US012446503B2

(12) United States Patent
Ward et al.

(10) Patent No.: US 12,446,503 B2
(45) Date of Patent: Oct. 21, 2025

(54) POLYPLOID HYBRID POTATO BREEDING

(71) Applicant: Ohalo Genetics, Inc., Aptos, CA (US)

(72) Inventors: Judson Arthur Ward, Watsonville, CA (US); Jason A. Peiffer, Hendersonville, NC (US); Lien Diana Bertier, Santa Cruz, CA (US); Morgan Edward Mccaw, Aptos, CA (US); Xingang Wang, Aptos, CA (US); Zachary Campbell Bower, Aptos, CA (US)

(73) Assignee: Ohalo Genetics, Inc., Aptos, CA (US)

( * ) Notice: Subject to any disclaimer, the term of this patent is extended or adjusted under 35 U.S.C. 154(b) by 0 days.

(21) Appl. No.: 18/504,893

(22) Filed: Nov. 8, 2023

(65) Prior Publication Data

US 2024/0147926 A1 May 9, 2024

Related U.S. Application Data

(60) Provisional application No. 63/497,670, filed on Apr. 21, 2023, provisional application No. 63/497,662, (Continued)

(51) Int. Cl.
*A01H 1/02* (2006.01)
*C12N 15/82* (2006.01)

(52) U.S. Cl.
CPC ......... *A01H 1/022* (2021.01); *C12N 15/8287* (2013.01); *C12N 15/8213* (2013.01); *C12N 15/8218* (2013.01); *C12N 15/8241* (2013.01)

(58) Field of Classification Search
None
See application file for complete search history.

(56) References Cited

U.S. PATENT DOCUMENTS 10,883,112 B2 1/2021 Mercier et al.
12,133,495 B2 11/2024 Albertsen et al.
(Continued)

FOREIGN PATENT DOCUMENTS

EP 4477069 A1 12/2024
WO WO-2012075195 A1 * 6/2012 ............ A01H 1/022
(Continued)

OTHER PUBLICATIONS

Jansky et al. “M6: A Diploid Potato Inbred Line for Use in Breeding and Genetics Research” 2014 J. of Plant Registrations doi: 10.3198/jpr2013.05.0024crg (5 total pages). (Year: 2014).*
(Continued)

*Primary Examiner* — Matthew R Keogh
*Assistant Examiner* — Rebecca Stephens
(74) *Attorney, Agent, or Firm* — Morrison & Foerster LLP

(57) ABSTRACT

The present inventions relate to a breeding system for the production of polyploid potato seeds, plants, or plant parts where cycles of meiosis, syngamy, and selection are used for interpopulation improvement of progenitor lines, and sexual polyploidization occurs during hybrid production by inducing clonal gamete formation in the parents that are to be crossed. Reciprocal recurrent selection can be used to inform selection of candidate potato lines that are either advanced to a gene editing or genetic modification system or crossed and selected to induce clonal gamete formation by arresting meiotic recombination and chromosome reduction. Crosses of parent plants bearing clonal gametes are planned and executed based upon predicted heterotic performance at the polyploid level. The final product is a homogeneous population of hybrid polyploid potato seed, or derivative thereof,
(Continued)

bearing both parents' complete nuclear genomes. In some instances, the method is used to generate seedless plants.

5 Claims, 59 Drawing Sheets

Specification includes a Sequence Listing.

Related U.S. Application Data filed on Apr. 21, 2023, provisional application No. 63/461,174, filed on Apr. 21, 2023, provisional application No. 63/423,768, filed on Nov. 8, 2022, provisional application No. 63/423,765, filed on Nov. 8, 2022.

(56) References Cited

U.S. PATENT DOCUMENTS

| | | | |
|---|---|---|---|
| 2005/0064474 | A1 | 3/2005 | Urniv et al. |
| 2009/0075829 | A1 | 3/2009 | Bush et al. |
| 2009/0117617 | A1 | 5/2009 | Holmes et al. |
| 2012/0042408 | A1 | 2/2012 | Mercier et al. |
| 2012/0142062 | A1 | 6/2012 | Doyon et al. |
| 2019/0098858 | A1 | 4/2019 | Albertsen et al. |
| 2019/0300900 | A1 | 10/2019 | Sirizzotti et al. |
| 2020/0362366 | A1 | 11/2020 | Davey et al. |
| 2021/0002657 | A1 | 1/2021 | Bass et al. |
| 2021/0054390 | A1 | 2/2021 | Chen et al. |
| 2021/0363537 | A1 | 11/2021 | Wang et al. |
| 2024/0150778 | A1 | 5/2024 | Ward et al. |
| 2024/0409950 | A1 | 12/2024 | Ward et al. |

FOREIGN PATENT DOCUMENTS

| | | | | |
|---|---|---|---|---|
| WO | WO-2017161264 A1 * | 9/2017 | ............... | A01H 1/08 |
| WO | WO-2024256682 A1 | 12/2024 | | |

OTHER PUBLICATIONS

Peloquin et al. 1999 "Perspectives: Anecdotal, Historical and Critical Commentaries on Genetics" Genetics 153:1493-1499. (Year: 1999).*

Brownfield and Kohler "Unreduced Gamete Formation in Plants: Mechanisms and Prospects" 2011 J. Experimental Botany 62(5):1659-1668. (Year: 2011).*

Mieulet et al. "Turning Rice Meiosis Into Mitosis" 2016 Cell Research 26:1242-1254 (Year: 2016).*

Jansky and Spooner "The Evolution of Potato Breeding" in Plant Breeding Reviews (vol. 41, First edition, Ed. Irwin Goldman, publisher John Wiley & Sons, Inc.) 2018 (46 total pages). (Year: 2018).*

D'Erfurth et al. "Turning Meiosis into Mitosis" 2009 PLoS Biology 7(6): e1000124 (doi:10.1371/journal.pbio.1000124 (10 total pages). (Year: 2009).*

Beurdeley et al., (2013). "Compact designer TALENs for efficient genome engineering," Nature Communications, 4:1762, 8 pages.

Brownfield et al., (2011). "Unreduced gamete formation in plants: mechanisms and prospects," Journal of Experimental Botany, 62(5):1659-1668.

Cao et al., (2014). "PEG-mediated transient gene expression and silencing system in maize mesophyll protoplasts: a valuable tool for signal transduction study in maize," Acta Physiologiae Plantarum, 36(5):1271-1281.

Cermak et al., (2011). "Efficient design and assembly of custom TALEN and other TAL effector-based constructs for DNA targeting," Nucleic Acids Research, 39(12):e82, 11 pages.

Clasen et al., (2016). "Improving cold storage and processing traits in potato through targeted gene knockout," Plant Biotechnology Journal, 14(1):169-176.

Colle et al., (2019). "Haplotype-phased genome and evolution of phytonutrient pathways of tetraploid blueberry," GigaScience, 8(3):giz012, 15 pages.

D'Erfurth et al., (2009). "Turning Meiosis into Mitosis," PLoS Biology, 7(6):e1000124, 10 pages.

Dhed'a et al., (1991). "Plant regeneration in cell suspension cultures of the cooking banana cv. Bluggoes'(*Musa* spp. ABB group)," Fruits, 46(2):125-135.

Doyle et al., (2012). "TAL Effector-Nucleotide Targeter (TALE-NT) 2.0: tools for TAL effector design and target prediction," Nucleic Acids Research, 40:W117-122.

Fossi et al., (2019). "Regeneration of Solanum tuberosum plants from protoplasts induces widespread genome instability," Plant Physiology, 180(1):78-86.

Gabsalilow et al., (2013). "Site- and strand-specific nicking of DNA by fusion proteins derived from MutH and I-Scel or TALE repeats," Nucleic Acids Research, 41:e83, 11 pages.

Gallais, (1984). "An Analysis Of Heterosis Vs. Inbreeding Effects With An Autotetraploid Cross-Fertilized Plant: *Medicago sativa* L.," Genetics, 106(1):123-137.

Groose et al., (1989). "Progressive Heterosis in Autotetraploid Alfalfa: Studies Using Two Types of Inbreds," Crop Sci., 29:1173-1177.

Guo et al., (2013). "The draft genome of watermelon (*Citrullus lanatus*) and resequencing of 20 diverse accessions," Nature Genetics, 45:51-58.

Haicour et al., (2009). "Protoplast isolation and culture for banana regeneration via somatic embryogenesis," Fruits, 64(4):261-269.

Huy et al. (1997). "Protoplast isolation, culture, and cell differentiation in raspberry and blackberry cultivars (*Rubus* spp.)," Angewandte-Botanik 71(3-4): 131-137.

Jansky et al., (2016). "Reinventing potato as a diploid inbred line-based crop," Crop Science, 56(4):1412-1422.

Jeong et al., (2021). "Optimization of protoplast regeneration in the model plant Arabidopsis thaliana," Plant Methods, 17(1):21, 16 pages.

Jiang et al., (2021). "Concerted genomic and epigenomic changes accompany stabilization of *Arabidopsis* allopolyploids," Nature Ecology & Evolution, 5:1382-1393, 22 pages.

Kouranov et al., (2022). "Demonstration of targeted crossovers in hybrid maize using CRISPR technology,"Communications Biology, 5:53, 11 pages.

Li, (2013). "Aligning sequence reads, clone sequences and assembly contigs with Bwa- Mem," arXiv, 1303.3997, 3 pages.

Liu et al., (2022). "Establishment of a DNA-free genome editing and protoplast regeneration method in cultivated tomato (*Solanum lycopersicum*)," Plant Cell Rep., 41(9):1843-1852.

Masters et al., (2020). "Agrobacterium Mediated Immature Embryo Transformation of Recalcitrant Maize Inbred Lines Using Morphogenic Genes," J. Vis. Exp., (156):e60782, 11 pages.

McCaw et al., (2020). "Development of a Transformable Fast-Flowering Mini-Maize as a Tool for Maize Gene Editing," Frontiers in Genome Editing, 2:622227, 14 pages.

McKenna et al., (2010). "The Genome Analysis Toolkit: a MapReduce framework for analyzing next-generation DNA sequencing data," Genome Research, 20(9):1297-1303.

Nicolia et al., (2015). "Targeted gene mutation in tetraploid potato through transient TALEN expression in protoplasts," Journal of Biotechnology, 204:17-24.

Nishiyama et al., (2007). "Embryological studies on cross-incompatibility between 2x and 4x in Brassica," Japanese Journal of Genetics, 41(1):27-42.

Noli et al., (2013). "Criteria for the definition of similarity thresholds for identifying essentially derived varieties," Plant Breeding, 132(6):525-531.

O'Leary et al., (2015). "Reference sequence (RefSeq) database at NCBI: current status, taxonomic expansion, and functional annotation," Nucleic Acids Res., 44(1)1):D733- D745.

Ott et al., (2017). "tGBS® genotyping-by-sequencing enables reliable genotyping of heterozygous loci," Nucleic acids research, 45(21): e178, 12 pages.

Panis et al., (1993). "Plant regeneration through direct somatic embryogenesis from protoplasts of banana (*Musa* spp.)," Plant Cell Reports, 12(7):403-407.

(56) References Cited

OTHER PUBLICATIONS

Clot et al., (2024). "Crossover shortage in potato is caused by StMSH4 mutant alleles and leads to either highly uniform unreduced pollen or sterility," Genetics, 226(1):iyad194, 13 pages.
Peloquin et al., (1999). "Meiotic Mutants in Potato: Valuable Variants," Genetics, 153:1493-1499.
Porto et al., (2020). "Base editing: advances and therapeutic opportunities," Nature Reviews Drug Discovery, 19(12):839-859, 60 pages.
Qiu et al., (2018). "Regeneration of Blueberry Cultivars through Indirect Shoot Organogenesis," HortScience, 53(7):1045-1049.
Ren et al., (2017). "Novel technologies in doubled haploid line development," Plant Biotechnol J, 15:1361-1370.
Rizzo et al., (2022). "Climate and agronomy, not genetics, underpin recent maize yield gains in favorable environments," PNAS, 119(4):e2113629119, 6 pages.
Sprunck et al., (2012). "Egg cell-secreted EC1 triggers sperm cell activation during double fertilization," Science, 338(6110):1093-1097.
Tian et al. (2017. "Efficient CRISPR/Cas9-based gene knockout in watermelon" Plant Cell Rep 36:399-406.
UniProt Consortium, (2019). "UniProt: a worldwide hub of protein knowledge," Nucleic Acids Res., 47(D1):D506-D515.
University of Hohenheim, (2020). "Heterotic groups," available online at <https://weizen.uni-hohenheim.de/en/111475>, 3 pages.
Vanburen et al., (2016). "The genome of black raspberry (Rubus occidentalis)," The Plant Journal, 87(6):535-547.
Veillet et al., (2019). "The Solanum tuberosum GBSSI gene: a target for assessing gene and base editing in tetraploid potato," Plant Cell Reports, 38(9):1065-1080, 34 pages.
Vernet et al., (2022). "High-frequency synthetic apomixis in hybrid rice," Nature Comm, 13:7963, 13 pages.
Vijayakumar et al., (2021). "High temperature induced changes in quality and yield parameters of tomato (*Solanum lycopersicum* L.) and similarity coefficients among genotypes using SSR markers," Heliyon. 7(2):e05988, 15 pages.
Vivian-Smith et al., (1999). "Genetic analysis of growth-regulator-induced parthenocarpy in *Arabidopsis*," Plant Physiology, 121(2):437-452.
Washburn et al., (2014). "Polyploids as a "model system" for the study of heterosis," Plant Reprod, 27:1-5.
Washburn et al., (2019). "Progressive heterosis in genetically defined tetraploid maize," Journal of Genetics and Genomics, 46:389-396.
Watanabe, (2015). "Potato genetics, genomics, and applications," Breed Sci., 65(1):53- 68.
Wu et al. (2018). "A Simple Method for Isolation of Soybean Protoplasts and Application to Transient Gene Expression Analyses," Journal of Visualized Experiments, 131:e57258, 7 pages.
Wu et al. (2020). "Establishment of a PEG-mediated protoplast transformation system based on DNA and CRISPR/Cas9 ribonucleoprotein complexes for banana," BMC Plant Biology, 20:425, 10 pages.
Wu et al., (2014). "Target specificity of the CRISPR-Cas9 system," Quant Biol., 2(2):59- 70, 19 pages.
Wu et al., (2019). "Genome of 'Charleston Gray', the principal American watermelon cultivar, and genetic characterization of 1,365 accessions in the U.S. National Plant Germplasm System watermelon collection," Plant Biotechnol J., 17(12): 2246-2258.
Yanik et al., (2013). "TALE-PvuII fusion proteins—novel tools for gene targeting," PLoS One, 8:e82539, 13 pages.
Yoo et al., (2007). "Arabidopsis mesophyll protoplasts: a versatile cell system for transient gene expression analysis," Nature Protocols, 2(7):1565-1572.
Yu et al., (2011). "Generation of transgenic watermelon resistant to Zucchini yellow mosaic virus and Papaya ringspot virus type W," Plant Cell Rep, 30:359-371, 19 pages.
Arisumi, (1982). "Endosperm balance Nos. among New Guinea-Indonesian Impatiens species," Journal of Heredity, 73(3):240-242.
Birchler, (1993). "Dosage analysis of maize endosperm development," Annu Rev Genet., 27:181-204.
Dalamu et al., (2023). "Genetic Diversity and Population Structure Analyses Using Simple Sequence Repeat Markers and Phenotypic Traits in Native Potato Collection in India," Potato Research: 1-25.
Dhir et al., (1992). "Regeneration of fertile plants from protoplasts of soybean (*Glycine max* L. Merr.): genotypic differences in culture response," Plant Cell Reports, 11:285-289.
Galbraith et al., (1983). "Rapid flow cytometric analysis of the cell cycle in intact plant tissues," Science, 220(4601): 1049-1051.
Heslop-Harrison et al., (1970). "Evaluation of pollen viability by enzymatically induced fluorescence; intracellular hydrolysis of fluorescein diacetate," Stain Technology, 45(3):115-120.
Jarl et al., (1995). "Protoplast regeneration and fusion in Cucumis: melon x cucumber," Plant Cell, Tissue and Organ Culture, 43:259-265.
Jones et al., (2019). "Maize transformation using the morphogenic genes Baby Boom and Wuschel2," Transgenic Plants, pp. 81-93.
Klein et al., (1987). "High-velocity microprojectiles for delivering nucleic acids into living cells," Nature, 327:70-73.
Krens et al., (1982). "In vitro transformation of plant protoplasts with Ti-plasmid DNA," Nature, 296:72-74.
Larkin (1976). "Purification and viability determinations of plant protoplasts," Planta, 128(3):213-216.
Linsmaier et al., (1965). "Organic growth factor requirements of tobacco tissue cultures," Physiol. Plant., 18(1):100-127.
Lloyd et al., (1980). "Commercially-feasible micropropagation of mountain laurel, Kalmia latifolia, by use of shoot-tip culture," Proc. Int. Plant Prop. Soc., 30:421-427.
Masson et al., (1987). "Plant regeneration from protoplasts of diploid potato derived from crosses of Solanum tuberosum with wild *Solanum* species," Plant Science, 53(2):167- 176.
Mok et al., (1975). "Breeding value of 2n pollen (diplandroids) in tetraploid x diploid crosses in potatoes," Theor. Appl. Genet., 46(6):307-314.
Murashige et al., (1962). "A revised medium for rapid growth and bioassays with tobacco tissue cultures," Physiologia Plantarum, 15(3):473-497.
Negrutiu et al., (1987). "Hybrid genes in the analysis of transformation conditions : I. Setting up a simple method for direct gene transfer in plant protoplasts," Plant. Mol. Biol., 8:363-373.
Ortiz et al., (1992). "The importance of Endosperm Balance Number in potato breeding and the evolution of tuber-bearing *Solanum* species," Euphytica, 60:105-113.
Paz et al., (1997). "Genetic Diversity Based on Randomly Amplified Polymorphic DNA (RAPD) and Its Relationship with the Performance of Diploid Potato Hybrids," Journal of the American Society for Horticultural Sci., 122(6):740-747.
Popescu et al., (2000). "High frequency shoot regeneration from leaf-derived callus in raspberry (*Rubus idaeus* L.)," Eucarpia Symposium On Fruit Breeding And Genetics, 538:667-670.
Shahin (1985). "Totipotency of tomato protoplasts," Theoretical and Applied Genetics, 69(3):235-240.
Shillito et al., (1985). "High Efficiency Direct Gene Transfer to Plants," Bio/Technol., 3:1099-1102.
Vosman et al., (2004). "The establishment of 'essential derivation' among rose varieties, using AFLP, " Theoretical and Applied Genetics, 109:1718-1725.
Wan et al., (1989). "Efficient production of doubled haploid plants through colchicine treatment of anther-derived maize callus," Theor. Appl. Genet., 77:889-892.
Wang et al., (2020). "Biolistic DNA delivery in maize immature embryos," Biolistic DNA Delivery in Plants: Methods and Protocols, pp. 177-195.
Werner et al., (1991). "Occurrence and mechanisms of 2n egg formation in 2x potato," Genome, 34(6):975-982.
Werner et al., (2015). "Inheritance and Two Mechanisms of 2n Egg Formation in 2x Potatoes," Journal of Heredity, 81(5):371-374.
Crossway et al., (1986). "Integration of foreign DNA following microinjection of tobacco mesophyll protoplasts," Mol. Gen. Genet., 202:179-185.
Genbank, (2014). "Accession No. AC216275, Zea maya cultivar B73 chromosome 5 clone CH201-219E6, * Sequencing in Progress * , 5 unordered pieces," available online at <https://www.ncbi.nlm.nih.gov/nuccore/AC21 6275>, 2 pages.

(56) References Cited

OTHER PUBLICATIONS

Genbank, (2005). "Accession No. AC155415, *Zea mays* strain B73 clone ZMMBBb0209015, * Sequencing in Progress * , 19 unordered pieces," available online at <https://www.ncbi.nlm.nih.gov/nuccore/AC1 55415>, 2 pages.
Genbank, (2000). "Accession No. AC009273, Sequence of Bac T1N6 from *Arabidopsis thaliana* chromosome 1, complete sequence," available online at <https://www.ncbi.nlm.nih.gov/nuccore/A0009273>, 2 pages.
Genbank, (2020). "Accession No. CP055239, Solanum tuberosum cultivar Solyntus chromosome 6," available online at <https://www.ncbi.nlm.nih.gov/nuccore/0P055239>, 2 pages.
Genbank, (2020). "Accession No. CP046692, Solanum tuberosum cultivar MSH/14-112 chromosome 6," available online at <https://www.ncbi.nlm.nih.gov/nuccore/CP046692>, 1 page.
Genbank, (2020). "Accession No. CP055240, Solanum tuberosum cultivar Solyntus chromosome 7," available online at <https://www.ncbi.nlm.nih.gov/nuccore/CP055240>, 1 page.
Genbank, (2020). "Accession No. CP046700, Solanum tuberosum cultivar MSH/14-112 chromosome 7," available online at <https://www.ncbi.nlm.nih.gov/nuccore/CP046700>, 1 page.
Genbank, (2020). "Accession No. CP055244, Solanum tuberosum cultivar Solyntus chromosome 11," available online at <https://www.ncbi.nlm.nih.gov/nuccore/CP055244>, 2 pages.
Genbank, (2020). Accession No. CP046691, Solanum tuberosum cultivar MSH/14-112 chromosome 11, available online at <https://www.ncbi.nlm.nih.gov/nuccore/0P046691>, 1 page.
International Search Report and Written Opinion received for International Patent Application No. PCT/US2023/079146 mailed on May 21, 2024, 20 pages.
Mahoney et al., (2019). "Sexual and Apomictic Seed Reproduction in *Aronia* Species with Different Ploidy Levels," HortScience, 54(4):642-646.
Max Planck Institute for Plant Breeding Research, (2024). "Like dad and like mum . . . all in one plant," available online at <www.sciencedaily.com/releases/2024/05/240513150437.htm>, 3 pages.
Max Planck Institute for Plant Breeding Research, (2024). "Mitosis instead of Meiosis: Researchers breed tomato plants that contain the complete genetic material of both parent plants," available online at <https://www.mpipz.mpg.de/pr-underwood-2024-05- en>, 3 pages.
Wang et al., (2024). "Harnessing clonal gametes in hybrid crops to engineer polyploid genomes," Nat Genet, 56(6): 1075-1079, 12 pages.
D'Erfurth et al., (2010). "The Cyclin-A CYCA1;2/TAM is Required for the Meiosis I to Meiosis II Transition and Cooperates with OSD1 for the Prophase to First Meiotic Division Transition," PLoS Genetics, 6(6):e1000989, 12 pages.
Guo et al., (2017). "Transcriptome analysis of neotetraploid rice reveals specific differential gene expressions associated with fertility and heterosis," Scientific Reports, 7:40139, 11 pages.
Kronholm et al., (2012). "Genetic basis of adaptation in *Arabidopsis thaliana*: local adaptation at the seed dormancy Qtl DOG1," Evolution, 66(7):2287-302.
Qian et al., (2024). "Genetic manipulation of the genes for clonal seeds results in sterility in cotton," BMC Plant Biology, 24:946, 12 pages.
Tiwari, (2022). "Chapter 9: Conventional True Potato Seed (TPS) to Diploid Hybrid Potato Technologies," Potato Improvement In The Post-Genomics Era, pp. 231-247.
Xie et al., (2019). "A strategy for generating rice apomixis by gene editing," JIPB, 61(8):911-916.

* cited by examiner

REC8, potato

```
Consensus                           MFYSHQLLARKAPLGQIXXXATLHSKLNRKKLSKLNIINICEQILNPSVPMALRLSGILM  60
StRec8 - WT                         .................WMA........................................  60
StRec8 - E-PED482-14761 allele 1    .................???----------------------------------------  60
StRec8 - E-PED482-14761 allele 2    .................???----------------------------------------  60

Consensus                           GGVVIVYERKVKLLYEDVTRLMVQINEAWKVKAATDPTLLPKGKSQAKYAAVTLPENREE  120
StRec8 - WT                         ............................................................  120
StRec8 - E-PED482-14761 allele 1    ------------------------------------------------------------  120
StRec8 - E-PED482-14761 allele 2    ------------------------------------------------------------  120

Consensus                           ELPEIEQTLRNPDTVTPMDFEQTSYFTMQVCKFNNRKLTMIKWFDFPSLSFGYSICFAIL  180
StRec8 - WT                         ............................................................  180
StRec8 - E-PED482-14761 allele 1    ------------------------------------------------------------  180
StRec8 - E-PED482-14761 allele 2    ------------------------------------------------------------  180

Consensus                           SDTTWIRVGNISENKIIIDNFYMRVQLNSRMFNVQRLDNADLYDKPNAQKEPAKDLHQVD  240
StRec8 - WT                         ............................................................  240
StRec8 - E-PED482-14761 allele 1    ------------------------------------------------------------  240
StRec8 - E-PED482-14761 allele 2    ------------------------------------------------------------  240

Consensus                           PDNITLAEHFESHHTDMFNHFERYHDEQFDIEGDEETQMNYTQPEDAQIPSTPVPSPPRE  300
StRec8 - WT                         ............................................................  300
StRec8 - E-PED482-14761 allele 1    ------------------------------------------------------------  300
StRec8 - E-PED482-14761 allele 2    ------------------------------------------------------------  300

Consensus                           QAHQPDEIPDRHPEDQVKQQSDEVEEAFEQRQDQQRPKPARRRARKATGLAIDHEQTIIS  360
StRec8 - WT                         ............................................................  360
StRec8 - E-PED482-14761 allele 1    ------------------------------------------------------------  360
StRec8 - E-PED482-14761 allele 2    ------------------------------------------------------------  360

Consensus                           GDIYQSWLQSSSDIASRKRKKRKTLRVLHSMKIARMMEMPPIALLEGLFTNGNKEVHYPA  420
StRec8 - WT                         ............................................................  420
StRec8 - E-PED482-14761 allele 1    ------------------------------------------------------------  420
StRec8 - E-PED482-14761 allele 2    ------------------------------------------------------------  420

Consensus                           FLLKLWMRNTQPPHDSPSGKTSPPYPPEPSYTSPGERMGNLEPPFEYFQSGVGSPAVGIS  480
StRec8 - WT                         ............................................................  480
StRec8 - E-PED482-14761 allele 1    ------------------------------------------------------------  480
StRec8 - E-PED482-14761 allele 2    ------------------------------------------------------------  480

Consensus                           IEKQRANLNNNKIPPEILMEDLRTNLTNMGLHPTVANGVKETDHMATPGSGDEPRSIPSS  540
StRec8 - WT                         ............................................................  540
StRec8 - E-PED482-14761 allele 1    ------------------------------------------------------------  540
StRec8 - E-PED482-14761 allele 2    ------------------------------------------------------------  540

Consensus                           GSGHGLLSQNSVTNSSRSNKKRPHSSSKHSGNGLQPVAEENPWHDPTPNFKLTRLSELSE  600
StRec8 - WT                         ............................................................  600
StRec8 - E-PED482-14761 allele 1    ------------------------------------------------------------  600
StRec8 - E-PED482-14761 allele 2    ------------------------------------------------------------  600

Consensus                           NGFTQDNEILMETGPTQTQHPFITQPLDMMTDSIRMQLKSHFDTPGSAEAECLNELTLGM  660
StRec8 - WT                         ............................................................  660
StRec8 - E-PED482-14761 allele 1    ------------------------------------------------------------  660
StRec8 - E-PED482-14761 allele 2    ------------------------------------------------------------  660

Consensus                           TKKQAACLFYQTCVLATRDFIKVEQELPYGNILISRGAKM                      700
StRec8 - WT                         ........................................                      700
StRec8 - E-PED482-14761 allele 1    ----------------------------------------                       20
StRec8 - E-PED482-14761 allele 2    ----------------------------------------                       20
```

FIG. 15A

CYCA1, potato

```
Consensus                           MMTTQNRRSSVSSAVAKRQAMAANSSGLENNQTGKLNAGAAKKRPALSNISNHTTVSARN   60
StTAM - WT                          ............................................................   60
StTAM - E-PED482-14761 allele 1     ............................................................   60
StTAM - E-PED482-14761 allele 2     ............................................................   60

Consensus                           SISHSSKLAPCTSKIVSIKKNISSGTAXXXXXXSXXXXXXXXXXZXXXXXXXXJXXJXLP  120
StTAM - WT                          ..........................VLPASS.VRPSSKPVSIQRSDAVVPKITAIP..  120
StTAM - E-PED482-14761 allele 1     ..........................--HPPL.DQAANLFLFKEVMQLCLRSLPFLF..  118
StTAM - E-PED482-14761 allele 2     ..........................VQHPPL.DQAANLFLFKEVMQLCLRSLPFLF..  120

Consensus                           XXXXXXJXXXXXDXXLVSMDESMSTSDTVRSPEVEYIDDLESAAVDSIEKKACSTLYISE  180
StTAM - WT                          ATCSMDISPSHS.GS.............................................  180
StTAM - E-PED482-14761 allele 1     PAAWTFLHLTQM.H*---------------------------------------------  178
StTAM - E-PED482-14761 allele 2     PAAWTFLHLTQM.H*---------------------------------------------  180

Consensus                           HIKAAAADICKRDVLVDLESGDKIVNIDNNLVDPQLCATMACDIYTHLRASEAKKRPSTD  240
StTAM - WT                          ............................................................  240
StTAM - E-PED482-14761 allele 1     ------------------------------------------------------------  238
StTAM - E-PED482-14761 allele 2     ------------------------------------------------------------  240

Consensus                           FMAKVQKDINPSMRAILIDWLVEVAEEYRLVPDTLHLTINYIDRYLSGNLMDRQRLQLLG  300
StTAM - WT                          ............................................................  300
StTAM - E-PED482-14761 allele 1     ------------------------------------------------------------  298
StTAM - E-PED482-14761 allele 2     ------------------------------------------------------------  300

Consensus                           VACMMIASKYEEICAPQVEEFCYITDNTYFKEEVLQMESTVLNYLKFEMTAPTAKCFLRR  360
StTAM - WT                          ............................................................  360
StTAM - E-PED482-14761 allele 1     ------------------------------------------------------------  358
StTAM - E-PED482-14761 allele 2     ------------------------------------------------------------  360

Consensus                           FVRAAQGLNEVLSLQLEHLASYIAELSLLEYNMLSYAPSLIAASAIFLAKYILLPSVKPW  420
StTAM - WT                          ............................................................  420
StTAM - E-PED482-14761 allele 1     ------------------------------------------------------------  418
StTAM - E-PED482-14761 allele 2     ------------------------------------------------------------  420

Consensus                           NSTLRHYTLYQPSDLQDCVMALHSLCCNNNNSSLPAVREKYSQHKYKFVAKKYCPPTVPV  480
StTAM - WT                          ............................................................  480
StTAM - E-PED482-14761 allele 1     ------------------------------------------------------------  478
StTAM - E-PED482-14761 allele 2     ------------------------------------------------------------  480

Consensus                           EFFQNISS*AREM*EEASTSVFPIVCWINSWHSILYSL*LAMSMAELHSWFFSP*GALAE  540
StTAM - WT                          ............................................................  540
StTAM - E-PED482-14761 allele 1     ------------------------------------------------------------  538
StTAM - E-PED482-14761 allele 2     ------------------------------------------------------------  540

Consensus                           YLRL*SLTLTLQD*SLVLILFFSGLVSLVSLCTEEALLAVSLTQKLFSNDSLVELLQFVP  600
StTAM - WT                          ............................................................  600
StTAM - E-PED482-14761 allele 1     ------------------------------------------------------------  598
StTAM - E-PED482-14761 allele 2     ------------------------------------------------------------  600

Consensus                           ISIEKNITTDQSLDFSSCQMSNWCNSI*SCTEVG*RKKVEH                     641
StTAM - WT                          .........................................                     641
StTAM - E-PED482-14761 allele 1     -----------------------------------------                     133
StTAM - E-PED482-14761 allele 2     -----------------------------------------                     135
```

FIG. 15B

SPO11-1, potato

```
Consensus                                   MEGKRSNTQPLTLIRKIKGFTRSIVEDLARGRAPLIYIDRFRNYCTDTSGNCSCSSGLST  60
StSpo11-1 - WT                              ............................................................  60
StSpo11-1 - E-PED482-14761 allele 1         ............................................................  60
StSpo11-1 - E-PED482-14761 allele 2         ............................................................  60

Consensus                                   GKEAISLKRECHARRXXVXXXXXXXXXXXXXXZXXXXXXXXJXXXXXXXFKEQSVVDRAIN 120
StSpo11-1 - WT                              ...............LD.LLRVLVIVQQLLQENRHGSKRDIYYMHPTV............ 120
StSpo11-1 - E-PED482-14761 allele 1         ...............CF.ESSCDSSTTSARKQAWIKKRHILHASYCF*------------ 120
StSpo11-1 - E-PED482-14761 allele 2         ...............CF.ESSCDSSTTSARKQAWIKKRHILHASYCF*------------ 120

Consensus                                   DICILLQCSRHNLNVVSVGNGLVMGWLRYVESGRKINCISNPHTAYPIPVLVEEVDDIIS 180
StSpo11-1 - WT                              ............................................................ 180
StSpo11-1 - E-PED482-14761 allele 1         ------------------------------------------------------------ 180
StSpo11-1 - E-PED482-14761 allele 2         ------------------------------------------------------------ 180

Consensus                                   VAQYVLVVEKESVFQRLANDQFCKRNRCIVITGRGYPDVPTRRFLRLLIDKLHLPVYGLV 240
StSpo11-1 - WT                              ............................................................ 240
StSpo11-1 - E-PED482-14761 allele 1         ------------------------------------------------------------ 240
StSpo11-1 - E-PED482-14761 allele 2         ------------------------------------------------------------ 240

Consensus                                   DCDPYGFDILTTYKFGSLQMAYDATFLRVSEIQWLGVFVQDCDNYSIPQQCLLPLTTEDK 300
StSpo11-1 - WT                              ............................................................ 300
StSpo11-1 - E-PED482-14761 allele 1         ------------------------------------------------------------ 300
StSpo11-1 - E-PED482-14761 allele 2         ------------------------------------------------------------ 300

Consensus                                   RKVEAMLPRCYLQREVPQWRFELELLLHKGVKFEIEALSVHSLTFLSHEYLPSKIHNGGA 360
StSpo11-1 - WT                              ............................................................ 360
StSpo11-1 - E-PED482-14761 allele 1         ------------------------------------------------------------ 360
StSpo11-1 - E-PED482-14761 allele 2         ------------------------------------------------------------ 360

Consensus                                   VF                                                           362
StSpo11-1 - WT                              ..                                                           362
StSpo11-1 - E-PED482-14761 allele 1         --                                                           108
StSpo11-1 - E-PED482-14761 allele 2         --                                                           108
```

FIG. 15C

*rec8*, potato

```
PRS078                                                                                                                                ATG
StREC8-WT              GTTGAAGTTCCTTCATAGGATTTTCGGTATACGTTAAGTTTTCACATTTCAATTTGACTACGAAGAATGTTTAAATTGATGCTGTTTATATCTCTCTCTTTGCTGTGAAGGATG
StREC8-WT translation                                                                                                           -5'UTR-[M]
PED-PR-AB-rcs          GTTGAAGTTCCTTCATAGGATTTTCGGTATACGTTAAGTTTTCACATTTCAATTTGACTACGAAGAATGTTTAAATTGATGCTGTTTATATCTCTCTCTTTGCTGTGAA-----
PED-PR-AB-rcs          GTTGAAGTTCCTTCATAGGATTTTTTGTATACGTTAAGTTTTCACATTTCAATTTGGCTACGAAGAATGTTTAAATTGATGTTGTTTATATCTCTCTCTTTGCTGTGAAG----
PED-PR-AB-rso          GTTGAAGTTCCTTCATAGGATTTTCGGTATACGTTAAGTTTTCACATTTCAATTTGACTACGAAGAATGTTTAAATTGATGCTGTTTATATCTCTCTCTTTGCTGTGAA-----
PED-PR-AB-rso          GTTGAAGTTCCTTCATAGGATTTTTTGTATACGTTAAGTTTTCACATTTCAATTTGGCTACGAAGAATGTTTAAATTGATGTTGTTTATATCTCTCTCTTTGCTGTGA------
PED-PR-EF-rso-1        GTTGAAGTTCCTTCATAGGATTTTCGGTATACGTTAAGTTTTCACATTTCAATTTGACTACGAAGTATGTTTAAATTGATGTTGTTTATATCT--------------------
PED-PR-EF-rso-1        GTTGAAGTTCCTTCATAGGATTTTCGGTATACGTTAAGTTTTCACATTTCAATTTGACTACGAAGTATGTTTAAATTGATGTTGTTTATATCTCTCT--TTGCTG---------
PED-PR-EF-rso-2        GTTGAAGTTCCTTCATAGGATTTTCGGTATACGTTAAGTTTTCACATTTCAATTTGACTACGAAGTATGTTTAAATTGATGTTGTTTATATCT--------------------
PED-PR-EF-rso-2        GTTGAAGTTCCTTCATAGGATTTTCGGTATACGTTAAGTTTTCACATTTCAATTTGACTACGAAGTATGTTTAAATTGATGTTGTTTATATCTCTCT--TTGCTG---------
PED-PR-EF-rcs          GTTGAAGTTCCTTCATAGGATTTTCGGTATACGTTAAGTTTTCACATTTCAATTTGACTACGAAGTATGTTTAAATTGATGTTGTTTATATCTCTCT--TTGCTGTGAA-----
PED-PR-EF-rcs          GTTGAAGTTCCTTCATAGGATTTTCGGTATACGTTAAGTTTTCACATTTCAATTTGACTACGAAGTATGTTTAAATTGATGTTGTTTATATCTCTCT--TTGCTGTGA------
PED-PR-AB-sp           GTTGAAGTTCCTTCATAGGATTTTTTGTATACGTTAAGTTTTCACATTTCAATTTGGCTACGAAGAATGTTTAAATTGATGTTGTTTATATCTCTCTCTTTGCTGTGAATACGT

GCGGCCACTCTACACTC
GCGGCCACTCTACACTCGAAACTCAATAGGAAAAAGCTTAGTAAACTCAATATTATTAACATCTGGTGAGGCGTTGTCTTCCACTACTACGTTGAACTGCCTTTA  219
[A][A][T][L][H][S][K][L][N][R][K][K][L][S][K][L][N][I][I][N][I]-intron-
-----CACTCTACACTCGAAACTCAATAGGAAAAAGCTTAGTAAACTCAATATTATTAACATCTGGTGAGGCGTTGTCTTCCACTACTACGTTGAACTGCCTTTA  209
-CGGCCACTCTACACTCGAAACTCAATAGGAAAAAGCTTAGTAAACTCAATATAATTAACATCTGGTGATGCGTTTTCTTCCACTACTACGTTGAACTGCCTTTA  214
--GGCCACTCTACACTCGAAACTCAATAGGAAAAAGCTTAGTAAACTCAATATTATTAACATCTGGTGAGGCGTTGTCTTCCACTACTACGTTGAACTGCCTTTA  212
--GGCCACTCTACACTCGAAACTCAATAGGAAAAAGCTTAGTAAACTCAATATAATTAACATCTGGTGATGCGTTTTCTTCCACTACTACGTTGAACTGCCTTTA  211
-CGGCCACTCTACACTCGAAACTCAATAGGAAAAAGCTTAGTAAACTCAATATTATTAACATCTGGTGATGCGTTTTCTTCCACTACTACGTTGAACTGCCTTTA  197
----------------------------GGAAAAAGCTTAGTAAACTCAATATTATTAACATCTGGTGATGCGTTTTCTTCCACTACTACGTTGAACTGCCTTTA  180
-CGGCCACTCTACACTCGAAACTCAATAGGAAAAAGCTTAGTAAACTCAATATTATTAACATCTGGTGATGCGTTTTCTTCCACTACTACGTTGAACTGCCTTTA  197
----------------------------GGAAAAAGCTTAGTAAACTCAATATTATTAACATCTGGTGATGCGTTTTCTTCCACTACTACGTTGAACTGCCTTTA  180
--GGCCACTCTACACTCGAAACTCAATAGGAAAAAGCTTAGTAAACTCAATATTATTAACATCTGGTGATGCGTTTTCTTCCACTACTACGTTGAACTGCCTTTA  210
--GGCCACTCTACACTCGAAACTCAATAGGAAAAAGCTTAGTAAACTCAATATTATTAACATCTGGTGATGCGTTTTCTTCCACTACTACGTTGAACTGCCTTTA  209
GCATGGCATTCCCTCTTCAGGGATATAGCTTCCTTGCCAGTCGACAAACCAGAGCTGCAAGAGCTACATAAATTAAACAAAGACCATTAATAC------------  207
```

FIG. 15D

*cyca1*, potato

```
PRS658                                                                                                     CTCAGGGACTGCTGTTCTG
StCYCA1-WT               GTTGTGACTAACTTGGAATCATTTTTGACTTTGGAAGGCACCATGTACGTCCAAGATTGTAAGCATTAAGAAGAACATTTCCTCAGGGACTGCTGTTCTG
StCYCA1-WT translation                             -intron-[A][P][C][T][S][K][I][V][S][I][K][K][N][I][S][S][G][T][A][V][L]
PED-PR-AB-rcs            GTTGTGACTAACTTGGAATCATTTTTGACTTTGGAAGGCACCATGTACGTCCAAGATTGTAAGCATTAAGAAGAACATTTCCTCAGGGACTGCTGTTC--
PED-PR-AB-rcs            GTTGTGACTAACTTGGAATCATTTTTGACTTTGGAAGGCACCATGTACGTCCAAGATTGTAAGCATTAAGAAGAACATTTCCTCAGGGACTGC-------
PED-PR-EF-rcs            GTTGTGACTAACTTGGAATCATTTTTGACTTTGGAAGGCACCATGTACGTCCAAGATTGTAAGCATTAAGAAGAACATTTCCTCAGGGACTGCTGT----
PED-PR-EF-rcs            GTTGTGACTAACTTGGAATCATTTTTGACTTTGGAAGGCACCATGTACGTCCAAGATTGTAAGCATTAAGAAGAACATTTCCTCAG--------------

                         C
                         CCAGCATCCTCCTCTGTCAGACCAAGCAGCAAACCTGTTTCTATTCAAAGAAGTGATGCAGTTGTGCCTAAGATCACTGCCATTCCTCTTCCTGCCACCT  200
                         [P][A][S][S][S][V][R][P][S][S][K][P][V][S][I][Q][R][S][D][A][V][V][P][K][I][T][A][I][P][L][P][A][T]
                         --AGCATCCTCCTCTGTCAGACCAAGCAGCAAACCTGTTTCTATTCAAAGAAGTGATGCAGTTGTGCCTAAGATCACTGCCATTCCTCTTCCTGCCACCT  196
                         ---GCATCCTCCTCTGTCAGACCAAGCAGCAAACCTGTTTCTATTCAAAGAAGTGATGCAGTTGTGCCTAAGATCACTGCCATTCCTCTTCCTGCCACCT  198
                         ---GCATCCTCCTCTGTCAGACCAAGCAGCAAACCTGTTTCTATTCAAAGAAGTGATGCAGTTGTGCCTAAGATCACTGCCATTCCTCTTCCTGCCACCT  193
                         --------------------ACCAAGCAGCAAACCTGTTTCTATTCAAAGAAGTGATGCAGTTGTGCCTAAGATCACTGCCATTCCTCTTCCTGCCACCT  166
```

FIG. 15E

*spo11-1*, potato

```
PRS257                                                                                                                                CTTGGTGAGTCTAGGGAGAG
StSPO11-1-WT               GTATTAATGGTCTTTGTTTAATTTATGTAGCTCTTGCAGCTCTGGTTTGTCTACTGGCAAGGAAGCTATATCCCTGAAGAGGGAATGCCATGCACGTAGGCTTGGTGAGTCTAGGGAGAGTAAA
StSPO11-1-WT translation                           -intron-[S][C][S][S][G][L][S][T][G][K][E][A][I][S][L][K][R][E][C][H][A][R][R][L]-intron-
PED-PR-AB-rso              GTATTAATGGTCTTTGTTTAATTTATGTAGCTCTTGCAGCTCTGGTTTGTCTACTGGCAAGGAAGCTATATCCCTGAAGAGGGAATGCCATGCACG--------------CTAGGGAGAGTAAA
PED-PR-AB-rso              GTATTAATGGTCTTTGTTTAATTTATGTAGCTCTTGCAGCTCTGGTTTGTCGACTGGCAAGGAAGCTATATCCCTGAAGAGGGAATGCCATGCACGT--------TGAGTCTAGGGAGAGTAAA
PED-PR-AB-sp               GTATTAATGGTCTTTGTTTAATTTATGTAGCTCTTGCAGCTCTGGTTTGTCTACTGGCAAGGAAGCTATATCCCTGAAGAGGGAATGCCATGCACGTA-----GGTGAGTCTAGGGAGAGTAAA
PED-PR-AB-sp                     CAGTTCAACGTAGTAGTGGAAGAAAACGCATCACCAGATGTTAATTATATTGAGTTTACTAAGCTTTTTCCTATTGAGTTTCGAGTGTAGAGTGGCCGGTGAGTCTAGGGAGAGTAAA
PED-PR-AB-rcs              GTATTAATGGTCTTTGTTTAATTTATGTAGCTCTTGCAGCTCTGGTTTGTCTACTGGCAAGGAAGCTATATCCCTGAAGAGGGAATGCCATGCACGTA-----GGTGAGTCTAGGGAGAGTAAA
PED-PR-AB-rcs              GTATTAATGGTCTTTGTTTAATTTATGTAGCTCTTGCAGCTCTGGTTTGTCGACTGGCAAGGAAGCTATATCCCTGAAGAGGGAATGCCATGCACGTA-----GGTGAGTCTAGGGAGAGTAAA
PED-PR-AD-sp               GTATTAATGGTCTTTGTTTAATTTATGTAGCTCTTGCAGCTCTGGTTTGTCTACTGGCAAGGAAGCTATATCCCTGAAGAGGGAATGCCATGCACGTTGG---------TCTAGGGAGAGTAAA
PED-PR-AD-sp               GTATTAATGGTCTTTGTTTAATTTATGTAGCTCTTGCAGCTCTGGTTTGTCGACTGGCAAGGAAGCTATATCCCTGAAGAGGGAATGCCATGCACGTA-----G-TGAGTCTAGGGAGAGTAAA
PED-PR-EF-rcs              GTATTAATGGTCTTTGTTTAATTTATGTAGCTCTTGCAGCTCTGGTTTGTCGACCGGCAAGGAAGCTATATCCCTGAAGAGGGAATGCCATGCACGTA-----GGTGAGTCTAGGGAGAGTAAA
PED-PR-EF-rcs              GTATTAATGGTCTTTGTTTAATTTATGTAGCTCTTGCAGCTCTGGTTTGTCGACTGGCAAGGAAGCTATATCCCTGAAGAGGGAATGCCAAGCACGTA-----GGTGAGTCTAGGGAGAGTAAA
PED-PR-EF-rso-1            GTATTAATGGTCTTTGTTTAATTTATGTAGCTCTTGCAGCTCTGGTTTGTCGACCGGCAAGGAAGCTATATCCCTGAAGAGGGAATGCCATGCACGTA-----GGTGAGTCTAGGGAGAGTAAA
PED-PR-EF-rso-1            GTATTAATGGTCTTTGTTTAATTTATGTAGCTCTTGCAGCTCTGGTTTGTCGACTGGCAAGGAAGCTATATCCCTGAAGAGGGAATGCCAAGCACGTA--------GAGTCTAGGGAGAGTAAA
PED-PR-EF-rso-2            GTATTAATGGTCTTTGTTTAATTTATGTAGCTCTTGCAGCTCTGGTTTGTCGACCGGCAAGGAAGCTATATCCCTGAAGAGGGAATGCCATGCACGTA-----GGTGAGTCTAGGGAGAGTAAA
PED-PR-EF-rso-2            GTATTAATGGTCTTTGTTTAATTTATGTAGCTCTTGCAGCTCTGGTTTGTCGACTGGCAAGGAAGCTATATCCCTGAAGAGGGAATGCCAAGCACGTA--------GAGTCTAGGGAGAGTAAA

                          CAATACTTGTATATTGTATCTGCTGATCTTCATCACATAGTTGGACAAGAAATGATATGATAGTGAAAAGGGTAG   199

                          CAATACTTGTATATTGTATCTGCTGATCTTCATCACATAGTTGGACAAGAAATGATATGATAGTGAAAAGGGTAG   185
                          TAATACTTGTATATTTTATCTGCTGATCTTCATCACATAGTTGGACAAGAAATGACATGATAGTGAAGAGGGTAG   191
                          CAATACTTGTATATTGTATCTGCTGATCTTCATCACATAGTTGGACAAGAAATGATATGATAGTGAAAAGGGTAG   194
                          TAATACTTGTATATTTTATCTGCTGATCTTCATCACATAGTTGGACAAGAAATGACATGATAGTGAAGAGGGTAG   193
                          CAATACTTGTATATTGTATCTGCTGATCTTCATCACATAGTTGGACAAGAAATGATATGATAGTGAAAAGGGTAG   194
                          TAATACTTGTATATTTTATCTGCTGATCTTCATCACAGAGTGGGACAAGAAATGACATGATAGTGAAGAGGGTAG   194
                          CAATACTTGTATATTGTATCTGCTGATCTTCATCACATAGTTGGACAAGAAATGATATGATAGTGAAAAGGGTAG   198
                          TAATACTTGTATATTTTATCTGCTGATCTTCATCACATAGTTGGACAAGAAATGACATGATAGTGAAGAGGGTAG   193
                          CAATACTTGTATATTTTATCTACTGATCTTCATCACATAGTTGGACAAGATATGATATGATAGTGAAGGGGGTAG   194
                          TAATACTTGTATATTTTATCTGCTGATCTTCATCACATAGTTGGACAAGAAATGATATGATAGTGAAGAGGG---   191
                          CAATACTTGTATATTTTATCTACTGATCTTCATCACATAGTTGGACAAGATATGATATGATAGTGAAGGGGGTAG   194
                          TAATACTTGTATATTTTATCTGCTGATCTTCATCACATAGTTGGACAAGAAATGATATGATAGTGAAGAGGGTAG   191
                          CAATACTTGTATATTTTATCTACTGATCTTCATCACATAGTTGGACAAGATATGATATGATAGTGAAGGGGGTAG   194
                          TAATACTTGTATATTTTATCTGCTGATCTTCATCACATAGTTGGACAAGAAATGATATGATAGTGAAGAGGGTAG   191
```

FIG. 15F

FIG. 17K
BPP1
(PED-PR-CC-o x PED-PR-AB-sp)
SPP2
(PED-PR-CC-o x PED-PR-AB)

FIG. 18G
BPP2
(PED-PR-EF-rso-1 x PED-PR-AB-sp)
SPP1
(PED-PR-EF-o x PED-PR-AABB)

BPP4

SEQUENCE LISTING

```
Sequence total quantity: 193
SEQ ID NO: 1            moltype = AA  length = 700
FEATURE                 Location/Qualifiers
source                  1..700
                        mol_type = protein
                        organism = Solanum tuberosum
SEQUENCE: 1
MFYSHQLLAR KAPLGQIWMA ATLHSKLNRK KLSKLNIINI CEQILNPSVP MALRLSGILM  60
GGVVIVYERK VKLLYEDVTR LMVQINEAWK VKAATDPTLL PKGKSQAKYA AVTLPENREE  120
ELPEIEQTLR NPDTVTMMDF EQTSYFTMQV CKFNNRKLTM IKWFDFPSLS FGYSICFAIL  180
SDTTWIRVGN ISENKIIIDN FYMRVQLNSR MFNVQRLDNA DLYDKPNAQK EPAKDLHQVD  240
PDNITLAEHF ESHHTDMFNH FERYHDEQFD IEGDEETQMN YTQPEDAQIP STPVPSPPRE  300
QAHQPDEIPD RHPEDQVKQQ SDEVEEAFEQ RQDQQRPKPA RRRARKATGL AIDHEQTIIS  360
GDIYQSWLQS SSDIASRKRK KRKTLRVLHS MKIARMMEMP PIALLEGLFT NGNKEVHYPA  420
PLLKLWMRNT QPPHDSPSGK TSPPYPPEPS YTSPGERMGN LEPPFEYFQS GVGSPAVGIS  480
IEKQRANLNN NKIPPEILME DLRTNLTNMG LHPTVANGVK ETDHMATPGS GDEPRSIPSS  540
GSGHGLLSQN SVTNSSRSNK KRPHSSSKHS GNGLQPVAEE NPWHDPTPNF KLTRLSELSE  600
NGFTQDNEIL METGPTQTQH PFITQPLDMM TDSIRMQLKS HFDTPGSAEA ECLNELTLGM  660
TKKQAACLFY QTCVLATRDF IKVEQELPYG NILISRGAKM                       700
```

```
SEQ ID NO: 2            moltype = AA  length = 362
FEATURE                 Location/Qualifiers
source                  1..362
                        mol_type = protein
                        organism = Solanum tuberosum
SEQUENCE: 2
MEGKRSNTQP LTLIRKIKGF TRSIVEDLAR GRAPLIYIDR FRNYCTDTSG NCSCSSGLST  60
GKEAISLKRE CHARRLDVLL RVLVIVQQLL QENRHGSKRD IYYMHPTVFK EQSVVDRAIN  120
DICILLQCSR HNLNVVSVGN GLVMGWLRYV ESGRKINCIG NPHTAYPIPV LVEEVDDIIS  180
VAQYVLVVEK ESVFQRLAND QFCKRNRCIV ITGRGYPDVP TRRFLRLLID KLHLPVYGLV  240
DCDPYGFDIL TTYKFGSLQM AYDATFLRVS EIQWLGVFVQ DCDNYSIPQQ CLLPLTTEDK  300
RKVEAMLPRC YLQREVPQWR FELELLLHKG VKFEIEALSV HSLTFLSHEY LPSKIHNGGA  360
VF                                                                362

SEQ ID NO: 3            moltype = AA  length = 451
FEATURE                 Location/Qualifiers
source                  1..451
                        mol_type = protein
                        organism = Solanum tuberosum
SEQUENCE: 3
MKLKMNKASD LSSISVLPPH ARRPSVVPSA AESSVFGKSQ PSQVRSQQQS QQSFSQGFSS  60
QQAIYSQLSQ SSLDDFVPNE QRLGSQEREN SAKRMSCLPH INYTREETQM QLSKPSTNYL  120
RKWSVPESKY QIEELEHKIG MVETSLSRQG MILDSIQSDI MQVNRGTKEI LMEMESLRPK  180
LVSHDELLQL MNKEREDLKA SLEGTFKSMF EELRENKYQE NIRDLLSLLR AMPNKLEMCI  240
LQLQTDLSKT LAKEIQIISP RPDCHGKKHE TAPVDPPKVI NDCSLPREVK FLKKDQKTTT  300
PPKIEMGSWT TVKINQTCMK QKNPIRSHTQ NEAFQKLLPL YEMGSWTTVK NNQTCMKQKI  360
PIRSLTQNEA FQQKIPIRSH TQNGAFQQER GHRITIESDE DIDAGFSCLL EENGTENPGI  420
YPLDDAKEES ARILRKARRR KRKHFNTIII D                                451

SEQ ID NO: 4            moltype = AA  length = 255
FEATURE                 Location/Qualifiers
source                  1..255
                        mol_type = protein
                        organism = Solanum tuberosum
SEQUENCE: 4
MAEGRDRLSR QEDPIDIYSR RRRSMGRGGI EIFEDESPES SSRAPIQTTA ETGRMAGTSG  60
GRGGIGRIGF GSPRNRRGRN SLRTPTRVIG RQNISPAGQG RNRGRHSVLP AWYPRTPLRD  120
ITSIVRAIER TRARLRESEG EQLESVVPQD HTDLGPSEST SGAQLEHTNS LITPRPKTRS  180
RYHTRSVGKV PKILLDITNQ STSEDSECLT PQRKLLNSID TVEKDVMEEL HKLKRTPGAR  240
KEERDKRVKT LMSMR                                                  255

SEQ ID NO: 5            moltype = AA  length = 488
FEATURE                 Location/Qualifiers
source                  1..488
                        mol_type = protein
                        organism = Solanum tuberosum
SEQUENCE: 5
MMTTQNRRSS VSSAVAKRQA MAANSSGLEN NQTGKLNAGA AKKRPALSNI SNHTTVSARN  60
SISHSSKLAP CTSKIVSIKK NISSGTAVLP ASSSVRPSSK PVSIQRSDAV VPKITAIPLP  120
ATCSMDISPS HSDGSLVSMD ESMSTSDTVR SPEVEYIDDL ESAAVDSIEK KACSTLYISE  180
HIKAAAADIC KRDVLVDLES GDKIVNIDNN LVDPQLCATM ACDIYTHLRA SEAKKRPSTD  240
FMAKVQKDIN PSMRAILIDW LVEVAEEYRL VPDTLHLTIN YIDRYLSGNL MDRQRLQLLG  300
VACMMIASKY EEICAPQVEE FCYITDNTYF KEEVLQMEST VLNYLKFEMT APTAKCFLRR  360
FVRAAQGLNE VLSLQLEHLA SYIAELSLLE YNMLSYAPSL IAASAIFLAK YILLPSVKPW  420
NSTLRHYTLY QPSDLQDCVM ALHSLCCNNN NSSLPAVREK YSQHKYKFVA KKYCPPTVPV  480
EFFQNISS                                                          488

SEQ ID NO: 6            moltype = AA  length = 487
FEATURE                 Location/Qualifiers
source                  1..487
                        mol_type = protein
                        organism = Solanum tuberosum
SEQUENCE: 6
MMTTQNRRSS VSSAVAKRQA MAANSSGLEN NQTGKLNAGA AKKRPALSNI SNHTTVSARN  60
SISHSSKLAP CTSKIVSIKK NISSGTAVLP ASSSVRPSSK PVSIQRSDAV VPKITAIPLP  120
ATCSMDISPS HSDGSLVSMD ESMSTSDTVR SPEVEYIDDL ESAAVDSIEK KACSTLYISE  180
HIKAAADICK RDVLVDLESG DKIVNIDNNL VDPQLCATMA CDIYTHLRAS EAKKRPSTDF  240
MAKVQKDINP SMRAILIDWL VEVAEEYRLV PDTLHLTINY IDRYLSGNLM DRQRLQLLGV  300
ACMMIASKYE EICAPQVEEF CYITDNTYFK EEVLQMESTV LNYLKFEMTA PTAKCFLRRF  360
VRAAQGLNEV LSLQLEHLAS YIAELSLLEY NMLSYAPSLI AASAIFLAKY ILLPSVKPWN  420
STLRHYTLYQ PSDLQDCVMA LHSLCCNNNN SSLPAVREKY SQHKYKFVAK KYCPPTVPVE  480
FFQNISS                                                           487

SEQ ID NO: 7            moltype = AA  length = 483
FEATURE                 Location/Qualifiers
source                  1..483
                        mol_type = protein
                        organism = Solanum tuberosum
```

```
SEQUENCE: 7
MMTTQNRRSS VSSAVAKRQA MAANSSGLEN NQTGKLNAGA AKKRPALSNI SNHTTVSARN  60
SISHSSKLAP CTSKIVSIKK NISSGTAVLP ASSSVRPSSK PVSIQRSDAV VPKITAIPLP  120
ATCSMDISPS HSDGSLVSMD ESMSTSDTVR SPEVEYIDDL ESAAVDSIEK KACSTLYISE  180
HIKAAAADIC KRDVLVDLES GDKIVNIDNN LVDPQLCATM ACDIYTHLRA SEAKKRPSTD  240
FMAKVQKDIN PSMRAILIDW LVEVAEEYRL VPDTLHLTIN YIDRYLSGNL MDRQRLQLLG  300
VACMMIASKY EEICAPQVEE FCYITDNTYF KEEVLQMEST VLNYLKFEMT APTAKCFLRR  360
FVRAAQGLNE LEHLASYIAE LSLLEYNMLS YAPSLIAASA IFLAKYILLP SVKPWNSTLR  420
HYTLYQPSDL QDCVMALHSL CCNNNNSSLP AVREKYSQHK YKFVAKKYCP PTVPVEFFQN  480
ISS                                                                483

SEQ ID NO: 8           moltype = AA  length = 614
FEATURE                Location/Qualifiers
source                 1..614
                       mol_type = protein
                       organism = Solanum tuberosum
SEQUENCE: 8
MWRNNERVYM SPARGFLTPP PKWRSPASDK DQRWPTHAQS AKADLFHVIH KVPSGDSPYV  60
RAKHVQLIDK DPGKAISLFW AAINSGDRVD SALKDMAVVM KQLDRSDEAI EAIKSFRNLC  120
PSESQESIDN ILIELYKRSG RLEEEIELLE LKLKNVEEGI AFGGKRTKIA RSQGKKVQIT  180
IEKEYARLLG NLAWSYMQLN NFKLAEEYYR KALSLESDKN KQSNLAICLM HMNKIAEARF  240
LLQSIKASDR WQMDESCTKS FERATQMLAE LETHGIQNSK EQVEEMREVR IDSSTSDEHD  300
CRGHEKTHPP PFTASGPPKH FLTQPRRYSC SLNDGGWLNK DSVSACSRRL LFEQTSNNEN  360
VQLVVNHNFN KLISANDMSE GASLVRGQVL TRSWGNGANV ESECDLQPPY SKWKNNSSGN  420
DGSDQISLEL SKSPTESLAD ITSARKYSGD GSKDCWSSTL TYRDTVTLED TTEHLESTNL  480
KPLNLPACTS KKSWADMVEE DELGLQFHET PGKYSDENEN IDSNIINLSQ NIDTLRLNEG  540
YHTQPGREAR RSLCFDQNDR KEKCSSDFQG KVLKSGSLNS LPPIGDIAYQ TPVTLMRRNR  600
LQVFRDITPE SPKP                                                    614

SEQ ID NO: 9           moltype = AA  length = 835
FEATURE                Location/Qualifiers
source                 1..835
                       mol_type = protein
                       organism = Solanum tuberosum
SEQUENCE: 9
MADKLEISSI EEDKKIPVFT VLKNGAILKN IFLLDNPPPG SNQESEIEEI LVVGRHPDCN  60
ITLEHPSISR FHLRIHSKPS SLSLSVTDLS SVHGTWISGK KLESGVKVEL KEGDRMQLGG  120
SSRVYRLHWV PISHAYDLEN PFVPTLGESE PEESTQEEQH QDESGFSLQN DQIQKEDYDM  180
VQGLDSSFSG MSSLPRLRSL TPPAPPMLDK YGAANQNLPG NIHEEGEISL LQPAYQTDKE  240
NSTPEALLVS GQSPNENADG TPPRSQQRCS SIWSRRGKPS NVQIQTGKDR AMNEKIDMET  300
EVESINREIA GTVSVSKDLF ASGNKDKEEE VFTPDKENHT PSSLFLGSMK KSCLSEMTNR  360
SDRKSVLSTM DETDEEIFTP DKENMTPETR RLRLMKKIGS QHQIKHPKLF KSSSLKLVVE  420
PRFNQAAGCV SHKKEKLGST TKSTQSDMDE NDEEIFTLDK ENMTPDTRLM RSMKKIGKLE  480
DLKHLESFKF SLDNVVGTPF CSEKDNLTNK VLVEQKSTIL ASRYPARLEV NTVKNRMDRV  540
PLQSLLVNYP VKTSSISPEE NIKLRDYPIK HPETTELCPF SNESVMEQKR WTIVVDTGSL  600
LNKESRKSLQ LLQGLRGTYM IIPRTVIREL DCMKRRASLF RRTTEVSAAL EWIEDCMINA  660
KSWIHVQSCA EETRAVAPTP PATAPLSLFS EENDMFPVGL HQFSPHSGLM EFASPTAEDH  720
ILEYALFFKR TNRNGQLVLL SNDLTMKIKA MAEGLNCETA EEFRESLVNP FSERFLWKDS  780
SPRGRTWSCE DDFVLRETYY HGPPKKPSVS GEAAKGLKLI LLHNSHFRHH ISTAS       835

SEQ ID NO: 10          moltype = AA  length = 823
FEATURE                Location/Qualifiers
source                 1..823
                       mol_type = protein
                       organism = Solanum tuberosum
SEQUENCE: 10
MAEKQESLGK PNSQSEEEKK IPVFTVLKNG AILKNIFLLD NPPATHVAIT ANQEFEEILV  60
VGRHPDCNIV LEHPSISRFH LRIHSNPSSH SLSVIDLSSV HGSWISGNKI EPGVRVELKE  120
GDKMKLGGSR REYMLHWIPI SRAYDLENPF VAPLGEAEPF KEMDEKEHQD ENGFALQNEG  180
DDLVQDQDSS FSCSSLLPYI KCPTPSAPPM PEEMKSSFPY GDEEVNINPL EKIHGESEIS  240
LLQPAYEPDQ ENSSPRALLV SGGFRTENAD STPVRSQQRC LNIWSRRGKC SSVQIQTGRD  300
RAFIERVDID TEVHTLDHEK VAMESVFNDP FSSGNKDEDH AFTPDKENHV PSSLLLGSEK  360
NSCLTDGQTT KPMLSCCMDE NGEENFTLDK VDFSANTHSP RSMKKMSCSE QIKNPKSLRS  420
SPMKETFDSI LTQAEGLEYY TENVGSSTIP PNMSKNSEQI FTPDKENMTP DSYSMRSIKK  480
GNMEEVKQRK PFAKENLNDK VLEEKISASL SSRNKARMEV TMLKNRTDRV PFQPLLVTNS  540
PNKTKSESPE RKVKLNAKPV KCQEIMEAYP FANNNAREEK RRWTMVVDIT SLLNKESRKA  600
LQLLQGLKGT CLIIPRIVLR ELDYMKRRAS FFRRATEVFA AIDWIDDCMV NAKSWVHVQS  660
CVEETRPVAP TPPATAPPYF FNEENGIFPV GSVLSSPHCG LAEIVSPTAD DHILEYALLF  720
KRTNRDGQLV LLSNDLTMKI KAMAEGIICE TAEDFQESLV NPFSERFLWK DSSPRGSTWS  780
CVDDFVLGPL RKTSKSGQAA KGLKLILLHN SHYRQICSGS TVS                    823

SEQ ID NO: 11          moltype = AA  length = 485
FEATURE                Location/Qualifiers
source                 1..485
                       mol_type = protein
                       organism = Solanum tuberosum
SEQUENCE: 11
MACLFGCFKI KDVTLPATPG SSSESNRVSQ STPAKEPMVS RNRSPLSSLF TEENEETNTL  60
GCKEVENLSL DTPMPQLDTN DLRNQAKFLK ACGTLPETPA EIRNFSMKCK DLSAPMEEVE  120
```

```
PLKVNSWPSD TTYQKLNLNS LSDQPTPVKI DGVKTHSGSF VHTPSSCLTD GQSDQSLSKS  180
FINGNENSST PIFIEVKANL ARNDNKASAA SPITAPTAQY RYRSVHFESE SDLSSMSSKC  240
ISSETSQSSE QSESSGNYNA SKYSPYPTPL KLSDEMQTPG TVFPAYLDRM GIAKTARIRS  300
QYVYPVLNPV DDVSQLKELS DEDSFSTQDS NSRLFSSHTT DSDQRPEEAT RISELGMSGF  360
GESAANKDSK PPSINQVQSK QHLGPVHYGR TPRDRPIIGL VAAHWNDDET SRISPKWWDG  420
NGIPNSTNKY KEDQKVSWHA TPFEERLEKA LSEETNISQR TQHSGTTPIA VHEAEESNTA  480
TSQVR                                                             485

SEQ ID NO: 12           moltype = AA  length = 628
FEATURE                 Location/Qualifiers
source                  1..628
                        mol_type = protein
                        organism = Solanum lycopersicum
SEQUENCE: 12
MFYSHQLLAR KAPLGQIWMA ATLHSKLNRK KLSKLNIINI CEQILNPSVP MALRLSGILM  60
GGVVIVYEHK VKLLYEDVTR LMVQINEAWK VKAATDPTLL PKGKSQAKYA AITLPENREE  120
ELPEIEQTLR NPDTVTMMDF EQTSYFTMRL DNADLYDKPN AQEEPAKDLH QVDPDNITLA  180
ERFESHHTDM FNHFERFDIE GDEETQMNYT QPEDAQIPST PVQSPPREQA HQPDEIPDRH  240
PEDQVKQQSD EVKEAFEQRQ DQQRPKPARR RTRKATSLAI DHEQTIISGD IYQSWLQSSS  300
DIASRKRKKR KTLSVLPSMK IARMMEMPPI ALLEGLFTNG NKEVHYPAPL LKLWMRNTQP  360
PHDSPSGKTS PPFPPEPSYT SPGERMGNLE PPFEYFQGGV GSPAVGISIE KQRANLNNNK  420
IPPEILMEDL RTNLTNMGLH PTETNGVKET DHMATPGSGD EPRSIPSSGS GHGLLSQNSV  480
TDSSRSNKKR PHSSLKHSGN GLQPVAEENP WHDPTLNFKL TRLSELSENG FTQDNEILME  540
TGPTQTQHPF ITQPLDMMTD SIRIQLKSHF DTPGSAEAEC LNELTLGMTK KQAACLFYQT  600
CVLATRDFVK VEQELPYGNI LISRGAKM                                    628

SEQ ID NO: 13           moltype = AA  length = 383
FEATURE                 Location/Qualifiers
source                  1..383
                        mol_type = protein
                        organism = Solanum lycopersicum
SEQUENCE: 13
MEGKRSNTRP LTLLRKIKGF TRSIVEDLAR GRPPLIYIER FRNYCTDTSG NCSCSSGLST  60
GKEAISLKRE CHARRLDVML RVLLIVQQLL QENRHGSKRD IYYMHPTVFK EQSVVDRAIN  120
DICILLQCSR HNLNVVSVGN GLVMGWLRYV ESGRKIDCIS NPNTAYPIPV LVEEVDDIIS  180
VAQYVIVVEK ESVFQRLAND QFCKRNRCIV ITGRGYPDVP TRRFLRLLID KLHLPVYGLV  240
DCDPYGFDIL TTYKFGSLQM AYDATFLRVS EIQWLGVFVQ DCDNYSIPQQ CLLPLTAEDK  300
RKIEAMLPRC YLQREVPQWR FELELLLHKG VKFEIEALSV HSLTFLSHEY LPSKIHNGGL  360
KILSLNQMIL HQNRLKTPIS LNS                                         383

SEQ ID NO: 14           moltype = AA  length = 441
FEATURE                 Location/Qualifiers
source                  1..441
                        mol_type = protein
                        organism = Solanum lycopersicum
SEQUENCE: 14
MKLKMNKASD LSSISVLPPH ARRPSVVPSA AESSVFGKSQ PSQVRSQQQS QQSFSQGFSS  60
QQAVYSQLSQ SSLDDFVPNE QRLGSQEREN SAKRMSCLPH INYTREETQM QLSKPSTNYL  120
RKWSVPESKY QIEELEHKIG MVETLLSRQG MILDSIQSDI MQVNRGTKEM LMEMESLRPK  180
LVSHDELLQL MNKDREDLKA SLEGTFKSMF EELRENKYQE NIRDLSSLLR AMPNKLEMCI  240
LQLQTDLSKT LAKEIQIIAP RPDFHGQKHE TAPVDPPKGI NDCIPPREVK LLKKDQKTTT  300
PPKIEMGSWT TVKINQTCMK QKIPIRSHTQ NEAFQQKIPI RSHTQNEAFQ QTIPIRSHTQ  360
NGAFQQKIPI RSHTENGAFQ QERGCRITIE SDEDIDAGFS CLLEENGTGI YPLDDAKEES  420
ARILRKARRR KRKHFNTIII D                                           441

SEQ ID NO: 15           moltype = AA  length = 255
FEATURE                 Location/Qualifiers
source                  1..255
                        mol_type = protein
                        organism = Solanum lycopersicum
SEQUENCE: 15
MAEGRDRLSR QEDPIDIYSR RRRSMGRGGI EIFEDESPES SSRAPIQTTA EAGRMAGTSG  60
GRGGIGRIGF GSPRNRRGRN LFRTPARVIG RQNISPTGQG RNRGRHSVLP AWYPRTPLRD  120
ITSIVRAIER TRARLRESEG EQLESVVPQD HTDLGPSEST SGAQLEHTNS LITPRPKTRS  180
RYHTRSVGKV PKILLDITNQ STSEDAECLT PQRKLLNSID TVEKHVMEEL HKLKRTPSAR  240
KQERDKRVKT LMSMR                                                  255

SEQ ID NO: 16           moltype = AA  length = 490
FEATURE                 Location/Qualifiers
source                  1..490
                        mol_type = protein
                        organism = Solanum lycopersicum
SEQUENCE: 16
MMTTQNRRSS AVAKRQAMAA NSSGLEHNQT GKLNAKKRPA LSNISNNTTV SARNSVSHSS  60
KLAPCTSKIV NIKKNTSACN SNAVSSGTAV LPASSSVRPS SKPVSIQRSD AVVPKITVIP  120
VPATCSMDIS PSHSDGSLVS MDESMSNSDT VRSPEVEYID DHELAAVDSI EKKACSTLYI  180
SEHVKAAAAD ICKRDVLVDL ESGDKIMNID NNLVDPQLCA TMACDIYKHL RASEAKKRPS  240
TDFMAKVQKD INPSMRAILI DWLVEVAEEY RLVPDTLHLT INYIDRYLSG NLMDRQRLQL  300
LGVACMMIAS KYEEICAPQV EEFCYITDNT YFKEEVLQME SAVLNYLKFE MTAPTAKCFL  360
```

```
RRFVRAAQGL NEVLSLQLEH LASYIAELSL LEYNMLCYAP SLIAASAIFL AKYILLPSVK  420
PWNSTLRHYT LYQPSDLRDC VLALHSLCCN NNNSSLPAVR EKYSQHKYKF VAKKYCPPTV  480
PVEFFQNISS                                                        490

SEQ ID NO: 17           moltype = RNA  length = 20
FEATURE                 Location/Qualifiers
source                  1..20
                        mol_type = unassigned RNA
                        organism = Solanum tuberosum
SEQUENCE: 17
ctttcagtgg aaagcttacg                                             20

SEQ ID NO: 18           moltype = RNA  length = 20
FEATURE                 Location/Qualifiers
source                  1..20
                        mol_type = unassigned RNA
                        organism = Solanum tuberosum
SEQUENCE: 18
ctctttcttg agaacccaat                                             20

SEQ ID NO: 19           moltype = RNA  length = 20
FEATURE                 Location/Qualifiers
source                  1..20
                        mol_type = unassigned RNA
                        organism = Solanum tuberosum
SEQUENCE: 19
gcactctata atgcagaaca                                             20

SEQ ID NO: 20           moltype = RNA  length = 20
FEATURE                 Location/Qualifiers
source                  1..20
                        mol_type = unassigned RNA
                        organism = Solanum tuberosum
SEQUENCE: 20
aaggtcccct ccaggctagc                                             20

SEQ ID NO: 21           moltype = RNA  length = 20
FEATURE                 Location/Qualifiers
source                  1..20
                        mol_type = unassigned RNA
                        organism = Solanum tuberosum
SEQUENCE: 21
ccacatcacg taaattaaaa                                             20

SEQ ID NO: 22           moltype = RNA  length = 20
FEATURE                 Location/Qualifiers
source                  1..20
                        mol_type = unassigned RNA
                        organism = Solanum tuberosum
SEQUENCE: 22
atggaagcgc tatctacctt                                             20

SEQ ID NO: 23           moltype = RNA  length = 20
FEATURE                 Location/Qualifiers
source                  1..20
                        mol_type = unassigned RNA
                        organism = Solanum tuberosum
SEQUENCE: 23
aatatgcaac atgcctgaat                                             20

SEQ ID NO: 24           moltype = RNA  length = 20
FEATURE                 Location/Qualifiers
source                  1..20
                        mol_type = unassigned RNA
                        organism = Solanum tuberosum
SEQUENCE: 24
aacgctttcc ctccattttc                                             20

SEQ ID NO: 25           moltype = RNA  length = 20
FEATURE                 Location/Qualifiers
source                  1..20
                        mol_type = unassigned RNA
                        organism = Solanum tuberosum
SEQUENCE: 25
gcaggattta ctcgttccat                                             20

SEQ ID NO: 26           moltype = RNA  length = 20
FEATURE                 Location/Qualifiers
source                  1..20
```

```
                        mol_type = unassigned RNA
                        organism = Solanum tuberosum
SEQUENCE: 26
gttgtggaaa aggaatcagg                                            20

SEQ ID NO: 27           moltype = RNA  length = 20
FEATURE                 Location/Qualifiers
source                  1..20
                        mol_type = unassigned RNA
                        organism = Solanum tuberosum
SEQUENCE: 27
tgtagctctt gcagctctgg                                            20

SEQ ID NO: 28           moltype = RNA  length = 20
FEATURE                 Location/Qualifiers
source                  1..20
                        mol_type = unassigned RNA
                        organism = Solanum tuberosum
SEQUENCE: 28
agttgtggaa aaggaatcag                                            20

SEQ ID NO: 29           moltype = RNA  length = 20
FEATURE                 Location/Qualifiers
source                  1..20
                        mol_type = unassigned RNA
                        organism = Solanum tuberosum
SEQUENCE: 29
agcaagacct tggctaaaga                                            20

SEQ ID NO: 30           moltype = RNA  length = 20
FEATURE                 Location/Qualifiers
source                  1..20
                        mol_type = unassigned RNA
                        organism = Solanum tuberosum
SEQUENCE: 30
gttgagagtt cttgtgatag                                            20

SEQ ID NO: 31           moltype = RNA  length = 20
FEATURE                 Location/Qualifiers
source                  1..20
                        mol_type = unassigned RNA
                        organism = Solanum tuberosum
SEQUENCE: 31
ctctccctag actcaccaag                                            20

SEQ ID NO: 32           moltype = RNA  length = 20
FEATURE                 Location/Qualifiers
source                  1..20
                        mol_type = unassigned RNA
                        organism = Solanum tuberosum
SEQUENCE: 32
ccacaactaa aacgtattga                                            20

SEQ ID NO: 33           moltype = RNA  length = 20
FEATURE                 Location/Qualifiers
source                  1..20
                        mol_type = unassigned RNA
                        organism = Solanum tuberosum
SEQUENCE: 33
gagtgtagag tggccgccat                                            20

SEQ ID NO: 34           moltype = RNA  length = 20
FEATURE                 Location/Qualifiers
source                  1..20
                        mol_type = unassigned RNA
                        organism = Solanum tuberosum
SEQUENCE: 34
aagcatgaat tactctgcag                                            20

SEQ ID NO: 35           moltype = RNA  length = 20
FEATURE                 Location/Qualifiers
source                  1..20
                        mol_type = unassigned RNA
                        organism = Solanum tuberosum
SEQUENCE: 35
cagttgatcc agataatatc                                            20

SEQ ID NO: 36           moltype = RNA  length = 20
FEATURE                 Location/Qualifiers
```

```
source                1..20
                      mol_type = unassigned RNA
                      organism = Solanum tuberosum
SEQUENCE: 36
ggtttagata tctaatcgtc                                              20

SEQ ID NO: 37         moltype = RNA  length = 20
FEATURE               Location/Qualifiers
source                1..20
                      mol_type = unassigned RNA
                      organism = Solanum tuberosum
SEQUENCE: 37
atagtatctg caaatgaagt                                              20

SEQ ID NO: 38         moltype = RNA  length = 20
FEATURE               Location/Qualifiers
source                1..20
                      mol_type = unassigned RNA
                      organism = Solanum tuberosum
SEQUENCE: 38
aagttatttc gtggattgag                                              20

SEQ ID NO: 39         moltype = RNA  length = 20
FEATURE               Location/Qualifiers
source                1..20
                      mol_type = unassigned RNA
                      organism = Solanum tuberosum
SEQUENCE: 39
taggtcatca atgattgtag                                              20

SEQ ID NO: 40         moltype = RNA  length = 20
FEATURE               Location/Qualifiers
source                1..20
                      mol_type = unassigned RNA
                      organism = Solanum tuberosum
SEQUENCE: 40
aaaggtaaat ctggatcgac                                              20

SEQ ID NO: 41         moltype = RNA  length = 20
FEATURE               Location/Qualifiers
source                1..20
                      mol_type = unassigned RNA
                      organism = Solanum tuberosum
SEQUENCE: 41
cataatgtac catcgtgaaa                                              20

SEQ ID NO: 42         moltype = RNA  length = 20
FEATURE               Location/Qualifiers
source                1..20
                      mol_type = unassigned RNA
                      organism = Solanum tuberosum
SEQUENCE: 42
cgaagcatac ccatgagaat                                              20

SEQ ID NO: 43         moltype = RNA  length = 20
FEATURE               Location/Qualifiers
source                1..20
                      mol_type = unassigned RNA
                      organism = Solanum tuberosum
SEQUENCE: 43
accttgcatg aggaggaaga                                              20

SEQ ID NO: 44         moltype = RNA  length = 20
FEATURE               Location/Qualifiers
source                1..20
                      mol_type = unassigned RNA
                      organism = Solanum tuberosum
SEQUENCE: 44
tgatttggta ttttcaggtg                                              20

SEQ ID NO: 45         moltype = RNA  length = 20
FEATURE               Location/Qualifiers
source                1..20
                      mol_type = unassigned RNA
                      organism = Solanum tuberosum
SEQUENCE: 45
gtggatcgac tggagcggtt                                              20

SEQ ID NO: 46         moltype = RNA  length = 20
```

```
FEATURE                 Location/Qualifiers
source                  1..20
                        mol_type = unassigned RNA
                        organism = Solanum tuberosum
SEQUENCE: 46
tatctctctc tttgctgtga                                              20

SEQ ID NO: 47           moltype = RNA  length = 21
FEATURE                 Location/Qualifiers
source                  1..21
                        mol_type = unassigned RNA
                        organism = Solanum tuberosum
SEQUENCE: 47
cctcatatca actacacacg a                                            21

SEQ ID NO: 48           moltype = RNA  length = 21
FEATURE                 Location/Qualifiers
source                  1..21
                        mol_type = unassigned RNA
                        organism = Solanum tuberosum
SEQUENCE: 48
tctcaagcga gctcttgttc t                                            21

SEQ ID NO: 49           moltype = RNA  length = 20
FEATURE                 Location/Qualifiers
source                  1..20
                        mol_type = unassigned RNA
                        organism = Solanum tuberosum
SEQUENCE: 49
ctattgagtt tcgagtgtag                                              20

SEQ ID NO: 50           moltype = RNA  length = 20
FEATURE                 Location/Qualifiers
source                  1..20
                        mol_type = unassigned RNA
                        organism = Solanum tuberosum
SEQUENCE: 50
gacgtggggt gatcaaagaa                                              20

SEQ ID NO: 51           moltype = RNA  length = 20
FEATURE                 Location/Qualifiers
source                  1..20
                        mol_type = unassigned RNA
                        organism = Solanum tuberosum
SEQUENCE: 51
agtctcttct cgtgtgtagt                                              20

SEQ ID NO: 52           moltype = RNA  length = 20
FEATURE                 Location/Qualifiers
source                  1..20
                        mol_type = unassigned RNA
                        organism = Solanum tuberosum
SEQUENCE: 52
atcaccccac gtccaaaaac                                              20

SEQ ID NO: 53           moltype = RNA  length = 20
FEATURE                 Location/Qualifiers
source                  1..20
                        mol_type = unassigned RNA
                        organism = Solanum tuberosum
SEQUENCE: 53
gctttatata gttctggatg                                              20

SEQ ID NO: 54           moltype = RNA  length = 20
FEATURE                 Location/Qualifiers
source                  1..20
                        mol_type = unassigned RNA
                        organism = Solanum tuberosum
SEQUENCE: 54
ctccataggc cattgaaaga                                              20

SEQ ID NO: 55           moltype = RNA  length = 20
FEATURE                 Location/Qualifiers
source                  1..20
                        mol_type = unassigned RNA
                        organism = Solanum tuberosum
SEQUENCE: 55
ctttcaggaa ctgaccattt                                              20
```

```
SEQ ID NO: 56          moltype = RNA  length = 20
FEATURE                Location/Qualifiers
source                 1..20
                       mol_type = unassigned RNA
                       organism = Solanum tuberosum
SEQUENCE: 56
gcactttacc aacagatctg                                        20

SEQ ID NO: 57          moltype = RNA  length = 20
FEATURE                Location/Qualifiers
source                 1..20
                       mol_type = unassigned RNA
                       organism = Solanum tuberosum
SEQUENCE: 57
atgtcaatgc gctgattttc                                        20

SEQ ID NO: 58          moltype = RNA  length = 21
FEATURE                Location/Qualifiers
source                 1..21
                       mol_type = unassigned RNA
                       organism = Solanum tuberosum
SEQUENCE: 58
cttatgagtg ttagtggctg c                                      21

SEQ ID NO: 59          moltype = RNA  length = 21
FEATURE                Location/Qualifiers
source                 1..21
                       mol_type = unassigned RNA
                       organism = Solanum tuberosum
SEQUENCE: 59
ctcccagatt ccacataccg c                                      21

SEQ ID NO: 60          moltype = RNA  length = 20
FEATURE                Location/Qualifiers
source                 1..20
                       mol_type = unassigned RNA
                       organism = Solanum tuberosum
SEQUENCE: 60
tgaaccgatc gatgtagatc                                        20

SEQ ID NO: 61          moltype = RNA  length = 20
FEATURE                Location/Qualifiers
source                 1..20
                       mol_type = unassigned RNA
                       organism = Solanum tuberosum
SEQUENCE: 61
ttggccgctc cagcattcaa                                        20

SEQ ID NO: 62          moltype = RNA  length = 20
FEATURE                Location/Qualifiers
source                 1..20
                       mol_type = unassigned RNA
                       organism = Solanum tuberosum
SEQUENCE: 62
gaaggcacca tgtacgtcca                                        20

SEQ ID NO: 63          moltype = RNA  length = 20
FEATURE                Location/Qualifiers
source                 1..20
                       mol_type = unassigned RNA
                       organism = Solanum tuberosum
SEQUENCE: 63
atatgttctg agatgtagag                                        20

SEQ ID NO: 64          moltype = RNA  length = 20
FEATURE                Location/Qualifiers
source                 1..20
                       mol_type = unassigned RNA
                       organism = Solanum tuberosum
SEQUENCE: 64
ttccagcagc agatatatgc                                        20

SEQ ID NO: 65          moltype = RNA  length = 20
FEATURE                Location/Qualifiers
source                 1..20
                       mol_type = unassigned RNA
                       organism = Solanum tuberosum
SEQUENCE: 65
ttatgctcca tcactcattg                                        20
```

```
SEQ ID NO: 66          moltype = RNA  length = 20
FEATURE                Location/Qualifiers
source                 1..20
                       mol_type = unassigned RNA
                       organism = Solanum tuberosum
SEQUENCE: 66
acaattaact acattgatcg                                              20

SEQ ID NO: 67          moltype = RNA  length = 20
FEATURE                Location/Qualifiers
source                 1..20
                       mol_type = unassigned RNA
                       organism = Solanum tuberosum
SEQUENCE: 67
gggcaacttg atggacagac                                              20

SEQ ID NO: 68          moltype = RNA  length = 20
FEATURE                Location/Qualifiers
source                 1..20
                       mol_type = unassigned RNA
                       organism = Solanum tuberosum
SEQUENCE: 68
ttacgatgcg atcatcatgc                                              20

SEQ ID NO: 69          moltype = RNA  length = 20
FEATURE                Location/Qualifiers
source                 1..20
                       mol_type = unassigned RNA
                       organism = Solanum tuberosum
SEQUENCE: 69
ctcagggact gctgttctgc                                              20

SEQ ID NO: 70          moltype = RNA  length = 20
FEATURE                Location/Qualifiers
source                 1..20
                       mol_type = unassigned RNA
                       organism = Solanum tuberosum
SEQUENCE: 70
tctatttttt attccagcag                                              20

SEQ ID NO: 71          moltype = RNA  length = 20
FEATURE                Location/Qualifiers
source                 1..20
                       mol_type = unassigned RNA
                       organism = Solanum tuberosum
SEQUENCE: 71
gaaactccta acagaactct                                              20

SEQ ID NO: 72          moltype = DNA  length = 20
FEATURE                Location/Qualifiers
source                 1..20
                       mol_type = unassigned DNA
                       organism = Solanum tuberosum
SEQUENCE: 72
ctttcagtgg aaagcttacg                                              20

SEQ ID NO: 73          moltype = DNA  length = 20
FEATURE                Location/Qualifiers
source                 1..20
                       mol_type = unassigned DNA
                       organism = Solanum tuberosum
SEQUENCE: 73
ctctttcttg agaacccaat                                              20

SEQ ID NO: 74          moltype = DNA  length = 20
FEATURE                Location/Qualifiers
source                 1..20
                       mol_type = unassigned DNA
                       organism = Solanum tuberosum
SEQUENCE: 74
gcactctata atgcagaaca                                              20

SEQ ID NO: 75          moltype = DNA  length = 20
FEATURE                Location/Qualifiers
source                 1..20
                       mol_type = unassigned DNA
                       organism = Solanum tuberosum
SEQUENCE: 75
```

```
aaggtcccct ccaggctagc                                              20

SEQ ID NO: 76          moltype = DNA  length = 20
FEATURE                Location/Qualifiers
source                 1..20
                       mol_type = unassigned DNA
                       organism = Solanum tuberosum
SEQUENCE: 76
ccacatcacg taaattaaaa                                              20

SEQ ID NO: 77          moltype = DNA  length = 20
FEATURE                Location/Qualifiers
source                 1..20
                       mol_type = unassigned DNA
                       organism = Solanum tuberosum
SEQUENCE: 77
atggaagcgc tatctacctt                                              20

SEQ ID NO: 78          moltype = DNA  length = 20
FEATURE                Location/Qualifiers
source                 1..20
                       mol_type = unassigned DNA
                       organism = Solanum tuberosum
SEQUENCE: 78
aatatgcaac atgcctgaat                                              20

SEQ ID NO: 79          moltype = DNA  length = 20
FEATURE                Location/Qualifiers
source                 1..20
                       mol_type = unassigned DNA
                       organism = Solanum tuberosum
SEQUENCE: 79
aacgctttcc ctccattttc                                              20

SEQ ID NO: 80          moltype = DNA  length = 20
FEATURE                Location/Qualifiers
source                 1..20
                       mol_type = unassigned DNA
                       organism = Solanum tuberosum
SEQUENCE: 80
gcaggattta ctcgttccat                                              20

SEQ ID NO: 81          moltype = DNA  length = 20
FEATURE                Location/Qualifiers
source                 1..20
                       mol_type = unassigned DNA
                       organism = Solanum tuberosum
SEQUENCE: 81
gttgtggaaa aggaatcagg                                              20

SEQ ID NO: 82          moltype = DNA  length = 20
FEATURE                Location/Qualifiers
source                 1..20
                       mol_type = unassigned DNA
                       organism = Solanum tuberosum
SEQUENCE: 82
tgtagctctt gcagctctgg                                              20

SEQ ID NO: 83          moltype = DNA  length = 20
FEATURE                Location/Qualifiers
source                 1..20
                       mol_type = unassigned DNA
                       organism = Solanum tuberosum
SEQUENCE: 83
agttgtggaa aaggaatcag                                              20

SEQ ID NO: 84          moltype = DNA  length = 20
FEATURE                Location/Qualifiers
source                 1..20
                       mol_type = unassigned DNA
                       organism = Solanum tuberosum
SEQUENCE: 84
agcaagacct tggctaaaga                                              20

SEQ ID NO: 85          moltype = DNA  length = 20
FEATURE                Location/Qualifiers
source                 1..20
                       mol_type = unassigned DNA
                       organism = Solanum tuberosum
```

```
SEQUENCE: 85
gttgagagtt cttgtgatag                                              20

SEQ ID NO: 86           moltype = DNA  length = 20
FEATURE                 Location/Qualifiers
source                  1..20
                        mol_type = unassigned DNA
                        organism = Solanum tuberosum
SEQUENCE: 86
ctctccctag actcaccaag                                              20

SEQ ID NO: 87           moltype = DNA  length = 20
FEATURE                 Location/Qualifiers
source                  1..20
                        mol_type = unassigned DNA
                        organism = Solanum tuberosum
SEQUENCE: 87
ccacaactaa aacgtattga                                              20

SEQ ID NO: 88           moltype = DNA  length = 20
FEATURE                 Location/Qualifiers
source                  1..20
                        mol_type = unassigned DNA
                        organism = Solanum tuberosum
SEQUENCE: 88
gagtgtagag tggccgccat                                              20

SEQ ID NO: 89           moltype = DNA  length = 20
FEATURE                 Location/Qualifiers
source                  1..20
                        mol_type = unassigned DNA
                        organism = Solanum tuberosum
SEQUENCE: 89
aagcatgaat tactctgcag                                              20

SEQ ID NO: 90           moltype = DNA  length = 20
FEATURE                 Location/Qualifiers
source                  1..20
                        mol_type = unassigned DNA
                        organism = Solanum tuberosum
SEQUENCE: 90
cagttgatcc agataatatc                                              20

SEQ ID NO: 91           moltype = DNA  length = 20
FEATURE                 Location/Qualifiers
source                  1..20
                        mol_type = unassigned DNA
                        organism = Solanum tuberosum
SEQUENCE: 91
ggtttagata tctaatcgtc                                              20

SEQ ID NO: 92           moltype = DNA  length = 20
FEATURE                 Location/Qualifiers
source                  1..20
                        mol_type = unassigned DNA
                        organism = Solanum tuberosum
SEQUENCE: 92
atagtatctg caaatgaagt                                              20

SEQ ID NO: 93           moltype = DNA  length = 20
FEATURE                 Location/Qualifiers
source                  1..20
                        mol_type = unassigned DNA
                        organism = Solanum tuberosum
SEQUENCE: 93
aagttatttc gtggattgag                                              20

SEQ ID NO: 94           moltype = DNA  length = 20
FEATURE                 Location/Qualifiers
source                  1..20
                        mol_type = unassigned DNA
                        organism = Solanum tuberosum
SEQUENCE: 94
taggtcatca atgattgtag                                              20

SEQ ID NO: 95           moltype = DNA  length = 20
FEATURE                 Location/Qualifiers
source                  1..20
                        mol_type = unassigned DNA
```

```
                        organism = Solanum tuberosum
SEQUENCE: 95
aaaggtaaat ctggatcgac                                                20

SEQ ID NO: 96           moltype = DNA  length = 20
FEATURE                 Location/Qualifiers
source                  1..20
                        mol_type = unassigned DNA
                        organism = Solanum tuberosum
SEQUENCE: 96
cataatgtac catcgtgaaa                                                20

SEQ ID NO: 97           moltype = DNA  length = 20
FEATURE                 Location/Qualifiers
source                  1..20
                        mol_type = unassigned DNA
                        organism = Solanum tuberosum
SEQUENCE: 97
cgaagcatac ccatgagaat                                                20

SEQ ID NO: 98           moltype = DNA  length = 20
FEATURE                 Location/Qualifiers
source                  1..20
                        mol_type = unassigned DNA
                        organism = Solanum tuberosum
SEQUENCE: 98
accttgcatg aggaggaaga                                                20

SEQ ID NO: 99           moltype = DNA  length = 20
FEATURE                 Location/Qualifiers
source                  1..20
                        mol_type = unassigned DNA
                        organism = Solanum tuberosum
SEQUENCE: 99
tgatttggta ttttcaggtg                                                20

SEQ ID NO: 100          moltype = DNA  length = 20
FEATURE                 Location/Qualifiers
source                  1..20
                        mol_type = unassigned DNA
                        organism = Solanum tuberosum
SEQUENCE: 100
gtggatcgac tggagcggtt                                                20

SEQ ID NO: 101          moltype = DNA  length = 20
FEATURE                 Location/Qualifiers
source                  1..20
                        mol_type = unassigned DNA
                        organism = Solanum tuberosum
SEQUENCE: 101
tatctctctc tttgctgtga                                                20

SEQ ID NO: 102          moltype = DNA  length = 21
FEATURE                 Location/Qualifiers
source                  1..21
                        mol_type = unassigned DNA
                        organism = Solanum tuberosum
SEQUENCE: 102
cctcatatca actacacacg a                                              21

SEQ ID NO: 103          moltype = DNA  length = 21
FEATURE                 Location/Qualifiers
source                  1..21
                        mol_type = unassigned DNA
                        organism = Solanum tuberosum
SEQUENCE: 103
tctcaagcga gctcttgttc t                                              21

SEQ ID NO: 104          moltype = DNA  length = 20
FEATURE                 Location/Qualifiers
source                  1..20
                        mol_type = unassigned DNA
                        organism = Solanum tuberosum
SEQUENCE: 104
ctattgagtt tcgagtgtag                                                20

SEQ ID NO: 105          moltype = DNA  length = 20
FEATURE                 Location/Qualifiers
source                  1..20
```

```
                          mol_type = unassigned DNA
                          organism = Solanum tuberosum
SEQUENCE: 105
gacgtggggt gatcaaagaa                                              20

SEQ ID NO: 106            moltype = DNA  length = 20
FEATURE                   Location/Qualifiers
source                    1..20
                          mol_type = unassigned DNA
                          organism = Solanum tuberosum
SEQUENCE: 106
agtctcttct cgtgtgtagt                                              20

SEQ ID NO: 107            moltype = DNA  length = 20
FEATURE                   Location/Qualifiers
source                    1..20
                          mol_type = unassigned DNA
                          organism = Solanum tuberosum
SEQUENCE: 107
atcaccccac gtccaaaaac                                              20

SEQ ID NO: 108            moltype = DNA  length = 20
FEATURE                   Location/Qualifiers
source                    1..20
                          mol_type = unassigned DNA
                          organism = Solanum tuberosum
SEQUENCE: 108
gctttatata gttctggatg                                              20

SEQ ID NO: 109            moltype = DNA  length = 20
FEATURE                   Location/Qualifiers
source                    1..20
                          mol_type = unassigned DNA
                          organism = Solanum tuberosum
SEQUENCE: 109
ctccataggc cattgaaaga                                              20

SEQ ID NO: 110            moltype = DNA  length = 20
FEATURE                   Location/Qualifiers
source                    1..20
                          mol_type = unassigned DNA
                          organism = Solanum tuberosum
SEQUENCE: 110
ctttcaggaa ctgaccattt                                              20

SEQ ID NO: 111            moltype = DNA  length = 20
FEATURE                   Location/Qualifiers
source                    1..20
                          mol_type = unassigned DNA
                          organism = Solanum tuberosum
SEQUENCE: 111
gcactttacc aacagatctg                                              20

SEQ ID NO: 112            moltype = DNA  length = 20
FEATURE                   Location/Qualifiers
source                    1..20
                          mol_type = unassigned DNA
                          organism = Solanum tuberosum
SEQUENCE: 112
atgtcaatgc gctgattttc                                              20

SEQ ID NO: 113            moltype = DNA  length = 21
FEATURE                   Location/Qualifiers
source                    1..21
                          mol_type = unassigned DNA
                          organism = Solanum tuberosum
SEQUENCE: 113
cttatgagtg ttagtggctg c                                            21

SEQ ID NO: 114            moltype = DNA  length = 21
FEATURE                   Location/Qualifiers
source                    1..21
                          mol_type = unassigned DNA
                          organism = Solanum tuberosum
SEQUENCE: 114
ctcccagatt ccacataccg c                                            21

SEQ ID NO: 115            moltype = DNA  length = 20
FEATURE                   Location/Qualifiers
```

```
source                  1..20
                        mol_type = unassigned DNA
                        organism = Solanum tuberosum
SEQUENCE: 115
tgaaccgatc gatgtagatc                                                20

SEQ ID NO: 116          moltype = DNA  length = 20
FEATURE                 Location/Qualifiers
source                  1..20
                        mol_type = unassigned DNA
                        organism = Solanum tuberosum
SEQUENCE: 116
ttggccgctc cagcattcaa                                                20

SEQ ID NO: 117          moltype = DNA  length = 20
FEATURE                 Location/Qualifiers
source                  1..20
                        mol_type = unassigned DNA
                        organism = Solanum tuberosum
SEQUENCE: 117
gaaggcacca tgtacgtcca                                                20

SEQ ID NO: 118          moltype = DNA  length = 20
FEATURE                 Location/Qualifiers
source                  1..20
                        mol_type = unassigned DNA
                        organism = Solanum tuberosum
SEQUENCE: 118
atatgttctg agatgtagag                                                20

SEQ ID NO: 119          moltype = DNA  length = 20
FEATURE                 Location/Qualifiers
source                  1..20
                        mol_type = unassigned DNA
                        organism = Solanum tuberosum
SEQUENCE: 119
ttccagcagc agatatatgc                                                20

SEQ ID NO: 120          moltype = DNA  length = 20
FEATURE                 Location/Qualifiers
source                  1..20
                        mol_type = unassigned DNA
                        organism = Solanum tuberosum
SEQUENCE: 120
ttatgctcca tcactcattg                                                20

SEQ ID NO: 121          moltype = DNA  length = 20
FEATURE                 Location/Qualifiers
source                  1..20
                        mol_type = unassigned DNA
                        organism = Solanum tuberosum
SEQUENCE: 121
acaattaact acattgatcg                                                20

SEQ ID NO: 122          moltype = DNA  length = 20
FEATURE                 Location/Qualifiers
source                  1..20
                        mol_type = unassigned DNA
                        organism = Solanum tuberosum
SEQUENCE: 122
gggcaacttg atggacagac                                                20

SEQ ID NO: 123          moltype = DNA  length = 20
FEATURE                 Location/Qualifiers
source                  1..20
                        mol_type = unassigned DNA
                        organism = Solanum tuberosum
SEQUENCE: 123
ttacgatgcg atcatcatgc                                                20

SEQ ID NO: 124          moltype = DNA  length = 20
FEATURE                 Location/Qualifiers
source                  1..20
                        mol_type = unassigned DNA
                        organism = Solanum tuberosum
SEQUENCE: 124
ctcagggact gctgttctgc                                                20

SEQ ID NO: 125          moltype = DNA  length = 20
```

```
FEATURE                Location/Qualifiers
source                 1..20
                       mol_type = unassigned DNA
                       organism = Solanum tuberosum
SEQUENCE: 125
tctatttttt attccagcag                                             20

SEQ ID NO: 126         moltype = DNA  length = 20
FEATURE                Location/Qualifiers
source                 1..20
                       mol_type = unassigned DNA
                       organism = Solanum tuberosum
SEQUENCE: 126
gaaactccta acagaactct                                             20

SEQ ID NO: 127         moltype = DNA  length = 263
FEATURE                Location/Qualifiers
source                 1..263
                       mol_type = unassigned DNA
                       organism = Solanum tuberosum
SEQUENCE: 127
tcagggagga tagcaacttt taattatcat tcctaccctt ttcactatca tatcatttct  60
tgtccaacta tgtgatgaag atcagcagat acaatataca agtattgttt actctcccta  120
gactcaccta cgtgcatggc attccctctt cagggatata gcttccttgc cagtagacaa  180
accagagctg caagagctac ataaattaaa caaagaccat taatactacc acgacatttg  240
gatggtcttt attagccatt caa                                         263

SEQ ID NO: 128         moltype = DNA  length = 266
FEATURE                Location/Qualifiers
source                 1..266
                       mol_type = unassigned DNA
                       organism = Solanum tuberosum
SEQUENCE: 128
cagttcaacg tagtagtgga agaaaacgca tcaccagatg ttaattatat tgagtttact  60
aagcttttc ctattgagtt tcgagtgtag agtggccggt gagtctaggg agagtaaata  120
atacttgtat attttatctg ctgatcttca tcacatagtt ggacaagaaa tgacatgata  180
gtgaagaggg taggaatgat aattaaatgt tgctatcctc cctgaaaagt gacaaaatta  240
ccagggtaac tatttccccg ttaagt                                      266

SEQ ID NO: 129         moltype = DNA  length = 219
FEATURE                Location/Qualifiers
source                 1..219
                       mol_type = unassigned DNA
                       organism = Solanum tuberosum
SEQUENCE: 129
tgttctgtat tcgttgaagt tccttcatag gattttttgt atacgttaag ttttcacatt  60
tcaatttggc tacgaagaat gtttaaattg atgttgttta tatctctctc tttgctgtga  120
atacgtgcat ggcattccct cttcagggat atagcttcct tgccagtcga caaaccagag  180
ctgcaagagc tacataaatt aaacaaagac cattaatac                        219

SEQ ID NO: 130         moltype =   length =
SEQUENCE: 130
000

SEQ ID NO: 131         moltype = DNA  length = 224
FEATURE                Location/Qualifiers
source                 1..224
                       mol_type = unassigned DNA
                       organism = Solanum tuberosum
SEQUENCE: 131
gtatctaatg taatgtattc gttgaagttc cttcatagga ttttcggtat acgttaagtt  60
ttcacatttc aatttgacta cgaagtatgt ttaaattgat gttgtttata tctcggccac  120
tctacactcg aaactcaata ggaaaaagct tagtaaactc aatattatta acatctggtg  180
atgcgttttc ttccactact acgttgaact gcctttattc cttg                  224

SEQ ID NO: 132         moltype = DNA  length = 202
FEATURE                Location/Qualifiers
source                 1..202
                       mol_type = unassigned DNA
                       organism = Solanum tuberosum
SEQUENCE: 132
gttgaagttc cttcatagga ttttcggtat acgttaagtt ttcacatttc aatttgacta  60
cgaagtatgt ttaaattgat gttgtttata tctctctttg ctgggaaaaa gcttagtaaa  120
ctcaatatta ttaacatctg gtgatgcgtt ttcttccact actacgttga actgccttta  180
ttccttgttg attttgagta at                                          202

SEQ ID NO: 133         moltype = DNA  length = 238
FEATURE                Location/Qualifiers
source                 1..238
```

```
                        mol_type = unassigned DNA
                        organism = Solanum tuberosum
SEQUENCE: 133
catttttcag ggaggatagc aacttttaat tatcattcct accccccttca ctatcatatc  60
atatcttgtc caactatgtg atgaagatca gtagataaaa tatacaagta ttgtttactc  120
tccctagact cacctacgtg catggcattc cctcttcagg gatatagctt ccttgccggt  180
cgacaaacca gagctgcaag agctacataa attaaacaaa gaccattaat actaccac    238

SEQ ID NO: 134          moltype = DNA  length = 245
FEATURE                 Location/Qualifiers
source                  1..245
                        mol_type = unassigned DNA
                        organism = Solanum tuberosum
SEQUENCE: 134
cttttcaggg aggatagcaa catttaatta tcattcctac cctcttcact atcatatcat  60
ttcttgtcca actatgtgat gaagatcagc agataaaata tacaagtatt atttactctc  120
cctagactct acgtgcttgg cattccctct tcagggatat agcttccttg ccagtcgaca  180
aaccagagct gcaagagcta cataaattaa acaaagacca ttaatactac cacgacattt  240
ggatg                                                              245

SEQ ID NO: 135          moltype =   length =
SEQUENCE: 135
000

SEQ ID NO: 136          moltype =   length =
SEQUENCE: 136
000

SEQ ID NO: 137          moltype = DNA  length = 242
FEATURE                 Location/Qualifiers
source                  1..242
                        mol_type = unassigned DNA
                        organism = Solanum tuberosum
SEQUENCE: 137
atctaatgtt ctgtattcgt tgaagttcct tcataggatt ttttgtatac gttaagtttt  60
cacatttcaa tttggctacg aagaatgttt aaattgatgt tgtttatatc tctctctttg  120
ctgtgaggcc actctacact cgaaactcaa taggaaaaag cttagtaaac tcaatataat  180
taacatctgg tgatgcgttt tcttccacta ctacgttgaa ctgcctttat tccttgttga  240
tt                                                                 242

SEQ ID NO: 138          moltype = DNA  length = 292
FEATURE                 Location/Qualifiers
source                  1..292
                        mol_type = unassigned DNA
                        organism = Solanum tuberosum
SEQUENCE: 138
gtcttttgct tttctgtatc taatgtaatg tattcgttga agttccttca taggattttc  60
ggtatacgtt aagttttcac atttcaattt gactacgaag aatgtttaaa ttgatgctgt  120
ttatatctct ctctttgctg tgaaggccac tctacactcg aaactcaata ggaaaaagct  180
tagtaaactc aatattatta acatctggtg aggcgttgtc ttccactact acgttgaact  240
gcctttattc cttgttgatt ttgagtaatc atcttctgca atttcttttg tc          292

SEQ ID NO: 139          moltype = DNA  length = 234
FEATURE                 Location/Qualifiers
source                  1..234
                        mol_type = unassigned DNA
                        organism = Solanum tuberosum
SEQUENCE: 139
ttaattatca ttcctaccct cttcactatc atgtcatttc ttgtccaact atgtgatgaa  60
gatcagcaga taaaatatac aagtattatt tactctccct agactcaacg tgcatggcat  120
tccctcttca gggatatagc ttccttgcca gtcgacaaac cagagctgca agagctacat  180
aaattaaaca aagaccatta atactaccac gacatttgga tggtctttat tagc        234

SEQ ID NO: 140          moltype = DNA  length = 520
FEATURE                 Location/Qualifiers
source                  1..520
                        mol_type = unassigned DNA
                        organism = Solanum tuberosum
SEQUENCE: 140
ccccaccccca ctccaccttc cccccatggt gcatcctgtg taacttcaag gaaagggagg  60
ctcatatagg aaaacagaag aacagaaaag tcaacttaac ggggaaatag ttctcctggt  120
aattttgtca tttttcaggg aggatagcaa cttttaatta tcattcctac ccttttcact  180
atcatatcat ttcttgtcca actatgtgat gaagatcagc agatacaata tacaagtatt  240
gtttactctc cctagcgtgc atggcattcc ctcttcaggg atatagcttc cttgccagta  300
gacaaaccag agctgcaaga gctacataaa ttaaacaaag accattaata ctaccacgac  360
atttggatgg tctttattag ccattcaaac tccaacttca gtaaatttca ttgtttttat  420
aactccattc aacataacaa ttaccactag tacttattag tgtctcagta taggcaatgg  480
cttctatgaa caaatctctc agtatagact gtgctcattc                        520
```

```
SEQ ID NO: 141          moltype = DNA  length = 259
FEATURE                 Location/Qualifiers
source                  1..259
                        mol_type = unassigned DNA
                        organism = Solanum tuberosum
SEQUENCE: 141
gggaggatag caacatttaa ttatcattcc taccctcttc actatcatgt catttcttgt  60
ccaactatgt gatgaagatc agcagataaa atatacaagt attatttact ctccctagac  120
tcactacgtg catggcattc cctcttcagg gatatagctt ccttgccagt cgacaaacca  180
gagctgcaag agctacataa attaaacaaa gaccattaat actaccacga catttggatg  240
gtctttatta gccattcaa                                               259

SEQ ID NO: 142          moltype = DNA  length = 491
FEATURE                 Location/Qualifiers
source                  1..491
                        mol_type = unassigned DNA
                        organism = Solanum tuberosum
SEQUENCE: 142
ccaccttccc cccatggtgc atcctgtgta acttcaagga aagggaggct catataggaa  60
aacagaagaa cagaaaagtc aacttaacgg ggaaatagtt ctcctggtaa ttttgtcatt  120
tttcagggag gatagcaact tttaattatc attcctaccc ttttcactat catatcattt  180
cttgtccaac tatgtgatga agatcagcag atacaatata caagtattgt ttactctccc  240
tagaccaacg tgcatggcat tccctcttca gggatatagc ttccttgcca gtagacaaac  300
cagagctgca agagctacat aaattaaaca aagaccatta atactaccac gacatttgga  360
tggtctttat tagccattca aactccaact tcagtaaatt tcattgtttt tataactcca  420
ttcaacataa caattaccac tagtacttat tagtgtctca gtataggcaa tggcttctat  480
gaacaaatct c                                                       491

SEQ ID NO: 143          moltype = DNA  length = 488
FEATURE                 Location/Qualifiers
source                  1..488
                        mol_type = unassigned DNA
                        organism = Solanum tuberosum
SEQUENCE: 143
gctacacgcc ttcttctcga tggaatcaac tgcagccgat tcaaggtcat ctatgtattc  60
gacctccgga cttctcactg tgtcagaagt tgacatagat tcatccatgg agactaatga  120
tccatctgag tgagatggag aaatgtccat gctgcaggtg gcaggaagag gaatggcagt  180
gatcttaggc acaactgcat cacttctttg aatagaaaca ggtttgctgc ttggtctgag  240
gaaatgttct tcttaatgct tacaatcttg gacgtacatg gtgccttcca aagtcaaaaa  300
tgattccaag ttagtcacaa cttcagatac aagaagcaat ctttttcaa tttacacaca  360
ttgcaaaaca gtatattaaa taaaaggtta atcccaactg tgaaaactaa aaaatatcaa  420
aagttgctta acttcttctg ctcatttgtg taatgataat caaattaaga acagtaatat  480
aatcattt                                                           488

SEQ ID NO: 144          moltype = DNA  length = 515
FEATURE                 Location/Qualifiers
source                  1..515
                        mol_type = unassigned DNA
                        organism = Solanum tuberosum
SEQUENCE: 144
gctacacgcc ttcttctcga tggaatcaac tgcagccgat tcaaggtcat ctatgtattc  60
gacctccgga cttctcactg tgtcagaagt tgacatagat tcatccatgg agactaatga  120
tccatctgag tgagatggag aaatgtccat gctgcaggtg gcaggaagag gaatggcagt  180
gatcttaggc acaactgcat cacttctttg aatagaaaca ggtttgctgc ttggtctgac  240
agaggaggat gcacagcagt ccctgaggaa atgttcttct taatgcttac aatcttggac  300
gtacatggtg ccttccaaag tcaaaaatga ttccaagtta gtcacaactt cagatacaag  360
aagcaatctt ttttcaattt acacacattg caaaacagta tattaaataa aaggttaatc  420
ccaactgtga aaactaaaaa atatcaaaag ttgcttaact tcttctgctc atttgtgtaa  480
tgataatcaa attaagaaca gtaatataat cattt                             515

SEQ ID NO: 145          moltype = DNA  length = 253
FEATURE                 Location/Qualifiers
source                  1..253
                        mol_type = unassigned DNA
                        organism = Solanum tuberosum
SEQUENCE: 145
tgtattcgtt gaagttcctt cataggattt tcggtatacg ttaagttttc acatttcaat  60
ttgactacga agtatgttta aattgatgtt gtttatatct ctctttgctg tgaggccact  120
ctacactcga aactcaatag gaaaaagctt agtaaactca atattattaa catctggtga  180
tgcgttttct tccactacta cgttgaactg cctttattcc ttgttgattt tgagtaatca  240
tcttctgcaa ttt                                                     253

SEQ ID NO: 146          moltype = DNA  length = 235
FEATURE                 Location/Qualifiers
source                  1..235
                        mol_type = unassigned DNA
                        organism = Solanum tuberosum
SEQUENCE: 146
tctaatgtaa tgtattcgtt gaagttcctt cataggattt tcggtatacg ttaagttttc  60
```

```
acatttcaat ttgactacga agtatgttta aattgatgtt gtttatatct ctctttgctg  120
tgaaggccac tctacactcg aaactcaata ggaaaaagct tagtaaactc aatattatta  180
acatctggtg atgcgttttc ttccactact acgttgaact gcctttattc cttgt       235

SEQ ID NO: 147         moltype = DNA  length = 196
FEATURE                Location/Qualifiers
source                 1..196
                       mol_type = unassigned DNA
                       organism = Solanum tuberosum
SEQUENCE: 147
ccctcttcac tatcatatca tttcttgtcc aactatgtga tgaagatcag cagataaaat  60
atacaagtat tatttactct ccctagactc acctacgtgc ttggcattcc ctcttcaggg  120
atatagcttc cttgccagtc gacaaaccag agctgcaaga gctacataaa ttaaacaaag  180
accattaata ctacca                                                 196

SEQ ID NO: 148         moltype = DNA  length = 234
FEATURE                Location/Qualifiers
source                 1..234
                       mol_type = unassigned DNA
                       organism = Solanum tuberosum
SEQUENCE: 148
cattcctacc cccttcacta tcatatcata tcttgtccaa ctatgtgatg aagatcagta  60
gataaaatat acaagtattg tttactctcc ctagactcac ctacgtgcat ggcattccct  120
cttcagggat atagcttcct tgccggtcga caaaccagag ctgcaagagc tacataaatt  180
aaacaaagac cattaatact accacaacat ttggatggtc tttattagcc attc        234

SEQ ID NO: 149         moltype = DNA  length = 288
FEATURE                Location/Qualifiers
source                 1..288
                       mol_type = unassigned DNA
                       organism = Solanum tuberosum
SEQUENCE: 149
tggagactaa tgatccatct gagtgagatg gagaaatgtc catgctgcag gtggcaggaa  60
gaggaatggc agtgatctta ggcacaactg catcacttct ttgaatagaa acaggtttgc  120
tgcttggtct gacagaggag gatgcgcagt ccctgaggaa atgttcttct taatgcttac  180
aatcttggac gtacatggtg ccttccaaag tcaaaaatga ttccaagtta gtcacaactt  240
cagatacaag aagcaatctt ttttcaattt acacacattg caaaacag               288

SEQ ID NO: 150         moltype = DNA  length = 294
FEATURE                Location/Qualifiers
source                 1..294
                       mol_type = unassigned DNA
                       organism = Solanum tuberosum
SEQUENCE: 150
tggagactaa tgatccatct gagtgagatg gagaaatgtc catgctgcag gtggcaggaa  60
gaggaatggc agtgatctta ggcacaactg catcacttct ttgaatagaa acaggtttgc  120
tgcttggtct gacagaggag gatgctgaac agcagtccct gaggaaatgt tcttcttaat  180
gcttacaatc ttggacgtac atggtgcctt ccaaagtcaa aaatgattcc aagttagtca  240
caacttcaga tacaagaagc aatctttttt caatttacac acattgcaaa acag        294

SEQ ID NO: 151         moltype = DNA  length = 239
FEATURE                Location/Qualifiers
source                 1..239
                       mol_type = unassigned DNA
                       organism = Solanum tuberosum
SEQUENCE: 151
taatgttctg tattcgttga agttccttca taggattttt tgtatacgtt aagttttcac  60
atttcaattt ggctacgaag aatgtttaaa ttgatgttgt ttatatctct ctctttgctg  120
tgaagcggcc actctacact cgaaactcaa taggaaaaag cttagtaaac tcaatataat  180
taacatctgg tgatgcgttt tcttccacta ctacgttgaa ctgcctttat tccttgttg   239

SEQ ID NO: 152         moltype = DNA  length = 415
FEATURE                Location/Qualifiers
source                 1..415
                       mol_type = unassigned DNA
                       organism = Solanum tuberosum
SEQUENCE: 152
gttttgcgtt ttaaactttc atatatcgca attcctgtag tggatcatct tttggtcttt  60
tgcttttctg tatctaatgt aatgtattcg ttgaagttcc ttcataggat tttcggtata  120
cgttaagttt tcacatttca atttgactac gaagaatgtt taaattgatg ctgtttatat  180
ctctctcttt gctgtgaaca ctctacactc gaaactcaat aggaaaaagc ttagtaaact  240
caatattatt aacatctggt gaggcgttgt cttccactac tacgttgaac tgcctttatt  300
ccttgttgat tttgagtaat catcttctgc aatttctttt gtcacagtga acaaatctta  360
aatccatcag tcccgatggc tctgaggctc tctggaattc tcatgggtat gcttc       415

SEQ ID NO: 153         moltype = DNA  length = 278
FEATURE                Location/Qualifiers
source                 1..278
                       mol_type = unassigned DNA
```

```
                         organism = Solanum tuberosum
SEQUENCE: 153
taattttgtc acttttcagg gaggatagca acatttaatt atcattccta ccctcttcac  60
tatcatgtca tttcttgtcc cactctgtga tgaagatcag cagataaaat atacaagtat  120
tatttactct ccctagactc acctacgtgc atggcattcc ctcttcaggg atatagcttc  180
cttgccagtc gacaaaccag agctgcaaga gctacataaa ttaaacaaag accattaata  240
ctaccacgac atttggatgg tctttattag ccattcaa                          278

SEQ ID NO: 154           moltype = DNA  length = 282
FEATURE                  Location/Qualifiers
source                   1..282
                         mol_type = unassigned DNA
                         organism = Solanum tuberosum
SEQUENCE: 154
tttttcaggg aggatagcaa cttttaatta tcattcctac ccttttcact atcatatcat  60
ttcttgtcca actatgtgat gaagatcagc agatacaata tacaagtatt gtttactctc  120
cctagactca cctacgtgca tggcattccc tcttcaggga tatagcttcc ttgccagtag  180
acaaaccaga gctgcaagag ctacataaat taaacaaaga ccattaatac taccacgaca  240
tttggatggt ctttattagc cattcaaact ccaacttcag ta                     282

SEQ ID NO: 155           moltype =   length =
SEQUENCE: 155
000

SEQ ID NO: 156           moltype = DNA  length = 240
FEATURE                  Location/Qualifiers
source                   1..240
                         mol_type = unassigned DNA
                         organism = Solanum tuberosum
SEQUENCE: 156
ttttgctttc tgtatctaat gtaatgtatt cgttgaagtt ccttcatagg attttcggta  60
tacgttaagt tttcacattt caatttgact acgaagtatg tttaaattga tgttgtttat  120
atctcggcca ctctacactc gaaactcaat aggaaaaagc ttagtaaact caatattatt  180
aacatctggt gatgcgtttt cttccactac tacgttgaac tgcctttatt ccttgttgat  240

SEQ ID NO: 157           moltype = DNA  length = 220
FEATURE                  Location/Qualifiers
source                   1..220
                         mol_type = unassigned DNA
                         organism = Solanum tuberosum
SEQUENCE: 157
atgtaatgta ttcgttgaag ttccttcata ggattttcgg tatacgttaa gttttcacat  60
ttcaatttga ctacgaagta tgtttaaatt gatgttgttt atatctctct ttgctgggaa  120
aaagcttagt aaactcaata ttattaacat ctggtgatgc gttttcttcc actactacgt  180
tgaactgcct ttattccttg ttgattttga gtaatcatct                        220

SEQ ID NO: 158           moltype = DNA  length = 240
FEATURE                  Location/Qualifiers
source                   1..240
                         mol_type = unassigned DNA
                         organism = Solanum tuberosum
SEQUENCE: 158
ttatcattcc taccccccttc actatcatat catatcttgt ccaactatgt gatgaagatc  60
agtagataaa atatacaagt attgtttact ctccctagac tcacctacgt gcatggcatt  120
ccctcttcag ggatatagct tccttgccgg tcgacaaacc agagctgcaa gagctacata  180
aattaaacaa agaccattaa tactaccaca acatttggat ggtctttatt agccattcaa  240

SEQ ID NO: 159           moltype = DNA  length = 208
FEATURE                  Location/Qualifiers
source                   1..208
                         mol_type = unassigned DNA
                         organism = Solanum tuberosum
SEQUENCE: 159
attcctaccc tcttcactat catatcattt cttgtccaac tatgtgatga agatcagcag  60
ataaaatata caagtattat ttactctccc tagactctac gtgcttggca ttccctcttc  120
agggatatag cttccttgcc agtcgacaaa ccagagctgc aagagctaca taaattaaac  180
aaagaccatt aatactacca cgacatttt                                    208

SEQ ID NO: 160           moltype = AA  length = 535
FEATURE                  Location/Qualifiers
source                   1..535
                         mol_type = protein
                         organism = Gossypium barbadense
SEQUENCE: 160
MFYSRELLAR KASLGQIWLL GTRQAKLDRR KANKLDIARL CEEILNPPVP IALRLSSILM  60
GGVVILYEKK VMFLHDDANR FLVEIRNAWK VMNEPTLLPK RKEKAKRKSI TLPENDETSM  120
GFTNVGELEE EISMGPGDSF RLADDNDITL FDLFQPNSNI HGQFERFEEA DEGTQVNFTL  180
DEHIQIPTTP IPSPSQKEPQ RAGGTQERHP EHQLDQQFNK NKEARDQQRQ GSVKQRRKPK  240
GIITDEEQTV ISNHVYHSWL HDTSDIASRI RRKNSGPASI LSTFKIAKLM ELPSTVIMDD  300
```

```
MLLKGNQEIS YPEPLLDLWK KCSQPLHDSP SDLHSGVGSP SHAASIEVQR ANVVNKVTPA  360
GINQFVSPGN SGDAVRYTGS SVSGDGVPSG NLEVNIERVG SKKKNLQSTS KNSGSLDTVV  420
EVFHEADTDY QLSRPKRKNL EPDHDFLVET QLTMETPADD PPDMMTENIK KHMKTHFETP  480
GAPQVESLQN LAAGLNKKGA AQLFYRTCVL ASQGFLKVQQ KVAFGDIFIS KGAKM        535

SEQ ID NO: 161          moltype = AA  length = 627
FEATURE                 Location/Qualifiers
source                  1..627
                        mol_type = protein
                        organism = Arabidopsis thaliana
SEQUENCE: 161
MLRLESLIVT VWGPATLLAR KAPLGQIWMA ATLHAKINRK KLDKLDIIQI CEEILNPSVP  60
MALRLSGILM GGVVIVYERK VKLLFDDVNR FLVEINGAWR TKSVPDPTLL PKGKTHARKE  120
AVTLPENEEA DFGDFEQTRN VPKFGNYMDF QQTFISMRLD ESHVNNNPEP EDLGQQFHQA  180
DAENITLFEY HGSFQTNNET YDRFERFDIE GDDETQMNSN PREGAEIPTT LIPSPPRHHD  240
IPEGVNPTSP QRQEQQENRR DGFAEQMEEQ NIPDKEEHDR PQPAKKRARK TATSAMDYEQ  300
TIIAGHVYQS WLQDTSDILC RGEKRKVRGT IRPDMESFKR ANMPPTQLFE KDSSYPPQLY  360
QLWSKNTQVL QTSSSESRHP DLRAEQSPGF VQERMHNHHQ TDHHERSDTS SQNLDSPAEI  420
LRTVRTGKGA SVESMMAGSR ASPETINRQA ADINVTPFYS GDDVRSMPST PSARGAASIN  480
NIEISSKSRM PNRKRPNSSP RRGLEPVAEE RPWEHREYEF EFSMLPEKRF TADKEILFET  540
ASTQTQKPVC NQSDEMITDS IKSHLKTHFE TPGAPQVESL NKLAVGMDRN AAAKLFFQSC  600
VLATRGVIKV NQAEPYGDIL IARGPNM                                      627

SEQ ID NO: 162          moltype = AA  length = 604
FEATURE                 Location/Qualifiers
source                  1..604
                        mol_type = protein
                        organism = Rubus occidentalis
SEQUENCE: 162
MFYSHSLLAR KAPLGEICEE ILNPAAPMAL RLSSILMGGV VIVYERKVKL LYGTVPVELN  60
EAWKVKSNTD STVLPKKRAQ AKKEAITLPE PEDTDLGGDI DIEQSLDFSH HATLFQQQTG  120
YFLMQLDSVD VGEPLNENAG EGDQHQNFHQ ADPEDITLPE RFDPSDAYGD LFNHRYERFE  180
IEGDDLDFTA GERTQIRAPS PNYIIPSPPS PNYIIPSPPR QDQRQEVQQP HHVFDEMVQM  240
QEVQENAQQR QGPLRGRRRK RRAPVMDNDQ TIHPAHVYQS WLQDTSDIVS RRRRNPKPKN  300
IMSTVKIGKL MEQPASVLMG CLFKPGSGET YYPPPLLELW KEKPTHDSPS ALTSPPLQPE  360
PSSWSPPERQ TYQDSPVEEF HSGGGSQSFA TPTEQIRTNL VNNDVPPELM DELRANLNGM  420
RGADTKLATP GNSGDERRSI PSTSSGKGVN KNSSEVNSGR SNRKRRYSSI HSNDGLEPVS  480
EDNGCHHPDP NFNVSRLSGI EQELLMETGP TQTPQPIIDQ PLEKMTDDIR KELKSYFEAP  540
GGPEVESLDK LTAGMNRKGA ALLFYQTCVL ATRNFVKVEQ KAPYEDILIT RGPNITEVEE  600
LVLK                                                               604

SEQ ID NO: 163          moltype = AA  length = 527
FEATURE                 Location/Qualifiers
source                  1..527
                        mol_type = protein
                        organism = Citrullus lanatus
SEQUENCE: 163
MFYSHQLLAR KAPLGQIWMA ATMHAKINRR KLDNEEILNP SVPMALRLSG ILMGGVVIVY  60
ERKVKILYED VTRLLVEINE AWKVKAAPEP TVIPKGKSLA KKEAVTRPEK DPKDVSYNTS  120
PMRFQQTAFF TMRLDSVDEP YNSDKTVEDD PFDIEEDEDT QPNFASVDQT QIPATFKDSP  180
PPQDKYPEGP PDAEVQDQHL ESNVNQPAYE STELRQQRTG AMSTMKIATL MDLPPVVLSE  240
RLFTDGSREV YYPAPLLELW MRSIRQPPDS PSERNSAPLP PEPSLSSLPE RVNFSDHMDF  300
SFEGHQSGVG SQSFGASMEK LMTRRVNDSN QAEIPEELGP NIMDNVMRMT ERNQVVTPGN  360
SVNGVRSVSS SASGHGDLSN NLGTNSVRSN KKRPYSSSRQ SSGGLEPVAE ENPWHHHSDP  420
NFKLARLSEN DPDLLEETAR TQTQVTQPAI KHPPADKITD SIRTQMKAHF DTPGAASTES  480
LNNLAAGMNR KAAAMLFYQT CVLASSDYLK VNQQVPFGDI FISKGTK                527

SEQ ID NO: 164          moltype = AA  length = 617
FEATURE                 Location/Qualifiers
source                  1..617
                        mol_type = protein
                        organism = Prunus avium
SEQUENCE: 164
MFYSHQLLAR KAPLGQIWMA ATMHAKINRR KLDKLDIIKI CEEILNPSVP MALRLSGILM  60
GGVVIVYERK VKLLYDDVTR LLVEINEAWK AKSVADPTVL PKGKSQARKE AVTLPENEDI  120
DIEGMLNFSN GATTMFQQTS YFAMRLDSVD EQYVNNDAGE EDPPQQFHQA EAENITLPER  180
FDSCQQADAYL YSRLERFDIE GDEETQLNFT SGEHTQIHIP PSPPRDEHQK ADTIQDDQHP  240
EQQVNQPEEC QEFRQKVRMK QVQERQGPIR RKTRRTQASA MDFEQTIIPG HLYQSWLQNS  300
SDIVSRRGRK RKRTDVMATM KIVNLMELPP IVLIGDLFTT GSRDIYYPRP LLDLWMKSTR  360
TPHASPSERT TPPLPPEPSS STLPGRQQYE DPPFEDYSGV GSQSLETSID KQRRHSGMTR  420
GNSDPAQVVL EGLTANLENN GLGGTDANPM VTPGNSDDVR SIPSSASGQA IPSEANSGRS  480
NRKRPYSASG HSSVRLEPVF EVNHPDVNFE LSRLHEHGPT SEIDFFVETG PTQTQKPIND  540
QPLDKTTDSI RRLLKSHFDT AGAPQVESLD HLTAGRTRKE AAIFFYKTCV LATHDAIKVE  600
QKVAYGEILI SRGPKMG                                                 617

SEQ ID NO: 165          moltype = AA  length = 624
FEATURE                 Location/Qualifiers
source                  1..624
                        mol_type = protein
```

```
                         organism = Vaccinium corymbosum
SEQUENCE: 165
MFYSHQLLAR KAPLGQIWMA ATMHAKMNRK KLDKLNIIKI CEEILNPSVP MALRLSGILM  60
GGVVIVYKRK VKFLYDDVNR FLVEINEAWK VKSVPDPTLL PKGKSQAKYE TVTLPDINQE  120
AELGEIEQSL NYTNTTMRFQ ETAYFSMRLD NVDEPFINND PREGPQSEQH HQVDADNITL  180
FERFDSYQTD TNLYSRFERF DIEGDDETQA NFTSQERTQI PSSLIPSPPR PAEPRKSDEI  240
LDQHPEDQVY HQPDEGKAAS QDLQRQGPTR RKARKPAAFA MDYEQTIIPG HMYQSWLQSA  300
SDIVSRRGRK RKRFNAMSTM KIGNLMDLPP MVLLCGLFGS GKREVHYPAP LLELWVRSTE  360
PPHDSPSGKT SPPQPPEPSA SSLADRARYN DSMGFLYEDV HGGLGSQSFG VSIEKQRTNV  420
NVNEIPTEVL MEDLRNNFVN NGVRVNEANV MVTPGNSGDE VRSIHSSGSG QGFQSHTSEG  480
NSGRSNKKRP NSSSRHSGSG LEPVAEENPW QHPDPNFKLA RLSENGLTPE NDLLAETGPT  540
QTQQPIMTPR IDQITNSIRM QLKTHFDTLG PSEKESLNQL AFGMNKKRAA HLFYHTCVLA  600
SRDFVRVEQH VPYGDILISR GAKM                                      624

SEQ ID NO: 166           moltype = AA  length = 747
FEATURE                  Location/Qualifiers
source                   1..747
                         mol_type = protein
                         organism = synthetic construct
VARIANT                  37
                         note = Xaa = L or I
VARIANT                  46
                         note = Xaa = N or D
VARIANT                  147
                         note = Xaa = N or D
VARIANT                  243
                         note = Xaa = Q or E
VARIANT                  319
                         note = Xaa = Q or E
VARIANT                  644
                         note = Xaa = L or I
VARIANT                  1..747
                         note = Xaa = Any Amino Acid, or no amino acid (except at
                          positions 37, 46, 147, 243, 319 and 644)
SEQUENCE: 166
MFYSHQLIVT VWGPATLLAR KAPLGQIWMA ATXHAKXNRK KLDKLXIIXI CEEILNPSVP  60
MALRLSGILM GGVVIVYERK VKLLYDDVTR LLVEINEAWK VKSXXDPTLL PKGKSQAKKE  120
AVTLPEINXE XDLGEDIDIE QTLNXXXXXT XMXFQQTXYF XMRLCKFNNR KLTMIKWFDF  180
PSLSFGYSIC FAILSDTTWI RVGNISENKI IIDNFYMRVQ LNSDXXVXXX XDDXXXXNNX  240
XXXXXPXXXF HQXDXDNITL XERFXSXXTD XXXXXXRFHD ERFDIEGDEE TQXNFTXXEX  300
TQIPXTSPNX XIPSPPRXXX XXXXPDXXXX DXHPEXQVXQ QXFXDEXXEA XXXQXQDQQR  360
QGPXRRRARK XXXXAMDXEQ TIIXGHXYQS WLQXXSDIXS RXRRRKRKXX XXMSTMKIAX  420
LMELPPXVLX EXLFTXGXXE VXYPAPLLXL WMRXTQPPHD SPSXXTSPPL PPEPSXXSXX  480
ERXXXXDXPF FXXEXXXSGV GSQSXGXSIE KQRANXNXXV XNXXPPEXLM EXLRXNLXNN  540
GXXXTXXNXV KETDHVTPGN SGDEVRSIPS SXSGXGXXSI XNSEXNSKXR SXNKKRPXSS  600
SXHSXXGLEP VAEENPWHHH PDPNFKLTRL SRLSENGFTX DXXXLXETGP TQTQVTXPXI  660
XHQPLDMMTD SIRXQLKSHF DTPGAPEVES LNXLXAGMNX KXAAXLFYQT CVLATRDFXK  720
VEQXVPYGDI LISRGAKITE VEELVXM                                   747

SEQ ID NO: 167           moltype = AA  length = 461
FEATURE                  Location/Qualifiers
source                   1..461
                         mol_type = protein
                         organism = Citrullus lanatus
SEQUENCE: 167
MEGNRGSLER IGILRKITEL TKSMIVELSN GSSKMISIDR FKSYCTNSLE NWFNLSEGKE  60
TLTLQRESHV RRLDVLLRVL LIIQQLLREN RHSSKRDIYY MHPSVFTDQS VVDRAINDIC  120
ILLQCSRHNL NVGDTLQQRS IAVFFKSYSL CLEAASDDPF NLCPLDRLVM GWLRFSEAGR  180
RFDCIKKPNS AHFIPVQVEE VTDIASPADY ILVVEKESGE GYSDKSWFHG SRKLNFKFYF  240
DQLKYLVSYF ERPVFQRLAN DRFCSRNRCI VITGRGYPDV PTRRFLRILV DVLALPAFCL  300
VDCDPYGFDI LTTYRFGSMQ MAYDAKYLRI PQLQWLGAFA SDSEKYNLPE QCLIPLTLQG  360
EGSCIQTHTH TLTLYAFSNV NFGISDILSF LVNLSDKRRT EALLQRCYLR REVPQWRLEL  420
DSMLQRGVKF EIEALSVHNI SFLSEEYLPS KIKNELTTGK F                    461

SEQ ID NO: 168           moltype = AA  length = 365
FEATURE                  Location/Qualifiers
source                   1..365
                         mol_type = protein
                         organism = Rubus occidentalis
SEQUENCE: 168
MEGKRSRWSS QPRPRDLLRK IKGFTRAIVE DLSNGRSPEI PIDRFRNYCS NPSANCYCSS  60
DLPKGKETLT LRRESHVHRL DVLLRVLVVV QQLLQENRHA SKRDIYYMHP SIFSDQSVVD  120
RAINDICILL QCSRHNLNVV SVGKGTFQHF SECCKVNNIM AYPVPVNVEE VKDIVSVAQY  180
ILVVEKESVF QRLANDQFCN SNRCIVITGR GYPDISTRRF LGLLVDTLHL PIYCLVDCDP  240
YGFDILSTYR FGSLVRPPDQ SINLSSTQMA YDAKFLRVPE IIWLGAFPLD SEKYHLPQQC  300
LLPLTAEDKR KTEAMLQRCY LEREVPQWRL ELQLMLESGV KFELEALSSL LMGVMGQAML  360
RKHIH                                                           365

SEQ ID NO: 169           moltype = AA  length = 409
```

```
FEATURE                Location/Qualifiers
source                 1..409
                       mol_type = protein
                       organism = Vaccinium corymbosum
SEQUENCE: 169
MEGTRSNTQP SDLLKKIKDV LLRVLLIVQQ LLQENRHGSK RDIYYMHPSV FQGESGFCFG  60
IHFLLRFFSS SLYRGHSLVM GWLRFHEAER KFDCISSLNT AQPVPVHVED VKDLVSVAHY  120
ILVVEKESVF QRLANDQFCN KNRCIVITGR GYPDVPTRRF LRLLMEKLSL PAYCLVDCDP  180
YGFDILMTYR FGSMQMAYDA KFLRLPEIHW LGVFPSDGEK YGIPQQCHLP LTAEGEMDTF  240
EKAFFNHKSR TEAMLLRCYL QREVPHWRSE LELLLQRGVK FEIEALSVHS LSFLAEEYIP  300
LKIKGEYSVT IDTEEGLAKV SGEVDPNVLL SAIGKSSKHA ELKWVQLKSP TPQNRSHYYH  360
NDDMGKSYGP YSLSYGQDYY GYGQPIEPPH TGRRRALLEA EGRWCDALS             409

SEQ ID NO: 170         moltype = AA  length = 362
FEATURE                Location/Qualifiers
source                 1..362
                       mol_type = protein
                       organism = Arabidopsis thaliana
SEQUENCE: 170
MEGKFAISES TNLLQRIKDF TQSVVVDLAE GRSPKISINQ FRNYCMNPEA DCLCSSDKPK  60
GQEIFTLKKE PQTYRIDMLL RVLLIVQQLL QENRHASKRD IYYMHPSAFK AQSIVDRAIG  120
DICILFQCSR YNLNVVSVGN GLVMGWLKFR EAGRKFDCLN SLNTAYPVPV LVEEVEDIVS  180
LAEYILVVEK ETVFQRLAND MFCKTNRCIV ITGRGYPDVS TRRFLRLLME KLHLPVHCLV  240
DCDPYGFEIL ATYRFGSMQM AYDIESLRAP DMKWLGAFPS DSEVYSVPKQ CLLPLTEEDK  300
KRTEAMLLRC YLKREMPQWR LELETMLKRG VKFEIEALSV HSLSFLSEVY IPSKIRREVS  360
SP                                                               362

SEQ ID NO: 171         moltype = AA  length = 313
FEATURE                Location/Qualifiers
source                 1..313
                       mol_type = protein
                       organism = Gossypium barbadense
SEQUENCE: 171
MEGIRSSTRS RDLLRKIKEF TLSILEDLSE GLSPLIFIQS FRTYCTNLDS ICSCRSNQPS  60
GHEILTFQKE SHVHRIDVLL RVLLIVQQLL QENKHASKRD IYYMHPLIFS DQSVVDRAIN  120
DICILLQCSR HNLNVVSVGN GLVMGWLRFF EAGRKFDCIN SPNTAHTVPV LVEDVKDLVS  180
AALYILVVEK ESVFQRLEND KFCSKNRCIV ITGRGYPDVP TRRFLRLLVD KLCLPVYCLV  240
DCDPYGFDIL ATYRFGSMQM AYDAKFLRVP QIQWLGAFPS DSENYDLPKQ CLLPLTIEGD  300
TYSKDQWLPP APS                                                   313

SEQ ID NO: 172         moltype = AA  length = 365
FEATURE                Location/Qualifiers
source                 1..365
                       mol_type = protein
                       organism = Prunus avium
SEQUENCE: 172
MEGKHSRWSS QPRPCDLLRK IREFTRAIVE DLSNGRSPEI LIDRFRNYCT KPDSNCDCSS  60
DLPILKETLT LRRESHLRRL DVLLRVLVIV QQLLQENRHG SKRDIYYMHP SVFSDQSIVD  120
RAINDICILM QCSRHNLNVV SVGKGLVMGW LRFSEAGNMF DCINRPNTAF PVPIHVEEVK  180
DIVSVAKYIL VVEKESVFQR LANDQFCNTN HCIVITGRGY PDISTRRFLG LLVDTLHLPT  240
YCLVDCDPYG FDILSTYRFG SMQMAYDAKF LRVPEILWLG GFPLDSEKYL LPQQCLLPLT  300
AQDKRKTEAM LRRCYLQREV PRWRLELQLM LERGVKFELE ALSVHELNFL SAVYIPSKIQ  360
GGVYI                                                            365

SEQ ID NO: 173         moltype = AA  length = 578
FEATURE                Location/Qualifiers
source                 1..578
                       mol_type = protein
                       organism = synthetic construct
VARIANT                486
                       note = Xaa = L or I
VARIANT                386
                       note = Xaa = Q or E
VARIANT                401
                       note = Xaa = N or D
VARIANT                484
                       note = Xaa = Q or E
VARIANT                1..578
                       note = Xaa = Any Amino Acid, or no amino acid (except at
                        positions 486, 386, 401 and 484)
SEQUENCE: 173
MEGKRSRWSS XTRPXDLLRK IKXFTRSIVE DLSXGRSPXI XIDRFRNYCT NXXXNCXCSS  60
XLPXGKEXLT LXRESHXRRL DVLLRVLLIV QQLLQENRHG SKRDIYYMHP SVFXDQSVVD  120
RAINDICILL QCSRHNLNVG DXLQVRSIAV FFKSYSXCLE AASDDPFSVG PLNGLVMGWL  180
RFXEAGRKFD CIXXPNTAYP VPVLVEEVKD IVSVAXYILV VEKESGEGYS DKSWFHGSRK  240
LNFKFYFXQL XYVVSYFERP VFQRLANDQF CXXNRCIVIT GRGYPDVPTR RFLRLLVDKL  300
HLPVYCLVDC DPYGFDILXT YRFGSMVXPP DQSINLSSTQ MAYDAKFLRV PEIQWLGAFP  360
SDSEKYXLPQ QCLLPLTAEG EXXXXXXXXH TLTLYAFDNV XFGISDXLSF LVNLXXKRKT  420
EAMLXRCYLQ REVPQWRLEL ELMLXRGVKF EIEALSVHSL XFLSXEYLPS KIXNXXXXXX  480
```

```
XXXXXXXXXX XXXXPXXLLS AIGKSXKHAE LKWVQLKSPT PQNRSHYYHN DDMGKSYGPY  540
SLSYGQDYYG YGQPIEPPHT GRRRALLEAE GRWCDALS                          578

SEQ ID NO: 174          moltype = AA  length = 451
FEATURE                 Location/Qualifiers
source                  1..451
                        mol_type = protein
                        organism = Arabidopsis thaliana
SEQUENCE: 174
MKMNINKACD LKSISVFPPN LRRRSAEPQA SQQLRSQQSQ QSFSQGPSSS QRGCGGFSQM  60
TQSSIDELLI NDQRFSSQER DLSLKKVSSC LPPINHKRED SQLVASRSSS GLSRRWSSAS  120
IGESKLAQIS EELEQRFGMM ETSLSRFGMM LDSIQSDIMQ ANRGTKEVFL ETERIQQKLT  180
LQDTSLQQLR KEQADSKASL DGGVKFILEE FSKDPNQEKL QKILQMLTTI PEQVETALQK  240
IQREICHTFT REIQVLASLR TPEPRVRVPT APQVKAKENL PEQRGQAAKV LTSLKMPEPR  300
VQVPAAPQAK ENFPEQRGPV AKSNSFCNTT LKTKQPQFPR NPNDASARAV KPYLSPKIQV  360
GCWKTVKPEK SNFKKRATRK PVKSESTRTQ FEQCSVVIDS DEEDIDGGFS CLINENTRGT  420
NFEWDAEKET ERILRTARRT KRKFGNPIII N                                 451

SEQ ID NO: 175          moltype = AA  length = 411
FEATURE                 Location/Qualifiers
source                  1..411
                        mol_type = protein
                        organism = Citrullus lanatus
SEQUENCE: 175
MRLKINKACD LSSISVLPPQ SRHARSNALT TGQQAPQLRS QPSQQSFSQG LSSQHGMYSQ  60
LSQNSFDEVV TNEQRFSSQD RENSIKKNSF FTPLSYSRED CQMALSKSST SLTQRWKSTP  120
LPDSKCQVGE ELDRRLGTIE NSLNKFGKIL DSLHSDILQL NKGMKQVSLD VEGIWQKMLV  180
NSSSLQSMNK EHDDMKATLD GGFKLISDLL KKDAHQERLH EISDVLSSLE KQVQASQLKL  240
KNDFISTFTQ EMKAIVCTLK NPLQKFPPRS IQSPEGTACL DVPSQKRHRC KIQSASPNVC  300
IRATAVQKEE VGRWKSVKVG KTFCTSSVVK KDDPKKVIPF SEQCLVLERE YRVIVDSDEE  360
IERSFSCLIE EKKTGENVRY YSIEDAKEES ARILRKARRQ KRKYCNPIII N            411

SEQ ID NO: 176          moltype = AA  length = 442
FEATURE                 Location/Qualifiers
source                  1..442
                        mol_type = protein
                        organism = Vaccinium corymbosum
SEQUENCE: 176
MKLKINKACD LSSISVLPPH TSVVVTALFD SKRRSSLVPN GPESSVFGKR QASQLLSQPS  60
QQSFSQGVSS QQGMFSQLSQ NSLDDIVTNN QRISSQEREN PVKKLSCLPP ISYTLEESQM  120
PVSRSSSNLM RKWNSGSALD HRSQTSEELE RRIGMIETSM NRFGMIMDSV QSDIMQVNKG  180
TKEALMEIED VRQKIIANGN LLQLMDKGQQ DIKTNLVGGI KSLTDQVGQD IDGEKLKEIS  240
SMISALPEQI DVSLHKMQSE LCTKITQEIQ AMACSLKIPS QKSQNPPTPA VLLAKDRSCR  300
SVQQQMQPLK DPEMPPKICG KTTLLPKIEV GSWTSVKTEQ ATRKKQKQKR MSPIEVHKQM  360
MVMQDRECRI PIESDEEIDG GFSCLLEGKE TDPVQYLKQA TDTFHTPHLG NYSMAEAKEE  420
TQRILRKARR RKRRHSNTII LD                                           442

SEQ ID NO: 177          moltype = AA  length = 402
FEATURE                 Location/Qualifiers
source                  1..402
                        mol_type = protein
                        organism = Gossypium barbadense
SEQUENCE: 177
MKLKINKACD LGSISVFPPH TRRSSLPPSV PQSSQLRSQP SQQSFSQGIS SQHALFSQIS  60
QSSLDEIVTT DQRFGSQERE NTASKFSCLA PTNFTREDSQ VPISRSSTNI IRKWNPVSAP  120
EHRCQTSEEL EHRLSVIETS LNRFGMILDS VQSDIMQVNK GTKELLLEME GMRQRSIAED  180
TSLQLMIKGQ EDIKASLDGS MKAVSDQLNN DKYRDKLQQI FLVLSALPEQ MEASLIKVRN  240
ELCNTFTNEI KAIDCKTLSQ KAPVAAAILP KSTGCSVTPR TKPLAVKKQA VPPKIYEQNT  300
VAAEVEKGGW KSVKMKQCAT NERASCKEND KRKGVSSVEQ ETFRILIESD EEIDAGFSCL  360
LNDKQTDDAM NILIEEAKEE TERILRKARR RKRKPLNPII IN                     402

SEQ ID NO: 178          moltype = AA  length = 407
FEATURE                 Location/Qualifiers
source                  1..407
                        mol_type = protein
                        organism = Prunus avium
SEQUENCE: 178
MKLKINKACD LSSISVLPQH TRRQNAAPNG PQASQLRSQP SEQSFSQGFS SQHGMFSQLS  60
QNSLSDVLTN DQRFGSQERE NSVKKIACLP PISHAREESQ MQISRSSTNF MRKWSSASGS  120
DHRWQTSEEF EHRIGMMETS LNKFGMILDS VQSDVMQVNK GMKEVSMEME AMRQKLTAQD  180
NSLQLMSKGQ EDFKASLDGG IKSMSEQLSK NTYQDKLQEM FLVLSALPGK IEIIEASLLK  240
SQNKLHDSFV KEMQKMICSQ NQSTSIQKCE ISSILSPKGV AASRAIPQGK PQPIKSSAVP  300
PKACVQAVVV PKTETGGWKT VKAEKAVFSD SGFRKVQKPN RFTSIQKERE CRVIIESDEE  360
IDGAFSCLLD DKETDVDMAA EVKEETQRIL RRARRRKRKL CNTIIIN                407

SEQ ID NO: 179          moltype = AA  length = 451
FEATURE                 Location/Qualifiers
source                  1..451
                        mol_type = protein
```

```
                         organism = Rubus occidentalis
SEQUENCE: 179
MKLKINKACD LSSISVLPPH TRRSNSVPHG PQSSQLQLRS QPSEQSFSQG LSSQYGMFSQ  60
LSQTSLDALT DQRSQERENS VKKISCLPPI SHAREESQMQ ISRTSNNHMR KWSSVSGSDH  120
RCQISEEFEH RIGMMETSLS KFGMILDSVQ SDVMQVKKGT KEVSLEMEAI QQKLMVQDSS  180
LQLMNKGQED FKTTFDAGIK SMLEQLSKNP NQDKLQEMFL VLSALPEKIE ASLLSSQNKL  240
HNSFIKEVQK LLCPIQTCQN QITPIQTCKA LSILSPKTAA SPAILKAEQK PKRKYVRKCK  300
VPSLPSPKGD AFHAIPQQKP QLINKASERL RNPALDSHST VPPKVCVQPA VVPTTETGGW  360
KTVKAGNATS IDRVPQKVQK HNRITCVQQE REGRVIIESD EDIDGGFSCL LDEKDTDIKN  420
YMIEEVNQET ERILRRARRR KRKCCNPIII N                                451

SEQ ID NO: 180           moltype = AA  length = 499
FEATURE                  Location/Qualifiers
source                   1..499
                         mol_type = protein
                         organism = synthetic construct
VARIANT                  127
                         note = Xaa = L or I
VARIANT                  471
                         note = Xaa = L or I
VARIANT                  236
                         note = Xaa = N or D
VARIANT                  1..499
                         note = Xaa = Any Amino Acid, or no amino acid (except at
                          positions 127, 471 and 236)
SEQUENCE: 180
MKLKINKACD LSSISVLPPH TXVVVTALFD SXRRSSXVPX GPESSVFGKS QXSQLRSQQP  60
SQQSFSQGXS SQQRGCGMFS QLSQSSLDDX VTNDQRFGSQ ERENSXKKXS SCLPPIXYTR  120
EESQMQXSRS STNXXRKWSS XSXPXXXLXQ ISEELEHRIG MXETSLXRFG MILDSVQSDI  180
MQVNKGTKEV LXEMEXXRQK LXXXDXSLQL MNKGQEDXKA SLDGGXKSMX EQLXKXXYQE  240
KLQEIXXVLS ALPEXXEIIE ASLLKXQNXL XXTFTKEIQX IXCXXXXXXX XXQXXPXXXX  300
XXXXXXXXXR XXXXXKXXXX KKXXXPPKIX XXXXXXXKXE FXXXXXPXGX WKSVKXXXXX  360
TXXXAFXKXX PXXSXXXVXP XXXPXTXXGQ WXXXXXXTQN XAFQQKIPXX XXXXXXXXQQ  420
ERECRXXIES DEEXIDGGFS CLLEEKXTDX VXYLKQATDT FHTPXXXXYX XXXAKEETXR  480
ILRKARRRKR KXXNXIIIN                                              499

SEQ ID NO: 181           moltype = AA  length = 262
FEATURE                  Location/Qualifiers
source                   1..262
                         mol_type = protein
                         organism = Prunus avium
SEQUENCE: 181
MAEARDRLSR PPVDLADTYA QWLSRNRSIY IDPPEQVLQV VPDLSRTPAR QRAPTALGFG  60
ATGVVGGGGL LRSSLRTSRT GNARGRIPFG FTTPARENTP PAGSSRRRRG RSSNSVLPSW  120
YPRTPLQDIS AVVRAIERRR ARLGENDGQH TEGQVPQGRN ILDQYLLVPG AQLEHGVPVT  180
PYSAVRTKHC PPPSVGRVQK IIREATNTQT AEGEFLTPQK KLLNSIDTVE KVVMEELQRL  240
KRTPSAKKAE REKRVRTLMS MR                                          262

SEQ ID NO: 182           moltype = AA  length = 250
FEATURE                  Location/Qualifiers
source                   1..250
                         mol_type = protein
                         organism = Rubus occidentalis
SEQUENCE: 182
MPAESRFRLE RPFDIAEAFS QRRSGSLAVL IDERGELLES PARSRALATP VHQRRLGFWA  60
TGGGVGHGLA RSRLRTPRAA IGHGQENMPP VGSSNRRRGR VSNSVLPSWY PRTPLRDITA  120
ITRAIERRRA RLGEENGETS RGQVPSQQVQ DASPEHEVPA TTPSTIKKRP CPPPSVRKVH  180
KILLEVAYQP DDGEFLTPQK KLLNSIDKVE NVVMEELQRL KRTPSAKKAE REKRHKADGS  240
LRYGGYALVT                                                        250

SEQ ID NO: 183           moltype = AA  length = 243
FEATURE                  Location/Qualifiers
source                   1..243
                         mol_type = protein
                         organism = Arabidopsis thaliana
SEQUENCE: 183
MPEARDRTER PVDYSTIFAN RRRHGILLDE PDSRLSLIES PVNPDIGSIG GTGGLVRGNF  60
TTWRPGNGRG GHTPFRLPQG RENMPIVTAR RGRGGGLLPS WYPRTPLRDI THIVRAIERR  120
RGAGTGGDDG RVIEIPTHRQ VGVLESPVPL SGEHKCSMVT PGPSVGFKRS CPPSTAKVQK  180
MLLDITKEIA EEEAGFITPE KKLLNSIDKV EKIVMAEIQK LKSTPQAKRE EREKRVRTLM  240
TMR                                                               243

SEQ ID NO: 184           moltype = AA  length = 257
FEATURE                  Location/Qualifiers
source                   1..257
                         mol_type = protein
                         organism = Gossypium barbadense
SEQUENCE: 184
MAESRDRLGR AVDIAEVFAR RRSGPLGILS DESMDLLGSP VRQSVTRRSM GVVGVTTSTA  60
```

```
RGVGLRRGGS FGTPRIGIRR SRNLYRSTGR ENASVTPSPL GRGRGRGTGS VLPSWYPRTP  120
LRDITAVVRA IERRRARLGD GEGQIVETPI LPHDETILGS NMSSVSQLEH NFSTPASTTR  180
LKPCPPSVRN VSKILLNVTN QKHEESSEEL LTPQKKLLNS IDTVEKAVIE ELNKMKKTPS  240
AKKAERQHKV RTLMSMR                                                 257

SEQ ID NO: 185         moltype = AA  length = 249
FEATURE                Location/Qualifiers
source                 1..249
                       mol_type = protein
                       organism = Citrullus lanatus
SEQUENCE: 185
MSEARDRLER QVDHAEVFAR RRSEGILDEQ EMNSHLIGTP IARATTTPTA QQRPTNPGPG  60
GGGSNPRRTF GSPISGGIGR NRFLYRSPVF NRENTAASSS RRNRSRGRNS VLPIWYPRTP  120
LRDITAVVRA IERTRARLRE NEGQGSDNSP APSDERALEY SVSVAGDHQE PSISLVTPKP  180
TVGKVPKIIL GIANQNVVGA ETLTPQKKLL NSIDKVEKVV MEELQKLKKT PSAKKAEREK  240
RVRTLMSFR                                                          249

SEQ ID NO: 186         moltype = AA  length = 255
FEATURE                Location/Qualifiers
source                 1..255
                       mol_type = protein
                       organism = Vaccinium corymbosum
SEQUENCE: 186
MPESRDRLSR PDEVRATFAR QRQSIGGIAI LLDEEQPEVG TPFRWGATAM TGTRGPMGVA  60
STRGGRGVRR GSLGTPRSST RNRRGQENMA SGSFRRGRGR GRSTNSVLPS WYPRTPLRDV  120
TYVVRAIERR RAASLRESEG LQIGSPMPQD QNVLVPSEPT SGAQLEHNLS LVTPNPTVRM  180
KKPCQPSVGK VPKILLDITH QTAAGSDCLT PQKKLLNSID TVEKVVMEEL RKLKSTPSAK  240
KAERQNRVRT LMSMR                                                   255

SEQ ID NO: 187         moltype = AA  length = 278
FEATURE                Location/Qualifiers
source                 1..278
                       mol_type = protein
                       organism = synthetic construct
VARIANT                57
                       note = Xaa = Q or E
VARIANT                71
                       note = Xaa = L or I
VARIANT                153
                       note = Xaa = Q or E
VARIANT                1..278
                       note = Xaa = Any Amino Acid, or no amino acid (except at
                        positions 57, 71 and 153)
SEQUENCE: 187
MPAEXRDRLS RPPVDXAXXF ARRRRSXXGX XXXXXXXXXX LXXXPXRXXX XXXTXXXXGX  60
XXGXXGGGGG XXRXXFGTPR XGIXRGRNRX XXXXXXXGRE NXXPXGSSRR GRGRGXNSVL  120
PSWYPRTPLR DITAXVRAIE RRRXARLXEX EGXXXEXSXV PQDXXXLGPS ESXSGAQLEH  180
XXSLVTPXPX XRXKXXXPPS VGKVPKILLD ITNQXXXESX XEXLTPQKKL LNSIDTVEKV  240
VMEELQKLKR TPSAKKAERE KRVRTLMSMR YGGYALVT                          278

SEQ ID NO: 188         moltype = AA  length = 501
FEATURE                Location/Qualifiers
source                 1..501
                       mol_type = protein
                       organism = Citrullus lanatus
SEQUENCE: 188
MSAHNRRPSF SSSTSSSLAK RQASSASSSD NVGKVMAVPP HLAKKRAPLG NLTNFKNVSH  60
SAAKSSVPPA IMVPCATKAV KARKSSPART RSTNLTTTNT TTLLDVKTTN AIAPSNVTAF  120
SRTDATAVSS SMDVSPSKSD GVSVSLDETM STCDSFKSPD VEYLDNTDVP AVDSVERKTK  180
SSLCISGPAP ISSQAPVKGS ICNRDVITEM ETDGDIVDVD TDFMDPQQCA TIACDIYKHL  240
RASEAKKRPS TDFMEKIQKD INSNMRAILI DWLVEVAEEY RLVPDTLYLT VNYIDRYLSG  300
NSMDRQRLQL LGVACMMIAS KYEEICAPQV EEFCYITDNT YFKDEVLEME SSVLNYLKFE  360
MTAPTPKCFL RRFVRAAQGA TDEVSSMQLE CLANFLAELS LIEYSMLCYA PSLVAASAIF  420
LAKFILLPTK RPWNSTLQHY THYQPSDLVD CVKDLHRLCC NTHNSSLPAI REKYSQHKYK  480
HVAKKYCPPT IPPEFFQNQT Q                                            501

SEQ ID NO: 189         moltype = AA  length = 490
FEATURE                Location/Qualifiers
source                 1..490
                       mol_type = protein
                       organism = Vaccinium corymbosum
SEQUENCE: 189
MSNQNRRSSV TTSTSSSLAK RHAENLGKAQ PYVAKKRPAL ANVTNQRHGS QNGPRSLVSG  60
SSNMVPCMTK VANAKKISST CISNASFSRS TLPVAVNVKP SVAVSSKSSP FIKYDDFPRI  120
PAPDAPCGMD ISSPHSDGSS VSMDETMSSC DSLKSPEFEY VDNTEIAAVD SIERRTSSKL  180
YISEHMEAAE TVCKRDIIVG VGTDEEFVDV DDNFMDPQLC ATMACDIYKH LRATEAKKRP  240
STDFMERVQK DINASMRAIL VDWLVEVAEE YRLVPDTLYL TINYLDRYLS GNTMDRQRLQ  300
LLGVACMMIA AKYEEICAPQ VEEFCYITDN TYFKEEVLQM ESAVLNYMKF EMTAPTAKCF  360
LRRFVRAAQG VNEAPSMQLE CLANYLAELS LLEYNMLCYA PSVIAASAIF LAKYILIPSK  420
```

-continued

```
RPWNSTLRHY THYQPCDLSD CVKALHSLCC NSQSSSLPAI REKYSLHKYK FVAKKYCPPA  480
IPAEYFQNLS                                                         490

SEQ ID NO: 190          moltype = AA  length = 442
FEATURE                 Location/Qualifiers
source                  1..442
                        mol_type = protein
                        organism = Arabidopsis thaliana
SEQUENCE: 190
MSSSSRNLSQ ENPIPRPNLA KTRTSLRDVG NRRAPLGDIT NQKNGSRNPS PSSTLVNCSN  60
KIGQSKKAPK PALSRNWNLG ILDSGLPPKP NAKSNIIVPY EDTELLQSDD SLLCSSPALS  120
LDASPTQSDP SISTHDSLTN HVVDYMVEST TDDGNDDDDD EIVNIDSDLM DPQLCASFAC  180
DIYEHLRVSE VNKRPALDYM ERTQSSINAS MRSILIDWLV EVAEEYRLSP ETLYLAVNYV  240
DRYLTGNAIN KQNLQLLGVT CMMIAAKYEE VCVPQVEDFC YITDNTYLRN ELLEMESSVL  300
NYLKFELTTP TAKCFLRRFL RAAQGRKEVP SLLSECLACY LTELSLLDYA MLRYAPSLVA  360
ASAVFLAQYT LHPSRKPWNA TLEHYTSYRA KHMEACVKNL LQLCNEKLSS DVVAIRKKYS  420
QHKYKFAAKK LCPTSLPQEL FL                                           442

SEQ ID NO: 191          moltype = AA  length = 490
FEATURE                 Location/Qualifiers
source                  1..490
                        mol_type = protein
                        organism = Gossypium barbadense
SEQUENCE: 191
MSTQKGNRRS SFSSSTTSSL AKRHASSSEN VGKVMASLAK KRVPLTNITN QKQSSSSKSS  60
ALASSLVPSS NKIQKARKTQ SVTNVGLSGH VLPPTNERRS SVLPPKVVPS LPTGNEVVLP  120
PPPVQCSMEF SPSKSDGLSS VSLDETMSTC DSFKSPEVEY IDNHDVSAIG SIERKTFSNL  180
CISDHDVVAT GASICNRDAV AEKEADDMVI DVDDNFMDPQ LCATFACDIY KHLRASEVKK  240
RPSTDFMETI QKDINSSMRA ILIDWLVEVA EEYRLVPDTL YLTVSYIDRY LSGNTMNRQR  300
LQLLGVACMM IASKYEEICA PQVEEFCYIT DNTYFKDEVL EMESSVLNYL KFEMTAPTAK  360
CFLRRFVRAA QGINEVPSMQ LECMANYIAE LSLLEYSMLC YPPSLIAASA IFLAKFILLP  420
SKKPWNSTLQ HFTLYKPSDL FECVKELHRL CCNNNNSTLP AIREKYSQHK YKCVAKKYCP  480
PSIPSDFFHN                                                         490

SEQ ID NO: 192          moltype = AA  length = 498
FEATURE                 Location/Qualifiers
source                  1..498
                        mol_type = protein
                        organism = Prunus avium
SEQUENCE: 192
MSTQNRRSAF PSSLAKRQAL SSSSSSSSAS GNVGKVVAAE PHLAKKRAPL SNLTNRNSVS  60
NNGLRSSGGS SCTLVPCTNK IAKVKKGPPA CTGNKGVSAS SLPASFNVKP SAVVHPKVTP  120
APRSDEAVPS SFALPGPCSM DVSPSKSDGN SVSMDETMSS CDSFKSPEVE YIDNNDVPAI  180
DSINRKTFSN LYISDHAETT GIACKREVLV ELEAEDKIAD LDNSLMDPQL CATIACDIYK  240
HLRASEVKKR PSTDFMEKTQ KDINPSMRAI LIDWLVEVAE EYRLVPDTLY LTVNYIDRYL  300
SGNPMNRQRL QLLGVACMMI ASKYEEICAP QVEEFCYITD NTYFKEEVLQ MESDVLNYLK  360
FEMTAPTTKC FLRRFVRAAQ GANEGISMHL ECLANYLAEL SLLEYSMLCY APSLVAASAI  420
FLANFILLPS KRPWNATLQH YTLYQPSDLR DCVKDLHRLC SNSQSSSLPA IREKYSQHKY  480
KHVAKKYCPP TIPSEYQT                                                498

SEQ ID NO: 193          moltype = AA  length = 515
FEATURE                 Location/Qualifiers
source                  1..515
                        mol_type = protein
                        organism = synthetic construct
VARIANT                 54
                        note = Xaa = N or D
VARIANT                 180
                        note = Xaa = N or D
VARIANT                 232
                        note = Xaa = N or D
VARIANT                 318
                        note = Xaa = N or D
VARIANT                 362
                        note = Xaa = Q or E
VARIANT                 410
                        note = Xaa = L or I
VARIANT                 416
                        note = Xaa = L or I
VARIANT                 1..515
                        note = Xaa = Any Amino Acid, or no amino acid (except at
                         positions 54, 180, 232, 318, 362, 410 and 416)
SEQUENCE: 193
MXXXXGNRXX XXXXXXXXXX XXXXXXSXXX AXXXXGKXXA XXXXXAXXRX XLXXXXNXXX  60
XSXXXXXXXX XXXXXXXXXX XKXXXXXKXX XXXXSXXXXX XXXXXXXXXX XXXXXXXXXX  120
XXXXXXXXXX XXXXXXXXXX XXXXXXXSXX XSDGLXXVSX DXXXSXXDXX XXXXXXYXDX  180
XXXXAXXSXX XXXXXXLXIS XXXXXXXXXX VKGSICXRXX XXXXXXXXXX XXXDXXXXDP  240
QXCAXXACDI YXHLRXXEXX KRPXXDXMXX XQXXINXXMR XILXDWLVEV AEEYRLXPXT  300
LXLXXXYXDR YLXGNXXXXQ XLQLLGVXCM MIAXKYEEXC XPQVEXFCYI TDNTYXXXEX  360
```

-continued

| | |
|---|---|
| LXMESXVLNY XKFEXTXPTX KCFLRRFXRA AQGXXXXXXS XXXEXXAXXX XELSLXXYXM | 420 |
| LXYXPSXXAA SAXFLAXXXL XPXXXPWNXT LXHXTXYXXX XXXXCVXXLX XLCXXXXXSX | 480 |
| XXAXRXKYSX HKYKXXAKKX CPXXXPXXXX XNXXX | 515 |

POLYPLOID HYBRID POTATO BREEDING

CROSS-REFERENCE TO RELATED APPLICATIONS

This application claims the benefit of priority to U.S. Provisional Application No. 63/423,765, filed on Nov. 8, 2022, to U.S. Provisional Application No. 63/423,768, filed on Nov. 8, 2022, to U.S. Provisional Application No. 63/497,670, filed Apr. 21, 2023, and to U.S. Provisional Application No. 63/461,174, filed Apr. 21, 2023, and to U.S. Provisional Application No. 63/497,662, filed Apr. 21, 2023, each of which is incorporated by reference herein in its entirety.

REFERENCE TO AN ELECTRONIC SEQUENCE LISTING

The content of the electronic sequence listing (197072000400subseqlist.xml; Size: 209,202 bytes; and Date of Creation: May 23, 2024) is herein incorporated by reference in its entirety.

FIELD

The inventions relate generally to the field of agricultural science, and specifically to crop improvement and systems of breeding novel hybrid polyploid potato cultivars. The inventions also relate to population improvement methods to desirably alter the genetic composition of diploid potato breeding populations for accelerated production of uniform hybrid polyploid potato seeds, potato plants, and potato plant parts suitable for cultivation. The inventions further relate to potato plant materials obtained by this process.

BACKGROUND

The growing human population, a desire to reduce the environmental impact of agriculture, and consumer food preferences ensure a constant need for improved varieties of crops. Crop breeding has been used as a way to improve crop characteristics, yields, and robustness to environmental pressure for millennia. Despite growth in crop yields in the 20th century, crop yields have begun to plateau in recent decades, signaling a need for improved breeding methods (e.g., Rizzo (2021). Climate and agronomy, not genetics, underpin recent maize yield gains in favorable environments. Proceedings of the National Academy of Sciences 119 (4): e2113629119). In some staple and specialty crops, the most widely-grown cultivars are polyploid. For example, the most preferred and widely-grown varieties of potato are autotetraploids. This creates immense complexity in breeding such varieties due to the increased inefficiency of artificial selection in polyploid plant species, and, in some cases, the requirement for vegetative propagation of the varieties, which is less desirable compared to seed-based propagation. For such polyploid crops, there is an even greater need for innovative breeding techniques for the development of improved varieties.

Hybrid crops are widely grown and preferred because they tend to exhibit more robust growth, higher yields, and resilience to environmental stressors compared to their inbred or open-pollinated counterparts. This phenomenon is known as heterosis, or "hybrid vigor", and reflects the tendency of a cross-bred plant to show superior quality due to extensive heterozygosity in the plant's genome. Hybrid seed is typically produced by a single cross of fully inbred parent plants with different sets of alleles, resulting in a biallelic hybrid plant with two sets of alleles (also known as haplotypes) contributing to heterosis. In a further extension of the mechanism of heterosis, polyploid crops can exhibit progressive heterosis; for example, the additional hybrid vigor in a multiallelic double-cross tetraploid hybrid plant that is not found in its biallelic single-cross tetraploid parents or in its more inbred grandparents. Progressive heterosis has been documented in a number of tetraploid species including alfalfa, potato, and tetraploid maize (Gallais. (1984). An analysis of heterosis vs. inbreeding effects with an autotetraploid cross-fertilized plant: *Medicago sativa* L. *Genetics* 106, 123-137; Groose et al. 1989. Progressive heterosis in autotetraploid alfalfa: studies using two types of inbreds. Crop Sci. 29, 1173-1177; Mok and Peloquin. 1975. Breeding value of 2n pollen (diplandroids) in tetraploid x diploid crosses in potatoes. *Theor. Appl. Genet.* 46, 307-314; Washburn et al. 2013. Polyploids as a "model system" for the study of heterosis. *Plant Reprod* 27:1-5; Washburn et al. 2019. Progressive heterosis in genetically defined tetraploid maize (*J Genet Genomics.* 46 (8): 389-396) has resulted in increased above ground biomass and several other agronomically desirable traits. However, due to the need to cross heterozygous single-cross parents to generate double-cross polyploid hybrids, it is not feasible to generate a uniform population of true-breeding seed while taking advantage of progressive heterosis with current breeding techniques.

Prior research has established methods that allow plant geneticists to arrest meiosis in plants and replace it with a mitosis-like division in germline cells, resulting in formation of clonal gametes that contain the complete nonrecombinant genome of the parent. One such method, known as MiMe (Mitosis instead of Meiosis; d'Erfurth et al. 2009. Turning meiosis into mitosis. *PLoS Biol* 7, no. 6: e1000124.) is achieved through a triple knockout of three genes encoding gene products involved in meiosis, specifically, (1) a component of sister chromatid cohesion during the first division of meiosis, (2) a component of DNA double strand breakage during meiotic recombination, and (3) a component of progression through the second division of meiosis. This technology for MiMe is well-developed, but commercial development of MiMe has only begun in a select few applications (e.g., see US20190098858A1, US20120042408A1, and U.S. Pat. No. 10,883,112B2). These current applications of MiMe that are in development have only focused on generation of apomictic seed from diploid plants. However, the application of MiMe to develop novel and enhanced breeding techniques for plants at the polyploid level has not yet been realized.

BRIEF SUMMARY

Provided herein are novel methods of breeding polyploid potato plants and genetically uniform potato populations that apply MiMe in innovative ways to accelerate breeding and produce potato plants or potato populations that are either very difficult to produce by traditional breeding or simply cannot be produced by traditional breeding.

In particular, certain methods leverage the production of clonal gametes to unlock the potential of progressive heterosis in breeding of polyploid potatoes. First, a diverse set of plant lines of a given ploidy is obtained, improved using traditional breeding methods, and organized into heterotic groups based on the predicted heterotic performance of their haplotypes when combined in potato plants of higher ploidy. Then, candidate lines together comprising three or more haplotypes are selected from the set of plant lines, and one or more candidate lines are induced to form clonal gametes by a method such as MiMe. The clonal gametes are then crossed (for example, with other gametes such as clonal gametes, haploid gametes derived from a fully inbred individual, or other types of unreduced gametes that would result in three or more haplotypes) to produce a homogenous population of multiallelic polyploid seed comprising the three or more haplotypes of the candidate lines. The polyploid seed is then grown, the potato plants are evaluated for the characteristics desired in the breeding program, and the heterotic performance of the haplotypes comprised by the potato plants is used to guide the breeding and selection of lines for further rounds of breeding. Exemplary embodiments of these methods are depicted in FIGS. 5-13C. For many species this method allows, for the first time, the production of genetically uniform true potato seed comprising three or more haplotypes, thus allowing for practical application of progressive heterosis in polyploids.

Certain related methods provided herein leverage the production of clonal gametes to unlock the potential of progressive heterosis in breeding of seedless polyploid crops. The method may be applied to the breeding and production of genetically-uniform populations of polyploid potato seeds yielding seedless plants, which provides advantages including, but not limited to, a means of manipulating source-sink carbon flux in root vegetable and tuber crops. In such methods, candidate potato lines, which may together comprise two, three, four, or more haplotypes, are selected, and two or more candidate potato lines are induced to form clonal gametes by a method such as MiMe, to produce two parent MiMe potato plants each having MiMe alleles at two or more MiMe loci on each set of chromosomes that confer clonal gamete formation. The parent MiMe potato plants are selected such that a) the wild-type (non-MiMe) alleles of the first parent MiMe potato plants partially complement the MiMe alleles conferring clonal gamete formation of the second parent MiMe potato plant, and vice versa; and b) the parent MiMe potato plants have at least one MiMe locus in common with MiMe alleles at that locus on all sets of chromosomes. The clonal gametes are then crossed to produce a homogenous population of multiallelic polyploid seed comprising the two, three, or more haplotypes candidate lines, which, due to the genotypes of the parent MiMe potato plants, have only MiMe alleles at one or more MiMe loci on all sets of chromosomes, and at least one non-MiMe allele at all other MiMe loci. Thus, the population of polyploid seed has neither a normal meiosis phenotype nor a clonal gamete formation phenotype, and therefore produces inviable gametes and seedless plants. The polyploid seed is then grown, the potato plants are evaluated for the characteristics desired in the breeding program, and the heterotic performance of the haplotypes comprised by the potato plants is used to guide the breeding and selection of lines for further rounds of breeding. Exemplary embodiments of these methods are depicted in FIGS. 5-13C. For many species this method allows, for the first time, the production of genetically uniform seed of a crop comprising three or more haplotypes which, upon germination, produce potato plants bearing inviable gametes, thus allowing for practical application of progressive heterosis in polyploids.

In one aspect, the present disclosure provides a population of polyploid potato seed comprising three or more haplotypes of the same or related species of potato plant, wherein at least 50% of the population of polyploid potato seed are genetically uniform, and wherein the population was obtained from a single potato plant or a set of potato plants such as, for example, a set of F1 hybrids. In some embodiments, the present disclosure provides a population of polyploid potato seed comprising a subpopulation of genetically uniform polyploid potato seed in an amount of at least 50% of the total number of seeds, the genetically uniform polyploid potato seed comprising three or more haplotypes of the same or related species of potato plant, wherein the population was obtained from a single potato plant or a set of potato plants such as, for example, of F1 hybrids. The polyploid potato seed (e.g., the subpopulation of genetically uniform seed) may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid potato seed are genetically uniform. In certain embodiments, the population of polyploid potato seed has an average pairwise genetic uniformity of at least 80%, at least 85%, at least 90%, at least 95%, at least 96%, at least 97%, at least 98%, at least 99%, or 100% as measured by the Jaccard similarity coefficient. In certain embodiments, the population of polyploid potato seed comprises the subpopulation of genetically uniform polyploid potato seed in an amount of at least 70%, at least 90%, at least 95%, at least 96%, at least 97%, at least 98%, or at least 99% of the total number of seeds. In certain embodiments, each pair of seeds in the subpopulation of genetically uniform polyploid potato seed has a pairwise identity of at least 95%, at least 96%, at least 97%, at least 98%, at least 99%, or 100% as measured by the Jaccard similarity coefficient. In certain embodiments, the polyploid potato seed (e.g., the subpopulation of genetically uniform seed) comprises four or more haplotypes of the same or related species of potato plant. In some embodiments, germination of a seed of the population of polyploid seed or the subpopulation of genetically uniform polyploid seed results in a sterile plant that produces inviable gametes.

In some embodiments, the polyploid potato seed (e.g., the subpopulation of genetically uniform potato seed) comprises one or more genetic modifications resulting in decreased expression of one or more, two or more, or three or more MiMe loci. The seed may comprise one or more genetic modifications resulting in decreased expression of MiMe loci including, but not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In some embodiments, the polyploid potato seed (e.g., the subpopulation of genetically uniform seed) comprises one or more genetic modifications resulting in altered activity of one or more, two or more, or three or more MiMe components. In some embodiments, the altered activity includes, for example, a dominant negative, constitutively active or null mutant of the one or more MiMe components. In one embodiment, the polyploid potato seed (e.g., the subpopulation of genetically uniform seed) comprises one or more genetic modifications resulting in decreased expression of REC8, SWITCH1/DYAD, or a combination thereof. In another embodiment, the polyploid seed (e.g., the subpopulation of genetically uniform seed) comprises one or more genetic modifications resulting in decreased expression of OSD1, CYCA1, TDM1, PC1, PC2, FC, or any combination thereof. In another embodiment, the polyploid potato seed (e.g., the subpopulation of genetically uniform seed) comprises one or more genetic modifications resulting in decreased expression of PAIR1, SPO11-1, SPO11-2, PRD1, PRD2, DFO, MTOPVIB, DSY1, SY1, SY2, SY3, SY4, or any combination thereof. In yet another embodiment, the polyploid potato seed (e.g., the subpopulation of genetically uniform seed) comprises one or more genetic modifications resulting in decreased expression of PS1, JASON, or a combination thereof. The polyploid potato seed may comprise genetic modifications in any combination of MiMe loci described herein. The one or more genetic modifications may include, but are not limited to, modification of an enhancer in the MiMe loci, modification of a promoter of the MiMe loci, modification of a coding region in the MiMe loci, modification of methylation status of the MiMe loci, expression of a repressor protein that targets the DNA or an mRNA of the MiMe loci, and expression of an RNA interference construct that targets an mRNA from the MiMe loci.

In certain embodiments, the population of polyploid potato seed or the subpopulation of genetically uniform polyploid potato seed has a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the population of polyploid or the subpopulation of genetically uniform polyploid potato seed has a partial MiMe genotype comprising (a) one or more MiMe alleles conferring decreased expression of one or more MiMe loci of each of the first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof.

In certain embodiments, the population of polyploid potato seed or the subpopulation of genetically uniform polyploid potato seed has a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments, the population of polyploid potato seed or the subpopulation of genetically uniform polyploid potato seed has a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis comprise PS1, JASON, or a combination thereof.

In certain embodiments, the population of polyploid potato seed or the subpopulation of genetically uniform polyploid potato seed has (i) at least a first and second haplotype, each comprising one or more MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the MiMe locus of the component of progression through the first division of meiosis of the third haplotype is PS1 or JASON. In still additional variations, the one or more MiMe loci of the component of progression through the second division of meiosis of the first and second haplotype comprise OSD1, CYCA1, TDM1, PC1, PC2, FC, or any combination thereof. In yet additional variations, the locus of the component of progression through the second division of meiosis of the third haplotype is OSD1, CYCA1, TDM1, PC1, PC2, or FC.

In certain embodiments, the population of polyploid potato seed or the subpopulation of genetically uniform polyploid potato seed has (i) at least a first and second haplotype, each comprising one or more MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis of the first and second haplotype comprise PS1, JASON, or a combination thereof. In still additional variations, the MiMe locus of the component of progression through the first division of meiosis of the third haplotype is PS1 or JASON. In yet additional variations, the MiMe locus of the component of progression through the second division of meiosis of the third haplotype is OSD1, CYCA1, TDM1, PC1, PC2 or FC.

In some embodiments, the population of polyploid potato seed or the subpopulation of genetically uniform polyploid potato seed has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid potato seed or the subpopulation of genetically uniform polyploid potato seed has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the population of polyploid potato seed or the subpopulation of genetically uniform polyploid potato seed has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid potato seed or the subpopulation of genetically uniform polyploid potato seed has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid potato seed or the subpopulation of genetically uniform polyploid potato seed has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid potato seed or the subpopulation of genetically uniform polyploid potato seed has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid potato seed or the subpopulation of genetically uniform polyploid potato seed has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid potato seed or the subpopulation of genetically uniform polyploid potato seed has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the population of polyploid potato seed or the subpopulation of genetically uniform polyploid potato seed has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid potato seed or the subpopulation of genetically uniform polyploid potato seed has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid potato seed or the subpopulation of genetically uniform polyploid potato seed has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid potato seed or the subpopulation of genetically uniform polyploid potato seed has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the population of polyploid potato seed or the subpopulation of genetically uniform polyploid potato seed has a complete MiMe genotype comprising (i) an os allele, wherein the subpopulation of genetically uniform polyploid potato seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid potato seed or the subpopulation of genetically uniform polyploid potato seed has a partial MiMe genotype comprising (i) an os allele, wherein the subpopulation of genetically uniform polyploid potato seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid potato seed or the subpopulation of genetically uniform polyploid potato seed has a complete MiMe genotype comprising (i) a ps allele, wherein the subpopulation of genetically uniform polyploid potato seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid potato seed or the subpopulation of genetically uniform polyploid potato seed has a partial MiMe genotype comprising (i) a ps allele, wherein the subpopulation of genetically uniform polyploid potato seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In another aspect, the present disclosure provides a population of polyploid potato seed having a partially-complemented MiMe genotype comprising (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component, wherein at least 50% of the population of polyploid potato seed are genetically uniform, and wherein the population was obtained from a single potato plant or a set of potato plants such as, for example, a set of F1 hybrids. In some embodiments, the present disclosure provides a population of polyploid potato seed comprising a subpopulation of genetically uniform polyploid potato seed in an amount of at least 50% of the total number of seeds, the genetically uniform polyploid potato seed comprising a partially-complemented MiMe genotype comprising (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component, and wherein the population was obtained from a single potato plant or a set of potato plants such as, for example, a set of F1 hybrids. The polyploid potato seed (e.g., the subpopulation of genetically uniform seed) may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid potato seed are genetically uniform. In certain embodiments, the population of polyploid potato seed has an average pairwise genetic uniformity of at least 80%, at least 85%, at least 90%, at least 95%, at least 96%, at least 97%, at least 98%, at least 99%, or 100% as measured by the Jaccard similarity coefficient. In certain embodiments, the population of polyploid potato seed comprises the subpopulation of genetically uniform polyploid potato seed in an amount of at least 70%, at least 90%, at least 95%, at least 96%, at least 97%, at least 98%, or at least 99% of the total number of seeds. In certain embodiments, each pair of seeds in the subpopulation of genetically uniform polyploid potato seed has a pairwise identity of at least 95%, at least 96%, at least 97%, at least 98%, at least 99%, or 100% as measured by the Jaccard similarity coefficient. In some embodiments, the partially-complemented genotype comprises only MiMe alleles at one or more MiMe loci of a third MiMe component. In other embodiments, the partially-complemented genotype comprises one or more MiMe alleles and one or more non-MiMe alleles at a first MiMe locus of the third MiMe component, and one or more MiMe alleles and one or more non-MiMe alleles at a second MiMe locus of the third MiMe component. In certain embodiments, the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

In another aspect, the present disclosure provides a population of polyploid potato seed having a partially-complemented MiMe genotype comprising (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein at least 50% of the population of polyploid potato seed are genetically uniform, and wherein the population was obtained from a single parent potato plant or a set of potato plants, such as, for example, a set of F1 hybrids. In some embodiments, the present disclosure provides a population of polyploid potato seed comprising a subpopulation of genetically uniform polyploid potato seed in an amount of at least 50% of the total number of seeds, the genetically uniform polyploid potato seed comprising a partially-complemented MiMe genotype comprising (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, and wherein the population was obtained from a single parent potato plant or a set of potato plants, such as, for example, a set of F1 hybrids. The polyploid potato seed (e.g., the subpopulation of genetically uniform seed) may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid potato seed are genetically uniform. In certain embodiments, the population of polyploid potato seed has an average pairwise genetic uniformity of at least 80%, at least 85%, at least 90%, at least 95%, at least 96%, at least 97%, at least 98%, at least 99%, or 100% as measured by the Jaccard similarity coefficient. In certain embodiments, the population of polyploid potato seed comprises the subpopulation of genetically uniform polyploid potato seed in an amount of at least 70%, at least 90%, at least 95%, at least 96%, at least 97%, at least 98%, or at least 99% of the total number of seeds. In certain embodiments, each pair of seeds in the subpopulation of genetically uniform polyploid potato seed has a pairwise identity of at least 95%, at least 96%, at least 97%, at least 98%, at least 99%, or 100% as measured by the Jaccard similarity coefficient. In some embodiments, the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

In another aspect, the present disclosure provides a population of polyploid potato seed having a partially-complemented MiMe genotype comprising (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein at least 50% of the population of polyploid potato seed are genetically uniform, and wherein the population was obtained from a single parent potato plant or a set of potato plants, such as, for example, a set of F1 hybrids. In some embodiments, the present disclosure provides a population of polyploid potato seed comprising a subpopulation of genetically uniform polyploid potato seed in an amount of at least 50% of the total number of seeds, the genetically uniform polyploid potato seed comprising a partially-complemented MiMe genotype comprising (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, and wherein the population was obtained from a single parent potato plant or a set of potato plants, such as, for example, a set of F1 hybrids. The polyploid potato seed (e.g., the subpopulation of genetically uniform seed) may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid potato seed are genetically uniform. In certain embodiments, the population of polyploid potato seed has an average pairwise genetic uniformity of at least 80%, at least 85%, at least 90%, at least 95%, at least 96%, at least 97%, at least 98%, at least 99%, or 100% as measured by the Jaccard similarity coefficient. In certain embodiments, the population of polyploid potato seed comprises the subpopulation of genetically uniform polyploid potato seed in an amount of at least 70%, at least 90%, at least 95%, at least 96%, at least 97%, at least 98%, or at least 99% of the total number of seeds. In certain embodiments, each pair of seeds in the subpopulation of genetically uniform polyploid potato seed has a pairwise identity of at least 95%, at least 96%, at least 97%, at least 98%, at least 99%, or 100% as measured by the Jaccard similarity coefficient. In some embodiments, the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

In some embodiments of the foregoing aspects, the first MiMe component is a component of sister chromatid cohesion during the first division of meiosis. In some variations, the one or more MiMe loci of the first MiMe component comprise REC8, SWITCH1/DYAD, or a combination thereof. In one variation, the MiMe locus of the first MiMe component is REC8. In certain embodiments, the second MiMe component is a component of DNA double strand breakage during meiotic recombination. In some variations, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation, the first MiMe locus of the second MiMe component is PAIR1 and the second MiMe locus of the second MiMe component is SPO11-1. In further embodiments, the third MiMe component is a component of progression through the second division of meiosis. In some embodiments, the partially-complemented MiMe genotype comprises only MiMe alleles at one or more MiMe loci of the third MiMe component. In some variations, the one or more MiMe loci of the third MiMe component comprise OSD1, CYCA1, TDM1, PC1, PC2, FC, or any combination thereof. In one variation, the MiMe locus of the third MiMe component is OSD1. In other embodiments, the partially-complemented MiMe genotype comprises one or more MiMe alleles and one or more non-MiMe alleles at a first MiMe locus of the third MiMe component, and one or more MiMe alleles and one or more non-MiMe alleles at a second MiMe locus of the third MiMe component. In some variations, the first MiMe locus and the second MiMe locus of the third MiMe component comprise OSD1, CYCA1, TDM1, PC1, PC2, FC, or any combination thereof. In one embodiment, the partially-complemented MiMe genotype comprises only MiMe alleles at one or more MiMe loci of the third MiMe component, wherein the one or more MiMe loci having only MiMe alleles of the first MiMe component comprise REC8, the first MiMe locus of the second MiMe component is PAIR1, the second MiMe locus of the second MiMe component is SPO11-1, and the one or more MiMe loci having only MiMe alleles of the third MiMe component comprise OSD1. In some embodiments, the polyploid potato seed (e.g., the subpopulation of genetically uniform polyploid potato seed) comprises one or more genetic modifications resulting in altered activity of one or more, two or more, or three or more MiMe components. In some embodiments, the altered activity includes, for example, a dominant negative, constitutively active or null mutant of the one or more MiMe components In some embodiments of the foregoing aspects, the population of polyploid potato seed or the subpopulation of genetically uniform polyploid potato seed has a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more only MiMe alleles at one or more SPO11-1 loci, wherein each of the MiMe alleles at the SPO11-1 locus comprise one or more genetic modifications resulting in decreased expression of SPO11-1.

In some embodiments of the foregoing aspects, the population of polyploid potato seed or the subpopulation of genetically uniform polyploid potato seed has a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

In some embodiments of the foregoing aspects, the population of polyploid potato seed or the subpopulation of genetically uniform polyploid potato seed has a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

In some embodiments of the foregoing aspects, the population of polyploid potato seed or the subpopulation of genetically uniform polyploid potato seed has a partially complemented MiMe genotype comprising (i) a ps allele, wherein the subpopulation of genetically uniform polyploid potato seed is heterozygous for the ps allele, (ii) an os allele, wherein the subpopulation of genetically uniform polyploid potato seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1.

In some embodiments of the foregoing aspects, the population of polyploid potato seed or the subpopulation of genetically uniform polyploid potato seed has a partially complemented MiMe genotype comprising (i) an os allele, wherein the subpopulation of genetically uniform polyploid potato seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

In another aspect, the present disclosure provides a method of producing a population of polyploid potato seed described herein, the method comprising: (a) providing clonal gametes from a pair of parent MiMe potato plants that together comprise three or more haplotypes; and (b) crossing the clonal gametes to produce the population of polyploid potato seed. In some embodiments, at least 50% of the population of polyploid potato seed are genetically uniform and comprise three or more haplotypes. In some embodiments, at least 70%, at least 90%, at least 95%, at least 96%, at least 97%, at least 98%, or at least 99% of the population of polyploid potato seed produced by said method are genetically uniform. In some embodiments, the population of polyploid potato seed comprises a subpopulation of genetically uniform seed in an amount of at least 50% of the total number of seeds, the subpopulation of genetically uniform seed comprising three or more haplotypes. In certain embodiments, the population of polyploid potato seed comprises a subpopulation of genetically uniform seed in an amount of at least 70%, at least 90%, at least 95%, at least 96%, at least 97%, at least 98%, or at least 99% of the total number of seeds. In certain embodiments, the polyploid potato seed (e.g., the subpopulation of genetically uniform polyploid potato seed) produced by said method comprises four or more haplotypes of the same or related species of potato. The population of polyploid potato seed or the subpopulation of genetically uniform polyploid potato seed may be, for example, triploid, tetraploid, pentaploid, hexaploid, heptaploid, or octoploid. In some embodiments, germination of a seed of the population of polyploid seed produced by said method (e.g., germination of a seed of the subpopulation of genetically uniform polyploid seed) results in a sterile plant that produces inviable gametes.

In some embodiments, the method of producing the population of polyploid potato seed comprises producing a population of polyploid potato seed comprising one or more genetic modifications resulting in decreased expression of one or more, two or more, or three or more MiMe loci. The population of polyploid potato seed or the subpopulation of genetically uniform polyploid potato seed may comprise one or more genetic modifications resulting in decreased expression of MiMe loci including, but not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In one embodiment, the polyploid potato seed produced by said method, or the subpopulation of genetically uniform polyploid potato seed, comprises one or more genetic modifications resulting in decreased expression of REC8, SWITCH1/DYAD, or a combination thereof. In another embodiment, the polyploid potato seed produced by said method, or the subpopulation of genetically uniform polyploid potato seed, comprises one or more genetic modifications resulting in decreased expression of OSD1, CYCA1, TDM1, PC1, PC2, FC, or a combination thereof. In another embodiment, the polyploid potato seed produced by said method, or the subpopulation of genetically uniform polyploid potato seed, comprises one or more genetic modifications resulting in decreased expression of PAIR1, SPO11-1, SPO11-2, PRD1, PRD2, DFO, MTOPVIB, DSY1, SY1, SY2, SY3, SY4, or a combination thereof. In yet another embodiment, the polyploid potato seed produced by said method comprises one or more genetic modifications resulting in decreased expression of PS1, JASON, or a combination thereof. The polyploid potato seed produced by said method, or the subpopulation of genetically uniform polyploid potato seed, may comprise genetic modifications in any combination of MiMe loci described herein. The genetic modifications may include, but are not limited to, modification of an enhancer in the MiMe loci, modification of a promoter of the MiMe loci, modification of a coding region in the MiMe loci, modification of methylation status of the MiMe loci, expression of a repressor protein that targets the DNA or an mRNA of the MiMe loci, and expression of an RNA interference construct that targets an mRNA from the MiMe loci.

In certain embodiments, the population of polyploid potato seed produced by said method, or the subpopulation of genetically uniform polyploid potato seed, comprises a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the population of polyploid potato seed produced by said method, or the subpopulation of genetically uniform polyploid potato seed, comprises a partial MiMe genotype comprising (a) one or more MiMe alleles conferring decreased expression of one or more MiMe loci of each of the first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof.

In certain embodiments, the population of polyploid potato seed produced by said method, or the subpopulation of genetically uniform polyploid potato seed, has a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments, the population of polyploid potato seed produced by said method, or the subpopulation of genetically uniform polyploid potato seed, has a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis comprise PS1, JASON, or a combination thereof.

In another aspect, the present disclosure provides a method of producing a population of polyploid potato seed described herein having a partially-complemented MiMe genotype, the method comprising (a) providing clonal gametes from a first parent MiMe potato plant, wherein the first parent MiMe potato plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; (b) providing clonal gametes from a second parent MiMe potato plant, wherein the second parent MiMe potato plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component; and (c) crossing the clonal gametes from the first and second parent MiMe potato plants to produce the population of polyploid potato seed having a partially-complemented MiMe genotype. In some embodiments, at least 50% of the population of polyploid potato seed are genetically uniform and comprise two, three, or more haplotypes. In some embodiments, the population of polyploid potato seed comprises a subpopulation of genetically uniform seed in an amount of at least 50% of the total number of seeds, the subpopulation of genetically uniform seed comprising the partially-complemented MiMe genotype. In certain embodiments, at least one of the MiMe loci having only MiMe alleles of the first MiMe component of the first parent MiMe potato plant is the same as at least one of the MiMe loci having only MiMe alleles of the first MiMe component of the second parent MiMe potato plant. In some embodiments, at least one of the MiMe loci having only MiMe alleles of the third MiMe component of the first parent MiMe potato plant is the same as at least one of the MiMe loci having only MiMe alleles of the third MiMe component of the second parent MiMe potato plant. In other embodiments, the one or more MiMe loci having only MiMe alleles of the third MiMe component of the first parent MiMe potato plant are distinct from the one or more MiMe loci having only MiMe alleles of the third MiMe component of the second parent MiMe potato plant. In some embodiments, the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

In another aspect, the present disclosure provides a method of producing a population of polyploid potato seed having a partially-complemented MiMe genotype described herein, the method comprising (a) providing clonal gametes from a first parent MiMe potato plant, wherein the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; (b) providing clonal gametes from a second parent MiMe potato plant, wherein the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component; and (c) crossing the clonal gametes from the first and second parent MiMe potato plants to produce the population of polyploid potato seed having a partially-complemented MiMe genotype. In some embodiments, at least 50% of the population of polyploid potato seed are genetically uniform and comprise two, three, or more haplotypes. In some embodiments, the population of polyploid potato seed comprises a subpopulation of genetically uniform seed in an amount of at least 50% of the total number of seeds, the subpopulation of genetically uniform seed comprising the partially-complemented MiMe genotype. In some embodiments at least one of the MiMe loci having only MiMe alleles of the first MiMe component of the first parent MiMe potato plant is the same as at least one of the MiMe loci having only MiMe alleles of the first MiMe component of the second parent MiMe potato plant. In certain embodiments, the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

In yet another aspect, the present disclosure provides a method of producing a population of polyploid potato seed having a partially-complemented MiMe genotype described herein, the method comprising (a) providing clonal gametes from a first parent MiMe potato plant, wherein the first parent MiMe potato plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination; (b) providing clonal gametes from a second parent MiMe potato plant, wherein the second parent MiMe potato plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and (c) crossing the clonal gametes from the first and second parent MiMe potato plants to produce the population of polyploid potato seed having a partially-complemented MiMe genotype. In some embodiments, at least 50% of the population of polyploid potato seed are genetically uniform and comprise two, three, or more haplotypes. In some embodiments, the population of polyploid potato seed comprises a subpopulation of genetically uniform seed in an amount of at least 50% of the total number of seeds, the subpopulation of genetically uniform seed comprising the partially-complemented MiMe genotype. In some embodiments, at least one of the MiMe loci having only MiMe alleles of the first MiMe component of the first parent MiMe potato plant is the same as at least one of the MiMe loci having only MiMe alleles of the first MiMe component of the second parent MiMe potato plant. In certain embodiments, the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

In some embodiments of the foregoing methods, the first MiMe component is a component of sister chromatid cohesion during the first division of meiosis. In some variations of said method, the MiMe loci of the first MiMe component of both the first and second parent MiMe potato plants comprise REC8. In certain embodiments of said method, the second MiMe component is a component of DNA double strand breakage during meiotic recombination. In some variations of said method, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation of said method, the first MiMe locus of the second MiMe component is PAIR1 and the second MiMe locus of the second MiMe component is SPO11-1. In further embodiments of said method, the third MiMe component is a component of progression through the second division of meiosis. In some embodiments of said method, at least one of the MiMe loci having only MiMe alleles of the third MiMe component of the first parent MiMe potato plant is the same as at least one of the MiMe loci having only MiMe alleles of the third MiMe component of the second parent MiMe potato plant. In some variations, the MiMe loci having only MiMe alleles of the component of progression through the second division of meiosis comprise OSD1, CYCA1, TDM1, PC1, PC2, FC, or any combination thereof. In one variation, the MiMe locus having only MiMe alleles of the third MiMe component is OSD1. In other embodiments of said method, the one or more MiMe loci having only MiMe alleles of the third MiMe component of the first parent MiMe potato plant are distinct from the one or more MiMe loci having only MiMe alleles of the third MiMe component of the second parent MiMe potato plant. In some variations, the MiMe loci having only MiMe alleles of the third MiMe component comprise OSD1, CYCA1, TDM1, PC1, PC2, FC, or any combination thereof. In one variation of said method, the MiMe loci having only MiMe alleles of the first MiMe component comprise REC8, the first MiMe locus of the second MiMe component is PAIR1, the second MiMe locus of the second MiMe component is SPO11-1, and the MiMe loci having only MiMe alleles of the third MiMe component comprise OSD1.

In another aspect, the present disclosure provides a method of breeding a polyploid hybrid potato line, comprising: (a) obtaining a set of potato lines; (b) breeding the potato lines using traditional plant breeding methods to produce a set of candidate potato lines; (c) selecting two or more candidate potato lines together comprising three or more haplotypes; (d) generating two parent MiMe potato plants from the two or more candidate potato lines that together comprise the three or more haplotypes; (e) providing clonal gametes from each of the parent MiMe potato plants; (f) crossing the clonal gametes to produce a hybrid polyploid potato seed comprising the three or more haplotypes; (g) growing the hybrid polyploid potato seed to produce a hybrid polyploid potato plant comprising three or more haplotypes; and (h) evaluating one or more characteristics of the hybrid polyploid potato plant. The candidate potato lines and the parent MiMe potato plants may be any ploidy, including, but not limited to, haploid, monoploid, diploid, triploid, or tetraploid. In additional embodiments of said breeding method, the hybrid polyploid potato plant is tetraploid, pentaploid, hexaploid, heptaploid, or octoploid.

In some embodiments of said breeding method, step (d) comprises introducing a complete MiMe genotype directly into two candidate potato lines to produce the two parent MiMe potato plants. In other embodiments of said breeding method, step (d) comprises introducing a partial MiMe genotype into two candidate potato lines to produce two grandparent non-MiMe potato plants each having a partial MiMe genotype, crossing said grandparent non-MiMe potato plants each having a partial MiMe genotype to produce the first parent MiMe potato plant, and introducing a complete MiMe genotype directly into a third candidate line to produce the second parent MiMe potato plant. In yet other embodiments of said breeding method, step (d) comprises introducing a partial MiMe genotype into four candidate potato lines to produce four grandparent non-MiMe potato plants each having a partial MiMe genotype, and crossing pairs of said grandparent non-MiMe potato plants each having a partial MiMe genotype to produce the two parent MiMe potato plants. In certain embodiments, step (d) further comprises propagating parent MiMe potato plants to scale production of homogenous seed.

In some embodiments of said breeding method, the parent MiMe potato plants of step (d) each have a complete MiMe genotype comprising MiMe alleles that are naturally-occurring, introduced via genetic modification, or a combination thereof. In certain embodiments, the genetic modifications result in decreased expression of one or more, two or more, or three or more MiMe loci including, but not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In one embodiment, the genetic modifications result in decreased expression of REC8, SWITCH1/DYAD, or a combination thereof. In another embodiment, the genetic modifications result in decreased expression of OSD1, CYCA1, TDM1, PC1, PC2, FC, or any combination thereof. In another embodiment, the genetic modifications result in decreased expression of PAIR1, SPO11-1, SPO11-2, PRD1, PRD2, DFO, MTOPVIB, DSY1, SY1, SY2, SY3, SY4, or any combination thereof. In yet another embodiment, the genetic modifications result in decreased expression of PS1, JASON, or a combination thereof. In some embodiments, the one or more genetic modifications are introduced by gene editing, transgenesis, or a combination thereof. The genetic modifications may be achieved by any methods described herein, including, but not limited to, gene disruption, gene knockout, gene knockdown, gene silencing, RNA interference, induction of methylation, or any combination thereof.

In certain embodiments, the population of polyploid potato seed produced by said breeding method comprises a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the population of polyploid potato seed produced by said breeding method comprises a partial MiMe genotype comprising (a) one or more MiMe alleles conferring decreased expression of one or more MiMe loci of each of the first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof.

In certain embodiments, the population of polyploid potato seed produced by said breeding method has a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments, the population of polyploid potato seed produced by said breeding method has a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis comprise PS1, JASON, or a combination thereof.

In certain embodiments of said breeding method, the method of breeding a population of polyploid potato seed further comprises (i) repeating steps (b)-(h) or steps (c)-(h) using the one or more characteristics of the hybrid polyploid potato plant evaluated in step (h) to guide the breeding of lines of step (b), the selecting of candidate potato lines of step (c), or both. In some variations, the one or more characteristics includes the heterotic performance of the three or more haplotypes of the polyploid hybrid potato evaluated in step (h).

In some embodiments of said breeding method, the set of potato lines in step (a) are obtained from one or more of natural diversity, existing breeding programs, or dihaploid induction of polyploid potato lines. In certain embodiments of said breeding method, step (a) further comprises organizing the set of potato lines into three or more heterotic groups, wherein each heterotic group comprises a haplotype, and wherein the haplotypes are grouped based on observed or predicted heterotic performance when combined in the hybrid polyploid potato plant of step (g). In one variation, step (a) comprises organizing the set of lines into four or more heterotic groups. In certain embodiments, heterotic performance is predicted via genome prediction modeling. In some embodiments of said breeding method, step (b) comprises reciprocal recurrent selection, inbreeding one or more of the plant lines to homozygosity, production of a doubled haploid potato line (e.g., a doubled monoploid potato line), backcrossing, or any other method known in the art for creating potato lines with high degrees of homozygosity, or a combination thereof. The candidate potato lines of step (c) may be inbred potato lines, hybrid potato lines, or a combination thereof.

In another aspect, the present disclosure provides a method of producing a population of polyploid potato seed comprising: (a) providing clonal gametes from a pair of parent MiMe potato plants that together comprise three or more haplotypes that were selected using the methods of breeding described herein based upon the polyploid potato plant comprising said three or more haplotypes having one or more desired characteristics; and (b) crossing the clonal gametes to produce the population of polyploid potato seed, wherein at least 50% of the population of polyploid potato seed are genetically uniform and comprise three or more haplotypes. The polyploid potato seed produced by said method may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid potato seed produced by said method are genetically uniform. In certain embodiments, the polyploid potato seed produced by said method comprises four or more haplotypes of the same or related species of potato. In some variations of said method, potato lines are maintained via vegetative propagation, selfing, apomixis, cell culture, or any combination thereof. In some embodiments, said method further comprises maintaining an inventory of potato lines from which haplotypes may be selected for rapid deterministic stacking of the haplotypes. In some variations, the inventory of potato lines comprises one or more potato lines having a complete MiMe genotype that is maintained through vegetative propagation, hybridization with a haploid inducer, or a combination thereof. In additional variations, the inventory of potato lines comprises one or more potato lines having a partial MiMe genotype.

In another aspect, the present disclosure provides a method of producing a population of polyploid potato seed comprising: (a) providing clonal gametes from a parent MiMe potato plant; (b) providing haploid (e.g., monoploid) gametes from a homozygous parent non-MiMe potato plant; and (c) crossing the clonal gametes with the haploid (e.g., monoploid) gametes to produce the population of polyploid potato seed, wherein the clonal gametes and the haploid (e.g., monoploid) gametes together comprise three or more haplotypes, and wherein at least 50% of the population of polyploid potato seed are genetically uniform and comprise three or more haplotypes. The parent MiMe potato plant may be, for example, diploid, triploid, or tetraploid. The homozygous parent non-MiMe potato plant may be, for example, diploid or tetraploid. The polyploid potato seed produced by said method may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid potato seed produced by said method are genetically uniform. In certain embodiments, the polyploid potato seed produced by said method comprises four or more haplotypes of the same or related species of potato plant. In some embodiments, germination of a seed of the population of polyploid seed produced by said method results in a sterile plant that produces inviable gametes.

In some embodiments, the method of producing a population of polyploid potato seed comprises producing a population of polyploid potato seed comprising one or more genetic modifications resulting in decreased expression of one or more, two or more, or three or more MiMe loci. The seed may comprise one or more genetic modifications resulting in decreased expression of MiMe loci including, but not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In one embodiment, the polyploid potato seed produced by said method comprises one or more genetic modifications resulting in decreased expression of REC8, SWITCH1/DYAD, or a combination thereof. In another embodiment, the polyploid potato seed produced by said method comprises one or more genetic modifications resulting in decreased expression of OSD1, CYCA1, TDM1, PC1, PC2, FC, or a combination thereof. In another embodiment, the polyploid potato seed produced by said method comprises one or more genetic modifications resulting in decreased expression of PAIR1, SPO11-1, SPO11-2, PRD1, PRD2, DFO, MTOPVIB, DSY1, SY1, SY2, SY3, SY4, or a combination thereof. In yet another embodiment, the polyploid potato seed produced by said method comprises one or more genetic modifications resulting in decreased expression of PS1, JASON, or a combination thereof. The polyploid potato seed produced by said method may comprise genetic modifications in any combination of MiMe loci described herein. The genetic modifications may include, but are not limited to, modification of an enhancer in the MiMe loci, modification of a promoter of the MiMe loci, modification of a coding region in the MiMe loci, modification of methylation status of the MiMe loci, expression of a repressor protein that targets the DNA or an mRNA of the MiMe loci, and expression of an RNA interference construct that targets an mRNA from the MiMe loci.

In certain embodiments, the population of polyploid potato seed produced by said method comprises a partial MiMe genotype comprising (a) one or more MiMe alleles conferring decreased expression of one or more MiMe loci of each of the first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof.

In certain embodiments, the population of polyploid potato seed produced by said method has a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis comprise PS1, JASON, or a combination thereof.

In another aspect, the present disclosure provides a method of breeding a polyploid hybrid potato line, comprising: (a) obtaining a set of potato lines; (b) breeding the lines using traditional plant breeding methods to produce a set of candidate potato lines; (c) selecting two or more candidate potato lines together comprising three or more haplotypes; (d) generating a parent MiMe potato plant from one of the two or more candidate potato lines; (e) providing clonal gametes from the parent MiMe potato plant; (f) providing haploid (e.g., monoploid) gametes from a homozygous parent non-MiMe potato plant of one of the two or more candidate potato lines; (g) crossing the clonal gametes with the haploid (e.g., monoploid) gametes to produce a hybrid polyploid potato seed; (h) growing the hybrid polyploid potato seed to produce a hybrid polyploid potato plant; and (i) evaluating one or more characteristics of the hybrid polyploid potato plant, wherein the parent MiMe potato plant and the homozygous parent non-MiMe potato plant together comprise three or more haplotypes, wherein the crossing of step (g) results in the hybrid polyploid potato seed comprising three or more haplotypes, and wherein the growing of step (h) results in the hybrid polyploid potato plant comprising three or more haplotypes. The candidate potato lines, parent MiMe potato plant, and the homozygous parent non-MiMe potato plant may be any ploidy, including, but not limited to, haploid, monoploid, diploid, triploid, or tetraploid. In some embodiments of said breeding method, the hybrid polyploid potato plant is tetraploid, pentaploid, hexaploid, heptaploid, or octoploid.

In some embodiments of said breeding method, step (d) comprises introducing a complete MiMe genotype directly into a candidate potato line to produce the parent MiMe potato plant. In further embodiments of said breeding method, step (d) comprises introducing a partial MiMe genotype into two candidate potato lines to produce two grandparent non-MiMe potato plants each having a partial MiMe genotype, crossing said grandparent non-MiMe potato plants each having a partial MiMe genotype to produce the parent MiMe potato plant. In certain embodiments, step (d) further comprises propagating the parent MiMe potato plant to scale production of homogenous seed.

In some embodiments of said breeding method, the parent MiMe potato plant of step (d) has a complete MiMe genotype comprising MiMe alleles that are naturally-occurring, introduced via genetic modification, or a combination thereof. In certain embodiments, the genetic modifications result in decreased expression of one or more, two or more, or three or more MiMe loci including, but not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In one embodiment, the genetic modifications result in decreased expression of REC8, SWITCH1/DYAD, or a combination thereof. In another embodiment, the genetic modifications result in decreased expression of OSD1, CYCA1, TDM1, PC1, PC2, FC, or any combination thereof. In another embodiment, the genetic modifications result in decreased expression of PAIR1, SPO11-1, SPO11-2, PRD1, PRD2, DFO, MTOPVIB, DSY1, SY1, SY2, SY3, SY4, or any combination thereof. In yet another embodiment, the genetic modifications result in decreased expression of PS1, JASON, or a combination thereof. In some embodiments, the one or more genetic modifications are introduced by gene editing, transgenesis, or a combination thereof. The genetic modifications may be achieved by any methods described herein, including, but not limited to, gene disruption, gene knockout, gene knockdown, gene silencing, RNA interference, induction of methylation, or any combination thereof.

In certain embodiments, the population of polyploid potato seed produced by said breeding method comprises a partial MiMe genotype comprising (a) one or more MiMe alleles conferring decreased expression of one or more MiMe loci of each of the first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof.

In certain embodiments, the population of polyploid potato seed produced by said breeding method has a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis comprise PS1, JASON, or a combination thereof.

In certain embodiments of said breeding method, the method of breeding a population of polyploid potato seed further comprises (j) repeating steps (b)-(i) or steps (c)-(i) using the one or more characteristics of the hybrid polyploid potato plant evaluated in step (i) to guide the breeding of lines of step (b), the selecting of candidate potato lines of step (c), or both. In some variations, the one or more characteristics includes the heterotic performance of the three or more haplotypes of the polyploid hybrid potato evaluated in step (i).

In some embodiments of said breeding method, the set of potato lines in step (a) are obtained from one or more of natural diversity, existing breeding programs, or dihaploid induction of polyploid potato lines. In certain embodiments of said breeding method, step (a) further comprises organizing the set of potato lines into three or more heterotic groups, wherein each heterotic group comprises a haplotype, and wherein the haplotypes are grouped based on observed or predicted heterotic performance when combined in the hybrid polyploid potato plant of step (h). In one variation, step (a) comprises organizing the set of potato lines into four or more heterotic groups. In certain embodiments, heterotic performance is predicted via genome prediction modeling. In some embodiments of said breeding method, step (b) comprises reciprocal recurrent selection, inbreeding one or more of the potato lines to homozygosity, production of a doubled haploid potato line (e.g., a doubled monoploid potato line), backcrossing, or any other method known in the art for creating potato lines with high degrees of homozygosity, or a combination thereof. The candidate potato lines of step (c) may be inbred potato lines, hybrid potato lines, or a combination thereof.

In another aspect, the present disclosure provides a method of producing a population of polyploid potato seed comprising: (a) selecting three or more haplotypes using the method of breeding described herein based upon the polyploid potato plant comprising said three or more haplotypes having one or more desired characteristics; (b) providing clonal gametes from a parent MiMe potato plant; (c) providing haploid (e.g., monoploid) gametes from a homozygous parent non-MiMe potato plant; (d) crossing the clonal gametes with the haploid (e.g., monoploid) gametes to produce the population of polyploid potato seed; wherein the parent MiMe potato plant and the homozygous parent non-MiMe potato plant together comprise the three or more haplotypes selected in step (a), wherein the crossing of step (d) results in a population of polyploid potato seed comprising the three or more haplotypes selected in step (a), and wherein at least 50% of the population of polyploid potato seed are genetically uniform and comprise three or more haplotypes. The polyploid potato seed produced by said method may be, for example, triploid, tetraploid, pentaploid, hexaploid, heptaploid, or octoploid. In some embodiments, at least 70%, at least 90%, at least 95%, at least 96%, at least 97%, at least 98%, or at least 99% of the population of polyploid potato seed produced by said method are genetically uniform. In certain embodiments, the polyploid potato seed produced by said method comprises four or more haplotypes of the same or related species of potato. In some variations of said method, potato lines are maintained via vegetative propagation, selfing, apomixis, cell culture, or any combination thereof. In some embodiments, said method further comprises maintaining an inventory of potato lines from which haplotypes may be selected for rapid deterministic stacking of the haplotypes. In some variations, the inventory of potato lines comprises one or more potato lines having a complete MiMe genotype that is maintained through vegetative propagation, hybridization with a haploid inducer, or a combination thereof. In additional variations, the inventory of potato lines comprises one or more potato lines having a partial MiMe genotype.

In another aspect, the present disclosure provides a method of breeding a polyploid potato plant, comprising (a) obtaining a set of potato lines; (b) breeding the lines using traditional plant breeding methods to produce a set of candidate potato lines; (c) selecting one or more candidate potato lines; (d) generating a first parent MiMe potato plant from one of the candidate potato lines, wherein the first parent MiMe potato plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; (e) generating a second parent MiMe potato plant from one of the candidate potato lines, wherein the second parent MiMe potato plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component, wherein at least one of the MiMe loci having only MiMe alleles of the first MiMe component of the first parent MiMe potato plant is the same as at least one of the MiMe loci having only MiMe alleles of the first MiMe component of the second parent MiMe potato plant; (f) providing clonal gametes from each of the parent MiMe potato plants; (g) crossing the clonal gametes to produce a polyploid potato seed; (h) growing the polyploid potato seed to produce a polyploid potato plant; and (i) evaluating one or more characteristics of the polyploid potato plant. In some embodiments, at least one of the MiMe loci having only MiMe alleles of the third MiMe component of the first parent MiMe potato plant is the same as at least one of the MiMe loci having only MiMe alleles of the third MiMe component of the second parent MiMe potato plant. In other embodiments, the one or more MiMe loci having only MiMe alleles of the third MiMe component of the first parent MiMe potato plant are distinct from the one or more MiMe loci having only MiMe alleles of the third MiMe component of the second parent MiMe potato plant. In certain embodiments, the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

In some embodiments of said breeding method, the first MiMe component is a component of sister chromatid cohesion during the first division of meiosis. In some variations of said breeding method, the MiMe loci of the first MiMe component of both the first and second parent MiMe potato plants comprise REC8. In certain embodiments of said breeding method, the second MiMe component is a component of DNA double strand breakage during meiotic recombination. In some variations of said breeding method, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation of said breeding method, the first MiMe locus of the second MiMe component is PAIR1 and the second MiMe locus of the second MiMe component is SPO11-1. In further embodiments of said breeding method, the third MiMe component is a component of progression through the second division of meiosis. In some embodiments of said breeding method, at least one of the MiMe loci having only MiMe alleles of the third MiMe component of the first parent MiMe potato plant is the same as at least one of the MiMe loci having only MiMe alleles of the third MiMe component of the second parent MiMe potato plant. In some variations, the MiMe loci having only MiMe alleles of the component of progression through the second division of meiosis comprise OSD1, CYCA1, TDM1, PC1, PC2, FC, or any combination thereof. In one variation, the MiMe locus having only MiMe alleles of the third MiMe component is OSD1. In other embodiments of said breeding method, the one or more MiMe loci having only MiMe alleles of the third MiMe component of the first parent MiMe potato plant are distinct from the one or more MiMe loci having only MiMe alleles of the third MiMe component of the second parent MiMe potato plant. In some variations, the MiMe loci having only MiMe alleles of the third MiMe component comprise OSD1, CYCA1, TDM1, PC1, PC2, FC, or any combination thereof. In one variation of said breeding method, the MiMe loci having only MiMe alleles of the first MiMe component comprise REC8, the first MiMe locus of the second MiMe component is PAIR1, the second MiMe locus of the second MiMe component is SPO11-1, and the one or more MiMe loci having only MiMe alleles of the third MiMe component comprise OSD1.

In another aspect, the present disclosure provides a method of producing a population of polyploid potato seed comprising (a) providing clonal gametes from a pair of parent MiMe potato plants together comprising two or more haplotypes that were selected using the foregoing method of breeding based upon the polyploid potato plant comprising said two or more haplotypes having one or more desired characteristics, wherein: (i) the first parent MiMe potato plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; (ii) the second parent MiMe potato plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component; and (iii) at least one of the MiMe loci having only MiMe alleles of the first MiMe component of the first parent MiMe potato plant is the same as at least one of the MiMe loci having only MiMe alleles of the first MiMe component of the second parent MiMe potato plant; and (b) crossing the clonal gametes to produce the population of polyploid potato seed, wherein at least 50% of the population of polyploid potato seed are genetically uniform and comprise two or more haplotypes. In some embodiments, at least one of the MiMe loci having only MiMe alleles of the third MiMe component of the first parent MiMe potato plant is the same as at least one of the MiMe loci having only MiMe alleles of the third MiMe component of the second parent MiMe potato plant. In other embodiments, the one or more MiMe loci having only MiMe alleles of the third MiMe component of the first parent MiMe potato plant are distinct from the one or more MiMe loci having only MiMe alleles of the third MiMe component of the second parent MiMe potato plant.

In another aspect, the present disclosure provides a method of breeding a polyploid potato plant, comprising (a) obtaining a set of potato lines; (b) breeding the lines using traditional plant breeding methods to produce a set of candidate potato lines; (c) selecting one or more candidate potato lines; (d) generating a first parent MiMe potato plant from one of the candidate potato lines, wherein the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; (e) generating a second parent MiMe potato plant from one of the candidate potato lines, wherein the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component, and at least one of the MiMe loci having only MiMe alleles of the first MiMe component of the first parent MiMe potato plant is the same as at least one of the MiMe loci having only MiMe alleles of the first MiMe component of the second parent MiMe potato plant; (f) providing clonal gametes from each of the parent MiMe potato plants; (g) crossing the clonal gametes to produce a polyploid potato seed; (h) growing the polyploid potato seed to produce a polyploid potato plant; and (i) evaluating one or more characteristics of the polyploid potato plant. In some embodiments of said breeding method, the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

In another aspect, the present disclosure provides a method of producing a population of polyploid potato seed comprising (a) providing clonal gametes from a pair of parent MiMe potato plants together comprising two or more haplotypes that were selected using the foregoing method of breeding based upon the polyploid potato plant comprising said two or more haplotypes having one or more desired characteristics, wherein: (i) the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; (ii) the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component; and (iii) at least one of the MiMe loci having only MiMe alleles of the first MiMe component of the first parent MiMe potato plant is the same as at least one of the MiMe loci having only MiMe alleles of the first MiMe component of the second parent MiMe potato plant; and (b) crossing the clonal gametes to produce the population of polyploid potato seed wherein at least 50% of the population of polyploid potato seed are genetically uniform and comprise two or more haplotypes.

In another aspect, the present disclosure provides a method of breeding a polyploid potato plant, comprising (a) obtaining a set of potato lines; (b) breeding the lines using traditional plant breeding methods to produce a set of candidate potato lines; (c) selecting one or more candidate potato lines; (d) generating a first parent MiMe potato plant from one of the candidate potato lines, wherein the first parent MiMe potato plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination; (e) generating a second parent MiMe potato plant from one of the candidate potato lines, wherein the second parent MiMe potato plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component, and at least one of the MiMe loci having only MiMe alleles of the first MiMe component of the first parent MiMe potato plant is the same as at least one of the MiMe loci having only MiMe alleles of the first MiMe component of the second parent MiMe potato plant; (f) providing clonal gametes from each of the parent MiMe potato plants; (g) crossing the clonal gametes to produce a polyploid potato seed; (h) growing the polyploid potato seed to produce a polyploid potato plant; and (i) evaluating one or more characteristics of the polyploid potato plant. In some embodiments of said breeding method, the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

In another aspect, the present disclosure provides a method of producing a population of polyploid potato seed comprising (a) providing clonal gametes from a pair of parent MiMe potato plants together comprising two or more haplotypes that were selected using the foregoing method of breeding based upon the polyploid potato plant comprising said two or more haplotypes having one or more desired characteristics, wherein: (i) the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; (ii) the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component; and (iii) at least one of the MiMe loci having only MiMe alleles of the first MiMe component of the first parent MiMe potato plant is the same as at least one of the MiMe loci having only MiMe alleles of the first MiMe component of the second parent MiMe potato plant; and (b) crossing the clonal gametes to produce the population of polyploid potato seed, wherein at least 50% of the population of polyploid potato seed are genetically uniform and comprise two or more haplotypes.

In some embodiments of the foregoing breeding methods, steps (d) and (e) comprise introducing a complete MiMe genotype directly into two candidate potato lines to produce the two parent MiMe potato plants. In further embodiments of the foregoing breeding methods, steps (d) and (e) comprise introducing a partial MiMe genotype into two candidate potato lines to produce two grandparent non-MiMe potato plants each having a partial MiMe genotype, crossing said grandparent non-MiMe potato plants each having a partial MiMe genotype to produce the first parent MiMe potato plant, and introducing a complete MiMe genotype directly into a third candidate potato line to produce the second parent MiMe potato plant. In yet further embodiments of the foregoing breeding methods, steps (d) and (e) comprise introducing a partial MiMe genotype into four candidate potato lines to produce four grandparent non-MiMe potato plants each having a partial MiMe genotype, and crossing pairs of said grandparent non-MiMe potato plants each having a partial MiMe genotype to produce the two parent MiMe potato plants. In certain embodiments of the foregoing breeding methods, steps (d) and (e) further comprise propagating parent MiMe potato plants to scale production of homogenous seed.

In some embodiments of the foregoing breeding methods, the method further comprises (j) repeating steps (b)-(i) or steps (c)-(i) using the one or more characteristics of the polyploid potato plant evaluated in step (i) to guide the breeding of the potato lines of step (b), the selecting of candidate potato lines of step (c), or both. In certain embodiments of the foregoing breeding methods, the one or more characteristics includes the heterotic performance of the two, three, four, or more haplotypes of the polyploid potato plant evaluated in step (i). In some embodiments of the foregoing breeding methods, the set of potato lines in step (a) are obtained from one or more of: natural diversity, existing breeding programs, or dihaploid induction of polyploid potato lines. In certain embodiments of the foregoing breeding methods, step (a) further comprises organizing the set of potato lines into two, three, four, or more heterotic groups, wherein each heterotic group comprises a haplotype, and wherein the haplotypes are grouped based on observed or predicted heterotic performance when combined in the polyploid potato plant of step (i). In some variations, heterotic performance is predicted via genome prediction modeling. In some embodiments of the foregoing breeding methods, step (b) comprises reciprocal recurrent selection, inbreeding one or more of the potato lines to homozygosity, production of a doubled haploid potato line (e.g., a doubled monoploid potato line), backcrossing, or any other method known in the art for creating potato lines with high degrees of homozygosity, or a combination thereof. In some embodiments of the foregoing breeding methods, one or more of the candidate potato lines of step (c) are inbred potato lines. In further embodiments of the foregoing breeding methods, one or more of the candidate potato lines of step (c) are hybrid potato lines.

In some embodiments of any of the forgoing breeding methods, the first and second parent MiMe potato plants together comprise two, three, four, or more haplotypes, resulting in a polyploid potato plant comprising two, three, four, or more haplotypes. In some embodiments of the foregoing breeding methods, the potato lines are maintained via vegetative propagation, selfing, apomixis, cell culture, or any combination thereof. In further embodiments of the forgoing methods, the method further comprises maintaining an inventory of potato lines from which haplotypes may be selected for rapid deterministic stacking of the haplotypes. In some variations, the inventory of potato lines comprises one or more potato lines having a complete MiMe genotype that is maintained through vegetative propagation, hybridization with a haploid inducer, or a combination thereof. In additional variations, the inventory of potato lines comprises one or more potato lines having a partial MiMe genotype.

In some embodiments of the foregoing aspects and embodiments, the one or more MiMe loci of the component of sister chromatid cohesion during the first division of meiosis comprise REC8, SWITCH1/DYAD, or a combination thereof. In some embodiments of the foregoing aspects and embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In some embodiments of the foregoing aspects and embodiments, the one or more MiMe loci of the component of progression through the second division of meiosis comprise OSD1, CYCA1, TDM1, PC1, PC2, FC, or any combination thereof. In some embodiments of the foregoing aspects and embodiments, the one or more MiMe loci of the component of progression through the first division of meiosis comprise PS1, JASON, or a combination thereof.

In some embodiments of any of the foregoing aspects and embodiments, the MiMe alleles comprise alleles that are naturally-occurring, introduced via genetic modification, or a combination thereof. In certain embodiments of the foregoing aspects and embodiments, the MiMe alleles comprise one or more genetic modifications. In further embodiments of the foregoing aspects and embodiments, one or more of the genetic modifications are at MiMe loci encoding gene products of the MiMe components. In some variations, the genetic modifications comprise modification of an enhancer in the MiMe loci, modification of a promoter of the MiMe loci, modification of a coding region in the MiMe loci, modification of methylation status of the MiMe loci, expression of a repressor protein that targets the DNA or an mRNA of the MiMe loci, and expression of an RNA interference construct that targets an mRNA from the MiMe loci, or any combination thereof. In some embodiments of the foregoing aspects and embodiments, one or more genetic modifications are introduced by gene editing, transgenesis, or a combination thereof. In further embodiments of the foregoing aspects and embodiments, the decreased expression of the one or more MiMe loci is achieved by gene disruption, gene knockout, gene knockdown, gene silencing, RNA interference, induction of methylation, or any combination thereof.

In any of the foregoing aspects and embodiments, the population of polyploid potato seed may be, for example, triploid, tetraploid, pentaploid, hexaploid, heptaploid, or octoploid. In some embodiments of the foregoing aspects and embodiments, at least 50%, at least 70%, at least 80%, at least 90%, at least 95%, at least 96%, at least 97%, at least 98%, or at least 99% of the population of polyploid potato seed are genetically uniform. In some embodiments of the foregoing aspects and embodiments, the population of polyploid potato seed comprises a subpopulation of genetically uniform polyploid potato seed in an amount of at least 50%, at least at least 70%, at least 75%, at least 80%, at least 90%, at least 95%, at least 96%, at least 97%, at least 98%, or at least 99% of the total number of seeds. In certain embodiments of the foregoing aspects and embodiments, the polyploid potato seed (e.g., the subpopulation of genetically uniform polyploid potato seed) comprises two, three, four, or more haplotypes of the same or related species of potato. In some embodiments of the foregoing aspects and embodiments, germination of a seed of the population of polyploid potato seed, or a seed of the subpopulation of genetically uniform polyploid potato seed, results in a plant that produces inviable gametes. In some embodiments, germination of a seed of the population of polyploid potato seed, or a seed of the subpopulation of genetically uniform polyploid potato seed, results in a seedless potato plant.

In another aspect, the present disclosure provides a genetically modified potato plant, plant part, or plant cell. In some embodiments, the genetically modified potato plant, plant part, or plant cell comprises: i) three or more haplotypes; and ii) a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the genetically modified potato plant, plant part, or plant cell comprises: i) three or more haplotypes; and ii) a partial MiMe genotype comprising: (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations of the foregoing embodiments, the one or more MiMe loci of the component of sister chromatid cohesion during the first division of meiosis comprise REC8, SWITCH1/DYAD, or a combination thereof. In additional variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations of the foregoing embodiments, the one or more MiMe loci of the component of progression through the second division of meiosis comprise OSD1, CYCA1, TDM1, PC1, PC2, FC, or any combination thereof.

In some embodiments of said genetically modified potato plant, plant part, or plant cell, the present disclosure provides a genetically modified potato plant, plant part, or plant cell comprising: i) three or more haplotypes; and ii) a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments of this aspect, the genetically modified potato plant, plant part, or plant cell comprising: i) three or more haplotypes; and ii) a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiments, the one or more MiMe loci of the component of progression through the first division of meiosis comprise PS1, JASON, or a combination thereof.

In some embodiments of said genetically modified potato plant, plant part, or plant cell, the genetically modified potato plant, plant part, or plant cell comprises: (i) at least a first and second haplotype, each comprising one or more MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations of the foregoing embodiments, the one or more MiMe loci of the component of sister chromatid cohesion during the first division of meiosis comprise REC8, SWITCH1/DYAD, or a combination thereof. In additional variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations of the foregoing embodiments, the MiMe locus of the component of progression through the first division of meiosis of the third haplotype is PS1 or JASON. In still additional variations of the foregoing embodiments, the one or more MiMe loci of the component of progression through the second division of meiosis of the first and second haplotype comprise OSD1, CYCA1, TDM1, PC1, PC2, FC, or any combination thereof. In yet additional variations of the foregoing embodiments, the locus of the component of progression through the second division of meiosis of the third haplotype is OSD1, CYCA1, TDM1, PC1, PC2, or FC.

In some embodiments of said genetically modified potato plant, plant part, or plant cell, the genetically modified potato plant, plant part, or plant cell comprises: (i) at least a first and second haplotype, each comprising one or more MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiments, the one or more MiMe loci of the component of progression through the first division of meiosis of the first and second haplotype comprise PS1, JASON, or a combination thereof. In yet additional variations of the foregoing embodiments, the MiMe locus of the component of progression through the first division of meiosis of the third haplotype is PS1 or JASON. In still additional variations of the foregoing embodiments, the MiMe locus of the component of progression through the second division of meiosis of the third haplotype is OSD1, CYCA1, TDM1, PC1, PC2 or FC.

In some embodiments, the genetically modified potato plant, plant part, or plant cell has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the genetically modified potato plant, plant part, or plant cell has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the genetically modified potato plant, plant part, or plant cell has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the genetically modified potato plant, plant part, or plant cell has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the genetically modified potato plant, plant part, or plant cell has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1 In some embodiments, the genetically modified potato plant, plant part, or plant cell has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the genetically modified potato plant, plant part, or plant cell has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the genetically modified potato plant, plant part, or plant cell has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the genetically modified potato plant, plant part, or plant cell has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the genetically modified potato plant, plant part, or plant cell has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the genetically modified potato plant, plant part, or plant cell has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the genetically modified potato plant, plant part, or plant cell has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the genetically modified potato plant, plant part, or plant cell has a complete MiMe genotype comprising (i) an os allele, wherein the subpopulation of genetically uniform polyploid potato seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the genetically modified potato plant, plant part, or plant cell has a partial MiMe genotype comprising (i) an os allele, wherein the subpopulation of genetically uniform polyploid potato seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the genetically modified potato plant, plant part, or plant cell has a complete MiMe genotype comprising (i) a ps allele, wherein the subpopulation of genetically uniform polyploid potato seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1. In some embodiments, the genetically modified potato plant, plant part, or plant cell has a partial MiMe genotype comprising (i) a ps allele, wherein the subpopulation of genetically uniform polyploid potato seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some aspects, provided herein is a genetically modified potato plant, plant part, or plant cell having a partially-complemented MiMe genotype. In some embodiments, the genetically modified potato plant, plant part, or plant cell has a partially-complemented MiMe genotype comprising: (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some embodiments, the first MiMe component is a component of sister chromatid cohesion during the first division of meiosis. In some variations, the one or more MiMe loci of the first MiMe component comprise REC8, SWITCH1/DYAD, or a combination thereof. In one variation, the MiMe locus of the first MiMe component is REC8. In certain embodiments, the second MiMe component is a component of DNA double strand breakage during meiotic recombination. In some variations, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation, the first MiMe locus of the second MiMe component is PAIR1 and the second MiMe locus of the second MiMe component is SPO11-1. In further embodiments, the third MiMe component is a component of progression through the second division of meiosis. In some embodiments, the partially-complemented MiMe genotype comprises only MiMe alleles at one or more MiMe loci of the third MiMe component. In some variations, the one or more MiMe loci of the third MiMe component comprise OSD1, CYCA1, TDM1, PC1, PC2, FC, or any combination thereof. In one variation, the MiMe locus of the third MiMe component is OSD1. In other embodiments, the partially-complemented MiMe genotype comprises one or more MiMe alleles and one or more non-MiMe alleles at a first MiMe locus of the third MiMe component, and one or more MiMe alleles and one or more non-MiMe alleles at a second MiMe locus of the third MiMe component. In some variations, the first MiMe locus and the second MiMe locus of the third MiMe component comprise OSD1, CYCA1, TDM1, PC1, PC2, FC, or any combination thereof. In one embodiment, the partially-complemented MiMe genotype comprises only MiMe alleles at one or more MiMe loci of the third MiMe component, wherein the one or more MiMe loci having only MiMe alleles of the first MiMe component comprise REC8, the first MiMe locus of the second MiMe component is PAIR1, the second MiMe locus of the second MiMe component is SPO11-1, and the one or more MiMe loci having only MiMe alleles of the third MiMe component comprise OSD1.

In some embodiments, the present disclosure provides a genetically modified potato plant, plant part, or plant cell having a partially-complemented MiMe genotype comprising: (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiment, the one or more MiMe loci of the component of progression through the first division of meiosis comprise PS1, JASON, or a combination thereof.

In some embodiments, the present disclosure provides a genetically modified potato plant, plant part, or plant cell having a partially-complemented MiMe genotype comprising: (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiments, the one or more MiMe loci of the component of sister chromatid cohesion during the first division of meiosis comprise REC8, SWITCH1/DYAD, or a combination thereof. In yet additional variations of the foregoing embodiments, the one or more MiMe loci of the component of progression through the second division of meiosis comprise OSD1, CYCA1, TDM1, PC1, PC2, FC, or any combination thereof. In still additional variations of the foregoing embodiments, the one or more MiMe loci of the component of progression through the first division of meiosis comprise PS1, JASON, or a combination thereof.

In some embodiments, the genetically modified potato plant, plant part, or plant cell has a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more only MiMe alleles at one or more SPO11-1 loci, wherein each of the MiMe alleles at the SPO11-1 locus comprise one or more genetic modifications resulting in decreased expression of SPO11-1.

In some embodiments, the genetically modified potato plant, plant part, or plant cell has a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

In some embodiments, the genetically modified potato plant, plant part, or plant cell has a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

In some embodiments, the genetically modified potato plant, plant part, or plant cell has a partially complemented MiMe genotype comprising (i) a ps allele, wherein the subpopulation of genetically uniform polyploid potato seed is heterozygous for the ps allele, (ii) an os allele, wherein the subpopulation of genetically uniform polyploid potato seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1.

In some embodiments, the genetically modified potato plant, plant part, or plant cell has a partially complemented MiMe genotype comprising (i) an os allele, wherein the subpopulation of genetically uniform polyploid potato seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more comprise one or more genetic modifications resulting in decreased expression of SPO11-1 loci.

In some embodiments of said genetically modified potato plant, plant part, or plant cell, which may be combined with any of the preceding embodiments, the genetically modified potato plant, plant part, or plant cell is diploid, triploid, tetraploid, pentaploid, hexaploid, heptaploid, or octoploid. In additional embodiments which may be combined with any of the preceding embodiments, the genetically modified potato plant, plant part, or plant cell comprises two, three, four, or more haplotypes of the same or related species of potato. In certain embodiments, which may be combined with any of the preceding embodiments, the genetically modified potato plant part is a non-regenerable plant part. In certain embodiments, which may be combined with any of the preceding embodiments, the genetically modified potato plant cell is a non-regenerable plant cell. In certain embodiments, which may be combined with any of the preceding embodiments, the plant part is a flower, a pistil, a leaf, a stem, a petiole, a cutting, a tissue, a seed coat, an ovule, pollen, a tuber, a root, a rootstock, a scion, a fruit, a cotyledon, a hypocotyl, a protoplast, an embryo, an anther, or a portion thereof.

In another aspect, provided herein is a processed potato product derived from any of the foregoing embodiments of genetically modified potato plants, plant parts, or plant cells, wherein the processed potato product comprises a detectable amount of the one or more MiMe alleles of the genetically modified potato plant, plant part, or plant cell. In some embodiments, the product is selected from the group consisting of plant biomass, oil, meal, food starch, syrup, animal feed, flour, flakes, bran, lint, hulls, processed seed, puree, juice, juice concentrate, pulp, pomace, preserve, and sauce. In certain embodiments, the processed potato product is non-regenerable.

DESCRIPTION OF THE FIGURES

The present application can be understood by reference to the following description taken in conjunction with the accompanying figures.

FIG. 13A illustrates generation of a plant having a first exemplary partially-complemented MiMe genotype where MiMe loci are propagated at the parent stage and each parent has a different set of edited MiMe loci. FIG. 13B illustrates generation of a plant having a second exemplary partially-complemented MiMe genotype where MiMe loci are propagated at the parent stage and each parent has a different set of edited MiMe loci. FIG. 13C illustrates generation of a plant having a third exemplary partially-complemented MiMe genotype where MiMe loci are propagated at the parent stage and each parent has a different set of edited MiMe loci.

FIG. 14A shows the screening results where editing efficiency is displayed as the proportion edited (vertical axis, in percentage) across a range of selected protospacers (horizontal axis) across four different genes (horizontal axis, grey boxes). From left to right, the potato orthologs are listed for OSD1 ("StOsd1"), PAIR1 ("StPair1"), REC8 ("StRec8"), and SPO11-1 ("StSpo11-1"). FIG. 14B shows further results of screening, as in FIG. 14A, with the exception that the exhibited gene is the potato ortholog of CYCA1 ("StCyca1").

FIGS. 15A-15F show the resultant editing of MiMe alleles and disruption of MiMe components in edited potato lines. FIG. 15A shows the truncated, inactivated proteins resulting from insertion of a premature stop codon in edited rec8 alleles. FIG. 15B shows the truncated, inactivated proteins resulting from insertion of a premature stop codon in edited cyca1 alleles. FIG. 15C shows the truncated, inactivated proteins resulting from insertion of a premature stop codon in edited spo11-1 alleles. FIG. 15D shows an alignment of edited "scar" nucleotide sequences of edited rec8 alleles (bottom portion continues from the top portion). FIG. 15E shows an alignment of edited "scar" nucleotide sequences of edited cyca1 alleles (bottom portion continues from the top portion). FIG. 15F shows an alignment of edited "scar" nucleotide sequences of edited spo11-1 alleles (bottom portion continues from the top portion).

FIG. 16A shows a summary of the genotyping results at 52 triallelic markers across 19 progeny comprising the Boosted Potato Population 1 (BPP1). The vertical-axis corresponds to individual tetraploid progeny as well as the two diploid parent plants for reference. The horizontal-axis corresponds to individual triallelic markers distributed across 12 separate chromosomes. When referring to the axis, vertical and horizontal are in respect to the text for their respective figure. The coloration of each cell denotes the specific configuration of haplotypes observed at that marker (where A=M18, B=DM, and C=M6). Samples with markers that are "AABC" have three haplotypes. The parent genotypes are displayed along the top rows.

FIG. 16B shows a summary of the genotyping results at 60 tetra-allelic markers across 19 progeny comprising the Boosted Potato Population 2 (BPP2). The vertical-axis corresponds to individual tetraploid progeny as well as the two diploid parent plants for reference. The horizontal-axis corresponds to individual tetra-allelic markers distributed across 12 separate chromosomes. When referring to the axis, vertical and horizontal are in respect to the text for their respective figure. The coloration of each cell denotes the specific configuration of haplotypes observed at that marker (where A=DM, B=M6, and C=Atlantic Haplotype 1, and D=Atlantic Haplotype 2). Samples with markers that are "ABCD" have four haplotypes. The parent genotypes are displayed along the top rows.

FIG. 16C shows a summary of the genotyping results at 50 triallelic markers across 10 progeny comprising the Boosted Potato Population 3 (BPP3). The vertical-axis corresponds to individual tetraploid progeny as well as the two diploid parent plants for reference. The horizontal-axis corresponds to individual triallelic markers distributed across 12 separate chromosomes. When referring to the axis, vertical and horizontal are in respect to the text for their respective figure. The coloration of each cell denotes the specific configuration of haplotypes observed at that marker (where A=M18, B=DM, and C=M6). Samples with markers that are "ABBC" have three haplotypes. The parent genotypes are displayed along the top rows.

FIG. 16D summary of the genotyping results at 60 tetra-allelic markers across 12 progeny comprising the Boosted Potato Population 4 (BPP4). The vertical-axis corresponds to individual tetraploid progeny as well as the two diploid parent plants for reference. The horizontal-axis corresponds to individual tetra-allelic markers distributed across 12 separate chromosomes. When referring to the axis, vertical and horizontal are in respect to the text for their respective figure. The coloration of each cell denotes the specific configuration of haplotypes observed at that marker (where A=DM, B=M6, and C=Atlantic Haplotype 1, and D=Atlantic Haplotype 2). Samples with markers that are "ABCD" have four haplotypes. The parent genotypes are displayed along the top rows.

FIG. 16E shows a summary of the genotyping results at 60 tetra-allelic markers across 8 progeny comprising the Boosted Potato Population 5 (BPP5). The vertical-axis corresponds to individual tetraploid progeny as well as the two diploid parent plants for reference. The horizontal-axis corresponds to individual tetra-allelic markers distributed across 12 separate chromosomes. When referring to the axis, vertical and horizontal are in respect to the text for their respective figure. The coloration of each cell denotes the specific configuration of haplotypes observed at that marker (where A=DM, B=M6, and C=Atlantic Haplotype 1, and D=Atlantic Haplotype 2). Samples with markers that are "ABCD" have four haplotypes. The parent genotypes are displayed along the top rows.

FIG. 17A shows a photograph of one BPP1 potato plant ("BPP1 (Boosted)"), its grandparent plants ("Grandparent non-MiMe (PED-PR-AA)" and "Grandparent non-MiMe (PED-PR-BB)"), its parent plants ("Parent non-MiMe (PED-PR-CC-o)" and "Parent MiMe (PED-PR-AB-sp)"), and an elite commercial tetraploid at 12 days post-planting. FIG. 17B shows measurements of leaf surface area visible in FIG. 17A, comparing the aerial surface area ($cm^2$) for each individual plant from the photograph in FIG. 17A using ImageJ software.

FIG. 17C shows photographs of three BPP1 potato plants ("BPP1 (Boosted)"), its grandparent plants ("Grandparent non-MiMe (PED-PR-AA)" and "Grandparent non-MiMe (PED-PR-BB)"), its parent plants ("Parent non-MiMe (PED-PR-CC-o)" and "Parent MiMe (PED-PR-AB-sp)", and an elite commercial tetraploid at 12 days post-planting. FIG. 17D shows measurements of leaf surface area visible in FIG. 17C, comparing the aerial surface area ($cm^2$) for each individual plant from the photograph in FIG. 17C using ImageJ software.

FIG. 17E shows photographs of one BPP1 potato plant ("BPP1 (Boosted)"), its grandparent plants ("Grandparent non-MiMe (PED-PR-AA)" and "Grandparent non-MiMe (PED-PR-BB)"), its parent plants ("Parent non-MiMe (PED-PR-CC-o)" and "Parent MiMe (PED-PR-AB-sp)"), and an elite commercial tetraploid at 19 days post-planting. FIG. 17F shows measurements of leaf surface area visible in FIG. 17E, comparing the aerial surface area ($cm^2$) for each individual plant from the photograph in FIG. 17E using ImageJ software.

FIG. 17G shows photographs of one BPP1 potato plant ("BPP1 (Boosted)"), its grandparent plants ("Grandparent non-MiMe (PED-PR-AA)" and "Grandparent non-MiMe (PED-PR-BB))"), its parent plants ("Parent non-MiMe (PED-PR-CC-o)" and "Parent MiMe (PED-PR-AB-sp)"), and an elite commercial tetraploid at 26 days post-planting. FIG. 17H shows measurements of leaf surface area visible in FIG. 17G, comparing the aerial surface area ($cm^2$) for each individual plant from the photograph in FIG. 17G using ImageJ software.

FIG. 17I shows photographs of six BPP1 potato plants (right, "BPP1") resulting from the cross between a parent non-MiMe plant (PED-PR-CC-0) and a parent MiMe plant (PED-PR-AB-sp), compared to six SPP2 potato plants (left, "SPP2") resulting from the cross between two parent non-MiMe plants (PED-PR-CC-o and PED-PR-AB). All the plants are 16 days post-planting. FIG. 17J shows measurements of leaf surface area visible in FIG. 17I, comparing the aerial surface area ($cm^2$) for each individual plant from the photograph in FIG. 17I using ImageJ software. The aerial surface area mean and standard deviation for each plant population are represented in the graph by a cross and error bars, respectively.

FIG. 17K shows photographs of six BPP1 potato plants (right, "BPP1") resulting from the cross between a parent non-MiMe plant (PED-PR-CC-0) and a parent MiMe plant (PED-PR-AB-sp), compared to six SPP2 potato plants (left, "SPP2") resulting from the cross between two parent non-MiMe plants (PED-PR-CC-0 and PED-PR-AB). All the plants are 23 days post-planting.

FIG. 18A shows photographs of a BPP2 potato plant ("BPP2 (Boosted)") adjacent to its grandparent plants ("Grandparent non-MiMe (PED-PR-AA)" and "Grandparent non-MiMe (PED-PR-BB)"), parent plants ("Parent MiMe (PED-PR-AB-sp)" and "Parent MiMe (PED-PR-EF-rso-1)"), and an elite commercial tetraploid. All the plants are 23 days post-planting.

FIG. 18B shows photographs of a BPP2 potato plant ("BPP2 (Boosted)") adjacent to its grandparent plants ("Grandparent non-MiMe (PED-PR-AA)" and "Grandparent non-MiMe (PED-PR-BB)", parent plants ("Parent MiMe (PED-PR-AB-sp,)" and "Parent MiMe (PED-PR-EF-rso-1"), and an elite commercial tetraploid. All the plants are 23 days post-planting.

FIG. 18C shows photographs of a BPP2 potato plant ("BPP2 (Boosted)", 4 haplotypes) adjacent to tetraploid (4n) versions of its respective grandparent plants ("4n version of grandparent non-MiMe (PED-PR-AA), 1 haplotype" and "4n version of grandparent non-MiMe (PED-PR-BB), 1 haplotype") and parent plants ("4n version of PED-PR-AA x PED-PR-BB, 2 haplotypes" and "4n version of Atlantic dihaploid, 2 haplotypes"). All the plants are 23 days post-planting.

FIG. 18D shows photographs of a BPP2 potato plant ("BPP2 (Boosted), 4 haplotypes") adjacent to tetraploid (4n) versions of its respective grandparent plants ("4n version of grandparent non-MiMe (PED-PR-AA), 1 haplotype" and "4n version of grandparent non-MiMe (PED-PR-BB), 1 haplotype") and parent plants ("4n version of PED-PR-AA x PED-PR-BB, 2 haplotypes" and "4n version of Atlantic dihaploid, 2 haplotypes"). All the plants are 29 days post-planting.

FIG. 18E shows photographs of nine BPP2 potato plants (right, "BPP2 (PED-PR-EF-rso-1×PED-PR-AB-sp") resulting from the cross between a parent MiMe plant (PED-PR-AB-sp) and a parent MiMe plant (PED-PR-EF-rso-1), compared to eight potato plants (left, "SPP1 (PED-PR-EF-o x PED-PR-AABB") resulting from the cross between two parent non-MiMe plants (PED-PR-EF-o and PED-PR-AABB). One of the progeny plants from the non-MiMe cross failed to develop, which is why there are only eight instead of nine. All the plants are 16 days post-planting. FIG. 18F shows measurements of leaf surface area visible in FIG. 18E, comparing the aerial surface area ($cm^2$) for each individual plant from the photograph in FIG. 18E using ImageJ software. The aerial surface area mean and standard deviation for each plant population are represented in the graph by a cross and error bars, respectively.

FIG. 18G shows photographs of nine BPP2 potato plants (right, "BPP2 (PED-PR-EF-rso-1×PED-PR-AB-sp") resulting from the cross between a parent MiMe plant (PED-PR-AB-sp) and a parent MiMe plant (PED-PR-EF-rso-1), compared to eight potato plants (left, "SPP1 (PED-PR-EF-o x PED-PR-AABB") resulting from the cross between two parent non-MiMe plants (PED-PR-EF-o and PED-PR-AABB). One of the progeny plants from the non-MiMe cross failed to develop, which is why there are only eight instead of nine. All the plants are 23 days post-planting. FIG. 18H shows measurements of leaf surface area visible in FIG. 18G, comparing the aerial surface area ($cm^2$) for each individual plant from the photograph in FIG. 18G using ImageJ software. The aerial surface area mean and standard deviation for each plant population are represented in the graph by a cross and error bars, respectively.

FIG. 18I shows photographs of eight BPP2 potato plants (right, "BPP2 (PED-PR-EF-rso-1×PED-PR-AB-sp") resulting from the cross between a parent MiMe plant (PED-PR-AB-sp) and a parent MiMe plant (PED-PR-EF-rso-1), compared to eight potato plants (left, "SPP1 (PED-PR-EF-o x PED-PR-AABB") resulting from the cross between two parent non-MiMe plants (PED-PR-EF-o and PED-PR-AABB). One of the progeny from the non-MiMe cross failed to develop, which is why there are only eight instead of nine and, because of this, one of the BPP2 was removed so that both populations had the same number of individuals. All the plants are 29 days post-planting.

FIG. 19A shows a matrix for pairwise identity as estimated by the Jaccard similarity coefficient of 64 molecular markers genotyped between 19 tetraploid potato plants in Boosted Potato Population 1 (BPP1). FIG. 19B shows a matrix for pairwise identity as estimated by the Jaccard similarity coefficient of 52 molecular markers genotyped between 19 tetraploid potato plants in Boosted Potato Population 2 (BPP2). FIG. 19C shows a matrix for pairwise identity as estimated by the Jaccard similarity coefficient of 47 molecular markers genotyped between 10 tetraploid potato plants in Boosted Potato Population 3 (BPP3). FIG. 19D shows a matrix illustrating pairwise identity as estimated by the Jaccard similarity coefficient of 60 molecular markers genotyped between 12 tetraploid potato plants in Boosted Potato Population 4 (BPP4). FIG. 19E shows a matrix illustrating pairwise identity as estimated by the Jaccard similarity coefficient of 60 molecular markers genotyped between 8 tetraploid potato plants in Boosted Potato Population 5 (BPP5). FIG. 19F shows a matrix for pairwise identity as estimated by the Jaccard similarity coefficient of 56 molecular markers genotyped between 7 tetraploid potato plants in Standard Potato Population 1 (SPP1). FIG. 19G shows a matrix for pairwise identity as estimated by the Jaccard similarity coefficient of 52 molecular markers genotyped between 4 tetraploid potato plants in Standard Potato Population 2 (SPP2).

FIG. 20A shows images of the tubers. From left to right, displayed are the tubers of the first grandparent plant ("Grandparent non-MiMe PED-PR-AA (doubled monoploid DM1-3)") with average tuber weight [35.5 g]; the tubers of the second grandparent plant ("Grandparent non-MiMe PED-PR-BB (selfed M6)") with average tuber weight [5.2 g]; the tubers of the first parent plant ("Parent MiMe (spo11-1/ps) PED-PR-AB-sp") with average tuber weight [78.1 g]; the tubers of the second parent plant ("Parent non-MiMe PED-PR-CC-o") with average tuber weight [35.3 g]; and the tubers of the BPP1 plant ("BOOSTED progeny BPP1") with average tuber weight [161.2 g]. FIG. 20B shows plotted weights of the tubers displayed in FIG. 20A.

DETAILED DESCRIPTION

Figure 1:
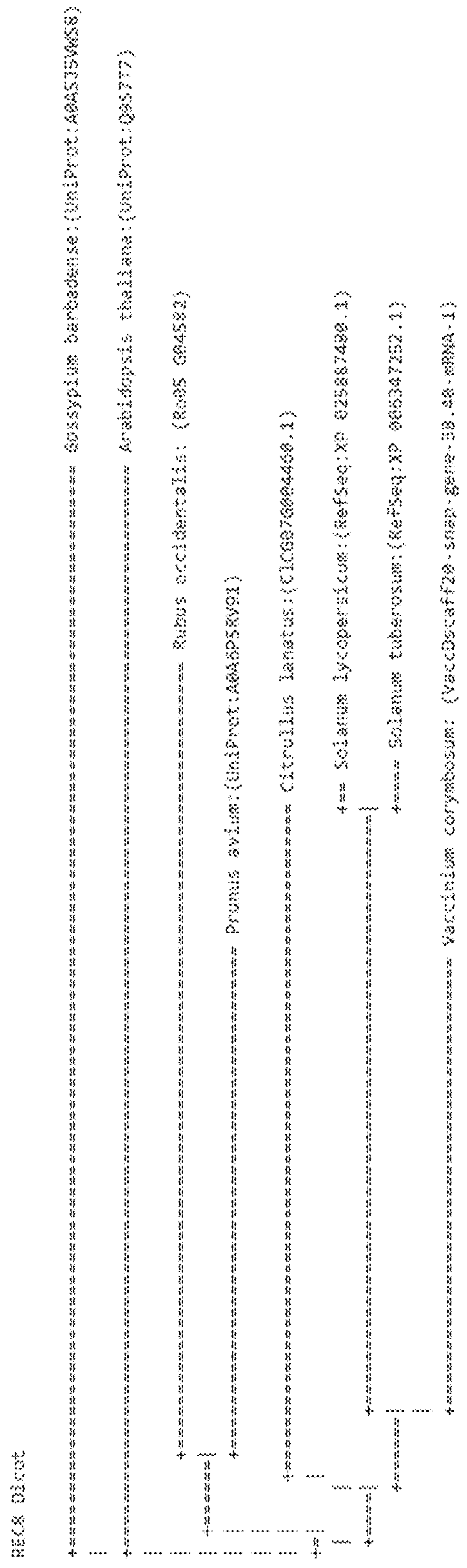
FIG. 1 depicts a phylogenetic tree of REC8 protein sequences from dicotyledonous plants.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Overview

In one aspect, described herein is a population of polyploid potato seed comprising three or more haplotypes of the same or related species of potato, wherein at least 50% of the population of polyploid potato seed is genetically uniform, and wherein the population was obtained from a single potato plant or a set of potato plants such as, for example, a set of genetically uniform F1 hybrids. In some embodiments, the population of polyploid potato seed comprises a subpopulation of genetically uniform polyploid potato seed in an amount of at least 50% of the total number of seed, the genetically uniform polyploid potato seed comprising three or more haplotypes of the same or related species of potato. The genetic uniformity of the seeds of the population addresses a long-felt need for genetically uniform populations of polyploid potato seed comprising three or more haplotypes with improved heterotic performance over the pairs of haplotypes present in existing hybrid plants. In some embodiments, the population of polyploid potato seed and/or the subpopulation of genetically uniform polyploid potato seed comprises one or more genetic modifications resulting in decreased expression of one or more MiMe loci. The population of polyploid potato seed and/or the subpopulation of genetically uniform polyploid potato seed may have a complete or partial MiMe genotype comprising MiMe alleles conferring decreased expression of MiMe loci of one or more MiMe components. In certain embodiments, germination of a seed of the population of polyploid potato seed and/or the subpopulation of genetically uniform polyploid potato seed results in a sterile plant that produces inviable gametes.

In another aspect, provided herein are methods of producing a population of polyploid potato seed comprising three or more haplotypes wherein at least 50% of the population of polyploid potato seed are genetically uniform. In some embodiments, the population of polyploid potato seed comprises a subpopulation of genetically uniform polyploid potato seed in an amount of at least 50% of the total number of seed, the genetically uniform polyploid potato seed comprising three or more haplotypes of the same or related species of potato. In some embodiments, the method comprises (a) providing clonal gametes from a pair of parent MiMe potato plants that together comprise three or more haplotypes; and (b) crossing the clonal gametes to produce the population of polyploid potato seed. In other embodiments, the method comprises (a) providing clonal gametes from a parent MiMe potato plant; (b) providing haploid (e.g., monoploid, dihaploid or higher ploidy) gametes from a homozygous parent non-MiMe potato plant; and (c) crossing the clonal gametes with the haploid (e.g., monoploid) gametes to produce the population of polyploid potato seed.

In yet another aspect, provided herein are methods of breeding a polyploid hybrid potato line comprising three or more haplotypes, the methods comprising: obtaining a set of lines of potato lines; breeding the lines using traditional plant breeding methods to produce a set of candidate potato lines; and selecting two or more candidate potato lines, together comprising three or more haplotypes, for crossing. In some embodiments, after the selection of candidate potato lines, the methods further comprise generating two parent MiMe potato plants from the two or more candidate potato lines; providing clonal gametes from each of the parent MiMe potato plants; and crossing the clonal gametes to produce a hybrid polyploid potato seed comprising the three or more haplotypes. In alternative embodiments, after the selection of candidate potato lines, the methods further comprise generating a single parent MiMe potato plant from one of the two or more candidate potato lines; providing clonal gametes from the parent MiMe potato plant; providing haploid (e.g., monoploid) gametes from a homozygous parent non-MiMe potato plant of one of the two or more candidate potato lines; and crossing the clonal gametes with the haploid (e.g., monoploid) gametes to produce a hybrid polyploid potato seed. In some embodiments, after the crossing of the clonal gametes or the crossing of the clonal gametes with the haploid (e.g., monoploid) gametes, the methods further comprise growing the hybrid polyploid potato seed to produce a hybrid polyploid potato plant and evaluating one or more characteristics of the hybrid polyploid potato plant.

In another aspect, described herein is a population of polyploid potato seed comprising a partially-complemented MiMe genotype, wherein at least 50% of the population of polyploid potato seed is genetically uniform, and wherein the population was obtained from a single potato plant or a set of potato plants such as, for example, a set of genetically uniform F1 hybrids. In some embodiments, the population of polyploid potato seed comprises a subpopulation of genetically uniform polyploid potato seed in an amount of at least 50% of the total number of seed, the genetically uniform seed comprising the partially-complemented MiMe genotype. The polyploid potato seed comprising the partially-complemented MiMe genotype may comprise one, two, three, or more haplotypes. The partially-complemented MiMe genotype of the population of polyploid potato seed results in a plant having neither a wild-type meiosis phenotype nor a MiMe phenotype. Thus, in some embodiments, germination of a seed of the population of polyploid potato seed or the subpopulation of genetically uniform polyploid potato seed results in a plant that produces inviable gametes. In some embodiments, the partially-complemented MiMe genotype comprises (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component. In certain embodiments, the partially-complemented MiMe genotype further comprises (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component.

In another aspect, provided herein are methods of producing a population of polyploid potato seed comprising a partially-complemented MiMe genotype wherein at least 50% of the population of polyploid potato seed are genetically uniform. In some embodiments, the population of polyploid potato seed comprises a subpopulation of genetically uniform polyploid potato seed in an amount of at least 50% of the total number of seed, the genetically uniform seed comprising the partially-complemented MiMe genotype. The polyploid potato seed comprising the partially-complemented MiMe genotype may comprise one, two, three, or more haplotypes. In some embodiments, the method comprises: (a) providing clonal gametes from a first parent MiMe potato plant; (b) providing clonal gametes from a second parent MiMe potato plant; and (c) crossing the clonal gametes to produce the population of polyploid potato seed comprising a partially-complemented MiMe genotype. In some embodiments, the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; and the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component. In certain embodiments, at least one of the MiMe loci having only MiMe alleles of the first MiMe component of the first parent MiMe potato plant is the same as at least one of the MiMe loci having only MiMe alleles of the first MiMe component of the second parent MiMe potato plant. In some embodiments, the first and second parent MiMe potato plants further have only MiMe alleles at one or more MiMe loci of a third MiMe component, wherein the one or more MiMe loci having only MiMe alleles of the third MiMe component of the first and second parent MiMe potato plants are the same or different.

In yet another aspect, provided herein are methods of breeding a polyploid potato plant, the methods comprising: obtaining a set of potato lines; breeding the potato lines using traditional plant breeding methods to produce a set of candidate potato lines; and selecting two or more candidate potato lines for crossing. In some embodiments, after the selection of candidate potato lines, the methods further comprise generating two parent MiMe potato plants from the two or more candidate potato lines. In some embodiments, the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; and the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component. In certain embodiments, at least one of the MiMe loci having only MiMe alleles of the first MiMe component of the first parent MiMe potato plant is the same as at least one of the MiMe loci having only MiMe alleles of the first MiMe component of the second parent MiMe potato plant. In some embodiments, the first and second parent MiMe potato plants further have only MiMe alleles at one or more MiMe loci of a third MiMe component, wherein the one or more MiMe loci having only MiMe alleles of the third MiMe component of the first and second parent MiMe potato plants are the same or different. In some embodiments, the method further comprises providing clonal gametes from each of the parent MiMe potato plants, crossing the clonal gametes to produce a polyploid potato seed, growing the polyploid potato seed to produce a polyploid potato plant, and evaluating one or more characteristics of the polyploid potato plant.

In some variations of the methods of breeding, the methods may further comprise repeating the steps of the method, using the one or more characteristics of the hybrid polyploid potato plant evaluated to guide the breeding of potato lines, the selecting of candidate potato lines, or both. In additional variations, the methods may further comprise organizing the set of potato lines into three or more heterotic groups, wherein each heterotic group comprises a haplotype, and wherein the haplotypes are grouped based on observed or predicted heterotic performance when combined in the hybrid polyploid potato plant. This method allows for deterministic combination of three or more haplotypes in a polyploid potato plant, addressing the need for plant breeding methods that yield predictable results on time scales shorter than those required for traditional breeding methods.

Definitions

As used herein, "potato" typically refers to the species *Solanum tuberosum* and other potato species in the genus *Solanum*. Moreover, it will be readily apparent to those of ordinary skill in the art that some varieties of *Solanum tuberosum* include genetic introgressions from related *Solanum* species, but that such varieties are still considered *Solanum tuberosum* unless otherwise noted. The terms "potato" and "potato plant" include the whole potato plant or any parts or derivatives thereof, such as plant organs (e.g., harvested or non-harvested flowers, leaves, etc.), plant cells, plant protoplasts, plant cell or tissue cultures from which whole plants can be regenerated, regenerable or non-regenerable plant cells, plant calli, plant cell clumps, and plant cells that are intact in plants, or parts of plants, such as embryos, pollen, ovules, ovaries (e.g., harvested tissues or organs), flowers, leaves, seeds, tubers, clonally propagated plants, roots, stems, cotyledons, hypocotyls, root tips, meristems, nodes, stolon tips and the like. The potato plant parts or derivatives thereof can also include any of the aforementioned plant parts in an encapsulated form such as, for example, shoot meristems, nodes, stolon tips, and the like, encapsulated in alginate, e.g., in a synthetic seed. Any developmental stage is also included, such as seedlings, immature and mature, etc.

As used herein, the term "seed" typically refers to a true seed rather than another plant part used for propagation. For example, the term "potato seed" as used herein refers to true potato seed rather than a potato tuber.

As used herein, "seedless plant" typically describes a plant or crop in which fruit produced contain inviable and/or poorly-developed seed. As used herein, seedless plants may or may not require pollen or fertilization to stimulate the development of the fruit. Fruit development may or may not involve initialization and abortion of a seed, leaving an incompletely developed seed. As used herein, "seedless" may refer to incomplete development of seed, lack of seed production, or otherwise inviable seed. A seedless plant may also refer to a plant that fails to produce fruits or seeds at all. For example, in a crop where seed development is required for fruit development failed formation of viable eggs, sperm or failed fertilization may result in no seed and no fruit of any kind.

As used herein, the term "non-regenerable" generally refers to a plant part, a plant cell, a processed plant product, or a portion of any of the foregoing, that cannot be induced to form a whole plant or that cannot be induced to form a whole plant that is capable of sexual and/or asexual reproduction.

As used herein, "ploidy" refers to the number of complete sets of chromosomes in a cell or organism. Ploidy may be annotated using "n" as the unit of complete sets of chromosomes. For example, a cell or organism with a single set of chromosomes may be referred to as "In", or the single set of chromosomes itself may be referred to as "In". A diploid cell or organism with two sets of chromosomes may be referred to as "2n"; a triploid cell or organism with three sets of chromosomes may be referred to as "3n"; and so on.

As used herein, "monoploid" refers to a cell or organism with a ploidy of 1n.

As used herein, "diploid" refers to a cell or organism with a ploidy of 2n.

As used herein, "polyploid" refers to a cell or organism with a ploidy of greater than 2n. "Polyploid" may refer to organisms which are triploid (3n), tetraploid (4n), pentaploid (5n), hexaploid (6n), heptaploid (7n), octoploid (8n), or higher ploidies (greater than 8n).

As used herein, "allele" refers to one of two or more alternative forms of a single gene or locus within the genome. As used herein, "monoallelic" typically describes the presence of a single allele at a given locus or set of loci within a cell or organism. As used herein, "biallelic" typically describes the presence of two different alleles at a given locus or set of loci within a cell or organism. As used herein, "multiallelic" typically describes the presence of three or more alleles at a given locus or set of loci within a cell or organism.

As used herein, "haplotype" refers to a distinct 1n set of chromosomes with a unique set of alleles. As used herein, each haplotype is distinct from other haplotypes in that it contains a set of alleles that confers a unique set of characteristics not conferred by other haplotypes. As used herein, as a feature of the present disclosure, each distinct haplotype need not be inherited from a different parent—a polyploid organism of the present disclosure may comprise three or more haplotypes inherited from two parents. As used herein, "monoallelic plant" typically refers to a plant line containing a single haplotype, "biallelic plant" typically refers to a plant line containing two haplotypes, and "multiallelic plant" typically refers to a plant line containing three or more haplotypes. In the case of allopolyploid plants that contain multiple subgenomes between which there is little to no recombination, as used herein, the term "three or more haplotypes" typically refers to three or more haplotypes of the same subgenome.

As used herein, "clonal" describes a body of DNA that is substantially identical to another body of DNA; or a set of cells or organisms that comprise such DNA. For example, mitosis results in two clonal genomes comprised by two clonal cells. Due to random errors in natural DNA replication, clonal bodies of DNA, clonal cells, or clonal organisms may not be completely identical. "Clonal" may describe two genomes that are not completely identical in sequence but that contain the same set of alleles.

As used herein, "genetically uniform" typically describes a set of individual plants, plant parts (e.g., seeds), or plant cells whose genomes are identical across at least 80% of loci, or are clonal. Genetic uniformity of a set of individual plants, plant parts (e.g., seeds), or plant cells may be measured using methods known in the art and described herein. For example, a set of genetic markers may be identified and used to determine the estimated pairwise identity of a pair of individuals, or to determine the average pairwise genetic uniformity of a population of individuals, using the Jaccard similarity coefficient. For example, a population of genetically uniform plants or seeds may consist of plants or seeds having genomes that are identical to one another across at least 80%, at least 85%, at least 90%, at least 95%, at least 96%, at least 97%, at least 98%, at least 99%, or 100% of genetic markers analyzed, or may consist of seeds having an average pairwise genetic uniformity of at least 80%, at least 85%, at least 90%, at least 95%, at least 96%, at least 97%, at least 98%, at least 99%, or 100% as measured by the Jaccard similarity coefficient. Additionally, each pair of seeds in a population of genetically uniform plants or seed may have genomes that have a pairwise identity of at least 95%, at least 96%, at least 97%, at least 98%, at least 99%, or 100% as measured by the Jaccard similarity coefficient.

As used herein, "expression" and "expression level" refer to the relative or absolute amount of a functional gene product present in a cell. As used herein, "gene products" include, but are not limited to, nucleic acids (e.g., RNA), post-transcriptionally modified nucleic acids (e.g., spliced RNA, poly-adenylated mRNA), proteins (e.g., enzymes, structural proteins, etc.), and post-translationally modified proteins (e.g., glycoproteins, lipoproteins, etc.). The function of the gene product refers to the wild-type, unmodified, uninhibited function of the gene product. As used herein, "decreased expression" refers to a relative decrease in the amount of a functional gene product of a gene or genetic locus, such as a MiMe locus, present in a cell. The decreased expression may refer to a decrease in the total amount of a gene product present in a cell (e.g., a decrease in the amount of a protein) or to a decrease in the amount of functional gene products present in a cell (e.g., a decrease in the percentage of proteins with wild-type function, e.g., an altered activity of the protein) or to a decrease in the function of gene products present in a cell (e.g., a decrease in the activity of proteins as compared to proteins with wild-type function, e.g., elimination of activity). The decreased expression may be of a gene product encoded at a certain genomic locus. Decreased expression also includes "non-expression" and "eliminated expression." As used herein, "non-expression" or "eliminated expression" refers to the absence of a functional gene product present in a cell, or to an expression level insufficient for detection of the gene product in the cell, or to an expression level insufficient to result in the function of the gene product within the cell, or to an activity level insufficient to result in the detectable activity of the gene product within the cell.

As used herein, "homozygous" describes a cell or organism in which all sets of chromosomes encode the same allele or set of alleles at a certain chromosomal locus, a set of chromosomal loci, or at all chromosomal loci. For example, a triploid cell or organism with the same allele at a specific locus in all three sets of chromosomes is homozygous for that allele. An organism may be homozygous for a specific allele or set of alleles at a certain chromosomal locus or set of chromosomal loci, or an organism may be homozygous for a haplotype. For example, a triploid cell or organism containing three copies of the same haplotype is homozygous for that haplotype. As used herein, "homozygous plant" typically refers to an inbred plant or plant line, a monoallelic plant or plant line, or a plant or plant line which is homozygous at all loci within its genome.

As used herein, "heterozygous" describes a cell or organism in which at least one set of chromosomes encodes an allele or set of alleles at a certain chromosomal locus or set of chromosomal loci that is distinct from those of the other sets of chromosomes within the cell or organism. For example, a triploid cell or organism having allele $a_1$ at locus A in two sets of chromosomes and having allele $a_2$ at locus A in the third set of chromosomes is heterozygous for alleles $a_1$ and $a_2$. An organism may be heterozygous for a specific set of alleles at a certain chromosomal locus or set of chromosomal loci, or an organism may be heterozygous for a haplotype. For example, a triploid cell or organism containing two copies of one first haplotype and one copy of a second haplotype is heterozygous for the first and second haplotype. As used herein, "heterozygous plant" typically refers to a biallelic or multiallelic plant or plant line containing two or more haplotypes.

As used herein, "crossing" refers to the act of forming a zygote from gametes of two distinct plants or plant lines. Crossing may refer to pollinating a plant or plant line using the pollen of a different plant or plant line.

As used herein, "related species of plant" refers to two or more species that, when crossed, result in viable seed.

As used herein, "hybrid" describes a plant comprising two or more haplotypes from the same or related species of plant.

As used herein, "F1 hybrid" refers to the first filial generation of hybrid seeds or plants resulting from the cross of parents comprising two or more haplotypes. For clarity, this refers to the first filial generation of the cross and not the first filial generation of the hybrids of a cross.

As used herein, "heterotic performance" refers to the performance of a set of two or more haplotypes in conferring certain desirable characteristics when combined in a hybrid plant. The desired characteristics of heterotic performance may include characteristics of plant vigor including, but not limited to, plant size, hardiness, fruit or grain yield, and the like.

As used herein, "MiMe" typically refers to a phenotype of a plant wherein the wild-type meiosis phenotype of the plant is disrupted in such a way that results in the formation of clonal female gametes and/or clonal male gametes. "MiMe" may refer to any one of several known methods to promote the formation of clonal female gametes and/or clonal male gametes in plants including, but not limited to, Mitosis instead of Meiosis as disclosed in d'Erfurth et al. (2009. Turning meiosis into mitosis. *PLoS Biol* 7, e1000124) and first division restitution without crossing over (FDR-NCO) as disclosed in Peloquin et al. (1999. Meiotic mutants in potato: valuable variants. *Genetics* 153:1493-1499), a prime example of FDR-NCO being spo11-1, ps1 mutants as disclosed in Brownfield and Kohler (2010. Unreduced gamete formation in plants: mechanisms and prospects. J Exp Bot 62:5, 1659-1668).

In organisms with a wild-type meiosis phenotype, meiosis in germline cells results in haploid gametes. As used herein, “haploid” typically refers to a cell or organism with a ploidy half that of the parent organism. As used herein, “haploid gametes” typically refers to gamete cells with a ploidy half that of the parent organism. For example, in a diploid (2n) organism with a wild-type meiosis phenotype, meiosis in germline cells results in 1n haploid gametes. In another example, in a tetraploid (4n) organism with a wild-type meiosis phenotype, meiosis in germline cells results in 2n haploid gametes. As used herein, “parent non-MiMe plant” typically refers to a plant with the wild-type meiosis phenotype wherein meiosis in germline cells results in haploid gametes (pollen and egg cells). As used herein, “homozygous parent non-MiMe plant” typically refers to an inbred parent non-MiMe parent, a monoallelic parent non-MiMe plant, or a parent non-MiMe plant which is homozygous at all loci within its genome. A homozygous parent non-MiMe plant may be produced through inbreeding, production of a doubled haploid line (e.g., a doubled monoploid line), or any other method known in the art for creating plant lines with high degrees of homozygosity.

In plants with the MiMe phenotype, meiosis is replaced by a mitosis-like process in male and/or female germline cells, resulting in clonal gametes. As used herein, “clonal gametes” typically refers to gametes which comprise unreduced, unrecombined copies of the parent plant’s genome and, therefore, have the same ploidy as, and are typically genetically identical to, the parent plant. Clonal gametes are produced when germline cells in the parent plant do not undergo recombination as they would in a normal meiotic process, and also undergo a first division restitution or a second division restitution, resulting in unreduced gametes. As a result, clonal gametes are typically both unreduced and unrecombined and therefore typically genetically identical to the parent plant. For example, in a diploid (2n) plant with a MiMe phenotype, germline cells undergo mitosis instead of meiosis, typically resulting in 2n unrecombined gametes, i.e., clonal gametes. In another example, in a tetraploid (4n) plant with a MiMe phenotype, germline cells undergo mitosis instead of meiosis, typically resulting in 4n unrecombined gametes, i.e., clonal gametes. Clonal gametes may refer to female clonal gametes, male clonal gametes, or a combination thereof.

As used herein, “unreduced, non-clonal gametes” typically refers to gametes which comprise unreduced, yet recombined, copies of the parent plant’s genome and, therefore, have the same ploidy as the parent plant, but are not genetically identical to the parent plant. Unreduced, non-clonal gametes are produced when germline cells in the parent plant undergo recombination as they would in a normal meiotic process, but undergo a first division restitution or a second division restitution, resulting in unreduced gametes. Therefore, even though unreduced, non-clonal gametes are unreduced, they are the result of a normal recombination process, and are therefore not genetically identical to the parent plant. For example, germline cells in a diploid (2n) plant that undergo a normal recombination process but undergo a first division restitution or a second division restitution result in 2n, recombined gametes, i.e., unreduced, non-clonal gametes. In another example, germline cells in a tetraploid (4n) plant that undergo a normal recombination process but undergo a first division restitution or a second division restitution result in 4n, recombined gametes, i.e., unreduced, non-clonal gametes. Unreduced, non-clonal gametes may refer to female clonal gametes, male clonal gametes, or a combination thereof.

As used herein, “MiMe component” typically refers to a gene function that contributes to a MiMe phenotype, including, but not limited to, genes and gene products involved in meiosis that may be modified or altered to disrupt a wild-type meiotic phenotype in a manner relevant to the formation of clonal female gametes and/or clonal male gametes via MiMe. MiMe components include (1) a component of sister chromatid cohesion during the first division of meiosis, (2) a component of DNA double strand breakage during meiotic recombination, (3) a component of progression through the second division of meiosis, and (4) a component of progression through the first division of meiosis. In general, each MiMe component includes one or more MiMe loci discussed further below. Further, generally, each MiMe locus may have MiMe alleles and non-MiMe alleles.

As used herein, “MiMe allele” typically refers to an allele at a MiMe locus that disrupts the normal meiotic function of a MiMe component (e.g., an allele that disrupts sister chromatid cohesion during the first division of meiosis). MiMe alleles may be naturally occurring MiMe alleles, or may be introduced into a plant line via genetic modification using the methods described herein.

As used herein, “non-MiMe allele” typically refers to any allele that contributes to wild-type function of a MiMe component that therefore does not contribute to conferring a MiMe phenotype in a plant. A non-MiMe allele typically refers to an allele at a MiMe locus that contributes to the wild-type meiotic function of a MiMe component (e.g., an allele that provides the wild-type function that contributes to sister chromatid cohesion during the first division of meiosis).

As used herein, “complete MiMe genotype” typically refers to any set of alleles that confers the MiMe phenotype in a plant. The individual alleles that make up the complete MiMe genotypes are referred to as MiMe alleles. The complete MiMe genotype may be naturally present in a plant or may be introduced via, for example, plant breeding, transgenic techniques, gene-editing techniques, or any combination thereof to introduce one or more naturally-occurring alleles, non-naturally-occurring alleles, or a combination thereof. A complete MiMe genotype may comprise any number of MiMe alleles that results in a MiMe phenotype, such as one, two, three, or more MiMe alleles. As used herein, “MiMe locus” and “MiMe loci” typically refers to any chromosomal locus or loci which may be the site of MiMe alleles, including genes and intergenic loci. A MiMe locus or MiMe loci may correspond to a specific MiMe component, for example, if the MiMe locus encodes a MiMe component gene product. A complete MiMe genotype may comprise MiMe alleles at any number of MiMe loci, such as one, two, three, or more MiMe loci. A complete MiMe genotype may comprise different alleles at the same MiMe locus on different sets of chromosomes and need not be homozygous to confer a MiMe phenotype. For example, a diploid plant with a complete MiMe genotype may have two different REC8 alleles each of which reduces or eliminates REC8 expression or activity such that the plant has two MiMe alleles for REC8 and thus exhibits disruption of sister chromatid cohesion during the first division of meiosis. Specific examples of complete MiMe genotypes are described in detail herein.

As used herein, “partial MiMe genotype” typically refers to a set of alleles that comprises both MiMe and non-MiMe alleles at one or more MiMe loci such that a plant with a partial MiMe genotype exhibits a wild-type meiosis phenotype. Two plants having compatible partial MiMe genotypes each exhibit a wild-type meiosis phenotype and may be crossed to produce F1 offspring having a complete MiMe genotype and, thus, a MiMe phenotype. As used herein, “compatible partial MiMe genotypes” typically refers to two or more partial MiMe genotypes that comprise sets of MiMe alleles at the same MiMe loci. For example, a partial MiMe genotype comprising MiMe alleles of REC8, SPO11-1, and OSD1 is compatible with another partial MiMe genotype that comprises the same or different MiMe alleles of REC8, SPO11-1, and OSD1. The MiMe alleles of a partial MiMe genotype may be combined with the MiMe alleles of the same or different partial MiMe genotype in a single cross to create a complete MiMe genotype and confer a MiMe phenotype in the F1 offspring. In general, where MiMe alleles and non-MiMe alleles are referred to together they are alleles of the same MiMe loci. The partial MiMe genotype may be naturally present in a plant or may be introduced via, for example, plant breeding, transgenic techniques, gene-editing techniques, or any combination thereof to introduce one or more naturally-occurring alleles, non-naturally-occurring alleles, or a combination thereof. A partial MiMe genotype may comprise any number of alleles, such as one, two, three, or more alleles. Further, a partial MiMe genotype may comprise MiMe alleles at any number of MiMe loci, such as one, two, three, or more MiMe loci. Specific examples of partial MiMe genotypes are described in detail herein.

As used herein, “partially-complemented MiMe genotype” typically refers to a set of alleles that comprises only MiMe alleles at each of one or more MiMe loci of a first MiMe component, both MiMe and non-MiMe alleles at a first MiMe locus of a second MiMe component, and both MiMe and non-MiMe alleles at a second MiMe locus of the second MiMe component. A plant with a partially-complemented MiMe genotype typically does not exhibit a wild-type meiosis phenotype because the first MiMe component has only MiMe alleles at each of one or more MiMe loci, disrupting wild-type meiosis. The plant will also not exhibit a MiMe phenotype due to the complementation of the MiMe alleles by the non-MiMe alleles of each of the first and second MiMe loci of the second MiMe component. Therefore, a plant with a partially-complemented MiMe genotype exhibits neither a wild-type meiosis phenotype nor a MiMe phenotype. A partially-complemented MiMe genotype may also include MiMe alleles for a third MiMe component, e.g., only MiMe alleles at each of one or more MiMe loci of a third MiMe component, or both MiMe and non-MiMe alleles at a first MiMe locus of a third MiMe component and both MiMe and non-MiMe alleles at a second MiMe locus of the third MiMe component. As used herein, a plant or genotype “comprising only MiMe alleles at a MiMe locus” is a plant or genotype wherein each set of chromosomes has a MiMe allele at said locus, thus conferring decreased expression (including non-expression or altered activity) of the functional gene product of said locus. Exemplary partially-complemented MiMe genotypes are shown in FIGS. 24A-24C and described in detail herein. The MiMe alleles of each MiMe locus having only MiMe alleles of the first MiMe component may comprise any number of distinct MiMe alleles on different sets of chromosomes and need not be homozygous, as long as there are no non-MiMe alleles at that locus on any set of chromosomes. The partially-complemented MiMe genotype may comprise, for example, one, two, three, or more MiMe alleles and one, two, three, or more non-MiMe alleles at each of the first and second MiMe loci of the second MiMe component, as long as at least one MiMe allele and at least one non-MiMe allele are present at each of the first and second MiMe loci of the second MiMe component. Further, a partially-complemented MiMe genotype may comprise MiMe alleles at more than three MiMe loci, such as four, five, or more MiMe loci. Specific examples of partially-complemented MiMe genotypes are described in detail herein.

As used herein, “parent MiMe plant” typically refers to a plant which has a complete MiMe genotype and exhibits a MiMe phenotype, and which may be a source of clonal gametes (pollen and/or egg cells).

As used herein, “introducing a complete MiMe genotype directly” typically refers to introducing genetic modifications resulting in a complete MiMe genotype into a plant or plant cell including using the methods described herein, selecting a plant or plant cell that has a complete MiMe genotype, if needed, and regenerating the cell that has the complete MiMe genotype into a plant that exhibits a MiMe phenotype, if needed.

As used herein, “grandparent non-MiMe plant having a partial MiMe genotype” typically refers to a plant which has a partial MiMe genotype and exhibits a wild-type meiosis phenotype. A grandparent non-MiMe plant having a partial MiMe genotype produces haploid gametes that may be crossed with haploid gametes from the same or another grandparent non-MiMe plant having a partial MiMe genotype to produce one or more seeds that have a complete MiMe genotype and can be grown to produce one or more parent MiMe plants.

As used herein, “introducing a partial MiMe genotype” refers to introducing genetic modifications resulting in a partial MiMe genotype into a plant or plant cell including using the methods described herein, selecting a plant or plant cell that has a partial MiMe genotype, if needed, and regenerating the cell that has a partial MiMe genotype into a plant that exhibits a wild-type meiosis phenotype. For example, introducing a partial MiMe genotype could include crossing a plant with a MiMe and a non-MiMe allele for a component of sister chromatid cohesion during the first division of meiosis and a MiMe and a non-MiMe allele for a component of DNA double strand breakage during meiotic recombination with a plant that has a MiMe and a non-MiMe allele for a component of progression through the second division of meiosis, and then selecting for offspring that are heterozygous for all three of the parental MiMe alleles and therefore have a partial MiMe genotype.

As used herein, “genetic modification” typically refers to any sequence or portion thereof within a nucleic acid molecule that differs from the sequence of an ancestral nucleic acid molecule. For example, a seed that contains an inserted or deleted genomic sequence that is not present in one of its parent plants comprises a genetic modification. A genetic modification may be naturally occurring or introduced. A genetic modification may be introduced via, for example: plant breeding to introduce a naturally-occurring genetic modification of one plant line into another plant line; transgenic methods; gene editing; chemical mutagenesis; and the like.

As used herein, “transgenesis” refers to the insertion of an exogenous genetic element into the genome of an organism. Any exogenous genetic element may be inserted via transgenesis, including, but not limited to, genes, protein coding sequences, non-protein coding sequences, regulatory sequences, spacer DNA, and the like.

As used herein, “gene editing” refers to a type of genetic modification in which DNA is inserted, deleted or substituted in the genome of an organism using one or more natural or engineered nucleases. Gene editing may be carried out using site-specific nucleases, guided nucleases, or a combination thereof. The nuclease creates one or more site-specific breaks, such as double-strand breaks (DSBs) at target loci in the genome. Each site-specific break may be repaired, for example via non-homologous end joining (NHEJ), resulting in a genetic modification in the genome at the target locus; or via homologous recombination of the target locus with a provided repair nucleic acid molecule comprising homology to the target genomic sequence and the desired genetic modification.

Populations of Polyploid Seed

In one aspect, described herein is a population of polyploid potato seed comprising three or more haplotypes of potato, wherein at least 50% of the population of polyploid potato seed are genetically uniform, and wherein the population was obtained from a single potato plant or a set of potato plants (e.g., a set of genetically uniform potato plants, e.g., a set of genetically uniform F1 hybrids). In some embodiments, the population of polyploid potato seed comprises a subpopulation of genetically uniform polyploid potato seed in an amount of at least 50% of the total number of seed, the genetically uniform seed comprising three or more haplotypes of potato. In some embodiments, the population of polyploid potato seed may have a complete MiMe genotype or a partial MiMe genotype.

In another aspect, described herein is a population of polyploid potato seed comprising a partially-complemented MiMe genotype, wherein at least 50% of the population of polyploid potato seed are genetically uniform, and wherein the population was obtained from a single potato plant or a set of potato plants (e.g., a set of genetically uniform potato plants, e.g., a set of genetically uniform F1 hybrids). In some embodiments, the population of polyploid potato seed comprises a subpopulation of genetically uniform polyploid potato seed in an amount of at least 50% of the total number of seed, the genetically uniform polyploid potato seed comprising the partially-complemented MiMe genotype. In some embodiments, the population of polyploid potato seed comprising the partially-complemented MiMe genotype may comprise one, two, three, or more haplotypes.

Haplotypes

In some embodiments, the population of polyploid potato seed or the subpopulation of genetically uniform polyploid potato seed comprises one, two, three, or more haplotypes. In some variations, the population of polyploid potato seed or the subpopulation of genetically uniform polyploid potato seed comprises two or more haplotypes, three or more haplotypes, four or more haplotypes, five or more haplotypes, six or more haplotypes, seven or more haplotypes, or eight or more haplotypes. In additional variations, the population of polyploid potato seed or the subpopulation of genetically uniform polyploid potato seed comprises two, three, four, five, six, seven, or eight haplotypes. In some embodiments wherein the polyploid potato seed is from an allopolyploid plant having multiple subgenomes, the two, three, or more haplotypes are two, three, or more haplotypes of the same subgenome.

Potato Plants

In some embodiments, the population of polyploid potato seed is a population of seed of the family Solanaceae comprising two, three, or more haplotypes from one or more species of potato. In certain embodiments, the population of polyploid potato seed is a population of potato seed comprising two, three, or more haplotypes from the same or related species of potato. In some variations, the population of potato seed comprises two, three, or more haplotypes of potato species or subspecies including, but not limited to, *Solanum chacoense, Solanum tuberosum, Solanum tuberosum* ssp. *andigena, Solanum tuberosum* ssp. *tuberosum, Solanum stenotomum, Solanum phureja, Solanum goniocalyx, Solanum ajanhuiri, Solanum chaucha, Solanum juzepczukii, Solanum curtilobum, Solanum brevicaule, Solanum fendleri, Solanum demissum*, and *Solanum bulbocastanum.*

In some embodiments, the population of polyploid potato seed comprises two, three, or more haplotypes of *Solanum tuberosum*. In some variations, the two, three, or more haplotypes may be from different subspecies of *Solanum tuberosum*, including without limitation *Solanum tuberosum* ssp. *andigena, Solanum tuberosum* ssp. *Tuberosum*, related *Solanum* species, including without limitation *Solanum chacoense*, or *Solanum tuberosum* having introgressions from related *Solanum* species, including without limitation *Solanum microdontum, Solanum berthaultii, Solanum tarijense, Solanum raphanifolium, Solanum verrucosum*, and the like.

Genetic Uniformity, Ploidy, and Origin

In some embodiments, at least 50% of the population of polyploid potato seed comprising two, three, or more haplotypes are genetically uniform. In some variations, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the population of polyploid potato seed comprising two, three, or more haplotypes are genetically uniform. In some embodiments, at least 50% of the population of polyploid potato seed produced are genetically uniform, wherein the polyploid potato seed comprises three or more haplotypes. In some variations, at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the population of polyploid potato seed produced are genetically uniform, wherein the polyploid potato seed comprises three or more haplotypes. In some embodiments, the population of polyploid potato seed has an average pairwise genetic uniformity of at least 80% as measured by the Jaccard similarity coefficient. In some variations, the population of polyploid potato seed has an average pairwise genetic uniformity of at least 80%, at least 85%, at least 90%, at least 91%, at least 92%, at least 93%, at least 94%, at least 95%, at least 96%, at least 97%, at least 98%, at least 99%, or 100% as measured by the Jaccard similarity coefficient. In one variation, the population of polyploid potato seed has an average pairwise genetic uniformity of at least 85% as measured by the Jaccard similarity coefficient. In another variation, the population of polyploid potato seed has an average pairwise identity of at least 90% as measured by the Jaccard similarity coefficient.

In some embodiments, the population of polyploid potato seed comprises a subpopulation of genetically uniform polyploid potato seed in an amount of at least 50% of the total number of seeds. In some variations, the population of polyploid potato seed comprises a subpopulation of genetically uniform polyploid potato seed in an amount of at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the total number of seeds. In some embodiments, each pair of the subpopulation of genetically uniform polyploid potato seed has a pairwise identity of at least about 90% as measured by the Jaccard similarity coefficient. In some embodiments, each pair of the subpopulation of genetically uniform polyploid potato seed has a pairwise identity of at least about 90%, at least about 95%, at least about 96%, at least about 97%, at least about 98%, at least about 99%, or about 100% as measured by the Jaccard similarity coefficient.

In some embodiments, the population of polyploid potato seed or the subpopulation of genetically uniform polyploid potato seed comprising two, three, or more haplotypes is triploid, tetraploid, pentaploid, hexaploid, heptaploid, or octoploid. In other embodiments, the population of polyploid potato seed or the subpopulation of genetically uniform polyploid potato seed comprising two, three, or more haplotypes has a ploidy of 9n, 10n, 11n, 12n, 13n, 14n, 15n, 16n, or higher.

In some embodiments, the population of polyploid potato seed was obtained from a single potato plant or a set of potato plants such as, for example, a set of F1 hybrids. In some embodiments, the population of polyploid potato seed was obtained from a single potato plant. In other embodiments, the population of polyploid potato seed was obtained from a set of F1 hybrids. In some variations, the population of polyploid potato seed was obtained from a set of two, three, four, five, 10, 20, 50, 100, or more F1 hybrids. In some additional variations, the population of polyploid potato seed was obtained from a set of genetically uniform potato plants, e.g., a set of F1 hybrids derived from the same inbred parents. In yet additional variations, the population of polyploid potato seed was obtained from a set of two, three, four, five, 10, 20, 50, 100, or more genetically uniform potato plants, e.g., genetically uniform F1 hybrids. In certain embodiments, the genetically uniform set of potato plants (e.g., the genetically uniform set of F1 hybrids) has an average pairwise genetic uniformity of at least 80%, at least 85%, at least 90%, at least 91%, at least 92%, at least 93%, at least 94%, at least 95%, at least 96%, at least 97%, at least 98%, at least 99%, or 100% as measured by the Jaccard similarity coefficient. In certain embodiments, each pair of the genetically uniform set of potato plants (e.g., the genetically uniform set of F1 hybrids) has a pairwise identity of at least about 90%, at least about 95%, at least about 96%, at least about 97%, at least about 98%, at least about 99%, or about 100% as measured by the Jaccard similarity coefficient.

Methods of measuring genetic uniformity are known in the art. One exemplary method of measuring genetic uniformity is by using the Jaccard similarity coefficient, also known as the Jaccard index or Jaccard similarity index. In the context of molecular plant genetics, the Jaccard index, Jaccard similarity index, or Jaccard similarity coefficient (Jaccard, P. (1908) Nouvelles Recherches sur 1a Distribution Florale. Bulletin de la Société Vaudoise des Sciences Naturelles. Vol. 44), is commonly applied to quantify the pairwise genetic similarity or uniformity of plants based on the presence or absence of shared alleles at loci spread throughout the genome. Exemplary methods of using the Jaccard similarity coefficient to measure genetic uniformity between two plants are described in Example 1 below and, for example, in Paz and SVeilleux (1997. Genetic diversity based on randomly amplified polymorphic DNA (RAPD) and its relationship with the performance of diploid potato hybrids. Journal of the American Society for Horticultural Sci. 122 (6): 740-747), Vosman et al. (2004. The establishment of 'essential derivation' among rose varieties, using AFLP. Theoretical and Applied Genetics. 109:1718-1725), Noli et al. (2013. Criteria for the definition of similarity thresholds for identifying essentially derived varieties. Plant Breeding. 132 (6): 525-531), Vijayakumar et al. (2021. High temperature induced changes in quality and yield parameters of tomato (*Solanum lycopersicum* L.) and similarity coefficients among genotypes using SSR markers. Heliyon. 7 (2)), and Dalamu et al. (2023. Genetic Diversity and Population Structure Analyses Using Simple Sequence Repeat Markers and Phenotypic Traits in Native Potato Collection in India. Potato Research: 1-25). The Jaccard similarity coefficient is defined as the ratio of the number of shared items to the total number of distinct items in the two sets. In the context of molecular plant genetics, it quantifies the proportion of shared alleles between two plants. The formula for calculating the Jaccard similarity coefficient is:

$$J(A,B)=|A\cap B|/|A\cup B|$$

Where A represents the set of unique alleles without duplication in one plant, B represents the set of unique alleles without duplication in the other plant, $|A\cap B|$ represents the number of shared alleles (the cardinality of the intersection) between the plants, and $|A\cup B|$ represents the number of distinct alleles (the cardinality of the union) between the plants. This formula computes the cardinality of the intersection (common elements) of two sets (the shared alleles) divided by the cardinality of the union (all alleles) of the two sets (all distinct alleles present). The resulting value of the Jaccard similarity coefficient ranges from 0 to 1, where 0 indicates no shared alleles, and 1 indicates complete uniformity. The average pairwise genetic uniformity of the populations was calculated as the average Jaccard similarity of all possible pairs of plants within the population. In the context of genetic pairwise similarity estimations, the size of A should be the same as, or very close to the size of B to avoid misinterpretation.

Genetic Modifications

In some embodiments, the polyploid potato seed (e.g., the subpopulation of genetically uniform polyploid potato seed) comprises one or more genetic modifications. Genetic modifications may be generated by modification of any nucleic acid sequence or genetic element by insertion, deletion, or substitution of one or more nucleotides in a nucleic acid molecule. This can occur by a replacement of at least one nucleotide, a deletion of at least one nucleotide, an insertion of at least one nucleotide, a chemical alteration of at least one nucleotide, or a combination thereof as long as the result is a detectable (e.g., by PCR, DNA sequencing, chromatography, etc.) change of nucleotide sequence compared to the sequence of the nucleic acid molecule prior to modification. Such modifications can be achieved by any of several well-known methods known in the art including, but not limited to, random mutagenesis, genome editing, insertion of a recombinant nucleic acid, crossing of an unmodified plant with a modified plant to introduce the modification of the modified plant into the unmodified plant, and the like. A genetic modification may be naturally occurring or non-naturally occurring.

The genetic modifications described herein may be present in any known genetic element including, but not limited to, protein-coding sequences, non-protein-coding sequences, promoter regions, 5' untranslated leaders, genes, exons, introns, poly-A signal sequences, 3' untranslated regions, regions encoding small RNAs (such as microRNAs and small-interfering RNAs), and any other sequences that affect transcription or translation of one or more nucleic acid sequences. In some embodiments, genetic modifications may include, but are not limited to, modifying or replacing nucleotide sequences of interest (such as a regulatory elements), gene disruption, gene knockout, gene knockdown, gene knock-in, gene silencing (including, e.g., by expressing an inverted repeat into a gene of interest), RNA interference (including, e.g., by insertion and/or expression of an RNA interference construct), modification of methylation status, modification of splicing sites, introducing alternate splicing sites, or any combination thereof. As used herein, gene disruption refers to the alteration or insertion of a sequence into a gene or locus that results in decreased expression (including non-expression or altered activity) of a functional protein gene product. A gene disruption may be achieved by introduction of a genetic modification in a protein-coding sequence, including, but not limited to, as a missense or nonsense mutation, or an insertion, deletion, or substitution. As used herein, a knockout is a genetic modification wherein a gene or gene product has been rendered completely inoperative. A knockout of a gene product may be achieved by introduction of a genetic modification in a protein-coding sequence of a gene or any non-protein-coding or regulatory sequence described herein. As used herein, a knockdown is a genetic modification wherein a gene or gene product has been rendered partially inoperative. A knockdown of a gene product may be achieved by introduction of a genetic modification in a protein-coding sequence of a gene or in a non-protein-coding or regulatory sequence, or insertion of a trans-acting element, such as a construct that expresses an inverted repeat of the gene product or a construct that expresses a DNA- or RNA-binding protein such as a transcriptional repressor which may include, for example, a deactivated targeted nuclease such as deactivated Cas9 (dCas9). As used herein, knock-in represents the replacement or insertion of a DNA sequence at a specific DNA locus in a cell. Knock-ins may include, but are not limited to, specific insertion of a heterologous amino acid coding sequence in a coding region of a gene, an insertion of a transcriptional regulatory element in a genetic locus, or any of several methods of inserting a DNA sequence into a cell that are known to one of ordinary skill in the art.

In certain embodiments, the polyploid potato seed (e.g., the subpopulation of genetically uniform polyploid potato seed) comprises one or more genetic modifications resulting in decreased expression (including non-expression or altered activity) of a gene product of a genomic locus. In some embodiments, genetic modifications resulting in decreased expression (including non-expression or altered activity) of a gene product or locus may include, but are not limited to, modification of an enhancer, modification of a promoter, modification of a 5' untranslated leader, modification of a coding region, modification of a non-coding region, insertion and/or expression of an RNA interference construct that targets an mRNA, modification of a region encoding a small RNA, modification of methylation status of a genomic locus, expression of a repressor protein that targets a DNA or mRNA sequence, and any other sequences that affect transcription or translation of one or more nucleic acid sequences. In some embodiments, genetic modifications resulting in decreased expression (including non-expression or altered activity) of a gene product or locus may include, but are not limited to, modifying or replacing nucleotide sequences of interest (such as a regulatory elements), gene disruption, gene knockout, gene knockdown, gene knock-in, gene silencing (including, e.g., by inserting and/or expressing an inverted repeat into a gene of interest), RNA interference (including, e.g., by insertion and/or expression of an RNA interference construct), expression of a repressor protein (e.g. dCas9), modification of methylation status of gene loci, modification of splicing sites, introducing alternate splicing sites, or any combination thereof. In some variations, the genetic modification is positioned in the first 70%, the first 60%, the first 50%, the first 40%, the first 30%, the first 20%, or the first 10% of the nucleotides of the coding sequence of the genomic locus following the start codon in the 3' direction. In certain variations, the genetic modification is positioned in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction.

In some embodiments, one or more genetic modifications each independently comprise an insertion, a deletion, one or more nucleotide changes, or an inversion that results in decreased expression of the one or more genomic loci (e.g., MiMe loci). In some variations, the insertion, the deletion, the one or more nucleotide changes, or the inversion eliminates expression (e.g., eliminates activity) of the genomic locus. In some variations, the insertion, the deletion, the one or more nucleotide changes, or the inversion is positioned in the first 70%, the first 60%, the first 50%, the first 40%, the first 30%, the first 20%, or the first 10% of the nucleotides of the coding sequence of the genomic locus following the start codon in the 3' direction. In certain variations, the insertion, the deletion, the one or more nucleotide changes, or the inversion is positioned in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction. In some embodiments, the insertion, the deletion, the one or more nucleotide changes, or the inversion eliminates expression (e.g., eliminates activity) of the genomic locus. In some variations, the insertion, the deletion, the one or more nucleotide changes, or the inversion results in a premature stop codon present in the first 70%, the first 60%, the first 50%, the first 40%, the first 30%, the first 20%, or the first 10% of the nucleotides of the coding sequence of the MiMe locus following the start codon in the 3' direction, thereby eliminating expression (e.g., activity) of the genomic locus. In some variations, the insertion, the deletion, the one or more nucleotide changes, or the inversion results in a premature stop codon present in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction, thereby eliminating expression (e.g., activity) of the genomic locus.

In some embodiments, the one or more genetic modifications comprise one or more polynucleotide sequences selected from the group consisting of SEQ ID NOs: 127-129, 131-134, 137-154, and 156-159. In certain embodiments, the one or more genetic modifications comprise one or more polynucleotide sequences each having at least 80%, at least 85%, at least 90%, at least 95%, at least 96%, at least 97%, at least 98%, or at least 99% identity or complementarity to a nucleotide sequence selected from the group consisting of SEQ ID NOs: 127-129, 131-134, 137-154, and 156-159.

MiMe Loci, MiMe Genotypes, and MiMe Components

In some embodiments, the polyploid potato seed (e.g., the subpopulation of genetically uniform polyploid potato seed) comprises one or more genetic modifications resulting in decreased expression (including non-expression or altered activity) of one or more MiMe loci. In some variations, the polyploid potato seed (e.g., the subpopulation of genetically uniform polyploid potato seed) comprises one or more genetic modifications resulting in a decreased amount of a functional gene product encoded at one or more MiMe loci. The gene products at the MiMe loci may include, but are not limited to, nucleic acids (e.g. RNA), post-transcriptionally modified nucleic acids (e.g. spliced RNA, poly-adenylated mRNA), proteins (e.g. enzymes, structural proteins, etc.), and post-translationally modified proteins (e.g. glycoproteins, lipoproteins, etc.). The function of the gene product at the MiMe locus refers to the wild-type, unmodified function of the gene product. The decreased expression of a MiMe locus may refer to a decrease in the total amount of a gene product encoded at a MiMe locus present in a cell (e.g. a decrease in the amount of a protein, including up to no detectable expression) or to a decrease in the amount of a functional gene product encoded at a MiMe locus present in a cell (e.g. a decrease in the percentage of proteins with wild-type function, or an increase in the percentage of proteins with altered activity). In some embodiments, the one or more genetic modifications resulting in decreased expression of one or more MiMe loci may include, but are not limited to, modification of an enhancer in the MiMe loci, modification of a promoter of the MiMe loci, modification of a coding region in the MiMe loci, modification of methylation status of the MiMe loci, expression of a repressor protein that targets the DNA or an mRNA of the MiMe loci, and expression of an RNA interference construct that targets an mRNA from the MiMe loci. In some embodiments, the polyploid potato seed (e.g., the subpopulation of genetically uniform polyploid potato seed) may comprise one or more genetic modifications resulting in non-expression of one or more MiMe loci. In some embodiments, the polyploid potato seed (e.g., the subpopulation of genetically uniform polyploid potato seed) may comprise one or more genetic modifications resulting in decreased expression (including non-expression or altered activity) of a combination of two or more MiMe loci.

In some embodiments, the polyploid potato seed comprises one or more genetic modifications resulting in decreased expression of one or more MiMe loci. In other embodiments, the polyploid potato seed (e.g., the subpopulation of genetically uniform polyploid potato seed) comprises one or more genetic modifications resulting in decreased expression of two or more MiMe loci. In yet another embodiment, the polyploid potato seed (e.g., the subpopulation of genetically uniform polyploid potato seed) comprises one or more genetic modifications resulting in decreased expression of three or more MiMe loci. In some variations, the MiMe loci may include, but are not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, PS1-LIKE PROTEIN, JASON, PC1, PC2, and FC. In one variation, the polyploid potato seed (e.g., the subpopulation of genetically uniform polyploid potato seed) comprises one or more genetic modifications resulting in decreased expression of REC8. In a second variation, the polyploid potato seed (e.g., the subpopulation of genetically uniform polyploid potato seed) comprises one or more genetic modifications resulting in decreased expression of OSD1. In a third variation, the polyploid potato seed (e.g., the subpopulation of genetically uniform polyploid potato seed) comprises one or more genetic modifications resulting in decreased expression of PAIR1. In a fourth variation, the polyploid potato seed (e.g., the subpopulation of genetically uniform polyploid potato seed) comprises one or more genetic modifications resulting in decreased expression of SPO11-1, SPO11-2, or a combination thereof. In a fifth variation, the polyploid potato seed (e.g., the subpopulation of genetically uniform polyploid potato seed) comprises one or more genetic modifications resulting in decreased expression of REC8 and SPO11-1. In a sixth variation, the polyploid potato seed (e.g., the subpopulation of genetically uniform polyploid potato seed) comprises one or more genetic modifications resulting in decreased expression of REC8 and OSD1. In a seventh variation, the polyploid potato seed (e.g., the subpopulation of genetically uniform polyploid potato seed) comprises one or more genetic modifications resulting in decreased expression of REC8 and PAIR1. In an eighth variation, the polyploid potato seed (e.g., the subpopulation of genetically uniform polyploid potato seed) comprises one or more genetic modifications resulting in decreased expression of OSD1 and SPO11-1. In a ninth variation, the polyploid potato seed (e.g., the subpopulation of genetically uniform polyploid potato seed) comprises one or more genetic modifications resulting in decreased expression of OSD1 and PAIR1. In a tenth variation, the polyploid potato seed (e.g., the subpopulation of genetically uniform polyploid potato seed) comprises one or more genetic modifications resulting in decreased expression of REC8, OSD1, and PAIR1. In an eleventh variation, the polyploid potato seed (e.g., the subpopulation of genetically uniform polyploid potato seed) comprises one or more genetic modifications resulting in decreased expression of REC8, OSD1, and SPO11-1. In a twelfth variation, the polyploid potato seed (e.g., the subpopulation of genetically uniform polyploid potato seed) comprises one or more genetic modifications resulting in decreased expression of PS1 and SPO11-1. In a thirteenth variation, the polyploid potato seed (e.g., the subpopulation of genetically uniform polyploid potato seed) comprises one or more genetic modifications resulting in decreased expression of PS1 and SY3. In a fifteenth variation, the polyploid potato seed (e.g., the subpopulation of genetically uniform polyploid potato seed) is potato seed and comprises one or more genetic modifications resulting in decreased expression of PS1-LIKE PROTEIN and SPO11-1. In a sixteenth variation, the polyploid potato seed (e.g., the subpopulation of genetically uniform polyploid potato seed) is potato seed and comprises one or more genetic modifications resulting in decreased expression of PS1-LIKE PROTEIN and SY3. In a seventeenth variation, the polyploid potato seed (e.g., the subpopulation of genetically uniform polyploid potato seed) is potato seed and comprises one or more genetic modifications resulting in altered activity of TDM1 (e.g., a dominant negative, constitutively active or null mutant of TDM1). In an eighteenth variation, the polyploid potato seed (e.g., the subpopulation of genetically uniform polyploid potato seed) is potato seed and comprises one or more genetic modifications resulting in decreased expression of PS1-LIKE PROTEIN and SPO11-1. In a nineteenth variation, the polyploid potato seed (e.g., the subpopulation of genetically uniform polyploid potato seed) is potato and comprises one or more genetic modifications resulting in decreased expression of PS1-LIKE PROTEIN and SY3. In a twentieth variation, the polyploid potato seed (e.g., the subpopulation of genetically uniform polyploid potato seed) comprises one or more genetic modifications resulting in decreased expression of REC8, OSD1, SPO11-1, and PAIR1. In a twenty-first variation, the polyploid potato seed (e.g., the subpopulation of genetically uniform polyploid potato seed) comprises one or more genetic modifications resulting in decreased expression of PS1 or PS1-LIKE PROTEIN, SY3, and SPO11-1. The polyploid potato seed (e.g., the subpopulation of genetically uniform polyploid potato seed) may comprise one or more genetic modifications resulting in decreased expression of any combination of MiMe loci described herein or known in the art. In some embodiments, the polyploid potato seed (e.g., the subpopulation of genetically uniform polyploid potato seed) may comprise one or more genetic modifications resulting in non-expression of any combination of MiMe loci described here or known in the art. In further embodiments, the polyploid potato seed (e.g., the subpopulation of genetically uniform polyploid potato seed) may comprise one or more genetic modifications resulting in decreased expression (including non-expression or altered activity) of a combination of two or more MiMe loci described here or known in the art.

In some embodiments, the polyploid potato seed (e.g., the subpopulation of genetically uniform polyploid potato seed) comprises one or more genetic modifications resulting in decreased expression of REC8, SWITCH1/DYAD, or a combination thereof. In some variations, the polyploid potato seed (e.g., the subpopulation of genetically uniform polyploid potato seed) comprises one or more genetic modifications resulting in decreased expression of REC8, SWITCH1/DYAD, or a combination thereof and one or more genetic modifications resulting in decreased expression of one or more additional MiMe loci. In additional variations, the polyploid potato seed (e.g., the subpopulation of genetically uniform polyploid potato seed) comprises one or more genetic modifications resulting in decreased expression of REC8, SWITCH1/DYAD, or a combination thereof and one or more genetic modifications resulting in decreased expression of one or more additional MiMe loci which may include, but are not limited to, OSD1, CYCA1, TDM1, PC1, PC2, and FC. In yet additional variations, the polyploid potato seed (e.g., the subpopulation of genetically uniform polyploid potato seed) comprises one or more genetic modifications resulting in decreased expression of REC8, SWITCH1/DYAD, or a combination thereof; one or more genetic modifications resulting in decreased expression of OSD1, CYCA1, TDM1, PC1, PC2, FC, or any combination thereof; and one or more genetic modifications resulting in decreased expression of one or more additional MiMe loci, which may include, but are not limited to, PAIR1, SPO11-1, SPO11-2, PRD1, PRD2, DFO, MTOPVIB, DSY1, SY1, SY2, SY3, and SY4.

In some embodiments, the polyploid potato seed (e.g., the subpopulation of genetically uniform polyploid potato seed) comprises one or more genetic modifications resulting in decreased expression of one or more MiMe loci which may include, but are not limited to, OSD1, CYCA1, TDM1, PC1, PC2, and FC. In some variations, the polyploid potato seed (e.g., the subpopulation of genetically uniform polyploid potato seed) comprises one or more genetic modifications resulting in decreased expression of OSD1, CYCA1, TDM1, PC1, PC2, FC, or any combination thereof and further comprises one or more genetic modifications resulting in decreased expression of one or more additional MiMe loci, which may include, but are not limited to, PAIR1, SPO11-1, SPO11-2, PRD1, PRD2, DFO, MTOPVIB, DSY1, SY1, SY2, SY3, and SY4.

In some embodiments, the polyploid potato seed (e.g., the subpopulation of genetically uniform polyploid potato seed) comprises one or more genetic modifications resulting in decreased expression of one or more MiMe loci which may include, but are not limited to, PAIR1, SPO11-1, SPO11-2, PRD1, PRD2, DFO, MTOPVIB, DSY1, SY1, SY2, SY3, and SY4. In some variations, the polyploid potato seed (e.g., the subpopulation of genetically uniform polyploid potato seed) comprises one or more genetic modifications resulting in decreased expression of PAIR1, SPO11-1, SPO11-2, PRD1, PRD2, DFO, MTOPVIB, DSY1, SY1, SY2, SY3, SY4, or any combination thereof, and further comprises one or more genetic modifications resulting in decreased expression of one or more additional MiMe loci, which may include, but are not limited to PS1, PS1-LIKE PROTEIN, and JASON.

In some embodiments, each of the one or more MiMe loci encodes a protein of a MiMe component as described herein. In certain embodiments, each of the one or more MiMe loci encodes a protein having an amino acid sequence selected from the group consisting of SEQ ID NOs: 1-16. In some variations, each of the one or more MiMe loci encodes a protein having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to an amino acid sequence selected from the group consisting of SEQ ID NOs: 1-16.

In some embodiments, the population of polyploid potato seed or the subpopulation of genetically uniform polyploid potato seed has a complete MiMe genotype. In alternative embodiments, the population of polyploid potato seed or the subpopulation of genetically uniform polyploid potato seed has a partial MiMe genotype. In still other embodiments, the population of polyploid potato seed or the subpopulation of genetically uniform polyploid potato seed has a partially-complemented MiMe genotype. In certain embodiments, the complete, partial, or partially-complemented MiMe genotype comprises one or more genetic modifications resulting in decreased expression of one or more MiMe loci. In other embodiments, the complete, partial, or partially-complemented MiMe genotype comprises one or more genetic modifications resulting in decreased expression of two or more MiMe loci. In yet another embodiment, the complete, partial, or partially-complemented MiMe genotype comprises one or more genetic modifications resulting in decreased expression of three or more MiMe loci. In some variations, the MiMe loci may include, but are not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, PS1-LIKE PROTEIN, JASON, PC1, PC2, and FC. In one variation, the complete, partial, or partially-complemented MiMe genotype comprises one or more genetic modifications resulting in decreased expression of REC8. In a second variation, the complete, partial, or partially-complemented MiMe genotype comprises one or more genetic modifications resulting in decreased expression of OSD1. In a third variation, the complete, partial, or partially-complemented MiMe genotype comprises one or more genetic modifications resulting in decreased expression of PAIR1. In a fourth variation, the complete, partial, or partially-complemented MiMe genotype comprises one or more genetic modifications resulting in decreased expression of SPO11-1, SPO11-2, or a combination thereof. In a fifth variation, the complete, partial, or partially-complemented MiMe genotype comprises one or more genetic modifications resulting in decreased expression of REC8 and SPO11-1. In a sixth variation, the complete, partial, or partially-complemented MiMe genotype comprises one or more genetic modifications resulting in decreased expression of REC8 and OSD1. In a seventh variation, the complete, partial, or partially-complemented MiMe genotype comprises one or more genetic modifications resulting in decreased expression of REC8 and PAIR1. In an eighth variation, the complete, partial, or partially-complemented MiMe genotype comprises one or more genetic modifications resulting in decreased expression of OSD1 and SPO11-1. In a ninth variation, the complete, partial, or partially-complemented MiMe genotype comprises one or more genetic modifications resulting in decreased expression of OSD1 and PAIR1. In a tenth variation, the complete, partial, or partially-complemented MiMe genotype comprises one or more genetic modifications resulting in decreased expression of REC8, OSD1, and PAIR1. In an eleventh variation, the complete, partial, or partially-complemented MiMe genotype comprises one or more genetic modifications resulting in decreased expression of REC8, OSD1, and SPO11-1. In a twelfth variation, the complete, partial, or partially-complemented MiMe genotype comprises one or more genetic modifications resulting in decreased expression of PS1 and SPO11-1. In a thirteenth variation, the complete, partial, or partially-complemented MiMe genotype comprises one or more genetic modifications resulting in decreased expression of PS1 and SY3. In a fifteenth variation, the population of polyploid potato seed is potato seed, and the complete, partial, or partially-complemented MiMe genotype comprises one or more genetic modifications resulting in decreased expression of PS1-LIKE PROTEIN and SPO11-1. In a sixteenth variation, the population of polyploid potato seed is potato seed, and the complete, partial, or partially-complemented MiMe genotype comprises one or more genetic modifications resulting in decreased expression of PS1-LIKE PROTEIN and SY3. In a seventeenth variation, the population of polyploid potato seed is potato seed, and the complete, partial, or partially-complemented MiMe genotype comprises one or more genetic modifications resulting in altered activity of TDM1 (e.g., a dominant negative, constitutively active or null mutant of TDM1). In an eighteenth variation, the polyploid potato seed is potato seed and the complete, partial, or partially-complemented MiMe genotype comprises one or more genetic modifications resulting in decreased expression of PS1-LIKE PROTEIN and SPO11-1. In a nineteenth variation, the polyploid seed is potato seed and the complete, partial, or partially-complemented MiMe genotype comprises one or more genetic modifications resulting in decreased expression of PS1-LIKE PROTEIN and SY3. In a twentieth variation, the complete, partial, or partially-complemented MiMe genotype comprises one or more genetic modifications resulting in decreased expression of REC8, OSD1, SPO11-1, and PAIR1. In a twenty-first variation, the complete, partial, or partially-complemented MiMe genotype comprises one or more genetic modifications resulting in decreased expression of PS1 or PS1-LIKE PROTEIN, SY3, and SPO11-1. The complete, partial, or partially-complemented MiMe genotype may comprise one or more genetic modifications resulting in decreased expression of any combination of MiMe loci described herein or known in the art, wherein a plant that has the complete MiMe genotype exhibits a MiMe phenotype. In some embodiments, the complete, partial, or partially-complemented MiMe genotype may comprise one or more genetic modifications resulting in non-expression of any combination of MiMe loci described here or known in the art wherein a plant that has the complete MiMe genotype exhibits a MiMe phenotype. In further embodiments, the complete, partial, or partially-complemented MiMe genotype may comprise one or more genetic modifications resulting in decreased expression (including non-expression or altered activity) of a combination of two or more MiMe loci described here or known in the art, wherein a plant that has the complete MiMe genotype exhibits a MiMe phenotype. Specific examples of complete MiMe genotypes are shown in Table 6.

In some embodiments, the complete, partial, or partially-complemented MiMe genotype comprises one or more genetic modifications resulting in decreased expression of REC8, SWITCH1/DYAD, or a combination thereof. In some variations, the complete, partial, or partially-complemented MiMe genotype comprises one or more genetic modifications resulting in decreased expression of REC8, SWITCH1/DYAD, or a combination thereof and one or more genetic modifications resulting in decreased expression of one or more additional MiMe loci. In additional variations, the complete, partial, or partially-complemented MiMe genotype comprises one or more genetic modifications resulting in decreased expression of REC8, SWITCH1/DYAD, or a combination thereof and one or more genetic modifications resulting in decreased expression of one or more additional MiMe loci, including, but not limited to, OSD1, CYCA1, TDM1, PC1, PC2, and FC. In yet additional variations, the complete, partial, or partially-complemented MiMe genotype comprises one or more genetic modifications resulting in decreased expression of REC8, SWITCH1/DYAD, or a combination thereof; one or more genetic modifications resulting in decreased expression of OSD1, CYCA1, TDM1, PC1, PC2, FC, or any combination thereof; and one or more genetic modifications resulting in decreased expression of one or more additional MiMe loci, including, but not limited to, PAIR1, SPO11-1, SPO11-2, PRD1, PRD2, DFO, MTOPVIB, DSY1, SY1, SY2, SY3, and SY4.

In some embodiments, the complete, partial, or partially-complemented MiMe genotype comprises one or more genetic modifications resulting in decreased expression of one or more MiMe loci including, but not limited to, OSD1, CYCA1, TDM1, PC1, PC2, and FC. In some variations, the complete, partial, or partially-complemented MiMe genotype comprises one or more genetic modifications resulting in decreased expression of OSD1, CYCA1, TDM1, PC1, PC2, FC, or any combination thereof and further comprises one or more genetic modifications resulting in decreased expression of one or more additional MiMe loci, including, but not limited to, PAIR1, SPO11-1, SPO11-2, PRD1, PRD2, DFO, MTOPVIB, DSY1, SY1, SY2, SY3, and SY4.

In some embodiments, the complete, partial, or partially-complemented MiMe genotype comprises one or more genetic modifications resulting in decreased expression of one or more MiMe loci including, but not limited to, PAIR1, SPO11-1, SPO11-2, PRD1, PRD2, DFO, MTOPVIB, DSY1, SY1, SY2, SY3, and SY4. In some variations, the complete, partial, or partially-complemented MiMe genotype comprises one or more genetic modifications resulting in decreased expression of PAIR1, SPO11-1, SPO11-2, PRD1, PRD2, DFO, MTOPVIB, DSY1, SY1, SY2, SY3, SY4, or any combination thereof, and further comprises one or more genetic modifications resulting in decreased expression of one or more additional MiMe loci, which may include, but are not limited to PS1, PS1-LIKE PROTEIN, and JASON.

In some embodiments, the population of polyploid potato seed or the subpopulation of genetically uniform polyploid potato seed has a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

In other embodiments, the population of polyploid potato seed or the subpopulation of genetically uniform polyploid potato seed has a partial MiMe genotype comprising (a) one or more MiMe alleles conferring decreased expression of one or more MiMe loci of each of a first, second, and third MiMe component; and (b) one or more non-MiMe alleles at the one or more MiMe loci of each of the first, second, and third MiMe components wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the partial MiMe genotype comprises one or more non-MiMe alleles at the one or more MiMe loci of each of the first, second, and third MiMe components. In other variations, the partial MiMe genotype comprises two or more non-MiMe alleles at the one or more MiMe loci of each of the first, second, and third MiMe components.

In some embodiments, the population of polyploid potato seed or the subpopulation of genetically uniform polyploid potato seed has a complete MiMe genotype comprising MiMe alleles conferring decreased expression of one or more MiMe loci each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In some variations, the population of polyploid potato seed or the subpopulation of genetically uniform polyploid potato seed having a complete MiMe genotype comprising MiMe alleles conferring decreased expression of MiMe loci of (2) a component of DNA double strand breakage during meiotic recombination and (4) a component of progression through the first division of meiosis exhibits a MiMe phenotype in male germline cells and/or produces clonal male gametes, and exhibits a wild-type meiosis phenotype in female germline cells and/or produces haploid female gametes.

In other embodiments, the population of polyploid potato seed or the subpopulation of genetically uniform polyploid potato seed has a partial MiMe genotype comprising (a) one or more MiMe alleles conferring decreased expression of one or more MiMe loci of each of a first and second MiMe component; and (b) one or more non-MiMe alleles at the one or more MiMe loci of each of the first and second MiMe components wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In some variations, the partial MiMe genotype comprises one or more non-MiMe alleles at the one or more MiMe loci of each of the first and second MiMe components. In other variations, the partial MiMe genotype comprises two or more non-MiMe alleles at the one or more MiMe loci of each of the first and second MiMe components.

In yet other embodiments, the population of polyploid potato seed or the subpopulation of genetically uniform polyploid potato seed has (i) at least a first and second haplotype, each comprising one or more MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the third haplotype comprises a non-MiMe allele at the one or more MiMe loci of one or more of the first, second, and third MiMe components.

In still other embodiments, the population of polyploid potato seed or the subpopulation of genetically uniform polyploid potato seed has (i) at least a first and second haplotype, each comprising one or more MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the third haplotype comprises a non-MiMe allele at the one or more MiMe loci of one or more of the first and second MiMe components.

In some embodiments, the population of polyploid potato seed or the subpopulation of genetically uniform polyploid potato seed has a partially-complemented MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the partially-complemented MiMe genotype comprises (a) only MiMe alleles at one or more MiMe loci of the first MiMe component; (b) one or more MiMe alleles and one or more non-MiMe alleles at a first MiMe locus of the second MiMe component, and one or more MiMe alleles and one or more non-MiMe alleles at a second MiMe locus of the second MiMe component; and (c) either (i) only MiMe alleles at one or more MiMe loci of the third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component. In some embodiments, the partially-complemented MiMe genotype comprises (a) only MiMe alleles at one or more MiMe loci of a component of sister chromatid cohesion during the first division of meiosis; (b) one or more MiMe alleles and one or more non-MiMe alleles at a first MiMe locus of a component of DNA double strand breakage during meiotic recombination, and one or more MiMe alleles and one or more non-MiMe alleles at a second MiMe locus of the component of DNA double strand breakage during meiotic recombination; and (c) either (i) only MiMe alleles at one or more MiMe loci of a component of progression through the second division of meiosis, or (ii) one or more MiMe alleles and one or more non-MiMe alleles at a first MiMe locus of a component of progression through the second division of meiosis, and one or more MiMe alleles and one or more non-MiMe alleles at a second MiMe locus of the component of progression through the second division of meiosis. Exemplary MiMe loci of each of said MiMe components are extensively described herein below. In one embodiment, the partially-complemented MiMe genotype comprises (a) only MiMe alleles of REC8; (b) one or more MiMe alleles and one or more non-MiMe alleles of SPO11-1, and one or more MiMe alleles and one or more non-MiMe alleles of PAIR1; and (c) only MiMe alleles of OSD1.

In other embodiments, the population of polyploid potato seed or the subpopulation of genetically uniform polyploid potato seed has a partially-complemented MiMe genotype comprising MiMe alleles conferring decreased expression of one or more MiMe loci each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In some variations, the population of polyploid potato seed or the subpopulation of genetically uniform polyploid potato seed having a partially-complemented MiMe genotype comprising MiMe alleles conferring decreased expression of MiMe loci of (2) a component of DNA double strand breakage during meiotic recombination and (4) a component of progression through the first division of meiosis exhibits neither a MiMe phenotype nor a wild-type meiosis phenotype in male germline cells and does not produce viable male gametes, and exhibits a wild-type meiosis phenotype in female germline cells and/or produces viable haploid female gametes. In some embodiments, the partially-complemented MiMe genotype comprises (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component. In certain embodiments, the partially-complemented MiMe genotype comprises (a) only MiMe alleles at one or more MiMe loci of a component of DNA double strand breakage during meiotic recombination; and (b) one or more MiMe alleles and one or more non-MiMe alleles at a first MiMe locus of a component of progression through the first division of meiosis, and one or more MiMe alleles and one or more non-MiMe alleles at a second MiMe locus of the component of progression through the first division of meiosis. In other embodiments, the partially-complemented MiMe genotype comprises (a) only MiMe alleles at one or more MiMe loci of a component of progression through the first division of meiosis; and (b) one or more MiMe alleles and one or more non-MiMe alleles at a first MiMe locus of a component of DNA double strand breakage during meiotic recombination and one or more MiMe alleles and one or more non-MiMe alleles at a second MiMe locus of the component of DNA double strand breakage during meiotic recombination. Exemplary MiMe loci of each of said MiMe components are extensively described below.

In some embodiments, the population of polyploid potato seed or the subpopulation of genetically uniform polyploid potato seed has a partially-complemented MiMe genotype comprising MiMe alleles conferring decreased expression of one or more MiMe loci of a first, second, third, and fourth MiMe component are selected from the group consisting of (1) a component of sister chromatid cohesion during the first division of meiosis, (2) a component of DNA double strand breakage during meiotic recombination, (3) a component of progression through the second division of meiosis, and (4) a component of progression through the first division of meiosis. In certain embodiments, the partially-complemented genotype comprises (a) only MiMe alleles at one or more MiMe loci of the first MiMe component, wherein the first MiMe component is a component of DNA double strand breakage during meiotic recombination; (b) one or more MiMe alleles and one or more non-MiMe alleles at one or more MiMe loci of the second MiMe component; (c) one or more MiMe alleles and one or more non-MiMe alleles at one or more MiMe loci of the third MiMe component; (d) one or more MiMe alleles and one or more non-MiMe alleles at one or more MiMe loci of the fourth MiMe component. In some embodiments, the partially-complemented genotype comprises (a) only MiMe alleles at one or more MiMe loci of a component of DNA double strand breakage during meiotic recombination; (b) one or more MiMe alleles and one or more non-MiMe alleles at one or more MiMe loci of a component of sister chromatid cohesion during the first division of meiosis; (c) one or more MiMe alleles and one or more non-MiMe alleles at one or more MiMe loci of a component of progression through the second division of meiosis; (d) one or more MiMe alleles and one or more non-MiMe alleles at one or more MiMe loci of a component of progression through the first division of meiosis. Exemplary MiMe loci of each of said MiMe components are extensively described below. In one variation, the partially-complemented genotype comprises (a) only MiMe alleles at SPO11-1; (b) one or more MiMe alleles and one or more non-MiMe alleles at REC8; (c) one or more MiMe alleles and one or more non-MiMe alleles at OSD1; (d) one or more MiMe alleles and one or more non-MiMe alleles at PS1 or JASON.

In certain embodiments, the complete MiMe genotype, the partial MiMe genotype, or the partiall-complemeneted MiMe genotype comprises one or more alleles that result in the production of unreduced (2n) gametes. The one or more alleles that result in the production of unreduced (2n) gametes can be a naturally occurring allele such as, for example, an os allele or a ps allele. os alleles are known in the art and described in, for example, J. E. Werner & S. J. Peloquin (Inheritance and Two Mechanisms of 2n Egg Fromation in 2× Potatoes, *Journal of Heredity*, Volume 81, Issue 5, September 1990, Pages 371-374) and J. E. Werner & S. J. Peloquin (Occurrence and mechanisms of 2n egg formation in 2× potato. Genome. 34 (6): 975-982). ps alleles are known in the art and described in, for example, Mok, D. W. S. & Peloquin, S. (1975. Breeding value of 2n pollen (diplandroids) in tetraploid×diploid crosses in potatoes. Theor. Appl. Genet. 46:307-314) and Watanabe K. (2015. Potato genetics, genomics, and applications. Breed Sci. 65 (1): 53-68).

In some embodiments, the population of polyploid potato seed or the subpopulation of genetically uniform polyploid potato seed has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid potato seed or the subpopulation of genetically uniform polyploid potato seed has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the population of polyploid potato seed or the subpopulation of genetically uniform polyploid potato seed has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid potato seed or the subpopulation of genetically uniform polyploid potato seed has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid potato seed or the subpopulation of genetically uniform polyploid potato seed has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid potato seed or the subpopulation of genetically uniform polyploid potato seed has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid potato seed or the subpopulation of genetically uniform polyploid potato seed has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid potato seed or the subpopulation of genetically uniform polyploid potato seed has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the population of polyploid potato seed or the subpopulation of genetically uniform polyploid potato seed has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid potato seed or the subpopulation of genetically uniform polyploid potato seed has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid potato seed or the subpopulation of genetically uniform polyploid potato seed has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In some embodiments, the population of polyploid potato seed or the subpopulation of genetically uniform polyploid potato seed has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the population of polyploid potato seed or the subpopulation of genetically uniform polyploid potato seed has a complete MiMe genotype comprising (i) an os allele, wherein the subpopulation of genetically uniform polyploid potato seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid potato seed or the subpopulation of genetically uniform polyploid potato seed has a partial MiMe genotype comprising (i) an os allele, wherein the subpopulation of genetically uniform polyploid potato seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid potato seed or the subpopulation of genetically uniform polyploid potato seed has a complete MiMe genotype comprising (i) a ps allele, wherein the subpopulation of genetically uniform polyploid potato seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1. In some embodiments, the population of polyploid potato seed or the subpopulation of genetically uniform polyploid potato seed has a partial MiMe genotype comprising (i) a ps allele, wherein the subpopulation of genetically uniform polyploid potato seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the population of polyploid potato seed or the subpopulation of genetically uniform polyploid potato seed has a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more only MiMe alleles at one or more SPO11-1 loci, wherein each of the MiMe alleles at the SPO11-1 locus comprise one or more genetic modifications resulting in decreased expression of SPO11-1.

In some embodiments, the population of polyploid potato seed or the subpopulation of genetically uniform polyploid potato seed has a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

In some embodiments, the population of polyploid potato seed or the subpopulation of genetically uniform polyploid potato seed has a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1.

In some embodiments, the population of polyploid potato seed or the subpopulation of genetically uniform polyploid potato seed has a partially complemented MiMe genotype comprising (i) a ps allele, wherein the subpopulation of genetically uniform polyploid potato seed is heterozygous for the ps allele, (ii) an os allele, wherein the subpopulation of genetically uniform polyploid potato seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1.

In some embodiments, the population of polyploid potato seed or the subpopulation of genetically uniform polyploid potato seed has a partially complemented MiMe genotype comprising (i) an os allele, wherein the subpopulation of genetically uniform polyploid potato seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

In some embodiments, the subpopulation of genetically uniform polyploid potato seed comprises one or more polynucleotide sequences selected from the group consisting of SEQ ID NOs: 127-129, 131-134, 137-154, and 156-159.

In some embodiments, the population of polyploid potato seed is from a potato plant, and the subpopulation of genetically uniform polyploid potato seed comprises one or more polynucleotide sequences selected from the group consisting of SEQ ID NOs: 127-129, 131-134, 137-154, and 156-159. In certain embodiments, the subpopulation of genetically uniform polyploid potato seed comprises a MiMe allele at each of one or more SPO11-1 loci, each independently comprising a polynucleotide sequence selected from the group consisting of SEQ ID NOs: 127-129. In certain embodiments, the subpopulation of genetically uniform polyploid potato seed comprises a) a MiMe allele at one or more REC8 loci, each independently comprising a polynucleotide sequence selected from the group consisting of SEQ ID NOs: 131 and 132; and/or b) a MiMe allele at one or more SPO11-1 loci, each independently comprising a polynucleotide sequence selected from the group consisting of SEQ ID NOs: 133 and 134. In certain embodiments, the subpopulation of genetically uniform polyploid potato seed comprises a) a MiMe allele at one or more REC8 loci, each independently comprising a polynucleotide sequence selected from the group consisting of SEQ ID NOs: 137 and 138; and/or b) a MiMe allele at one or more SPO11-1 loci, each independently comprising a polynucleotide sequence selected from the group consisting of SEQ ID NOs: 139 and 140. In certain embodiments, the subpopulation of genetically uniform polyploid potato seed comprises a MiMe allele at one or more SPO11-1 loci, each independently comprising a polynucleotide sequence selected from the group consisting of SEQ ID NOs: 141 and 142. In certain embodiments, the subpopulation of genetically uniform polyploid potato seed comprises a) a MiMe allele at one or more CYCA1 loci, each independently: comprising a polynucleotide sequence selected from the group consisting of SEQ ID NOs: 143 and 144; b) a MiMe allele at one or more REC8 loci, each independently comprising a polynucleotide sequence selected from the group consisting of SEQ ID NOs: 145 and 146; and/or c) a MiMe allele at one or more SPO11-1 loci, each independently comprising a polynucleotide sequence selected from the group consisting of SEQ ID NOs: 147 and 148. In certain embodiments, the subpopulation of genetically uniform polyploid potato seed comprises a) a MiMe allele at one or more CYCA1 loci, each independently comprising a polynucleotide sequence selected from the group consisting of SEQ ID NOs: 149 and 150; b) a MiMe allele at one or more REC8 loci, each independently comprising a polynucleotide sequence selected from the group consisting of SEQ ID NOs: 151 and 152; and/or c) a MiMe allele at one or more SPO11-1 loci, each independently comprising a polynucleotide sequence selected from the group consisting of SEQ ID NOs: 153 and 154. In certain embodiments, the subpopulation of genetically uniform polyploid potato seed comprises a) a MiMe allele at one or more REC8 loci, each independently comprising a polynucleotide sequence selected from the group consisting of SEQ ID NOs: 156 and 157; and/or b) a MiMe allele at one or more SPO11-1 loci, each independently comprising a polynucleotide sequence selected from the group consisting of SEQ ID NOs: 158 and 159. In some variations, each the one or more CYCA1 loci, the one or more REC8 loci, and/or the one or more SPO11-1 loci are present on a different homologous chromosome.

In some embodiments, the population of polyploid potato seed comprises one or more genetic modifications resulting in decreased expression of one or more MiMe loci. In certain embodiments, the genetic modification resulting in decreased expression of a MiMe locus is positioned in the first 70%, the first 60%, the first 50%, the first 40%, the first 30%, the first 20%, or the first 10% of the nucleotides of the coding sequence of the MiMe locus following the start codon in the 3' direction. In some embodiments, the genetic modification resulting in decreased expression of a MiMe locus is positioned in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the MiMe locus following the start codon in the 3' direction. In some embodiments, the genetic modification resulting in decreased expression of a MiMe locus is an insertion, a deletion, one or more nucleotide changes, or an inversion. In some variations, the insertion, the deletion, the one or more nucleotide changes, or the inversion eliminates expression (e.g., eliminates activity) of the MiMe locus. In certain embodiments, the insertion, the deletion, the one or more nucleotide changes, or the inversion is positioned in the first 70%, the first 60%, the first 50%, the first 40%, the first 30%, the first 20%, or the first 10% of the nucleotides of the coding sequence of the MiMe locus following the start codon in the 3' direction. In certain embodiments, the insertion, the deletion, the one or more nucleotide changes, or the inversion is positioned in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the MiMe locus following the start codon in the 3' direction. In certain embodiments, the insertion, the deletion, the one or more nucleotide changes, or the inversion results in a premature stop codon present in the first 70%, the first 60%, the first 50%, the first 40%, the first 30%, the first 20%, or the first 10% of the nucleotides of the coding sequence of the MiMe locus following the start codon in the 3' direction, thereby eliminating expression (e.g., activity) of the MiMe locus. In certain embodiments, the insertion, the deletion, the one or more nucleotide changes, or the inversion results in a premature stop codon present in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the MiMe locus following the start codon in the 3' direction, thereby eliminating expression (e.g., activity) of the MiMe locus.

In some embodiments, the one or more genetic modifications resulting in decreased expression of one or more MiMe loci comprise one or more sequences selected from the group consisting of SEQ ID NOs: 127-129, 131-134, 137-154, and 156-159.

Components of Sister Chromatid Cohesion During the First Division of Meiosis.

In some embodiments, the complete, partial, or partially-complemented MiMe genotype comprises one or more MiMe alleles conferring decreased expression of one or more MiMe loci of a component of sister chromatid cohesion during the first division of meiosis. In certain embodiments, the one or more MiMe loci of the component of sister chromatid cohesion during the first division of meiosis comprise REC8, SWITCH1/DYAD, or a combination thereof. One of skill in the art will understand that MiMe loci that are components of sister chromatid cohesion during the first division of meiosis are not limited to REC8 and SWITCH1/DYAD, and may include any loci encoding gene products required for sister chromatid cohesion during the first division of meiosis. By way of example only, a gene product of the component of sister chromatid cohesion during the first division of meiosis is exemplified by a REC8 protein and specifically by the REC8 protein sequences, sequence alignments, and percent identities described in "MiMe Gene Product Sequences" below. Representative REC8 protein sequences from dicotyledonous plants (SEQ ID NOs: 1 and 12) are provided in the sequence listing as outlined in Table 5, including eight native sequences and a consensus sequence identified by multiple sequence alignment of the eight native sequences (Sequence Alignment 1). Table 1 shows a matrix of percent identities of the REC8 protein sequences from dicotyledonous plants, and a phylogenetic tree showing the relationship between the sequences is shown in FIG. 1. The gene products of MiMe loci of the component of sister chromatid cohesion during the first division of meiosis include REC8 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to any one of the REC8 proteins of SEQ ID NOs: 1 and 12.

There is an abundance of known REC8 gene products from potato including the following, which sequence is hereby incorporated by reference in its form as of the effective filing date. Exemplary REC8 gene products from potato include those of, by way of example, *Solanum tuberosum* (XP 006347252.1).

A gene product of the component of sister chromatid cohesion during the first division of meiosis is also exemplified by a SWITCH1 protein. There is an abundance of known SWITCH1 gene products from potato including the following, which sequence is hereby incorporated by reference in its form as of the effective filing date. Exemplary SWITCH1 gene products from potato include those of, by way of example, *Solanum tuberosum* (M1BMI9).

Components of DNA Double Strand Breakage During Meiotic Recombination.

Figure 2:
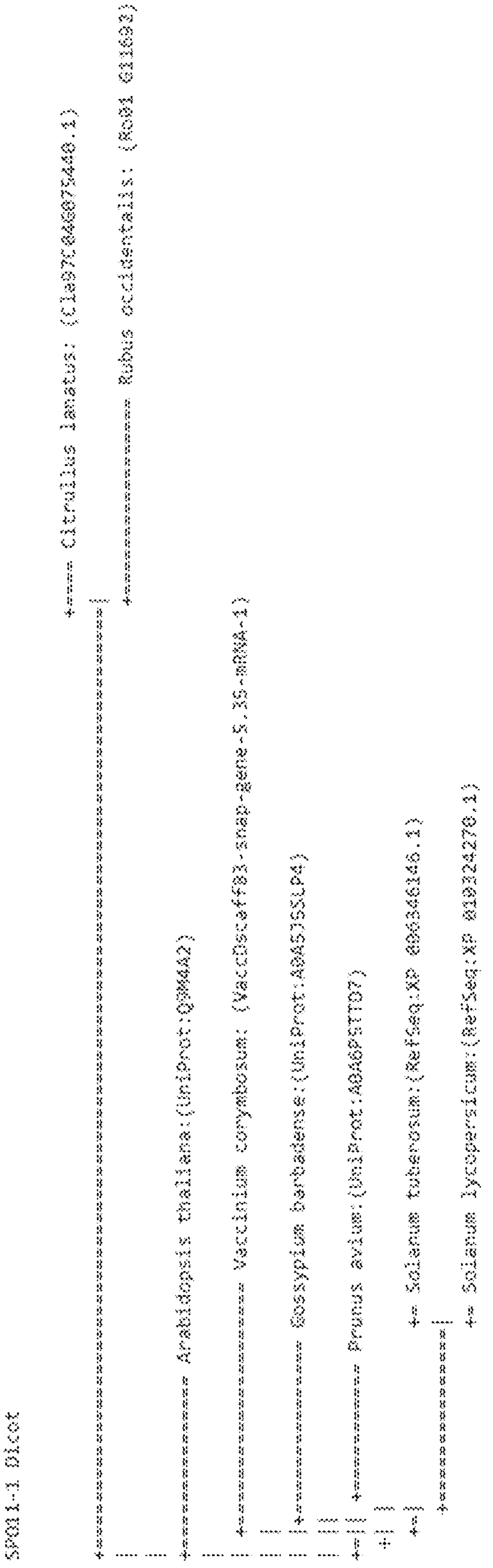
FIG. 2 depicts a phylogenetic tree of SPO11-1 protein sequences from dicotyledonous plants.

In some embodiments, the complete, partial, or partially-complemented MiMe genotype comprises one or more MiMe alleles conferring decreased expression of one or more MiMe loci of a component of DNA double strand breakage during meiotic recombination. In certain embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. One of skill in the art will understand that MiMe loci of the component of DNA double strand breakage during meiotic recombination are not limited to PAIR1, SPO11-1, SPO11-2, PRD1, PRD2, DFO, MTOPVIB, DSY1, SY1, SY2, SY3, and SY4 and may include any loci encoding gene products required for DNA double strand breakage during meiotic recombination. By way of example only, a gene product of the component of DNA double strand breakage during meiotic recombination is exemplified by a SPO11-1 protein and specifically by the SPO11-1 protein sequences, sequence alignments, and percent identities described in "MiMe Gene Product Sequences" below. Representative SPO11-1 protein sequences from dicotyledonous plants (SEQ ID NOs: 2 and 13) are provided in the sequence listing as outlined in Table 5, including eight native sequences and a consensus sequence identified by multiple sequence alignment of the eight native sequences (Sequence Alignment 2). Table 2 shows a matrix of percent identities of the SPO11-1 protein sequences from dicotyledonous plants, and a phylogenetic tree showing the relationship between the sequences is shown in FIG. 2. The gene products of MiMe loci of the component of DNA double strand breakage during meiotic recombination include SPO11-1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to any one of the SPO11-1 proteins of SEQ ID NOs: 2 and 13.

There is an abundance of known SPO11-1 gene products from potato including all of the following, which sequences are hereby incorporated by reference in their form as of the effective filing date. Exemplary SPO11-1 gene products from potato include those of, by way of example, *Solanum tuberosum* (XP 006346146.1, M1C0B8, and M1CP72).

A gene product of the component of DNA double strand breakage during meiotic recombination is also exemplified by a SPO11-2 protein. There is an abundance of known SPO11-2 gene products from potato including all of the following, which sequences are hereby incorporated by reference in their form as of the effective filing date. Exemplary SPO11-2 gene products from potato include those of, by way of example, *Solanum tuberosum* (XP 006344018.1, XP 006367265.1 and M1CP72) and *Solanum chacoense* (A0A0V0I1Z4).

Figure 3:
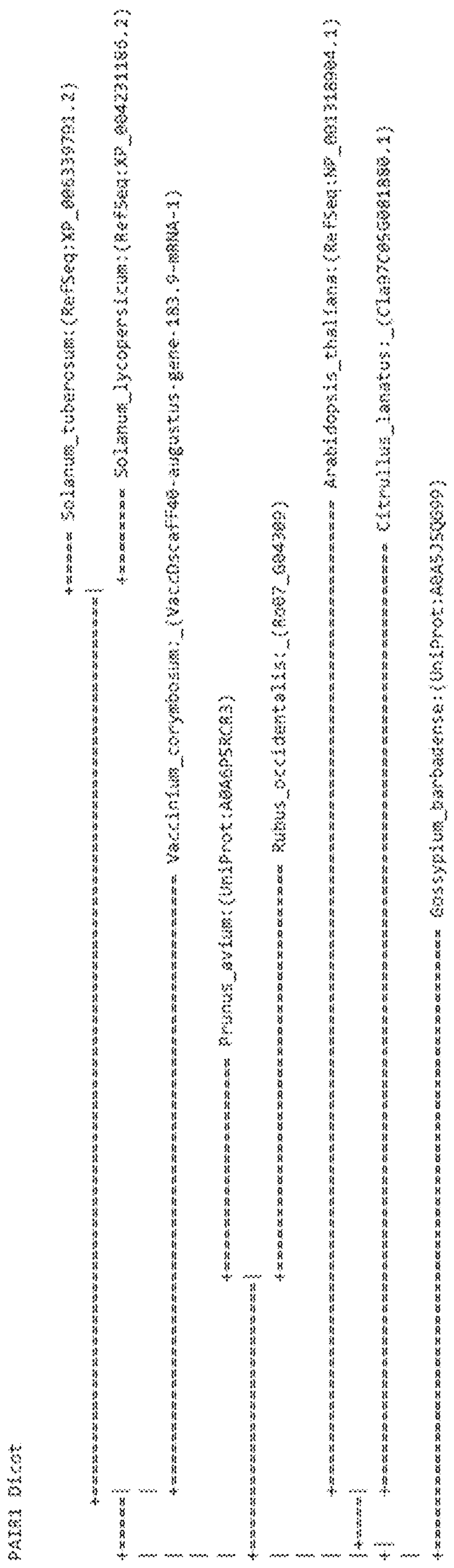
FIG. 3 depicts a phylogenetic tree of PAIR1 protein sequences from dicotyledonous plants.

A gene product of the component of DNA double strand breakage during meiotic recombination is also exemplified by a PAIR1 protein and specifically by the PAIR1 protein sequences, sequence alignments, and percent identities described in "MiMe Gene Product Sequences" below. Representative PAIR1 protein sequences from dicotyledonous plants (SEQ ID NOs: 3 and 14) are provided in the sequence listing as outlined in Table 5, including eight native sequences and a consensus sequence identified by multiple sequence alignment of the eight native sequences (Sequence Alignment 3). Table 3 shows a matrix of percent identities of the PAIR1 protein sequences from dicotyledonous plants, and a phylogenetic tree showing the relationship between the sequences is shown in FIG. 3. The gene products of MiMe loci of the component of DNA double strand breakage during meiotic recombination includes PAIR1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to any one of the PAIR1 proteins of SEQ ID NOs: 3 and 14.

There is an abundance of known PAIR1 gene products from potato including both of the following, which sequences are hereby incorporated by reference in their form as of the effective filing date. Exemplary PAIR1 gene products from potato include those of, by way of example, *Solanum tuberosum* (XP 006339791.2 and M0ZGU5).

A gene product of the component of DNA double strand breakage during meiotic recombination is also exemplified by a PRD1 protein. There is an abundance of known PRD1 gene products from potato including both of the following, which sequences are hereby incorporated by reference in their form as of the effective filing date. Exemplary PRD1 gene products from potato include those of, by way of example, *Solanum tuberosum* (XP 015163123.1 and M1CA99).

A gene product of the component of DNA double strand breakage during meiotic recombination is also exemplified by a PRD2 protein. There is an abundance of known PRD2 gene products from potato including all of the following, which sequences are hereby incorporated by reference in their form as of the effective filing date. Exemplary PRD2 gene products from potato include those of, by way of example, *Solanum tuberosum* (XP 015162530.1 and M1AS84).

A gene product of the component of DNA double strand breakage during meiotic recombination is also exemplified by a DFO protein. There is an abundance of known DFO gene products from potato including all of the following, which sequences are hereby incorporated by reference in their form as of the effective filing date. Exemplary DFO gene products from potato include those of, by way of example, *Solanum tuberosum* (XP 006350870.1 and M1CZR2).

A gene product of the component of DNA double strand breakage during meiotic recombination is also exemplified by a MTOPVIB protein. There is an abundance of known MTOPVIB gene products from potato including all of the following, which sequences are hereby incorporated by reference in their form as of the effective filing date. Exemplary MTOPVIB gene products from potato include those of, by way of example, *Solanum tuberosum* (XP 015166906.1, XP 015166907.1 and M1CGP5).

Components of Progression Through the Second Division of Meiosis

Figure 4:
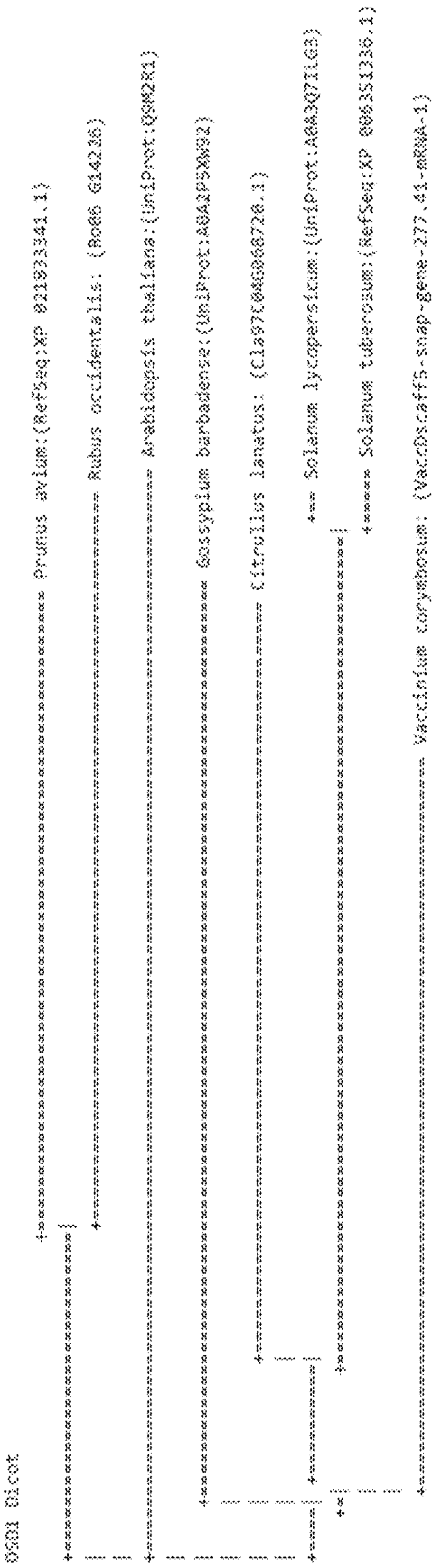
FIG. 4 depicts a phylogenetic tree of OSD1 protein sequences from dicotyledonous plants.

In some embodiments, the complete, partial, or partially-complemented MiMe genotype comprises one or more MiMe alleles conferring decreased expression of one or more MiMe loci of a component of progression through the second division of meiosis. Components of progression through the second division of meiosis include, for example, both (a) MiMe loci that encode gene products that are required for progression through the second division of meiosis and (b) MiMe loci that that are associated with second division restitution mechanisms, since the effective end result of both is as if the second division of meiosis did not occur, with the resulting gametes of each containing sister chromatids. Second division restitution (also known as nuclear restitution) mechanisms are known in the art and described in Brownfield and Kohler (2010. Unreduced gamete formation in plants: mechanisms and prospects. J Exp Bot 62:5, 1659-1668). In certain embodiments, the one or more MiMe loci of the component of progression through the second division of meiosis comprise OSD1, CYCA1, TDM1, PC1, PC2, FC, or any combination thereof. One of skill in the art will understand that MiMe loci of the component of progression through the second division of meiosis are not limited to OSD1, CYCA1, TDM1, PC1, PC2, and FC, and may include any loci encoding gene products required for progression through the second division of meiosis or associated with second division restitution mechanisms. By way of example only, a gene product of the component of progression through the second division of meiosis of the first division sister chromatid segregation is exemplified by an OSD1 protein and specifically by the OSD1 protein sequences, sequence alignments, and percent identities described in "MiMe Gene Product Sequences" below. Representative OSD1 protein sequences from dicotyledonous plants (SEQ ID NOs: 4 and 15) are provided in the sequence listing as outlined in Table 5, including eight native sequences and a consensus sequence identified by multiple sequence alignment of the eight native sequences (Sequence Alignment 4). Table 4A shows a matrix of percent identities of the OSD1 protein sequences from dicotyledonous plants, and a phylogenetic tree showing the relationship between the sequences is shown in FIG. 4. The gene products of MiMe loci of the component of progression through the second division of meiosis include OSD1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to any one of the OSD1 proteins of SEQ ID NOs: 4 and 15.

There is an abundance of known OSD1 gene products from potato including all of the following, which sequences are hereby incorporated by reference in their form as of the effective filing date. Exemplary OSD1 gene products from potato include those of, by way of example, A *Solanum chacoense* (A0A0V0HQ03) and *Solanum tuberosum* (XP 006351336.1).

By way of example only, a gene product of the component of progression through the second division of meiosis is also exemplified by a CYCA1 protein, also known as CYCLIN-A1 or TARDY ASYNCHRONOUS MEIOSIS (TAM), and specifically by the CYCA1 protein sequences, sequence alignments, and percent identities described in "MiMe Gene Product Sequences" below. Representative CYCA1 protein sequences from dicotyledonous plants (SEQ ID NOs: 5-7 and 16) are provided in the sequence listing as outlined in Table 5, including native sequences and a consensus sequence identified by multiple sequence alignment of the native sequences (Sequence Alignment 5). Table 4B shows a matrix of percent identities of the CYCA1 protein sequences from dicotyledonous plants. The gene products of MiMe loci of the component of progression through the second division of meiosis include CYCA1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to any one of the CYCA1 proteins of SEQ ID NOs: 5-7 and 16.

There is an abundance of known CYCA1 gene products from potato including all of the following, which sequences are hereby incorporated by reference in their form as of the effective filing date. Exemplary CYCA1 gene products from potato include those of, by way of example, *Solanum tuberosum* (XP 006351137.1, XP 006351136.1 and XP 006351138.1).

By way of example only, a gene product of the component of progression through the second division of meiosis is also exemplified by a TDM1 protein, and specifically by the TDM1 protein sequences and percent identities described herein. A representative TDM1 protein sequences from potato (SEQ ID NO: 8) is provided in the sequence listing as outlined in Table 5. The gene products of MiMe loci of the component of progression through the second division of meiosisinclude TDM1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to any one of the TDM1 proteins of SEQ ID NO: 8.

There is an abundance of known TDM1 gene products from potato including all of the following, which sequences are hereby incorporated by reference in their form as of the effective filing date. Exemplary TDM1 gene products from potato include those of, by way of example, *Solanum tuberosum* (XP 006350746.1, XP 006340757.1 and XP 006360343.1) and *Solanum chacoense* (A0A0V0I6U1).

Components of Progression Through the First Division of Meiosis

In some embodiments, the complete, partial, or partially-complemented MiMe genotype comprises one or more MiMe alleles conferring decreased expression of one or more MiMe loci of a component of progression through the first division of meiosis. Components of progression through the first division of meiosis include, for example, both (a) MiMe loci that encode gene products that are required for progression through the first division of meiosis and (b) MiMe loci that that are associated with first division restitution mechanisms, since the effective end result of both is as if the first division of meiosis did not occur, with the resulting gametes of each containing non-sister chromatids. First division restitution (also known as nuclear restitution) mechanisms are known in the art and described in Peloquin et al. (1999. Meiotic mutants in potato: valuable variants. *Genetics* 153:1493-1499) and Brownfield and Kohler (2010. Unreduced gamete formation in plants: mechanisms and prospects. J Exp Bot 62:5, 1659-1668). In certain embodiments, the one or more MiMe loci of the component of progression through the first division of meiosis comprise PS1, JASON, or a combination thereof. One of skill in the art will understand that MiMe loci of the component of progression through the first division of meiosis are not limited to PS1 and JASON, and may include any loci encoding gene products required for progression through the first division of meiosis or associated with first division restitution mechanisms. By way of example only, a gene product of the component of progression through the first division of meiosis is exemplified by PS1 protein or a PS1-like protein, and specifically by the PS1 and PS1-like protein sequences and percent identities described herein. A representative PS1 protein sequence (SEQ ID NO: 9) and a representative PS1-like protein sequence (SEQ ID NO: 10) are provided in the sequence listing as outlined in Table 5. The gene products of MiMe loci of the component of progression through the first division of meiosis include: a) PS1 proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the PS1 protein of SEQ ID NO: 9; and b) PS1-like proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the PS1-like protein of SEQ ID NO: 10.

There is an abundance of known PS1 gene products from potato including all of the following, which sequences are hereby incorporated by reference in their form as of the effective filing date. Exemplary PS1 gene products from potato include those of, by way of example, *Solanum tuberosum* (XP 006351164.1, XP 006353632.1 and M1AJ10) and *Solanum chacoense* (F5A7N5, F5A7N4, F5A7P1, A0A0V0H9T7 and A0A0V0GWE7).

By way of example only, a gene product of the component of progression through the first division of meiosis is also exemplified by a JASON protein, and specifically by the JASON protein sequences and percent identities described herein. A representative JASON protein sequence (SEQ ID NO: 11) is provided in the sequence listing as outlined in Table 5. The gene products of MiMe loci of the component of progression through the first division of meiosis include JASON proteins having at least 40%, 45%, 50%, 55%, 60%, 65%, 70%, 75%, 80%, 85%, 90%, 95% or 98% sequence identity, or at least 60%, 65%, 70%, 75%, 80%, 85%, 90%, 95% or 98% sequence similarity to the JASON protein of SEQ ID NO: 11.

There is an abundance of known JASON gene products from potato including all of the following, which sequences are hereby incorporated by reference in their form as of the effective filing date. Exemplary JASON gene products from potato include those of, by way of example, *Solanum tuberosum* (XP 006352001.1, XP 015160469.1 and M1CT79) and *Solanum chacoense* (A0A0V01DT0).

The sequences of the gene products listed above may be accessed using the given accession numbers in the RefGen, UniProt, and RefSeq databases, except for those marked with "MAKER". The identifiers of the sequences of the gene products marked with "MAKER" are MAKER-derived annotations of genome sequences of *Citrullus lanatus* cv 97103 v2.0 (Guo S et al. 2013. The draft genome of watermelon (*Citrullus lanatus*) and resequencing of 20 diverse accessions. *Nature Genetics* 45:51-58); *Citrullus lanatus* cv Charleston Gray v1.0 (Wu S. et al. 2019. Genome of 'Charleston Gray', the principal American watermelon cultivar, and genetic characterization of 1,365 accessions in the U.S. National Plant Germplasm System watermelon collection. Plant Biotechnol J), *Rubus occidentalis* v3.0 (VanBuren et al. 2016. The genome of black raspberry (*Rubus occidentalis*). *The Plant Journal.* 87 (6): 535-547), and *Vaccinium corymbosum* cv Draper v1.0 (Marivi Colle et al. 2019. Haplotype-phased genome and evolution of phytonutrient pathways of tetraploid blueberry, *GigaScience*, Volume 8, Issue 3).

Plants that Produce Inviable Gametes and Seedless Plants

In some embodiments, germination of a seed of the population of polyploid potato seed or of the subpopulation of genetically uniform polyploid potato seed results in a sterile plant that produces inviable gametes. For example, in some embodiments, the population of polyploid potato seed or the subpopulation of genetically uniform polyploid potato seed that has a partial MiMe genotype has a wild-type meiosis phenotype. In some variations, the population of polyploid potato seed or the subpopulation of genetically uniform polyploid potato seed that has a partial MiMe genotype and has a wild-type meiosis phenotype and is triploid, pentaploid, or heptaploid, such that germination of the seed results in a sterile plant that produces inviable gametes due to the non-even ploidy of the potato plant. In some embodiments, germination of a seed of the population of polyploid potato seed or the subpopulation of genetically uniform polyploid potato seed results in a plant that has a partially-complemented MiMe genotype and has neither a wild-type meiosis phenotype nor a MiMe phenotype. In some embodiments, germination of a seed of the population of polyploid potato seed or the subpopulation of genetically uniform polyploid potato seed results in a plant that produces inviable gametes due to the partially complemented MiMe genotype resulting in neither wild-type meiosis or MiMe. Accordingly, in some embodiments, germination of a seed of the population of polyploid potato seed or the subpopulation of genetically uniform polyploid potato seed results in a sterile plant that produces inviable gametes. In some embodiments, germination of a seed of the population of polyploid potato seed or the subpopulation of genetically uniform polyploid potato seed results in a plant that produces seedless fruit, no fruit, or a reduced amount of fruit compared to a potato plant having a wild-type meiosis phenotype. In some embodiments, germination of a seed of the population of polyploid potato seed or the subpopulation of genetically uniform polyploid potato seed results in a seedless plant.

Exemplary Populations of Polyploid Potato Seed

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, or at least about 95%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. The subpopulation of genetically uniform polyploid potato seed may have any complete MiMe genotype, partial MiMe genotype, or partially-complemented MiMe genotype described herein. In certain embodiments, the subpopulation of genetically uniform polyploid potato seed has a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid potato seed has a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In certain embodiments, the subpopulation of genetically uniform polyploid potato seed has a partial MiMe genotype comprising (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid potato seed has a partial MiMe genotype comprising (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In certain embodiments, the subpopulation of genetically uniform polyploid potato seed has a partially-complemented MiMe genotype comprising (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid potato seed has a partially-complemented MiMe genotype comprising (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In certain embodiments, the subpopulation of genetically uniform polyploid potato seed has a partially-complemented MiMe genotype comprising (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components. In some variations, the one or more MiMe loci of the component of sister chromatid cohesion during the first division of meiosis comprise REC8, SWITCH1/DYAD, or a combination thereof; the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof; the one or more MiMe loci of the component of progression through the second division of meiosis comprise OSD1, CYCA1, TDM1, PC1, PC2, FC, or any combination thereof; and/or the one or more MiMe loci of the component of progression through the first division of meiosis comprise PS1, JASON, or a combination thereof. In other variations, the one or more MiMe loci of the component of sister chromatid cohesion during the first division of meiosis comprise REC8; the one or more MiMe loci of the component of DNA double strand breakage during meiotic recombination comprise PAIR1, SPO11-1, SPO11-2, or any combination thereof; the one or more MiMe loci of the component of progression through the second division of meiosis comprise OSD1, CYCA1, TDM1, or any combination thereof; and/or the one or more MiMe loci of the component of progression through the first division of meiosis comprise PS1. In certain embodiments, the population of polyploid potato seed is from a potato plant. In certain embodiments, the population of polyploid potato seed is from a dicotyledonous plant. In some variations, the population of polyploid potato seed is from a potato plant In certain embodiments, germination of a seed of the subpopulation of genetically uniform polyploid potato seed results in a sterile plant that produces inviable gametes. In some embodiments, the subpopulation of genetically uniform polyploid potato seed comprises one or more polynucleotide sequences selected from the group consisting of SEQ ID NOs: 127-129, 131-134, 137-154, and 156-159. In some embodiments, the subpopulation of genetically uniform polyploid potato seed comprises one or more polynucleotide sequences selected from the group consisting of SEQ ID NOs: 127-129, 131-134, 137-154, and 156-159. In certain embodiments, the subpopulation of genetically uniform polyploid potato seed comprises a MiMe allele at one or more SPO11-1 loci, each independently comprising a polynucleotide sequence selected from the group consisting of SEQ ID NOs: 127-129. In certain embodiments, the subpopulation of genetically uniform polyploid potato seed comprises a) a MiMe allele at one or more REC8 loci, each independently comprising a polynucleotide sequence selected from the group consisting of SEQ ID NOs: 131 and 132; and/or b) a MiMe allele at one or more SPO11-1 loci, each independently comprising a polynucleotide sequence selected from the group consisting of SEQ ID NOS: 133 and 134. In certain embodiments, the subpopulation of genetically uniform polyploid potato seed comprises a) a MiMe allele at one or more REC8 loci, each independently comprising a polynucleotide sequence selected from the group consisting of SEQ ID NOs: 137 and 138; and/or b) a MiMe allele at one or more SPO11-1 loci, each independently comprising a polynucleotide sequence selected from the group consisting of SEQ ID NOs: 139 and 140. In certain embodiments, the subpopulation of genetically uniform polyploid potato seed comprises a MiMe allele at one or more SPO11-1 loci, each independently comprising a polynucleotide sequence selected from the group consisting of SEQ ID NOs: 141 and 142. In certain embodiments, the subpopulation of genetically uniform polyploid potato seed comprises a) a MiMe allele at one or more CYCA1 loci, each independently comprising a polynucleotide sequence selected from the group consisting of SEQ ID NOs: 143 and 144; b) a MiMe allele at one or more REC8 loci, each independently comprising a polynucleotide sequence selected from the group consisting of SEQ ID NOs: 145 and 146; and/or c) a MiMe allele at one or more SPO11-1 loci, each independently comprising a polynucleotide sequence selected from the group consisting of SEQ ID NOs: 147 and 148. In certain embodiments, the subpopulation of genetically uniform polyploid potato seed comprises a) a MiMe allele at one or more CYCA1 loci, each independently comprising a polynucleotide sequence selected from the group consisting of SEQ ID NOs: 149 and 150; b) a MiMe allele at one or more REC8 loci, each independently comprising a polynucleotide sequence selected from the group consisting of SEQ ID NOs: 151 and 152; and/or c) a MiMe allele at one or more SPO11-1 loci, each independently comprising a polynucleotide sequence selected from the group consisting of SEQ ID NOs: 153 and 154. In certain embodiments, the subpopulation of genetically uniform polyploid potato seed comprises a) a MiMe allele at one or more REC8 loci, each independently comprising a polynucleotide sequence selected from the group consisting of SEQ ID NOs: 156 and 157; and/orb) a MiMe allele at one or more SPO11-1 loci, each independently comprising a polynucleotide sequence selected from the group consisting of SEQ ID NOs: 158 and 159. In some variations, each the one or more CYCA1 loci, each of the one or more REC8 loci, each of the one or more PAIR1 loci, and/or each of the one or more SPO11-1 loci are present on a different homologous chromosome.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, or at least about 95%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. The subpopulation of genetically uniform polyploid potato seed may have any complete MiMe genotype, partial MiMe genotype, or partially-complemented MiMe genotype described herein. In certain embodiments, the subpopulation of genetically uniform polyploid potato seed has a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid potato seed has a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In certain embodiments, the subpopulation of genetically uniform polyploid potato seed has a partial MiMe genotype comprising (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid potato seed has a partial MiMe genotype comprising (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In certain embodiments, the subpopulation of genetically uniform polyploid potato seed has a partially-complemented MiMe genotype comprising (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In certain embodiments, the subpopulation of genetically uniform polyploid potato seed has a partially-complemented MiMe genotype comprising (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In certain embodiments, the subpopulation of genetically uniform polyploid potato seed has a partially-complemented MiMe genotype comprising (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components. In some variations, the one or more MiMe loci of the component of sister chromatid cohesion during the first division of meiosis comprise REC8; the one or more MiMe loci of the component of DNA double strand breakage during meiotic recombination comprise PAIR1, SPO11-1, SPO11-2, or any combination thereof; the one or more MiMe loci of the component of progression through the second division of meiosis comprise OSD1, CYCA1, or a combination thereof; and/or the one or more MiMe loci of the component of progression through the first division of meiosis comprise PS1. In certain embodiments, germination of a seed of the subpopulation of genetically uniform polyploid potato seed results in a sterile plant that produces inviable gametes. In some embodiments, the subpopulation of genetically uniform polyploid potato seed comprises one or more polynucleotide sequences selected from the group consisting of SEQ ID NOs: 127-129, 131-134, 137-154, and 156-159. In some embodiments, the subpopulation of genetically uniform polyploid potato seed comprises one or more polynucleotide sequences selected from the group consisting of SEQ ID NOs: 127-129, 131-134, 137-154, and 156-159. In certain embodiments, the subpopulation of genetically uniform polyploid potato seed comprises a MiMe allele at one or more SPO11-1 loci, each independently comprising a polynucleotide sequence selected from the group consisting of SEQ ID NOs: 127-129. In certain embodiments, the subpopulation of genetically uniform polyploid potato seed comprises a) a MiMe allele at one or more REC8 loci, each independently comprising a polynucleotide sequence selected from the group consisting of SEQ ID NOs: 131 and 132; and/or b) a MiMe allele at one or more SPO11-1 loci, each independently comprising a polynucleotide sequence selected from the group consisting of SEQ ID NOs: 133 and 134. In certain embodiments, the subpopulation of genetically uniform polyploid potato seed comprises a) a MiMe allele at one or more REC8 loci, each independently comprising a polynucleotide sequence selected from the group consisting of SEQ ID NOs: 137 and 138; and/or b) a MiMe allele at one or more SPO11-1 loci, each independently comprising a polynucleotide sequence selected from the group consisting of SEQ ID NOs: 139 and 140. In certain embodiments, the subpopulation of genetically uniform polyploid potato seed comprises a MiMe allele at one or more SPO11-1 loci, each independently comprising a polynucleotide sequence selected from the group consisting of SEQ ID NOs: 141 and 142. In certain embodiments, the subpopulation of genetically uniform polyploid potato seed comprises a) a MiMe allele at one or more CYCA1 loci, each independently comprising a polynucleotide sequence selected from the group consisting of SEQ ID NOS: 143 and 144; b) a MiMe allele at one or more REC8 loci, each independently comprising a polynucleotide sequence selected from the group consisting of SEQ ID NOs: 145 and 146; and/or c) a MiMe allele at one or more SPO11-1 loci, each independently comprising a polynucleotide sequence selected from the group consisting of SEQ ID NOs: 147 and 148. In certain embodiments, the subpopulation of genetically uniform polyploid potato seed comprises a) a MiMe allele at one or more CYCA1 loci, each independently comprising a polynucleotide sequence selected from the group consisting of SEQ ID NOs: 149 and 150; b) a MiMe allele at one or more REC8 loci, each independently comprising a polynucleotide sequence selected from the group consisting of SEQ ID NOs: 151 and 152; and/or c) a MiMe allele at one or more SPO11-1 loci, each independently comprising a polynucleotide sequence selected from the group consisting of SEQ ID NOs: 153 and 154. In certain embodiments, the subpopulation of genetically uniform polyploid potato seed comprises a) a MiMe allele at one or more REC8 loci, each independently comprising a polynucleotide sequence selected from the group consisting of SEQ ID NOs: 156 and 157; and/or b) a MiMe allele at one or more SPO11-1 loci, each independently comprising a polynucleotide sequence selected from the group consisting of SEQ ID NOs: 158 and 159. In some variations, each the one or more CYCA1 loci, each of the one or more REC8 loci, each of the one or more PAIR1 loci, and/or each of the one or more SPO11-1 loci are present on a different homologous chromosome.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises one or more rec8 alleles, each comprising a polynucleotide sequence selected from the group consisting of SEQ ID NOs: 128, 129, 131, 132, 137, 138, 145, 146, 151, 152, 156, and 157.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises one or more rec8 alleles, each comprising a polynucleotide sequence selected from the group consisting of SEQ ID NOs: 131, 132, 137, 138, 145, 146, 151, 152, 156, and 157.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the one or more CYCA1 loci comprise CYCA1-1, CYCA1-2, and/or CYCA1-3. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; b) one or more cyca1 alleles, each comprising a polynucleotide sequence selected from the group consisting of SEQ ID NOs: 143, 144, 149, and 150; and c) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the one or more CYCA1 loci comprise CYCA1-1, CYCA1-2, and/or CYCA1-3. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; b) one or more cyca1 alleles, each comprising a polynucleotide sequence selected from the group consisting of SEQ ID NOs: 143, 144, 149, and 150; and c) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the one or more CYCA1 loci comprise CYCA1-1, CYCA1-2, and/or CYCA1-3. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; and/or b) one or more cyca1 alleles, each comprising a polynucleotide sequence selected from the group consisting of SEQ ID NOs: 143, 144, 149, and 150.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the one or more CYCA1 loci comprise CYCA1-1, CYCA1-2, and/or CYCA1-3. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; and/or b) one or more cyca1 alleles, each comprising a polynucleotide sequence selected from the group consisting of SEQ ID NOs: 143, 144, 149, and 150.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises one or more rec8 alleles, each comprising a polynucleotide sequence selected from the group consisting of SEQ ID NOs: 131, 132, 137, 138, 145, 146, 151, 152, 156, and 157.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises one or more rec8 alleles, each comprising a polynucleotide sequence selected from the group consisting of SEQ ID NOs: 131, 132, 137, 138, 145, 146, 151, 152, 156, and 157.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a complete MiMe genotype comprising (i) an os allele, wherein the subpopulation of genetically uniform polyploid potato seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partial MiMe genotype comprising (i) an os allele, wherein the subpopulation of genetically uniform polyploid potato seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a complete MiMe genotype comprising (i) a ps allele, wherein the subpopulation of genetically uniform polyploid potato seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partial MiMe genotype comprising (i) a ps allele, wherein the subpopulation of genetically uniform polyploid potato seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more only MiMe alleles at one or more SPO11-1 loci, wherein each of the MiMe alleles at the SPO11-1 locus comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the one or more CYCA1 loci comprise CYCA1-1, CYCA1-2, and/or CYCA1-3. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; b) one or more cyca1 alleles, each comprising a polynucleotide sequence selected from the group consisting of SEQ ID NOs: 143, 144, 149, and 150; and/or c) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partially complemented MiMe genotype comprising (i) a ps allele, wherein the subpopulation of genetically uniform polyploid potato seed is heterozygous for the ps allele, (ii) an os allele, wherein the subpopulation of genetically uniform polyploid potato seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes of the same or related species of potato and a partially complemented MiMe genotype comprising (i) an os allele, wherein the subpopulation of genetically uniform polyploid potato seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1. In certain embodiments, the population was obtained from a single potato plant or a set of potato plants (e.g., a set of genetically uniform plants, e.g., a set of genetically uniform F1 hybrids). In certain embodiments, the subpopulation of genetically uniform polyploid potato seed is triploid, tetraploid, or pentaploid. In one embodiment, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of seeds, wherein each pair of seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient. In some variations, the population of polyploid potato seed is from a potato plant or a set of potato plants (e.g., a set of genetically uniform potato plants, e.g. a set of genetically uniform F1 hybrid potato plants), optionally wherein the one or more CYCA1 loci comprise CYCA1-1, CYCA1-2, and/or CYCA1-3. In some variations, the population of polyploid potato seed is from a potato plant or a set of potato plants (e.g., a set of genetically uniform potato plants, e.g. a set of genetically uniform F1 hybrid potato plants), optionally wherein the subpopulation of genetically uniform polyploid potato seed comprises a) one or more rec8 alleles, each comprising a polynucleotide sequence selected from the group consisting of SEQ ID NOs: 131, 132, 137, 138, 145, 146, 151, 152, 156, and 157; b) one or more cyca1 alleles, each comprising a polynucleotide sequence selected from the group consisting of SEQ ID NOs: 143, 144, 149, and 150; and/or c) one or more spo11-1 alleles, each comprising a polynucleotide sequence selected from the group consisting of SEQ ID NOs: 127, 128, 129, 133, 134, 139-142, 147, 148, 153, 154, 158, and 159.

In some embodiments, provided herein is a population of polyploid potato seed comprising a subpopulation of genetically uniform polyploid potato seed in an amount of at least 50% of the total number of seeds, the genetically uniform polyploid potato seed comprising three or more haplotypes and one or more polynucleotide sequences selected from the group consisting of SEQ ID NOs: 127-129, 131-134, 137-154, and 156-159. In certain embodiments, the population was obtained from a single potato plant or a set of potato plants (e.g., a set of genetically uniform potato plants, e.g., a set of genetically uniform potato F1 hybrids). In certain embodiments, the subpopulation of genetically uniform polyploid potato seed is tetraploid. In certain embodiments, the population of polyploid potato seed has an average pairwise genetic uniformity of at least 90% (e.g., at least about 90%, at least about 91%, at least about 92%, at least about 94%, at least about 95%, at least about 96%, at least about 97%, at least about 98%, at least about 99%, or about 100%) as measured by the Jaccard similarity coefficient. In certain embodiments, the population of polyploid potato seed comprises the subpopulation of genetically uniform polyploid potato seed in an amount of at least 50% (e.g., at least 50%, at least 60%, at least 70%, at least 75%, at least 80%, at least 85%, at least 90%, at least 95%, at least 96%, at least 97%, at least 98%, or at least 99%) of the total number of potato seeds, wherein each pair of potato seeds in the subpopulation of genetically uniform polyploid potato seed has a pairwise identity of at least about 95% (e.g., at least about 95%, at least about 96%, at least about 97%, at least about 98%, at least about 99%, or about 100%) as measured by the Jaccard similarity coefficient.

Methods of Producing Populations of Polyploid Potato Seed

In another aspect, provided herein are methods of producing a population of polyploid potato seed comprising three or more haplotypes wherein at least 50% of the population of polyploid potato seed are genetically uniform. In some embodiments, the population of polyploid potato seed comprises a subpopulation of genetically uniform polyploid potato seed in an amount of at least 50%, the genetically uniform polyploid potato seed comprising the three or more haplotypes. In some embodiments, the method comprises (a) providing clonal gametes from a pair of parent MiMe potato plants that together comprise three or more haplotypes; and (b) crossing the clonal gametes to produce the population of polyploid potato seed. In other embodiments, the method comprises (a) providing clonal gametes from a parent MiMe potato plant; (b) providing haploid gametes from a homozygous parent non-MiMe potato plant; and (c) crossing the clonal gametes with the haploid gametes to produce the population of polyploid potato seed. In other embodiments, the method comprises (a) providing clonal gametes from a parent MiMe potato plant; (b) providing haploid gametes from a homozygous parent non-MiMe potato plant; and (c) crossing the clonal gametes with the haploid gametes to produce the population of polyploid potato seed; wherein the clonal gametes and the haploid gametes together comprise three or more haplotypes. In still other embodiments, the method comprises (a) providing clonal gametes from a parent MiMe potato plant; (b) providing unreduced, non-clonal gametes from a homozygous parent plant; and (c) crossing the clonal gametes with the unreduced, non-clonal gametes to produce the population of polyploid potato seed; wherein the clonal gametes and the unreduced, non-clonal gametes together comprise three or more haplotypes.

In another aspect, provided herein are methods of producing a population of polyploid potato seed comprising a partially-complemented MiMe genotype wherein at least 50% of the population of polyploid potato seed are genetically uniform. In some embodiments, provided herein are methods of producing a population of polyploid potato seed comprising a subpopulation of genetically uniform polyploid potato seed in an amount of at least 50% of the total number of seeds, the subpopulation of genetically uniform seed comprising a partially-complemented MiMe genotype wherein at least 50% of the population of polyploid potato seed are genetically uniform. In some embodiments, the method comprises (a) providing clonal gametes from a first parent MiMe potato plant; (b) providing clonal gametes from a second parent MiMe potato plant; and (c) crossing the clonal gametes to produce the population of polyploid potato seed comprising a partially-complemented MiMe genotype. In certain embodiments, the polyploid seed (e.g., the subpopulation of genetically uniform seed) comprises one, two, three, or more haplotypes.

In some embodiments, at least 50% of the population of polyploid potato seed produced are genetically uniform. In some variations, at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the population of polyploid potato seed produced are genetically uniform. In some embodiments, at least 50% of the population of polyploid potato seed produced are genetically uniform, wherein the polyploid seed comprises two, three, or more haplotypes. In some variations, at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the population of polyploid potato seed produced are genetically uniform, wherein the polyploid seed comprises two, three, or more haplotypes.

In some embodiments, the population of polyploid potato seed comprises a subpopulation of genetically uniform polyploid potato seed in an amount of at least 50% of the total number of seeds. In some variations, the population of polyploid potato seed comprises a subpopulation of genetically uniform polyploid potato seed in an amount of at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the total number of seeds. In some embodiments, the subpopulation of genetically uniform polyploid potato seed comprises two, three, or more haplotypes. In some variations, the population of polyploid potato seed comprises a subpopulation of genetically uniform polyploid potato seed in an amount of at least 60%, least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, or at least 99.99% of the total number of seeds, wherein the genetically uniform polyploid potato seed comprises two, three, or more haplotypes. In certain variations, the subpopulation of genetically uniform polyploid potato seed has a complete MiMe genotype, a partial MiMe genotype, or a partially-complemented MiMe genotype.

Providing Clonal Gametes

In some embodiments, the method of producing a population of polyploid potato seed comprises providing clonal gametes. In some embodiments, providing clonal gametes comprises growing a plant with a complete MiMe genotype that exhibits a MiMe phenotype and allowing the plant to grow to a reproductive stage until clonal gametes form. In other embodiments, providing clonal gametes comprises generating a plant with a complete MiMe genotype that exhibits a MiMe phenotype and growing said plant to a reproductive stage until clonal gametes form. In some variations, providing clonal gametes further comprises collecting pollen comprising clonal gametes from a plant with a complete MiMe genotype that exhibits a MiMe phenotype.

In some embodiments, the method of producing a population of polyploid potato seed comprises providing clonal gametes from one or more parent MiMe potato plants. In some variations, the method of producing a population of polyploid potato seed comprises providing clonal gametes from a pair of parent MiMe potato plants. In some embodiments, providing clonal gametes comprises growing one or more parent MiMe potato plants and allowing them to grow to a reproductive stage until clonal gametes form. In other embodiments, providing clonal gametes comprises generating one or more parent MiMe potato plants and growing them to a reproductive stage until clonal gametes form. In some variations, providing clonal gametes further comprises collecting pollen comprising clonal gametes from one or more parent MiMe potato plants. In some additional variations, the pair of parent MiMe potato plants are diploid, triploid, tetraploid, pentaploid, hexaploid, heptaploid, octoploid, or any combination thereof.

In some embodiments, the method of producing a population of polyploid potato seed comprises providing clonal gametes from a pair of parent MiMe potato plants that together comprise three or more haplotypes. In some variations, the pair of parent MiMe potato plants together comprise three or more haplotypes, four or more haplotypes, five or more haplotypes, six or more haplotypes, seven or more haplotypes, or eight or more haplotypes. In additional variations, the pair of parent MiMe potato plants together comprise three, four, five, six, seven, or eight haplotypes. In some embodiments, the first parent MiMe potato plant comprises one or more haplotypes and the second parent MiMe potato plant comprises one or more haplotypes, wherein the parent MiMe potato plants together comprise two or more haplotypes. In some embodiments, the first parent MiMe potato plant comprises one haplotype and the second parent MiMe potato plant comprises two or more haplotypes, wherein the parent MiMe potato plants together comprise three or more haplotypes. In other embodiments, each of the parent MiMe potato plants comprises two or more haplotypes, wherein the parent MiMe potato plants together comprise four or more haplotypes.

Parent MiMe Potato Plant Genotypes

In some embodiments, each of the parent MiMe potato plants has a complete MiMe genotype. In certain embodiments, the complete MiMe genotype comprises one or more genetic modifications resulting in decreased expression of one or more MiMe loci. In other embodiments, the complete MiMe genotype comprises one or more genetic modifications resulting in decreased expression of two or more MiMe loci. In yet another embodiment, the complete MiMe genotype comprises one or more genetic modifications resulting in decreased expression of three or more MiMe loci. In some variations, the MiMe loci may include, but are not limited to, REC8, OSD1, CYCA1, TDM1, PAIR1, SPO11-1, SPO11-2, PRD1, PRD2, DFO, MTOPVIB, DSY1, SY1, SY2, SY3, SY4, SWITCH1/DYAD, PS1, JASON, PC1, PC2, and FC. In one variation, the complete MiMe genotype comprises one or more genetic modifications resulting in decreased expression of REC8. In a second variation, the complete MiMe genotype comprises one or more genetic modifications resulting in decreased expression of OSD1. In a third variation, the complete MiMe genotype comprises one or more genetic modifications resulting in decreased expression of PAIR1. In a fourth variation, the complete MiMe genotype comprises one or more genetic modifications resulting in decreased expression of SPO11-1, SPO11-2, or a combination thereof. In a fifth variation, the complete MiMe genotype comprises one or more genetic modifications resulting in decreased expression of REC8 and SPO11-1. In a sixth variation, the complete MiMe genotype comprises one or more genetic modifications resulting in decreased expression of REC8 and OSD1. In a seventh variation, the complete MiMe genotype comprises one or more genetic modifications resulting in decreased expression of REC8 and PAIR1. In an eighth variation, the complete MiMe genotype comprises one or more genetic modifications resulting in decreased expression of OSD1 and SPO11-1. In a ninth variation, the complete MiMe genotype comprises one or more genetic modifications resulting in decreased expression of OSD1 and PAIR1. In a tenth variation, the complete MiMe genotype comprises one or more genetic modifications resulting in decreased expression of REC8, OSD1, and PAIR1. In an eleventh variation, the complete MiMe genotype comprises one or more genetic modifications resulting in decreased expression of REC8, OSD1, and SPO11-1. In a twelfth variation, the complete MiMe genotype comprises one or more genetic modifications resulting in decreased expression of PS1 and SPO11-1. In a thirteenth variation, the complete MiMe genotype comprises one or more genetic modifications resulting in decreased expression of PS1 and SY3. The complete MiMe genotype may comprise one or more genetic modifications resulting in decreased expression of any combination of MiMe loci described herein or known in the art, wherein a potato plant that has the complete MiMe genotype exhibits a MiMe phenotype. In some embodiments, the complete MiMe genotype may comprise one or more genetic modifications resulting in non-expression of any combination of MiMe loci described here or known in the art wherein a potato plant that has the complete MiMe genotype exhibits a MiMe phenotype. In further embodiments, the complete MiMe genotype may comprise one or more genetic modifications resulting in decreased expression, non-expression, or a combination thereof of any combination of MiMe loci described here or known in the art, wherein a potato plant that has the complete MiMe genotype exhibits a MiMe phenotype. The parent MiMe potato plant may have any complete MiMe genotype known in the art or described herein, including, but not limited to, complete MiMe genotypes comprising MiMe alleles resulting in decreased expression of any of the MiMe loci described herein. Specific examples of complete MiMe genotypes are shown in Table 6.

In some embodiments, the complete MiMe genotype comprises one or more genetic modifications resulting in decreased expression of REC8, SWITCH1/DYAD, or a combination thereof. In some variations, the complete MiMe genotype comprises one or more genetic modifications resulting in decreased expression of REC8, SWITCH1/DYAD, or a combination thereof and one or more genetic modifications resulting in decreased expression of one or more additional MiMe loci. In additional variations, the complete MiMe genotype comprises one or more genetic modifications resulting in decreased expression of REC8, SWITCH1/DYAD, or a combination thereof and one or more genetic modifications resulting in decreased expression of one or more additional MiMe loci, including, but not limited to, OSD1, CYCA1, TDM1, PC1, PC2, and FC. In yet additional variations, the complete MiMe genotype comprises one or more genetic modifications resulting in decreased expression of REC8, SWITCH1/DYAD, or a combination thereof; one or more genetic modifications resulting in decreased expression of OSD1, CYCA1, TDM1, PC1, PC2, FC, or any combination thereof; and one or more genetic modifications resulting in decreased expression of one or more additional MiMe loci, including, but not limited to, PAIR1, SPO11-1, SPO11-2, PRD1, PRD2, DFO, MTOPVIB, DSY1, SY1, SY2, SY3, and SY4.

In some embodiments, the complete MiMe genotype comprises one or more genetic modifications resulting in decreased expression of one or more MiMe loci including, but not limited to, OSD1, CYCA1, TDM1, PC1, PC2, and FC. In some variations, the complete MiMe genotype comprises one or more genetic modifications resulting in decreased expression of OSD1, CYCA1, TDM1, PC1, PC2, FC, or any combination thereof and further comprises one or more genetic modifications resulting in decreased expression of one or more additional MiMe loci, including, but not limited to, PAIR1, SPO11-1, SPO11-2, PRD1, PRD2, DFO, MTOPVIB, DSY1, SY1, SY2, SY3, and SY4.

In some embodiments, the complete MiMe genotype comprises one or more genetic modifications resulting in decreased expression of one or more MiMe loci including, but not limited to, PAIR1, SPO11-1, SPO11-2, PRD1, PRD2, DFO, MTOPVIB, DSY1, SY1, SY2, SY3, and SY4. In some variations, the complete MiMe genotype comprises one or more genetic modifications resulting in decreased expression of PAIR1, SPO11-1, SPO11-2, PRD1, PRD2, DFO, MTOPVIB, DSY1, SY1, SY2, SY3, SY4, or any combination thereof, and further comprises one or more genetic modifications resulting in decreased expression of one or more additional MiMe loci, which may include, but are not limited to PS1 and JASON.

In some embodiments, the parent MiMe potato plant has a complete MiMe genotype comprising MiMe alleles conferring decreased expression of MiMe loci of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the parent MiMe potato plant has a complete MiMe genotype comprising MiMe alleles conferring decreased expression of MiMe loci of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In some variations, the parent MiMe potato plant having a complete MiMe genotype comprising MiMe alleles conferring decreased expression of MiMe loci of (2) a component of DNA double strand breakage during meiotic recombination and (4) a component of progression through the first division of meiosis exhibits a MiMe phenotype in male germline cells and/or produces clonal male gametes, and exhibits a wild-type meiosis phenotype in female germline cells and/or produces haploid female gametes. The parent MiMe potato plant may have any complete MiMe genotype known in the art or described herein, including, but not limited to, complete MiMe genotypes comprising MiMe alleles resulting in decreased expression of any of the MiMe loci described herein.

Parent MiMe Potato Plant Complementary Genotypes

In some embodiments, each of the parent MiMe potato plants has a complete MiMe genotype comprising MiMe alleles conferring decreased expression of MiMe loci of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some embodiments, (a) the first parent MiMe potato plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; (b) the second parent MiMe potato plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component; and (c) at least one of the MiMe loci having only MiMe alleles of the first MiMe component of the first parent MiMe potato plant is the same as at least one of the MiMe loci having only MiMe alleles of the first MiMe component of the second parent MiMe potato plant. In some variations, at least one of the MiMe loci having only MiMe alleles of the third MiMe component of the first parent MiMe potato plant is the same as at least one of the MiMe loci having only MiMe alleles of the third MiMe component of the second parent MiMe potato plant. In other variations, the one or more MiMe loci having only MiMe alleles of the third MiMe component of the first parent MiMe potato plant are distinct from the one or more MiMe loci having only MiMe alleles of the third MiMe component of the second parent MiMe potato plant. In some embodiments, (a) the first parent MiMe potato plant has only MiMe alleles at one or more MiMe loci of a component of sister chromatid cohesion during the first division of meiosis, only MiMe alleles at a first MiMe locus of a component of DNA double strand breakage during meiotic recombination, only non-MiMe alleles at a second MiMe locus of the component of DNA double strand breakage during meiotic recombination, and only MiMe alleles at one or more MiMe loci of a component of progression through the second division of meiosis; (b) the second parent MiMe potato plant has only MiMe alleles at one or more MiMe loci of the component of sister chromatid cohesion during the first division of meiosis, only non-MiMe alleles at the first MiMe locus of the component of DNA double strand breakage during meiotic recombination, only MiMe alleles at the second MiMe locus of component of DNA double strand breakage during meiotic recombination, and only MiMe alleles at one or more MiMe loci of the of a component of progression through the second division of meiosis; and (c) at least one of the MiMe loci having only MiMe alleles of the component of sister chromatid cohesion during the first division of meiosis of the first parent MiMe potato plant is the same as at least one of the MiMe loci having only MiMe alleles of the component of sister chromatid cohesion during the first division of meiosis of the second parent MiMe potato plant. In some variations, at least one of the MiMe loci having only MiMe alleles of the component of progression through the second division of meiosis of the first parent MiMe potato plant is the same as at least one of the MiMe loci having only MiMe alleles of the component of progression through the second division of meiosis of the second parent MiMe potato plant. In other variations, the one or more MiMe loci having only MiMe alleles of the component of progression through the second division of meiosis of the first parent MiMe potato plant are distinct from the one or more MiMe loci having only MiMe alleles of the component of progression through the second division of meiosis of the second parent MiMe potato plant. Exemplary MiMe loci of each of said MiMe components are extensively described below. In certain embodiments, (a) the first parent MiMe potato plant has only MiMe alleles at REC8, only MiMe alleles at SPO11-1, only non-MiMe alleles at PAIR1, and only MiMe alleles at OSD1; and (b) the second parent MiMe potato plant has only MiMe alleles at REC8, only non-MiMe alleles at SPO11-1, only MiMe alleles at PAIR1, and only MiMe alleles at OSD1.

In other embodiments, each of the parent MiMe potato plants has a complete MiMe genotype comprising MiMe alleles conferring decreased expression of MiMe loci of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In some variations, the parent MiMe potato plant having a complete MiMe genotype comprising MiMe alleles conferring decreased expression of MiMe loci of (2) a component of DNA double strand breakage during meiotic recombination and (4) a component of progression through the first division of meiosis exhibits a MiMe phenotype in male germline cells and/or produces clonal male gametes, and exhibits a wild-type meiosis phenotype in female germline cells and/or produces haploid female gametes. In some embodiments, (a) the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; (b) the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component; and (c) at least one of the MiMe loci having only MiMe alleles of the first MiMe component of the first parent MiMe potato plant is the same as at least one of the MiMe loci having only MiMe alleles of the first MiMe component of the second parent MiMe potato plant. In certain embodiments, (a) the first parent MiMe potato plant has only MiMe alleles at one or more MiMe loci of a component of DNA double strand breakage during meiotic recombination, only MiMe alleles at a first MiMe locus of a component of progression through the first division of meiosis, and only non-MiMe alleles at a second MiMe locus of the component of progression through the first division of meiosis; (b) the second parent MiMe potato plant has only MiMe alleles at one or more MiMe loci of the component of DNA double strand breakage during meiotic recombination, only non-MiMe alleles at the first MiMe locus of the component of progression through the first division of meiosis, and only MiMe alleles at the second MiMe locus of the component of progression through the first division of meiosis; and (c) at least one of the MiMe loci having only MiMe alleles of the component of DNA double strand breakage during meiotic recombination of the first parent MiMe potato plant is the same as at least one of the MiMe loci having only MiMe alleles of the component of DNA double strand breakage during meiotic recombination of the second parent MiMe potato plant. In certain embodiments, (a) the first parent MiMe potato plant has only MiMe alleles at one or more MiMe loci of a component of progression through the first division of meiosis, only MiMe alleles at a first MiMe locus of a the component of DNA double strand breakage during meiotic recombination, and only non-MiMe alleles at a second MiMe locus of the component of DNA double strand breakage during meiotic recombination; (b) the second parent MiMe potato plant has only MiMe alleles at one or more MiMe loci of the component of progression through the first division of meiosis, only non-MiMe alleles at the first MiMe locus of the component of DNA double strand breakage during meiotic recombination, and only MiMe alleles at the second MiMe locus of the component of DNA double strand breakage during meiotic recombination; and (c) at least one of the MiMe loci having only MiMe alleles of the component of progression through the first division of meiosis of the first parent MiMe potato plant is the same as at least one of the MiMe loci having only MiMe alleles of the component of progression through the first division of meiosis of the second parent MiMe potato plant. Exemplary MiMe loci of each of said MiMe components are extensively described below. The parent MiMe potato plant may have any complete MiMe genotype known in the art or described herein, including, but not limited to, complete MiMe genotypes comprising MiMe alleles resulting in decreased expression of any of the MiMe loci described herein.

In some embodiments, the first parent MiMe potato plant has a complete MiMe genotype comprising MiMe alleles conferring decreased expression of one or more MiMe loci of a first, second, and third MiMe component, wherein the first MiMe component is (2) a component of DNA double strand breakage during meiotic recombination, the second MiMe component is (1) a component of sister chromatid cohesion during the first division of meiosis and the third MiMe component is (3) a component of progression through the second division of meiosis, and the second parent MiMe potato plant has a complete MiMe genotype comprising MiMe alleles conferring decreased expression of MiMe loci of the first MiMe component and a fourth MiMe component, wherein the fourth MiMe component is (4) a component of progression through the first division of meiosis. In some variations, the second parent MiMe potato plant having a complete MiMe genotype comprising MiMe alleles conferring decreased expression of MiMe loci of (2) a component of DNA double strand breakage during meiotic recombination and (4) a component of progression through the first division of meiosis exhibits a MiMe phenotype in male germline cells and/or produces clonal male gametes, and exhibits a wild-type meiosis phenotype in female germline cells and/or produces haploid female gametes. In certain embodiments, (a) the first parent MiMe potato plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination; (b) the second parent MiMe potato plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of a fourth MiMe component; and (c) at least one of the MiMe loci having only MiMe alleles of the first MiMe component of the first parent MiMe potato plant is the same as at least one of the MiMe loci having only MiMe alleles of the first MiMe component of the second parent MiMe potato plant. In some variations, (a) the first parent MiMe potato plant has only MiMe alleles at one or more MiMe loci of a component is a component of DNA double strand breakage during meiotic recombination, only MiMe alleles one or more MiMe loci of a component of sister chromatid cohesion during the first division of meiosis, only MiMe alleles at one or more MiMe loci of a component of progression through the second division of meiosis, and only non-MiMe alleles at one or more MiMe loci of a component of progression through the first division of meiosis; and (b) the second parent MiMe potato plant has only MiMe alleles at the one or more MiMe loci of the component of DNA double strand breakage during meiotic recombination, only non-MiMe alleles at the one or more MiMe loci of the component of sister chromatid cohesion during the first division of meiosis, only non-MiMe alleles at the one or more MiMe loci of the component of progression through the second division of meiosis, and only MiMe alleles at the one or more MiMe loci of the component of progression through the first division of meiosis. Exemplary MiMe loci of each of said MiMe components are extensively described below. In one variation, (a) the first parent MiMe potato plant has only MiMe alleles at SPO11-1, only MiMe alleles at REC8, only MiMe alleles at OSD1, and only non-MiMe alleles at PS1 and JASON; (b) the second parent MiMe potato plant has only MiMe alleles at SPO11-1, only non-MiMe alleles at REC8, only non-MiMe alleles at OSD1, and only MiMe alleles at PS1 or JASON.

In some embodiments, the first parent MiMe potato plant, the second parent MiMe potato plant, or both has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1.

In some embodiments, the first parent MiMe potato plant, the second parent MiMe potato plant, or both has a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1.

In some embodiments, the first parent MiMe potato plant, the second parent MiMe potato plant, or both has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1.

In some embodiments, the first parent MiMe potato plant, the second parent MiMe potato plant, or both has a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1.

In some embodiments, the first parent MiMe potato plant, the second parent MiMe potato plant, or both has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. potato plant In some embodiments, the first parent MiMe potato plant, the second parent MiMe potato plant, or both has a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1.

In some embodiments, the first parent MiMe potato plant, the second parent MiMe potato plant, or both has a complete MiMe genotype comprising (i) an os allele, wherein the subpopulation of genetically uniform polyploid potato seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1.

In some embodiments, the first parent MiMe potato plant, the second parent MiMe potato plant, or both has a complete MiMe genotype comprising (i) a ps allele, wherein the subpopulation of genetically uniform polyploid potato seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1.

In some embodiments, the first parent MiMe potato plant, the second parent MiMe potato plant, or both comprise one or more polynucleotide sequences selected from the group consisting of SEQ ID NOs: 127-129, 131-134, 137-154, and 156-159. In certain embodiments, the first parent MiMe potato plant, the second parent MiMe potato plant, or both comprises a MiMe allele at one or more SPO11-1 loci, each independently comprising a polynucleotide sequence selected from the group consisting of SEQ ID NOs: 127-129. In certain embodiments, the first parent MiMe potato plant, the second parent MiMe potato plant, or both comprises a) a MiMe allele at one or more REC8 loci, each independently comprising a polynucleotide sequence selected from the group consisting of SEQ ID NOs: 131 and 132; and/or b) a MiMe allele at one or more SPO11-1 loci, each independently comprising a polynucleotide sequence selected from the group consisting of SEQ ID NOs: 133 and 134. In certain embodiments, the first parent MiMe potato plant, the second parent MiMe potato plant, or both comprises a) a MiMe allele at one or more REC8 loci, each independently comprising a polynucleotide sequence selected from the group consisting of SEQ ID NOs: 137 and 138; and/or b) a MiMe allele at one or more SPO11-1 loci, each independently comprising a polynucleotide sequence selected from the group consisting of SEQ ID NOs: 139 and 140. In certain embodiments, the first parent MiMe potato plant, the second parent MiMe potato plant, or both comprises a MiMe allele at one or more SPO11-1 loci, each independently comprising a polynucleotide sequence selected from the group consisting of SEQ ID NOs: 141 and 142. In certain embodiments, the first parent MiMe potato plant, the second parent MiMe potato plant, or both comprises a) a MiMe allele at one or more CYCA1 loci, each independently comprising a polynucleotide sequence selected from the group consisting of SEQ ID NOs: 143 and 144; b) a MiMe allele at one or more REC8 loci, each independently comprising a polynucleotide sequence selected from the group consisting of SEQ ID NOs: 145 and 146; and/or c) a MiMe allele at one or more SPO11-1 loci, each independently comprising a polynucleotide sequence selected from the group consisting of SEQ ID NOs: 147 and 148. In certain embodiments the first parent MiMe potato plant, the second parent MiMe potato plant, or both comprises a) a MiMe allele at one or more CYCA1 loci, each independently comprising a polynucleotide sequence selected from the group consisting of SEQ ID NOs: 149 and 150; b) a MiMe allele at one or more REC8 loci, each independently comprising a polynucleotide sequence selected from the group consisting of SEQ ID NOs: 151 and 152; and/or c) a MiMe allele at one or more SPO11-1 loci, each independently comprising a polynucleotide sequence selected from the group consisting of SEQ ID NOs: 153 and 154. In certain embodiments, the first parent MiMe potato plant, the second parent MiMe potato plant, or both comprises a) a MiMe allele at one or more REC8 loci, each independently comprising a polynucleotide sequence selected from the group consisting of SEQ ID NOs: 156 and 157; and/or b) a MiMe allele at one or more SPO11-1 loci, each independently comprising a polynucleotide sequence selected from the group consisting of SEQ ID NOs: 158 and 159. In some variations, each the one or more CYCA1 loci, each of the one or more REC8 loci, each of the one or more PAIR1 loci, and/or each of the one or more SPO11-1 loci are present on a different homologous chromosome.

Providing Haploid Gametes

In some embodiments, the method of producing a population of polyploid potato seed comprises providing haploid gametes from a homozygous parent non-MiMe potato plant. In some embodiments, providing haploid gametes comprises growing one or more homozygous parent non-MiMe potato plants and allowing them to grow to a reproductive stage until haploid gametes form. In some variations, providing haploid gametes further comprises collecting haploid pollen from one or more homozygous parent non-MiMe potato plants. In some additional variations, the one or more homozygous parent non-MiMe potato plants may be haploid, monoploid, diploid, triploid, tetraploid, pentaploid, hexaploid, heptaploid, octoploid, or any combination thereof. In some embodiments, the homozygous parent non-MiMe potato plant is diploid and the haploid gametes are monoploid gametes.

In some embodiments, the method of producing a population of polyploid potato seed comprises (a) providing clonal gametes from a parent MiMe potato plant; and (b) providing haploid (e.g., monoploid) gametes from a homozygous parent non-MiMe potato plant, wherein the clonal gametes and the haploid (e.g., monoploid) gametes together comprise three or more haplotypes. In some variations, the clonal gametes and the haploid gametes together comprise three or more haplotypes, four or more haplotypes, five or more haplotypes, six or more haplotypes, seven or more haplotypes, or eight or more haplotypes. In additional variations the clonal gametes and the haploid gametes together comprise three, four, five, six, seven, or eight haplotypes. In some embodiments, the haploid gametes comprise one haplotype and the clonal gametes comprise two or more haplotypes, wherein the clonal gametes and the haploid gametes together comprise three or more haplotypes.

Providing Unreduced, Non-Clonal Gametes

In some embodiments, the method of producing a population of polyploid potato seed comprises providing unreduced, non-clonal gametes. In some embodiments, the method of producing a population of polyploid potato seed comprises providing unreduced, non-clonal gametes from one or more parent plants. In certain embodiments, providing unreduced, non-clonal gametes comprises: growing a parent potato plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis; and allowing the parent potato plant to grow to a reproductive stage until unreduced, non-clonal gametes form. In other embodiments, providing unreduced, non-clonal gametes comprises: generating a parent potato plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis; and growing said parent potato plant to a reproductive stage until unreduced, non-clonal gametes form. In some variations, providing unreduced, non-clonal gametes further comprises collecting pollen comprising unreduced, non-clonal gametes from a parent potato plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis. The MiMe loci of a of a component of progression through the first division of meiosis may be any loci of a component of progression through the first division of meiosis known in the art or described herein, including, but not limited to, PS1 and JASON. The MiMe loci of a component of a component of progression through the second division of meiosis may be any loci of a component of a component of progression through the second division of meiosis known in the art or described herein, including, but not limited to, OSD1, CYCA1, TDM1, PC1, PC2, and FC. In certain embodiments, the parent potato plant is a plant of an inbred potato line. In some variations, the parent plant is diploid, triploid, tetraploid, pentaploid, hexaploid, heptaploid, octoploid, or any combination thereof.

Crossing Clonal Gametes

In some embodiments, the method of producing a population of polyploid potato seed comprises crossing the clonal gametes to produce the population of polyploid potato seed. In some variations, crossing the clonal gametes to produce the population of polyploid potato seed comprises contacting pollen comprising clonal gametes with the stigma of a pistil comprising clonal gametes. In some variations, crossing the clonal gametes to produce the population of polyploid potato seed comprises contacting pollen comprising clonal gametes of a first potato plant with the stigma of a pistil comprising clonal gametes of a second potato plant. In some embodiments, crossing the clonal gametes to produce the population of polyploid potato seed comprises contacting pollen comprising clonal gametes from a first parent MiMe potato plant with the stigma of a pistil comprising clonal gametes of a second parent MiMe potato plant. In some embodiments, the population of polyploid potato seed is produced by crossing the clonal gametes and allowing seeds to form.

In other embodiments, the method of producing a population of polyploid potato seed comprises crossing clonal gametes with haploid gametes to produce the population of polyploid potato seed. In one variation, crossing the clonal gametes with the haploid gametes to produce the population of polyploid potato seed comprises contacting pollen comprising clonal gametes with the stigma of a pistil comprising haploid gametes. In another variation, crossing the clonal gametes with the haploid gametes to produce the population of polyploid potato seed comprises contacting pollen comprising haploid gametes with the stigma of a pistil comprising clonal gametes. In some embodiments, crossing the clonal gametes with the haploid gametes to produce the population of polyploid potato seed comprises contacting pollen comprising clonal gametes from a parent MiMe potato plant with the stigma of a pistil comprising haploid gametes of a homozygous parent non-MiMe potato plant. In other embodiments, crossing the clonal gametes with the haploid gametes to produce the population of polyploid potato seed comprises contacting pollen comprising haploid gametes from a homozygous parent non-MiMe potato plant with the stigma of a pistil comprising clonal gametes of a parent MiMe potato plant. In some variations, the homozygous parent non-MiMe potato plant and the haploid gametes are monoploid gametes. In some embodiments, the population of polyploid potato seed is produced by crossing the clonal gametes with the haploid gametes and allowing seeds to form.

In yet other embodiments, the method of producing a population of polyploid potato seed comprises crossing clonal gametes with unreduced, non-clonal gametes to produce the population of polyploid potato seed. In one variation, crossing the clonal gametes with the unreduced, non-clonal gametes to produce the population of polyploid potato seed comprises contacting pollen comprising clonal gametes with the stigma of a pistil comprising unreduced, non-clonal gametes. In another variation, crossing the clonal gametes with the unreduced, non-clonal gametes to produce the population of polyploid potato seed comprises contacting pollen comprising unreduced, non-clonal gametes with the stigma of a pistil comprising clonal gametes. In some embodiments, crossing the clonal gametes with the unreduced, non-clonal gametes to produce the population of polyploid potato seed comprises contacting pollen comprising clonal gametes from a parent MiMe potato plant with the stigma of a pistil comprising unreduced, non-clonal gametes of a homozygous parent plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis. In some embodiments, crossing the clonal gametes with the unreduced, non-clonal gametes to produce the population of polyploid potato seed comprises contacting the stigma of a pistil comprising clonal gametes from a parent MiMe potato plant with pollen comprising unreduced, non-clonal gametes of a homozygous parent plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis. In some embodiments, the population of polyploid potato seed is produced by crossing the clonal gametes with the unreduced, non-clonal gametes and allowing seeds to form.

In some embodiments, crossing clonal gametes to produce the population of polyploid potato seed comprises (a) collecting pollen from a first parent MiMe potato plant having only MiMe alleles at the one or more MiMe loci of the component of DNA double strand breakage during meiotic recombination, only non-MiMe alleles at the one or more MiMe loci of the component of sister chromatid cohesion during the first division of meiosis, only non-MiMe alleles at the one or more MiMe loci of the component of progression through the second division of meiosis, and only MiMe alleles at the one or more MiMe loci of the component of progression through the first division of meiosis; and (b) contacting the pollen from the first parent MiMe potato plant with a stigma of a second parent MiMe potato plant having only MiMe alleles at one or more MiMe loci of a component is a component of DNA double strand breakage during meiotic recombination, only MiMe alleles one or more MiMe loci of a component of sister chromatid cohesion during the first division of meiosis, only MiMe alleles at one or more MiMe loci of a component of progression through the second division of meiosis, and only non-MiMe alleles at one or more MiMe loci of a component of progression through the first division of meiosis.

Methods of Breeding Polyploid Hybrid Potato Lines Comprising Three or More Haplotypes In yet another aspect, provided herein are methods of breeding a polyploid hybrid potato line comprising three or more haplotypes, comprising obtaining a set of potato lines; breeding the potato lines using traditional plant breeding methods to produce a set of candidate potato lines; and selecting two or more candidate potato lines together comprising three or more haplotypes for crossing. In some embodiments, after the selection of candidate potato lines, the methods further comprise generating two parent MiMe potato plants from the two or more candidate potato lines; providing clonal gametes from each of the parent MiMe potato plants; and crossing the clonal gametes to produce a hybrid polyploid potato seed comprising the three or more haplotypes. In alternative embodiments, after the selection of candidate potato lines, the methods further comprise generating a single parent MiMe potato plant from one of the two or more candidate potato lines; providing clonal gametes from the parent MiMe potato plant; providing haploid (e.g., monoploid) gametes from a homozygous parent non-MiMe potato plant of one of the two or more candidate potato lines; and crossing the clonal gametes with the haploid (e.g., monoploid) gametes to produce a hybrid polyploid potato seed. In yet additional embodiments, after the selection of candidate potato lines, the methods further comprise generating a single parent MiMe potato plant from one of the two or more candidate potato lines; providing clonal gametes from the parent MiMe potato plant; providing unreduced, non-clonal gametes from homozygous parent plant of one of the two or more candidate potato lines; and crossing the clonal gametes with the unreduced, non-clonal gametes to produce a hybrid polyploid potato seed. In some embodiments, after the crossing of the clonal gametes or the crossing of the clonal gametes with the haploid (e.g., monoploid) gametes, or crossing of the clonal gametes with unreduced, non-clonal gametes, the methods further comprise growing the hybrid polyploid potato seed to produce a hybrid polyploid potato plant and evaluating one or more characteristics of the hybrid polyploid potato plant.

In still another aspect, provided herein are methods of breeding hybrid polyploid potato plants, comprising obtaining a set of potato lines; breeding the lines using traditional plant breeding methods to produce a set of candidate potato lines; selecting two or more candidate potato lines for crossing; and generating a first parent MiMe potato plant and a second parent MiMe potato plants from the two or more candidate potato lines. In some embodiments, the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; and the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component. In certain embodiments, at least one of the MiMe loci having only MiMe alleles of the first MiMe component of the first parent MiMe potato plant is the same as at least one of the MiMe loci having only MiMe alleles of the first MiMe component of the second parent MiMe potato plant. In some embodiments, the first and second parent MiMe potato plants further have only MiMe alleles at one or more MiMe loci of a third MiMe component, wherein the one or more MiMe loci having only MiMe alleles of the third MiMe component of the first and second parent MiMe potato plants are the same or different. In certain embodiments, the parent MiMe potato plants together comprise two, three, or more haplotypes. In some embodiments, the methods further comprise providing clonal gametes from each of the parent MiMe potato plants; crossing the clonal gametes to produce a polyploid seed; growing the polyploid seed to produce a hybrid polyploid potato plant; and evaluating one or more characteristics of the hybrid polyploid potato plant.

Obtaining Plant Lines

In some embodiments, the method of breeding a polyploid hybrid potato line comprising two, three, or more haplotypes comprises obtaining a set of potato lines. In preferred embodiments, the set of potato lines is genetically diverse and comprises a large and diverse pool of haplotypes. In some embodiments, the method of breeding a polyploid hybrid potato line comprising two, three, or more haplotypes comprises obtaining a set of lines of the same or related species of potato. The set of potato lines may be obtained from any source and by any methods known in the art. In some embodiments, the set of lines is obtained from sources including, but not limited to, natural diversity, existing breeding programs, dihaploid induction of polyploid lines, or any combination thereof.

In some embodiments, the set of plant lines is a genetically diverse founder population of plants. These plants may be collected from existent diploid germplasm sources such as wild species, progenitor species and landraces or from recent diploid inbred line-based breeding efforts (Jansky et al. 2016. Reinventing potato as a diploid inbred line-based crop. Crop Science 56, no. 4:1412-1422). In some instances, these plants may have high genetic load and may not have undergone the narrowing of genetic variability attributable to the elite selection practices imposed on modern cultivated materials. As such, many possess traits promoting their fitness within non-agrarian environments in the case of wild progenitors, or have been adapted to vastly differing cultivation practices and agricultural environments in the case of landraces. In either instance, these founding plant materials may contain suites of both desirable and undesirable agronomic characteristics that may be recombined, selected, and complemented to develop a commercially viable product.

In some embodiments, the method of breeding a polyploid hybrid potato line comprising two, three, or more haplotypes comprises obtaining a set of diploid potato lines. The diploid potato lines may be obtained by any methods known in the art or described herein. In some variations, obtaining a set of diploid potato lines comprises dihaploid induction of polyploid lines. New diploid plant germplasm may be created from polyploid sources by one of several ploidy manipulation approaches to reduce the ploidy of a plant's progeny to the diploid level. One of the most frequent and practiced scenarios is the reduction of elite cultivated tetraploid source materials (2n=4x=48) to diploids (2n=2x=24) via ploidy reduction methods such as pseudogamy (a.k.a. gynogenesis or sperm-dependent parthenogenesis). This approach may provide an efficient means to create new diploid plants that are each a sampling of half the alleles of a tetraploid line. As such, these dihaploids are less likely to bear the genetic load of diploid wild progenitor species or landraces and are more apt to complement the germplasm sources attained by other methods described herein. Moreover, undesirable recessive alleles masked at the cultivated tetraploid level may be revealed phenotypically and selected against at the diploid level.

In certain embodiments, the obtaining a set of potato lines comprises creating reduced-ploidy plant lines by haploid induction of polyploid potato lines. Haploid induction may be achieved in a variety of plant species by, for example, interspecific hybridization with a haploid inducer, intraspecific hybridization with a haploid inducer, or modification of CENH3 activity or expression (e.g. by RNA interference and/or expression of a modified CENH3 protein). Methods of haploid induction are well known in the literature, and examples are described Wan, et al. (1989. Efficient production of doubled haploid plants through colchicine treatment of anther-derived maize callus. Theor. Appl. Genet., 77:889-892.) and Ren et al. (2017. Novel technologies in doubled haploid line development. Plant Biotechnol J 15, 1361-1370.) and references cited therein. In some variations, the obtaining a set of potato lines comprises haploid induction of one or more tetraploid lines to create one or more diploid lines. In other variations, the obtaining a set of potato lines comprises haploid induction of hexaploid, octoploid, or higher even-ploidy lines to create one or more lines of half the original ploidy.

Heterotic Groups

In some embodiments, the method of breeding a polyploid hybrid potato line comprises organizing the set of lines into two, three, or more heterotic groups, wherein each heterotic group comprises a haplotype, and wherein the haplotypes are grouped based on observed or predicted heterotic performance when combined in the hybrid polyploid potato plant. In some embodiments, the method of breeding a polyploid hybrid potato line comprises organizing the set of lines into four or more heterotic groups. In some variations, the method of breeding a polyploid hybrid potato line comprises organizing the set of lines into five or more heterotic groups, six or more heterotic groups, seven or more heterotic groups, or eight or more heterotic groups.

The obtained set of potato lines may be organized by assigning their membership into complementary heterotic groups based upon both their empirically-defined Endosperm Balance Number for the genus in question (Ortiz and Ehlenfeldt. 1992. The importance of Endosperm Balance Number in potato breeding and the evolution of tuber-bearing Solanum species. Euphytica 60, 105-113; Arisumi. 1982. Endosperm balance numbers among New Guinea-Indonesian Impatiens species, Journal of Heredity, 73:3, 240-242; Birchler. 1993. Dosage analysis of maize endosperm development. Annu Rev Genet. 27:181-204; Nishiyama et al. 2007. Embryological studies on cross-incompatibility between 2× and 4× in Brassica, Japanese Journal of Genetics, 41:1, 27-42) and heterotic patterns observed from preliminary estimation or prediction of their combining ability for traits and environments of interest at the diploid and polyploid levels. In this context, the combining ability is an estimation of the value of a plant as a parent as inferred by progeny testing in an established factorial or hierarchical mating design. Combining ability at the polyploid hybrid level is of primary importance; however, sufficient diploid hybrid performance is necessary to permit the diploid hybrid to serve as a parent for seed production. Furthermore, assessment of combining abilities at the simplified diploid level will better inform predictive models of genetic architecture.

In defining heterotic groups, the main goal is identifying subpopulations of the set of potato lines based on employment of a clustering procedure that maximizes some measure of interpopulation combining ability. Exhaustive evaluation of all possible parental combinations for the final polyploid hybrid, as in the case of a factorial mating scheme, is infeasible for all but a trivial number of potential parents (i.e. even a partial diallel ignoring reciprocal crosses scales at (n+3)!/(4! (n−1)!) crosses per n parents). Yet, hierarchical mating schemes necessitate an understanding and judgment of which set of "testers" or analogous constructs should serve as a relevant and efficient basis or frame of reference for inferring combining ability. The sample of testers selected invariably biases perceptions of existing heterotic patterns. Furthermore, the relative importance of traits and environments of interest used to infer these combining abilities are dynamic and depend upon market trends. As such, predictive modeling is essential and the process of assigning and refining heterotic groups and testers to represent them is one of iterative improvement and refinement throughout repeated cycles of the breeding process. Nonetheless, once preliminary heterotic group membership is assigned, interpopulation improvement of the diploid germplasm and development of polyploid hybrid plants may proceed.

Breeding Plant Lines

In some embodiments, the method of breeding a polyploid hybrid potato line comprising three or more haplotypes comprises breeding the lines using traditional plant breeding methods to produce a set of candidate potato lines. The method may comprise breeding the lines using any traditional plant breeding method known in the art or described herein. In some embodiments, the breeding of the lines comprises reciprocal recurrent selection. In additional embodiments, the breeding of the lines comprises inbreeding one or more of the lines to homozygosity. In some variations, the breeding of the lines comprises crossing, selfing (self-pollinating), and backcrossing the lines to produce candidate potato lines. In additional variations, the breeding of the lines comprises crossing pairs of the lines to generate an F1 (first filial) generation, followed by several generations of selfing (generating F2, F3, etc.). In yet additional variations, the breeding of the lines comprises backcrossing (BC) steps, whereby the offspring is backcrossed to one of the parental lines, termed the recurrent parent.

There are numerous steps that may be taken in breeding the potato lines using traditional plant breeding methods to produce a set of candidate potato lines. The choice of breeding method depends on the mode of plant reproduction and the heritability of the trait(s) being improved. Backcross breeding may be used to transfer one or a few favorable genes for a highly heritable trait into a desirable line. This approach has been used extensively for breeding disease-resistant lines. Various recurrent selection techniques may be used to improve quantitatively inherited traits controlled by numerous genes. The use of recurrent selection in self-pollinating crops depends on the ease of pollination, the frequency of successful hybrids from each pollination, and the number of hybrid offspring from each successful cross. A breeder can initially select and cross two or more parental lines, followed by repeated selfing and selection, producing many new genetic combinations. Moreover, a breeder can generate multiple different genetic combinations by crossing, selfing, generating mutations, or any combination thereof. A plant breeder can then select which lines to select as candidate potato lines. Recurrent selection techniques are reviewed in Vasal et al. (2004. Population Improvement Strategies for Crop Improvement. In: Plant Breeding. Springer, p 391-406).

The development of candidate potato lines for the methods described herein may include obtaining parental lines, crossing of these lines, and evaluating the crosses. Pedigree breeding and recurrent selection breeding methods may be used to develop candidate potato lines from breeding populations. Breeding programs may combine desirable traits from two or more varieties or various broad-based sources into breeding pools from which lines are developed by selfing and selection of desired phenotypes. The new lines may be further crossed with other lines and the hybrids from these crosses may be evaluated for potential selection as candidate potato lines.

Choice of breeding or selection methods depends on the mode of plant reproduction and the heritability of the trait(s) being improved. For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

In some embodiments, the breeding of the lines comprises inbreeding one or more of the lines to homozygosity. In some variations, inbreeding a plant line to homozygosity may comprise selfing plants of the line for two or more generations, such as for five to seven generations, to produce an inbred or homozygous plant line. Homozygous plant lines may also be developed by the production of double haploids. Double haploids are produced by generating a haploid plant from a heterozygous plant and the doubling of the genome of the haploid plant to produce a completely homozygous individual. The process of generating a haploid plant is also known as haploid induction. Haploid induction can be achieved in a variety of plants using methods well-known in the art and described herein. After a haploid plant is generated, genome doubling may occur spontaneously or may be achieved artificially using, for example, colchicine, amiprophos-mehtyl (APM), oryzalin, pronamide, trifluralin, or nitrous oxide. Methods of producing double haploids are well known in the literature, and examples are described Wan, et al. (1989. Efficient production of doubled haploid plants through colchicine treatment of anther-derived maize callus. Theor. Appl. Genet., 77:889-892.) and Ren et al. (2017. Novel technologies in doubled haploid line development. Plant Biotechnol J 15, 1361-1370.) and references cited therein.

Pedigree breeding is used commonly for the improvement of self-pollinating crops or inbred lines of cross-pollinating crops. Two parents which possess favorable, complementary traits are crossed to produce an F1 population. An F2 population is produced by selfing one or several F1s or by intercrossing two F1s (sib mating). Selection of the best individuals may begin in the F2 population; then, beginning in the F3, the best individuals in the best families may be selected. Replicated testing of families, or hybrid combinations involving individuals of these families, may follow in the F4 generation to improve the effectiveness of selection for traits with low heritability. At an advanced stage of inbreeding (i.e., F6 and F7), the best lines or mixtures of phenotypically similar lines may be tested for potential selection as candidate potato lines.

Mass and recurrent selections can be used to improve lines of either self- or cross-pollinating crops. A genetically variable population of heterozygous individuals may be either identified or created by intercrossing several different parents. The best plants are selected based on individual superiority, outstanding progeny, or heterotic performance. The selected plants are intercrossed to produce a new population in which further cycles of selection are continued.

Backcross breeding may be used to transfer genes for a simply inherited, highly heritable trait into a desirable homozygous line that is the recurrent parent. The source of the trait to be transferred is called the donor parent. The resulting plant is expected to have the attributes of the recurrent parent and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generational advancement is completed.

In addition to phenotypic observations, the genotype of a plant can also be examined during breeding to produce candidate potato lines. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs-which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of lines as parental varieties or ancestors of a plant by providing a means of tracking genetic profiles through crosses.

Mutation breeding may also be used in the breeding of plant lines to produce candidate potato lines. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into an existing line by traditional breeding techniques. Details of mutation breeding can be found in Principles of Cultivar Development by Fehr, Macmillan Publishing Company, 1993.

Additional non-limiting examples of breeding methods that may be used include, without limitation, those found in Allard (1960. Principles of Plant Breeding, John Wiley and Son, pp. 115-161). Simmonds (1979. Principles of Crop Improvement, Longman Group Limited), Sneep (1979. Plant Breeding Perspectives, Unipub), and Fehr and Walt (1987. Principles of Cultivar Development, pp. 261-286).

In certain embodiments, breeding the potato lines comprises generating and maintaining one or more plant lines having complete or partial MiMe genotypes. The one or more plant lines having complete or partial MiMe genotypes may be maintained via vegetative propagation, selfing, apomixis, cell culture, or any combination thereof. The MiMe alleles of the one or more plant lines having partial MiMe genotypes may be propagated across breeding cycles to reduce the number of required editing or transgenesis events to introduce partial or complete MiMe genotypes into candidate potato lines. In some embodiments, each of the heterotic groups may be further divided into two subgroups, resulting in each heterotic group containing a small subgroup of plant lines having a partial MiMe genotype, maintained through outbreeding and stabilizing selection for the partial MiMe genotype and a wild-type meiosis phenotype, and another larger subgroup of plant lines that do not comprise MiMe alleles. The subgroup containing the plant lines having a partial MiMe genotype may be slower-cycling during breeding, as genotyping and stabilizing selection for the partial MiMe genotype and wild-type meiosis phenotype may be undertaken in some or all progeny. Within this subgroup, a subset of all possible intragroup crosses, which are expected to bear some offspring possessing the partial MiMe genotype and a wild-type meiosis phenotype, is selected and realized by considering the following criteria: 1) per se performance of the plant line, 2) genotype or pedigree-based estimation or prediction of breeding value and combining ability with regard to complementing the alternate subgroup within the heterotic group as well as the other heterotic groups at the polyploid hybrid level, and 3) management of inbreeding with respect to both subgroups of the heterotic group. After genotyping and selecting the subset of realized recombinant diploid progeny having a partial MiMe genotype and a wild-type meiosis phenotype, these plants may serve in the following breeding roles: 1) field evaluations to improve the estimation or prediction of breeding values and combining abilities, 2) testers to aid heterotic group (re) assignment, 3) progenitors in recurrent cycles of diploid intergroup improvement to increase desirable allele frequencies and linkage disequilibria, and/or 4) great-grandparents in tetraploid hybrid plant development.

In some embodiments, breeding the potato lines comprises (i) introducing a partial MiMe genotype into one or more potato lines within a heterotic group to produce a plant line having a partial MiMe genotype, wherein the plant line having a partial MiMe genotype comprises one or more haplotypes, (ii) crossing the plant line having the partial MiMe genotype with itself or another plant line, and (iii) propagating the plant line having the partial MiMe genotype by selecting for the partial MiMe genotype in the offspring of the cross of step (ii). In some variations, step (ii) comprises crossing the plant line having the partial MiMe genotype with itself. In other variations, step (ii) comprises crossing the plant line having the partial MiMe genotype with another plant within the same heterotic group or a different heterotic group.

In some embodiments, haploid induction may be used to maintain polyploid potato lines having a complete MiMe genotype. In certain embodiments, maintaining a polyploid potato line having a complete MiMe genotype comprises crossing a polyploid potato plant having a complete MiMe genotype with a haploid inducer to produce progeny of the same ploidy as the plant having the complete MiMe genotype. In one variation, maintaining a polyploid potato line having a complete MiMe genotype comprises crossing a tetraploid plant having a complete MiMe genotype with a haploid inducer to produce tetraploid progeny.

Selecting Candidate Potato Lines

In some embodiments, the method of breeding a polyploid hybrid potato line comprising two, three, or more haplotypes comprises selecting two or more candidate potato lines together comprising two, three, or more haplotypes. In some variations, the method of breeding a hybrid polyploid potato plant comprises selecting two or more candidate potato lines together comprising three or more haplotypes or four or more haplotypes. In some embodiments, one or more of the candidate potato lines are inbred potato lines. In additional embodiments, one or more of the candidate potato lines are hybrid potato lines. In certain embodiments, the selecting of candidate potato lines is guided by the one or more characteristics of a hybrid polyploid potato plant comprising the two, three, or more haplotypes comprised by the two or more candidate potato lines. In certain embodiments, the selecting of candidate potato lines is guided by the one or more characteristics of a hybrid polyploid potato plant comprising the two or more haplotypes, three or more haplotypes, or four or more haplotypes comprised by the two or more candidate potato lines. In some variations, the selecting of candidate potato lines is guided by the observed or predicted heterotic performance of the two or more haplotypes, three or more haplotypes, or four or more haplotypes comprised by the two or more candidate potato lines.

Generating Parent MiMe Plants

In some embodiments, the method of breeding a polyploid hybrid potato line comprising two, three, or more haplotypes comprises generating one or more parent MiMe potato plants from one or more of the two or more candidate potato lines, wherein the parent MiMe potato plant has a complete MiMe genotype. In some variations, the method of breeding a polyploid hybrid potato line comprising two, three, or more haplotypes comprises generating two parent MiMe potato plants from two of the two or more candidate potato lines, wherein each of the parent MiMe potato plants has a complete MiMe genotype. In some embodiments, the method of breeding a hybrid polyploid potato plant comprises generating a first parent MiMe potato plant from one of the candidate potato lines and generating a second parent MiMe potato plant from one of the candidate potato lines, wherein the parent MiMe potato plant has a complete MiMe genotype. In some variations, the method of breeding a hybrid polyploid potato plant comprises generating two parent MiMe potato plants from two of the two or more candidate potato lines, wherein the parent MiMe potato plant has a complete MiMe genotype. In some embodiments, the complete MiMe genotypes of the one or more parent MiMe potato plants comprise alleles that are naturally-occurring, introduced via genetic modification, or a combination thereof. The one or more parent MiMe potato plants may have any complete MiMe genotype known in the art or described herein. The generating of the parent MiMe potato plants may comprise introducing any of the parent MiMe potato plant genotypes described herein (see “Parent MiMe Plant Genotypes” and “Parent MiMe Plant Complementary Genotypes”).

Figure 5:
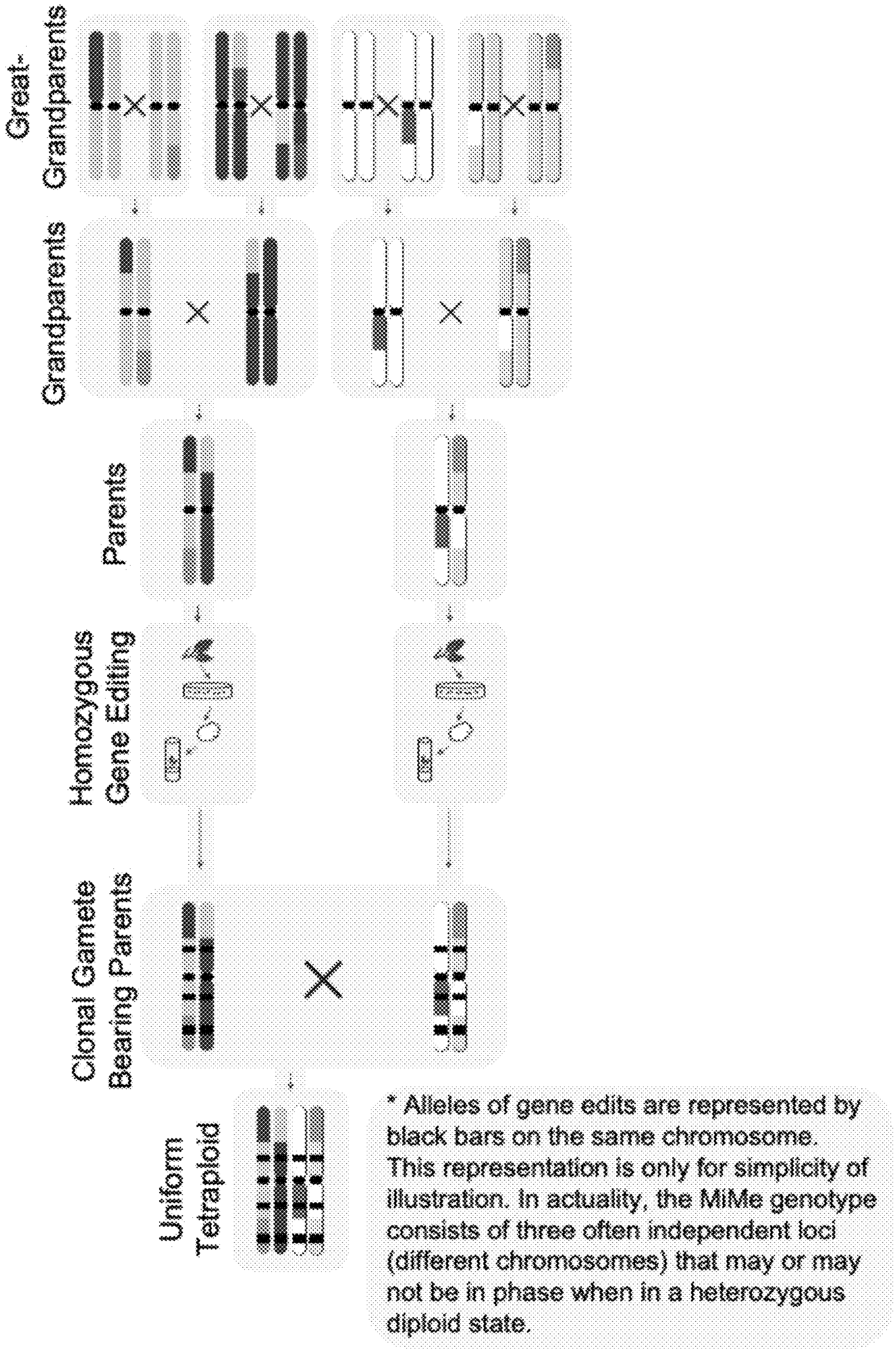
FIG. 5 illustrates an embodiment where homozygous gene editing occurs at the parent stage.
Figure 6:
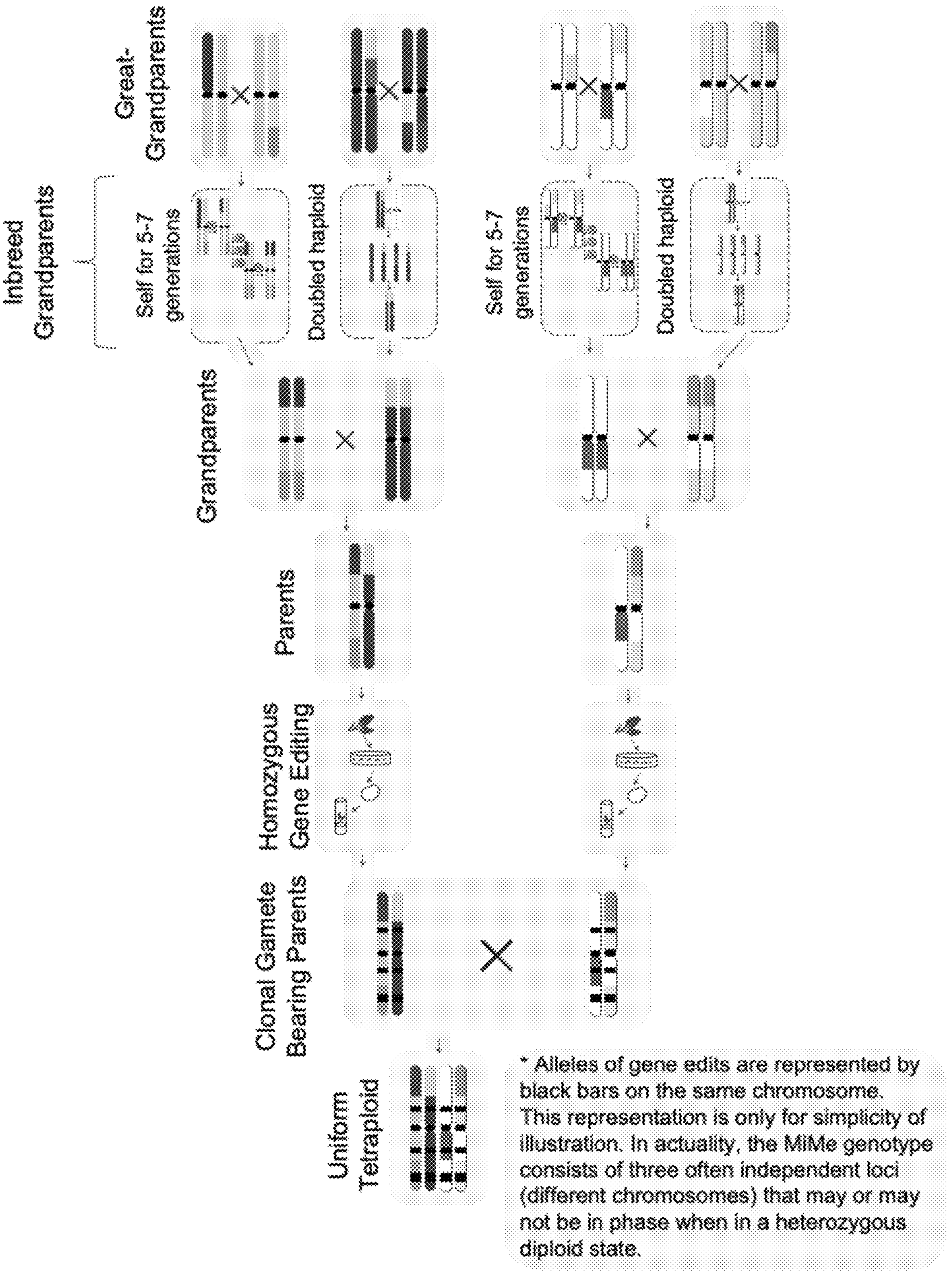
FIG. 6 illustrates an embodiment where grandparents are inbred and homozygous gene editing occurs at the parent stage.
Figure 12:
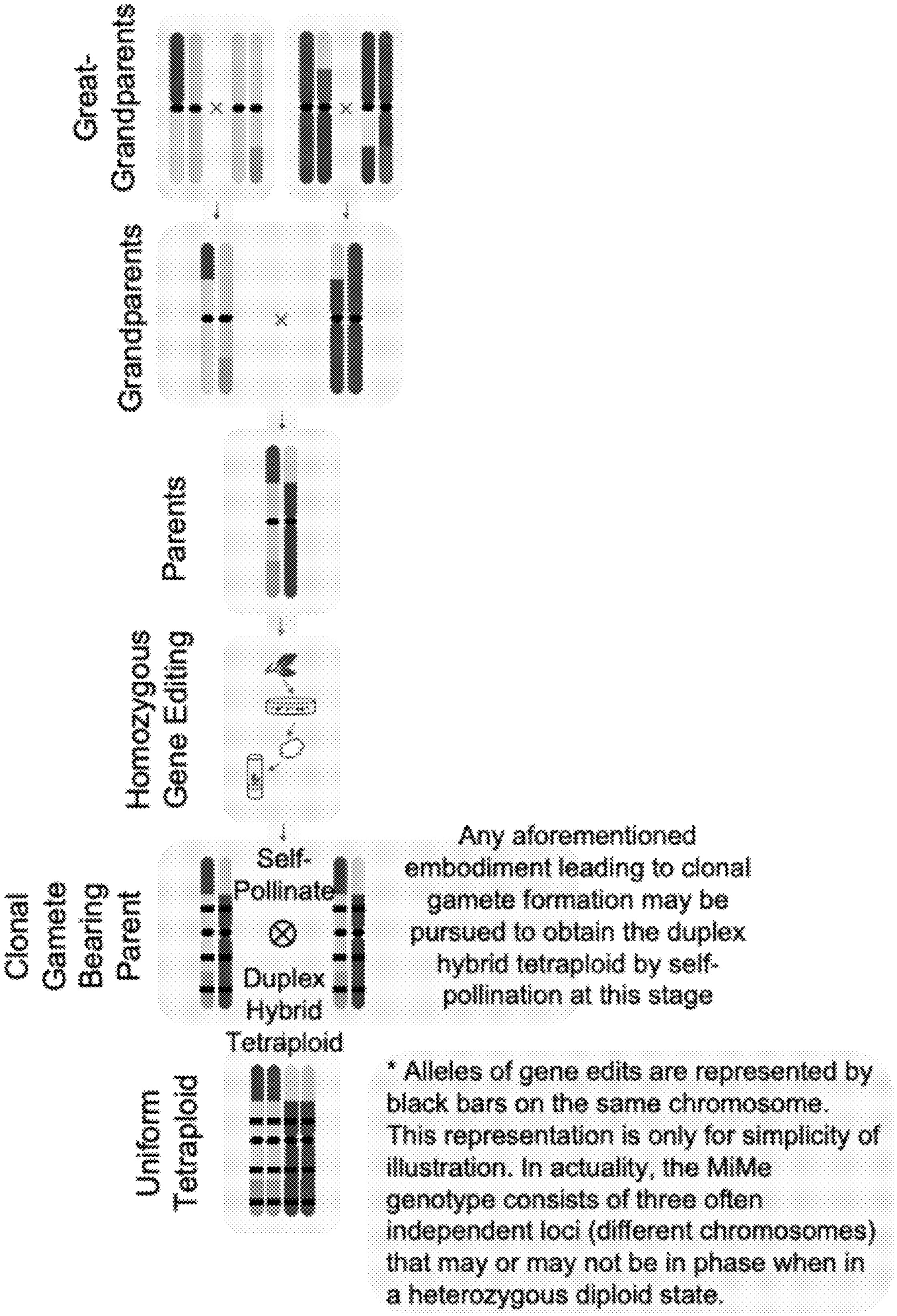
FIG. 12 illustrates an embodiment where unilateral editing results in sexual tetraploidization.
Figure 13A:
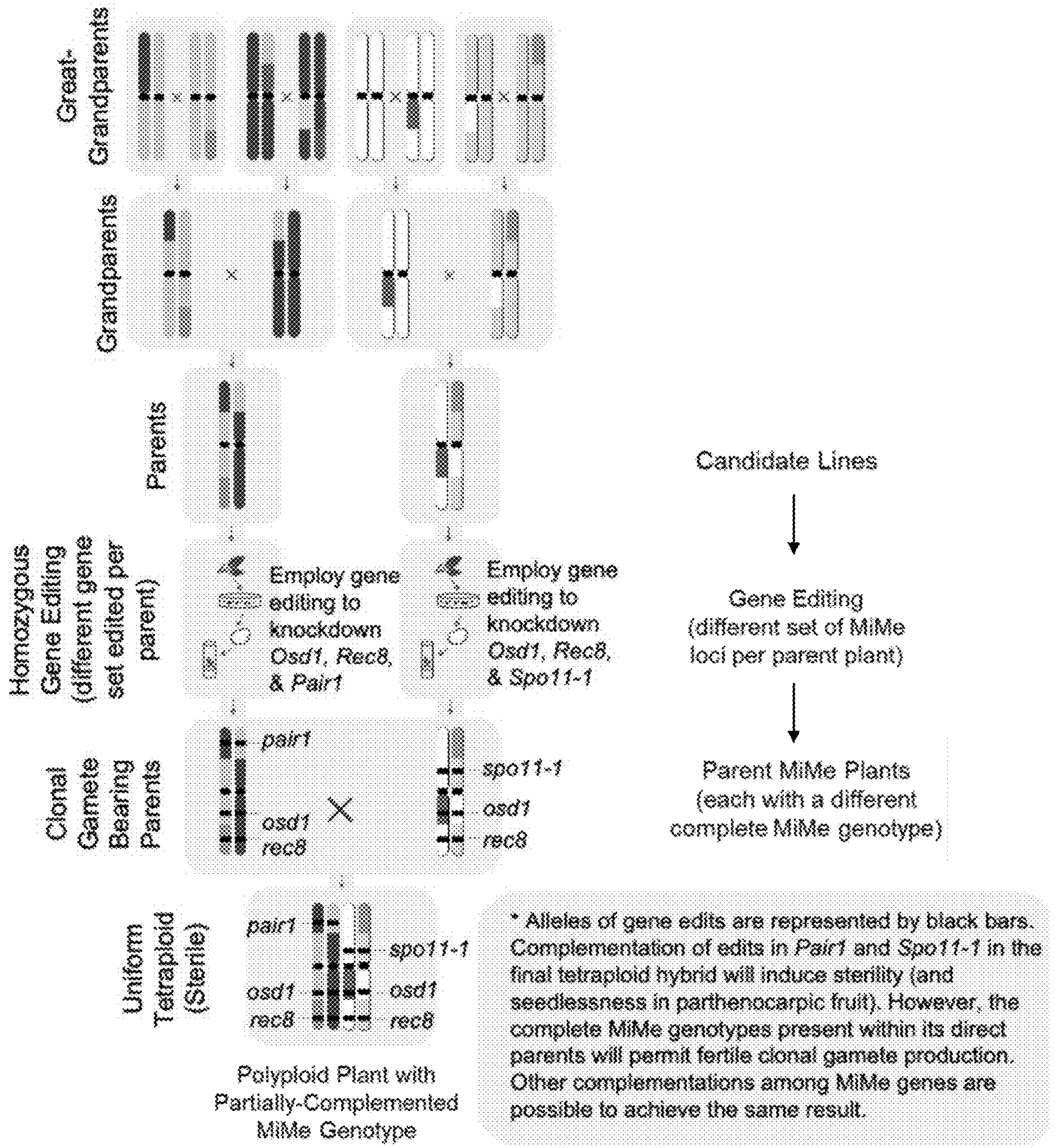
FIGS. 13A-13C illustrate embodiments where sterility of the polyploid hybrid seed is induced via complementation of one of the MiMe loci.
Figure 13B:
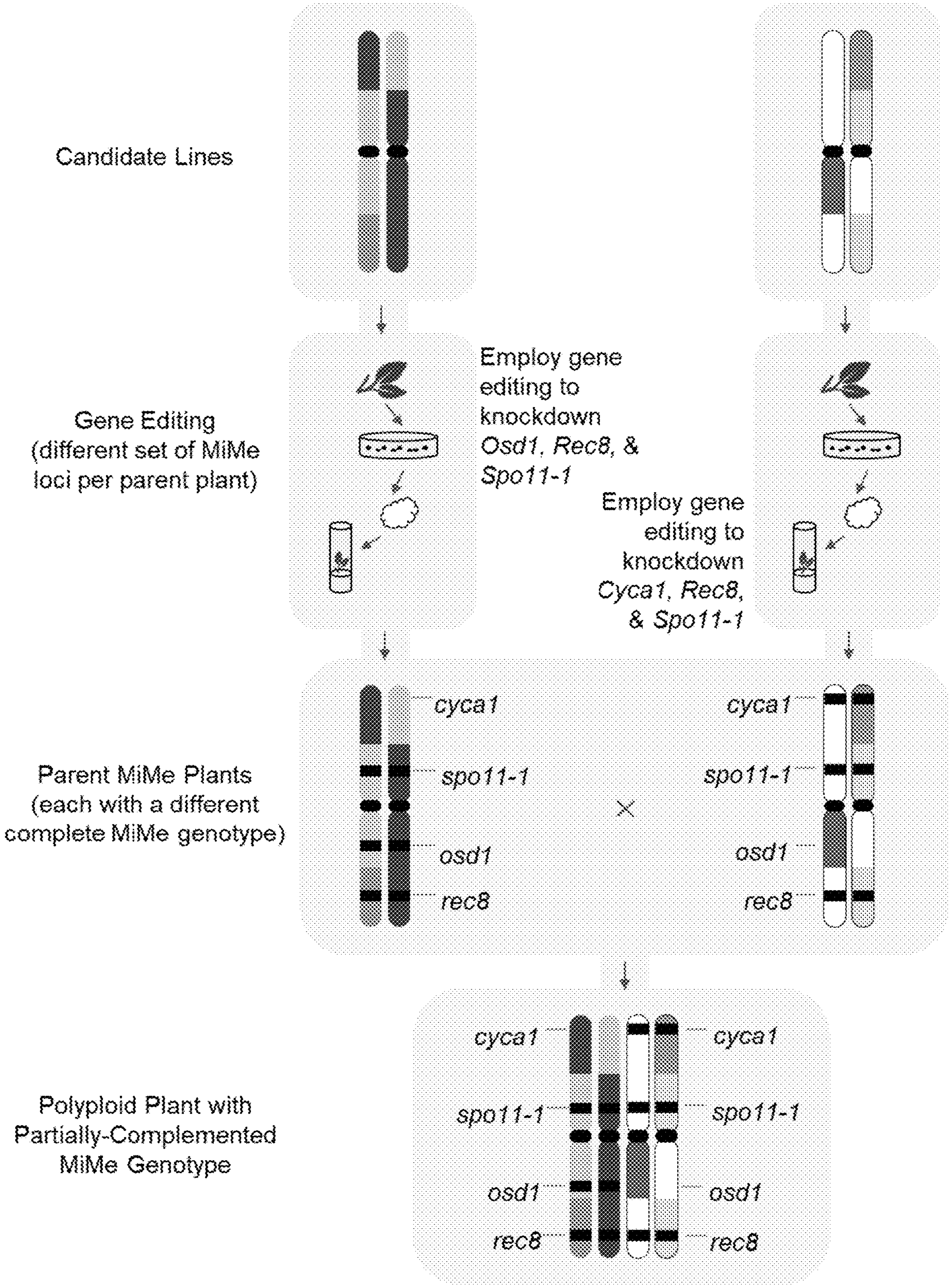
Figure 13C:
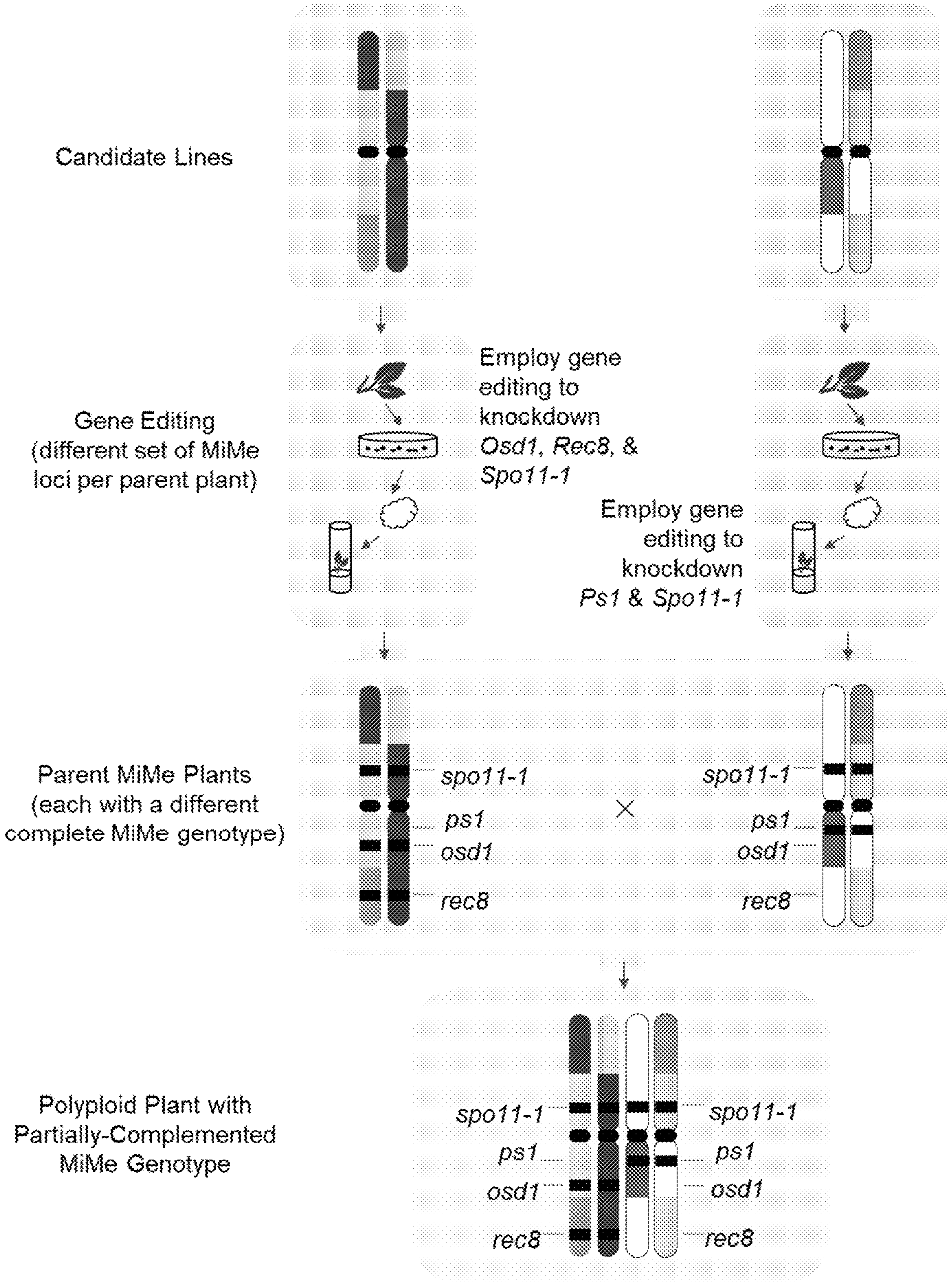

In certain embodiments, the generating of the one or more parent MiMe potato plants comprises introducing a complete MiMe genotype directly into one or more candidate potato lines to produce the one or more parent MiMe potato plants. In some variations, the generating of the two parent MiMe potato plants comprises introducing a complete MiMe genotype directly into two or more candidate potato lines to produce the two parent MiMe potato plants, for example, as shown in FIG. 5, 6, or 12.

Figure 7:
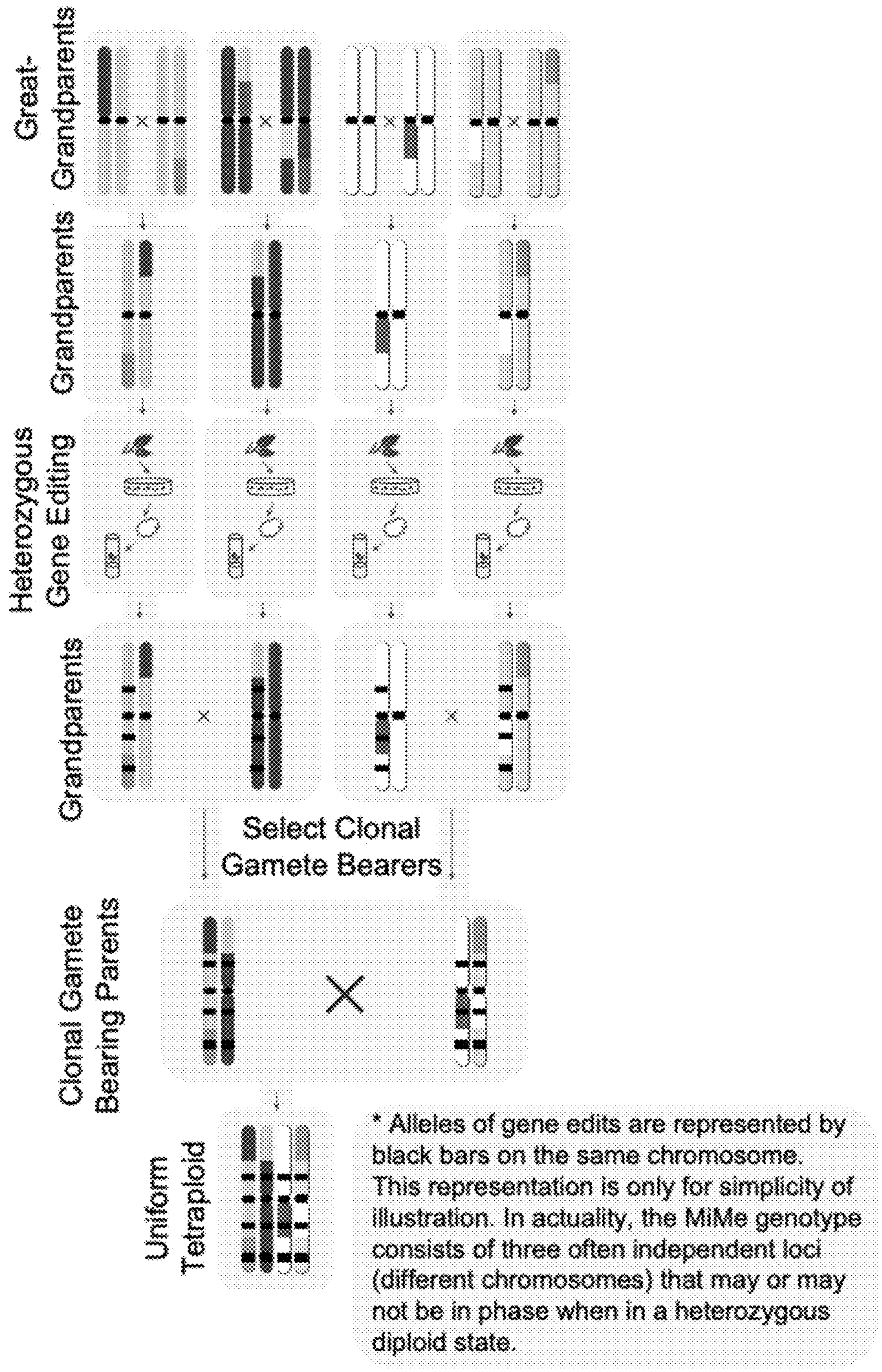
FIG. 7 illustrates an embodiment where heterozygous gene editing occurs at the grandparent stage.
Figure 8:
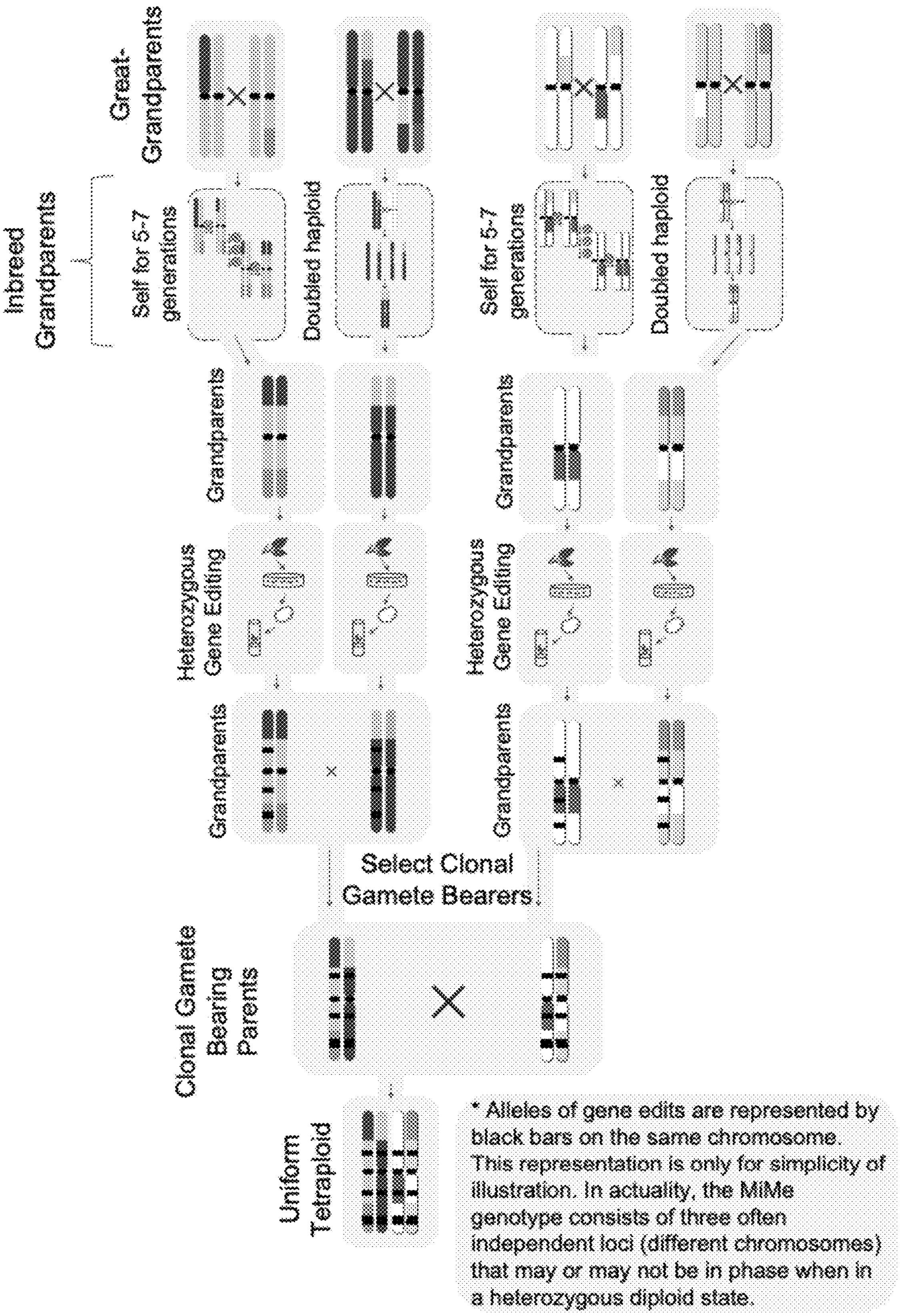
FIG. 8 illustrates an embodiment where grandparents are inbred and heterozygous gene editing at the grandparent stage.
Figure 9:
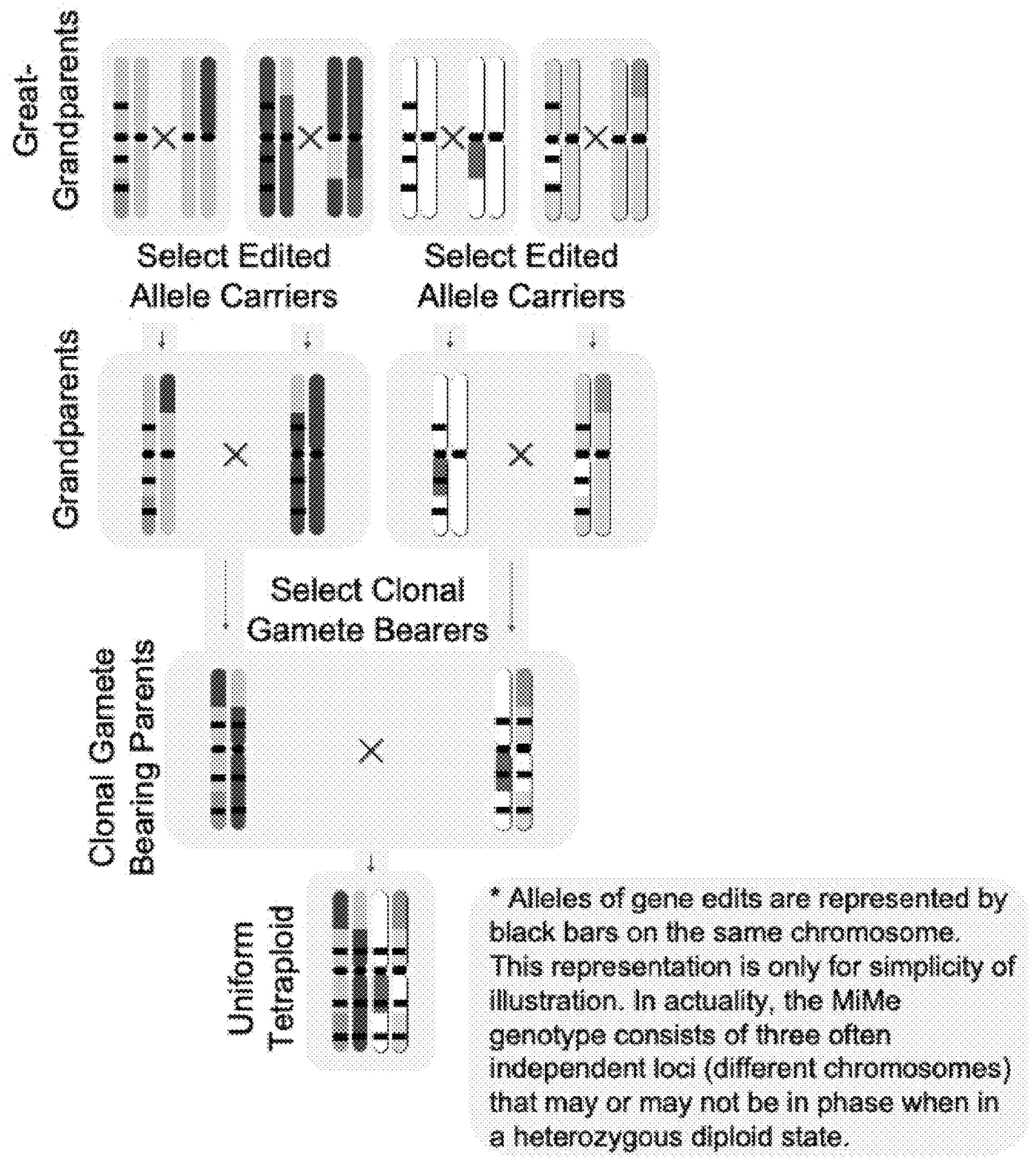
FIG. 9 illustrates an embodiment where MiMe loci are propagated at the grandparent stage.
Figure 10:
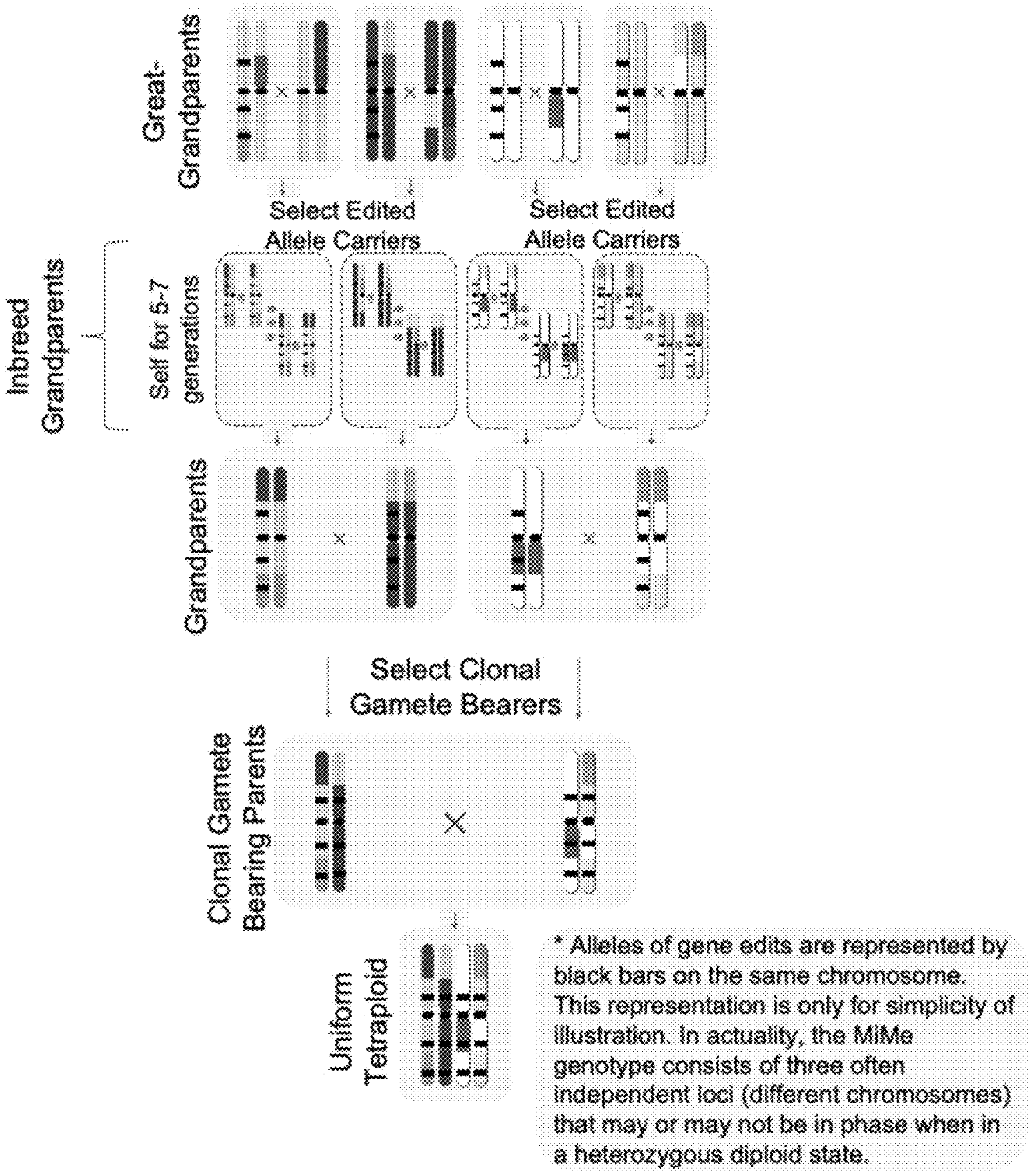
FIG. 10 illustrates an embodiment where grandparents are inbred and MiMe loci are propagated at the grandparent stage.
Figure 11:
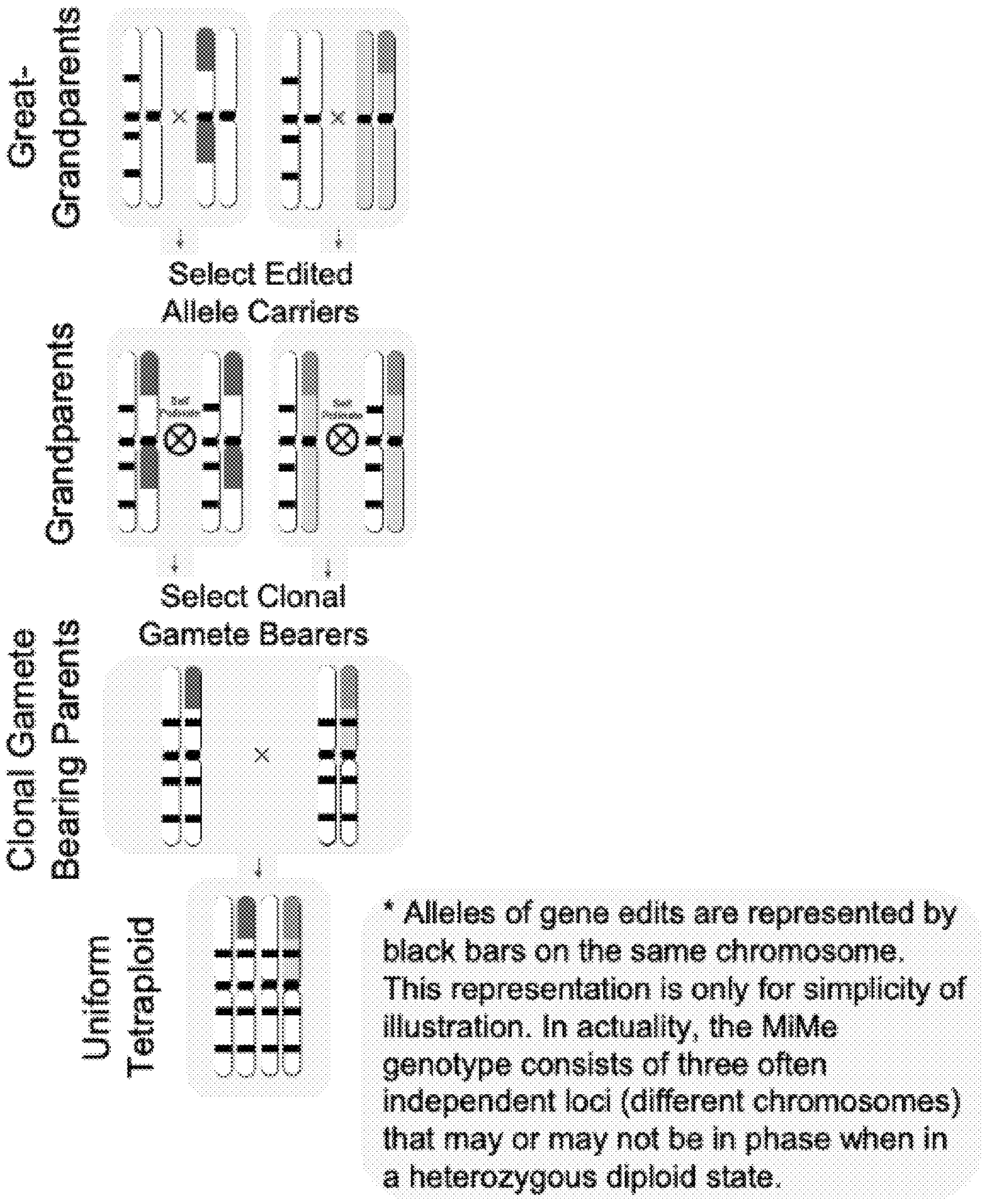
FIG. 11 illustrates an embodiment where MiMe loci are propagated at the great-grandparent stage.

In certain embodiments, the generating of the one or more parent MiMe potato plants comprises introducing a partial MiMe genotype into two or more candidate potato lines to produce two or more grandparent non-MiMe potato plants each having a partial MiMe genotype and crossing said grandparent non-MiMe potato plants each having a partial MiMe genotype to produce the one or more parent MiMe potato plants, for example, as shown in FIG. 7 or 8. In some embodiments, the generating of the two parent MiMe potato plants comprises introducing a partial MiMe genotype into four candidate potato lines to produce four grandparent non-MiMe potato plants each having a partial MiMe genotype, and crossing pairs of said grandparent non-MiMe potato plants each having a partial MiMe genotype to produce the two parent MiMe potato plants, for example, as shown in FIG. 7 or 8. In other embodiments, the generating of the two parent MiMe potato plants comprises introducing a partial MiMe genotype into two candidate potato lines to produce two grandparent non-MiMe potato plants each having a partial MiMe genotype, crossing said grandparent non-MiMe potato plants each having a partial MiMe genotype to produce the first parent MiMe potato plant, and introducing a complete MiMe genotype directly into a third candidate potato line to produce the second parent MiMe potato plant. In additional embodiments, the generating of the one or more parent MiMe potato plants comprises introducing a partial MiMe genotype into a candidate potato line to produce a great-grandparent non-MiMe potato plant having a partial MiMe genotype, crossing the great-grandparent non-MiMe potato plant having a partial MiMe genotype with one or more candidate potato lines together comprising one or more haplotypes to produce a grandparent non-MiMe potato plant having a partial MiMe genotype and comprising two or more haplotypes, and crossing or selfing the grandparent non-MiMe potato plant having the partial MiMe genotype and comprising two or more haplotypes to produce a parent MiMe potato plant comprising two or more haplotypes, for example, as shown in any one of FIGS. 9-11. In one variation, the generating of the two parent MiMe potato plants comprises introducing a partial MiMe genotype into a candidate potato line to produce a great-grandparent non-MiMe potato plant having a partial MiMe genotype, crossing the great-grandparent non-MiMe potato plant having a partial MiMe genotype with two candidate potato lines together comprising two or more haplotypes to produce two grandparent non-MiMe potato plants together comprising three or more haplotypes, and selfing each of the grandparent non-MiMe potato plants together comprising three or more haplotypes to produce two parent MiMe potato plants together comprising three or more haplotypes, for example, as shown in FIG. 10 or 11. In one variation, the generating of the two parent MiMe potato plants comprises introducing a partial MiMe genotype into a candidate potato line to produce a great-grandparent non-MiMe potato plant having a partial MiMe genotype, crossing the great-grandparent non-MiMe potato plant having a partial MiMe genotype with two candidate potato lines together comprising two or more haplotypes to produce two grandparent non-MiMe potato plants together comprising three or more haplotypes, and crossing pairs of the grandparent non-MiMe potato plants together comprising three or more haplotypes to produce two parent MiMe potato plants together comprising three or more haplotypes, for example, as shown in FIG. 9. Any combination of methods for generating one or more parent MiMe potato plants described herein can be used in any combination to generate parent MiMe potato plants for use in the methods described herein. The grandparent non-MiMe potato plant or great-grandparent non-MiMe potato plant may have any partial MiMe genotype known in the art or described herein, including, but not limited to, partial MiMe genotypes comprising MiMe alleles resulting in decreased expression of any of the MiMe loci described herein.

In some embodiments, the grandparent non-MiMe potato plant has a partial MiMe genotype comprising (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, the grandparent non-MiMe potato plant has a partial MiMe genotype comprising (a) one or more MiMe alleles conferring decreased expression of one or more MiMe loci of each of a first and second MiMe component; and (a) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. The grandparent non-MiMe potato plant or great-grandparent non-MiMe potato plant may have any partial MiMe genotype known in the art or described herein, including, but not limited to, partial MiMe genotypes comprising MiMe alleles resulting in decreased expression of any of the MiMe loci described herein.

In some embodiments, the generating of the parent MiMe potato plants comprises introducing a complete MiMe genotype into two candidate potato lines wherein (a) the first parent MiMe potato plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; (b) generating a second parent MiMe potato plant from one of the candidate potato lines, wherein the second parent MiMe potato plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component; (c) at least one of the MiMe loci having only MiMe alleles of the first MiMe component of the first parent MiMe potato plant is the same as at least one of the MiMe loci having only MiMe alleles of the first MiMe component of the second parent MiMe potato plant; and (d) either (1) at least one of the MiMe loci having only MiMe alleles of the third MiMe component of the first parent MiMe potato plant is the same as at least one of the MiMe loci having only MiMe alleles of the third MiMe component of the second parent MiMe potato plant, or (2) the one or more MiMe loci having only MiMe alleles of the third MiMe component of the first parent MiMe potato plant are distinct from the one or more MiMe loci having only MiMe alleles of the third MiMe component of the second parent MiMe potato plant. In some embodiments, the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. Exemplary MiMe loci of each of said MiMe components are extensively described herein.

In other embodiments, the generating of the parent MiMe potato plants comprises introducing a complete MiMe genotype into two candidate potato lines wherein (a) the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; (b) the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component; and (c) at least one of the MiMe loci having only MiMe alleles of the first MiMe component of the first parent MiMe potato plant is the same as at least one of the MiMe loci having only MiMe alleles of the first MiMe component of the second parent MiMe potato plant. In some embodiments, the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. Exemplary MiMe loci of each of said MiMe components are extensively described herein.

In some embodiments, the grandparent non-MiMe potato plant or the great-grandparent non-MiMe potato plant has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the grandparent non-MiMe potato plant or the great-grandparent non-MiMe potato plant has a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the grandparent non-MiMe potato plant or the great-grandparent non-MiMe potato plant has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the grandparent non-MiMe potato plant or the great-grandparent non-MiMe potato plant has a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the grandparent non-MiMe potato plant or the great-grandparent non-MiMe potato plant has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the grandparent non-MiMe potato plant or the great-grandparent non-MiMe potato plant has a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1.

In some embodiments, the grandparent non-MiMe potato plant or the great-grandparent non-MiMe potato plant has a partial MiMe genotype comprising (i) an os allele, wherein the grandparent non-MiMe potato plant or the great-grandparent non-MiMe potato plant is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the grandparent non-MiMe potato plant or the great-grandparent non-MiMe potato plant has a partial MiMe genotype comprising (i) a ps allele, wherein the grandparent non-MiMe potato plant or the great-grandparent non-MiMe potato plant is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1.

In some embodiments, the parent MiMe potato plant, the grandparent non-MiMe potato plant, the great-grandparent non-MiMe potato plant, or any combination thereof comprises one or more polynucleotide sequences selected from the group consisting of SEQ ID NOs: 127-129, 131-134, 137-154, and 156-159.

In some embodiments, the parent MiMe potato plant, the grandparent non-MiMe potato plant, the great-grandparent non-MiMe potato plant, or any combination thereof comprises one or more polynucleotide sequences selected from the group consisting of SEQ ID NOs: 127-129, 131-134, 137-154, and 156-159. In certain embodiments, parent MiMe potato plant, the grandparent non-MiMe potato plant, the great-grandparent non-MiMe potato plant, or any combination thereof comprises a MiMe allele at one or more SPO11-1 loci, each independently comprising a polynucleotide sequence selected from the group consisting of SEQ ID NOs: 127-129. In certain embodiments, parent MiMe potato plant, the grandparent non-MiMe potato plant, the great-grandparent non-MiMe potato plant, or any combination thereof comprises a) a MiMe allele at one or more REC8 loci, each independently comprising a polynucleotide sequence selected from the group consisting of SEQ ID NOs: 131 and 132; and/or c) a MiMe allele at one or more SPO11-1 loci, each independently comprising a polynucleotide sequence selected from the group consisting of SEQ ID NOs: 133 and 134. In certain embodiments, the parent MiMe potato plant, the grandparent non-MiMe potato plant, the great-grandparent non-MiMe potato plant, or any combination thereof comprises a) a MiMe allele at one or more REC8 loci, each independently comprising a polynucleotide sequence selected from the group consisting of SEQ ID NOs: 137 and 138; and/or b) a MiMe allele at one or more SPO11-1 loci, each independently comprising a polynucleotide sequence selected from the group consisting of SEQ ID NOs: 139 and 140. In certain embodiments, the parent MiMe potato plant, the grandparent non-MiMe potato plant, the great-grandparent non-MiMe potato plant, or any combination thereof comprises a MiMe allele at one or more SPO11-1 loci, each independently comprising a polynucleotide sequence selected from the group consisting of SEQ ID NOs: 141 and 142. In certain embodiments, the parent MiMe potato plant, the grandparent non-MiMe potato plant, the great-grandparent non-MiMe potato plant, or any combination thereof comprises a) a MiMe allele at one or more CYCA1 loci, each independently comprising a polynucleotide sequence selected from the group consisting of SEQ ID NOs: 143 and 144; b) a MiMe allele at one or more REC8 loci, each independently comprising a polynucleotide sequence selected from the group consisting of SEQ ID NOs: 145 and 146; and/or c) a MiMe allele at one or more SPO11-1 loci, each independently comprising a polynucleotide sequence selected from the group consisting of SEQ ID NOs: 147 and 148. In certain embodiments, the parent MiMe potato plant, the grandparent non-MiMe potato plant, the great-grandparent non-MiMe potato plant, or any combination thereof comprises a) a MiMe allele at one or more CYCA1 loci, each independently comprising a polynucleotide sequence selected from the group consisting of SEQ ID NOs: 149 and 150; b) a MiMe allele at one or more REC8 loci, each independently comprising a polynucleotide sequence selected from the group consisting of SEQ ID NOs: 151 and 152; and/or c) a MiMe allele at one or more SPO11-1 loci, each independently comprising a polynucleotide sequence selected from the group consisting of SEQ ID NOs: 153 and 154. In certain embodiments, the parent MiMe potato plant, the grandparent non-MiMe potato plant, the great-grandparent non-MiMe potato plant, or any combination thereof comprises a) a MiMe allele at one or more REC8 loci, each independently comprising a polynucleotide sequence selected from the group consisting of SEQ ID NOs: 156 and 157; and/or c) a MiMe allele at one or more SPO11-1 loci, each independently comprising a polynucleotide sequence selected from the group consisting of SEQ ID NOs: 158 and 159. In some variations, each the one or more CYCA1 loci, each of the one or more REC8 loci, and/or each of the one or more SPO11-1 loci are present on a different homologous chromosome.

Methods of Introducing Genetic Modifications

In some embodiments, the method of breeding a polyploid hybrid potato line comprising two, three, or more haplotypes comprises generating one or more parent MiMe potato plants from one or more of the two or more candidate potato lines, wherein the parent MiMe potato plant has a complete MiMe genotype, and wherein the complete MiMe genotype comprises alleles that are introduced via genetic modification. Generating a parent MiMe potato plant having a complete MiMe genotype may comprise introducing a complete MiMe genotype via genetic modification directly into a candidate potato line to produce the parent MiMe potato plant; introducing a partial MiMe genotype via genetic modification into two candidate potato lines to produce two grandparent non-MiMe plants each having a partial MiMe genotype, and crossing the grandparent non-MiMe potato plants each having a partial MiMe genotype to produce the parent MiMe potato plant; or a combination thereof. The MiMe alleles of a complete or partial MiMe genotype may be introduced via genetic modification by any means known in the art. In some embodiments, the genetic modifications are introduced by gene editing, transgenesis, or a combination thereof.

In some embodiments, the methods described herein comprise introducing one or more genetic modifications into one or more MiMe loci that result in the decreased expression of the one or more MiMe loci. In some embodiments, decreased expression a MiMe locus may be achieved by modifying or replacing nucleotide sequences of interest (such as a regulatory elements), gene disruption, gene knockout, gene knockdown, gene knock-in, gene silencing (including, e.g., by inserting and/or expressing an inverted repeat into a gene of interest), RNA interference (including, e.g., by insertion and/or expression of an RNA interference construct), expression of a repressor protein (e.g. dCas9), modification of methylation status of gene loci, modification of splicing sites, introducing alternate splicing sites, or any combination thereof. In some variations, the genetic modification is introduced into the first 70%, the first 60%, the first 50%, the first 40%, the first 30%, the first 20%, or the first 10% of the nucleotides of the coding sequence of the MiMe locus following the start codon in the 3' direction. In certain variations, the genetic modification is introduced into the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the MiMe locus following the start codon in the 3' direction. In certain variations, the genetic modification is introduced into a non-coding element of the MiMe locus (e.g., a promoter, an enhancer, a terminator, an intron, or the like).

In some embodiments, the decreased expression of each of the one or more of the MiMe loci is independently achieved by introducing an insertion, a deletion, one or more nucleotide changes, or an inversion into the MiMe locus that that results in decreased expression of the MiMe locus. In some variations, the insertion, the deletion, the one or more nucleotide changes, or the inversion is introduced into the first 70%, the first 60%, the first 50%, the first 40%, the first 30%, the first 20%, or the first 10% of the nucleotides of the coding sequence of the MiMe locus following the start codon in the 3' direction. In certain variations, the insertion, the deletion, the one or more nucleotide changes, or the inversion is introduced into the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction. In some variations, the insertion, the deletion, the one or more nucleotide changes, or the inversion eliminates expression (e.g., eliminates activity) of the MiMe locus. In some variations, the activity of the MiMe locus is eliminated by a premature stop codon introduced into the first 70%, the first 60%, the first 50%, the first 40%, the first 30%, the first 20%, or the first 10% of the nucleotides of the coding sequence of the MiMe locus following the start codon in the 3' direction. In certain variations, the activity of the MiMe locus is eliminated by a premature stop codon introduced into the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the MiMe locus following the start codon in the 3' direction.

In certain embodiments, the genetic modifications are introduced by gene editing. Any of several gene editing methods known in the art may be used to introduce the genetic modifications of the complete or partial MiMe genotype. In some variations, gene editing is performed with one or more natural or engineered nucleases including, but not limited to, RNA-guided nucleases, meganucleases, zinc finger nucleases (ZFNs), and transcription activator-like effector-based nucleases (TALENs). In further variations, gene editing is performed with RNA-guided nucleases including, but not limited to, Clustered Regularly Interspaced Short Palindromic Repeats (CRISPR) associated nucleases. Methods of gene editing are numerous, well-known and routine in the art, and are described in U.S. Ser. No. 17/045,747, U.S. Ser. No. 16/977,020, and U.S. Ser. No. 16/961,396, which are herein incorporated in their entirety.

An engineered nuclease may be a guided nuclease, which may function as a ribonucleoprotein (RNP) complex with a guide RNA. According to some embodiments, a guided nuclease may be selected from the group consisting of Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, CasZ, and homologs or modified versions thereof, Argonaute (non-limiting examples of Argonaute proteins include Thermus thermophilus Argonaute (TtAgo), Pyrococcus furiosus Argonaute (PfAgo), Natronobacterium gregoryi Argonaute (NgAgo), and homologs or modified versions thereof). According to some embodiments, a guided nuclease is a Cas9 or Cpf1 enzyme. The DNA construct or molecule encoding a guided nuclease, or the guided nuclease itself, may be delivered with or without a guide nucleic acid.

For guided nucleases, a guide nucleic acid molecule may be further provided to direct the guided nuclease to a target site in the genome of the plant via base-pairing or hybridization to cause a DSB or nick at or near the target site. The guide nucleic acid may be transformed or introduced into a plant cell or tissue as a guide nucleic acid molecule, or as a recombinant DNA molecule, construct or vector comprising a transcribable DNA sequence encoding the guide nucleic acid operably linked to a promoter or plant-expressible promoter. The promoter may be a constitutive promoter, a tissue-specific or tissue-preferred promoter, a developmental stage promoter, or an inducible promoter.

In some embodiments, the guide nucleic acid comprises a first segment comprising a nucleotide sequence that is complementary to a sequence in a target nucleic acid and a second segment that interacts with a guided nuclease protein. In some embodiments, the first segment of a guide comprising a nucleotide sequence that is complementary to a sequence in a target nucleic acid corresponds to a CRISPR RNA (crRNA or crRNA repeat). In some embodiments, the second segment of a guide comprising a nucleic acid sequence that interacts with a guided nuclease protein corresponds to a trans-acting CRISPR RNA (tracrRNA). In some embodiments, the guide nucleic acid comprises two separate nucleic acid molecules (a polynucleotide that is complementary to a sequence in a target nucleic acid and a polynucleotide that interacts with a guided nuclease protein) that hybridize with one another. In other embodiments, the guide nucleic acid is a single polynucleotide. In some embodiments, the guide nucleic acid may comprise DNA, RNA or a combination of DNA and RNA.

A protospacer-adjacent motif (PAM) may be present in the genome immediately adjacent and upstream to the 5' end of the genomic target site sequence complementary to the targeting sequence of the guide RNA, immediately downstream (3') to the sense (+) strand of the genomic target site (relative to the targeting sequence of the guide RNA) as known in the art. See, e.g., Wu, X. et al. 2014. Target specificity of the CRISPR-Cas9 system, Quant Biol. 2 (2): 59-70. The genomic PAM sequence on the sense (+) strand adjacent to the target site (relative to the targeting sequence of the guide RNA) may comprise 5'-NGG-3'. However, the corresponding sequence of the guide nucleic acid (immediately downstream (3') to the targeting sequence of the guide RNA) may generally not be complementary to the genomic PAM sequence.

The guide nucleic acid may typically be a non-coding RNA molecule that does not encode a protein. The targeting sequence of the guide nucleic acid may be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The targeting sequence may be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

In addition to the targeting sequence, a guide nucleic acid may further comprise one or more other structural or scaffold sequence(s), which may bind or interact with an RNA-guided endonuclease. Such scaffold or structural sequences may further interact with other RNA molecules (e.g., tracrRNA). Methods and techniques for designing targeting constructs and guide nucleic acids for genome editing and site-directed integration at a target site within the genome of a plant using a guided nuclease are known in the art.

An engineered nuclease may be a site-specific nuclease. Several site-specific nucleases, such as recombinases, zinc finger nucleases (ZFNs), meganucleases, and TALENs, are not nucleic acid-guided and instead rely on their protein structure to determine their target site for causing the DSB or nick, or they are fused, tethered or attached to a DNA-binding protein domain or motif. The protein structure of the site-specific nuclease (or the fused/attached/tethered DNA binding domain) may target the site-specific nuclease to the target site. According to many of these embodiments, non-nucleic acid-guided site-specific nucleases, such as recombinases, zinc finger nucleases (ZFNs), meganucleases, and TALENs, may be designed, engineered and constructed according to known methods to target and bind to a target site at or near the genomic locus of an endogenous gene of a plant to create a DSB or nick at such genomic locus to knockout or knockdown expression of the gene via repair of the DSB or nick, which may lead to the creation of a mutation or insertion of a sequence at the site of the DSB or nick, through cellular repair mechanisms, which may be guided by a donor template molecule.

In some embodiments, a site-specific nuclease is a recombinase. A recombinase may be a serine recombinase attached to a DNA recognition motif, a tyrosine recombinase attached to a DNA recognition motif, or other recombinase enzyme known in the art. A recombinase or transposase may be a DNA transposase or recombinase attached or fused to a DNA binding domain. Non-limiting examples of recombinases include a tyrosine recombinase attached, etc., to a DNA recognition motif provided herein is selected from the group consisting of a Cre recombinase, a gin recombinase, a Flp recombinase, and a Tnpl recombinase. In an aspect, a Cre recombinase or a Gin recombinase provided herein is tethered to a zinc-finger DNA-binding domain, or a transcription activator-like effector (TALE) DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

A site-specific nuclease may be a zinc finger nuclease (ZFN). ZFNs are synthetic proteins consisting of an engineered zinc finger DNA-binding domain fused to a cleavage domain (or a cleavage half-domain), which may be derived from a restriction endonuclease (e.g., FokI). The DNA binding domain may be canonical (C2H2) or non-canonical (e.g., C3H or C4). The DNA-binding domain can comprise one or more zinc fingers (e.g., 2, 3, 4, 5, 6, 7, 8, 9 or more zinc fingers) depending on the target site. Multiple zinc fingers in a DNA-binding domain may be separated by linker sequence(s). ZFNs can be designed to cleave almost any stretch of double-stranded DNA by modification of the zinc finger DNA-binding domain. ZFNs form dimers from monomers composed of a non-specific DNA cleavage domain (e.g., derived from the FokI nuclease) fused to a DNA-binding domain comprising a zinc finger array engineered to bind a target site DNA sequence. The DNA-binding domain of a ZFN may typically be composed of 3-4 (or more) zinc-fingers. The amino acids at positions-1, +2, +3, and +6 relative to the start of the zinc finger alpha-helix, which contribute to site-specific binding to the target site, can be changed and customized to fit specific target sequences. The other amino acids may form a consensus backbone to generate ZFNs with different sequence specificities.

Methods and rules for designing ZFNs for targeting and binding to specific target sequences are known in the art. See, e.g., US Patent App. Nos. 2005/0064474, 2009/0117617, and 2012/0142062. The FokI nuclease domain may require dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. A ZFN, as used herein, is broad and includes a monomeric ZFN that can cleave double stranded DNA without assistance from another ZFN. The term ZFN may also be used to refer to one or both members of a pair of ZFNs that are engineered to work together to cleave DNA at the same site. Without being limited by any theory, because the DNA-binding specificities of zinc finger domains can be re-engineered using one of various methods, customized ZFNs can theoretically be constructed to target nearly any target sequence (e.g., at or near a gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick.

A site-specific nuclease may be a TALEN enzyme. TALENs are artificial restriction enzymes generated by fusing the TALE DNA binding domain to a nuclease domain (e.g., FokI). When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the TALE DNA binding domain to a nuclease domain. In some aspects, the nuclease is selected from a group consisting of PvuII, MutH, TevI, FokI, AlwI, MlyI, SbfI, SdaI, StsI, CleDORF, Clo051, and Pept071. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN also refers to one or both members of a pair of TALENs that work together to cleave DNA at the same site.

Transcription activator-like effectors (TALEs) can be engineered to bind practically any DNA sequence, such as at or near the genomic locus of a gene in a plant. TALEs have a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. PLoS One. 8: e82539). MutH is capable of introducing strand-specific nicks in DNA (see Gabsalilow et al. 2013. Nucleic Acids Research. 41: e83). TevI introduces double-stranded breaks in DNA at targeted sites (see Beurdeley et al., 2013. Nature Communications. 4:1762).

The relationship between amino acid sequence and DNA recognition of the TALE binding domain allows for designable proteins. Software programs such as DNAWorks can be used to design TALE constructs. Other methods of designing TALE constructs are known to those of skill in the art. See Doyle et al., Nucleic Acids Research (2012) 40: W117-122; Cermak et al., Nucleic Acids Research (2011) 39: e82; and tale-nt.cac.cornelledu/about. In another aspect, a TALEN provided herein is capable of generating a targeted DSB.

A site-specific nuclease may be a meganuclease. Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some embodiments, a meganuclease may comprise a scaffold or base enzyme selected from the group consisting of I-CreI, I-CeuI, I-MsoI, I-SceI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease may be selected or engineered to bind to a genomic target sequence in a plant, such as at or near the genomic locus of a gene. In another aspect, a meganuclease provided herein is capable of generating a targeted DSB.

In some embodiments, gene editing comprises (a) inducing a DSB in the genome of a cell at a cleavage site at or near a recognition site for a natural or engineered nuclease by expressing in the cell the natural or engineered nuclease recognizing said recognition site and inducing said DSB at the cleavage site; (b) introducing into the cell a repair nucleic acid molecule comprising an upstream flanking region having homology to the DNA region upstream of the preselected site and/or a downstream flanking DNA region having homology to the DNA region downstream of the preselected site for allowing homologous recombination between said flanking region or regions and said DNA region or regions flanking said preselected site; and (c) selecting a cell wherein said repair nucleic acid molecule has been used as a template for making a modification of said genome at said preselected site. In other embodiments, gene editing comprises (a) inducing a DSB in the genome of a cell at a cleavage site at or near a recognition site for a natural or engineered nuclease by introducing into the cell the natural or engineered nuclease recognizing said recognition site and inducing said DSB at the cleavage site; (b) introducing into the cell a repair nucleic acid molecule comprising an upstream flanking region having homology to the DNA region upstream of the preselected site and/or a downstream flanking DNA region having homology to the DNA region downstream of the preselected site for allowing homologous recombination between said flanking region or regions and said DNA region or regions flanking said preselected site; and (c) selecting a cell wherein said repair nucleic acid molecule has been used as a template for making a modification of said genome at said preselected site.

As used herein, a repair nucleic acid molecule is a single-stranded or double-stranded DNA molecule or RNA molecule that is used as a template for modification of the genomic DNA at the preselected site in the vicinity of or at the cleavage site. As used herein, use as a template for modification of the genomic DNA, means that the repair nucleic acid molecule is copied or integrated at the preselected site by homologous recombination between the flanking region(s) and the corresponding homology region(s) in the target genome flanking the preselected site, optionally in combination with non-homologous end-joining (NHEJ) at one of the two ends of the repair nucleic acid molecule (e.g. in case there is only one flanking region). Integration by homologous recombination will allow precise joining of the repair nucleic acid molecule to the target genome up to the nucleotide level, while NHEJ may result in small insertions/deletions at the junction between the repair nucleic acid molecule and genomic DNA.

In some embodiments, the genetic modifications introduced by gene editing result in the decreased expression (including non-expression or altered activity) of one or more MiMe loci. In gene editing, the introduction of a DSB or nick may be used to introduce targeted genetic modifications in the genome of a plant. According to this approach, genetic modifications, such as deletions, insertions, inversions and/or substitutions may be introduced at a target site via imperfect repair of the DSB or nick to produce a knock-out or knock-down of a gene, or to produce a MiMe component with altered activity. Such genetic modifications may be generated by imperfect repair of the targeted locus even without the use of a donor template molecule, and can result in decreased expression (including non-expression or altered activity) of an endogenous gene product. For example, genetic modifications may be produced by an indel (insertion or deletion of nucleotide bases in a target DNA sequence through NHEJ), or by specific removal of sequence that reduces or completely destroys the function of a sequence or motif at or near the targeting site, or which results in an altered activity of a MiMe component such as the production of a dominant-negative MiMe component, a constitutively active MiMe component, a null mutant, or the like. Such embodiments may comprise a deletion or insertion which alters one or more post-translational modifications on the one or more MiMe components. The post-translational modifications can include phosphorylation, glycosylation, ubiquitination, nitrosylation, methylation, acetylation, lipidation and the like. Altered activity in a MiMe component can be achieved, for example, by deleting or otherwise disrupting one or more phosphorylation sites (e.g., Tyrosine phosphorylation site or Serine/Threonine phosphorylation site). In further embodiments, the motif which is disrupted is a proteolytic cleavage site. A knockout of a gene may be achieved by inducing a DSB or nick at or near the endogenous locus of the gene that results in non-expression of the gene product, whereas a knockdown of a gene may be achieved in a similar manner by inducing a DSB or nick at or near the endogenous locus of the gene that is repaired imperfectly at a site that does not affect the coding sequence of the gene in a manner that would eliminate the function of the gene product. For example, the site of the DSB or nick within the endogenous locus may be in the upstream or 5' region of the gene (e.g., a promoter and/or enhancer sequence) to affect or reduce its level of expression. Similarly, such targeted knockout or knockdown mutations of a gene may be generated with a donor template molecule to direct a particular or desired mutation at or near the target site via repair of the DSB or nick. The donor template molecule may comprise a homologous sequence with or without an insertion sequence and comprising one or more mutations, such as one or more deletions, insertions, inversions and/or substitutions, relative to the targeted genomic sequence at or near the site of the DSB or nick. For example, targeted knockout mutations of a gene may be achieved by substituting, inserting, deleting or inverting at least a portion of the gene, including, but not limited to, by introducing a frame shift or premature stop codon into a protein coding sequence of the gene. A deletion of a portion of a gene may also be introduced by generating DSBs or nicks at two target sites and causing a deletion of the intervening target region flanked by the target sites.

In some embodiments, the genetic modifications are introduced by transgenesis. Transgenes may include, but are not limited to, one or more protein-coding sequences operably linked to a plant-expressible promoter, one or more transcribable DNA sequences encoding an RNA molecule operably linked to a plant-expressible promoter, a gene of interest, a marker gene, or any combination thereof. Methods for the introduction of transgenes in plants are well-known and routine in the art. In some embodiments, transgenesis comprises (a) inducing a DSB in the genome of a cell at a cleavage site at or near a recognition site for a natural or engineered nuclease by expressing in the cell the natural or engineered nuclease recognizing said recognition site and inducing said DSB at the cleavage site; (b) introducing into the cell a repair nucleic acid molecule comprising an upstream flanking region having homology to the DNA region upstream of the preselected site, a downstream flanking DNA region having homology to the DNA region downstream of the preselected site, and a transgene region flanked by the upstream and downstream flanking DNA regions and comprising the transgene to be inserted at the preselected site; and (c) selecting a cell wherein said repair nucleic acid molecule has been used as a template for making a modification of said genome at said preselected site. In other embodiments, transgenesis comprises (a) inducing a DSB in the genome of a cell at a cleavage site at or near a recognition site for a natural or engineered nuclease by introducing into the cell the natural or engineered nuclease recognizing said recognition site and inducing said DSB at the cleavage site; (b) introducing into the cell a repair nucleic acid molecule comprising an upstream flanking region having homology to the DNA region upstream of the preselected site, a downstream flanking DNA region having homology to the DNA region downstream of the preselected site, and a transgene region flanked by the upstream and downstream flanking DNA regions and comprising the transgene to be inserted at the preselected site; and (c) selecting a cell wherein said repair nucleic acid molecule has been used as a template for making a modification of said genome at said preselected site.

In some embodiments, the genetic modification comprises introducing proteins, nucleic acids, or a combination thereof into a plant cell. The introduction of the proteins, nucleic acids, or combination thereof into the plant cell may be achieved by any of several means known and routinely-used in the art. In some embodiments, the introduction of the proteins, nucleic acids, or combination thereof into the plant cell comprises isolating protoplasts, transfecting the protoplasts, encapsulating the protoplasts, and regenerating plants from the protoplasts. In other embodiments, the introduction of the proteins, nucleic acids, or combination thereof into the plant cell comprises biolistic transformation. In certain embodiments, the introduction of the proteins, nucleic acids, or combination thereof into the plant cell comprises isolating immature plant embryos, bombarding the embryos with particles comprising nucleic acids, and regenerating plants from the immature embryos. Numerous additional transformation methods may be used to introduce the proteins, nucleic acids, or combination thereof into a suitable plant or plant cell. Transformation methods include the use of liposomes, electroporation, chemicals that increase free DNA uptake, injection of the DNA directly into the plant (cell) such as microinjection, particle gun bombardment, transformation using viruses or pollen and microprojection. Methods may be selected from the calcium/polyethylene glycol method for protoplasts (Krens et al. (1982) Nature 296:72-74; Negrutiu et al. (1987) Plant. Mol. Biol. 8:363-373); electroporation of protoplasts (Shillito et al. (1985) Bio/Technol. 3:1099-1102); microinjection into plant material (Crossway et al. (1986) Mol. Gen. Genet. 202:179-185); DNA or RNA-coated particle bombardment (Klein et al. (1987) Nature 327:70) infection with (non-integrative) viruses and the like.

In some embodiments, generating the parent MiMe potato plant, the grandparent non-MiMe potato plant, the great-grandparent non-MiMe potato plant, or any combination thereof comprises introducing an RNA-guided nuclease system (e.g., a CRISPR system) into a cell of a candidate potato plant line, wherein the RNA-guided nuclease system (e.g., a CRISPR system) is configured to bind to one or more target sequences of each of one or more MiMe loci. Exemplary target sequences for specific MiMe loci are provided in the sequence listing as outlined in Table 5, and also in Example 2. In certain embodiments, the one or more candidate potato lines are potato plant lines, and the one or more target sequences comprise a polynucleotide sequence selected from the group consisting of SEQ ID NOs: 72-126, or a variant thereof comprising 1, 2, 3, 4, or 5 nucleotide substitutions.

In certain embodiments, the CRISPR system comprises one or more nucleic acid molecules (e.g., one or more plasmids) encoding an expression cassette for expressing a Cas enzyme, and expression cassette for expressing a targeting RNA (e.g., a crRNA or gRNA molecule), or a combination thereof. In some variations, the targeting RNA and the Cas enzyme are encoded on separate nucleic acid molecules (e.g., separate plasmids). In other variations, the targeting RNA and the Cas enzyme are encoded on the same nucleic acid molecule (e.g., the same plasmid). In certain embodiments, the CRISPR system comprises ribonucleoproteins (RNPs) comprising a Cas enzyme complexed with a targeting RNA (e.g., a crRNA or gRNA molecule). Exemplary gRNA protospacer sequences for specific MiMe loci are provided in the sequence listing as outlined in Table 5, and also in Examples 2, 5, and 7. In certain embodiments, the one or more candidate potato lines are potato plant lines, and the targeting RNA (e.g., crRNA or gRNA) sequences comprises a polynucleotide sequence selected from the group consisting of SEQ ID NOs: 17-71, or a variant thereof comprising 1, 2, 3, 4, or 5 nucleotide substitutions.

In some embodiments, introducing the CRISPR system into the cell of the candidate potato plant line results in an insertion, a deletion, one or more nucleotide changes, or an inversion that results in decreased expression of the targeted MiMe locus. The one or more MiMe loci may comprise any MiMe loci known in the art or described herein. In some variations, the insertion, the deletion, the one or more nucleotide changes, or the inversion is positioned in the first 70%, the first 60%, the first 50%, the first 40%, the first 30%, the first 20%, or the first 10% of the nucleotides of the coding sequence of the genomic locus following the start codon in the 3' direction. In certain variations, the insertion, the deletion, the one or more nucleotide changes, or the inversion is positioned in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction. In some variations, the insertion, the deletion, the one or more nucleotide changes, or the inversion results in a premature stop codon present in the first 70%, the first 60%, the first 50%, the first 40%, the first 30%, the first 20%, or the first 10% of the nucleotides of the coding sequence of the MiMe locus following the start codon in the 3' direction, thereby eliminating expression (e.g., activity) of the genomic locus. In some variations, the insertion, the deletion, the one or more nucleotide changes, or the inversion results in a premature stop codon present in the first 100, the first 200, the first 300, the first 400, the first 500, the first 600, the first 700, the first 800, the first 900, the first 1000, the first 1250, the first 1500, the first 1750, the first 2000, the first 2500, or the first 3000 nucleotides of the coding sequence of the genomic locus following the start codon in the 3' direction, thereby eliminating expression (e.g., activity) of the genomic locus.

Crossing Clonal Gametes to Produce Hybrid Polyploid Seed

In some embodiments, the method of breeding a polyploid hybrid potato line comprises providing clonal gametes from two parent MiMe potato plants and crossing the clonal gametes to produce a hybrid polyploid seed comprising two, three, or more haplotypes. In other embodiments, the method of breeding a polyploid hybrid potato line comprises providing clonal gametes from a parent MiMe potato plant, providing haploid gametes from a homozygous parent non-MiMe potato plant, and crossing the clonal gametes with the haploid gametes to produce a hybrid polyploid seed. In some variations, the homozygous parent non-MiMe potato plant is diploid and the haploid gametes are monoploid gametes. In yet other embodiments, the method of breeding a polyploid hybrid potato line comprises providing clonal gametes from a parent MiMe potato plant, providing unreduced, non-clonal gametes from a homozygous parent plant, and crossing the clonal gametes with the unreduced, non-clonal gametes to produce a hybrid polyploid seed. Methods for providing clonal gametes, providing haploid gametes, providing unreduced, non-clonal gametes, crossing clonal gametes, crossing clonal gametes with haploid gametes, and crossing clonal gametes with unreduced, non-clonal gametes are described herein. In some embodiments, the method of breeding a polyploid hybrid potato line comprises growing the hybrid polyploid seed to produce a hybrid polyploid potato plant.

In some embodiments, the method of breeding a polyploid hybrid potato line comprises crossing the clonal gametes to produce the hybrid polyploid seed. In some variations, crossing the clonal gametes to produce the hybrid polyploid seed comprises contacting pollen comprising clonal gametes with the stigma of a pistil comprising clonal gametes. In some variations, crossing the clonal gametes to produce the hybrid polyploid seed comprises contacting pollen comprising clonal gametes of a first potato plant with the stigma of a pistil comprising clonal gametes of a second potato plant. In some embodiments, crossing the clonal gametes to produce the hybrid polyploid seed comprises contacting pollen comprising clonal gametes from a first parent MiMe potato plant with the stigma of a pistil comprising clonal gametes of a second parent MiMe potato plant. In some variations, the homozygous parent non-MiMe potato plant is diploid and the haploid gametes are monoploid gametes. In some embodiments, the hybrid polyploid seed is produced by crossing the clonal gametes and allowing seeds to form.

In other embodiments, the method of breeding a polyploid hybrid potato line comprises crossing the clonal gametes with the haploid gametes to produce the hybrid polyploid seed. In one variation, crossing the clonal gametes with the haploid gametes to produce the hybrid polyploid seed comprises contacting pollen comprising clonal gametes with the stigma of a pistil comprising haploid gametes. In another variation, crossing the clonal gametes with the haploid gametes to produce the hybrid polyploid seed comprises contacting pollen comprising haploid gametes with the stigma of a pistil comprising clonal gametes. In some embodiments, crossing the clonal gametes with the haploid gametes to produce the hybrid polyploid seed comprises contacting pollen comprising clonal gametes from a parent MiMe potato plant with the stigma of a pistil comprising haploid gametes of a homozygous parent non-MiMe potato plant. In other embodiments, crossing the clonal gametes with the haploid gametes to produce the hybrid polyploid seed comprises contacting pollen comprising haploid gametes from a homozygous parent non-MiMe potato plant with the stigma of a pistil comprising clonal gametes of a parent MiMe potato plant. In some embodiments, the population of polyploid potato seed is produced by crossing the clonal gametes with the haploid gametes and allowing seeds to form.

In yet other embodiments, the method of breeding a polyploid hybrid potato line comprises crossing clonal gametes with unreduced, non-clonal gametes to produce the hybrid polyploid seed. In one variation, crossing the clonal gametes with the unreduced, non-clonal gametes to produce the hybrid polyploid seed comprises contacting pollen comprising clonal gametes with the stigma of a pistil comprising unreduced, non-clonal gametes. In another variation, crossing the clonal gametes with the unreduced, non-clonal gametes to produce the hybrid polyploid seed comprises contacting pollen comprising unreduced, non-clonal gametes with the stigma of a pistil comprising clonal gametes. In some embodiments, crossing the clonal gametes with the unreduced, non-clonal gametes to produce the hybrid polyploid seed comprises contacting pollen comprising clonal gametes from a parent MiMe potato plant with the stigma of a pistil comprising unreduced, non-clonal gametes of a homozygous parent potato plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis. In some embodiments, crossing the clonal gametes with the unreduced, non-clonal gametes to produce the hybrid polyploid seed comprises contacting the stigma of a pistil comprising clonal gametes from a parent MiMe potato plant with pollen comprising unreduced, non-clonal gametes of a homozygous parent potato plant that is homozygous for (a) a MiMe allele conferring decreased expression of one or more MiMe loci of a component of progression through the first division of meiosis, or (b) a MiMe allele conferring decreased expression of one or more MiMe loci of a component of progression through the second division of meiosis. In some embodiments, the hybrid polyploid seed is produced by crossing the clonal gametes with the unreduced, non-clonal gametes and allowing seeds to form.

Evaluating Characteristics and Heterotic Performance

In some embodiments, the method of breeding a polyploid hybrid potato line comprises evaluating one or more characteristics of the hybrid polyploid potato plant. Methods for evaluating potato plant characteristics are numerous and well-known in the art. The one or more characteristics evaluated may include, but are not limited to, plant height, plant size, plant vigor, fruit yield, crop yield, disease resistance, pest resistance, and the like. The potato plants to be evaluated may then be grown under different geographical, climatic, and soil conditions, and further selections can be made during, and at the end of, the growing season. Promising advanced breeding lines are thoroughly tested and compared to appropriate standards in environments representative of the commercial target area(s) for three years at least. The best lines are candidate potatoes for new commercial cultivars. These processes, which lead to the final step of marketing and distribution, usually take from five to ten years from the time the first cross or selection is made.

In some embodiments, the one or more characteristics includes the heterotic performance of the two, three, or more haplotypes of the polyploid hybrid potato. In some embodiments, the heterotic performance of the two, three, or more haplotypes of the polyploid hybrid potato is used to guide the breeding of lines, the selecting of candidate potato lines, or both. In some embodiments, the heterotic performance is predicted via genome prediction modeling.

In some embodiments, the method of breeding a polyploid hybrid potato line comprises repeating the steps of the method using the one or more characteristics of the hybrid polyploid potato plant evaluated to guide the breeding of, the selecting of candidate potato lines, or both. In some variations, the method comprises repeating the steps of the method two, three, four, five, six, seven, eight, nine, or ten times or more. In additional variations, the repeating of the steps of the method iteratively informs a genome prediction model for improved prediction of heterotic performance. In certain variations, the improved prediction of heterotic performance allows for rapid combination of haplotypes with strong heterotic performance and acceleration of breeding programs.

Inventory and Maintenance of Potato Lines

In some embodiments, the method of breeding a hybrid polyploid potato plant line comprises maintaining the lines of the potato plant. In some variations, the potato lines are maintained via vegetative propagation, selfing, apomixis, cell culture, or any combination thereof. Additional methods of maintaining potato lines are well-known in the art. In some embodiments, the method of breeding a hybrid polyploid potato plant line comprises maintaining an inventory of potato lines from which haplotypes may be selected for rapid deterministic stacking of the haplotypes. In some variations, the inventory of lines comprises one or more potato lines having complete or partial MiMe genotypes that are maintained through vegetative propagation, hybridization with a haploid inducer, or a combination thereof. In additional variations, the inventory of lines may include, but is not limited to, the set of lines, candidate potato lines, potato lines comprising one or more MiMe alleles, potato lines having a partial MiMe genotype, potato lines having a complete MiMe genotype, grandparent non-MiMe potato plants having a partial MiMe genotype, parent MiMe potato plants, homozygous parent non-MiMe potato plants, or any combination thereof maintained by vegetative propagation, seed propagation, tissue culture, hybridization with a haploid inducer or any combination thereof. In some embodiments, maintaining the inventory of potato lines comprises maintaining pairs of parent MiMe potato plants having any of the complete MiMe genotypes or complementary genotypes described herein.

In some embodiments, haploid induction may be used to maintain polyploid potato plant lines having a complete MiMe genotype. In certain embodiments, maintaining the inventory of potato lines comprises crossing a polyploid potato plant having a complete MiMe genotype with a haploid inducer to produce progeny of the same ploidy as the plant having the complete MiMe genotype. In one variation, maintaining the inventory of potato lines comprises crossing a tetraploid potato plant having a complete MiMe genotype with a haploid inducer to produce tetraploid progeny.

Genetically Modified Plants, Plant Parts, Plant Cells, and Processed Plant Products In some aspects, provided herein are genetically modified potato plants, plant parts, and plant cells grown from a population of polyploid potato seed or a subpopulation of genetically uniform polyploid potato seed described herein. Also provided herein are processed plant products derived from the genetically modified potato plants, plant parts, or plant cells provided herein. In some embodiments, the genetically modified potato plant parts, genetically modified potato plant cells, and processed plant products provided herein are non-regenerable.

In some embodiments, genetically modified potato plants and genetically modified potato plant parts are provided herein. The genetically modified potato plants and plant parts may be grown from a population of polyploid potato seed or a subpopulation of genetically uniform polyploid potato seed comprising three or more haplotypes and one or more genetic modifications resulting in decreased expression of one or more MiMe loci described herein. Alternatively, the genetically modified potato plants and plant parts may be regenerated from a genetically modified potato plant cell wherein the genetically modified potato plant cell comprises three or more haplotypes and one or more genetic modifications resulting in decreased expression of one or more MiMe loci. Genetically modified potato plants can be obtained from a genetically modified potato seed. Genetically modified potato plant parts can be obtained by cutting, snapping, grinding or otherwise disassociating the part from the potato plant. The potato plant part may be any plant part known in the art, including, but not limited to, a flower, a pistil, a leaf, a stem, a petiole, a cutting, a tissue, a seed coat, an ovule, a microspore, pollen, a tuber, a stolon, a meristem, a root, a rootstock, a scion, a fruit, a cotyledon, a hypocotyl, a protoplast, an embryo, an anther, a seed, or any portion thereof. In certain embodiments, a genetically modified potato plant part provided herein is a non-regenerable portion of a genetically modified potato plant part. As used in this context, a "non-regenerable" portion of a genetically modified potato plant part refers to a portion that cannot be induced to form a whole potato plant or that cannot be induced to form a whole potato plant (e.g., through in vitro culture) that is capable of sexual and/or asexual reproduction. A non-regenerable portion of a genetically modified potato plant part may be a portion of a flower, a pistil, a leaf, a stem, a petiole, a cutting, a tissue, a seed coat, an ovule, a microspore, pollen, a tuber, a stolon, a root, a rootstock, a scion, a fruit, a cotyledon, a hypocotyl, a protoplast, an embryo, an anther, or any portion thereof.

In some embodiments, a non-regenerable or non-propagating potato plant cell is provided herein. As used in this context, a "non-regenerable plant cell" is a cell which cannot be regenerated into a whole potato plant that is capable of sexual and/or asexual reproduction through in vitro culture.

The non-regenerable potato cell may be in a potato plant or plant part described herein. The non-regenerable potato cell may be a cell in a seed, or in the seedcoat of said seed. Mature potato plant organs, including a mature leaf, a mature stem or a mature root, contain at least one non-regenerable cell. In certain embodiments, the non-regenerable potato plant cell is a somatic cell.

Also provided herein is a potato cell culture or tissue culture of non-regenerable or regenerable potato cells or tissue of a genetically modified potato plant or genetically modified potato plant part described herein, wherein the non-regenerable or regenerable potato cells comprise three or more haplotypes and one or more genetic modifications resulting in decreased expression of one or more MiMe loci described herein. Preferably, the regenerable potato cells are derived from embryos, protoplasts, meristematic cells, callus, microspores, pollen, leaves, tubers, stolons, anthers, stems, petioles, roots, root tips, fruits, seeds, flowers, cotyledons, and/or hypocotyls of a genetically modified potato plant or a genetically modified potato plant part grown from a population of polyploid potato seed or a subpopulation of genetically uniform polyploid potato seed described herein.

In some embodiments, provided herein is a processed potato product derived from a genetically modified potato plant, plant part, or plant cell described herein comprising three or more haplotypes and one or more genetic modifications resulting in decreased expression of one or more MiMe loci. In certain embodiments, the processed potato product contains sufficient nucleic acid (e.g., DNA or RNA) and/or protein material from the genetically modified potato plant, plant part, or plant cell to detect nucleic acid and/or protein sequences corresponding to the three haplotypes, the one or more genetic modifications resulting in decreased expression of one or more MiMe loci, or both. In some embodiments, the processed potato product is non-regenerable, i.e., cannot be induced to form a whole potato plant or that cannot be induced to form a whole potato plant that is capable of sexual and/or asexual reproduction.

A processed potato product may be a seed, a tuber, a fruit, a grain, a root, a stolon, a vegetable, or any potato plant part described herein, and may be blended as a commodity or other product which moves through commerce and is derived from a genetically modified potato plant or a genetically modified potato plant part. In some embodiments, the commodity or other product can be tracked through commerce by detecting nucleic acid and/or protein sequences of the genetically modified potato plant or plant part from which they were obtained. In certain embodiments, the processed potato product comprises a detectable amount of nucleotide and/or protein sequences corresponding to the three or more haplotypes and/or to the one or more genetic modifications resulting in decreased expression of one or more MiMe loci. In certain embodiments, the commodity or other potato product is produced in or maintained in the genetically modified potato plant or plant part from which the commodity or other product has been obtained. Such commodities or other products of commerce include, but are not limited to, potato plant parts, biomass, oil, meal, food starch, syrup, sugar, animal feed, flour, flakes, processed seed, seed, potato fries (French fries), wedges, shredded potato products (e.g., hash browns, tater tots), baked potatoes, fresh potatoes, mashed potatoes, dehydrated potatoes, pellets, abraded peels, steamed peels, potato slurry, puree, filter cake, gray starch, screen solids, pulp, potato protein concentrate, culled fries, culled crisps, crowns, batter, crumbles, nubbins, or material fermented for alcoholic beverage production. The processed potato product may be a food product that is processed by any means known in the art, e.g., canned, steamed, boiled, fried, blanched and/or frozen etc. The potato product may be produced for any purpose or industry, including but not limited to human consumption, animal consumption, dietary supplement, food product ingredient, pharmaceutical, textile, wood, paper, adhesive, binder, texture agent, filler, washing of boreholes or biofuel production.

In some embodiments, provided herein is a genetically modified potato plant, plant part, or plant cell comprising: i) three or more haplotypes; and ii) a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, provided herein is a genetically modified potato plant, plant part, or plant cell comprising: i) three or more haplotypes; and ii) a partial MiMe genotype comprising: (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof. In certain embodiments, the genetically modified potato plant part is a non-regenerable plant part. In certain embodiments, the genetically modified potato plant cell is a non-regenerable plant cell. genetically modified potato plant Also provided herein is germplasm of the genetically modified potato plant, the germplasm comprising the complete or partial MiMe genotype. Further provided herein is a genetically altered plant genome derived from the genetically modified potato plant, the genetically altered plant genome comprising the complete or partial MiMe genotype.

In some embodiments, provided herein is a genetically modified potato plant, plant part, or plant cell comprising: i) three or more haplotypes; and ii) a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments, provided herein is a genetically modified potato plant, plant part, or plant cell comprising: i) three or more haplotypes; and ii) a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In other variations, the one or more MiMe loci of the component of progression through the first division of meiosis comprise PS1, JASON, or a combination thereof. In certain embodiments, the genetically modified potato plant part is a non-regenerable plant part. Also provided herein is germplasm of the genetically modified potato plant, the germplasm comprising the complete or partial MiMe genotype. Further provided herein is a genetically altered plant genome derived from the genetically modified potato plant, the genetically altered plant genome comprising the complete or partial MiMe genotype.

In some embodiments, provided herein is a genetically modified potato plant, plant part, or plant cell comprising: (i) at least a first and second haplotype, each comprising one or more MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the MiMe locus of the component of progression through the first division of meiosis of the third haplotype is PS1 or JASON. In still additional variations, the one or more MiMe loci of the component of progression through the second division of meiosis of the first and second haplotype comprise OSD1, CYCA1, TDM1, PC1, PC2, FC, or any combination thereof. In yet additional variations, the locus of the component of progression through the second division of meiosis of the third haplotype is OSD1, CYCA1, TDM1, PC1, PC2, or FC. In certain embodiments, the genetically modified potato plant part is a non-regenerable plant part. In certain embodiments, the genetically modified potato plant cell is a non-regenerable plant cell. Also provided herein is germplasm of the genetically modified potato plant, the germplasm comprising the MiMe alleles of the genetically modified potato plant. Further provided herein is a genetically altered plant genome derived from the genetically modified potato plant, the genetically altered plant genome comprising the germplasm comprising the MiMe alleles of the genetically modified potato plant.

In some embodiments, provided herein is a genetically modified potato plant, plant part, or plant cell comprising: (i) at least a first and second haplotype, each comprising one or more MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis of the first and second haplotype comprise PS1, JASON, or a combination thereof. In yet additional variations, the MiMe locus of the component of progression through the first division of meiosis of the third haplotype is PS1 or JASON. In still additional variations, the MiMe locus of the component of progression through the second division of meiosis of the third haplotype is OSD1, CYCA1, TDM1, PC1, PC2 or FC. In certain embodiments, the genetically modified potato plant part is a non-regenerable plant part. In certain embodiments, the genetically modified potato plant cell is a non-regenerable plant cell. Also provided herein is germplasm of the genetically modified potato plant, the germplasm comprising the MiMe alleles of the genetically modified potato plant. Further provided herein is a genetically altered plant genome derived from the genetically modified potato plant, the genetically altered plant genome comprising the germplasm comprising the MiMe alleles of the genetically modified potato plant.

In some embodiments, provided herein is a genetically modified potato plant, plant part, or plant cell having a partially-complemented MiMe genotype. In some embodiments, the genetically modified potato plant, plant part, or plant cell has a partially-complemented MiMe genotype comprising: (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some embodiments, the first MiMe component is a component of sister chromatid cohesion during the first division of meiosis. In some variations, the one or more MiMe loci of the first MiMe component comprise REC8, SWITCH1/DYAD, or a combination thereof. In one variation, the MiMe locus of the first MiMe component is REC8. In certain embodiments, the second MiMe component is a component of DNA double strand breakage during meiotic recombination. In some variations, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation, the first MiMe locus of the second MiMe component is PAIR1 and the second MiMe locus of the second MiMe component is SPO11-1. In further embodiments, the third MiMe component is a component of progression through the second division of meiosis. In some embodiments, the partially-complemented MiMe genotype comprises only MiMe alleles at one or more MiMe loci of the third MiMe component. In some variations, the one or more MiMe loci of the third MiMe component comprise OSD1, CYCA1, TDM1, PC1, PC2, FC, or any combination thereof. In one variation, the MiMe locus of the third MiMe component is OSD1. In other embodiments, the partially-complemented MiMe genotype comprises one or more MiMe alleles and one or more non-MiMe alleles at a first MiMe locus of the third MiMe component, and one or more MiMe alleles and one or more non-MiMe alleles at a second MiMe locus of the third MiMe component. In some variations, the first MiMe locus and the second MiMe locus of the third MiMe component comprise OSD1, CYCA1, TDM1, PC1, PC2, FC, or any combination thereof. In one embodiment, the partially-complemented MiMe genotype comprises only MiMe alleles at one or more MiMe loci of the third MiMe component, wherein the one or more MiMe loci having only MiMe alleles of the first MiMe component comprise REC8, the first MiMe locus of the second MiMe component is PAIR1, the second MiMe locus of the second MiMe component is SPO11-1, and the one or more MiMe loci having only MiMe alleles of the third MiMe component comprise OSD1. Also provided herein is germplasm of the genetically modified potato plant, the germplasm comprising the partially-complemented MiMe genotype. Further provided herein is a genetically altered plant genome derived from the genetically modified potato plant, the genetically altered plant genome comprising the germplasm comprising the partially-complemented MiMe genotype.

In some embodiments, provided herein is a genetically modified potato plant, plant part, or plant cell having a partially-complemented MiMe genotype comprising: (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiment, the one or more MiMe loci of the component of progression through the first division of meiosis comprise PS1, JASON, or a combination thereof. Also provided herein is germplasm of the genetically modified potato plant, the germplasm comprising the partially-complemented MiMe genotype. Further provided herein is a genetically altered plant genome derived from the genetically modified potato plant, the genetically altered plant genome comprising the germplasm comprising the partially-complemented MiMe genotype.

In some embodiments, provided herein is a genetically modified potato plant, plant part, or plant cell having a partially-complemented MiMe genotype comprising: (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiments, the one or more MiMe loci of the component of sister chromatid cohesion during the first division of meiosis comprise REC8, SWITCH1/DYAD, or a combination thereof. In yet additional variations of the foregoing embodiments, the one or more MiMe loci of the component of progression through the second division of meiosis comprise OSD1, CYCA1, TDM1, PC1, PC2, FC, or any combination thereof. In still additional variations of the foregoing embodiments, the one or more MiMe loci of the component of progression through the first division of meiosis comprise PS1, JASON, or a combination thereof. Also provided herein is germplasm of the genetically modified potato plant, the germplasm comprising the partially-complemented MiMe genotype. Further provided herein is a genetically altered plant genome derived from the genetically modified potato plant, the genetically altered plant genome comprising the germplasm comprising the partially-complemented MiMe genotype.

In some embodiments which may be combined with any of the preceding embodiments, the genetically modified potato plant, plant part, or plant cell is diploid, triploid, tetraploid, pentaploid, hexaploid, heptaploid, or octoploid. In additional embodiments which may be combined with any of the preceding embodiments, the genetically modified potato plant, plant part, or plant cell comprises two, three, four, or more haplotypes of the same or related species of potato. In some embodiments, which may be combined with the foregoing embodiments, the genetically modified potato plant part is a non-regenerable plant part. In some embodiments which may be combined with the foregoing embodiments, the genetically modified potato plant cell is a non-regenerable plant cell. In certain embodiments, which may be combined with any of the previous embodiments, the plant part is a flower, a pistil, a leaf, a stem, a petiole, a cutting, a tissue, a seed coat, an ovule, pollen, a tuber, a root, a rootstock, a scion, a fruit, a cotyledon, a hypocotyl, a protoplast, an embryo, an anther, or a portion thereof.

In certain embodiments, which may be combined with any of the previous embodiments, the potato plant part is a flower, a pistil, a leaf, a stem, a petiole, a cutting, a tissue, a seed coat, an ovule, a microspore, pollen, a tuber, a stolon, a meristem, a root, a rootstock, a scion, a fruit, a cotyledon, a hypocotyl, a protoplast, an embryo, an anther, or a portion thereof.

In some embodiments, provided herein is a processed potato product derived from the genetically modified potato plant, plant part, or plant cell of any one of the preceding embodiments. In certain embodiments, the processed potato product comprises a detectable amount of the one or more MiMe alleles of the genetically modified potato plant, plant part, or plant cell. In certain embodiments, the potato product is selected from the group consisting of plant biomass, oil, meal, food starch, syrup, animal feed, flour, flakes, bran, lint, hulls, processed seed, puree, juice, juice concentrate, pulp, pomace, preserve, sauce, chips, crisps, or French fries. In some embodiments, the processed potato product is non-regenerable. In certain embodiments, the processed potato product contains sufficient nucleic acid (e.g., DNA or RNA) and/or protein material from the genetically modified potato plant, plant part, or plant cell to detect nucleic acid and/or protein sequences corresponding to the three haplotypes, the one or more genetic modifications resulting in decreased expression of one or more MiMe loci, or both.

In some embodiments, provided herein is a processed potato product derived from a genetically modified potato plant, plant part, or plant cell comprising: i) three or more haplotypes; and ii) a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In other embodiments, provided herein is a processed potato product derived from a genetically modified potato plant, plant part, or plant cell comprising: i) three or more haplotypes; and ii) a partial MiMe genotype comprising: (a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the one or more MiMe loci of the component of progression through the second division of meiosis comprise OSD1, CYCA1, TDM1, PC1, PC2, FC, or any combination thereof. In certain embodiments, the processed potato product comprises sufficient nucleic acid (e.g., DNA or RNA) and/or protein material from the genetically modified potato plant, plant part, or plant cell to detect nucleic acid and/or protein sequences corresponding to the three haplotypes, the MiMe alleles, or both in the processed potato product. In certain embodiments, the processed potato product is non-regenerable.

In some embodiments, provided herein is a processed potato product derived from a genetically modified potato plant, plant part, or plant cell comprising: i) three or more haplotypes; and ii) a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components. In other embodiments, provided herein is a processed potato product derived from a genetically modified potato plant, plant part, or plant cell comprising: i) three or more haplotypes; and ii) a partial MiMe genotype comprising: (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In other variations, the one or more MiMe loci of the component of progression through the first division of meiosis comprise PS1, JASON, or a combination thereof. In certain embodiments, the processed potato product comprises sufficient nucleic acid (e.g., DNA or RNA) and/or protein material from the genetically modified potato plant, plant part, or plant cell to detect nucleic acid and/or protein sequences corresponding to the three haplotypes, the MiMe alleles, or both in the processed potato product. In certain embodiments, the processed potato product is non-regenerable.

In some embodiments, provided herein is a processed potato product derived from a genetically modified potato plant, plant part, or plant cell comprising: (i) at least a first and second haplotype, each comprising one or more MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of sister chromatid cohesion during the first division of meiosis comprise REC8, SWITCH1/DYAD, or a combination thereof. In additional variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In yet additional variations, the MiMe locus of the component of progression through the first division of meiosis of the third haplotype is PS1 or JASON. In still additional variations, the one or more MiMe loci of the component of progression through the second division of meiosis of the first and second haplotype comprise OSD1, CYCA1, TDM1, PC1, PC2, FC, or any combination thereof. In yet additional variations, the locus of the component of progression through the second division of meiosis of the third haplotype is OSD1, CYCA1, TDM1, PC1, PC2, or FC. In certain embodiments, the processed potato product comprises sufficient nucleic acid (e.g., DNA or RNA) and/or protein material from the genetically modified potato plant, plant part, or plant cell to detect nucleic acid and/or protein sequences corresponding to the three haplotypes, the MiMe alleles, or both in the processed potato product. In certain embodiments, the processed potato product is non-regenerable.

In some embodiments, provided herein is a processed plant product derived from a genetically modified potato plant, plant part, or plant cell comprising: (i) at least a first and second haplotype, each comprising one or more MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components, and (ii) at least a third haplotype comprising (a) a MiMe allele conferring decreased expression of a MiMe locus of a component of progression through the first division of meiosis, or (b) a MiMe allele conferring decreased expression of a MiMe locus of a component of progression through the second division of meiosis. In some variations, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations, the one or more MiMe loci of the component of progression through the first division of meiosis of the first and second haplotype comprise PS1, JASON, or a combination thereof. In yet additional variations, the MiMe locus of the component of progression through the first division of meiosis of the third haplotype is PS1 or JASON. In still additional variations, the MiMe locus of the component of progression through the second division of meiosis of the third haplotype is OSD1, CYCA1, TDM1, PC1, PC2 or FC. In certain embodiments, the processed plant product comprises sufficient nucleic acid (e.g., DNA or RNA) and/or protein material from the genetically modified potato plant, plant part, or plant cell to detect nucleic acid and/or protein sequences corresponding to the three haplotypes, the MiMe alleles, or both in the processed potato product. In certain embodiments, the processed potato product is non-regenerable.

In some embodiments, provided herein is a processed plant product derived from a genetically modified potato plant, plant part, or plant cell having a partially-complemented MiMe genotype. In some embodiments, a processed plant product derived from a genetically modified potato plant, plant part, or plant cell having a partially-complemented MiMe genotype comprising: (a) only MiMe alleles at one or more MiMe loci of a first MiMe component; (b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components. In some embodiments, the first MiMe component is a component of sister chromatid cohesion during the first division of meiosis. In some variations, the one or more MiMe loci of the first MiMe component comprise REC8, SWITCH1/DYAD, or a combination thereof. In one variation, the MiMe locus of the first MiMe component is REC8. In certain embodiments, the second MiMe component is a component of DNA double strand breakage during meiotic recombination. In some variations, the first MiMe locus and the second MiMe locus of the second MiMe component comprise PAIR1, SPO11-1, SPO11-2, PRD1, PRD2, DFO, MTOPVIB, DSY1, SY1, SY2, SY3, SY4, or any combination thereof. In one variation, the first MiMe locus of the second MiMe component is PAIR1 and the second MiMe locus of the second MiMe component is SPO11-1. In further embodiments, the third MiMe component is a component of progression through the second division of meiosis. In some embodiments, the partially-complemented MiMe genotype comprises only MiMe alleles at one or more MiMe loci of the third MiMe component. In some variations, the one or more MiMe loci of the third MiMe component comprise OSD1, CYCA1, TDM1, PC1, PC2, FC, or any combination thereof. In one variation, the MiMe locus of the third MiMe component is OSD1. In other embodiments, the partially-complemented MiMe genotype comprises one or more MiMe alleles and one or more non-MiMe alleles at a first MiMe locus of the third MiMe component, and one or more MiMe alleles and one or more non-MiMe alleles at a second MiMe locus of the third MiMe component. In some variations, the first MiMe locus and the second MiMe locus of the third MiMe component comprise OSD1, CYCA1, TDM1, PC1, PC2, FC, or any combination thereof. In one embodiment, the partially-complemented MiMe genotype comprises only MiMe alleles at one or more MiMe loci of the third MiMe component, wherein the one or more MiMe loci having only MiMe alleles of the first MiMe component comprise REC8, the first MiMe locus of the second MiMe component is PAIR1, the second MiMe locus of the second MiMe component is SPO11-1, and the one or more MiMe loci having only MiMe alleles of the third MiMe component comprise OSD1. In some variations of the foregoing embodiments, the processed plant product is non-regenerable.

In some embodiments, provided herein is a processed plant product derived from a genetically modified potato plant, plant part, or plant cell having a partially-complemented MiMe genotype comprising: (a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiment, the one or more MiMe loci of the component of progression through the first division of meiosis comprise PS1, JASON, or a combination thereof. In some variations of the foregoing embodiments, the processed plant product is non-regenerable.

In some embodiments, provided herein is a processed plant product derived from a genetically modified potato plant, plant part, or plant cell having a partially-complemented MiMe genotype comprising: (a) only MiMe alleles at one or more MiMe loci of a first MiMe component, wherein the first MiMe component is a component of DNA double strand breakage during meiotic recombination; (b) one or more MiMe alleles and one or more non-MiMe alleles at one or more MiMe loci of a second MiMe component; (c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components. In some variations of the foregoing embodiments, the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof. In additional variations of the foregoing embodiments, the one or more MiMe loci of the component of sister chromatid cohesion during the first division of meiosis comprise REC8, SWITCH1/DYAD, or a combination thereof. In yet additional variations of the foregoing embodiments, the one or more MiMe loci of the component of progression through the second division of meiosis comprise OSD1, CYCA1, TDM1, PC1, PC2, FC, or any combination thereof. In still additional variations of the foregoing embodiments, the one or more MiMe loci of the component of progression through the first division of meiosis comprise PS1, JASON, or a combination thereof. In some variations of the foregoing embodiments, the processed plant product is non-regenerable.

In some embodiments, provided herein is a genetically modified potato plant, plant part, or plant cell, or a processed potato product derived therefrom, having a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell, comprises a) one or more rec8 alleles, each comprising a polynucleotide sequence selected from the group consisting of SEQ ID NOs: 131, 132, 137, 138, 145, 146, 151, 152, 156, and 157. Also provided herein is germplasm of the genetically modified potato plant, the germplasm comprising the complete MiMe genotype. Further provided herein is a genetically altered plant genome derived from the genetically modified potato plant, the genetically altered plant genome comprising the complete MiMe genotype.

In some embodiments, provided herein is a genetically modified potato plant, plant part, or plant cell, or a processed potato product derived therefrom, having a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified plant, plant part, or plant cell comrpises a) one or more rec8 alleles, each comprising a polynucleotide sequence selected from the group consisting of SEQ ID NOs: 131, 132, 137, 138, 145, 146, 151, 152, 156, and 157. Also provided herein is germplasm of the genetically modified potato plant, the germplasm comprising the partial MiMe genotype. Further provided herein is a genetically altered plant genome derived from the genetically modified potato plant, the genetically altered plant genome comprising the partial MiMe genotype.

In some embodiments, provided herein is a genetically modified potato plant, plant part, or plant cell, or a processed potato product derived therefrom, having a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comrpises a) one or more rec8 alleles, each comprising a polynucleotide sequence selected from the group consisting of SEQ ID NOS: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the complete MiMe genotype. Further provided herein is a genetically altered plant genome derived from the genetically modified potato plant, the genetically altered plant genome comprising the complete MiMe genotype.

In some embodiments, provided herein a genetically modified potato plant, plant part, or plant cell, or a processed potato product derived therefrom, having a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the partial MiMe genotype. Further provided herein is a genetically altered plant genome derived from the genetically modified potato plant, the genetically altered plant genome comprising the partial MiMe genotype.

In some embodiments, provided herein a genetically modified potato plant, plant part, or plant cell, or a processed potato product derived therefrom, having a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the one or more CYCA1 loci comprise CYCA1-1, CYCA1-2, and/or CYCA1-3. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; b) one or more spo11-1 alleles, each comprising a polynucleotide sequence selected from the group consisting of SEQ ID NOs: 127, 128, 129, 133, 134, 139-142, 147, 148, 153, 154, 158, and 159; and/or c) one or more cyca1 alleles, each comprising a polynucleotide sequence selected from the group consisting of SEQ ID NOs: 143, 144, 149, and 150. Also provided herein is germplasm of the genetically modified potato plant, the germplasm comprising the complete MiMe genotype. Further provided herein is a genetically altered plant genome derived from the genetically modified potato plant, the genetically altered plant genome comprising the complete MiMe genotype.

In some embodiments, provided herein is a genetically modified potato plant, plant part, or plant cell, or a processed potato product derived therefrom, having a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the one or more CYCA1 loci comprise CYCA1-1, CYCA1-2, and/or CYCA1-3. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; b) one or more spo11-1 alleles, each comprising a polynucleotide sequence selected from the group consisting of SEQ ID NOs: 127, 128, 129, 133, 134, 139-142, 147, 148, 153, 154, 158, and 159; and/or c) one or more cyca1 alleles, each comprising a polynucleotide sequence selected from the group consisting of SEQ ID NOs: 143, 144, 149, and 150. Also provided herein is germplasm of the genetically modified potato plant, the germplasm comprising the partial MiMe genotype. Further provided herein is a genetically altered plant genome derived from the genetically modified potato plant, the genetically altered plant genome comprising the partial MiMe genotype.

In some embodiments, provided herein a genetically modified potato plant, plant part, or plant cell, or a processed potato product derived therefrom, having a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the genetically modified potato plant, plant part, or plant cell, or processed potato product derived therefrom, is triploid, tetraploid, pentaploid, hexaploid, heptaploid, or octoploid. In some variations, the one or more CYCA1 loci comprise CYCA1-1, CYCA1-2, and/or CYCA1-3. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; and/or b) one or more cyca1 alleles, each comprising a polynucleotide sequence selected from the group consisting of SEQ ID NOs: 143, 144, 149, and 150. Also provided herein is germplasm of the genetically modified potato plant, the germplasm comprising the complete MiMe genotype. Further provided herein is a genetically altered plant genome derived from the genetically modified potato plant, the genetically altered plant genome comprising the complete MiMe genotype.

In some embodiments, provided herein a genetically modified potato plant, plant part, or plant cell, or a processed potato product derived therefrom, having a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the genetically modified potato plant, plant part, or plant cell, or processed potato product derived therefrom, is triploid, tetraploid, pentaploid, hexaploid, heptaploid, or octoploid. In some variations, the one or more CYCA1 loci comprise CYCA1-1, CYCA1-2, and/or CYCA1-3. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; and/or b) one or more cyca1 alleles, each comprising a polynucleotide sequence selected from the group consisting of SEQ ID NOs: 143, 144, 149, and 150. Also provided herein is germplasm of the genetically modified potato plant, the germplasm comprising the partial MiMe genotype. Further provided herein is a genetically altered plant genome derived from the genetically modified potato plant, the genetically altered plant genome comprising the partial MiMe genotype.

In some embodiments, provided herein is a genetically modified potato plant, plant part, or plant cell, or a processed potato product derived therefrom, having a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comprises a) one or more rec8 alleles, each comprising a polynucleotide sequence selected from the group consisting of SEQ ID NOS: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the complete MiMe genotype. Further provided herein is a genetically altered plant genome derived from the genetically modified potato plant, the genetically altered plant genome comprising the complete MiMe genotype.

In some embodiments, provided herein is a genetically modified potato plant, plant part, or plant cell, or a processed potato product derived therefrom, having a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the partial MiMe genotype. Further provided herein is a genetically altered plant genome derived from the genetically modified potato plant, the genetically altered plant genome comprising the partial MiMe genotype.

In some embodiments, provided herein is a genetically modified potato plant, plant part, or plant cell, or a processed potato product derived therefrom, having a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comprises one or more rec8 alleles, each comprising a polynucleotide sequence selected from the group consisting of SEQ ID NOs: 131, 132, 137, 138, 145, 146, 151, 152, 156, and 157. Also provided herein is germplasm of the genetically modified potato plant, the germplasm comprising the complete MiMe genotype. Further provided herein is a genetically altered plant genome derived from the genetically modified potato plant, the genetically altered plant genome comprising the complete MiMe genotype.

In some embodiments, provided herein is a genetically modified potato plant, plant part, or plant cell, or a processed potato product derived therefrom, having a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comprises one or more rec8 alleles, each comprising a polynucleotide sequence selected from the group consisting of SEQ ID NOs: 131, 132, 137, 138, 145, 146, 151, 152, 156, and 157. Also provided herein is germplasm of the genetically modified potato plant, the germplasm comprising the partial MiMe genotype. Further provided herein is a genetically altered plant genome derived from the genetically modified potato plant, the genetically altered plant genome comprising the partial MiMe genotype.

In some embodiments, provided herein is a genetically modified potato plant, plant part, or plant cell, or a processed potato product derived therefrom, having a complete MiMe genotype comprising (i) an os allele, wherein the genetically modified potato plant, plant part, or plant cell is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the complete MiMe genotype. Further provided herein is a genetically altered plant genome derived from the genetically modified potato plant, the genetically altered plant genome comprising the complete MiMe genotype.

In some embodiments, provided herein is a genetically modified potato plant, plant part, or plant cell, or a processed potato product derived therefrom, having a partial MiMe genotype comprising (i) an os allele, wherein the genetically modified potato plant, plant part, or plant cell is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the partial MiMe genotype. Further provided herein is a genetically altered plant genome derived from the genetically modified potato plant, the genetically altered plant genome comprising the partial MiMe genotype.

In some embodiments, provided herein is a genetically modified potato plant, plant part, or plant cell, or a processed potato product derived therefrom, having a complete MiMe genotype comprising (i) a ps allele, wherein the genetically modified potato plant, plant part, or plant cell is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell is a genetically modified potato plant, plant part, or plant cell, optionally comprising one or more spo11-1 alleles, each comprising a polynucleotide sequence selected from the group consisting of SEQ ID NOs: 127-129, 133, 134, 139-142, 147, 148, 153, 154, 158, and 159. Also provided herein is germplasm of the genetically modified potato plant, the germplasm comprising the complete MiMe genotype. Further provided herein is a genetically altered plant genome derived from the genetically modified potato plant, the genetically altered plant genome comprising the complete MiMe genotype.

In some embodiments, provided herein is a genetically modified potato plant, plant part, or plant cell, or a processed potato product derived therefrom, having a partial MiMe genotype comprising (i) a ps allele, wherein the genetically modified potato plant, plant part, or plant cell, is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comprises one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the partial MiMe genotype. Further provided herein is a genetically altered plant genome derived from the genetically modified potato plant, the genetically altered plant genome comprising the partial MiMe genotype.

In some embodiments, provided herein is a genetically modified potato plant, plant part, or plant cell, or a processed potato product derived therefrom, having a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more only MiMe alleles at one or more SPO11-1 loci, wherein each of the MiMe alleles at the SPO11-1 locus comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the partially complemented MiMe genotype. Further provided herein is a genetically altered plant genome derived from the genetically modified potato plant, the genetically altered plant genome comprising the partially complemented MiMe genotype.

In some embodiments, provided herein is a genetically modified potato plant, plant part, or plant cell, or a processed potato product derived therefrom, having a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the one or more CYCA1 loci comprise CYCA1-1, CYCA1-2, and/or CYCA1-3. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; b) one or more cyca1 alleles, each comprising a polynucleotide sequence selected from the group consisting of SEQ ID NOs: 143, 144, 149, and 150; and/or c) one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the partially complemented MiMe genotype. Further provided herein is a genetically altered plant genome derived from the genetically modified potato plant, the genetically altered plant genome comprising the partially complemented MiMe genotype.

In some embodiments, provided herein is a genetically modified potato plant, plant part, or plant cell, or a processed potato product derived therefrom, having a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the partially complemented MiMe genotype. Further provided herein is a genetically altered plant genome derived from the genetically modified potato plant, the genetically altered plant genome comprising the partially complemented MiMe genotype.

In some embodiments, provided herein is a genetically modified potato plant, plant part, or plant cell, or a processed potato product derived therefrom, having a partially complemented MiMe genotype comprising (i) a ps allele, wherein the genetically modified potato plant, plant part, or plant cell is heterozygous for the ps allele, (ii) an os allele, wherein the genetically modified potato plant, plant part, or plant cell is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; and/or b) one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the partially complemented MiMe genotype. Further provided herein is a genetically altered plant genome derived from the genetically modified potato plant, the genetically altered plant genome comprising the partially complemented MiMe genotype.

In some embodiments, provided herein is a genetically modified potato plant, plant part, or plant cell, or a processed potato product derived therefrom, having a partially complemented MiMe genotype comprising (i) an os allele, wherein the genetically modified potato plant, plant part, or plant cell is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1. In certain embodiments, the genetically modified potato plant, plant part, or plant cell, or processed potato product derived therefrom, is triploid, tetraploid, pentaploid, hexaploid, heptaploid, or octoploid. In some variations, the one or more CYCA1 loci comprise CYCA1-1, CYCA1-2, and/or CYCA1-3. In some variations, the genetically modified potato plant, plant part, or plant cell comprises a) one or more rec8 alleles, each comprising a polynucleotide sequence selected from the group consisting of SEQ ID NOs: 131, 132, 137, 138, 145, 146, 151, 152, 156, and 157; b) one or more cyca1 alleles, each comprising a polynucleotide sequence selected from the group consisting of SEQ ID NOs: 143, 144, 149, and 150; and/or c) one or more spo11-1 alleles, each comprising a polynucleotide sequence selected from the group consisting of SEQ ID NOs: 127, 128, 129, 133, 134, 139-142, 147, 148, 153, 154, 158, and 159. Also provided herein is germplasm of the genetically modified potato plant, the germplasm comprising the partially complemented MiMe genotype. Further provided herein is a genetically altered plant genome derived from the genetically modified potato plant, the genetically altered plant genome comprising the partially complemented MiMe genotype.

Sequences of MiMe Loci, Gene Products, and Alleles
Sequence Alignment 1: REC8 protein sequences
from dicotyledonous plants.
REC8 Dicots
Homologs identified by BLAST of Arabidopsis thaliana AT5G05490.1 from AGI -
TAIR10 map to dicot NCBI RefSeq,
UniProtKB, Vaccinium corymbosum Draper v1.0, Rubus
occidentalis v3.0, Citrullus lanatus (97103) v2.0, and
Citrullus lanatus (Charleston Gray) v1.0 protein databases

```
                                                         10        20        30        40        50        60        70        80        90       100
                                                 ----:----|----:----|----:----|----:----|----:----|----:----|----:----|----:----|----:----|----:----|
Consensus                          SEQ ID NO: 166 MFYSHQLIVTVWGPATLLARKAPLGQIHMAATXHAKJNRKKLDKLBIIXICEEILNPSVPMALRLSGILMGGVVIVYERKVKLLYDDVTRLLVEINEAWK
Gossypium barbadense:              SEQ ID NO: 160 ....RE.----------.....S.....LLG.RQ..LD.R.AN..D.ARL.......P..I.....S........L..K..MF.H..AN.F....RN...
(UniProt: A0A5JSVWS8)
Arabidopsis thaliana:              SEQ ID NO: 161 .LRLES.........................L...I........D..Q................................F...N.F.....G..R
(UniProt: Q95777)
Rubus occidentalis: (Ro05 G04582)  SEQ ID NO: 162 .....S.----------........E.----------------------.......AA.......S.................GT.P---..L.....
Citrullus lanatus:                 SEQ ID NO: 163 ......----------...............M...I..R...N-------.............................I..E.............
(C1CG076684460.1)
Prunus avium: (UniProt: A0A6PSRV91) SEQ ID NO: 164 ......----------...............M...I..R.....D..K...................................................
Vaccinium corymbosum: (VaccDscaff20-snap-gene-    ......----------...............M...M........N..K...........................K....F.....N.F.........
38.40-mRNA-1)*
Solanum lycopersicum:              SEQ ID NO: 12  ......----------...............L.S.L.....S..N..N...Q.......................H......E.....M.Q......
(RefSeq: XP_025887480.1)
Solanum tuberosum:                 SEQ ID NO: 1   ......----------...............L.S.L.....S..N..N...Q..............................E.....M.Q......
(RefSeq: XP_006347252.1)

                                                        110       120       130       140       150       160       170       180       190       200
                                                 ----:----|----:----|----:----|----:----|----:----|----:----|----:----|----:----|----:----|----:----|
Consensus                          SEQ ID NO: 166 VKSXXDPTLLPKGKSQAKKEAVTLPEINXEXDLGEDIDIEQTLNXXBXXTXMXFQQTXYFXMRLCKFNNRKLTMIKWFDFPSLSFGYSICFAILSDTTWI
Gossypium barbadense:              SEQ ID NO: 160 .MN--E......R.EK..RKSI....-.D.-------------------.S.G.TNVGEL----------------------------------------
(UniProt: A0A5JSVWS8)
Arabidopsis thaliana:              SEQ ID NO: 161 T..VP........TH.R........-.E.A.F.-.--F...R.VPKFGNY.D....-FIS..-------------------------------------
(UniProt: Q95777)
Rubus occidentalis: (Ro05 G04582)  SEQ ID NO: 162 ...NT.S.V...RRA......I....-PEDT...G......S.DFSHHA.LFQ-...G..L.Q.------------------------------------
Citrullus lanatus:                 SEQ ID NO: 163 ..AAPE..VI.....L.......R..-KDPK.------------VSYNTSP.R....AF.T..-------------------------------------
(C1CG076684460.1)
Prunus avium: (UniProt: A0A6PSRV91) SEQ ID NO: 164 A..VA...V........R........-.EDI.------..GM..FSNGA.T.-....S..A..-------------------------------------
Vaccinium corymbosum: (VaccDscaff20-snap-gene-    ...VP............Y.T....D..Q.AE..----...S..YTN--.T.R..E.A..S..-------------------------------------
38.40-mRNA-1)*
Solanum lycopersicum:              SEQ ID NO: 12  ..AAT............YA.I....-.R.EE.P.---.....RNPDTV.M.D.E..S..T..-------------------------------------
(RefSeq: XP_025887480.1)
Solanum tuberosum:                 SEQ ID NO: 1   ..AAT............YA......-.R.EE.P.---.....RNPDTV.M.D.E..S..T.QV-------------------------------------
(RefSeq: XP_006347252.1)

                                                        210       220       230       240       250       260       270       280       290       300
                                                 ----:----|----:----|----:----|----:----|----:----|----:----|----:----|----:----|----:----|----:----|
Consensus                          SEQ ID NO: 166 RVGNISENKIIIDNFYMRVQLNSDXXVXXXXDDXXXXNNXXXZXXPXXXFHQXDXDNITLXERFXSXXTDXXXXXXRFHDERFDIEGDEETQXNFTXXEX
Gossypium barbadense:              SEQ ID NO: 160 -------------------------E------------EEISMG.GDS.RLA.DND...FDL.QPNSN----IHGQ.--...E-.A..G..V...LD.H
(UniProt: A0A5JSVWS8)
Arabidopsis thaliana:              SEQ ID NO: 161 --------------------------LDE----SHV..NPEPEDLGQQ...A.AE....F.YHG.FQ.N-NETYD..--.........D...M.SNPR.G
```

-continued

Sequences of MiMe Loci, Gene Products, and Alleles
Sequence Alignment 1: REC8 protein sequences
from dicotyledonous plants.
REC8 Dicots
Homologs identified by BLAST of Arabidopsis thaliana AT5G05490.1 from AGI -
TAIR10 map to dicot NCBI RefSeq,
UniProtKB, Vaccinium corymbosum Draper v1.0, Rubus
occidentalis v3.0, Citrullus lanatus (97103) v2.0, and
Citrullus lanatus (Charleston Gray) v1.0 protein databases

```
(UniProt: Q95777)
Rubus occidentalis: (Ro05 G04582)    SEQ ID NO: 162 -----------------------.-S----V.VGEPL.ENAHEHDQHQN...A.PED...P...DPSDAYGDLFNH.Y--...E....D---LD..AG.R
Citrullus lanatus:                   SEQ ID NO: 163 ------------------------L--------------DSVDE.YNSDKTVED.P-------------------------....E..D..P..ASVDQ
(C1CG076684460.1)
Prunus avium: (UniProt: A0A6PSRV91)  SEQ ID NO: 164 -----------------------.S-.-----.EQYV..DAGEED.PQQ...AEAE....P...D.CQA.-AYLYS.L--...........L...SG.H
Vaccinium corymbosum: (VaccDscaff20-snap-gene-      -----------------------.N-.-----.EPFI..DPREGPQSEQH..V.A.....F...D.YQ..-TNLYS..--........D...A...SQ.R
38.40-mRNA-1)*
Solanum lycopersicum:                SEQ ID NO: 12  -----------------------.-N-------ADLYDKPNAQEE.AKDL..V.P.....A...E.HH..---MFNH.--...........M.Y.QP.D
(RefSeq: XP_025887480.1)
Solanum tuberosum:                   SEQ ID NO: 1   ......................RMFNVQRL.NADLYDKPNAQKE.AKDL..V.P.....A.H.E.HH..MFNHFE.Y...Q.........M.Y.QP.D
(RefSeq: XP_006347252.1)

                                                              310       320       330       340       350       360       370       380       390       400
                                                    ----:----|----:----|----:----|----:----|----:----|----:----|----:----|----:----|----:----|----:----|
Consensus                            SEQ ID NO: 166 TQIPXTSPNXXIPSPPRXZXXXXXPDXXXXDXHPEXQVXQQXFXDEXXEAXXXQXQDQQRQGPXRRRARKXXXXAMDXEQTIIXGHXYQSWLQXXSDIXS
Gossypium barbadense:                SEQ ID NO: 160 I...T.---P-....SQKE--PQRAGGT-QER...H.LD..F--NKNK..---R--......SVKQ.-..PKGIIT.E...V.SN.V.H...HDT...A.
(UniProt: A0A5JSVWS8)
Arabidopsis thaliana:                SEQ ID NO: 161 AE..T.---LI-.....HHDIPEGVNPTSPQRQEQQENRRDG.AEQME.QNIPDKEEHD.PQ.AKK....TATS...Y.....A..V......DT...LC
(UniProt: Q95777)
Rubus occidentalis: (Ro05 G04582)    SEQ ID NO: 162 ...RAP...YI.....SPN--YII.SPPRQ.QRQ.V.QPHHV.-..MVQMQEV.ENA......L.G.R..RRAPV..ND...HPA.V......DT...V.
Citrullus lanatus:                   SEQ ID NO: 163 ....A.---FKDSP..QQKYPEGP..AEVQ.Q.L.SN.N.PA----------------------------------Y.S.EL-----------------
(C1CG076684460.1)
Prunus avium: (UniProt: A0A6PSRV91)  SEQ ID NO: 164 ...HIP----------.DE--HQKA.TIQD.Q...Q..N.PEECQ.FRQK-VRMK.V.E....I..KT.RTQAS...F.....P..L......NS...V.
Vaccinium corymbosum: (VaccDscaff20-snap-gene-      ....SS----L......PA--EPRKSDEIL.Q...D..YH.P--..GKA.S----..L.....T..K...PAAF...Y.....P..M......SA...V.
38.40-mRNA-1)*
Solanum lycopersicum:                SEQ ID NO: 12  A...S.----PVQ....EQ--AHQ..EI-P.R...D..K..S--..VK..-FE.R.....PK.A...T..ATSL.I.H.....S.DI......SS...A.
(RefSeq: XP_025887480.1)
Solanum tuberosum:                   SEQ ID NO: 1   A...S.----PV.....EQ--AHQ..EI-P.R...D..K..S--..VE..-FE.R.....PK.A......ATGL.I.H.....S.DI......SS...A.
(RefSeq: XP_006347252.1)

                                                              410       420       430       440       450       460       470       480       490       500
                                                    ----:----|----:----|----:----|----:----|----:----|----:----|----:----|----:----|----:----|----:----|
Consensus                            SEQ ID NO: 166 RXRRRKRKXXXXMSTMKIAXLMELPPXVLXEXLFTXGXXEVXYPAPLLXLHMRXTQPPHDSPSXXTSPPLPPEPSXXSXXERXXXXDXPFFXXEXXXSGV
Gossypium barbadense:                SEQ ID NO: 160 .I..KNSGPASIL..F...K.....ST.IMDDMLLK.NQ.IS..E...D..KKCS..L....-----------------------.--------LH...
(UniProt: A0A5JSVWS8)
Arabidopsis thaliana:                SEQ ID NO: 161 .GEK..VRGT-IRPD.ESFKRANM..TQ.F.-------KDSS..PQ.YQ..SKN..VLQT.S.ESRH.D.RA.Q.PGFVQ..MHNHHQT---DMHER.DT
(UniProt: Q95777)
Rubus occidentalis: (Ro05 G04582)    SEQ ID NO: 162 .-...NP.PKNI...V..GK...Q.AS..MGC..KP.SG.TY..P...E..KE--K.T.....AL.....Q....SW.PP..QTYQ.S.---V.EFH..G
Citrullus lanatus:                   SEQ ID NO: 163 -----RQQRTGA.......T..D...V..S.R...D.SR..Y......E....SIRQ.P....ERN.A.......LS.LP..VNFS.HMD.SF.GHQ...
(C1CG076684460.1)
Prunus avium: (UniProt: A0A6PSRV91)  SEQ ID NO: 164 .-.G....RTDV.A....VN......I..IGD...T.SRDIY..R...D...KS.RT..A...ER.T........SSTLPG.QQYE.P..----EDY...
Vaccinium corymbosum: (VaccDscaff20-snap-gene-      .-.G....RFNA......GN..D...M..LCG..GS.KR..H......E..V.S.E.......GK....Q.....AS.LAD.ARYN.SMG.LY.DVHG.L
38.40-mRNA-1)*
```

-continued

Sequences of MiMe Loci, Gene Products, and Alleles
Sequence Alignment 1: REC8 protein sequences
from dicotyledonous plants.
REC8 Dicots
Homologs identified by BLAST of Arabidopsis thaliana AT5G05490.1 from AGI -
TAIR10 map to dicot NCBI RefSeq,
UniProtKB, Vaccinium corymbosum Draper v1.0, Rubus
occidentalis v3.0, Citrullus lanatus (97103) v2.0, and
Citrullus lanatus (Charleston Gray) v1.0 protein databases

```
Solanum lycopersicum:                 SEQ ID NO: 12  .-K.K...TLSVLPS....RM..M..IA.L.G...N.NK..H......K....N.........GK....F.....YT.PG..MGNLEP..----.YFQG..
(RefSeq: XP_025887480.1)
Solanum tuberosum:                    SEQ ID NO: 1   .-K.K...TLRVLHS....RM..M..IA.L.G...N.NK..H......K....N.........GK....Y.....YT.PG..MGNLEP..----.YFQ...
(RefSeq: XP_006347252.1)

                                                               510       520       530       540       550       560       570       580       590       600
                                                     ----:----|----:----|----:----|----:----|----:----|----:----|----:----|----:----|----:----|----:----|
Consensus                             SEQ ID NO: 166 GSQSXGXSIEKQRANXNXXVXNXXPPEXLMEXLRXNLXNNGXXXTXXNXVKETDHVTPGNSGDEVRSIPSSXSGXGXXSIXNSEXNSKXRSXNKKRPXSS
Gossypium barbadense:                 SEQ ID NO: 160 ..P.HAA...V..--A.--.V.KVT.AGINQFV----------S----------------......A..YTG..V..D.VP.-G.L.V.I-E.VGS..KNLQ.
(UniProt: A0A5JSVWS8)
Arabidopsis thaliana:                 SEQ ID NO: 161 S..NLDSPA.IL.--TV-RTGKGASV.SM.AGS.ASPETINRQAADI.--------...FY...D...M..TP.AR.AA..N.I.IS..S.MP.R...N..
(UniProt: Q95777)
Rubus occidentalis: (Ro05 G04582)     SEQ ID NO: 162 ....FATPT.QI.--T.-L.N.DV...-..DE..A..--..MRGADTKL------A........R.....TS..K.VNK-NS..V..-G..-.R..RY..
Citrullus lanatus:                    SEQ ID NO: 163 ....F.A.M..LM--TRR--V.DSNQAEIP.E.GP.IMD.VMRM.ER.Q.-----......VNG...VS..A..H.DL.-N.LGT..-V..-......Y..
(C1CG076684460.1)
Prunus avium: (UniProt: A0A6PSRV91)   SEQ ID NO: 164 ....LET..D...RHSGMTRG.SD.AQVVL.G.TA..E...LGG.DA.PM-----......-.D.......A..QAIP.----.A..-G..-.R...Y.A
Vaccinium corymbosum: (VaccDscaff20-snap-gene-       ....F.V......T.V.---V.EI.T.V...D..N.FV...VRVNEA.VM-----.............H..G..Q.FQ.-HT..G..-G..-......N..
38.40-mRNA-1)*
Solanum lycopersicum:                 SEQ ID NO: 12  ..PAV.I........L.---N.KI...I...D..T..T.M.LHP.ET.G......MATPG....P......G..H.LL.-Q..VTD.-S..-......H..
(RefSeq: XP_025887480.1)
Solanum tuberosum:                    SEQ ID NO: 1   ..PAV.I........L.---N.KI...I...D..T..T.M.LHP.VA.G......MATPG....P......G..H.LL.-Q..VT..-S..-......H..
(RefSeq: XP_006347252.1)

                                                               610       620       630       640       650       660       670       680       690       700
                                                     ----:----|----:----|----:----|----:----|----:----|----:----|----:----|----:----|----:----|----:----|
Consensus                             SEQ ID NO: 166 SXHSXXGLEPVAEENPWHHHPDPNFKLTRLSRLSENGFTXDXXJLXETGPTQTQVTXPXIXHQPLDMMTDSIRXQLKSHFDTPGAPEVESLNXLXAGMNX
Gossypium barbadense:                 SEQ ID NO: 160 TSKNSGS.DT.V.VFH--E-A.TDYQ.----..PKRKNLEP.HDF.V..QL.MET---.ADD--.P....EN.KKHM.T..E.....Q....QN.A..L.K
(UniProt: A0A5JSVWS8)
Arabidopsis thaliana:                 SEQ ID NO: 161 PRR---.........R..E.-REYE.EF---.M.P.KR..A.KEI.F..AS.....--K.VCN-.SDE.I....KSH..T..E.....Q.....K.AV..DR
(UniProt: Q95777)
Rubus occidentalis: (Ro05 G04582)     SEQ ID NO: 162 I-..ND.....S.D.GC..-.....NV---.....GI----EQEL.M.......P--Q.I.D-...EK...D..KE...Y.EA..G......DK.T....R
Citrullus lanatus:                    SEQ ID NO: 163 .RQ.SG..............S......A---.........----.PDL.E..AR......Q.A.K.P.A.KI.....T.M.A.......AST....N.A....R
(C1CG076684460.1)
Prunus avium: (UniProt: A0A6PSRV91)   SEQ ID NO: 164 .G..SVR....F.V.H----..V..E.----...H.H.P.SEIDFFV.........--K.IND-....KT.....RL.......A...Q....DH.T..RTR
Vaccinium corymbosum: (VaccDscaff20-snap-gene-       .R..GS...........Q.-.......---A......L.PENDL.A.........--Q.IMT-PRI.QI.N...M...T....L.PS.K....Q.AF...K
38.40-mRNA-1)*
Solanum lycopersicum:                 SEQ ID NO: 12  LK..GN..Q.........D-.TL........E.......Q.NEI.M.........--H.F.T-...........I..........SA.A.C..E.TL..TK
(RefSeq: XP_025887480.1)
Solanum tuberosum:                    SEQ ID NO: 1   .K..GN..Q.........D-.T.........E.......Q.NEI.M.........--H.F.T-...........M..........SA.A.C..E.TL..TK
(RefSeq: XP_006347252.1)

                                                               710       720       730       840
                                                     ----:----|----:----|----:----|----:----|----:--
```

-continued

Sequences of MiMe Loci, Gene Products, and Alleles
Sequence Alignment 1: REC8 protein sequences
from dicotyledonous plants.
REC8 Dicots
Homologs identified by BLAST of Arabidopsis thaliana AT5G05490.1 from AGI - TAIR10 map to dicot NCBI RefSeq, UniProtKB, Vaccinium corymbosum Draper v1.0, Rubus occidentalis v3.0, Citrullus lanatus (97103) v2.0, and Citrullus lanatus (Charleston Gray) v1.0 protein databases

| | | |
|---|---|---|
| Consensus | SEQ ID NO: 166 | KXAAXLFYQTCVLATRDFXKVEQXVPYGDILISRGAKITEVEELVXM |
| Gossypium barbadense: (UniProt: A0A5JSVWS8) | SEQ ID NO: 160 | .G..Q...R.....SQG.L..Q.K.AF...F..K...---------. |
| Arabidopsis thaliana: (UniProt: Q95777) | SEQ ID NO: 161 | NA..K..F.S......GVI..N.AE.......A..PN---------. |
| Rubus occidentalis: (Ro05 G04582) | SEQ ID NO: 162 | .G..L...........N.V....KA..E....T..PN........LK |
| Citrullus lanatus: (C1CG076684460.1) | SEQ ID NO: 163 | .A..M.........SS.YL..N.Q..F...F..K.T.---------- |
| Prunus avium: (UniProt: A0A6PSRV91) | SEQ ID NO: 164 | .E..IF..K......H.AI....K.A..E......P.--------MG |
| Vaccinium corymbosum: (VaccDscaff20-snap-gene-38.40-mRNA-1)* | | .R..H...H.....S...VR...H...........---------. |
| Solanum lycopersicum: (RefSeq: XP_025887480.1) | SEQ ID NO: 12 | .Q..C............V....EL...N.......---------. |
| Solanum tuberosum: (RefSeq: XP_006347252.1) | SEQ ID NO: 1 | .Q..C............I....EL...N.......---------. |

TABLE 1

| Percent identities of REC8 protein sequences from dicotyledonous plants. | | | | | | | |
|---|---|---|---|---|---|---|---|
| REC8 Dicot % ID | Gossypium barbadense: (UniProt: A0A5J5VWS8) | Arabidopsis thaliana: (UniProt: Q9S7T7) | Rubus occidentalis: (Ro05-G04582) | Citrullus lanatus: (ClCG07-G004460.1) | Prunus avium: (UniProt: A0A6P5RV91) | Vaccinium corymbosum: (VaccDscaff20-snap-gene-38.40-mRNA-1) | Solanum lycopersicum: (RefSeq: XP_02588-7480.1) |
| Arabidopsis thaliana: (UniProt: Q9S7T7) | 33.073 | | | | | | |
| Rubus occidentalis: (Ro05-G04582) | 35.349 | 37.349 | | | | | |
| Citrullus lanatus: (ClCG07-G004460.1) | 34.967 | 34.202 | 36.687 | | | | |
| Prunus avium: (UniProt: A0A6P5RV91) | 38.915 | 45.092 | 50 | 45.938 | | | |
| Vaccinium corymbosum: (VaccDscaff20-snap-gene-38.40-mRNA-1) | 39.905 | 44.275 | 49.158 | 48.742 | 60.377 | | |
| Solanum lycopersicum: (RefSeq: XP_02588-7480.1) | 37.915 | 42.857 | 44.36 | 43.906 | 52.812 | 59.781 | |
| Solanum tuberosum: (RefSeq: XP_00634-7252.1) | 33.949 | 39.31 | 40.582 | 40.028 | 48.091 | 54.249 | 85.714 |

Seqience Alignment 2: SP011-1 protein sequences from dicotyledonous plants.
SP011-1 Dicots
Homologs identified by BLAST of Arabidopsis thaliana AT3613170.1 from AGI - TAIR10 map to dicot NCBI RefSeq, UniProtKB, Vaccinium corymbosum Draper v1.0, Rubus occidentalis v3.0, Citrullus lanatus (97103) v2.0, and Citrullus lanatus (Charleston Gray) v1.0 protein databases

```
                                                      10        20        30        40        50        60        70        80        90       100
                                                ----:----|----:----|----:----|----:----|----:----|----:----|----:----|----:----|----:----|----:----|
Consensus                      SEQ ID NO: 173 MEGKRSRWSSXTRPXDLLRKIKXFTRSIVEDLSXGRSPXIXIDRFRNYCTNXXXNCXCSSXLPXGKEXLTLXRESHXRRLDVLLRVLLIVQQLLQENRHG
Citrullus lanatus: (Cla97C04G075440.1)        ...N.G----SLERIGI....TEL.K.MIVE..N.S.KM.S....KS....SLE.WF---N.SE...T...Q....V...........I....R...S
*C1CG096021210.1**
Rubus occidentalis:            SEQ ID NO: 168 ..........SP..R.......G...A......N....E.P........S.PSA..Y...D..K...T...R....VH.........VV..........A
(Ro01 G11692) *Ro03_G32130
Vaccinium corymbosum:                         ...T..----N.Q.S...K..-----------------------------------------------------------....................
(VaccDscaff83-snap-gene-5.35-mRNA-1)*
Arabidopsis thaliana:          SEQ ID NO: 170 ....FA----ISESTN..QR..D..Q.V.V..AE....K.S.NQ.....M.PEAD.L...DK,K.Q.FI..KK.PQTY.I.M.................A
(UniProt: Q9M4A2)
Gossypium barbadense:          SEQ ID NO: 171 ...I..----S..SR.......E..L..L....E.L..L.R.QS..T....LDSI.S.R.NQ.S.H.I..FQK...VH.I.................K.A
(UniProt:A0A5J5SLP4)
Prunus avium:                  SEQ ID NO: 172 ....H.....QP..C......RE...A......N....E.L.........KPDS..D...D..IL..T...R....L..........V............
(UniProt:A0A6P5TTD7)
Solanum tuberosum:             SEQ ID NO: 2   ......----N.Q.LT.I....G.........AR..A.L.Y.........DTSG..S...G.ST...AIS.K..C.A..........V............
(RefSeq:XP_006346146.1)
Solanum lycopersicum:          SEQ ID NO: 13  ......----N...LT......G.........AR..P.L.Y.E.......DTSG..S...G.ST...AIS.K..C.A.....M.................
(RefSeq:XP_010324270.1)

                                                     110       120       130       140       150       160       170       180       190       200
                                                ----:----|----:----|----:----|----:----|----:----|----:----|----:----|----:----|----:----|----:----|
Consensus                      SEQ ID NO: 173 SKRDIYYMHPSVFXDQSWDRAINDICILLQCSRHNLNVGDXLQVRSIAVFFKSYSXCLEAASDDPFSVGPLNGLVMGWLRFXEAGRKFDCIXXPNTAYP
Citrullus lanatus: (Cla97C04G075440.1)        .............T.........................T..Q...........L...........NLC..DR.......S....R....KK..S.HF
*C1CG096021210.1**
Rubus occidentalis:            SEQ ID NO: 168 ...........I.S.......................--V-------------------------..-----K.TFQHFSECC.VNN.----M...
(Ro01 G11692) *Ro03_G32130
Vaccinium corymbosum:                         .............QGE.GFCFG.HFLLRFFSS.LYRGH-----------------S-----------------------.......H..E......SSL...Q.
(VaccDscaff83-snap-gene-5.35-mRNA-1)*
Arabidopsis thaliana:          SEQ ID NO: 170 ...........A.KA..I.....G.....F....Y...-----.----------------------..--........K.R.........LNSL.....
(UniProt: Q9M4A2)
Gossypium barbadense:          SEQ ID NO: 171 ..........LI.S........................-----.----------------------..--.........F.........NS....HT
(UniProt:A0A5J5SLP4)
Prunus avium:                  SEQ ID NO: 172 .............S....I..........M.........-----.----------------------..--K.........S...NM....NR....F.
(UniProt:A0A6P5TTD7)
Solanum tuberosum:             SEQ ID NO: 2   ..........T..KE.......................-----.----------------------..--.........YV.S...IN..GN.H....
(RefSeq:XP_006346146.1)
Solanum lycopersicum:          SEQ ID NO: 13  ..........T..KE.......................-----.----------------------..--.........YV.S...I...SN......
(RefSeq:XP_010324270.1)
```

-continued

Seqience Alignment 2: SP011-1 protein sequences from dicotyledonous plants.
SP011-1 Dicots
Homologs identified by BLAST of Arabidopsis thaliana AT3613170.1 from AGI -
TAIR10 map to dicot NCBI RefSeq, UniProtKB,
Vaccinium corymbosum Draper v1.0, Rubus occidentalis v3.0,
Citrullus lanatus (97103) v2.0, and
Citrullus lanatus (Charleston Gray) v1.0 protein databases

```
                                                210       220       230       240       250       260       270       280       290       300
                                       ----:----|----:----|----:----|----:----|----:----|----:----|----:----|----:----|----:----|----:----|
Consensus                 SEQ ID NO: 173 VPVLVEEVKDIVSVAXYILVVEKESGEGYSDKSWFHGSRKLNFKFYFXQLXYVVSYFERPVFQRLANDQFCXXNRCIVITGRGYPDVPTRRFLRLLVDKL
Citrullus lanatus: (Cla97C04G075440.1)   I..Q....T..A.P.D..............................D..K.L................R..SR.....................I...V.
*C1CG096021210.1**
Rubus occidentalis:       SEQ ID NO: 168 ...N...........Q.........---------------------V-------------...........NS..............IS.....G...T.
(Ro01 G11692) *Ro03_G32130
Vaccinium corymbosum:                    ...H..D...L....H.........------------------------V----------...........NK.......................ME..
(VaccDscaff83-snap-gene-5.35-mRNA-1)*
Arabidopsis thaliana:     SEQ ID NO: 170 ........E....L.E........T--------------------------.--------........M..KT...............S.......ME..
(UniProt: Q9M4A2)
Gossypium barbadense:     SEQ ID NO: 171 ......D...L..A.L.........--------------------------.--------.....E..K..SK...........................
(UniProt:A0A5J5SLP4)
Prunus avium:             SEQ ID NO: 172 ..IH...........K.........--------------------------.--------...........NT.H............IS.....G...T.
(UniProt:A0A6P5TTD7)
Solanum tuberosum:        SEQ ID NO: 2   I.......D..I...Q.V.......--------------------------.--------...........KR.......................I...
(RefSeq:XP_006346146.1)
Solanum lycopersicum:     SEQ ID NO: 13  I.......D..I...Q.VI......--------------------------.--------...........KR.......................I...
(RefSeq:XP_010324270.1)

                                                310       320       330       340       350       360       370       380       390       400
                                       ----:----|----:----|----:----|----:----|----:----|----:----|----:----|----:----|----:----|----:----|
Consensus                 SEQ ID NO: 173 HLPVYCLVDCDPYGFDILXTYRFGSMVXPPDQSINLSSTQMAYDAKFLRVPEIQWLGAFPSDSEKYXLPQQCLLPLTAEGEXXXXXXXXHTLTLYAFDNV
Citrullus lanatus: (Cla97C04G075440.1)   A..AF.............T.......-------------.......Y..I.QL......A......N..E...I...LQ..GSCIQTHT........S..
*C1CG096021210.1**
Rubus occidentalis:       SEQ ID NO: 168 ...I..............S......L.R.........................I......L.....H............---------------------
(Ro01 G11692) *Ro03_G32130
Vaccinium corymbosum:                    S..A..............M.......-Q-----------..........L...H...V....G...GI....H........MDTFEKAF-----------
(VaccDscaff83-snap-gene-5.35-mRNA-1)*
Arabidopsis thaliana:     SEQ ID NO: 170 ....H..........E..A.......-------------.....IES..A.DMK..........V.SV.K.......E.------------------.--
(UniProt: Q9M4A2)
Gossypium barbadense:     SEQ ID NO: 171 C.................A.......-------------............Q............N.D..K.......I.---------------------
(UniProt:A0A5J5SLP4)
Prunus avium:             SEQ ID NO: 172 ...T..............S.......-------------..............L...G..L.....L...........Q------------------.--
(UniProt:A0A6P5TTD7)
Solanum tuberosum:        SEQ ID NO: 2   .....G............T..K...L-------------......T....S......V.VQ.CDN.SI.........T.------------------.--
(RefSeq:XP_006346146.1)
Solanum lycopersicum:     SEQ ID NO: 13  .....G............T..K...L-------------......T....S......V.VQ.CDN.SI...........------------------.--
(RefSeq:XP_010324270.1)

                                                410       420       430       440       450       460       470       480       490       500
```

-continued

Seqience Alignment 2: SPO11-1 protein sequences from dicotyledonous plants.
SPO11-1 Dicots
Homologs identified by BLAST of Arabidopsis thaliana AT3613170.1 from AGI - TAIR10 map to dicot NCBI RefSeq, UniProtKB, Vaccinium corymbosum Draper v1.0, Rubus occidentalis v3.0, Citrullus lanatus (97103) v2.0, and Citrullus lanatus (Charleston Gray) v1.0 protein databases

```
                                               ----:----|----:----|----:----|----:----|----:----|----:----|----:----|----:----|----:----|----:----|
Consensus                      SEQ ID NO: 173  BFGISDXLSFLVNLXXKRKTEAMLXRCYLQREVPQWRLELELMLXRGVKFEIEALSVHSLXFLSXEYLPSKIXNXXXXXXXXXXXXXXXXXXXXXXXLLS
Citrullus lanatus: (Cla97C04G075440.1)         N.....I.......SD..R...L.Q....R..........DS..Q.............NIS...E.......K.ELTTGKF-------------------
*C1CG096021210.1**
Rubus occidentalis:            SEQ ID NO: 168  D---------------........Q....E..........Q...ES.....L....SLLMGVMGQAM.RKH.H---------------------------
(Ro01 G11692) *Ro03_G32130
Vaccinium corymbosum:                          ------F-------NH.SR.....L.........H..S....L.Q...............S..AR..I.L..KGEVSVTIDTEEGLAKVSGEVD.NV...
(VaccDscaff83-snap-gene-5.35-mRNA-1)*
Arabidopsis thaliana:          SEQ ID NO: 170  ----------------.KR.....L....K..M........T..K...............S...EV.I....RREVSSP---------------------
(UniProt: Q9M4A2)
Gossypium barbadense:          SEQ ID NO: 171  ----------------------------------------------------------GDTYSKDQW..PAPS---------------------------
(UniProt:A0A5J5SLP4)
Prunus avium:                  SEQ ID NO: 172  ----------------........R.........R.....Q...E......L......E.N...AV.I....QGGVYI----------------------
(UniProt:A0A6P5TTD7)
Solanum tuberosum:             SEQ ID NO: 2    ----------------...V....P............F....L.HK..............T...H.......H.GGAVF---------------------
(RefSeq:XP_006346146.1)
Solanum lycopersicum:          SEQ ID NO: 13   ----------------...I....P............F....L.HK..............T...H.......H.GGLKILSLNQMILHQNRLKT.IS.--
(RefSeq:XP_010324270.1)

Consensus                      SEQ ID NO: 173  AIGKSXKHAELKWVQLKSPTPQNRSHYYHNDDMGKSYGPYSLSYGQDYYGYGQPIEPPHTGRRRALLEAEGRWCDALS
Citrullus lanatus: (Cla97C04G075440.1)         ------------------------------------------------------------------------------
*C1CG096021210.1**
Rubus occidentalis:            SEQ ID NO: 168  ------------------------------------------------------------------------------
(Ro01 G11692) *Ro03_G32130
Vaccinium corymbosum:                          .....S........................................................................
(VaccDscaff83-snap-gene-5.35-mRNA-1)*
Arabidopsis thaliana:          SEQ ID NO: 170  ------------------------------------------------------------------------------
(UniProt: Q9M4A2)
Gossypium barbadense:          SEQ ID NO: 171  ------------------------------------------------------------------------------
(UniProt:A0A5J5SLP4)
Prunus avium:                  SEQ ID NO: 172  ------------------------------------------------------------------------------
(UniProt:A0A6P5TTD7)
Solanum tuberosum:             SEQ ID NO: 2    ------------------------------------------------------------------------------
(RefSeq:XP_006346146.1)
Solanum lycopersicum:          SEQ ID NO: 13   -----N-----------------------------------------------------------------------.
(RefSeq:XP_010324270.1)
```

*SEQ ID NO: 169
**SEQ ID NO: 167

TABLE 2

Percent identities of SPO11-1 protein sequences from dicotyledonous plants.

| SPO11-1 Dicot % ID | Citrullus lanatus: (Cla97C04G-075440.1)* ClCG09G-021210.1 | Rubus occidentalis: (Ro01G11692)* Ro03__G32130 | Vaccinium corymbosum: (VaccDscaff83-snap-gene-5.35-mRNA-1) | Arabidopsis thaliana: (UniProt: Q9M4A2) | Gossypium barbadense: (UniProt: A0A5J5SLP4) | Prunus avium: (UniProt: A0A6P5TTD7) | Solanum tuberosum: (RefSeq: XP__00634-6146.1) |
|---|---|---|---|---|---|---|---|
| Rubus occidentalis: (Ro01G11692)* Ro03__G32130 | 46.985 | | | | | | |
| Vaccinium corymbosum: (VaccDscaff83-snap-gene-5.35-mRNA-1) | 35.599 | 37.678 | | | | | |
| Arabidopsis thaliana: (UniProt: Q9M4A2) | 49.353 | 59.424 | 43.396 | | | | |
| Gossypium barbadense: (UniProt: A0A5J5SLP4) | 45.474 | 57.333 | 36.134 | 59.669 | | | |
| Prunus avium: (UniProt: A0A6P5TTD7) | 52.778 | 74.278 | 43.659 | 68.579 | 61.37 | | |
| Solanum tuberosum: (RefSeq: XP__00634-6146.1) | 50.647 | 64.921 | 42.977 | 66.851 | 59.392 | 71.585 | |
| Solanum lycopersicum: (RefSeq: XP__01032-4270.1) | 48.861 | 61.042 | 44.025 | 63.708 | 56.919 | 67.959 | 90.601 |

Sequence Alignment 3: PAIR1 protein sequences from dicotyledonous plants
PAIR1 Dicots
Homologs identified by BLAST of Arabidopsis thaliana AT1601690.2 from AGI - TAIR10 map to dicot NCBI RefSeq, UniProtKB, Vaccinium corymbosum Draper v1.0, Rubus occidentalis v3.0, Citrullus lanatus (97103) v2.0, and Citrullus lanatus (Charleston Gray) v1.0 protein databases

```
                                                10        20        30        40        50        60        70        80        90       100
                                       ----:----|----:----|----:----|----:----|----:----|----:----|----:----|----:----|----:----|----:----|
Consensus                 SEQ ID NO: 180  MKLKINKACDLSSISVLPPHTXVVVTALFDSXRRSSXVPXGPESSVFGKSQXSQLRSQQPSQQSFSQGXSSQQRGCGMFSQLSQSSLDDXVTNDQRFGSQ
Arabidopsis_thaliana:     SEQ ID NO: 174  ..MN.......K....F..NL-----------..R.AE.QA---------SQ.....-Q........P..S.....G...MT...I.ELLI.....S..
(RefSeq:NP_001318904.1)
Citrullus_lanatus:_       SEQ ID NO: 175  .R................QSR---------HA..NALTT.Q--------.AP....-.........L...H---.Y.....N.F.EV...E...S..
(Cla97C05G081880.1)
Solanum_tuberosum:        SEQ ID NO: 3    ....M...S...........A-----------..P.V..SAA.........P..V....Q........F....---AIY..........F.P.E..L...
(RefSeq:XP_006339791.2)
Solanum_lycopersicum:     SEQ ID NO: 14   ....M...S...........A-----------..P.V..SAA.........P..V....Q........F....---AIY..........F.P.E..L...
(RefSeq:XP_004231186.2)
Vaccinium_corymbosum:_                    ....................S.........K....L..N.........R.A...L..-.........V....---........N....I...N..IS..
(VaccDscaff40-augustus-gene-183.9-mRNA-1)*
Gossypium_barbadense:     SEQ ID NO: 177  ..........G....F....------------....LP.SV.--------.S.........-.........I...H---AL...I......EI..T.......
(UniProt: A0ASJ5QG99)
Prunus_avium:             SEQ ID NO: 178  ..................Q..-----------..QNAA.N..---------.A......-..E......F...H---.........N..S.VL.........
(UniProt:A0A6P5RCR3)
Rubus_occidentalis:_      SEQ ID NO: 179  ....................-----------...NS..H..Q.------SQL.....-..E......L...Y---.........T...AL--T...--..
(Ro07_G04309)

                                               110       120       130       140       150       160       170       180       190       200
                                       ----:----|----:----|----:----|----:----|----:----|----:----|----:----|----:----|----:----|----:----|
Consensus                 SEQ ID NO: 180  ERENSXKKXSSCLPPIXYTREESQMQJSRSSTNXXRKQSSXSXPXXXKXQISEELEHRIGMXETSLXRFGMILDSCQSDIMQVNKGTKEVLXEMEXXRQK
Arabidopsis_thaliana:     SEQ ID NO: 174  ..DL.L..V.......NHK..D..LVa....SGLS.R...A.IGESK.A.......Q.F..M....S....M...I......A.R.....FL.T.RIQ..
(RefSeq:NP_001318904.1)
Citrullus_lanatus:_       SEQ ID NO: 175  D....I..N-.FFT.LS.S..DC..AL.K...SLTQR.K.TPL.DSK-C.VG...DR.L.TI.N..NK..K....LH...L.L...M.Q.SLDV.GIW..
(Cla97C05G081880.1)
Solanum_tuberosum:        SEQ ID NO: 3    .....A.RM-....H.N.....T...L.KP...YL...---.V.ESK-Y..-.....K...V....S.Q......I........R....I.M...SL.P.
(RefSeq:XP_006339791.2)
Solanum_lycopersicum:     SEQ ID NO: 14   .....A.RM-....H.N.....T...L.KP...YL...---.V.ESK-Y..-.....K...V..L.S.Q......I........R....M.M...SL.P.
(RefSeq:XP_004231186.2)
Vaccinium_corymbosum:_                    ....PV..L-......S..L.....PV....S.LM...N.G.ALDHR-S.T.....R....I...MN.....M................A.M.I.DV...
(VaccDscaff40-augustus-gene-183.9-mRNA-1)*
Gossypium_barbadense:     SEQ ID NO: 177  ....TAS.F-...A.TNF...D..VPI......II...NPV.A.EHR-C.T.......LSVI....N.....................L.L...GM..R
(UniProt: A0ASJ5QG99)
Prunus_avium:             SEQ ID NO: 178  .....V..I-A.....SHA.......I......FM.....A.GSDHR-W.T...F......M....NK...........V......M...SM...AM...
(UniProt:A0A6P5RCR3)
Rubus_occidentalis:_      SEQ ID NO: 179  .....V..I-......SHA.......I..T.N.HM.....V.GSDHR-C............M....SK...........V...K......SL...AIQ..
(Ro07_G04309)
```

-continued

Sequence Alignment 3: PAIR1 protein sequences from dicotyledonous plants
PAIR1 Dicots
Homologs identified by BLAST of Arabidopsis thaliana AT1601690.2 from AGI - TAIR10 map to dicot NCBI RefSeq, UniProtKB, Vaccinium corymbosum Draper v1.0, Rubus occidentalis v3.0, Citrullus lanatus (97103) v2.0, and Citrullus lanatus (Charleston Gray) v1.0 protein databases

```
                                                         210       220       230       240       250       260       270       280       290       300
                                                 ----:----|----:----|----:----|----:----|----:----|----:----|----:----|----:----|----:----|----:----|
Consensus                          SEQ ID NO: 180  LXXXDXSLQLMNKGQEDXKASLDGGXKSMXEQLXKBXYQEKLQEIXXVLSALPEXXEIIEASLLKXQNXLXXTFTKEIQXIXCXXXXXXXXXQXXPXXXX
Arabidopsis_thaliana:              SEQ ID NO: 174  .TLQ.T...QLR.E.A.S.......V.FIL.EFS.DPN.....K.LQM.TTI..QV---.TA.Q.I.REICH...R...VLA-SLRTPEPRVRVPTAPQV
(RefSeq:NP_001318904.1)
Citrullus_lanatus:_                SEQ ID NO: 175  MLVNSS...S...EHD.M..T....F.LISDL.K.DAH..R.H..SD...S.EKQVQ----..Q..LK.DFIS...Q.MKA.V.TLK---NPL.KF.PRSI
(Cla97C05G081880.1)
Solanum_tuberosum:                 SEQ ID NO: 3    .VSH.EL......ER..L....E.TF...F.E.RENK...NIRDLLSL.R.M.NKL.---MCI.QL.TD.SK.LA....I.SPRPDCHGKKHETA.VDPP
(RefSeq:XP_006339791.2)
Solanum_lycopersicum:              SEQ ID NO: 14   .VSH.EL......DR..L....E.TF...F.E.RENK...NIRDLSSL.R.M.NKL.---MCI.QL.TD.SK.LA....I.APRPDFHGQKHETA.VDPP
(RefSeq:XP_004231186.2)
Vaccinium_corymbosum:_                             IIANGNL....D...Q.I.TN.V..I..LTD.VGQDIDG...K..SSMI.....QI---DV..H.M.SE.CTKI.Q...AMA.SLKIPSQKS.NP.TPAV
(VaccDscaff40-augustus-gene-183.9-mRNA-1)*
Gossypium_barbadense:              SEQ ID NO: 177  SIAE.T.....I.....I......SM.AVSD..NNDK.RD...Q.FL.......QM.----...I.VR.E.CN...N..KA.D.K-----TLS.KA.VAAA
(UniProt: A0ASJ5QG99)
Prunus_avium:                      SEQ ID NO: 178  .TAQ.N.....S.....F.......I...S...S.NT..D....MFL......GKI.........S..K.HDS.V..M.KMI.SQN-QSTSI.KCEISSI
(UniProt:A0A6P5RCR3)
Rubus_occidentalis:_               SEQ ID NO: 179  .MVQ.S...........F.TTF.A.I...L...S.NPN.D....MFL.......KI.----....SS..K.HNS.I..V.KLL.PIQTCQNQITPIQTCKA
(Ro07_G04309)

                                                         310       320       330       340       350       360       370       380       390       400
                                                 ----:----|----:----|----:----|----:----|----:----|----:----|----:----|----:----|----:----|----:----|
Consensus                          SEQ ID NO: 180  XXXXXXXXXRXXXXXKXXXXKKXXXPPKIXXXXXXXXXKXEFXXXXXPXGXWKSVKXXXXXXTXXXAFXKXXPXXSXXXVXPXXXPXTXXGQWXXXXXXXTQN
Arabidopsis_thaliana:              SEQ ID NO: 174  KAKENLPEQ.GQAAKVLTSL.MPE--.RVQVPAAPQA.EN.PEQRG.VAKSN.FCNTTLK.KQPQ.PRNPNDA.ARA.K.YLS.KIQV.C.KTVKPEKS.
(RefSeq:NP_001318904.1)
Citrullus_lanatus:_                SEQ ID NO: 175  QSPEGTAC-LDVPSQ.RHRC.IQSAS.NVCIRATAVQ.E.-------V.R.....VGKTFCTSSWK.DD.---K-------------------------
(Cla97C05G081880.1)
Solanum_tuberosum:                 SEQ ID NO: 3    KVINDCSLP.EVKFL.KD--Q.TTT....EMGSWTTV.IN-------QTCM.QKNPIRSH.QNE..Q.LL.LYEMGSWTTVKNNQ.CMK.KIPIRSL...
(RefSeq:XP_006339791.2)
Solanum_lycopersicum:              SEQ ID NO: 14   KGINDCIPP.EVKLL.KD--Q.TTT....EMGSWTTV.IN-------QTCM.QKIPIRSH.QNE..QQKI.IR.H-------TQNEAFQ.TIPIRSH...
(RefSeq:XP_004231186.2)
Vaccinium_corymbosum:_                             LLAKDRSCRSVQQQMQPL--.DPEM....CGKTTLLP.I.-------V.S.T...TEQATRKKQKQKRMS.I----------------------E----
(VaccDscaff40-augustus-gene-183.9-mRNA-1)*
Gossypium_barbadense:              SEQ ID NO: 177  ILPKSTGC-SVTPRT.PLAV..QAV....YEQNTVAAEV.-------K.G.....MKQCA.NER.SC.E-----N------------------------
(UniProt: A0ASJ5QG99)
Prunus_avium:                      SEQ ID NO: 178  LSPKGVAAS.AIPQG.PQPI.SSAV...ACVQAVWVP.T.-------T.G..T..AEKAVFSDSG.R.------V------------------------
(UniProt:A0A6P5RCR3)
Rubus_occidentalis:_               SEQ ID NO: 179  LSILSPKTAASPAIL.AEQKP.RKYVR.CKVPSLPSP.GD-AFHAI.QQKPQLINKASERLRNP.LDSHSTVPPKVC.Q.AVV.T.ET.G.KTVKAGNAT
(Ro07_G04309)
```

-continued

Sequence Alignment 3: PAIR1 protein sequences from dicotyledonous plants
PAIR1 Dicots
Homologs identified by BLAST of Arabidopsis thaliana AT1601690.2 from AGI - TAIR10 map to dicot NCBI RefSeq, UniProtKB, Vaccinium corymbosum Draper v1.0, Rubus occidentalis v3.0, Citrullus lanatus (97103) v2.0, and Citrullus lanatus (Charleston Gray) v1.0 protein databases

```
                                                      410        420        430        440        450        460        470        480        490        500
                                                ----:----|----:----|----:----|----:----|----:----|----:----|----:----|----:----|----:----|----:----|
Consensus                   SEQ ID NO: 180   XAFQQKIPXXXXXXXXXXQQERECRXXIESDEEXIDGGFSCLLEEKXTDXVXYLKQATDTFHTPXXXXYXJXXAKEETXRILRKARRRKRKXXNXIIIN
Arabidopsis_thaliana:       SEQ ID NO: 174   --.KKRATRKPVKSESTRT.FEQ.SVV.D.............IN.NTRG---------------T---NFEWD.EK..E....T...T...FG.P....
(RefSeq:NP_001318904.1)
Citrullus_lanatus:_         SEQ ID NO: 175   --------KVIPFSEQCLVL...Y.VIVD..-.E.ERS....I...K.GE--------------NVRY.SIED....SA........Q...YC.P....
(Cla97C05G081880.1)
Solanum_tuberosum:          SEQ ID NO: 3     E.......IRSHTQNGAF....GH.IT....-.D..A........NG.EN---------------PGI.PLDD....SA............HF.T...D
(RefSeq:XP_006339791.2)
Solanum_lycopersicum:       SEQ ID NO: 14    G.......IRSHTENGAF....G..IT....-.D..A........NG.G------------------I.PLDD....SA............HF.T...D
(RefSeq:XP_004231186.2)
Vaccinium_corymbosum:_                       -----------VHKQMMVM.D....IP....-.E..........G.E..P.Q............HLGN.SMAE.....Q...........RHS.T..LD
(VaccDscaff40-augustus-gene-183.9-mRNA-1)*
Gossypium_barbadense:       SEQ ID NO: 177   ----------DKRKGVSSVEQETF.IL....-.E..A......ND.Q..D-A--------------MNILIEE.....E............PL.P....
(UniProt: A0ASJ5QG99)
Prunus_avium:               SEQ ID NO: 178   ---------QKPNRFTSI.K.....VI....-.E...A.....DD.E.-------------------VDMAAEV....Q....R.......LC.T....
(UniProt:A0A6P5RCR3)
Rubus_occidentalis:_        SEQ ID NO: 179   SIDRVPQKVQKHNRITCV.....G.VI....-.D.........D..D..--I--------------KN.MIEEVNQ..E....R.......CC.P....
(Ro07_G04309)
```

*SEQ ID NO: 176

TABLE 3

| Percent identities of PAIR1 protein sequences from dicotyledonous plants. | | | | | | | |
|---|---|---|---|---|---|---|---|
| PAIR1 Dicot % ID | Arabidopsis thaliana: (RefSeq: NP_00131-8904.1) | Citrullus lanatus: (Cla97C05-G081880.1) | Solanum tuberosum: (RefSeq: XP_00633-9791.2 | Solanum lycopersicum: (RefSeq: XP_00423-1186.2) | Vaccinium corymbosum: (VaccDscaff40-augustus-gene-183.9-mRNA-1) | Gossypium barbadense: (UniProt: A0A5J5QG99) | Prunus avium: (UniProt: A0A6P5RCR3) |
| Citrullus lanatus: (Cla97C05-G081880.1) | 35.205 | | | | | | |
| Solanum tuberosum: (RefSeq: XP_00633-9791.2 | 35.381 | 34.348 | | | | | |
| Solanum lycopersicum: (RefSeq: XP_00423-1186.2) | 35.821 | 34.658 | 90.466 | | | | |
| Vaccinium corymbosum: (VaccDscaff40-augustus-gene-183.9-mRNA-1) | 36.105 | 40.98 | 40.249 | 41.263 | | | |
| Gossypium barbadense: (UniProt: A0A5J5QG99) | 37.961 | 45.631 | 40.611 | 40.889 | 51.007 | | |
| Prunus avium: (UniProt: A0A6P5RCR3) | 38.261 | 47.722 | 40.652 | 41.333 | 51.333 | 55.474 | |
| Rubus occidentalis: (Ro07_G04309) | 41.379 | 37.609 | 40.302 | 39.827 | 41.309 | 44.079 | 57.86 |

Sequence Alignment 4A: OSD1 sequences from dicotyledonous plants.
OSD1 Dicots
v3.0, Citrullus lanatus (97103) v2.0, and Citrullus lanatus (Charleston Gray) v1.0 protein databases
Homologs identified by BLAST of Arabidopsis thaliana AT3G57860.1 from AGI - TAIR10 map to dicot NCBI RefSeq,
UniProtKB, Vaccinium corymbosum Draper v1.0, Rubus occidentalis

```
                                                                    10        20        30        40        50        60        70        80        90       100
                                                           ----:----|----:----|----:----|----:----|----:----|----:----|----:----|----:----|----:----|----:----|
Consensus                             SEQ ID NO: 187 MPAEXRDRLSRPPVDXAXXFARRRRSXXGXXXXXXXXXXXLXXXPXRXXXXXXTXXZXGXXXGXXGGGGGJXRXXFGTPRXGIXRGRNRXXXXXXXXGRE
Prunus avium:(RefSeq:XP_021833341.1) SEQ ID NO: 181 .-..A.........L.DTY.QWLSRNRSIYIDPPEQVLQVVPDLS.TPARQRAPTAL.FGATGVV....LL.SSLR.S.T.--NA.G.IPFGFTTPA..
Rubus occidentalis: (Ro06 G14226)    SEQ ID NO: 182 ....S.F..E..-F.I.EA.SQ-...--.SLAVLIDERGE.LES.A.SRALATPVHQRRLGFWAT...V.HGLA----------.S.L.TPRAAIGH.Q.
Arabidopsis thaliana:                 SEQ ID NO: 183 .-P.A...TE..-..YSTI..N...H--.ILLDEPDSRLS.IES.VNP-----------DI.SI..T..LV.GN.T.W.P.--N..GGHTPFRLPQ...
(UniProt:Q9M2R1)
Gossypium                             SEQ ID NO: 184 ....S....G.A-..I.EV.....SGPL.IL---SDESMD.LGS.V.QSVTRRSMGVV.VTTSTAR.V.LRRGGS.....I..R.S..LYRSTGRENASV
barbadense:(UniProt:A0A2P5XW92)
Citrullus lanatus:                    SEQ ID NO: 185 .-S.A....E.Q-..H.EV.....SE---GILDEQEMNSH.IGT.IARATTTP.AQQRPTNP.P-....SNP.RT..S.IS.-GI....FLYRSPVFN..
(Cla97C046068720.1)
Vaccinium corymbosum:                                -P.S........-DEVRAT...Q.Q.I-.GIAILLDEEQPEVGT.F.WGATAM.GTRGPMGVASTR..R.VR.GSL....SS---T...RGQENMAS.SF
(VaccDscaffS-snap-gene-277.41-mRNA-1)*
Solanum lycopersicum:                 SEQ ID NO: 15  .-..G......Q-E.PIDIYS.....---MGRGGIEIFEDESPESSSRAPIQT.-AEA.RMA.TS..R..IG.IG..S..NR--....LFRTPARVI..Q
(UniProt:ABA3Q7ILG3)
Solanum tuberosum:                    SEQ ID NO: 4   .-..G......Q-E.PIDIYS.....---MGRGGIEIFEDESPESSSRAPIQT.-AET.RMA.TS..R..IG.IG..S..NR--....SLRTPTRVI..Q
(RefSeq:XP_006351336.1)

                                                                   110       120       130       140       150       160       170       180       190       200
                                                           ----:----|----:----|----:----|----:----|----:----|----:----|----:----|----:----|----:----|----:----|
Consensus                             SEQ ID NO: 187 NXXPXGSSRRGRGRGXNSVLPSWYPRTPLRDITAXVRAIERRRXARLXEXEGZXXEXSXVPQDXXXLGPSESXSGAQLEHXXSLVTPXPXXRXXXXXPPS
Prunus avium:(RefSeq:XP_021833341.1) SEQ ID NO: 181 ..TP.A....R...SS............Q..S.V........-...G.ND.QHT.-GQ...GRNI.DQYLLVP......GVP-...YSAV.T.HCP...
Rubus occidentalis: (Ro06 G14226)    SEQ ID NO: 182 .MP.V...N.R...VS.................IT.......-...G.EN.ETSR-GQ..---------.QQVQD.SP..EVPAT..-STIKKRPCP...
Arabidopsis thaliana:                 SEQ ID NO: 183 .MPIVT---AR....-GGL.............HI........G.GTGGDD.RVI.---I.T-HRQV.VL..PVPLSG..KC.M...G.SVGF.RSC...
(UniProt:Q9M2R1)
Gossypium barbadense:                 SEQ ID NO: 184 TSP.L.---......TG................V........-...GDG..QIV.TPIL.H.ETI..-.NMS.VS....NF.--..ASTT.L.PC-...
(UniProt:A0A2P5XW92)
Citrullus lanatus:                    SEQ ID NO: 185 .TA-AS....N.S..R.....I...........V......T.-...R.N..QGSDN.PA.S.ERA.EY.V.VA.DHQ.PSI....----------K.T
(Cla97C046068720.1)
Vaccinium corymbosum:                                RRG------.....ST..............V.YV........A.S.R.S..LQIG-.PM...QNV.V...PT.......NL.....N.TV.M.KPCQ..
(VaccDscaffS-snap-gene-277.41-mRNA-1)*
Solanum lycopersicum:                 SEQ ID NO: 15  .IS.T.---Q..N..RH....A...........SI......T.-...R.S..EQL.-.V....HTD......T.......TN..I..R.KT.-SRYHTR.
(UniProt:ABA3Q7ILG3)
Solanum tuberosum:                    SEQ ID NO: 4   .IS.A.---Q..N..RH....A...........SI......T.-...R.S..EQL.-.V....HTD......T.......TN..I..R.KT.-SRYHTR.
(RefSeq:XP_006351336.1)
```

-continued

Sequence Alignment 4A: OSD1 sequences from dicotyledonous plants.
OSD1 Dicots
v3.0, Citrullus lanatus (97103) v2.0, and Citrullus lanatus (Charleston Gray) v1.0 protein databases
Homologs identified by BLAST of Arabidopsis thaliana AT3G57860.1 from AGI - TAIR10 map to dicot NCBI RefSeq,
UniProtKB, Vaccinium corymbosum Draper v1.0, Rubus occidentalis

```
                                                     210       220       230       240       250       260       270
                                                 ----:----|----:----|----:----|----:----|----:----|----:----|----:---
Consensus                           SEQ ID NO: 187 VGKVPKILLDITNQXXXESXXEXLTPQKKLLNSIDTVEKVVMEELQKLKRTPSAKKAEREKRVRTLMSMRYGGYALVT
Prunus avium:(RefSeq:XP_021833341.1) SEQ ID NO: 181 ..R.Q..IREA..TQTA.-GE-F......................R.....................--------
Rubus occidentalis: (Ro06 G14226)    SEQ ID NO: 182 .R..H....EVAY.PDDG-EF--............K..N.......R...............HKADG.L.........
Arabidopsis thaliana:               SEQ ID NO: 183 TA..Q.M.....KEIAE.-EAGFI..E........K...I..A.I....S..Q..RE.........T..--------
(UniProt:Q9M2R1)
Gossypium barbadense:               SEQ ID NO: 184 .RN.S....NV...KHE..SE.L................A.I...N.M.K.........QHK.......--------
(UniProt:A0A2P5XW92)
Citrullus lanatus:                  SEQ ID NO: 185 .......I.G.A..NVVG--A.T............K............K.................F.--------
(Cla97C046068720.1)
Vaccinium corymbosum:                              ............H.TAAG--SDC.....................R...S.........QN.......--------
(VaccDscaffS-snap-gene-277.41-mRNA-1)*
Solanum lycopersicum:               SEQ ID NO: 15  ..............STS.-DA.C....R...........H.....H........R.Q..D...K.....--------
(UniProt:ABA3Q7ILG3)
Solanum tuberosum:                  SEQ ID NO: 4   ..............STS.-DS.C....R...........H.....H......G.R.E..D...K.....--------
(RefSeq:XP_006351336.1)
```

*SEQ ID NO: 186

TABLE 4A

Percent identities of OSD1 protein sequences from dicotyledonous plants.

| OSD1 Dicot % ID | *Prunus avium*: (RefSeq: XP_021833341.1) | *Rubus occidentalis*: (Ro06 G14226) | *Arabidopsis thaliana*: (UniProt: Q9M2R1) | *Gossypium barbadense*: (UniProt: A0A2P5XW92) | *Citrullus lanatus*: (Cla97C04G068720.1) | *Vaccinium corymbosum*: (VaccDscaff5-snap-gene-277.41-mRNA-1) | *Solanum lycopersicum*: (UniProt: A0A3Q7ILG3) |
|---|---|---|---|---|---|---|---|
| *Rubus occidentalis*: (Ro06 G14226) | 45.588 | | | | | | |
| *Arabidopsis thaliana*: (UniProt: Q9M2R1) | 41.887 | 37.778 | | | | | |
| *Gossypium barbadense*: (UniProt: A0A2P5XW92) | 46.442 | 41.455 | 40.377 | | | | |
| *Citrullus lanatus*: (Cla97C04G068720.1) | 45.865 | 40.959 | 40.909 | 45.113 | | | |
| *Vaccinium corymbosum*: (VaccDscaff5-snap-gene-277.41-mRNA-1) | 47.17 | 41.176 | 41.154 | 49.434 | 47.909 | | |
| *Solanum lycopersicum*: (UniProt: A0A3Q7ILG3) | 44.697 | 38.889 | 40.698 | 47.348 | 49.042 | 49.615 | |
| *Solanum tuberosum*: (Ref Seq: XP_006351336.1) | 44.697 | 38.148 | 40.698 | 46.591 | 48.276 | 49.615 | 96.471 |

Sequence Alignment 5: CYCA1 protein sequences from dicotyledonous plants.
CYCA1 Dicots
Homologs identified by BLAST of Arabidopsis thaliana AT1G7390 from AGI - TAIR10 map to dicot NCBI RefSeq, UniProtKB, Vaccinium corymbosum Draper v1.0, Rubus occidentalis (not included in this alignment) v3.0, Citrullus lanatus (97103) v2.0, and Citrullus lanatus (Charleston Gray) v1.0 protein databases

```
                                                    10        20        30        40        50        60        70        80        90        100
                                            ----:----|----:----|----:----|----:----|----:----|----:----|----:----|----:----|----:----|----:----|
Consensus                    SEQ ID NO: 193  MXXXXGNRXXXXXXXXXXXXXXXXXSXXXAXXXXGKXXAXXXXXAXXRXXLXBXXXXXXXSXXXXXXXXXXXXXXXXXXXXXXKXXXXXKXXXXXXSXXXXX
Citrullus lanatus:           SEQ ID NO: 188  .SAH--..RPSFSSSTSSSLAKRQAS.ASS-SDNV..VM.VPPHL.KK.AP.GNLT.FKNV.HSAAKSSVPPAI-MVPCAT.AVKAR.SSPART-RSTNL
(Cla97C086148690.1)
Vaccinium corymbosum:                        .SNQ--..RSSVTTSTSSSLAKRHA-------ENL..A---QPYV.KK.PA.ANVT.QRHG.QNGPRSLVSGSSNMVPCMT.VANAK.ISSTCI-SNASF
(VaccDscaff2-augustus-gene-199.26-mRNA-1)*
Solanum lycopersicum:        SEQ ID NO: 16   .MTTQ-..RSS---AVAKRQAMAANS.GLE-HNQT..L------N.KK.PA.SNIS.NTTV.---ARNSVSHSSKLAPCTS.IVNIK.NTSACN.NAVSS
(RefSeq:NP_001233762.1)
Arabidopsis thaliana:        SEQ ID NO: 190  .SSSS--.NLSQENPIPRPNLAKTRT.----LRDV.----------NR.AP.GDIT.QKNG.-----RNPSPSSTLVNCSN.IGQSK.APKPAL.RNWNL
(RefSeq:NP_177863.2)
Gossypium barbadense:        SEQ ID NO: 191  .STQK...RSSFSSSTTSSLAKRHAS.----SENV..V---MASL.KK.VP.TNIT.QKQS.---SSKSSALASSLVPSSN.IQKAR.TQSV---TNVGL
(UniProt:A0A2PSVPW8)
Prunus avium:                SEQ ID NO: 192  .STQ--..RSAFPSSLAKRQALSSSS.SSS.SGNV..WV.AEPHL.KK.AP.SNLT.RNSV.NNGLRSSGGSSCTLVPCTN.IAKVK.GPPAC---TGNK
(RefSeq:XP_021806552.1)
Solanum tuberosum:           SEQ ID NO: 5    .MTTQ-..RSSVSSAVAKRQAMAANS.GLE-NNQT..L---NAGA.KK.PA.SNIS.HTTV.---ARNSISHSSKLAPCTS.IVSIK.--------NISS
(RefSeq:XP_006351136.1)

                                                   110       120       130       140       150       160       170       180       190       200
                                            ----:----|----:----|----:----|----:----|----:----|----:----|----:----|----:----|----:----|----:----|
Consensus                    SEQ ID NO: 193  XXXXXXXXXXXXXXXXXXXXXXXXXXXXXXXXXXXXXXXXXXXXXXXXXXXXXSXXXSDG-
                                             LXXVSXDXXXSXXDXXXXXXXXYXDBXXXXAXXSXXXXXXXXLXIS
Citrullus lanatus:           SEQ ID NO: 188  T--TTNTTTLLDVKTTNAIAPSNVTAFSRTDATAVSS------SMDV.PSK...-VS..L.ETM.TC.SFKSPDVE.L.NTDVP.VD.VERKTKSS.C..
(Cla97C086148690.1)
Vaccinium corymbosum:                        S--RSTLPVAVNVKPSVAVSSKSSPFIKYDDFPRIPAP-DAPCGMDI.SPH...-SS..M.ETM.SC.SLKSPEFE.V.NTEIA.VD.IERRTSSK.Y..
(VaccDscaff2-augustus-gene-199.26-mRNA-1)*
Solanum lycopersicum:        SEQ ID NO: 16   G--TAVLPASSSVRPSSKPVSIQRSDAVVPKITVIPVP--ATCSMDI.PSH...-SL..M.ESM.NS.TVRSPEVE.I.DHELA.VD.IEKKACST.Y..
(RefSeq:NP_001233762.1)
Arabidopsis thaliana:        SEQ ID NO: 190  GILDSGLPPKPNAKSNIIVPYEDTELLQSDDSLLCSSPA---LSLDA.PTQ.---------.PSI.TH.SLTNHWD.M-----------VESTTDDG----
(RefSeq:NP_177863.2)
Gossypium barbadense:        SEQ ID NO: 191  SG--HVLPPTNERRSSVLPPKVVPSLPTGNEVVLPPPP--VQCSMEF.PSK....SS..L.ETM.TC.SFKSPEVE.I.NHDVS.IG.IERKTFSN.C..
(UniProt:A0A2PSVPW8)
Prunus avium:                SEQ ID NO: 192  GVSASSLPASFNVKPSAVVHPKVTPAPRSDEAVPSSFALPGPCSMDV.PSK...-NS..M.ETM.SC.SFKSPEVE.I.NNDVP.ID.INRKTFSN.Y..
(RefSeq:XP_021806552.1)
Solanum tuberosum:           SEQ ID NO: 5    G--TAVLPASSSVRPSSKPVSIQRSDAVVPKITAIPLP--ATCSMDI.PSH...-SL..M.ESM.TS.TVRSPEVE.I.DLESA.VD.IEKKACST.Y..
(RefSeq:XP_006351136.1)
```

-continued

Sequence Alignment 5: CYCA1 protein sequences from dicotyledonous plants.
CYCA1 Dicots
Homologs identified by BLAST of Arabidopsis thaliana AT1G7390 from AGI -
TAIR10 map to dicot NCBI RefSeq, UniProtKB, Vaccinium corymbosum Draper v1.0,
Rubus occidentalis (not included in this alignment) v3.0, Citrullus lanatus (97103) v2.0, and
Citrullus lanatus (Charleston Gray) v1.0 protein databases

```
                                                      210       220       230       240       250       260       270       280       290       300
                                              ----:----|----:----|----:----|----:----|----:----|----:----|----:----|----:----|----:----|----:----|
Consensus                   SEQ ID NO: 193    XXXXXXXXXXVKGSICXRXXXXXXXXXXXXXXBXDXXXXDPQXCAXXACDIYXHLRXXEXXKRPXXDXMXXXQXXINXXMRXILXDWLVEVAEEYRLXPXT
Citrullus lanatus:          SEQ ID NO: 188    GPAPISSQAP......N.DVITEMETDGDIVDV.TDFM...Q..TI.....K...AS.AK...ST.F.EKI.KD..SN..A..I............V.D.
(Cla97C086148690.1)
Vaccinium corymbosum:                         EHMEAAETV------.K.DIIVGVGTDEEFVDV.DNFM...L..TM.....K...AT.AK...ST.F.ERV.KD..AS..A..V............V.D.
(VaccDscaff2-augustus-gene-199.26-mRNA-1)*
Solanum lycopersicum:       SEQ ID NO: 16     EHVKAAAAD-----..K.DVLVDLESGDKIMNI.NNLV...L..TM.....K...AS.AK...ST.F.AKV.KD..PS..A..I............V.D.
(RefSeq:NP_001233762.1)
Arabidopsis thaliana:       SEQ ID NO: 190    ----------------------NDDDDDEIVNI.SDLM...L..SF.....E...VS.VN...AL.Y.ERT.SS..AS..S..I............S.E.
(RefSeq:NP_177863.2)
Gossypium barbadense:       SEQ ID NO: 191    DHDVVATGA----...N.DAVAEKEADDMVIDV.DNFM...L..TF.....K...AS.VK...ST.F.ETI.KD..SS..A..I............V.D.
(UniProt:A0A2PSVPW8)
Prunus avium:               SEQ ID NO: 192    DHAETTGIAC------K.EVLVELEAEDKIADL.NSLM...L..TI.....K...AS.VK...ST.F.EKT.KD..PS..A..I............V.D.
(RefSeq:XP_021806552.1)
Solanum tuberosum:          SEQ ID NO: 5      EHIKAAAAD-----..K.DVLVDLESGDKIVNI.NNLV...L..TM.....T...AS.AK...ST.F.AKV.KD..PS..A..I............V.D.
(RefSeq:XP_006351136.1)

                                                      310       320       330       340       350       360       370       380       390       400
                                              ----:----|----:----|----:----|----:----|----:----|----:----|----:----|----:----|----:----|----:----|
Consensus                   SEQ ID NO: 193    LXLXXXYXDRYLXGNXXBXQXLQLLGVXCMMIAXKYEEXCXPQVEXFCYITDNTYXXXEXLZMESXVLNYXKFEXTXPTXKCFLRRFXRAAQGXXXXXXS
Citrullus lanatus:          SEQ ID NO: 188    .Y.TVN.I....S..SMDR.R......A.....S....I.A....E.........FKD.V.E...S....L...M.A..P.......V.....ATDEVS.
(Cla97C086148690.1)
Vaccinium corymbosum:                         .Y.TIN.I....S..TMDR.R......A.....A....I.A....E.........FKE.V.Q...A....M...M.A..A.......V.....VNE-AP.
(VaccDscaff2-augustus-gene-199.26-mRNA-1)*
Solanum lycopersicum:       SEQ ID NO: 16     .H.TIN.I....S..LMDR.R......A.....S....I.A....E.........FKE.V.Q...A....L...M.A..A.......V.....LNE-VL.
(RefSeq:NP_001233762.1)
Arabidopsis thaliana:       SEQ ID NO: 190    .Y.AVN.V....T..AINK.N......T.....A....V.V....D.........LRN.L.E...S....L...L.T..A.......L.....RKE-VP.
(RefSeq:NP_177863.2)
Gossypium barbadense:       SEQ ID NO: 191    .Y.TVS.I....S..TMNR.R......A.....S....I.A....E.........FKD.V.E...S....L...M.A..A.......V.....INE-VP.
(UniProt:A0A2PSVPW8)
Prunus avium:               SEQ ID NO: 192    .Y.TVN.I....S..PMNR.R......A.....S....I.A....E.........FKE.V.Q...D....L...M.A..T.......V.....ANEGI-.
(RefSeq:XP_021806552.1)
Solanum tuberosum:          SEQ ID NO: 5      .Y.TIN.I....S..LMDR.R......A.....S....I.A....E.........FKE.V.Q...T....L...M.A..A.......V.....LNE-VL.
(RefSeq:XP_006351136.1)
```

-continued

Sequence Alignment 5: CYCA1 protein sequences from dicotyledonous plants.
CYCA1 Dicots
Homologs identified by BLAST of Arabidopsis thaliana AT1G7390 from AGI - TAIR10 map to dicot NCBI RefSeq, UniProtKB, Vaccinium corymbosum Draper v1.0, Rubus occidentalis (not included in this alignment) v3.0, Citrullus lanatus (97103) v2.0, and Citrullus lanatus (Charleston Gray) v1.0 protein databases

```
                                                      410       420       430       440       450       460       470       480       490       500
                                                  ----:----|----:----|----:----|----:----|----:----|----:----|----:----|----:----|----:----|----:----|
Consensus                          SEQ ID NO: 193 XXXEXXAXXJXELSLJXYXMLXYXPSXXAASAXFLAXXXLXPXXXPWNXTLXHXTXYXXXXXXXCVXXLXXLCXXXXXSXXXAXRXKYSXHKYKXXAKKX
Citrullus lanatus:                 SEQ ID NO: 188 MQL.CL.NFLA....IE.S..C.A..LV....I...KFI.L.TKR...S..Q.Y.H.QPSDLVD..KD.HR..CNTHN.SLP.I.E...Q....HV...Y
(Cla97C086148690.1)
Vaccinium corymbosum:                             MQL.CL.NYLA....LE.N..C.A..VI....I...KYI.I.SKR...S..R.Y.H.QPCDLSD..KA.HS..CNSQS.SLP.I.E...L....FV...Y
(VaccDscaff2-augustus-gene-199.26-mRNA-1)*
Solanum lycopersicum:              SEQ ID NO: 16  LQL.HL.SYIA....LE.N..S.A..LI....I...KYI.L.SVK...S..R.Y.L.QPSDLQD..MA.HS..CNNNN.SLP.V.E...Q....FV...Y
(RefSeq:NP_001233762.1)
Arabidopsis thaliana:              SEQ ID NO: 190 LLS.CL.CYLT....LD.A..R.A..LV....V...QYT.H.SRK...A..E.Y.S.RAKHMEA..KN.LQ..NEKLS.DWV.I.K...Q....FA...L
(RefSeq:NP_177863.2)
Gossypium barbadense:              SEQ ID NO: 191 MQL.CM.NYIA....LE.S..C.P..LI....I...KFI.L.SKK...S..Q.F.L.KPSDLFE..KE.HR..CNNNN.TLP.I.E...Q....CV...Y
(UniProt:A0A2PSVPW8)
Prunus avium:                      SEQ ID NO: 192 MHL.CL.NYLA....LE.S..C.A..LV....I...NFI.L.SKR...A..Q.Y.L.QPSDLRD..KD.HR..SNSQS.SLP.I.E...Q....HV...Y
(RefSeq:XP_021806552.1)
Solanum tuberosum:                 SEQ ID NO: 5   LDL.HL.SYIA....LE.N..C.A..LI....I...KYI.L.SVK...S..R.Y.L.QPSDLRD..LA.HS..CNNNN.SLP.V.E...Q....FV...Y
(RefSeq:XP_006351136.1)

                                                      510
                                                  ----:----|----:
Consensus                          SEQ ID NO: 193 CPXXXPXXXXXXXXX
Citrullus lanatus:                 SEQ ID NO: 188 ..PTI.SEYQT----
(Cla97C086148690.1)
Vaccinium corymbosum:                             ..PAI.AEYFQ.LS-
(VaccDscaff2-augustus-gene-199.26-mRNA-1)*
Solanum lycopersicum:              SEQ ID NO: 16  ..PTV.VEFFQ.ISS
(RefSeq:NP_001233762.1)
Arabidopsis thaliana:              SEQ ID NO: 190 ..TSL.QELFL----
(RefSeq:NP_177863.2)
Gossypium barbadense:              SEQ ID NO: 191 ..PSI.SDFFH.---
(UniProt:A0A2PSVPW8)
Prunus avium:                      SEQ ID NO: 192 ..PTI.PEFFQ.QTQ
(RefSeq:XP_021806552.1)
Solanum tuberosum:                 SEQ ID NO: 5   ..PTV.VEFFQ.ISS
(RefSeq:XP_006351136.1)
```

*SEQ ID NO: 189

TABLE 4B

| Percent identities of CYCA1 sequences from dicotyledonous plants. | | | | | | |
|---|---|---|---|---|---|---|
| TAM (CYCA1) Dicot % ID | Citrullus lanatus: (Cla97C08-G148690.1) | Vaccinium corymbosum: (VaccDscaff2-augustus-gene-199.26-mRNA-1) | Solanum lycopersicum: (RefSeq: NP__00123-3762.1) | Arabidopsis thaliana: (RefSeq: NP__177863.2) | Gossypium barbadense: (UniProt: A0A2P5VPW8) | Prunus avium: (RefSeq: XP__02180-6552.1) |
| Vaccinium corymbosum: (VaccDscaff2-augustus-gene-199.26-mRNA-1) | 63.511 | | | | | |
| Solanum lycopersicum: (RefSeq: NP__00123-3762.1) | 59.646 | 66.2 | | | | |
| Arabidopsis thaliana: (RefSeq: NP__177863.2) | 44.99 | 45.984 | 44.758 | | | |
| Gossypium barbadense: (UniProt: A0A2P5VPW8) | 67.647 | 64.729 | 63.4 | 47.581 | | |
| Prunus avium: (RefSeq: XP__02180-6552.1) | 68.102 | 64.95 | 64.44 | 47.515 | 67.061 | |
| Solanum tuberosum: (RefSeq: XP__00635-1136.1) | 59.961 | 65.531 | 93.347 | 44.89 | 63.783 | 64.032 |

TABLE 5

| Table of SEQ ID NOs. | | | |
|---|---|---|---|
| SEQ ID NO. | Sequence | Plant Type | Sequence Source (Accession) |
| 1 | REC8 protein | dicot | *Solanum tuberosum* (RefSeq: XP 006347252.1) |
| 2 | SPO11-1 protein | dicot | *Solanum tuberosum* (RefSeq: XP__006346146.1) |
| 3 | PAIR1 protein | dicot | *Solanum tuberosum* (RefSeq: XP__006339791.2) |
| 4 | OSD1 protein | dicot | *Solanum tuberosum* (RefSeq: XP 006351336.1) |
| 5 | CYCA1-1 protein | dicot | *Solanum tuberosum* (RefSeq: XP__006351136.1) |
| 6 | CYCA1-2 protein | dicot | *Solanum tuberosum* (RefSeq: XP__006351137.1) |
| 7 | CYCA1-3 protein | dicot | *Solanum tuberosum* (RefSeq: XP__006351138.1) |
| 8 | TDM1 protein | dicot | *Solanum tuberosum* (RefSeq: XP__006350746.1) |
| 9 | PS1 protein | dicot | *Solanum tuberosum* (RefSeq: XP__006351164.1) |
| 10 | PS1-LIKE PROTEIN | dicot | *Solanum tuberosum* (RefSeq: XP__006353632.1) |
| 11 | JASON protein | dicot | *Solanum tuberosum* (RefSeq: XP__006352001.1) |
| 12 | REC8 protein | dicot | *Solanum lycopersicum* (RefSeq: XP 025887480.1) |
| 13 | SPO11-1 protein | dicot | *Solanum lycopersicum* (RefSeq: XP__010324270.1) |
| 14 | PAIR1 protein | dicot | *Solanum lycopersicum* (RefSeq: XP__004231186.2) |
| 15 | OSD1 protein | dicot | *Solanum lycopersicum* (UniProt: A0A3Q7ILG3) |
| 16 | CYCLIN-A1 (CYCA1) protein | dicot | *Solanum lycopersicum* (RefSeq: NP__001233762.1) |

TABLE 5-continued

| Table of SEQ ID NOs. | | | |
|---|---|---|---|
| SEQ ID NO. | Sequence | Plant Type | Sequence Source (Accession) |
| 17 | PAIR1-targeting region of gRNA | dicot | *Solanum tuberosum* |
| 18 | PAIR1-targeting region of gRNA | dicot | *Solanum tuberosum* |
| 19 | SPO11-1-targeting region of gRNA | dicot | *Solanum tuberosum* |
| 20 | PAIR1-targeting region of gRNA | dicot | *Solanum tuberosum* |
| 21 | PAIR1-targeting region of gRNA | dicot | *Solanum tuberosum* |
| 22 | SPO11-1-targeting region of gRNA | dicot | *Solanum tuberosum* |
| 23 | PAIR1-targeting region of gRNA | dicot | *Solanum tuberosum* |
| 24 | SPO11-1-targeting region of gRNA | dicot | *Solanum tuberosum* |
| 25 | SPO11-1-targeting region of gRNA | dicot | *Solanum tuberosum* |
| 26 | SPO11-1-targeting region of gRNA | dicot | *Solanum tuberosum* |
| 27 | SPO11-1-targeting region of gRNA | dicot | *Solanum tuberosum* |
| 28 | SPO11-1-targeting region of gRNA | dicot | *Solanum tuberosum* |

TABLE 5-continued

| SEQ ID NO. | Sequence | Plant Type | Sequence Source (Accession) |
|---|---|---|---|
| Table of SEQ ID NOs. | | | |
| 29 | PAIR1-targeting region of gRNA | dicot | *Solanum tuberosum* |
| 30 | SPO11-1-targeting region of gRNA | dicot | *Solanum tuberosum* |
| 31 | SPO11-1-targeting region of gRNA | dicot | *Solanum tuberosum* |
| 32 | SPO11-1-targeting region of gRNA | dicot | *Solanum tuberosum* |
| 33 | REC8-targeting region of gRNA | dicot | *Solanum tuberosum* |
| 34 | REC8-targeting region of gRNA | dicot | *Solanum tuberosum* |
| 35 | REC8-targeting region of gRNA | dicot | *Solanum tuberosum* |
| 36 | REC8-targeting region of gRNA | dicot | *Solanum tuberosum* |
| 37 | PAIR1-targeting region of gRNA | dicot | *Solanum tuberosum* |
| 38 | REC8-targeting region of gRNA | dicot | *Solanum tuberosum* |
| 39 | PAIR1-targeting region of gRNA | dicot | *Solanum tuberosum* |
| 40 | SPO11-1-targeting region of gRNA | dicot | *Solanum tuberosum* |
| 41 | REC8-targeting region of gRNA | dicot | *Solanum tuberosum* |
| 42 | REC8-targeting region of gRNA | dicot | *Solanum tuberosum* |
| 43 | PAIR1-targeting region of gRNA | dicot | *Solanum tuberosum* |
| 44 | REC8-targeting region of gRNA | dicot | *Solanum tuberosum* |
| 45 | PAIR1-targeting region of gRNA | dicot | *Solanum tuberosum* |
| 46 | REC8-targeting region of gRNA | dicot | *Solanum tuberosum* |
| 47 | PAIR1-targeting region of gRNA | dicot | *Solanum tuberosum* |
| 48 | OSD1-targeting region of gRNA | dicot | *Solanum tuberosum* |
| 49 | REC8-targeting region of gRNA | dicot | *Solanum tuberosum* |
| 50 | OSD1-targeting region of gRNA | dicot | *Solanum tuberosum* |
| 51 | PAIR1-targeting region of gRNA | dicot | *Solanum tuberosum* |
| 52 | OSD1-targeting region of gRNA | dicot | *Solanum tuberosum* |
| 53 | OSD1-targeting region of gRNA | dicot | *Solanum tuberosum* |
| 54 | OSD1-targeting region of gRNA | dicot | *Solanum tuberosum* |
| 55 | PAIR1-targeting region of gRNA | dicot | *Solanum tuberosum* |
| 56 | OSD1-targeting region of gRNA | dicot | *Solanum tuberosum* |
| 57 | OSD1-targeting region of gRNA | dicot | *Solanum tuberosum* |
| 58 | SPO11-1-targeting region of gRNA | dicot | *Solanum tuberosum* |
| 59 | SPO11-1-targeting region of gRNA | dicot | *Solanum tuberosum* |
| 60 | SPO11-1-targeting region of gRNA | dicot | *Solanum tuberosum* |
| 61 | CYCA1-targeting region of gRNA | dicot | *Solanum tuberosum* |

TABLE 5-continued

| SEQ ID NO. | Sequence | Plant Type | Sequence Source (Accession) |
|---|---|---|---|
| Table of SEQ ID NOs. | | | |
| 62 | CYCA1-targeting region of gRNA | dicot | *Solanum tuberosum* |
| 63 | CYCA1-targeting region of gRNA | dicot | *Solanum tuberosum* |
| 64 | CYCA1-targeting region of gRNA | dicot | *Solanum tuberosum* |
| 65 | CYCA1-targeting region of gRNA | dicot | *Solanum tuberosum* |
| 66 | CYCA1-targeting region of gRNA | dicot | *Solanum tuberosum* |
| 67 | CYCA1-targeting region of gRNA | dicot | *Solanum tuberosum* |
| 68 | CYCA1-targeting region of gRNA | dicot | *Solanum tuberosum* |
| 69 | CYCA1-targeting region of gRNA | dicot | *Solanum tuberosum* |
| 70 | CYCA1-targeting region of gRNA | dicot | *Solanum tuberosum* |
| 71 | CYCA1-targeting region of gRNA | dicot | *Solanum tuberosum* |
| 72 | PAIR1 target sequence | dicot | *Solanum tuberosum* |
| 73 | PAIR1 target sequence | dicot | *Solanum tuberosum* |
| 74 | SPO11-1 target sequence | dicot | *Solanum tuberosum* |
| 75 | PAIR1 target sequence | dicot | *Solanum tuberosum* |
| 76 | PAIR1 target sequence | dicot | *Solanum tuberosum* |
| 77 | SPO11-1 target sequence | dicot | *Solanum tuberosum* |
| 78 | PAIR1 target sequence | dicot | *Solanum tuberosum* |
| 79 | SPO11-1 target sequence | dicot | *Solanum tuberosum* |
| 80 | SPO11-1 target sequence | dicot | *Solanum tuberosum* |
| 81 | SPO11-1 target sequence | dicot | *Solanum tuberosum* |
| 82 | SPO11-1 target sequence | dicot | *Solanum tuberosum* |
| 83 | SPO11-1 target sequence | dicot | *Solanum tuberosum* |
| 84 | PAIR1 target sequence | dicot | *Solanum tuberosum* |
| 85 | SPO11-1 target sequence | dicot | *Solanum tuberosum* |
| 86 | SPO11-1 target sequence | dicot | *Solanum tuberosum* |
| 87 | SPO11-1 target sequence | dicot | *Solanum tuberosum* |
| 88 | REC8 target sequence | dicot | *Solanum tuberosum* |
| 89 | REC8 target sequence | dicot | *Solanum tuberosum* |
| 90 | REC8 target sequence | dicot | *Solanum tuberosum* |
| 91 | REC8 target sequence | dicot | *Solanum tuberosum* |
| 92 | PAIR1 target sequence | dicot | *Solanum tuberosum* |
| 93 | REC8 target sequence | dicot | *Solanum tuberosum* |

TABLE 5-continued

Table of SEQ ID NOs.

| SEQ ID NO. | Sequence | Plant Type | Sequence Source (Accession) |
|---|---|---|---|
| 94 | PAIR1 target sequence | dicot | *Solanum tuberosum* |
| 95 | SPO11-1 target sequence | dicot | *Solanum tuberosum* |
| 96 | REC8 target sequence | dicot | *Solanum tuberosum* |
| 97 | REC8 target sequence | dicot | *Solanum tuberosum* |
| 98 | PAIR1 target sequence | dicot | *Solanum tuberosum* |
| 99 | REC8 target sequence | dicot | *Solanum tuberosum* |
| 100 | PAIR1 target sequence | dicot | *Solanum tuberosum* |
| 101 | REC8 target sequence | dicot | *Solanum tuberosum* |
| 102 | PAIR1 target sequence | dicot | *Solanum tuberosum* |
| 103 | OSD1 target sequence | dicot | *Solanum tuberosum* |
| 104 | REC8 target sequence | dicot | *Solanum tuberosum* |
| 105 | OSD1 target sequence | dicot | *Solanum tuberosum* |
| 106 | PAIR1 target sequence | dicot | *Solanum tuberosum* |
| 107 | OSD1 target sequence | dicot | *Solanum tuberosum* |
| 108 | OSD1 target sequence | dicot | *Solanum tuberosum* |
| 109 | OSD1 target sequence | dicot | *Solanum tuberosum* |
| 110 | PAIR1 target sequence | dicot | *Solanum tuberosum* |
| 111 | OSD1 target sequence | dicot | *Solanum tuberosum* |
| 112 | OSD1 target sequence | dicot | *Solanum tuberosum* |
| 113 | SPO11-1 target sequence | dicot | *Solanum tuberosum* |
| 114 | SPO11-1 target sequence | dicot | *Solanum tuberosum* |
| 115 | SPO11-1 target sequence | dicot | *Solanum tuberosum* |
| 116 | CYCA1 target sequence | dicot | *Solanum tuberosum* |
| 117 | CYCA1 target sequence | dicot | *Solanum tuberosum* |
| 118 | CYCA1 target sequence | dicot | *Solanum tuberosum* |
| 119 | CYCA1 target sequence | dicot | *Solanum tuberosum* |
| 120 | CYCA1 target sequence | dicot | *Solanum tuberosum* |
| 121 | CYCA1 target sequence | dicot | *Solanum tuberosum* |
| 122 | CYCA1 target sequence | dicot | *Solanum tuberosum* |
| 123 | CYCA1 target sequence | dicot | *Solanum tuberosum* |
| 124 | CYCA1 target sequence | dicot | *Solanum tuberosum* |
| 125 | CYCA1 target sequence | dicot | *Solanum tuberosum* |
| 126 | CYCA1 target sequence | dicot | *Solanum tuberosum* |
| 127 | spo11 allele | dicot | *Solanum tuberosum* PED-PR-AB-sp |
| 128 | spo11:rec8 allele (trans-location) | dicot | *Solanum tuberosum* PED-PR-AB-sp |
| 129 | rec8:spo11 allele (trans-location) | dicot | *Solanum tuberosum* PED-PR-AB-sp |
| 131 | rec8 allele | dicot | *Solanum tuberosum* PED-PR-EF-rso-1 |
| 132 | rec8 allele | dicot | *Solanum tuberosum* PED-PR-EF-rso-1 |
| 133 | spo11 allele | dicot | *Solanum tuberosum* PED-PR-EF-rso-1 |
| 134 | spo11 allele | dicot | *Solanum tuberosum* PED-PR-EF-rso-1 |
| 137 | rec8 allele | dicot | *Solanum tuberosum* PED-PR-AB-rso |
| 138 | rec8 allele | dicot | *Solanum tuberosum* PED-PR-AB-rso |
| 139 | spo11 allele | dicot | *Solanum tuberosum* PED-PR-AB-rso |
| 140 | spo11 allele | dicot | *Solanum tuberosum* PED-PR-AB-rso |
| 141 | spo11 allele | dicot | *Solanum tuberosum* PED-PR-AD-sp |
| 142 | spo11 allele | dicot | *Solanum tuberosum* PED-PR-AD-sp |
| 143 | tam (cyca1) allele | dicot | *Solanum tuberosum* PED-PR-EF-rcs |
| 144 | tam (cyca1) allele | dicot | *Solanum tuberosum* PED-PR-EF-rcs |
| 145 | rec8 allele | dicot | *Solanum tuberosum* PED-PR-EF-rcs |
| 146 | rec allele | dicot | *Solanum tuberosum* PED-PR-EF-rcs |
| 147 | spo11 allele | dicot | *Solanum tuberosum* PED-PR-EF-rcs |
| 148 | spo11 allele | dicot | *Solanum tuberosum* PED-PR-EF-rcs |
| 149 | tam (cyca1) allele | dicot | *Solanum tuberosum* PED-PR-AB-rcs |
| 150 | tam (cyca1) allele | dicot | *Solanum tuberosum*m PED-PR-AB-rcs |
| 151 | rec8 allele | dicot | *Solanum tuberosum* PED-PR-AB-rcs |
| 152 | rec8 allele | dicot | *Solanum tuberosum* PED-PR-AB-rcs |
| 153 | spo11 allele | dicot | *Solanum tuberosum* PED-PR-AB-res |
| 154 | spo11 allele | dicot | *Solanum tuberosum* PED-PR-AB-rcs |
| 156 | rec8 allele | dicot | *Solanum tuberosum* PED-PR-EF-rso-2 |
| 157 | rec8 allele | dicot | *Solanum tuberosum* PED-PR-EF-rso-2 |
| 158 | spo11 allele | dicot | *Solanum tuberosum* PED-PR-EF-rso-2 |
| 159 | spo11 allele | dicot | *Solanum tuberosum* PED-PR-EF-rso-2 |

TABLE 6

Exemplary combinations of in MiMe alleles of parent MiMe plants having a complete MiMe genotype.

| Genotype | Complete MiMe Genotype |
|---|---|
| 1 | rec8, spo11-1, cyca1 |
| 2 | rec8, pair1, cyca1 |
| 3 | rec8, pair1, spo11-1, cyca1 |
| 4 | rec8, spo11-1, TDM1* |
| 5 | rec8, pair1, TDM1* |
| 6 | rec8, pair1, spo11-1, TDM]* |
| 7 | rec8, spo11-1, TDM1*, cyca1 |
| 8 | rec8, pair1, TDM1*, cyca1 |
| 9 | rec8, pair1, spo11-1, TDM1*, cyca1 |
| 10 | spo11-1, ps1 |
| 10 | spo11-1, ps1, ps1-like |
| 11 | spo11-1, ps1-like |

TABLE 6-continued

| Exemplary combinations of in MiMe alleles of parent MiMe plants having a complete MiMe genotype. | |
|---|---|
| Genotype | Complete MiMe Genotype |
| 12 | spo11-1, ps1-like, jason |
| 13 | spo11-1, jason |
| 14 | spo11-1, ps1, ps1-like, jason |
| 15 | pair1, ps1 |
| 16 | pair1, spo11-1, ps1 |
| 17 | spo11-1, ps1, ps1-like |
| 18 | pair1, spo11-1, ps1, ps1-like |
| 19 | pair1, ps1-like |
| 20 | pair1, spo11-1, ps1-like |
| 21 | pair1, ps1-like, jason |
| 22 | pair1, spo11-1, ps1-like, jason |
| 23 | pair1, jason |
| 24 | pair1, spo11-1, jason |
| 25 | pair1, ps1, ps1-like, jason |
| 26 | pair1, spo11-1, ps1, ps1-like, jason |
| 27 | rec8, spo11-1, osd1 |
| 28 | rec8, pair1, osd1 |
| 29 | rec8, pair1, spo11-1, osd1 |
| 30 | rec8, spo11-1, os |
| 31 | rec8, pair1, os |
| 32 | rec8, pair1, spo11-1, os |
| 33 | spo11-1, ps |
| 34 | spo11-1, ps, ps1 |
| 35 | spo11-1, ps, ps1, ps1-like |
| 36 | spo11-1, ps, ps1-like |
| 37 | spo11-1, ps, jason |
| 38 | spo11-1, ps, ps1, jason |
| 39 | spo11-1, ps, ps1-like, jason |
| 40 | spo11-1, ps, ps1, ps1-like, jason |
| 41 | pair1, ps |
| 42 | pair1, ps, ps1 |
| 43 | pair1, ps, ps1, ps1-like |
| 44 | pair1, ps, ps1-like |
| 45 | pair1, ps, jason |
| 46 | pair1, ps, ps1, jason |
| 47 | pair1, ps, ps1-like, jason |
| 48 | pair1, ps, ps1, ps1-like, jason |
| 49 | pair1, spo11-1, ps |
| 50 | pair1, spo11-1, ps, ps1 |
| 51 | pair1, spo11-1, ps, ps1, ps1-like |
| 52 | pair1, spo11-1, ps, ps1-like |
| 53 | pair1, spo11-1, ps, jason |
| 54 | pair1, spo11-1, ps, ps1, jason |
| 55 | pair1, spo11-1, ps, ps1-like, jason |
| 56 | pair1, spo11-1, ps, ps1, ps1-like, jason |

*Dominant mutation

ENUMERATED EMBODIMENTS

The following enumerated embodiments are representative of some aspects of the invention.

1. A population of polyploid potato seed comprising a subpopulation of genetically uniform polyploid potato seed in an amount of at least 50% of the total number of seeds, the genetically uniform polyploid potato seed comprising three or more haplotypes of the same or related species of potato, wherein the population was obtained from a single potato plant or a set of F1 hybrids.
2. The population of embodiment 1, wherein the subpopulation of genetically uniform polyploid potato seed is triploid, tetraploid, pentaploid, hexaploid, heptaploid, or octoploid.
3. The population of embodiment 1 or 2, wherein the population of polyploid potato seed has an average pairwise genetic uniformity of at least 80%, at least 85%, at least 90%, at least 95%, at least 96%, at least 97%, at least 98%, at least 99%, or 100% as measured by the Jaccard similarity coefficient.
4. The population of any one of embodiments 1-3, wherein the population of polyploid potato seed comprises the subpopulation of genetically uniform polyploid potato seed in an amount of at least 70%, at least 90%, at least 95%, at least 96%, at least 97%, at least 98%, or at least 99% of the total number of seeds.
5. The population of embodiment 1-4, wherein each pair of seeds in the subpopulation of genetically uniform polyploid potato seed has a pairwise identity of at least 95%, at least 96%, at least 97%, at least 98%, at least 99%, or 100% as measured by the Jaccard similarity coefficient.
6. The population of any one of embodiments 1-5, wherein the subpopulation of genetically uniform polyploid potato seed has a complete MiMe genotype comprising:
   (A)
   MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or
   (B)
   MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components.
7. The population of any one of embodiments 1-5, wherein the subpopulation of genetically uniform polyploid potato seed has a partial MiMe genotype comprising:
   (A)
   (a) one or more MiMe alleles conferring decreased expression of one or more MiMe loci of each of a first, second, and third MiMe component; and
   (b) one or more non-MiMe alleles at the one or more MiMe loci of each of the first, second, and third MiMe component,
   wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or
   (B)
   (a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

8. The population of any one of embodiments 1-5, wherein the subpopulation of genetically uniform polyploid potato seed has a partially-complemented MiMe genotype comprising:

(A)

(a) only MiMe alleles at one or more MiMe loci of a first MiMe component;

(b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;

(B)

(a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; or (C)

(a) only MiMe alleles at one or more MiMe loci of a first MiMe component, wherein the first MiMe component is a component of DNA double strand breakage during meiotic recombination;

(b) one or more MiMe alleles and one or more non-MiMe alleles at one or more MiMe loci of a second MiMe component;

(c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

9. The population of any one of embodiments 6-8f, wherein:

(1) the one or more MiMe loci of the component of sister chromatid cohesion during the first division of meiosis comprise REC8, SWITCH1/DYAD, or a combination thereof;

(2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;

(3) the one or more MiMe loci of the component of progression through the second division of meiosis comprise OSD1, CYCA1, TDM1, PC1, PC2, FC, or any combination thereof; and/or (4) the one or more MiMe loci of the component of progression through the first division of meiosis comprise PS1, JASON, or a combination thereof.

10. The population of any one of embodiments 1-9, wherein the subpopulation of genetically uniform polyploid potato seed comprises:

(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a complete MiMe genotype comprising (i) an os allele, wherein the subpopulation of genetically uniforms seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(14) a partial MiMe genotype comprising (i) an os allele, wherein the subpopulation of genetically uniforms seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(15) a complete MiMe genotype comprising (i) a ps allele, wherein the subpopulation of genetically uniforms seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1;

(16) a partial MiMe genotype comprising (i) a ps allele, wherein the subpopulation of genetically uniforms seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(17) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(18) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(19) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(20) a partially complemented MiMe genotype comprising (i) a ps allele, wherein the subpopulation of genetically uniforms seed is heterozygous for the ps allele, (ii) an os allele, wherein the subpopulation of genetically uniforms seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1; or

(21) a partially complemented MiMe genotype comprising (i) an os allele, wherein the subpopulation of genetically uniforms seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

11. The population of any one of embodiments 1-9, wherein the subpopulation of genetically uniform polyploid potato seed comprises one or more polynucleotide sequences selected from the group consisting of SEQ ID NOs: 127-129, 131-134, 137-154, and 156-159.

12. The population of any one of embodiments 1-11, wherein germination of a seed of the subpopulation of genetically uniform polyploid potato seed results in a sterile plant that produces inviable gametes.

13. The population of any one of embodiments 1-12, wherein the population of polyploid potato seed comprises three or more haplotypes from *Solanum tuberosum.*

14. A method of producing the population of polyploid potato seed of any one of embodiments 1-13, the method comprising:

(a) generating a first parent MiMe potato plant and a second parent MiMe potato plant by introducing genetic modifications into one or more candidate potato lines to produce MiMe alleles in germplasm of a first parent MiMe potato plant, a second parent MiMe potato plant, and/or progenitors thereof, wherein the first parent MiMe potato plant and the second parent MiMe potato plant each comprise a complete MiMe genotype, and each of the progenitors comprises a partial MiMe genotype, wherein if progenitors are generated, the progenitors are further crossed to generate the first parent MiMe potato plant, the second parent MiMe potato plant, or both;

(b) providing clonal gametes from the first parent MiMe potato plant and the second parent MiMe potato plant that together comprise the three or more haplotypes; and (c) crossing the clonal gametes to produce the population of polyploid potato seed;

wherein the population of polyploid potato seed comprises a subpopulation of genetically uniform polyploid potato seed in an amount of at least 50% of the total number of seeds, the subpopulation of genetically uniform polyploid potato seed comprising the three or more haplotypes.

15. The method of embodiment 14, wherein the subpopulation of genetically uniform polyploid potato seed has a partially-complemented MiMe genotype, wherein:

(A)

(a) the first parent MiMe potato plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and (b) the second parent MiMe potato plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;

wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein either (i) at least one of the MiMe loci having only MiMe alleles of the third MiMe component of the first parent MiMe potato plant is the same as at least one of the MiMe loci having only MiMe alleles of the third MiMe component of the second parent MiMe potato plant, or (ii) the one or more MiMe loci having only MiMe alleles of the third MiMe component of the first parent MiMe potato plant are distinct from the one or more MiMe loci having only MiMe alleles of the third MiMe component of the second parent MiMe potato plant;

wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

(B)

(a) the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; and (b) the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component;

wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and (C)

(a) the first parent MiMe potato plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;

(b) the second parent MiMe potato plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

16. A method of producing the population of polyploid potato seed of any one of embodiments 1-13, the method comprising:

(a) generating a first parent MiMe potato plant by introducing genetic modifications into one or more candidate potato lines to produce MiMe alleles in germplasm of the first parent MiMe potato plant or progenitors thereof, wherein the first parent MiMe potato plant comprises a complete MiMe genotype, and each of the progenitors comprises a partial MiMe genotype, wherein if progenitors are generated, the progenitors are further crossed to generate the first parent MiMe potato plant;

(b) providing clonal gametes from the first parent MiMe potato plant;

(c) providing haploid gametes from a homozygous parent non-MiMe potato plant; and (d) crossing the clonal gametes with the haploid gametes to produce the population of polyploid potato seed, wherein the clonal gametes and the haploid gametes together comprise three or more haplotypes, optionally wherein step (a) comprises generating the first parent MiMe potato plant, the second parent MiMe potato plant, or both.

17. A method of breeding a polyploid hybrid potato line, the method comprising:

(a) obtaining a set of potato lines;

(b) breeding the potato lines using traditional plant breeding methods to produce a set of candidate potato lines;

(c) selecting two or more candidate potato lines together comprising three or more haplotypes;

(d) generating a first parent MiMe potato plant and a second parent MiMe potato plant from the two or more candidate potato lines that together comprise the three or more haplotypes;

(e) providing clonal gametes from each of the first and second parent MiMe potato plants;

(f) crossing the clonal gametes to produce a hybrid polyploid seed comprising the three or more haplotypes;

(g) growing the hybrid polyploid seed to produce a hybrid polyploid potato plant comprising three or more haplotypes; and (h) evaluating one or more characteristics of the hybrid polyploid potato plant;

the method optionally further comprising (i) repeating steps (b)-(h) or steps (c)-(h) using the one or more characteristics of the hybrid polyploid potato plant evaluated in step (h) to guide the breeding of potato lines of step (b), the selecting of candidate potato lines of step (c), or both.

18. The method of embodiment 17, wherein:

(A)

(a) the first parent MiMe potato plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and (b) the second parent MiMe potato plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;

wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein either (i) at least one of the MiMe loci having only MiMe alleles of the third MiMe component of the first parent MiMe potato plant is the same as at least one of the MiMe loci having only MiMe alleles of the third MiMe component of the second parent MiMe potato plant, or (ii) the one or more MiMe loci having only MiMe alleles of the third MiMe component of the first parent MiMe potato plant are distinct from the one or more MiMe loci having only MiMe alleles of the third MiMe component of the second parent MiMe potato plant;

wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

(B)

(a) the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; and (b) the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component;

wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and (C)

(a) the first parent MiMe potato plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;

(b) the second parent MiMe potato plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

19. A method of breeding a polyploid hybrid potato line, the method comprising:

(a) obtaining a set of potato lines;

(b) breeding the potato lines using traditional plant breeding methods to produce a set of candidate potato lines;

(c) selecting two or more candidate potato lines together comprising three or more haplotypes;

(d) generating a first parent MiMe potato plant from one of the two or more candidate potato lines;

(e) providing clonal gametes from the first parent MiMe potato plant;

(f) providing haploid gametes from a homozygous parent non-MiMe potato plant of one of the two or more candidate potato lines;

(g) crossing the clonal gametes with the haploid gametes to produce a hybrid polyploid seed;

(h) growing the hybrid polyploid seed to produce a hybrid polyploid potato plant; and (i) evaluating one or more characteristics of the hybrid polyploid potato plant, wherein the first parent MiMe potato plant and the homozygous parent non-MiMe potato plant together comprise three or more haplotypes, wherein the crossing of step (g) results in the hybrid polyploid seed comprising three or more haplotypes, and wherein the growing of step (h) results in the hybrid polyploid potato plant comprising three or more haplotypes;

the method optionally further comprising (j) repeating steps (b)-(i) or steps (c)-(i) using the one or more characteristics of the hybrid polyploid potato plant evaluated in step (i) to guide the breeding of potato lines of step (b), the selecting of candidate potato lines of step (c), or both.

20. The method of any one of embodiments 14-19, wherein the first parent MiMe potato plant, the second parent MiMe potato plant, the parent non-MiMe potato plant, or any combination thereof are diploid, triploid, or tetraploid and the hybrid polyploid potato plant is tetraploid, pentaploid, hexaploid, heptaploid, or octoploid.

21. The method of any one of embodiments 14-20, wherein generating the first parent MiMe potato plant, the second parent MiMe potato plant, or both comprises:

(1) introducing a complete MiMe genotype directly into two candidate potato lines to produce the first parent MiMe potato plant, the second parent MiMe potato plant, or both;

(2) introducing a partial MiMe genotype into two candidate potato lines to produce two grandparent non-MiMe potato plants each having a partial MiMe genotype and crossing the grandparent non-MiMe potato plants each having a partial MiMe genotype to produce the first parent MiMe potato plant, optionally wherein generating the first parent MiMe potato plant, the second parent MiMe potato plant, or both further comprises introducing a complete MiMe genotype directly into a third candidate potato line to produce the second parent MiMe potato plant; or (3) introducing a partial MiMe genotype into four candidate potato lines to produce four grandparent non-MiMe potato plants each having a partial MiMe genotype, and crossing pairs of said grandparent non-MiMe potato plants each having a partial MiMe genotype to produce the first and second parent MiMe potato plants, optionally wherein generating the first parent MiMe potato plant, the second parent MiMe potato plant, or both further comprises propagating the first parent MiMe potato plant, the second parent MiMe potato plant, the grandparent non-MiMe potato plants, or any combination thereof to scale production of homogenous seed.

22. The method of any one of embodiments 14-21, wherein the first parent MiMe potato plant, the second parent MiMe potato plant, the hybrid polyploid potato plant, or any combination thereof has a complete MiMe genotype comprising:

(A)

MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or (B)

MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components.

23. The method of any one of embodiments 17-22, wherein each grandparent non-MiMe potato plant, the hybrid polyploid potato plant, or a combination thereof has a partial MiMe genotype comprising:

(A)

(a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or (B)

(a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

24. The method of embodiment 18, 22, or 23, wherein:

(1) the one or more MiMe loci of the component of sister chromatid cohesion during the first division of meiosis comprise REC8, SWITCH1/DYAD, or a combination thereof;

(2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;

(3) the one or more MiMe loci of the component of progression through the second division of meiosis comprise OSD1, CYCA1, TDM1, PC1, PC2, FC, or any combination thereof; and/or (4) the one or more MiMe loci of the component of progression through the first division of meiosis comprise PS1, JASON, or a combination thereof.

25. The method of any one of embodiments 17-24, wherein the hybrid polyploid potato plant comprises:

(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a complete MiMe genotype comprising (i) an os allele, wherein the subpopulation of genetically uniforms seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(14) a partial MiMe genotype comprising (i) an os allele, wherein the subpopulation of genetically uniforms seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(15) a complete MiMe genotype comprising (i) a ps allele, wherein the subpopulation of genetically uniforms seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1;

(16) a partial MiMe genotype comprising (i) a ps allele, wherein the subpopulation of genetically uniforms seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(17) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(18) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(19) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(20) a partially complemented MiMe genotype comprising (i) a ps allele, wherein the subpopulation of genetically uniforms seed is heterozygous for the ps allele, (ii) an os allele, wherein the subpopulation of genetically uniforms seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1; or

(21) a partially complemented MiMe genotype comprising (i) an os allele, wherein the subpopulation of genetically uniforms seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

26. The method of any one of embodiments 17-25, wherein one or more of the candidate potato lines of step (c) are inbred potato lines, hybrid potato lines, or a combination thereof.

27. The method of any one of embodiments 21-26, wherein the complete MiMe genotype, the partial MiMe genotype, or both are introduced by gene editing, transgenesis, or a combination thereof.

28. The method of embodiment 22-27, wherein the decreased expression of one or more of the MiMe loci is each independently achieved by gene disruption, gene knockout, gene knockdown, gene silencing, RNA interference, or induction of methylation.

29. The method of embodiment 22-28, wherein the decreased expression of one or more of the MiMe loci is each independently achieved by introducing into each candidate potato line or a progenitor thereof an insertion, a deletion, one or more nucleotide changes, or an inversion that results in decreased expression of the MiMe locus, optionally including a step of selection for decreased expression of the MiMe locus.

30. The method of embodiment 29, wherein the insertion, the deletion, the one or more nucleotide changes, or the inversion eliminates expression of the MiMe locus, optionally wherein the expression of the MiMe locus is eliminated by a premature stop codon present in the 70%, the first 60%, the first 50%, the first 40%, the first 30%, the first 20%, or the first 10% of the nucleotides of the coding sequence of the MiMe locus following the start codon in the 3' direction.

31. A method of producing a population of polyploid potato seed comprising:
    (a) providing clonal gametes from a pair of parent MiMe potato plants together comprising three or more haplotypes that were selected using the method of breeding of any one of embodiments 17, 18, and 20-30 based upon the polyploid potato plant comprising the three or more haplotypes having one or more desired characteristics; and
    (b) crossing the clonal gametes to produce the population of polyploid potato seed;
    wherein the population of polyploid potato seed comprises a subpopulation of genetically uniform polyploid potato seed in an amount of at least 50% of the total number of seeds, the subpopulation of genetically uniform polyploid potato seed comprising the three or more haplotypes.

32. A method of producing a population of polyploid potato seed comprising:
    (a) selecting three or more haplotypes using the method of breeding of any one of embodiments 19-30 based upon the polyploid potato plant comprising said three or more haplotypes having one or more desired characteristics;
    (b) providing clonal gametes from a parent MiMe potato plant;
    (c) providing haploid gametes from a homozygous parent non-MiMe potato plant;
    (d) crossing the clonal gametes with the haploid gametes to produce the population of polyploid potato seed;
    wherein the parent MiMe potato plant and the homozygous parent non-MiMe potato plant together comprise the three or more haplotypes selected in step (a), wherein the crossing of step (d) results in a population of polyploid potato seed comprising a subpopulation of genetically uniform polyploid potato seed in an amount of at least 50% of the total number of seeds, the subpopulation of genetically uniform polyploid potato seed comprising the three or more haplotypes.

33. The method of embodiment 31 or 32, wherein the population of polyploid potato seed has an average pairwise genetic uniformity of at least 80%, at least 85%, at least 90%, at least 95%, at least 96%, at least 97%, at least 98%, at least 99%, or 100% as measured by the Jaccard similarity coefficient.

34. The method of any one of embodiments 31-33, wherein the population of polyploid potato seed comprises the subpopulation of genetically uniform polyploid potato seed in an amount of at least 70%, at least 90%, at least 95%, at least 96%, at least 97%, at least 98%, or at least 99% of the total number of seeds.

35. The method of any one of embodiments 31-34, wherein each pair of seeds in the subpopulation of genetically uniform polyploid potato seed has a pairwise identity of at least 95%, at least 96%, at least 97%, at least 98%, at least 99%, or 100% as measured by the Jaccard similarity coefficient.

36. A genetically modified potato plant, plant part, or plant cell comprising:
    (A) three or more haplotypes; and
    (B)
      (i) a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;
      ii) a partial MiMe genotype comprising:
        (a) one or more MiMe alleles conferring decreased expression of one or more MiMe loci of each of a first, second, and third MiMe component; and
        (b) one or more non-MiMe alleles at the one or more MiMe loci of each of the first, second, and third MiMe component,
        wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;
      iii) a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components;
      iv) a partial MiMe genotype comprising:
        (a) one or more MiMe alleles conferring decreased expression of one or more MiMe loci of each of the first and second MiMe component; and
        (b) one or more non-MiMe alleles at the one or more MiMe loci of each of the first and second MiMe component,
        wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components;

v) a partially complemented MiMe genotype comprising:

(a) only MiMe alleles at one or more MiMe loci of a first MiMe component;

(b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;

vi) a partially complemented MiMe genotype comprising:

(a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; or vii) a partially complemented MiMe genotype comprising:

(a) only MiMe alleles at one or more MiMe loci of a first MiMe component, wherein the first MiMe component is a component of DNA double strand breakage during meiotic recombination;

(b) one or more MiMe alleles and one or more non-MiMe alleles at one or more MiMe loci of a second MiMe component;

(c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

37. The genetically modified potato plant, plant part, or plant cell of embodiment 36, wherein:

(1) the one or more MiMe loci of the component of sister chromatid cohesion during the first division of meiosis comprise REC8, SWITCH1/DYAD, or a combination thereof;

(2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;

(3) the one or more MiMe loci of the component of progression through the second division of meiosis comprise OSD1, CYCA1, TDM1, PC1, PC2, FC, or any combination thereof; and/or (4) the one or more MiMe loci of the component of progression through the first division of meiosis comprise PS1, JASON, or a combination thereof.

38. The genetically modified potato plant, plant part, or plant cell of embodiment 36 or 37, comprising:

(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a complete MiMe genotype comprising (i) an os allele, wherein the subpopulation of genetically uniforms seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(14) a partial MiMe genotype comprising (i) an os allele, wherein the subpopulation of genetically uniforms seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(15) a complete MiMe genotype comprising (i) a ps allele, wherein the subpopulation of genetically uniforms seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1;

(16) a partial MiMe genotype comprising (i) a ps allele, wherein the subpopulation of genetically uniforms seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(17) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(18) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(19) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(20) a partially complemented MiMe genotype comprising (i) a ps allele, wherein the subpopulation of genetically uniforms seed is heterozygous for the ps allele, (ii) an os allele, wherein the subpopulation of genetically uniforms seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1; or

(21) a partially complemented MiMe genotype comprising (i) an os allele, wherein the subpopulation of genetically uniforms seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

39. The genetically modified potato plant, plant part, or plant cell of any one of embodiments 36-38, comprising one or more polynucleotide sequences selected from the group consisting of SEQ ID NOs: 127-129, 131-134, 137-154, and 156-159.

40. The genetically modified potato plant, plant part, or plant cell of any one of embodiments 36-39, wherein:
(i) the genetically modified potato plant part is a non-regenerable plant part; or
(ii) the genetically modified potato plant cell is a non-regenerable plant cell.

41. The genetically modified potato plant, plant part, or plant cell of any one of embodiments 36-40, wherein the plant part is a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, an anther, or a portion thereof.

42. A processed potato product derived from the genetically modified potato plant, plant part, or plant cell of any one of embodiments 36-41 wherein the processed potato product comprises a detectable amount of the one or more MiMe alleles of the genetically modified potato plant, plant part, or plant cell.

43. The processed potato product of embodiment 42, wherein the processed potato product:
(i) is selected from the group consisting of plant biomass, oil, meal, food starch, syrup, animal feed, flour, flakes, bran, lint, hulls, and processed seed; and/or
(ii) is non-regenerable.

44. Germplasm of the population of polyploid potato seeds of any one of embodiments 1-13.

45. A population of polyploid potato seed comprising a subpopulation of genetically uniform polyploid potato seed in an amount of at least 50% of the total number of seeds, the genetically uniform polyploid potato seed comprising three or more haplotypes of the same or related species of potato, wherein the population was obtained from a single potato plant or a set of F1 hybrids, wherein the subpopulation of genetically uniform polyploid potato seed comprise (A) (1) a germplasm genetic modification means for inhibiting sister chromatid cohesion during the first division of meiosis, (2) a germplasm genetic modification means for inhibiting DNA double strand breakage during meiotic recombination, and (3) a germplasm genetic modification means for inhibiting progression through the second division of meiosis; or (B) (2) a germplasm genetic modification means for preventing DNA double strand breakage during meiotic recombination, and (4) a germplasm genetic modification means for preventing progression through the first division of meiosis;
wherein each of the germplasm genetic modifications are (i) a complete set that achieves the inhibition, (ii) a partial set that does not achieve inhibition, or (iii) partially complemented at one or more of the genetic modification means and achieve sterility.

46. The population of embodiment 45, wherein the subpopulation of genetically uniform polyploid potato seed is triploid, tetraploid, pentaploid, hexaploid, heptaploid, or octoploid.

47. The population of embodiment 45 or 46, wherein the population of polyploid potato seed has an average pairwise genetic uniformity of at least 80%, at least 85%, at least 90%, at least 95%, at least 96%, at least 97%, at least 98%, at least 99%, or 100% as measured by the Jaccard similarity coefficient.

48. The population of any one of embodiments 45-47, wherein the population of polyploid potato seed comprises the subpopulation of genetically uniform polyploid potato seed in an amount of at least 70%, at least 90%, at least 95%, at least 96%, at least 97%, at least 98%, or at least 99% of the total number of seeds.

49. The population of embodiment 45-48, wherein each pair of seeds in the subpopulation of genetically uniform polyploid potato seed has a pairwise identity of at least 95%, at least 96%, at least 97%, at least 98%, at least 99%, or 100% as measured by the Jaccard similarity coefficient.

50. The population of any one of embodiments 45-49, wherein the subpopulation of genetically uniform polyploid potato seed has a complete MiMe genotype comprising the complete set of germplasm genetic modification means as follows:
(A)
(1) the germplasm genetic modification means for inhibiting sister chromatid cohesion during the first division of meiosis comprise only MiMe alleles at one or more MiMe loci of a component of sister chromatid cohesion during the first division of meiosis, (2) the germplasm genetic modification means for inhibiting DNA double strand breakage during meiotic recombination comprise only MiMe alleles at one or more MiMe loci of a component of DNA double strand breakage during meiotic recombination, and (3) the germplasm genetic modification means for inhibiting progression through the second division of meiosis comprise only MiMe alleles at one or more Mime loci of progression through the second division of meiosis; or
(B)
(2) the germplasm genetic modification means for inhibiting DNA double strand breakage during meiotic recombination comprise only MiMe alleles at one or more MiMe loci of a component of DNA double strand breakage during meiotic recombination, and (4) the germplasm genetic modification means for inhibiting progression through the first division of meiosis comprise only MiMe alleles at one or more MiMe loci of a component of progression through the first division of meiosis.

51. The population of any one of embodiments 45-49, wherein the subpopulation of genetically uniform polyploid potato seed has a partial MiMe genotype comprising the partial set of germplasm genetic modification means as follows:
(A)
(1) the germplasm genetic modification means for inhibiting sister chromatid cohesion during the first division of meiosis comprise at least one MiMe allele and at least one non-MiMe allele at one or more MiMe loci for a component of sister chromatid cohesion during the first division of meiosis comprise, (2) the germplasm genetic modification means for inhibiting DNA double strand breakage during meiotic recombination comprise at least one MiMe allele and at least one non-MiMe allele at one or more MiMe loci for a component of DNA double strand breakage during meiotic recombination, and (3) the germplasm genetic modification means for inhibiting progression through the second division of meiosis comprise at least one MiMe allele and at least one non-MiMe allele at one or more MiMe loci for a component of progression through the second division of meiosis; or (B)

(2) the germplasm genetic modification means for inhibiting DNA double strand breakage during meiotic recombination comprise at least one MiMe allele and at least one non-MiMe allele at one or more MiMe loci for a component of DNA double strand breakage during meiotic recombination, and (4) the germplasm genetic modification means for inhibiting progression through the first division of meiosis comprise at least one MiMe allele and at least one non-MiMe allele at one or more MiMe loci for a component of progression through the first division of meiosis.

52. The population of any one of embodiments 45-49, wherein the subpopulation of genetically uniform polyploid potato seed has a partially-complemented MiMe genotype comprising the partially complemented set of germplasm genetic modification means as follows:

(A)

(1) the germplasm genetic modification means for inhibiting sister chromatid cohesion during the first division of meiosis comprises at least one MiMe allele at at least a first MiMe locus of a component of sister chromatid cohesion during the first division of meiosis, (2) the germplasm genetic modification means for inhibiting DNA double strand breakage during meiotic recombination comprises at least one MiMe allele at at least a first MiMe locus of a component of DNA double strand breakage during meiotic recombination, and (3) the germplasm genetic modification means for inhibiting progression through the second division of meiosis comprises at least one MiMe allele at at least a first MiMe locus of a component of progression through the second division of meiosis, wherein at least one of (1), (2), and (3) comprise one or more MiMe alleles and one or more non-MiMe alleles at the first MiMe locus of the component, and one or more MiMe alleles and one or more non-MiMe alleles at a second MiMe locus of the component, and wherein one or both of the others of (1), (2), and (3) comprise only MiMe alleles at at least the first MiMe locus of the component; or (B)

(2) the germplasm genetic modification means for inhibiting DNA double strand breakage during meiotic recombination comprises at least one MiMe allele at at least a first MiMe locus of a component of DNA double strand breakage during meiotic recombination, and (4) the germplasm genetic modification means for preventing progression through the first division of meiosis comprises at least one MiMe allele at at least a first MiMe locus of a component of progression through the first division of meiosis, wherein one of (2) and (4) comprises one or more MiMe alleles and one or more non-MiMe alleles at the first MiMe locus of the component, and one or more MiMe alleles and one or more non-MiMe alleles at a second MiMe locus of the component, and the other of (2) and (4) comprises only MiMe alleles at at least the first MiMe locus of the component; or (C)

(2) the germplasm genetic modification means for inhibiting DNA double strand breakage during meiotic recombination comprise at least one MiMe allele at at least a first MiMe locus of a component of DNA double strand breakage during meiotic recombination;

(1) the germplasm genetic modification means for inhibiting sister chromatid cohesion during the first division of meiosis comprises at least one MiMe allele and at least one non-MiMe allele at one or more MiMe loci for a component of sister chromatid cohesion during the first division of meiosis;

(3) the germplasm genetic modification means for inhibiting progression through the second division of meiosis comprises at least one MiMe allele and at least one non-MiMe allele at one or more MiMe loci for a component of progression through the second division of meiosis; and (4) the germplasm genetic modification means for inhibiting progression through the first division of meiosis comprise at least one MiMe allele and at least one non-MiMe allele at one or more MiMe loci for a component of progression through the first division of meiosis.

53. The population of any one of embodiments 50-52, wherein:

(1) the one or more MiMe loci of the component of sister chromatid cohesion during the first division of meiosis comprise REC8, SWITCH1/DYAD, or a combination thereof;

(2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;

(3) the one or more MiMe loci of the component of progression through the second division of meiosis comprise OSD1, CYCA1, TDM1, PC1, PC2, FC, or any combination thereof; and/or (4) the one or more MiMe loci of the component of progression through the first division of meiosis comprise PS1, JASON, or a combination thereof.

54. The population of any one of embodiments 45-53, wherein the subpopulation of genetically uniform polyploid potato seed comprises:

(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a complete MiMe genotype comprising (i) an os allele, wherein the subpopulation of genetically uniforms seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(14) a partial MiMe genotype comprising (i) an os allele, wherein the subpopulation of genetically uniforms seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(15) a complete MiMe genotype comprising (i) a ps allele, wherein the subpopulation of genetically uniforms seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1;

(16) a partial MiMe genotype comprising (i) a ps allele, wherein the subpopulation of genetically uniforms seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(17) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(18) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(19) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(20) a partially complemented MiMe genotype comprising (i) a ps allele, wherein the subpopulation of genetically uniforms seed is heterozygous for the ps allele, (ii) an os allele, wherein the subpopulation of genetically uniforms seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1; or

(21) a partially complemented MiMe genotype comprising (i) an os allele, wherein the subpopulation of genetically uniforms seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

55. The population of any one of embodiments 45-54, wherein the subpopulation of genetically uniform polyploid potato seed comprises one or more polynucleotide sequences selected from the group consisting of SEQ ID NOs: 127-129, 131-134, 137-154, and 156-159.

56. The population of any one of embodiments 45-55, wherein germination of a seed of the subpopulation of genetically uniform polyploid potato seed results in a sterile plant that produces inviable gametes.

57. The population of any one of embodiments 45-56, wherein the population of polyploid potato seed comprises three or more haplotypes from *Solanum tuberosum.*

58. A method of producing the population of polyploid potato seed of any one of embodiments 45-57, the method comprising:

(0) generating a first parent MiMe potato plant and a second parent MiMe potato plant by introducing genetic modifications into germplasms of one or more candidate potato lines to generate the first parent MiMe potato plant, the second parent MiMe potato plant, and/or progenitors thereof, wherein the first parent MiMe potato plant and the second parent MiMe potato plant together comprise three or more haplotypes, and wherein each of the first parent MiMe potato plant, the second parent MiMe potato plant, and/or the progenitors thereof comprises:

(A) (1) a germplasm genetic modification means for inhibiting sister chromatid cohesion during the first division of meiosis, (2) a germplasm genetic modification means for inhibiting DNA double strand breakage during meiotic recombination, and (3) a germplasm genetic modification means for inhibiting progression through the second division of meiosis; or (B) (2) a germplasm genetic modification means for preventing DNA double strand breakage during meiotic recombination, and (4) a germplasm genetic modification means for preventing progression through the first division of meiosis;

wherein each of the germplasm genetic modifications are (i) a complete set that achieves the inhibition, or (ii) a partial set that does not achieve inhibition;

wherein if progenitors are generated, the progenitors are further crossed to generate the first parent MiMe potato plant, the second parent MiMe potato plant, or both, and wherein the generating the first parent MiMe potato plant, the second parent MiMe potato plant, and/or the progenitors thereof comprises selecting for plants comprising the germplasm genetic modification means after introducing the germplasm genetic modification means;

(a) providing clonal gametes from the first parent MiMe potato plant and the second parent MiMe potato plant that together comprise the three or more haplotypes; and (b) crossing the clonal gametes to produce the population of polyploid potato seed;

wherein the population of polyploid potato seed comprises a subpopulation of genetically uniform polyploid potato seed in an amount of at least 50% of the total number of seeds, the subpopulation of genetically uniform polyploid potato seed comprising the three or more haplotypes.

59. The method of embodiment 58, wherein the subpopulation of genetically uniform polyploid potato seed has a partially-complemented MiMe genotype, wherein:

(A)

(a) the first parent MiMe potato plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and (b) the second parent MiMe potato plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;

wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein either (i) at least one of the MiMe loci having only MiMe alleles of the third MiMe component of the first parent MiMe potato plant is the same as at least one of the MiMe loci having only MiMe alleles of the third MiMe component of the second parent MiMe potato plant, or (ii) the one or more MiMe loci having only MiMe alleles of the third MiMe component of the first parent MiMe potato plant are distinct from the one or more MiMe loci having only MiMe alleles of the third MiMe component of the second parent MiMe potato plant;

wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

(B)

(a) the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; and (b) the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component;

wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and (C)

(a) the first parent MiMe potato plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;

(b) the second parent MiMe potato plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

60. A method of producing the population of polyploid potato seed of any one of embodiments 45-57, the method comprising:

(0) generating a first parent MiMe potato plant by introducing genetic modifications into germplasms of one or more candidate potato lines to generate the first parent MiMe potato plant or progenitors thereof, and wherein each of the first parent MiMe potato plant or the progenitors thereof comprises:

(A) (1) a germplasm genetic modification means for inhibiting sister chromatid cohesion during the first division of meiosis, (2) a germplasm genetic modification means for inhibiting DNA double strand breakage during meiotic recombination, and (3) a germplasm genetic modification means for inhibiting progression through the second division of meiosis; or (B) (2) a germplasm genetic modification means for preventing DNA double strand breakage during meiotic recombination, and (4) a germplasm genetic modification means for preventing progression through the first division of meiosis;

wherein each of the germplasm genetic modifications are (i) a complete set that achieves the inhibition, (ii) a partial set that does not achieve inhibition, or (iii) partially complemented at one or more of the genetic modification means and achieve sterility;

wherein if progenitors are generated, the progenitors are further crossed to generate the first parent MiMe potato plant, and wherein the generating the first parent MiMe potato plant and/or the progenitors thereof comprises selecting for plants comprising the germplasm genetic modification means after introducing the germplasm genetic modification means;

(a) providing clonal gametes from the first parent MiMe potato plant;

(b) providing haploid gametes from a homozygous parent non-MiMe potato plant; and (c) crossing the clonal gametes with the haploid gametes to produce the population of polyploid potato seed, wherein the clonal gametes and the haploid gametes together comprise three or more haplotypes, optionally wherein step (a) comprises generating the first parent MiMe potato plant, the second parent MiMe potato plant, or both.

61. A method of breeding a polyploid hybrid potato line, the method comprising:

(a) obtaining a set of potato lines;

(b) breeding the potato lines using traditional plant breeding methods to produce a set of candidate potato lines;

(c) selecting two or more candidate potato lines together comprising three or more haplotypes;

(d) generating a first parent MiMe potato plant and a second parent MiMe potato plant from the two or more candidate potato lines that together comprise the three or more haplotypes;

(e) providing clonal gametes from each of the first and second parent MiMe potato plants;

(f) crossing the clonal gametes to produce a hybrid polyploid seed comprising the three or more haplotypes;

(g) growing the hybrid polyploid seed to produce a hybrid polyploid potato plant comprising three or more haplotypes; and (h) evaluating one or more characteristics of the hybrid polyploid potato plant;

the method optionally further comprising (i) repeating steps (b)-(h) or steps (c)-(h) using the one or more characteristics of the hybrid polyploid potato plant evaluated in step (h) to guide the breeding of potato lines of step (b), the selecting of candidate potato lines of step (c), or both.

62. The method of embodiment 61, wherein:
(A)
(a) the first parent MiMe potato plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and
(b) the second parent MiMe potato plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;
wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;
wherein either (i) at least one of the MiMe loci having only MiMe alleles of the third MiMe component of the first parent MiMe potato plant is the same as at least one of the MiMe loci having only MiMe alleles of the third MiMe component of the second parent MiMe potato plant, or (ii) the one or more MiMe loci having only MiMe alleles of the third MiMe component of the first parent MiMe potato plant are distinct from the one or more MiMe loci having only MiMe alleles of the third MiMe component of the second parent MiMe potato plant;
wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.
(B)
(a) the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; and
(b) the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component;
wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;
wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and
(C)
(a) the first parent MiMe potato plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;
(b) the second parent MiMe potato plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and
wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;
wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

63. A method of breeding a polyploid hybrid potato line, the method comprising:
(a) obtaining a set of potato lines;
(b) breeding the potato lines using traditional plant breeding methods to produce a set of candidate potato lines;
(c) selecting two or more candidate potato lines together comprising three or more haplotypes;
(d) generating a first parent MiMe potato plant from one of the two or more candidate potato lines;
(e) providing clonal gametes from the first parent MiMe potato plant;
(f) providing haploid gametes from a homozygous parent non-MiMe potato plant of one of the two or more candidate potato lines;
(g) crossing the clonal gametes with the haploid gametes to produce a hybrid polyploid seed;
(h) growing the hybrid polyploid seed to produce a hybrid polyploid potato plant; and
(i) evaluating one or more characteristics of the hybrid polyploid potato plant, wherein the first parent MiMe potato plant and the homozygous parent non-MiMe potato plant together comprise three or more haplotypes, wherein the crossing of step (g) results in the hybrid polyploid seed comprising three or more haplotypes, and wherein the growing of step (h) results in the hybrid polyploid potato plant comprising three or more haplotypes;

the method optionally further comprising (j) repeating steps (b)-(i) or steps (c)-(i) using the one or more characteristics of the hybrid polyploid potato plant evaluated in step (i) to guide the breeding of potato lines of step (b), the selecting of candidate potato lines of step (c), or both.

64. The method of any one of embodiments 58-64, wherein the first parent MiMe potato plant, the second parent MiMe potato plant, the parent non-MiMe potato plant, or any combination thereof are diploid, triploid, or tetraploid and the hybrid polyploid potato plant is tetraploid, pentaploid, hexaploid, heptaploid, or octoploid.

65. The method of any one of embodiments 58-64, wherein generating the first parent MiMe potato plant, the second parent MiMe potato plant, or both comprises:

(1) introducing a complete MiMe genotype directly into two candidate potato lines to produce the first parent MiMe potato plant, the second parent MiMe potato plant, or both;

(2) introducing a partial MiMe genotype into two candidate potato lines to produce two grandparent non-MiMe potato plants each having a partial MiMe genotype and crossing the grandparent non-MiMe potato plants each having a partial MiMe genotype to produce the first parent MiMe potato plant, optionally wherein generating the first parent MiMe potato plant, the second parent MiMe potato plant, or both further comprises introducing a complete MiMe genotype directly into a third candidate potato line to produce the second parent MiMe potato plant; or (3) introducing a partial MiMe genotype into four candidate potato lines to produce four grandparent non-MiMe potato plants each having a partial MiMe genotype, and crossing pairs of said grandparent non-MiMe potato plants each having a partial MiMe genotype to produce the first and second parent MiMe potato plants, optionally wherein generating the first parent MiMe potato plant, the second parent MiMe potato plant, or both further comprises propagating the first parent MiMe potato plant, the second parent MiMe potato plant, the grandparent non-MiMe potato plants, or any combination thereof to scale production of homogenous seed.

66. The method of any one of embodiments 58-65, wherein the first parent MiMe potato plant, the second parent MiMe potato plant, the hybrid polyploid potato plant, or any combination thereof has a complete MiMe genotype comprising:

(A)

MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or 66.

(B)

MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components.

67. The method of any one of embodiments 61-66, wherein each grandparent non-MiMe potato plant, the hybrid polyploid potato plant, or a combination thereof has a partial MiMe genotype comprising:

(A)

(a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components; or (B)

(a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components.

68. The method of embodiment 18, 66, or 67, wherein:

(1) the one or more MiMe loci of the component of sister chromatid cohesion during the first division of meiosis comprise REC8, SWITCH1/DYAD, or a combination thereof;

(2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;

(3) the one or more MiMe loci of the component of progression through the second division of meiosis comprise OSD1, CYCA1, TDM1, PC1, PC2, FC, or any combination thereof; and/or (4) the one or more MiMe loci of the component of progression through the first division of meiosis comprise PS1, JASON, or a combination thereof.

69. The method of any one of embodiments 61-68, wherein the hybrid polyploid potato plant comprises:

(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a complete MiMe genotype comprising (i) an os allele, wherein the subpopulation of genetically uniforms seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(14) a partial MiMe genotype comprising (i) an os allele, wherein the subpopulation of genetically uniforms seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(15) a complete MiMe genotype comprising (i) a ps allele, wherein the subpopulation of genetically uniforms seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1;

(16) a partial MiMe genotype comprising (i) a ps allele, wherein the subpopulation of genetically uniforms seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(17) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(18) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(19) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(20) a partially complemented MiMe genotype comprising (i) a ps allele, wherein the subpopulation of genetically uniforms seed is heterozygous for the ps allele, (ii) an os allele, wherein the subpopulation of genetically uniforms seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1; or

(21) a partially complemented MiMe genotype comprising (i) an os allele, wherein the subpopulation of genetically uniforms seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

70. The method of any one of embodiments 61-69, wherein one or more of the candidate potato lines of step (c) are inbred potato lines, hybrid potato lines, or a combination thereof.

71. The method of any one of embodiments 65-70, wherein the complete MiMe genotype, the partial MiMe genotype, or both are introduced by gene editing, transgenesis, or a combination thereof.

72. The method of embodiment 66-71, wherein the decreased expression of one or more of the MiMe loci is each independently achieved by gene disruption, gene knockout, gene knockdown, gene silencing, RNA interference, or induction of methylation.

73. The method of embodiment 66-71, wherein the decreased expression of one or more of the MiMe loci is each independently achieved by introducing into each candidate potato line an insertion, a deletion, one or more nucleotide changes, or an inversion that results in decreased expression of the MiMe locus, optionally including a step of selection for decreased expression of the MiMe locus.

74. The method of embodiment 73, wherein the insertion, the deletion, the one or more nucleotide changes, or the inversion eliminates expression of the MiMe locus, optionally wherein the expression of the MiMe locus is eliminated by a premature stop codon present in the 70%, the first 60%, the first 50%, the first 40%, the first 30%, the first 20%, or the first 10% of the nucleotides of the coding sequence of the MiMe locus following the start codon in the 3' direction.

75. A method of producing a population of polyploid potato seed comprising:

(a) providing clonal gametes from a pair of parent MiMe potato plants together comprising three or more haplotypes that were selected using the method of breeding of any one of embodiments 61, 62, and 64-74 based upon the polyploid potato plant comprising the three or more haplotypes having one or more desired characteristics; and (b) crossing the clonal gametes to produce the population of polyploid potato seed;

wherein the population of polyploid potato seed comprises a subpopulation of genetically uniform polyploid potato seed in an amount of at least 50% of the total number of seeds, the subpopulation of genetically uniform polyploid potato seed comprising the three or more haplotypes.

76. A method of producing a population of polyploid potato seed comprising:

(a) selecting three or more haplotypes using the method of breeding of any one of embodiments 63-74 based upon the polyploid potato plant comprising said three or more haplotypes having one or more desired characteristics;

(b) providing clonal gametes from a parent MiMe potato plant;

(c) providing haploid gametes from a homozygous parent non-MiMe potato plant;

(d) crossing the clonal gametes with the haploid gametes to produce the population of polyploid potato seed;

wherein the parent MiMe potato plant and the homozygous parent non-MiMe potato plant together comprise the three or more haplotypes selected in step (a), wherein the crossing of step (d) results in a population of polyploid potato seed comprising a subpopulation of genetically uniform polyploid potato seed in an amount of at least 50% of the total number of seeds, the subpopulation of genetically uniform polyploid potato seed comprising the three or more haplotypes.

77. The method of embodiment 75 or 76, wherein the population of polyploid potato seed has an average pairwise genetic uniformity of at least 80%, at least 85%, at least 90%, at least 95%, at least 96%, at least 97%, at least 98%, at least 99%, or 100% as measured by the Jaccard similarity coefficient.

78. The method of any one of embodiments 75-77, wherein the population of polyploid potato seed comprises the subpopulation of genetically uniform polyploid potato seed in an amount of at least 70%, at least 90%, at least 95%, at least 96%, at least 97%, at least 98%, or at least 99% of the total number of seeds.

79. The method of any one of embodiments 75-78, wherein each pair of seeds in the subpopulation of genetically uniform polyploid potato seed has a pairwise identity of at least 95%, at least 96%, at least 97%, at least 98%, at least 99%, or 100% as measured by the Jaccard similarity coefficient.

80. A genetically modified potato plant, plant part, or plant cell comprising:

(A) three or more haplotypes; and (B)

(i) a complete MiMe genotype comprising MiMe alleles conferring decreased expression of one or more MiMe loci of each of a first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;

ii) a partial MiMe genotype comprising:

(a) one or more MiMe alleles conferring decreased expression of one or more MiMe loci of each of a first, second, and third MiMe component; and (b) one or more non-MiMe alleles at the one or more MiMe loci of each of the first, second, and third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;

iii) a complete MiMe genotype comprising MiMe alleles conferring decreased expression of one or more MiMe loci of each of a first and second MiMe component, wherein the first MiMe component and the second MiMe component are selected from the group consisting of (2) a component of DNA double strand breakage during meiotic recombination and (4) a component of progression through the first division of meiosis, and each of the first MiMe component and the second MiMe component are different MiMe components;

iv) a partial MiMe genotype comprising:

(a) one or more MiMe alleles conferring decreased expression of one or more MiMe loci of each of the first and second MiMe component; and (b) one or more non-MiMe alleles at the one or more MiMe loci of each of the first and second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components;

v) a partially complemented MiMe genotype comprising:

(a) only MiMe alleles at one or more MiMe loci of a first MiMe component;

(b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components;

vi) a partially complemented MiMe genotype comprising:

(a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; or vii) a partially complemented MiMe genotype comprising:

(a) only MiMe alleles at one or more MiMe loci of a first MiMe component, wherein the first MiMe component is a component of DNA double strand breakage during meiotic recombination;

(b) one or more MiMe alleles and one or more non-MiMe alleles at one or more MiMe loci of a second MiMe component;

(c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

81. The genetically modified potato plant, plant part, or plant cell of embodiment 80, wherein:
(1) the one or more MiMe loci of the component of sister chromatid cohesion during the first division of meiosis comprise REC8, SWITCH1/DYAD, or a combination thereof;
(2) the one or more MiMe loci of the component of DNA double strand breakage during meiotic recombination comprise PAIR1, SPO11-1, SPO11-2, PRD1, PRD2, DFO, MTOPVIB, DSY1, SY1, SY2, SY3, SY4, or any combination thereof;
(3) the one or more MiMe loci of the component of progression through the second division of meiosis comprise OSD1, CYCA1, TDM1, PC1, PC2, FC, or any combination thereof; and/or
(4) the one or more MiMe loci of the component of progression through the first division of meiosis comprise PS1, JASON, or a combination thereof.

82. The genetically modified potato plant, plant part, or plant cell of embodiment 80 or 81, comprising:
(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;
(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;
(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;
(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;
(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;
(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a complete MiMe genotype comprising (i) an os allele, wherein the subpopulation of genetically uniforms seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(14) a partial MiMe genotype comprising (i) an os allele, wherein the subpopulation of genetically uniforms seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(15) a complete MiMe genotype comprising (i) a ps allele, wherein the subpopulation of genetically uniforms seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1;

(16) a partial MiMe genotype comprising (i) a ps allele, wherein the subpopulation of genetically uniforms seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(17) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(18) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(19) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(20) a partially complemented MiMe genotype comprising (i) a ps allele, wherein the subpopulation of genetically uniforms seed is heterozygous for the ps allele, (ii) an os allele, wherein the subpopulation of genetically uniforms seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1; or

(21) a partially complemented MiMe genotype comprising (i) an os allele, wherein the subpopulation of genetically uniforms seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

83. The genetically modified potato plant, plant part, or plant cell of any one of embodiments 80-82, comprising one or more polynucleotide sequences selected from the group consisting of SEQ ID NOs: 127-129, 131-134, 137-154, and 156-159.

84. The genetically modified potato plant, plant part, or plant cell of any one of embodiments 80-83, wherein:
(i) the genetically modified potato plant part is a non-regenerable plant part; or
(ii) the genetically modified potato plant cell is a non-regenerable plant cell.

85. The genetically modified potato plant, plant part, or plant cell of any one of embodiments 80-84, wherein the plant part is a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, an anther, or a portion thereof.

86. A processed potato product derived from the genetically modified potato plant, plant part, or plant cell of any one of embodiments 80-85 wherein the processed potato product comprises a detectable amount of the one or more MiMe alleles of the genetically modified potato plant, plant part, or plant cell.

87. The processed potato product of embodiment 86, wherein the processed potato product:
(i) is selected from the group consisting of plant biomass, oil, meal, food starch, syrup, animal feed, flour, flakes, bran, lint, hulls, and processed seed; and/or
(ii) is non-regenerable.

88. Germplasm of the population of polyploid potato seeds of any one of embodiments 45-59.

89. A population of polyploid potato seed comprising a subpopulation of genetically uniform polyploid potato seed in an amount of at least 50% of the total number of seeds, the genetically uniform polyploid potato seed comprising three or more haplotypes of the same or related species of potato, wherein the population was obtained from a single potato plant or a set of F1 hybrids, wherein the subpopulation of genetically uniform polyploid potato seed comprise (A) (1) one or more MiMe alleles at each of one or more MiMe loci of a component of sister chromatid cohesion during the first division of meiosis comprising REC8, SWITCH1/DYAD, or a combination thereof, (2) one or more MiMe alleles at each of one or more MiMe loci of a component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (3) one or more MiMe alleles at each of one or more MiMe loci of the component of progression through the second division of meiosis comprising OSD1, CYCA1, TDM1, PC1, PC2, FC, or any combination thereof; or (B) (2) one or more MiMe alleles at each of one or more MiMe loci of the component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (4) one or more MiMe alleles at each of one or more MiMe loci of the component of progression through the first division of meiosis comprise PS1, JASON, or a combination thereof;

wherein each of the of the MiMe alleles comprises a germplasm genetic modification, wherein at least one seed, or a plant grown therefrom, of the population of polyploid potato seed has been selected for lack of expression of each of the one or more MiMe loci, and wherein the subpopulation of genetically uniform polyploid potato seeds comprises (i) a complete MiMe genotype comprising only MiMe alleles at each of the one or more MiMe loci, (ii) a partial MiMe genotype comprising at least one MiMe allele and at least one non-MiMe allele at each of the one or more MiMe loci, or (iii) a partially complemented MiMe genotype comprising only MiMe alleles at a first MiMe locus of the one or more MiMe loci and at least one MiMe allele and at least one non-MiMe allele at a second MiMe locus of the one or more MiMe loci.

90. The population of embodiment 89, wherein the subpopulation of genetically uniform polyploid potato seed is triploid, tetraploid, pentaploid, hexaploid, heptaploid, or octoploid.

91. The population of embodiment 89 or 90, wherein the population of polyploid potato seed has an average pairwise genetic uniformity of at least 80%, at least 85%, at least 90%, at least 95%, at least 96%, at least 97%, at least 98%, at least 99%, or 100% as measured by the Jaccard similarity coefficient.

92. The population of any one of embodiments 89-91, wherein the population of polyploid potato seed comprises the subpopulation of genetically uniform polyploid potato seed in an amount of at least 70%, at least 90%, at least 95%, at least 96%, at least 97%, at least 98%, or at least 99% of the total number of seeds.

93. The population of embodiment 89-92, wherein each pair of seeds in the subpopulation of genetically uniform polyploid potato seed has a pairwise identity of at least 95%, at least 96%, at least 97%, at least 98%, at least 99%, or 100% as measured by the Jaccard similarity coefficient.

94. The population of any one of embodiments 89-93, wherein the subpopulation of genetically uniform polyploid potato seed has a partially-complemented MiMe genotype comprising:

(A)

(a) only MiMe alleles at one or more MiMe loci of a first MiMe component;

(b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) the component of sister chromatid cohesion during the first division of meiosis, (2) the component of DNA double strand breakage during meiotic recombination, and (3) the component of progression through the second division of meiosis, and each of the first MiMe component, the second MiMe component, and the third MiMe component are different MiMe components;

(B)

(a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) the component of DNA double strand breakage during meiotic recombination and (4) the component of progression through the first division of meiosis and each of the first MiMe component and the second MiMe component are different MiMe components; or (C)

(a) only MiMe alleles at one or more MiMe loci of a first MiMe component, wherein the first MiMe component is the component of DNA double strand breakage during meiotic recombination;

(b) one or more MiMe alleles and one or more non-MiMe alleles at one or more MiMe loci of a second MiMe component;

(c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) the component of sister chromatid cohesion during the first division of meiosis, (3) the component of progression through the second division of meiosis, and (4) the component of progression through the first division of meiosis, and each of the second MiMe component, the third MiMe component, and the fourth MiMe component are different MiMe components.

95. The population of any one of embodiments 89-94, wherein the subpopulation of genetically uniform polyploid potato seed comprises:

(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a complete MiMe genotype comprising (i) an os allele, wherein the subpopulation of genetically uniforms seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(14) a partial MiMe genotype comprising (i) an os allele, wherein the subpopulation of genetically uniforms seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(15) a complete MiMe genotype comprising (i) a ps allele, wherein the subpopulation of genetically uniforms seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1;

(16) a partial MiMe genotype comprising (i) a ps allele, wherein the subpopulation of genetically uniforms seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(17) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(18) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(19) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(20) a partially complemented MiMe genotype comprising (i) a ps allele, wherein the subpopulation of genetically uniforms seed is heterozygous for the ps allele, (ii) an os allele, wherein the subpopulation of genetically uniforms seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1; or

(21) a partially complemented MiMe genotype comprising (i) an os allele, wherein the subpopulation of genetically uniforms seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

96. The population of any one of embodiments 89-95, wherein the subpopulation of genetically uniform polyploid potato seed comprises one or more polynucleotide sequences selected from the group consisting of SEQ ID NOs: 127-129, 131-134, 137-154, and 156-159.

97. The population of any one of embodiments 89-96, wherein germination of a seed of the subpopulation of genetically uniform polyploid potato seed results in a sterile plant that produces inviable gametes.

98. The population of any one of embodiments 89-97, wherein the population of polyploid potato seed comprises three or more haplotypes of *Solanum tuberosum.*

99. A method of producing the population of polyploid potato seed of any one of embodiments 89-98, the method comprising:

(a) generating a first parent MiMe potato plant and a second parent MiMe potato plant by introducing genetic modifications into one or more candidate potato lines to produce MiMe alleles in germplasm of a first parent MiMe potato plant, a second parent MiMe potato plant, and/or progenitors thereof, wherein the first parent MiMe potato plant and the second parent MiMe potato plant each comprise a complete MiMe genotype, and each of the progenitors comprises a partial MiMe genotype, wherein if progenitors are generated, the progenitors are further crossed to generate the first parent MiMe potato plant, the second parent MiMe potato plant, or both;

(b) providing clonal gametes from the first parent MiMe potato plant and the second parent MiMe potato plant that together comprise the three or more haplotypes; and (c) crossing the clonal gametes to produce the population of polyploid potato seed;

wherein the population of polyploid potato seed comprises a subpopulation of genetically uniform polyploid potato seed in an amount of at least 50% of the total number of seeds, the subpopulation of genetically uniform polyploid potato seed comprising the three or more haplotypes.

100. The method of embodiment 99, wherein the subpopulation of genetically uniform polyploid potato seed has a partially-complemented MiMe genotype, wherein:

(A)

(a) the first parent MiMe potato plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and (b) the second parent MiMe potato plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;

wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein either (i) at least one of the MiMe loci having only MiMe alleles of the third MiMe component of the first parent MiMe potato plant is the same as at least one of the MiMe loci having only MiMe alleles of the third MiMe component of the second parent MiMe potato plant, or (ii) the one or more MiMe loci having only MiMe alleles of the third MiMe component of the first parent MiMe potato plant are distinct from the one or more MiMe loci having only MiMe alleles of the third MiMe component of the second parent MiMe potato plant;

wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

(B)

(a) the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; and (b) the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component;

wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and (C)

(a) the first parent MiMe potato plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;

(b) the second parent MiMe potato plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

101. A method of producing the population of polyploid potato seed of any one of embodiments 1-98, the method comprising:

(a) generating a first parent MiMe potato plant by introducing genetic modifications into one or more candidate potato lines to produce MiMe alleles in germplasm of the first parent MiMe potato plant or progenitors thereof, wherein the first parent MiMe potato plant comprises a complete MiMe genotype, and each of the progenitors comprises a partial MiMe genotype, wherein if progenitors are generated, the progenitors are further crossed to generate the first parent MiMe potato plant;

(b) providing clonal gametes from the parent MiMe potato plant;

(c) providing haploid gametes from a homozygous parent non-MiMe potato plant; and (d) crossing the clonal gametes with the haploid gametes to produce the population of polyploid potato seed, wherein the clonal gametes and the haploid gametes together comprise three or more haplotypes, optionally wherein step (a) comprises generating the first parent MiMe potato plant, the second parent MiMe potato plant, or both.

102. A method of breeding a polyploid hybrid potato line, the method comprising:

(a) obtaining a set of potato lines;

(b) breeding the potato lines using traditional plant breeding methods to produce a set of candidate potato lines;

(c) selecting two or more candidate potato lines together comprising three or more haplotypes;

(d) generating a first parent MiMe potato plant and a second parent MiMe potato plant from the two or more candidate potato lines that together comprise the three or more haplotypes;

(e) providing clonal gametes from each of the first and second parent MiMe potato plants;

(f) crossing the clonal gametes to produce a hybrid polyploid seed comprising the three or more haplotypes;

(g) growing the hybrid polyploid seed to produce a hybrid polyploid potato plant comprising three or more haplotypes; and (h) evaluating one or more characteristics of the hybrid polyploid potato plant, wherein the first parent MiMe potato plant, the second parent MiMe potato plant, and the hybrid polyploid potato plant each independently comprise:

(A) (1) one or more MiMe alleles at each of one or more MiMe loci of a component of sister chromatid cohesion during the first division of meiosis comprising REC8, SWITCH1/DYAD, or a combination thereof, (2) one or more MiMe alleles at each of one or more MiMe loci of a component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (3) one or more MiMe alleles at each of one or more MiMe loci of the component of progression through the second division of meiosis comprising OSD1, CYCA1, TDM1, PC1, PC2, FC, or any combination thereof; or (B) (2) one or more MiMe alleles at each of one or more MiMe loci of the component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (4) one or more MiMe alleles at each of one or more MiMe loci of the component of progression through the first division of meiosis comprise PS1, JASON, or a combination thereof;

wherein each of the of the MiMe alleles comprises a germplasm genetic modification, wherein the method comprises selecting the first parent MiMe potato plant, the second parent MiMe potato plant, the hybrid polyploid potato plant, or any combination thereof for lack of expression of the one or more MiMe loci, and wherein the first parent MiMe potato plant and the second parent MiMe potato plant each independently comprise a complete MiMe genotype comprising only MiMe alleles at each of the one or more MiMe loci, and wherein the hybrid polyploid potato plant comprises (i) a complete MiMe genotype comprising only MiMe alleles at each of the one or more MiMe loci, or (ii) a partially complemented MiMe genotype comprising only MiMe alleles at a first MiMe locus of the one or more MiMe loci and at least one MiMe allele and at least one non-MiMe allele at a second MiMe locus of the one or more MiMe loci; the method optionally further comprising (i) repeating steps (b)-(h) or steps (c)-(h) using the one or more characteristics of the hybrid polyploid potato plant evaluated in step (h) to guide the breeding of potato lines of step (b), the selecting of candidate potato lines of step (c), or both.

103. The method of embodiment 102, wherein:

(A)

(a) the first parent MiMe potato plant has only MiMe alleles at one or more MiMe loci of a first MiMe component, only MiMe alleles at a first MiMe locus of a second MiMe component, only non-MiMe alleles at a second MiMe locus of the second MiMe component, and only MiMe alleles at one or more MiMe loci of a third MiMe component; and (b) the second parent MiMe potato plant has only MiMe alleles at one or more MiMe loci of the first MiMe component, only non-MiMe alleles at the first MiMe locus of the second MiMe component, only MiMe alleles at the second MiMe locus of the second MiMe component, and only MiMe alleles at one or more MiMe loci of the third MiMe component;

wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein either (i) at least one of the MiMe loci having only MiMe alleles of the third MiMe component of the first parent MiMe potato plant is the same as at least one of the MiMe loci having only MiMe alleles of the third MiMe component of the second parent MiMe potato plant, or (ii) the one or more MiMe loci having only MiMe alleles of the third MiMe component of the first parent MiMe potato plant are distinct from the one or more MiMe loci having only MiMe alleles of the third MiMe component of the second parent MiMe potato plant;

wherein the first MiMe component, the second MiMe component, and the third MiMe component are selected from the group consisting of (1) a component of sister chromatid cohesion during the first division of meiosis, (2) a component of DNA double strand breakage during meiotic recombination, and (3) a component of progression through the second division of meiosis, and each of the first MiMe component, the second MiMe component, and the third MiMe component are different MiMe components.

(B)

(a) the first parent MiMe potato plant has only MiMe alleles at one or more MiMe loci of a first MiMe component, only MiMe alleles at a first MiMe locus of a second MiMe component, and only non-MiMe alleles at a second MiMe locus of the second MiMe component; and (b) the second parent MiMe potato plant has only MiMe alleles at one or more MiMe loci of the first MiMe component, only non-MiMe alleles at the first MiMe locus of the second MiMe component, and only MiMe alleles at the second MiMe locus of the second MiMe component;

wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein the first MiMe component and the second MiMe component are selected from the group consisting of (2) a component of DNA double strand breakage during meiotic recombination and (4) a component of progression through the first division of meiosis and each of the first MiMe component and the second MiMe component are different MiMe components; and (C)

(a) the first parent MiMe potato plant has only MiMe alleles at one or more MiMe loci of a first MiMe component, only MiMe alleles one or more MiMe loci of a second MiMe component, only MiMe alleles at one or more MiMe loci of a third MiMe component, and only non-MiMe alleles at one or more MiMe loci of a fourth MiMe component, wherein the first MiMe component is a component of DNA double strand breakage during meiotic recombination;

(b) the second parent MiMe potato plant has only MiMe alleles at the one or more MiMe loci of the first MiMe component, only non-MiMe alleles at the one or more MiMe loci of the second MiMe component, only non-MiMe alleles at the one or more MiMe loci of the third MiMe component, and only MiMe alleles at the one or more MiMe loci of the fourth MiMe component; and wherein at least one of the MiMe loci having only MiMe alleles of the first MiMe component of the first parent MiMe potato plant is the same as at least one of the MiMe loci having only MiMe alleles of the first MiMe component of the second parent MiMe potato plant;

wherein the second MiMe component, the third MiMe component, and the fourth MiMe component are selected from the group consisting of (1) a component of sister chromatid cohesion during the first division of meiosis, (3) a component of progression through the second division of meiosis, and (4) a component of progression through the first division of meiosis, and each of the second MiMe component, the third MiMe component, and the fourth MiMe component are different MiMe components.

104. A method of breeding a polyploid hybrid potato line, the method comprising:

(a) obtaining a set of potato lines;

(b) breeding the potato lines using traditional plant breeding methods to produce a set of candidate potato lines;

(c) selecting two or more candidate potato lines together comprising three or more haplotypes;

(d) generating a first parent MiMe potato plant from one of the two or more candidate potato lines;

(e) providing clonal gametes from the first parent MiMe potato plant;

(f) providing haploid gametes from a homozygous parent non-MiMe potato plant of one of the two or more candidate potato lines;

(g) crossing the clonal gametes with the haploid gametes to produce a hybrid polyploid seed;

(h) growing the hybrid polyploid seed to produce a hybrid polyploid potato plant; and (i) evaluating one or more characteristics of the hybrid polyploid potato plant, wherein the first parent MiMe potato plant and the homozygous parent non-MiMe potato plant together comprise three or more haplotypes, wherein the crossing of step (g) results in the hybrid polyploid seed comprising three or more haplotypes, and wherein the growing of step (h) results in the hybrid polyploid potato plant comprising three or more haplotypes;

wherein the first parent MiMe potato plant and the hybrid polyploid potato plant each independently comprise:

(A) (1) one or more MiMe alleles at each of one or more MiMe loci of a component of sister chromatid cohesion during the first division of meiosis comprising REC8, SWITCH1/DYAD, or a combination thereof, (2) one or more MiMe alleles at each of one or more MiMe loci of a component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (3) one or more MiMe alleles at each of one or more MiMe loci of the component of progression through the second division of meiosis comprising OSD1, CYCA1, TDM1, PC1, PC2, FC, or any combination thereof; or (B) (2) one or more MiMe alleles at each of one or more MiMe loci of the component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (4) one or more MiMe alleles at each of one or more MiMe loci of the component of progression through the first division of meiosis comprise PS1, JASON, or a combination thereof;

wherein each of the of the MiMe alleles comprises a germplasm genetic modification, wherein the method comprises screening the first parent MiMe potato plant, the hybrid polyploid potato plant, or any combination thereof for lack of expression of the one or more MiMe loci, and wherein the first parent MiMe potato comprises a complete MiMe genotype comprising only MiMe alleles at each of the one or more MiMe loci, the parent non-MiMe potato plant comprises only non-MiMe alleles at each of the one or more MiMe loci, and the hybrid polyploid potato plant comprises a partial MiMe genotype comprising at least one MiMe allele and at least one non-MiMe allele at each of the one or more MiMe loci, the method optionally further comprising (j) repeating steps (b)-(i) or steps (c)-(i) using the one or more characteristics of the hybrid polyploid potato plant evaluated in step (i) to guide the breeding of potato lines of step (b), the selecting of candidate potato lines of step (c), or both.

105. The method of any one of embodiments 101-104, wherein the first parent MiMe potato plant, the second parent MiMe potato plant, the parent non-MiMe potato plant, or any combination thereof are diploid, triploid, or tetraploid and the hybrid polyploid potato plant is tetraploid, pentaploid, hexaploid, heptaploid, or octoploid.

106. The method of any one of embodiments 101-105, wherein generating the first parent MiMe potato plant, the second parent MiMe potato plant, or both comprises:

(1) introducing a complete MiMe genotype directly into two candidate potato lines to produce the first parent MiMe potato plant, the second parent MiMe potato plant, or both;

(2) introducing a partial MiMe genotype into two candidate potato lines to produce two grandparent non-MiMe potato plants each having a partial MiMe genotype and crossing the grandparent non-MiMe potato plants each having a partial MiMe genotype to produce the first parent MiMe potato plant, optionally wherein generating the first parent MiMe potato plant, the second parent MiMe potato plant, or both further comprises introducing a complete MiMe genotype directly into a third candidate potato line to produce the second parent MiMe potato plant; or (3) introducing a partial MiMe genotype into four candidate potato lines to produce four grandparent non-MiMe potato plants each having a partial MiMe genotype, and crossing pairs of said grandparent non-MiMe potato plants each having a partial MiMe genotype to produce the first and second parent MiMe potato plants, optionally wherein generating the first parent MiMe potato plant, the second parent MiMe potato plant, or both further comprises propagating the first parent MiMe potato plant, the second parent MiMe potato plant, the grandparent non-MiMe potato plants, or any combination thereof to scale production of homogenous seed.

107. The method of any one of embodiments 102-106, wherein the hybrid polyploid potato plant comprises:

(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a complete MiMe genotype comprising (i) an os allele, wherein the subpopulation of genetically uniforms seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(14) a partial MiMe genotype comprising (i) an os allele, wherein the subpopulation of genetically uniforms seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(15) a complete MiMe genotype comprising (i) a ps allele, wherein the subpopulation of genetically uniforms seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1;

(16) a partial MiMe genotype comprising (i) a ps allele, wherein the subpopulation of genetically uniforms seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(17) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(18) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(19) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(20) a partially complemented MiMe genotype comprising (i) a ps allele, wherein the subpopulation of genetically uniforms seed is heterozygous for the ps allele, (ii) an os allele, wherein the subpopulation of genetically uniforms seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1; or

(21) a partially complemented MiMe genotype comprising (i) an os allele, wherein the subpopulation of genetically uniforms seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

108. The method of any one of embodiments 102-107, wherein one or more of the candidate potato lines of step (c) are inbred potato lines, hybrid potato lines, or a combination thereof.

109. The method of any one of embodiments 102-108, wherein the complete MiMe genotype, the partial MiMe genotype, or both are introduced by gene editing, transgenesis, or a combination thereof.

110. The method of embodiment 102-109, wherein the decreased expression of one or more of the MiMe loci is each independently achieved by gene disruption, gene knockout, gene knockdown, gene silencing, RNA interference, or induction of methylation.

111. The method of embodiment 102-110, wherein the decreased expression of one or more of the MiMe loci is each independently achieved by introducing into each candidate potato line or a progenitor thereof an insertion, a deletion, one or more nucleotide changes, or an inversion that results in decreased expression of the MiMe locus, optionally including a step of selection for decreased expression of the MiMe locus.

112. The method of embodiment 111, wherein the insertion, the deletion, the one or more nucleotide changes, or the inversion eliminates expression of the MiMe locus, optionally wherein the expression of the MiMe locus is eliminated by a premature stop codon present in the 70%, the first 60%, the first 50%, the first 40%, the first 30%, the first 20%, or the first 10% of the nucleotides of the coding sequence of the MiMe locus following the start codon in the 3' direction.

113. A method of producing a population of polyploid potato seed comprising:

(a) providing clonal gametes from a pair of parent MiMe potato plants together comprising three or more haplotypes that were selected using the method of breeding of any one of embodiments 102, 103, and 105-112 based upon the polyploid potato plant comprising the three or more haplotypes having one or more desired characteristics; and (b) crossing the clonal gametes to produce the population of polyploid potato seed;

wherein the population of polyploid potato seed comprises a subpopulation of genetically uniform polyploid potato seed in an amount of at least 50% of the total number of seeds, the subpopulation of genetically uniform polyploid potato seed comprising the three or more haplotypes.

114. A method of producing a population of polyploid potato seed comprising:

(a) selecting three or more haplotypes using the method of breeding of any one of embodiments 104-112 based upon the polyploid potato plant comprising said three or more haplotypes having one or more desired characteristics;

(b) providing clonal gametes from a parent MiMe potato plant;

(c) providing haploid gametes from a homozygous parent non-MiMe potato plant;

(d) crossing the clonal gametes with the haploid gametes to produce the population of polyploid potato seed;

wherein the parent MiMe potato plant and the homozygous parent non-MiMe potato plant together comprise the three or more haplotypes selected in step (a), wherein the crossing of step (d) results in a population of polyploid potato seed comprising a subpopulation of genetically uniform polyploid potato seed in an amount of at least 50% of the total number of seeds, the subpopulation of genetically uniform polyploid potato seed comprising the three or more haplotypes.

115. The method of embodiment 113 or 114, wherein the population of polyploid potato seed has an average pairwise genetic uniformity of at least 80%, at least 85%, at least 90%, at least 95%, at least 96%, at least 97%, at least 98%, at least 99%, or 100% as measured by the Jaccard similarity coefficient.

116. The method of any one of embodiments 113-115, wherein the population of polyploid potato seed comprises the subpopulation of genetically uniform polyploid potato seed in an amount of at least 70%, at least 90%, at least 95%, at least 96%, at least 97%, at least 98%, or at least 99% of the total number of seeds.

117. The method of any one of embodiments 113-116, wherein each pair of seeds in the subpopulation of genetically uniform polyploid potato seed has a pairwise identity of at least 95%, at least 96%, at least 97%, at least 98%, at least 99%, or 100% as measured by the Jaccard similarity coefficient.

118. A genetically modified potato plant, plant part, or plant cell comprising:

(A) three or more haplotypes; and (B)

(a) (1) one or more MiMe alleles at each of one or more MiMe loci of a component of sister chromatid cohesion during the first division of meiosis comprising REC8, SWITCH1/DYAD, or a combination thereof, (2) one or more MiMe alleles at each of one or more MiMe loci of a component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (3) one or more MiMe alleles at each of one or more MiMe loci of the component of progression through the second division of meiosis comprising OSD1, CYCA1, TDM1, PC1, PC2, FC, or any combination thereof; or (b) (2) one or more MiMe alleles at each of one or more MiMe loci of the component of DNA double strand breakage during meiotic recombination comprising PAIR1, SPO11-1, SPO11-2, PRD1, PRD2, DFO, MTOPVIB, DSY1, SY1, SY2, SY3, SY4, or any combination thereof, and (4) one or more MiMe alleles at each of one or more MiMe loci of the component of progression through the first division of meiosis comprise PS1, JASON, or a combination thereof;

wherein each of the of the MiMe alleles comprises a germplasm genetic modification comprising introduction of a premature in-frame stop codon present in the first 30% of the nucleotides of the coding sequence of the MiMe locus following the start codon in the 3' direction, thereby generating a MiMe allele, and wherein the subpopulation of genetically uniform polyploid potato seeds comprises (i) a complete MiMe genotype comprising only MiMe alleles at each of the one or more MiMe loci, (ii) a partial MiMe genotype comprising at least one MiMe allele and at least one non-MiMe allele at each of the one or more MiMe loci, or (iii) a partially complemented MiMe genotype comprising only MiMe alleles at a first MiMe locus of the one or more MiMe loci and at least one MiMe allele and at least one non-MiMe allele at a second MiMe locus of the one or more MiMe loci wherein the partially-complemented MiMe genotype comprises:

(i)

(a) only MiMe alleles at one or more MiMe loci of a first MiMe component;

(b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) the component of sister chromatid cohesion during the first division of meiosis, (2) the component of DNA double strand breakage during meiotic recombination, and (3) the component of progression through the second division of meiosis, and each of the first MiMe component, the second MiMe component, and the third MiMe component are different MiMe components;

(ii)

(a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) the component of DNA double strand breakage during meiotic recombination and (4) the component of progression through the first division of meiosis and each of the first MiMe component and the second MiMe component are different MiMe components; or (iii)

(a) only MiMe alleles at one or more MiMe loci of a first MiMe component, wherein the first MiMe component is the component of DNA double strand breakage during meiotic recombination;

(b) one or more MiMe alleles and one or more non-MiMe alleles at one or more MiMe loci of a second MiMe component;

(c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) the component of sister chromatid cohesion during the first division of meiosis, (3) the component of progression through the second division of meiosis, and (4) the component of progression through the first division of meiosis, and each of the second MiMe component, the third MiMe component, and the fourth MiMe component are different MiMe components.

119. The genetically modified potato plant, plant part, or plant cell of embodiment 118, comprising:

(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a complete MiMe genotype comprising (i) an os allele, wherein the subpopulation of genetically uniforms seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(14) a partial MiMe genotype comprising (i) an os allele, wherein the subpopulation of genetically uniforms seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(15) a complete MiMe genotype comprising (i) a ps allele, wherein the subpopulation of genetically uniforms seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1;

(16) a partial MiMe genotype comprising (i) a ps allele, wherein the subpopulation of genetically uniforms seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(17) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(18) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(19) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(20) a partially complemented MiMe genotype comprising (i) a ps allele, wherein the subpopulation of genetically uniforms seed is heterozygous for the ps allele, (ii) an os allele, wherein the subpopulation of genetically uniforms seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1; or

(21) a partially complemented MiMe genotype comprising (i) an os allele, wherein the subpopulation of genetically uniforms seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

120. The genetically modified potato plant, plant part, or plant cell of embodiment 118 or 119, comprising one or more polynucleotide sequences selected from the group consisting of SEQ ID NOs: 127-129, 131-134, 137-154, and 156-159.

121. The genetically modified potato plant, plant part, or plant cell of any one of embodiments 118-120, wherein:

(i) the genetically modified potato plant part is a non-regenerable plant part; or (ii) the genetically modified potato plant cell is a non-regenerable plant cell.

122. The genetically modified potato plant, plant part, or plant cell of any one of embodiments 118-121, wherein the plant part is a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, an anther, or a portion thereof.

123. A processed potato product derived from the genetically modified potato plant, plant part, or plant cell of any one of embodiments 118-122 wherein the processed potato product comprises a detectable amount of the one or more MiMe alleles of the genetically modified potato plant, plant part, or plant cell.

124. The processed potato product of embodiment 123, wherein the processed potato product:

(i) is selected from the group consisting of plant biomass, oil, meal, food starch, syrup, animal feed, flour, flakes, bran, lint, hulls, and processed seed; and/or (ii) is non-regenerable.

125 Germplasm of the population of polyploid potato seeds of any one of embodiments 89-98.

126. A method of producing comprising a subpopulation of genetically uniform polyploid potato seed in an amount of at least 50% of the total number of seeds, the genetically uniform polyploid potato seed comprising three or more haplotypes of the same or related species of potato, wherein the population was obtained from a single potato plant or a set of F1 hybrids, the method comprising:

(1)

(a) generating a first parent MiMe potato plant and a second parent MiMe potato plant;

(b) providing clonal gametes from the first parent MiMe potato plant and the second parent MiMe potato plant that together comprise the three or more haplotypes; and (c) crossing the clonal gametes to produce the population of polyploid potato seed, or (2)

(a) generating a first parent MiMe potato plant;

(b) providing clonal gametes from the parent MiMe potato plant;

(c) providing haploid gametes from a homozygous parent non-MiMe potato plant; and (d) crossing the clonal gametes with the haploid gametes to produce the population of polyploid potato seed, wherein the generating in step (a) comprises introducing the following MiMe alleles (A) or (B) at the following MiMe loci by (i) introducing genetic modifications in the MiMe loci and selecting for lack of expression at the MiMe loci, (ii) introducing an expression construct for a silencing RNA targeting the MiMe loci, or (iii) introducing a natural MiMe allele or selecting a first parent MiMe potato plant, a second parent MiMe potato plant or a progenitor with the natural allele for use in combination with (i) and/or (ii) for other MiMe alleles;

wherein genetic modifications and/or expression constructs are introduced into one or more candidate potato lines to produce MiMe alleles in germplasm of a first parent MiMe potato plant, a second parent MiMe potato plant, and/or progenitors thereof, wherein the first parent MiMe potato plant and the second parent MiMe potato plant each comprise a complete MiMe genotype, and each of the progenitors comprises a partial MiMe genotype, wherein if progenitors are generated, the progenitors are further crossed to generate the first parent MiMe potato plant, the second parent MiMe potato plant, or both:

(A) (1) one or more MiMe alleles at one or more MiMe loci of a component of sister chromatid cohesion during the first division of meiosis comprising REC8 (i.e., a gene encoding a protein having at least 60% sequence identity to XP 006347252.1), SWITCH1/DYAD (i.e., a gene encoding a protein having at least 60% sequence identity to M1BMI9), or a combination thereof, (2) one or more MiMe alleles at one or more MiMe loci of a component of DNA double strand breakage during meiotic recombination comprising PAIR1 (i.e., a gene encoding a protein having at least 60% sequence identity to one of XP 006339791.2 and M0ZGU5), SPO11-1 (i.e., a gene encoding a protein having at least 60% sequence identity to one of XP 006346146.1, M1C0B8, and M1CP72), SPO11-2 (i.e., a gene encoding a protein having at least 60% sequence identity to one of XP 006344018.1, XP 006367265.1 and M1CP72), PRD1 (i.e., a gene encoding a protein having at least 60% sequence identity to one of XP 015163123.1 and M1CA99), PRD2 (i.e., a gene encoding a protein having at least 60% sequence identity to one of XP 015162530.1 and M1AS84), DFO (i.e., a gene encoding a protein having at least 60% sequence identity to one of XP 006350870.1 and M1CZR2), MTOPVIB (i.e., a gene encoding a protein having at least 60% sequence identity to one of XP 015166906.1, XP 015166907.1 and MICGP5), DSY1, SY1, SY2, SY3, SY4, or any combination thereof, and (3) a natural os allele or one or more MiMe alleles at one or more MiMe loci of the component of progression through the second division of meiosis comprising OSD1 (i.e., a gene encoding a protein having at least 60% sequence identity to one of XP 006351336.1), CYCA1 (i.e., a gene encoding a protein having at least 60% sequence identity to one of XP 006351137.1, XP 006351136.1 and XP 006351138.1), TDM1 (i.e., a gene encoding a protein having at least 60% sequence identity to one of XP 006350746.1, XP 006340757.1 and XP 006360343.1), PC1, PC2, FC, or any combination thereof; or (B) (2) one or more MiMe alleles at one or more MiMe loci of the component of DNA double strand breakage during meiotic recombination comprising PAIR1 (i.e., a gene encoding a protein having at least 60% sequence identity to one of XP 006339791.2 and M0ZGU5), SPO11-1 (i.e., a gene encoding a protein having at least 60% sequence identity to one of XP 006344018.1, XP 006367265.1 and M1CP72), SPO11-2, PRD1, PRD2, DFO, MTOPVIB, DSY1, SY1, SY2, SY3, SY4, or any combination thereof, and (4) a natural ps allele or one or more MiMe alleles at one or more MiMe loci of the component of progression through the first division of meiosis comprise PS1 (i.e., a gene encoding a protein having at least 60% sequence identity to one of XP 006351164.1, XP 006353632.1 and M1AJ10), JASON (i.e., a gene encoding a protein having at least 60% sequence identity to one of XP 006352001.1, XP 015160469.1 and M1CT79), or a combination thereof;

wherein the subpopulation of genetically uniform polyploid potato seeds comprises (i) a complete MiMe genotype comprising only MiMe alleles at each of the one or more MiMe loci, (ii) a partial MiMe genotype comprising at least one MiMe allele and at least one non-MiMe allele at each of the one or more MiMe loci, or (iii) a partially complemented MiMe genotype comprising only MiMe alleles at a first MiMe locus of the one or more MiMe loci and at least one MiMe allele and at least one non-MiMe allele at a second MiMe locus of the one or more MiMe loci.

127. The method of embodiment 126, wherein the subpopulation of genetically uniform polyploid potato seed is triploid, tetraploid, pentaploid, hexaploid, heptaploid, or octoploid.

128. The method of embodiment 126 or 127, wherein the population of polyploid potato seed has an average pairwise genetic uniformity of at least 80%, at least 85%, at least 90%, at least 95%, at least 96%, at least 97%, at least 98%, at least 99%, or 100% as measured by the Jaccard similarity coefficient.

129. The population of any one of embodiments 126-128, wherein the population of polyploid potato seed comprises the subpopulation of genetically uniform polyploid potato seed in an amount of at least 70%, at least 90%, at least 95%, at least 96%, at least 97%, at least 98%, or at least 99% of the total number of seeds.

130. The population of embodiment 126-129, wherein each pair of seeds in the subpopulation of genetically uniform polyploid potato seed has a pairwise identity of at least 95%, at least 96%, at least 97%, at least 98%, at least 99%, or 100% as measured by the Jaccard similarity coefficient.

131. The population of any one of embodiments 126-130, wherein the subpopulation of genetically uniform polyploid potato seed has a partially-complemented MiMe genotype comprising:

(A)

(a) only MiMe alleles at one or more MiMe loci of a first MiMe component;

(b) one or more MiMe alleles and one or more non-MiMe alleles at a first MiMe locus of a second MiMe component, and one or more MiMe alleles and one or more non-MiMe alleles at a second MiMe locus of the second MiMe component; and (c) either (i) only MiMe alleles at one or more MiMe loci of a third MiMe component, or (ii) one or more MiMe alleles and one or more non-MiMe alleles at a first MiMe locus of the third MiMe component, and one or more MiMe alleles and one or more non-MiMe alleles at a second MiMe locus of the third MiMe component, wherein the first MiMe component, the second MiMe component, and the third MiMe component are selected from the group consisting of (1) the component of sister chromatid cohesion during the first division of meiosis, (2) the component of DNA double strand breakage during meiotic recombination, and (3) the component of progression through the second division of meiosis, and each of the first MiMe component, the second MiMe component, and the third MiMe component are different MiMe components;

(B)

(a) only MiMe alleles at one or more MiMe loci of a first MiMe component; and (b) one or more MiMe alleles and one or more non-MiMe alleles at a first MiMe locus of a second MiMe component, and one or more MiMe alleles and one or more non-MiMe alleles at a second MiMe locus of the second MiMe component, wherein the first MiMe component and the second MiMe component are selected from the group consisting of (2) the component of DNA double strand breakage during meiotic recombination and (4) the component of progression through the first division of meiosis and each of the first MiMe component and the second MiMe component are different MiMe components; or (C)

(a) only MiMe alleles at one or more MiMe loci of a first MiMe component, wherein the first MiMe component is the component of DNA double strand breakage during meiotic recombination;

(b) one or more MiMe alleles and one or more non-MiMe alleles at one or more MiMe loci of a second MiMe component;

(c) one or more MiMe alleles and one or more non-MiMe alleles at one or more MiMe loci of a third MiMe component; and (d) one or more MiMe alleles and one or more non-MiMe alleles at one or more MiMe loci of a fourth MiMe component, wherein the second MiMe component, the third MiMe component, and the fourth MiMe component are selected from the group consisting of (1) the component of sister chromatid cohesion during the first division of meiosis, (3) the component of progression through the second division of meiosis, and (4) the component of progression through the first division of meiosis, and each of the second MiMe component, the third MiMe component, and the fourth MiMe component are different MiMe components.

132. The method of any one of embodiments 126-131, wherein the subpopulation of genetically uniform polyploid potato seed comprises:

(1) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(2) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(3) a complete MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(4) a partial MiMe genotype comprising (i) at least one MiMe allele and at least one non-MiMe allele at one or more OSD1 loci, wherein each of the MiMe alleles at the one or more OSD1 loci comprise one or more genetic modifications resulting in decreased expression of OSD1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(5) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(6) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(7) a complete MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(8) a partial MiMe genotype comprising (i) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(9) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(10) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(11) a complete MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more PAIR1 loci, wherein each of the MiMe alleles at the one or more PAIR1 loci comprise one or more genetic modifications resulting in decreased expression of PAIR1;

(12) a partial MiMe genotype comprising (i) at least one MiMe allele and at least one non-MiMe allele at one or more TDM1 loci, wherein each of the MiMe alleles at the one or more TDM1 loci comprise one or more genetic modifications resulting in decreased expression of TDM1, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1;

(13) a complete MiMe genotype comprising (i) an os allele, wherein the subpopulation of genetically uniforms seed is homozygous for the os allele, (ii) only MiMe alleles at one or more REC8 loci, wherein each of the MiMe alleles at the one or more REC8 loci comprise one or more genetic modifications resulting in decreased expression of REC8, and (iii) only MiMe alleles at one or more SPO11-1 loci, wherein each of the MiMe alleles at the one or more SPO11-1 loci comprise one or more genetic modifications resulting in decreased expression of SPO11-1;

(14) a partial MiMe genotype comprising (i) an os allele, wherein the subpopulation of genetically uniforms seed is heterozygous for the os allele, (ii) at least one MiMe allele and at least one non-MiMe allele at one or more REC8 loci, wherein each of the MiMe alleles at the one or more REC8 loci comprise one or more genetic modifications resulting in decreased expression of REC8, and (iii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(15) a complete MiMe genotype comprising (i) a ps allele, wherein the subpopulation of genetically uniforms seed is homozygous for the ps allele, and (ii) only MiMe alleles at one or more SPO11-1 loci, wherein each of the MiMe alleles at the one or more SPO11-1 loci comprise one or more genetic modifications resulting in decreased expression of SPO11-1;

(16) a partial MiMe genotype comprising (i) a ps allele, wherein the subpopulation of genetically uniforms seed is heterozygous for the ps allele, and (ii) at least one MiMe allele and at least one non-MiMe allele at one or more SPO11-1 loci, wherein each of the MiMe alleles at the one or more SPO11-1 loci comprise one or more genetic modifications resulting in decreased expression of SPO11-1;

(17) a partially complemented MiMe genotype comprising (i) only MiMe alleles at one or more OSD1 loci, wherein each of the MiMe alleles at the one or more OSD1 loci comprise one or more genetic modifications resulting in decreased expression of OSD1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(18) a partially complemented MiMe genotype comprising (i) only MiMe alleles at one or more CYCA1 loci, wherein each of the MiMe alleles at the one or more CYCA1 loci comprise one or more genetic modifications resulting in decreased expression of CYCA1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(19) a partially complemented MiMe genotype comprising (i) only MiMe alleles at one or more TDM1 loci, wherein each of the MiMe alleles at the one or more TDM1 loci comprise one or more genetic modifications resulting in decreased expression of TDM1, (ii) only MiMe alleles at one or more REC8 loci, wherein each of the MiMe alleles at the one or more REC8 loci comprise one or more genetic modifications resulting in decreased expression of REC8, (iii) at least one MiMe allele and at least one non-MiMe allele at one or more PAIR1 loci, wherein each of the MiMe alleles at the one or more PAIR1 loci comprise one or more genetic modifications resulting in decreased expression of PAIR1, and (iv) at least one MiMe allele and at least one non-MiMe allele at one or more SPO11-1 loci, wherein each of the MiMe alleles at the SPO11-1 locus comprise one or more genetic modifications resulting in decreased expression of SPO11-1;

(20) a partially complemented MiMe genotype comprising (i) a ps allele, wherein the subpopulation of genetically uniforms seed is heterozygous for the ps allele, (ii) an os allele, wherein the subpopulation of genetically uniforms seed is heterozygous for the os allele, (iii) at least one MiMe allele and at least one non-MiMe allele at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the SPO11-1 locus comprise one or more genetic modifications resulting in decreased expression of SPO11-1; or

(21) a partially complemented MiMe genotype comprising (i) an os allele, wherein the subpopulation of genetically uniforms seed is heterozygous for the os allele, (ii) at least one MiMe allele and at least one non-MiMe allele at one or more CYCA1 loci, wherein each of the MiMe alleles at the one or more CYCA1 loci comprise one or more genetic modifications resulting in decreased expression of CYCA1, (iii) only MiMe alleles at one or more REC8 loci, wherein each of the MiMe alleles at the one or more REC8 loci comprise one or more genetic modifications resulting in decreased expression of REC8, and (iv) only MiMe alleles at one or more SPO11-1 loci, wherein each of the MiMe alleles at the one or more SPO11-1 loci comprise one or more genetic modifications resulting in decreased expression of SPO11-1.

133. The population of any one of embodiments 126-132, wherein the subpopulation of genetically uniform polyploid potato seed comprises one or more polynucleotide sequences selected from the group consisting of SEQ ID NOs: 448-466, 468-471, 474-491, and 493-496.

134. The population of any one of embodiments 126-133, wherein germination of a seed of the subpopulation of genetically uniform polyploid potato seed results in a sterile plant that produces inviable gametes.

EXAMPLES

The presently disclosed subject matter will be better understood by reference to the following Examples, which are provided as exemplary of the inventions, and not by way of limitation.

Example 1: General Methods

GM: Methods

GM1: Identifying Homologs of Genes Underlying MiMe-Like Phenotype Across Plant Species Core genes involved in the conversion of meiosis to mitosis (mitosis instead of meiosis or MiMe) were identified through alignment with any of the canonical reference sequences for REC8, OSD1, PAIR1, SPO11-1, JASON, CYCA1 (also known as CYCLIN-A1 or as TARDY ASYNCHRONOUS MEIOSIS (TAM)), TDM1, PS1, and/or PS1-LIKE as shown in Table 5 (SEQ ID NOs 1-16). For example, core MiMe genes from various plant genomes were identified through alignment with the *Arabidopsis thaliana* sequences of REC8, OSD1, CYCA1, PAIR1, and SPO11-1. Amino acid sequences of the protein isoforms predicted from open reading frames of these genes were aligned to the NCBI RefSeq (O'Leary et al. (2016) Reference sequence (RefSeq) database at NCBI: current status, taxonomic expansion, and functional annotation. Nucleic Acids Res. 44 (D1): D733-D745), UniProtKB Swiss-Prot and TrEMBL (The UniProt Consortium (2019) UniProt: a worldwide hub of protein knowledge, Nucleic Acids Res. 47 (D1): D506-D515, https://doi.org/10.1093/nar/gkyl049) protein databases as well as MAKER-derived annotations. These alignments were performed using default parameters (gap opening penalty=11, gap extension penalty=1, E-value=10, word size=3, max score=25, query filter=SEG, substitution matrix=BLOSUM 62) in Protein-Protein BLAST 2.11.0+ (O'Leary et al. (2016)). For example, core MiMe genes in a plant's genome may be identified through alignment with the REC8, OSD1, PAIR1, and SPO11-1 sequences from *Arabidopsis thaliana.*

Candidate potato orthologs were further validated through alignments between the identified orthologs and canonical protein sequences in Table 5 using Clustal Omega-1.2.4 with default parameters (substitution matrix=GONNET) for protein-protein alignments. The canonical protein sequences used were those from *Arabidopsis thaliana* for dicots. In some cases, the canonical protein sequences available were from *Arabidopsis thaliana*. Results were filtered for relevant species and were further manually curated to remove spurious alignments. Orthologs with an amino acid consensus greater than 20% when aligning *A. thaliana* against dicot (class Magnoliopsida) protein databases were considered as candidate potato orthologs with a preference for the highest conservation of amino acid sequence and exon structure relative to the canonical set (SEQ ID NOs: 1-16) shown in Table 5.

GM1.1: Identification of Target DNA Sequences for crRNA Design

The protein Blast results were aligned to a genomic database using BLAST's "tblastn" search, specifically the Protein Query-Translated Subject BLAST 2.11.0+ with default parameters (gap opening penalty=11, gap extension penalty=1, E-value=10, word size=3, max score=25, query filter=SEG, query genetic code=universal, substitution matrix=BLOSUM 62). The corresponding nucleotide sequences of identified orthologs and any putative paralogs were extracted from this search, including 5 kb upstream of each gene, using custom shell scripts. These sequences were then aligned to each other using Clustal Omega-1.2.4 with default parameters (substitution matrix=GONNET). Most likely candidate sequences, with the highest identity to the canonical sequences and with the most conserved exon structure were used to design CRISPR RNA (crRNA) for an appropriate CRISPR-associated (Cas) nuclease.

GM1.2: Design of crRNA for DNA Editing with a Cas Nuclease

For each species of interest, the most probable candidate sequences identified from the protein BLAST, tblastn, and Clustal Omega workflows were targeted for crRNA design in Geneious Prime 2020.0.3, with protospacer adjacent motif (PAM) sites near each candidate identified for an appropriate Cas nuclease. crRNA with high specificity targeting the first or second exons or promoter sequences were generally preferred, but high-scoring crRNA targeting later exons were also selected. Resulting sequences were exported and scaffolds for an appropriate Cas nuclease were added. Functional crRNAs were synthesized by IDT (Integrated DNA Technologies, Newark, NJ, USA) using standard RNA synthesis. The process was repeated for each target gene, including REC8, OSD1, PAIR1, SPO11-1, JASON, CYCA1 (e.g., CYCA1-1, CYCA1-2 and CYCA1-3 from potato), TDM1, PS1, and/or PS1-LIKE. crRNA were screened for editing efficiency in protoplasts.

GM2: Ribonucleoprotein Preparation

To prepare ribonucleoproteins (RNPs), 2 μL of New England Biolabs buffer (NEBuffer™) 2.1 (10× stock) was placed into a 1.5 mL microcentrifuge tube with 10-600 pmol of crRNA and with an equal amount of the selected Cas nuclease protein. The final volume was adjusted to 20 μL using nuclease-free water. The solution was prepared fresh and used after a 15-minute incubation at room temperature.

GM3: Sequence-Based Edit Confirmation

Primers were designed to amplify each gene, and protoplasts were generated. Further details on plant selection, plant growth, protoplast generation, and protoplast transfection, are provided in the species-specific protocols in the Examples below.

Some transfected protoplasts were incubated at room temperature for 24 to 48 hours, then lysed and one or more long-range direct polymerase chain reactions (PCRs) were performed on the crude lysates. Other transfected protoplasts were regenerated, and DNA was then extracted from these protoplasts' regenerated callus, leaf, or other plant tissue. PCR products were pooled by transfection sample and a seqWell™ (Beverly, MA, USA) library preparation was performed to generate an Illumina (Illumina, San Diego, CA, USA) library. Samples were loaded onto an Illumina iSeq (Illumina, San Diego, CA, USA) and sequenced with a paired-end 150 nt sequencing kit. Sequences were analyzed by aligning FASTQ files to reference sequences and mutations adjacent to target sites for each gene were tabulated relative to a control. Editing efficiency was calculated based on the frequency of observed mutations in the reads obtained for a given sample, and this information was used to calculate how many plants should be screened to identify the multi-gene knockouts required to induce the clonal gamete production.

PCR amplicons were used to prepare Illumina sequencing libraries using plex Well 96 kits (seqWell™, Beverly, MA, USA) and libraries were sequenced on an Illumina iSeq (Illumina, San Diego, CA, USA). FASTQ data sets were aligned to the corresponding reference genomes using the BWA-MEM algorithm (Li, H. (2013) Aligning sequence reads, clone sequences and assembly contigs with BWA-MEM. arXiv preprint arXiv: 1303.3997) and variants were visualized and quantified using custom scripts. Editing efficiency was calculated as the fraction of reads in an edited sample with on-target mutations relative to an unedited control. Editing efficiency was determined for each guide and used to estimate the minimum number of plants needed to recover the required multi-gene knockout.

GM4: Flow Cytometry

Flow cytometry was performed on parent plants and on the progeny using the methods of Galbraith et al. 1983 (Rapid flow cytometric analysis of the cell cycle in intact plant tissues. Science. 220 (4601): 1049-1051). Further details on parent plant selection and methods of crossing are provided in the species-specific protocols in the Examples below. Briefly, intact nuclei were extracted, filtered, and stained with propidium iodide as per instructions of the CyStain® PI Absolute P kit (Sysmex America, Lincolnshire, IL, USA). DNA content of nuclei was determined by applying the samples to a BD Accuri C6 Flow Cytometer. Gating was performed and genomic DNA content was calculated by comparing the peak area for the sample to the known position of a control with known ploidy. The ploidy of the unknown samples was determined based on relative comparison to each control.

GM5: Analysis of genetic uniformity using the Jaccard similarity coefficient The Jaccard similarity coefficient was used to measure genetic uniformity of populations of seeds. The Jaccard index, Jaccard similarity index, or Jaccard similarity coefficient (Jaccard, P. (1908) Nouvelles Recherches sur 1a Distribution Florale. Bulletin de la Société Vaudoise des Sciences Naturelles. Vol. 44) is a metric used to compare the similarity of two sets. In the context of molecular plant genetics, the Jaccard index, Jaccard similarity index, or Jaccard similarity coefficient, is commonly applied to quantify the pairwise genetic similarity or uniformity of plants based on the presence or absence of shared alleles at loci spread throughout the genome (Paz and Veilleux (1997). Genetic diversity based on randomly amplified polymorphic DNA (RAPD) and its relationship with the performance of diploid potato hybrids. Journal of the American Society for Horticultural Sci. 122 (6): 740-747; Vosman et al. (2004). The establishment of 'essential derivation' among rose varieties, using AFLP. Theoretical and Applied Genetics. 109:1718-1725; Noli et al. (2013). Criteria for the definition of similarity thresholds for identifying essentially derived varieties. Plant Breeding. 132 (6): 525-531; Vijayakumar et al. (2021) High temperature induced changes in quality and yield parameters of tomato (*Solanum lycopersicum* L.) and similarity coefficients among genotypes using SSR markers. Heliyon. 7 (2); Dalamu et al. (2023). Genetic Diversity and Population Structure Analyses Using Simple Sequence Repeat Markers and Phenotypic Traits in Native Potato Collection in India. Potato Research: 1-25).

The Jaccard similarity coefficient is defined as the ratio of the number of shared items to the total number of distinct items in the two sets. In the context of molecular plant genetics, it can be used to quantify the proportion of shared alleles between two plants.

The formula for calculating the Jaccard similarity coefficient is:

$$J(A,B)=|A\cap B|/|A\cup B|$$

Where A represents the set of unique alleles without duplication in one plant, B represents the set of unique alleles without duplication in the other plant, $|A\cap B|$ represents the number of shared alleles (the cardinality of the intersection) between the plants, and $|A\cup B|$ represents the number of distinct alleles (the cardinality of the union) between the plants. This formula computes the cardinality of the intersection (common elements) of two sets (the shared alleles) divided by the cardinality of the union (all alleles) of the two sets (all distinct alleles present). The resulting value of the Jaccard similarity coefficient ranges from 0 to 1, where 0 indicates no shared alleles, and 1 indicates complete uniformity. The average pairwise genetic uniformity of the populations of seed was calculated as the average Jaccard similarity coefficient of all possible pairs of plants within the population. In the context of genetic pairwise similarity estimations, the size of A should be the same as, or very close to, the size of B to avoid misinterpretation.

Genotyping results found in the Examples below (such as in Example 2's section PR5, Example 5's section ZR4, and Example 7's section AR5) were encoded so that each allele at each locus represents a unique member of the set of total alleles. The number of shared alleles between each pair of progeny were divided by the total number of distinct alleles present in the two plants, and the results are the Jaccard index, Jaccard similarity index, or Jaccard similarity coefficient.

GM6: Population Genotyping

All relevant parent and progeny plants were sequenced via whole genome shotgun (WGS) sequencing. DNA samples were sequenced by Novogene. Libraries were prepared using the NEBNext® Ultra™ II for DNA Library Prep kit, and paired-end 2×150 reads were sequenced on an Illumina NovaSeq 6000 or NovaSeq X plus. Germline SNPs and small indels were called in all relevant parents using a standard whole genome variant calling pipeline. WGS data was aligned to a reference genome with BWA-MEM (Li, H. (2013) Aligning sequence reads, clone sequences and assembly contigs with BWA-MEM. arXiv preprint arXiv: 1303.3997). PCR duplicates were removed and SNPs and small indels were called and jointly genotyped with GATK (McKenna, A et al. (2010) The Genome Analysis Toolkit: a MapReduce framework for analyzing next-generation DNA sequencing data. Genome research, 20 (9), pp. 1297-1303). Tri-allelic and tetra-allelic markers were established to genotype populations.

Tri-allelic (containing three alleles) markers were used when one parent was expected to contribute one distinct haplotype while the other parent was expected to contribute two distinct haplotypes. Pairs of SNPs that were close enough to be directly phased by 150 bp Illumina reads were used. Each SNP was unique/exclusive to one of the parents. One SNP/parent was homozygous while the other was heterozygous (REF/ALT or ALT1/ALT2). To genotype progeny, the inventors looked for the presence of both ALT alleles (one from each parent) as well as the presence of the reference allele or second alternate allele of the heterozygous SNPs. If all alleles were observed and phasing was consistent with parental haplotypes, then the locus was genotyped as tri-allelic.

Tetra-allelic (containing four alleles) markers were used when both parents were expected to contribute two distinct haplotypes. Trios of SNPs that were close enough to be directly phased by 150 bp Illumina reads were used. One SNP was unique/exclusive to one parent and the two other SNPs were unique/exclusive to the other parent. All SNPs were heterozygous. The ALT alleles of the two SNPs exclusive to the same parent were on opposing haplotypes. To genotype progeny, the inventors looked for the presence of all three ALT alleles (one from one parent and two from the other) as well as the presence of the reference allele or second alternate allele of the solo heterozygous SNPs. If all alleles were observed and phasing was consistent with parental haplotypes, then the locus was genotyped as tetra-allelic.

After establishing markers, markers were filtered, genotyped, and checked for quality across all progenies (via WGS data) using a combination of manual and custom automated techniques.

Example 2: Generating Genetically Uniform Tetraploid Hybrid Potato

PM: Methods

PM1: Plant Materials and Protoplast Isolation

Plants from potato accessions that were selected and tested included F1 hybrids between the doubled monoploid DM 1-3 516 R44 (*Solanum tuberosum* Group Phureja, also referred to as "DM1-3" or "DM") and the diploid S7 inbred M6 (*Solanum chacoense*); F1 hybrids between the doubled monoploid DM 1-3 516 R44 (*Solanum tuberosum* Group Phureja) and M18 (the diploid S5 inbred diploid derived from the dihaploid *S. tuberosum* ssp. *tuberosum* clone US-W4); and dihaploid *Solanum tuberosum* ssp. *tuberosum* lines derived from the tetraploid commercial cultivar Atlantic.

The plant material was propagated in vitro via internode cuttings on Murashige & Skoog Modified BC Potato Medium containing sucrose and grown under 16-hour day with cool white fluorescent lighting. Approximately one gram of leaves from 2-3 week old explants were removed under aseptic conditions and placed in sterile water. Other diploid *Solanum* spp. were also selected and propagated in the same manner.

Leaves were sliced into thin sections approximately 1 mm in width and incubated in digest solution overnight. (See, e.g., Clasen et al. (2016). Improving cold storage and processing traits in potato through targeted gene knockout. Plant biotechnology journal, 14 (1), 169-176; Fossi et al. (2019). Regeneration of *Solanum tuberosum* plants from protoplasts induces widespread genome instability. Plant physiology, 180 (1), 78-86; Masson et al. (1987). Plant regeneration from protoplasts of diploid potato derived from crosses of *Solanum tuberosum* with wild *Solanum* species. Plant Science, 53 (2), 167-176; Nicolia et al. (Nicolia et al. (2015) Targeted gene mutation in tetraploid potato through transient TALEN expression in protoplasts. Journal of biotechnology. 204:17-24; Veillet et al. (2019). The *Solanum tuberosum* GBSS1 gene: a target for assessing gene and base editing in tetraploid potato. Plant cell reports, 38 (9), 1065-1080). Sliced leaves in the digest solution were then incubated overnight at 24° C. The next day, protoplasts were liberated from the leaf tissue with 15-minute shaking at 40 RPM at room temperature.

Protoplasts were harvested through 100 μm sterile cell filters into sterile 50 mL conical tubes and centrifuged at 100×g for 5 minutes. Supernatant was removed and replaced with wash solution (See, e.g., Clasen et al. 2016; Fossi et al. 2019; Masson et al. 1987; Nicolia et al. 2015; Veillet et al. 2019). Cells were then gently resuspended by rocking and slowly layered onto a 0.43 M sucrose solution. Tubes were centrifuged at 100×g for 15 minutes. After 15 minutes, a thick dark band of protoplasts appeared at the interface of the two solutions. This band was harvested in one continuous motion using a sterile serological pipette and combined with transformation buffer (See, e.g., Clasen et al. 2016; Fossi et al. 2019; Masson et al. 1987; Nicolia et al 2015; Veillet et al. 2019). Harvested cells were quantified using a Burker hemocytometer and stored at 4° C. in the dark until transfection. A sample was reserved to test cell viability using FDA staining as described by Larkin (1976. Purification and viability determinations of plant protoplasts. Planta. 128 (3): 213-216).

PM2: Protoplast Transfection

Transfection proceeded as described in the art. (See, e.g., Clasen et al. 2016; Fossi et al. 2019; Masson et al. 1987; Nicolia et al 2015; Veillet et al. 2019). Protoplasts were centrifuged at 50×g for 10 minutes and resuspended in a volume of transformation buffer to achieve a cell density of $1\times10^6$ protoplasts/mL. 20 μL of freshly prepared RNP as described in section GM2 was added to the bottom of a 15 mL round bottom tube and 100 μL of protoplasts suspended in the transformation buffer were mixed with the RNP solution. Next, 120 μL of PEG solution was added and gently mixed by rotating the tubes. After a 15-minute incubation at room temperature the protoplasts were washed twice following centrifugation at 50×g for 10 minutes using a wash solution consisting of 0.4M D-Mannitol, 15 mM $CaCl_2$), and 5 mM HEPES (4-(2-hydroxyethyl)-1-piperazineethanesulfonic acid). A final centrifugation was performed and transfected cells were resuspended in culture medium. (See, e.g., Clasen et al. 2016; Fossi et al. 2019; Masson et al. 1987; Nicolia et al 2015; Veillet et al. 2019).

The protoplasts were transfected with RNPs designed to target MiMe loci identified as described in GM1 and prepared as described in GM2

PM3: Encapsulation and Regeneration of Plants

An equal volume of transfected cells was combined with a 3.2% sodium alginate solution and then gently mixed together. The resulting solution was pipetted on top of setting agar to solidify the alginate matrix, creating alginate lenses. Lenses were incubated for 30 minutes at room temperature and then transferred to a new petri dish with 20 mL of culture medium.

Plant regeneration protocols proceeded as described in the art. (See, e.g., Clasen et al. 2016; Fossi et al. 2019; Masson et al. 1987; Nicolia et al 2015; Veillet et al. 2019). The alginate lenses in culture medium were placed at 24° C. in the dark for about 3-4 weeks, during which time cell division and signs of mini calli induction were: observed through an inverted microscope. When mini-calli reached 1 mm in size, culture medium was replaced with a first callus induction medium as described in the art (see, e.g., Clasen et al. 2016; Fossi et al. 2019; Masson et al. 1987; Nicolia et al 2015; Veillet et al. 2019) and light was gradually increased by first covering and then removing layers of cheesecloth under cool white fluorescent bulbs. After 3-6 weeks, or when minicalli reach approximately 2 mm in diameter, the mini calli were liberated from the alginate using a citric acid solution consisting of 20 mM sodium citrate and 0.5 M sorbitol. Mini calli were then washed in callus induction medium and incubated in a second callus induction medium, then replacing the second callus induction medium with a freshly prepared solution on a weekly basis. (See, e.g., Clasen et al. 2016; Fossi et al. 2019; Masson et al. 1987; Nicolia et al 2015; Veillet et al. 2019). Finally, large green calli of 3-5 mm were removed and placed on Petri dishes with shoot induction media. (See, e.g., Clasen et al. 2016; Fossi et al. 2019; Masson et al. 1987; Nicolia et al 2015; Veillet et al. 2019). Calli were then transferred every 2 weeks to a fresh shoot induction medium until shoots emerged, in about 2-3 months. When shoots reached a size of approximately 1 cm on shoot induction media, they were excised from the calli and transferred to Murashige & Skoog Modified BC Potato Medium with sucrose and 16-hour day length under cool white fluorescent bulbs.

Plants were then propagated by nodal segments and genotyped using the same sequencing methods described in Example 1's section GM3. Plants containing bi-allelic mutations in target MiMe genes were further multiplied and prepared for planting.

PM4: Plant Growth and Crossing Conditions

Once plants had completely regenerated in vitro from protoplasts, rooted plantlets were transferred from tissue culture into 1-gallon pots with peat substrate and grown under greenhouse conditions with a continued 16-hour day-length. Freshly transplanted in vitro plants were covered with humidity domes for up to 3 days.

Regenerated plants with confirmed edits in each target gene, including REC8, CYCA1, and PAIR1 and/or SPO11, were transplanted from tissue culture into peat substrate as described in the previous paragraph. When plants produced flowers, pollen was collected from the male and cross pollinations were performed. About 4-6 weeks after pollination, berries were harvested and potato true seeds were extracted, dried, and prepared for planting.

PM5: Potato True Seed Germination and Genotyping

Following extraction, potato true seeds were surface disinfected for 20 minutes in a sonic bath using a ten percent bleach solution containing 20 μL of Tween 20 (Sigma) in a final volume of 50 mL. Disinfected potato true seeds were rinsed twice with sterile deionized water and were germinated in Murashige & Skoog (M&S) Modified BC Potato Medium with sucrose and 16-hour day length under cool white fluorescent bulbs. For in vitro germination, berries were surface disinfected and sliced open under aseptic conditions. Embryos were removed carefully and plated directly. Plants were transferred every two weeks to fresh medium and leaves were removed for DNA extraction during this process.

High-quality genomic DNA was extracted from the leaves of randomly selected plants of each population and used for genotyping through Qiagen DNeasy Plant Mini kits (Cat. No. 69104) (QIAGEN, Germantown, MD, USA). Purity was determined using a spectrophotometer, Nanodrop™ One-C (ThermoFisher, Waltham, MA, USA), and DNA was quantified on a fluorometer, Qubit™ Flex Fluorometer (Cat. No. Q33327) (ThermoFisher, Waltham, MA, USA). Samples were adjusted to a final concentration of 20 ng/μL. Markers were established and populations were genotyped as described in GM6.

PR: Results

PR1: Guide RNA Screening

Figure 14A:
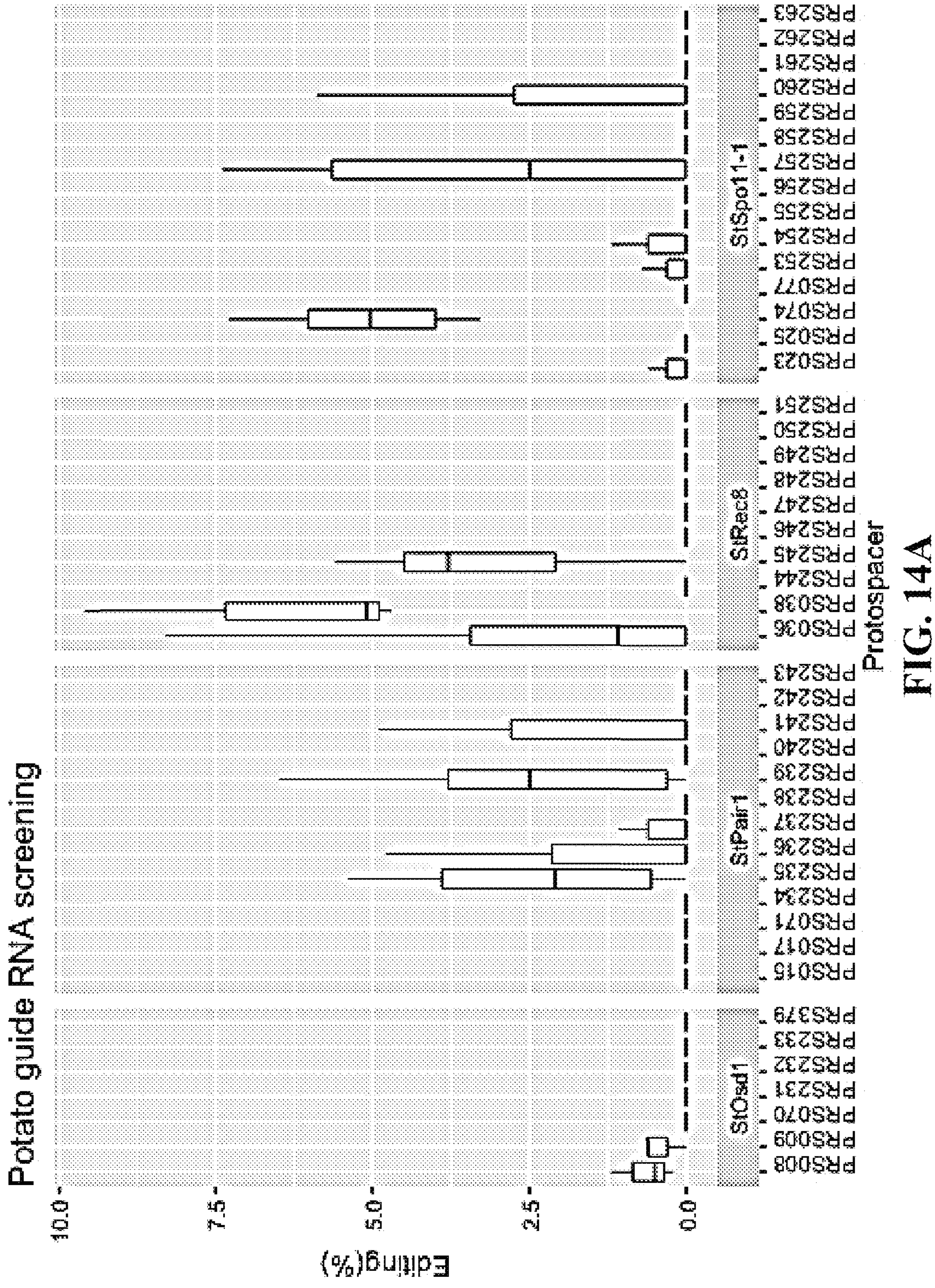
FIGS. 14A-14B show the screening results for guide RNA screening for edits in potato.
Figure 14B:
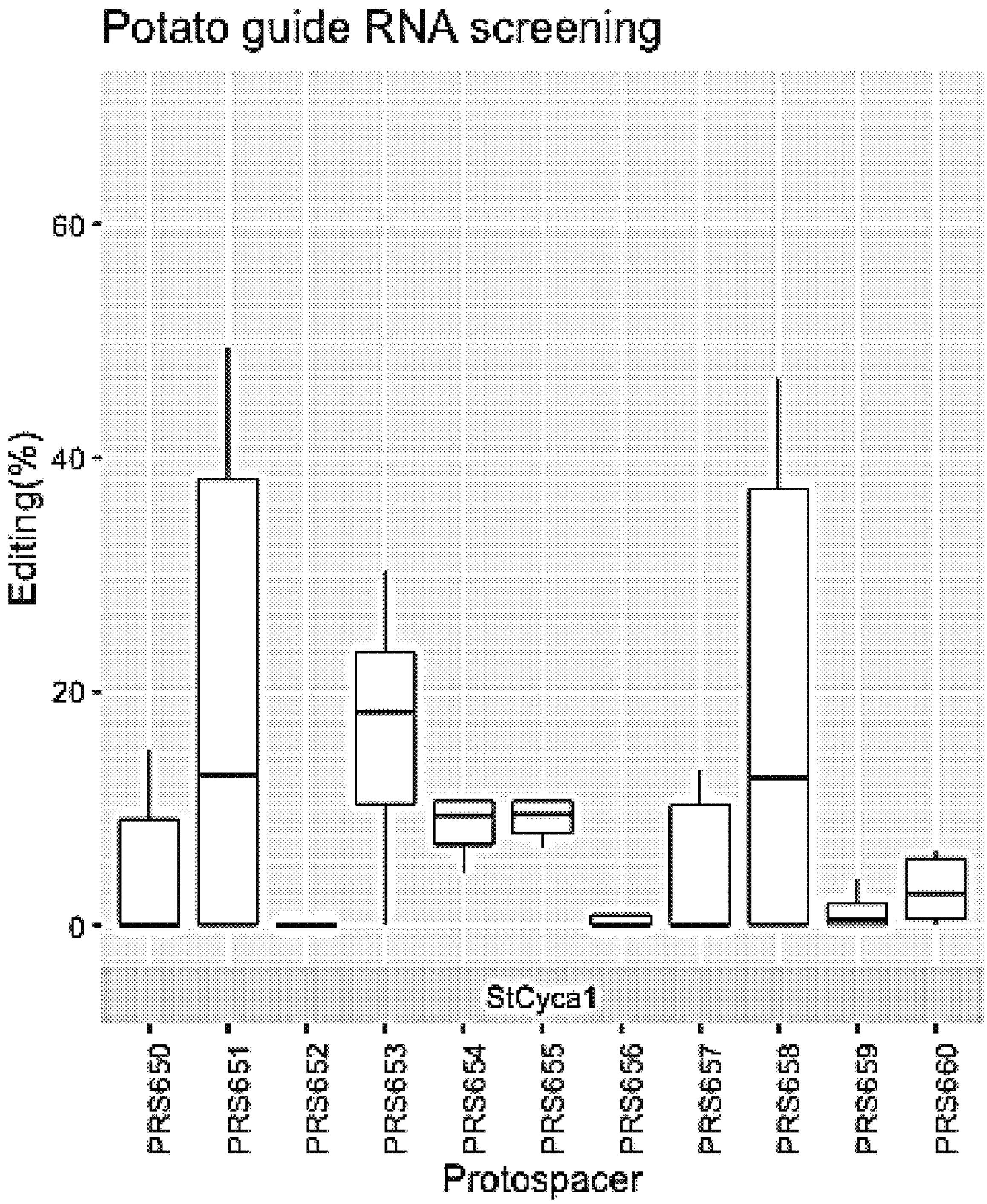

A total of 57 guide RNAs (SEQ ID NOs: 17-71, shown in Table 7A) targeting conserved regions of the OSD1, CYCA1, SPO11-1, REC8, or PAIR1 genes provided by SEQ ID NOs: 72-126, shown in Table 7B, were transfected in triplicate in protoplasts from the *Solanum tuberosum* or *Solanum chacoense* accessions described in section PM1. Editing efficiency was calculated by sequencing as described in Example 1's section GM3, and the resulting data presented in FIG. 14A and FIG. 14B. Based on this data, guide RNAs SEQ ID NO: 50 and SEQ ID NO: 52 were chosen for editing the OSD1 gene; guide RNA SEQ ID NO: 69 was chosen for editing the CYCA1 gene; guide RNAs SEQ ID NO: 47, SEQ ID NO: 39 and SEQ ID NO: 29 were chosen for editing the PAIR1 gene; guide RNA SEQ ID NO: 33 was chosen for editing the REC8 gene; and guide RNA SEQ ID NO: 31 was chosen for editing the SPO11-1 gene.

TABLE 7A

Sequences for guide RNAs targeting MiMe genes in potato.

| SEQ ID NO. | PRSG# | Guide RNA sequence |
|---|---|---|
| 17 | PRS234G | CUUUCAGUGGAAAGCUUACG |
| 18 | PRS242G | CUCUUUCUUGAGAACCCAAU |
| 19 | PRS259G | GCACUCUAUAAUGCAGAACA |
| 20 | PRS235G | AAGGUCCCCUCCAGGCUAGC |
| 21 | PRS243G | CCACAUCACGUAAAUUAAAA |
| 22 | PRS260G | AUGGAAGCGCUAUCUACCUU |
| 23 | PRS236G | AAUAUGCAACAUGCCUGAAU |
| 24 | PRS253G | AACGCUUUCCCUCCAUUUUC |
| 25 | PRS261G | GCAGGAUUUACUCGUUCCAU |
| 26 | PRS254G | GUUGUGGAAAAGGAAUCAGG |
| 27 | PRS262G | UGUAGCUCUUGCAGCUCUGG |
| 28 | PRS255G | AGUUGUGGAAAAGGAAUCAG |
| 29 | PRS239G | AGCAAGACCUUGGCUAAAGA |
| 30 | PRS256G | GUUGAGAGUUCUUGUGAUAG |
| 31 | PRS257G | CUCUCCCUAGACUCACCAAG |
| 32 | PRS258G | CCACAACUAAAACGUAUUGA |
| 33 | PRS036G | GAGUGUAGAGUGGCCGCCAU |
| 34 | PRS246G | AAGCAUGAAUUACUCUGCAG |
| 35 | PRS247G | CAGUUGAUCCAGAUAAUAUC |
| 36 | PRS248G | GGUUUAGAUAUCUAAUCGUC |
| 37 | PRS237G | AUAGUAUCUGCAAAUGAAGU |

TABLE 7A-continued

| Sequences for guide RNAs targeting MiMe genes in potato. | | |
|---|---|---|
| SEQ ID NO. | PRSG# | Guide RNA sequence |
| 38 | PRS249G | AAGUUAUUUCGUGGAUUGAG |
| 39 | PRS238G | UAGGUCAUCAAUGAUUGUAG |
| 40 | PRS263G | AAAGGUAAAUCUGGAUCGAC |
| 41 | PRS250G | CAUAAUGUACCAUCGUGAAA |
| 42 | PRS251G | CGAAGCAUACCCAUGAGAAU |
| 43 | PRS240G | ACCUUGCAUGAGGAGGAAGA |
| 44 | PRS244G | UGAUUUGGUAUUUUCAGGUG |
| 45 | PRS241G | GUGGAUCGACUGGAGCGGUU |
| 46 | PRS245G | UAUCUCUCUCUUUGCUGUGA |
| 47 | PRS071G | CCUCAUAUCAACUACACACGA |
| 48 | PRS070G | UCUCAAGCGAGCUCUUGUUCU |
| 49 | PRS038G | CUAUUGAGUUUCGAGUGUAG |
| 50 | PRS008G | GACGUGGGGUGAUCAAAGAA |
| 51 | PRS015G | AGUCUCUUCUCGUGUGUAGU |
| 52 | PRS009G | AUCACCCCACGUCCAAAAAC |
| 53 | PRS231G | GCUUUAUAUAGUUCUGGAUG |
| 54 | PRS232G | CUCCAUAGGCCAUUGAAAGA |
| 55 | PRS017G | CUUUCAGGAACUGACCAUUU |
| 56 | PRS233G | GCACUUUACCAACAGAUCUG |
| 57 | PRS379G | AUGUCAAUGCGCUGAUUUUC |
| 58 | PRS074G | CUUAUGAGUGUUAGUGGCUGC |
| 59 | PRS077G | CUCCCAGAUUCCACAUACCGC |
| 60 | PRS025G | UGAACCGAUCGAUGUAGAUC |
| 61 | PRS650G | UUGGCCGCUCCAGCAUUCAA |
| 62 | PRS651G | GAAGGCACCAUGUACGUCCA |
| 63 | PRS652G | AUAUGUUCUGAGAUGUAGAG |
| 64 | PRS653G | UUCCAGCAGCAGAUAUAUGC |
| 65 | PRS654G | UUAUGCUCCAUCACUCAUUG |
| 66 | PRS655G | ACAAUUAACUACAUUGAUCG |
| 67 | PRS656G | GGGCAACUUGAUGGACAGAC |
| 68 | PRS657G | UUACGAUGCGAUCAUCAUGC |
| 69 | PRS658G | CUCAGGGACUGCUGUUCUGC |
| 70 | PRS659G | UCUAUUUUUUAUUCCAGCAG |
| 71 | PRS660G | GAAACUCCUAACAGAACUCU |

TABLE 7B

| Sequences for conserved regions of MiMe genes targeted in potato. | | |
|---|---|---|
| SEQ ID NO. | PRS# | Target DNA sequence |
| 72 | PRS234 | CTTTCAGTGGAAAGCTTACG |
| 73 | PRS242 | CTCTTTCTTGAGAACCCAAT |
| 74 | PRS259 | GCACTCTATAATGCAGAACA |
| 75 | PRS235 | AAGGTCCCCTCCAGGCTAGC |
| 76 | PRS243 | CCACATCACGTAAATTAAAA |
| 77 | PRS260 | ATGGAAGCGCTATCTACCTT |
| 78 | PRS236 | AATATGCAACATGCCTGAAT |
| 79 | PRS253 | AACGCTTTCCCTCCATTTTC |
| 80 | PRS261 | GCAGGATTTACTCGTTCCAT |
| 81 | PRS254 | GTTGTGGAAAAGGAATCAGG |
| 82 | PRS262 | TGTAGCTCTTGCAGCTCTGG |
| 83 | PRS255 | AGTTGTGGAAAAGGAATCAG |
| 84 | PRS239 | AGCAAGACCTTGGCTAAAGA |
| 85 | PRS256 | GTTGAGAGTTCTTGTGATAG |
| 86 | PRS257 | CTCTCCCTAGACTCACCAAG |
| 87 | PRS258 | CCACAACTAAAACGTATTGA |
| 88 | PRS036 | GAGTGTAGAGTGGCCGCCAT |
| 89 | PRS246 | AAGCATGAATTACTCTGCAG |
| 90 | PRS247 | CAGTTGATCCAGATAATATC |
| 91 | PRS248 | GGTTTAGATATCTAATCGTC |
| 92 | PRS237 | ATAGTATCTGCAAATGAAGT |
| 93 | PRS249 | AAGTTATTTCGTGGATTGAG |
| 94 | PRS238 | TAGGTCATCAATGATTGTAG |
| 95 | PRS263 | AAAGGTAAATCTGGATCGAC |
| 96 | PRS250 | CATAATGTACCATCGTGAAA |
| 97 | PRS251 | CGAAGCATACCCATGAGAAT |
| 98 | PRS240 | ACCTTGCATGAGGAGGAAGA |
| 99 | PRS244 | TGATTTGGTATTTTCAGGTG |
| 100 | PRS241 | GTGGATCGACTGGAGCGGTT |
| 101 | PRS245 | TATCTCTCTCTTTGCTGTGA |
| 102 | PRS071 | CCTCATATCAACTACACACGA |
| 103 | PRS070 | TCTCAAGCGAGCTCTTGTTCT |
| 104 | PRS038 | CTATTGAGTTTCGAGTGTAG |
| 105 | PRS008 | GACGTGGGGTGATCAAAGAA |
| 106 | PRS015 | AGTCTCTTCTCGTGTGTAGT |
| 107 | PRS009 | ATCACCCCACGTCCAAAAAC |
| 108 | PRS231 | GCTTTATATAGTTCTGGATG |
| 109 | PRS232 | CTCCATAGGCCATTGAAAGA |

TABLE 7B-continued

| Sequences for conserved regions of MiMe genes targeted in potato. | | |
|---|---|---|
| SEQ ID NO. | PRS# | Target DNA sequence |
| 110 | PRS017 | CTTTCAGGAACTGACCATTT |
| 111 | PRS233 | GCACTTTACCAACAGATCTG |
| 112 | PRS379 | ATGTCAATGCGCTGATTTTC |
| 113 | PRS074 | CTTATGAGTGTTAGTGGCTGC |
| 114 | PRS077 | CTCCCAGATTCCACATACCGC |
| 115 | PRS025 | TGAACCGATCGATGTAGATC |
| 116 | PRS650 | TTGGCCGCTCCAGCATTCAA |
| 117 | PRS651 | GAAGGCACCATGTACGTCCA |
| 118 | PRS652 | ATATGTTCTGAGATGTAGAG |
| 119 | PRS653 | TTCCAGCAGCAGATATATGC |
| 120 | PRS654 | TTATGCTCCATCACTCATTG |
| 121 | PRS655 | ACAATTAACTACATTGATCG |
| 122 | PRS656 | GGGCAACTTGATGGACAGAC |
| 123 | PRS657 | TTACGATGCGATCATCATGC |
| 124 | PRS658 | CTCAGGGACTGCTGTTCTGC |
| 125 | PRS659 | TCTATTTTTATTCCAGCAG |
| 126 | PRS660 | GAAACTCCTAACAGAACTCT |

PR2: Generation of MiMe Parent Plants

Regenerated plants were screened using the sequencing methods described in section GM3. About 1% of regenerated plants screened (roughly 200 plants out of 20,000 total plants) had mutations predicted to result in either nonfunctional or non-expressed MiMe alleles, resulting in a MiMe genotype. The screened plants with these mutations were selected for crosses. These mutations were predicted to result in (i) either nonfunctional or non-expressed rec8, cyca1, and spo11-1 alleles; (ii) either nonfunctional or non-expressed rec8 and spo11-1 alleles in combination with the os allele; or (iii) either nonfunctional or non-expressed spo11-1 allele in combination with the ps allele.

Select potato plants were given designations according to the following format. The first part of the designation, "PED-PR", was used to indicate plants involved in the potato results. The second part of the designation uses capital letters to indicate the haplotypes the selected plants contain (see Table 8A). The third part of the designation uses lower case letters to indicate which edits or natural alleles were used in the selected plants (see Table 8B).

TABLE 8A

| Letter codes in PED-PR designations to indicate the haplotypes the selected plants contain. Haplotype | |
|---|---|
| DM1-3 516 R44 | A |
| M6 | B |
| M18 selfed | C |
| M18 | D |

TABLE 8A-continued

| Letter codes in PED-PR designations to indicate the haplotypes the selected plants contain. Haplotype | |
|---|---|
| Atlantic Dihaploid | E |
| Atlantic Dihaploid | F |

TABLE 8B

| Letter codes in PED-PR designations to indicate which edits or natural alleles were used in the selected plants. Edits or natural alleles | |
|---|---|
| rec8 | r |
| cyca1 | c |
| spo11-1 | s |
| ps | p |
| os | o |

Two unique plants designated PED-PR-AB-rcs and PED-PR-EF-res were chosen to move forward as parent MiMe plants for crossing, each of which had bi-allelic edits resulting in a MiMe genotype for rec8, cyca1 and spo11-1, and each of which produced both male and female clonal gametes. The parent MiMe plant PED-PR-AB-rcs (rec8/cyca1/spo11-1) was derived from an F1 cross between DM 1-3 516 R44 and M6. The parent MiMe plant PED-PR-EF-rcs (rec8/cyca1/spo11-1) was derived from an Atlantic dihaploid.

Three additional unique plants designated PED-PR-EF-rso-2, PED-PR-AB-rso and PED-PR-EF-rso-1 were chosen to move forward as parent MiMe plants for crossing, each of which had bi-allelic edits resulting in a MiMe genotype for rec8 and spo11-1 in combination with the os allele. All three parent MiMe plants PED-PR-EF-rso-2 (rec8/spo11-1/os), PED-PR-AB-rso (rec8/spo11-1/os) and PED-PR-EF-rso-1 (rec8/spo11-1/os) produced male sterility and female clonal gametes. The parent MiMe plants PED-PR-EF-rso-2 (rec8/spo11-1/os) and PED-PR-EF-rso-1 (rec8/spo11-1/os) were each derived from an Atlantic dihaploid. The parent MiMe plant PED-PR-AB-rso (rec8/spo11-1/os) was derived from an F1 cross between DM1-3 516 R44 and M6.

Two unique plants designated PED-PR-AB-sp and PED-PR-AD-sp were chosen to move forward as parent MiMe plants for crossing, each of which had bi-allelic edits resulting in a MiMe genotype for spo11-1 in combination with the ps allele. Both parent MiMe plants produced male clonal gametes and female sterility. The parent MiMe plant PED-PR-AB-sp (spo11-1/ps) was derived from an F1 cross between DM 1-3 516 R44 and M6. The parent MiMe plant PED-PR-AD-sp (spo11-1/ps) was derived from an F1 cross between DM 1-3 516 R44 and M18.

Microscopic analysis of microsporogenesis showed that these parent MiMe plants produced dyads instead of tetrads and produced viable pollen (except in the male sterile plants). Plants with expected female clonal gametes were confirmed by test crosses with 1n and 2n pollen.

As an example, edits to the parent MiMe plant PED-PR-AB-rcs (rec8/cyca1/spo11-1) are illustrated in FIGS. 15A-15F. In that figure, the predicted protein sequences are illustrated with respect to the unedited wildtype protein sequence and a consensus sequence, wherein an "X" in the consensus sequence indicates that there is no consensus for that amino acid position; wherein a dot (".") in the parent MiMe plant sequence indicates that the respective amino acid matches the consensus sequence; and wherein a dash ("-") in the parent MiMe plant sequence indicates that the respective amino acid is present in the consensus sequence but is absent in the parent MiMe plant sample sequence. Frameshift inducing deletions in both alleles of rec8 (FIGS. 15A and 15D), cyca1 (FIGS. 15B and 15E) and spo11-1 (FIGS. 15C and 15F) result in premature stop codons. Premature stop codons are denoted by an asterisk ("*") in FIGS. 15A-15C.

PR2b: Generation of Control, Non-MiMe Parent Plants

Four unique plants designated PED-PR-EF-o, PED-PR-AABB, PED-PR-CC-o and PED-PR-AB, respectively, were chosen as parent non-MiMe plants for control crosses. PED-PR-EF-o was a dihaploid derived from the tetraploid *S. tuberosum* cultivar "Atlantic". PED-PR-AABB was derived from a tetraploidized hybrid between the *S. tuberosum* Group Phureja doubled monoploid "DM1-3 516 R44" and the S7 inbred *S. chacoense* "M6". PED-PR-CC-o was derived from a self of the *S. tuberosum* S5 inbred "M18". M18 was derived from 5 generations of selfing of the *S. tuberosum* dihaploid "US-W4". PED-PR-AB was derived from a hybrid between the *S. tuberosum* Group Phureja doubled monoploid "DM1-3 516 R44" and the S7 inbred *S. chacoense* "M6".

PR3a: Generation of Genetically Uniform Tetraploid Potato True Seed

Parent MiMe plants were crossed using hand pollination. Potato true seeds resulting from crosses were germinated following the procedures described in section PM5. In total, five genetically uniform populations of tetraploid potato true seed with either three or four haplotypes were created from the parent MiMe plants described in section PR2. The parent MiMe plants used in the crosses to generate the genetically uniform populations are outlined in Table 8C.

The first genetically uniform population of tetraploid potato true seed, referred to herein as Boosted Potato Population 1 ("BPP1"), consisted of 20 individuals with three haplotypes, derived from a cross between a female unedited selfed M18 potato plant PED-PR-CC-o and a male parent MiMe plant PED-PR-AB-sp (spo11-1/ps), which together comprise three haplotypes.

The second genetically uniform population of tetraploid potato true seed, referred to herein as Boosted Potato Population 2 ("BPP2"), consisted of 36 individuals with four haplotypes, derived from a cross between a female parent MiMe plant PED-PR-EF-rso-1 (rec8/spo11-1/os) and a male parent MiMe plant PED-PR-AB-sp (spo11-1/ps), which together comprise four haplotypes.

The third genetically uniform population of tetraploid potato true seed, referred to herein as Boosted Potato Population 3 ("BPP3"), consisted of 10 individuals with three haplotypes, derived from a cross between a female parent MiMe plant PED-PR-AB-rso (rec8/spo11-1/os) and a male parent MiMe plant PED-PR-AD-sp (spo11-1/ps), which together comprise three haplotypes.

The fourth genetically uniform population of tetraploid potato true seed, referred to herein as Boosted Potato Population 4 ("BPP4"), consisted of 12 individuals with four haplotypes, derived from a cross between a female parent MiMe plant PED-PR-EF-rso-2 (rec8/spo11-1/os) and a male parent MiMe plant PED-PR-AB-rcs expected to produce male and female clonal gametes (rec8/cyca1/spo11-1), which together comprise four haplotypes.

The fifth genetically uniform population of tetraploid potato true seed, referred to herein as Boosted Potato Population 5 ("BPP5"), consisted of 8 individuals with four haplotypes, derived from a cross between a female parent MiMe plant PED-PR-EF-rcs (rec8/cyca1/spo11-1) and a male parent MiMe plant PED-PR-AB-rcs (rec8/cyca1/spo11-1), which together comprise four haplotypes.

PR3b: Generation of Standard Tetraploid Potato True Seed

The first standard population of tetraploid potato true seed, referred to herein as Standard Potato Population 1 ("SPP1"), consisted of 8 individuals with four haplotypes, derived from a cross between a female parent non-MiMe plant PED-PR-EF-o and a male parent non-MiMe plant PED-PR-AABB.

The second standard population of diploid potato true seed, referred to herein as Standard Potato Population 2 ("SPP2"), consisted of 6 individuals with two haplotypes, derived from a cross between a female unedited selfed M18 PED-PR-CC-o and a male parent non-MiMe plant PED-PR-AB.

The parent plants used in the crosses to generate SPP1 and SPP2 are outlined in Table 8C.

TABLE 8C

Parent potato plants selected for crossing and the resulting potato populations

| | | Male Parent | | | | |
|---|---|---|---|---|---|---|
| | | PED-PR-AB-rcs | PED-PR-AB-sp | PED-PR-AB | PED-PR-AABB | PED-PR-AD-sp |
| Female Parent | PED-PR-AB-rso | | | | | BPP3 |
| | PED-PR-CC-o | | BPP1 | SPP2 | | |
| | PED-PR-EF-rcs | BPP5 | | | | |
| | PED-PR-EF-rso-1 | | BPP2 | | | |
| | PED-PR-EF-rso-2 | BPP4 | | | | |
| | PED-PR-EF-o | | | | SPP1 | |

PR4: Flow Cytometry

For each individual, young leaf tissue was used for flow cytometry. All parent MiMe plants described in section PR2 and used in the crosses described in section PR3 were shown to be diploid, having mean peak fluorescences consistent with diploid control plants. All individuals from BPP1, BPP2, BPP3, BPP4, and BPP5 were shown to be tetraploid with mean peak fluorescence values double that of diploid control plants, except for one triploid from BPP1 which was excluded from further analysis.

PR5: Genotypic Evaluation

DNA samples were sequenced by Novogene. Libraries were prepared using the NEBNext® Ultra™ II for DNA Library Prep kit and paired-end 2×150 reads were sequenced on an Illumina NovaSeq 6000. Reads were aligned to the reference genome with BWA-MEM (v0.7.17-r1188) (Li, H. 2013) and alignments were sorted and indexed with samtools (v1.15.1). Markers were established and populations were genotyped as described in GM6.

For the parent non-MiMe plant PED-PR-CC-o and the MiMe plant PED-PR-AB-sp, DNA samples were sequenced to a depth of 25,923,949,200 bp, and 31,814,370,300 bp, respectively. For the BPP1 progeny plants, DNA samples were sequenced to an average depth of 51,874,541,384 bp. For the parent MiMe plant PED-PR-EF-rso-1, DNA sample was sequenced to a depth of 28,961,600,100 bp. For the BPP2 progeny plants, DNA samples were sequenced to an average depth of 52,349,190,474 bp. For the parent MiMe plants PED-PR-AB-rso and PED-PR-AD-sp, DNA samples were sequenced to a depth of 42,150,801,600 bp and 22,856,602,500 bp, respectively. For the BPP3 progeny plants, DNA samples were sequenced to an average depth of 52,905,004,980 bp.

For the parent MiMe plants PED-PR-AB-rcs, PED-PR-EF-rcs, and PED-PR-EF-rso-2, DNA samples were sequenced to a depth of 35,057,119,200 bp, 33,124,974,900 bp, and 38,116,453,200 bp respectively. For the BPP4 progeny plants, DNA samples were sequenced to an average depth of 49,270,594,500 bp. For the BPP5 progeny plants, DNA samples were sequenced to an average depth of 50,083,712,663 bp.

For the SPP1 progeny plants, DNA samples were sequenced to an average depth of 47,781,003,814 bp. For the SPP2 progeny plants, DNA samples were sequenced to an average depth of 28,116,787,950 bp.

Figure 16A:
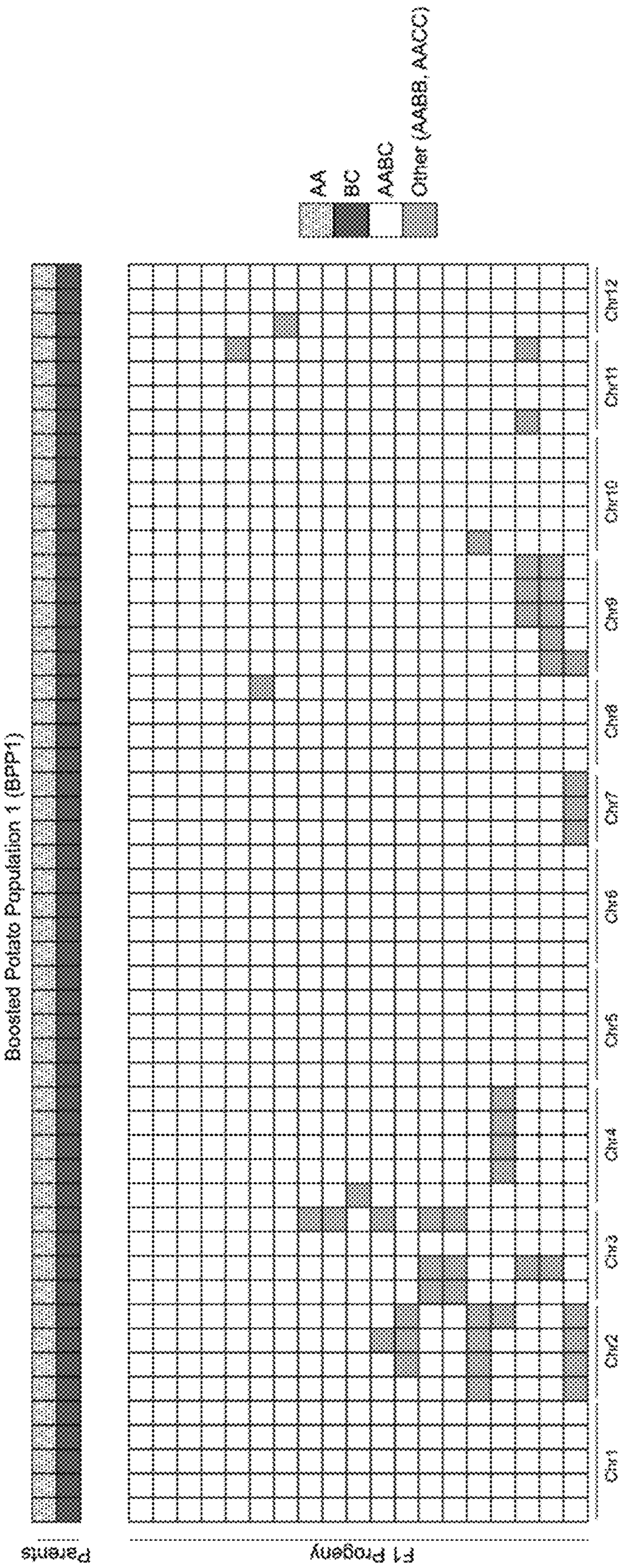
FIGS. 16A-16E show genotyping results of 50-60 tri- or tetra-allelic markers across generated MiMe progeny of potato.
Figure 19A:
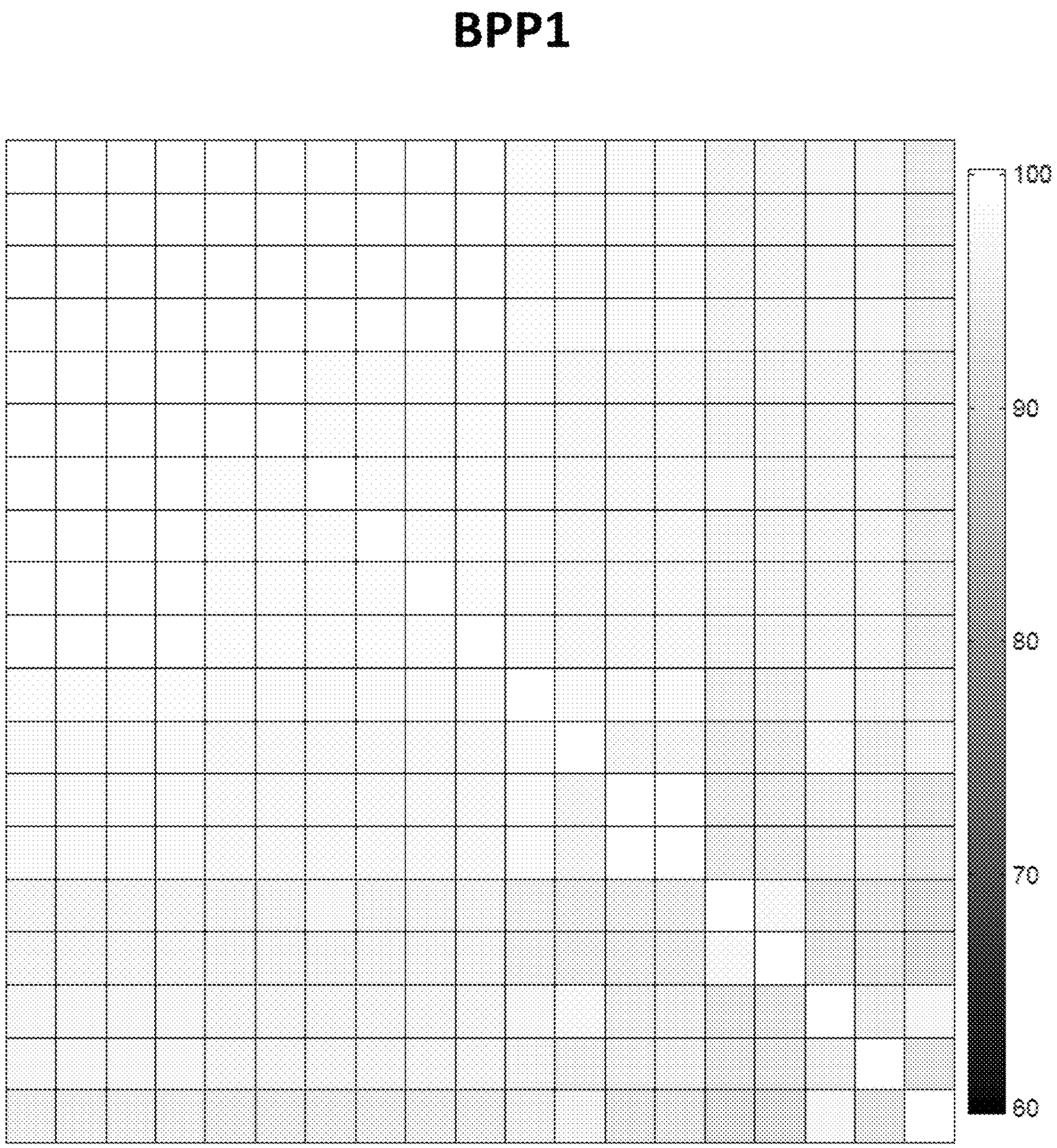
FIGS. 19A-19G show the superior uniformity of plants grown from populations of polyploid seed produced by the methods described herein as compared to control populations.
Figure 21:
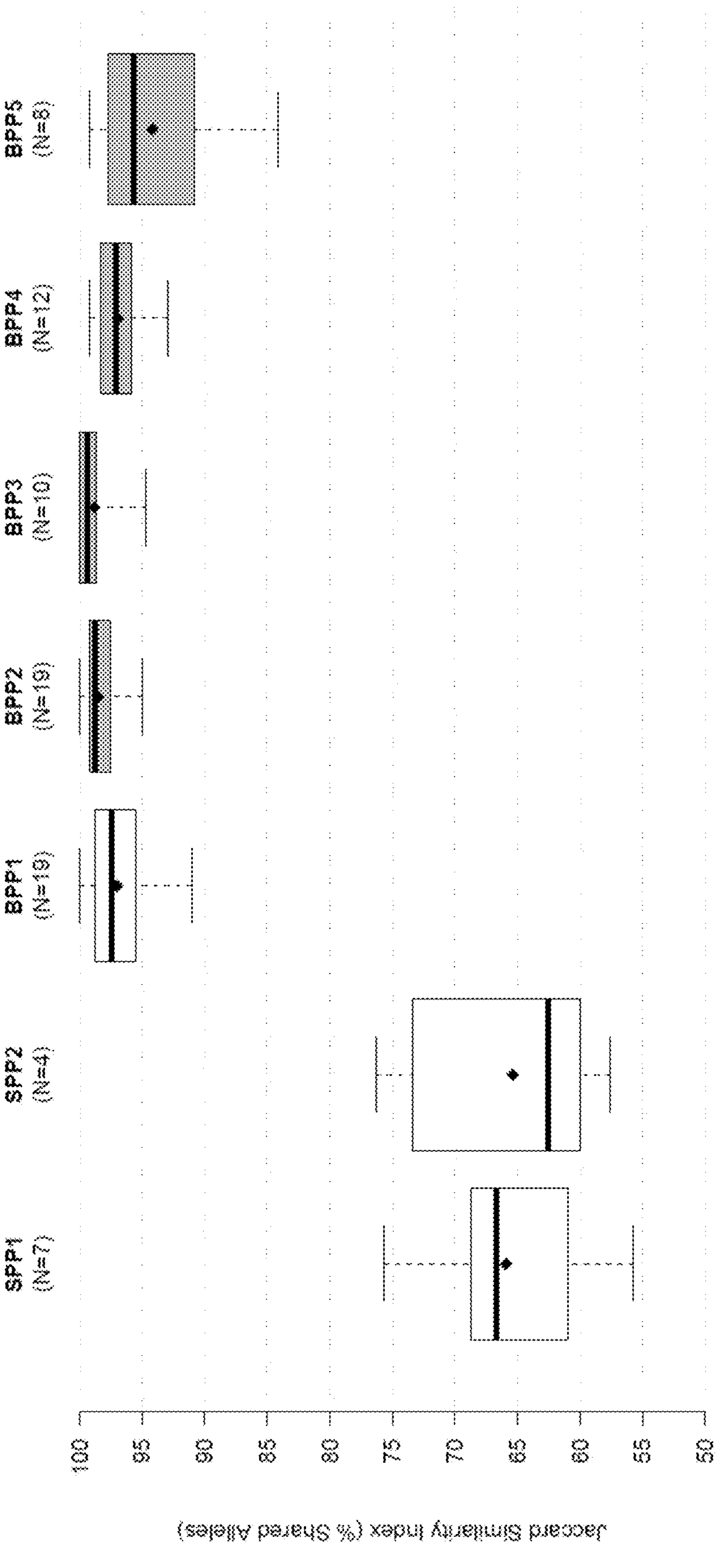
FIG. 21 illustrates the expected pairwise identity (or percentage of shared alleles as estimated by the Jaccard similarity coefficient among genotypes) of randomly selected individuals within each population (SPP1-Standard Potato Population 1, SPP2-Standard Potato Population 2, BPP1-Boosted Potato Population 1, BPP2-Boosted Potato Population 2, BPP3-Boosted Potato Population 3, BPP4-Boosted Potato Population 4, BPP5-Boosted Potato Population 5). The diamonds denote the expected or mean pairwise identity between genotyped plants in each population. The black bars are the median or second quartile. The boxes each represent the interquartile range from the first to the third quartile, and the dashed whiskers display the minimum and maximum pairwise identity between genotyped individuals in each population.

After filtering for high quality markers, a genotype matrix was assembled for BPP1 (FIG. 16A). Across the BPP1 population, the average pairwise genetic uniformity as measured by the Jaccard similarity coefficient was 97.0%. These data are illustrated by the population uniformity graph in FIG. 21 and the matrix in FIG. 19A.

Figure 16B:
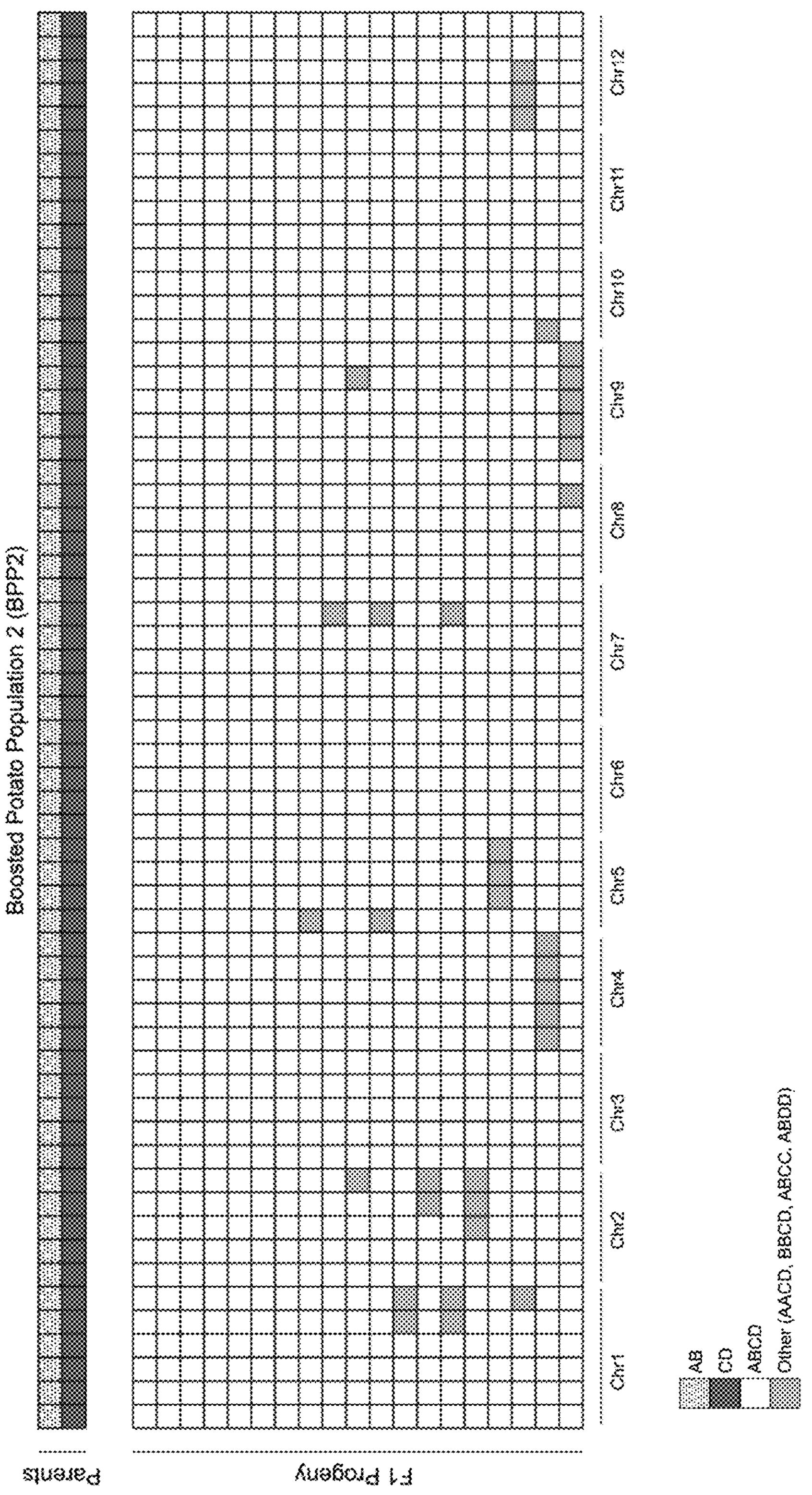
Figure 19B:
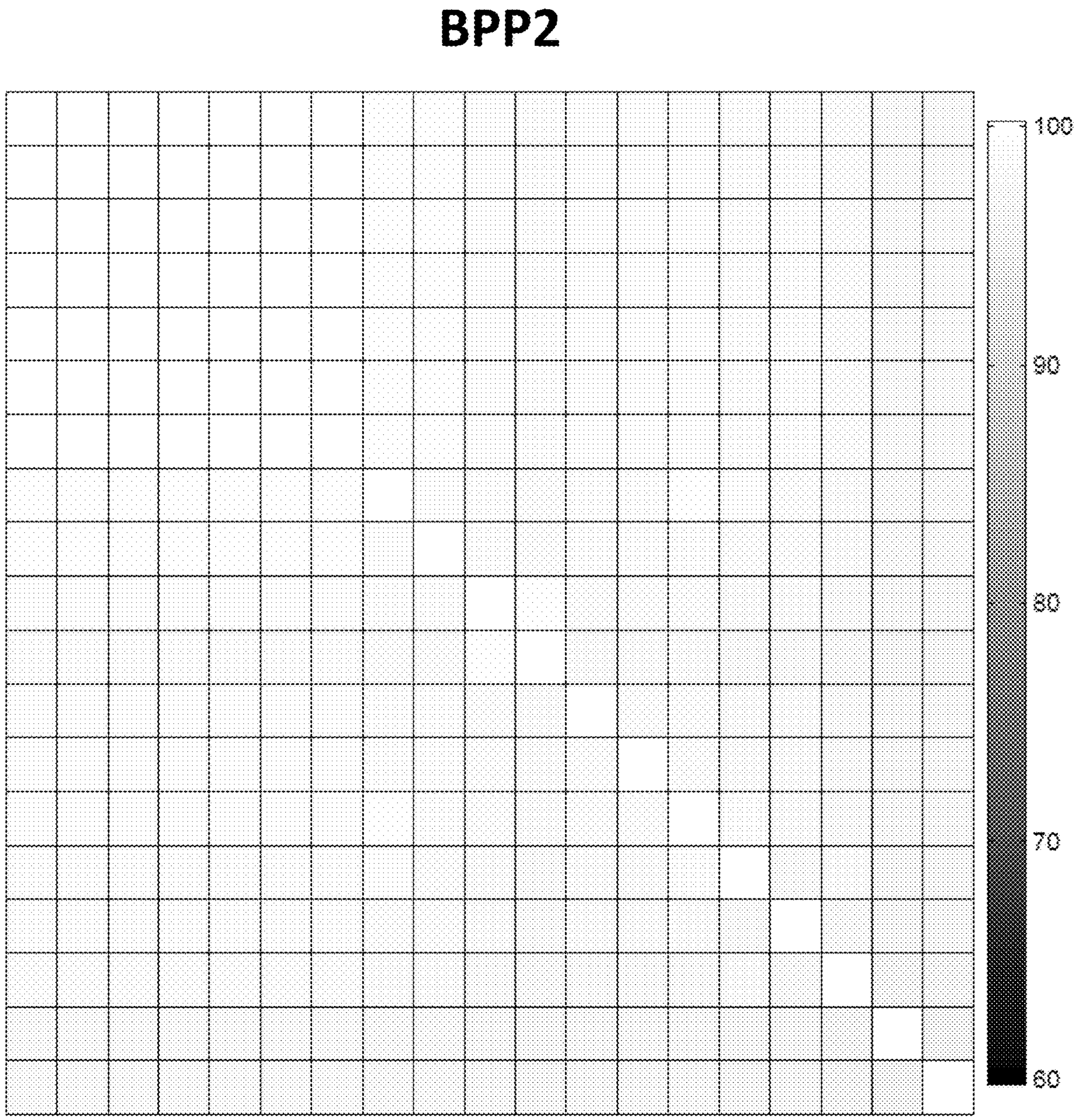

After filtering for high quality markers, a genotype matrix was assembled for BPP2 (FIG. 16B). Across the BPP2 population, the average pairwise genetic uniformity as measured by the Jaccard similarity coefficient was 98.5%. These data are illustrated by the population uniformity graph in FIG. 21 and the matrix in FIG. 19B.

Figure 16C:
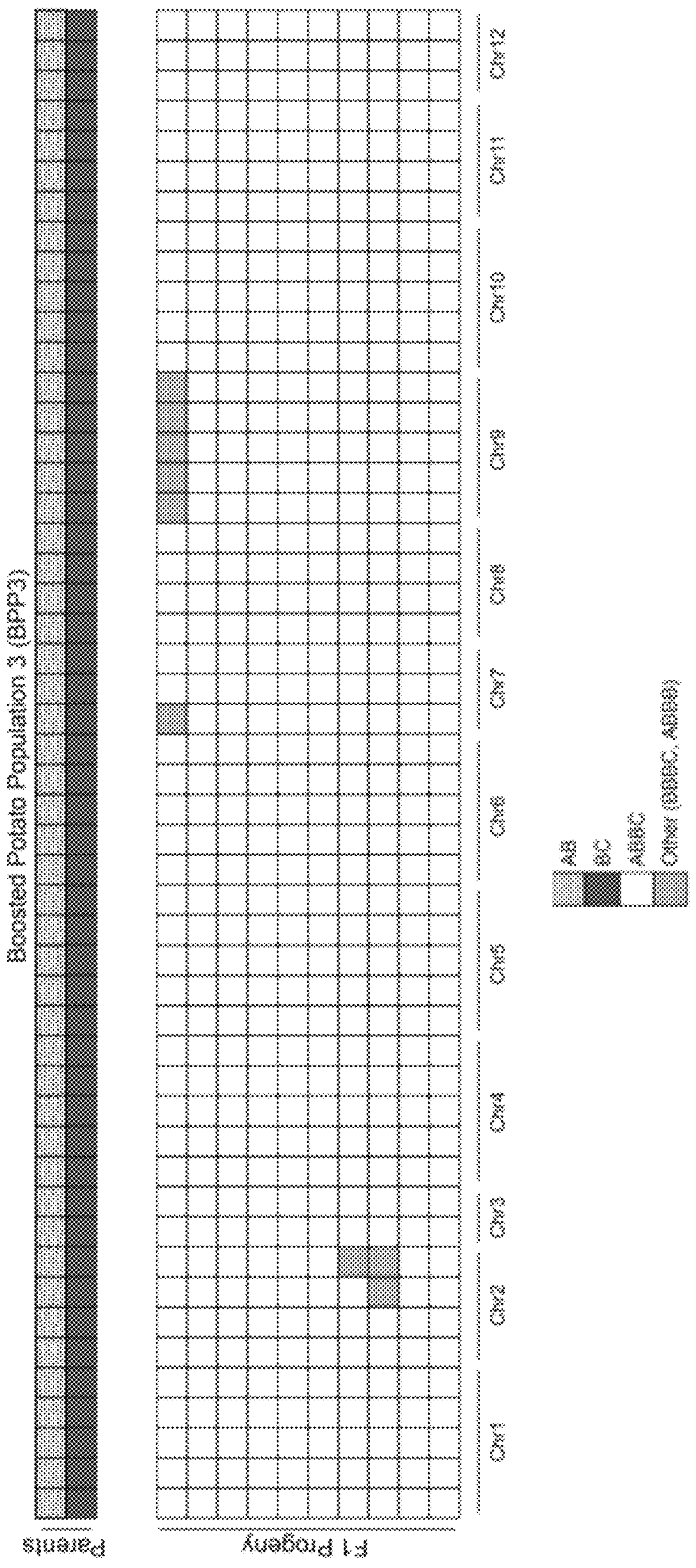
Figure 19C:
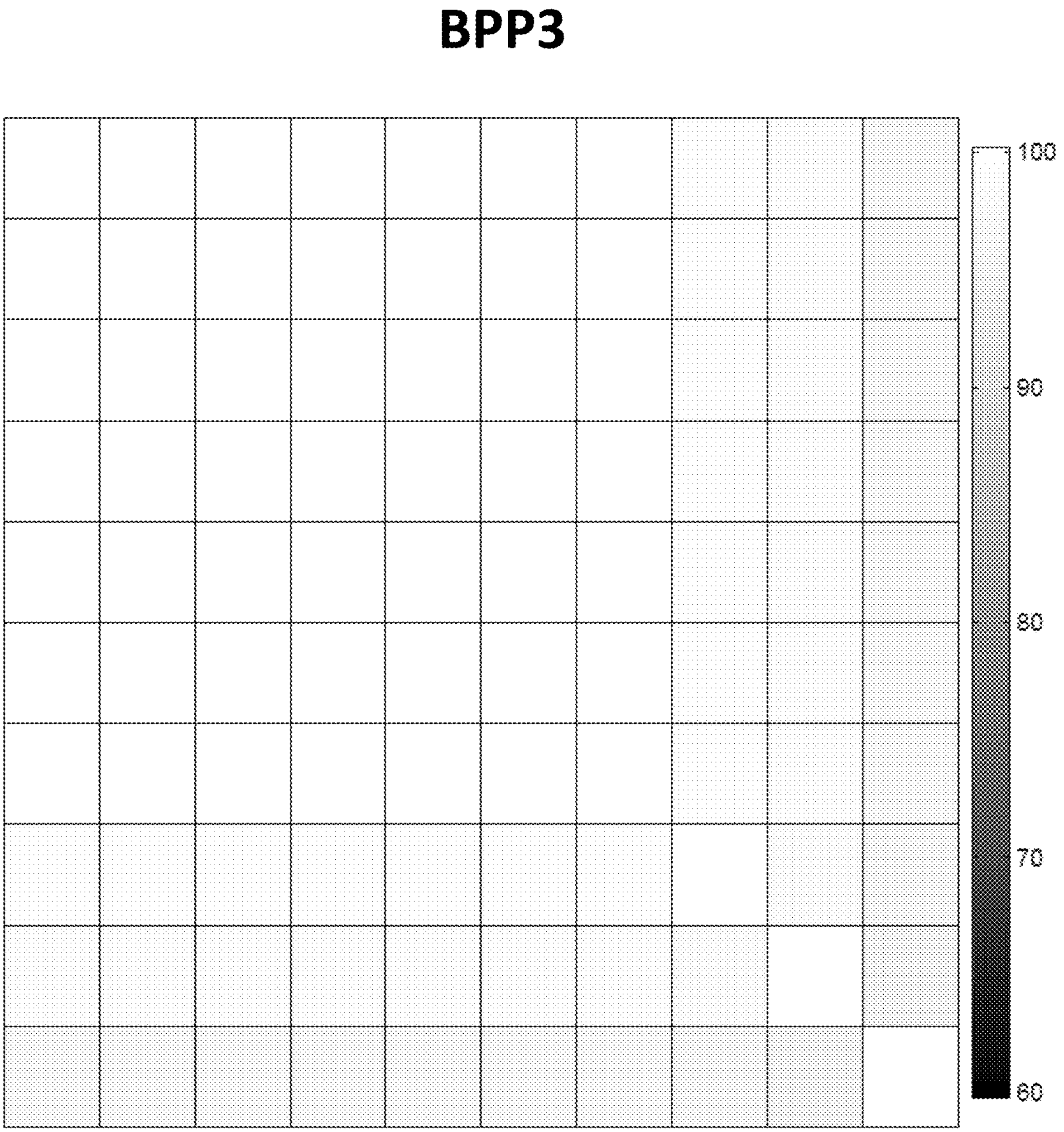

After filtering for high quality markers, a genotype matrix was assembled for BPP3 (FIG. 16C). Across the BPP3 population, the average pairwise genetic uniformity as measured by the Jaccard similarity coefficient was 98.8%. These data are illustrated by the population uniformity graph in FIG. 21 and the matrix in FIG. 19C.

Figure 16D:
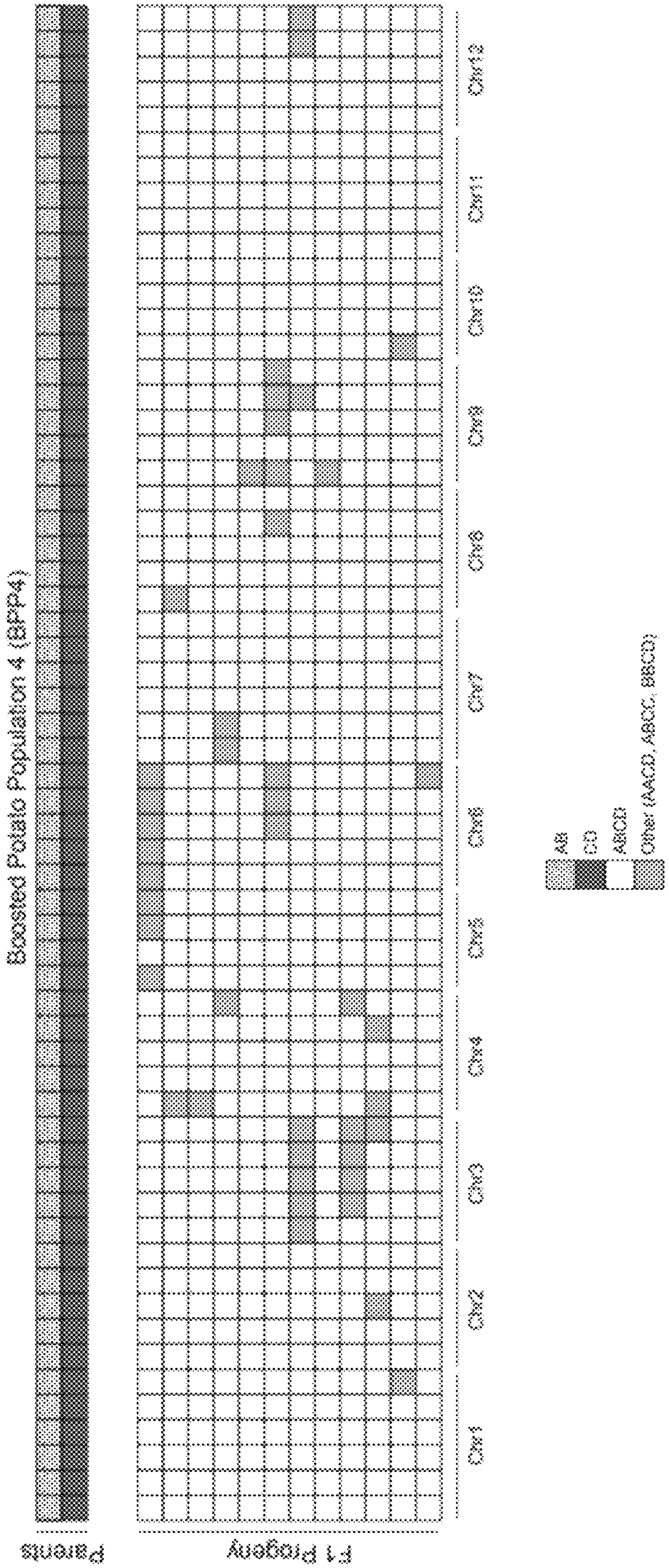
Figure 19D:
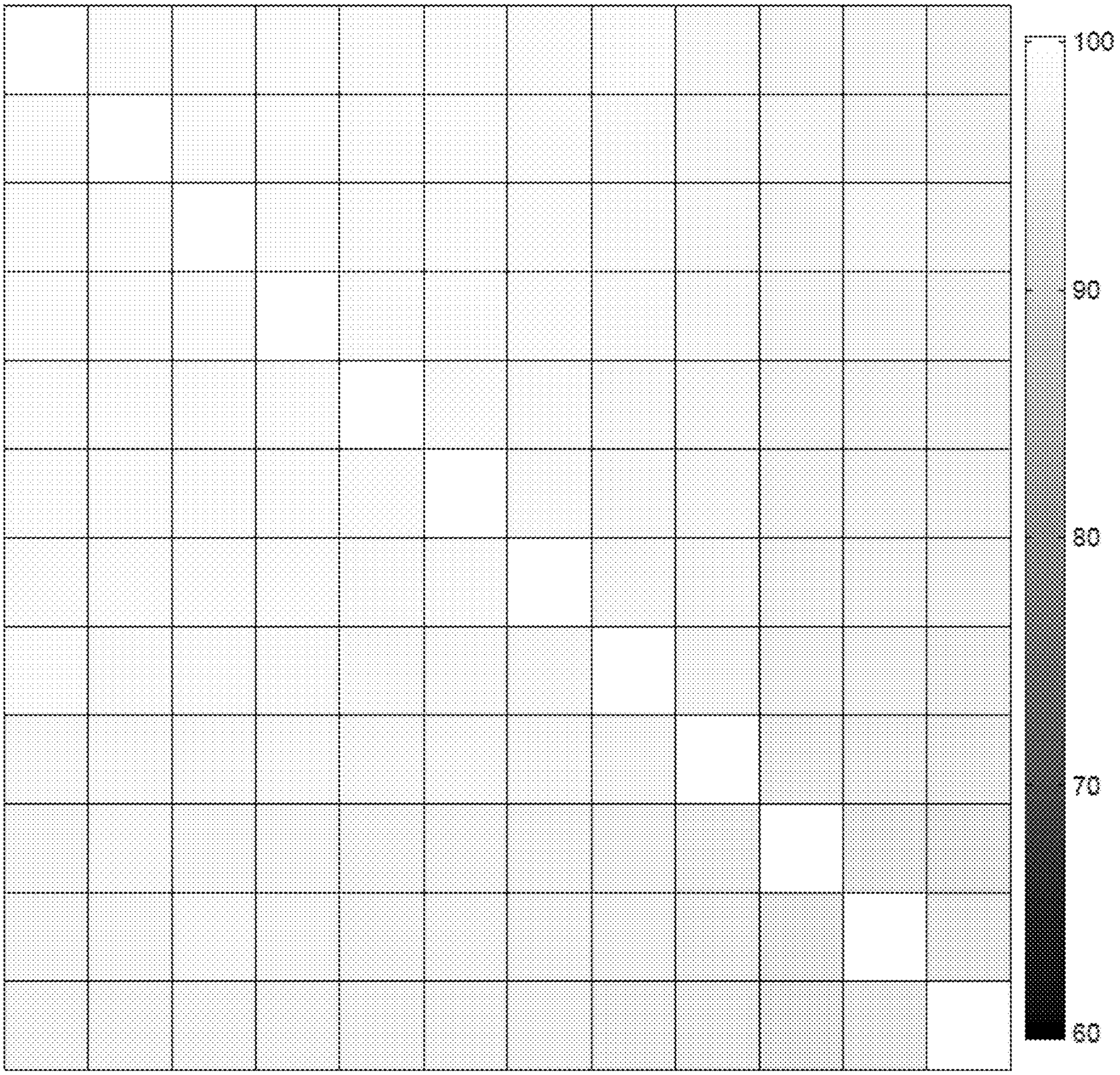

After filtering for high quality markers, a genotype matrix was assembled for BPP4 (FIG. 16D). Across the BPP4 population, the average pairwise genetic uniformity as measured by the Jaccard similarity coefficient was 96.9%. These data are illustrated by the population uniformity graph in FIG. 21 and the matrix in FIG. 19D.

Figure 16E:
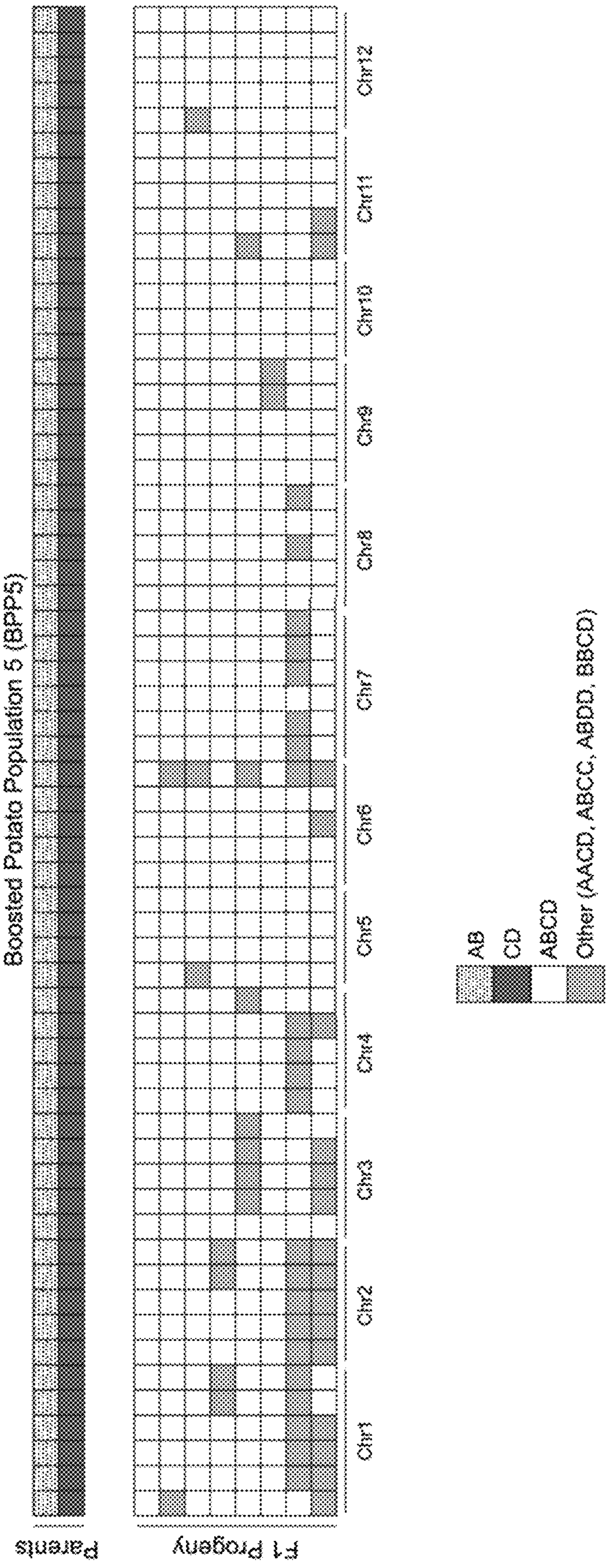
Figure 19E:
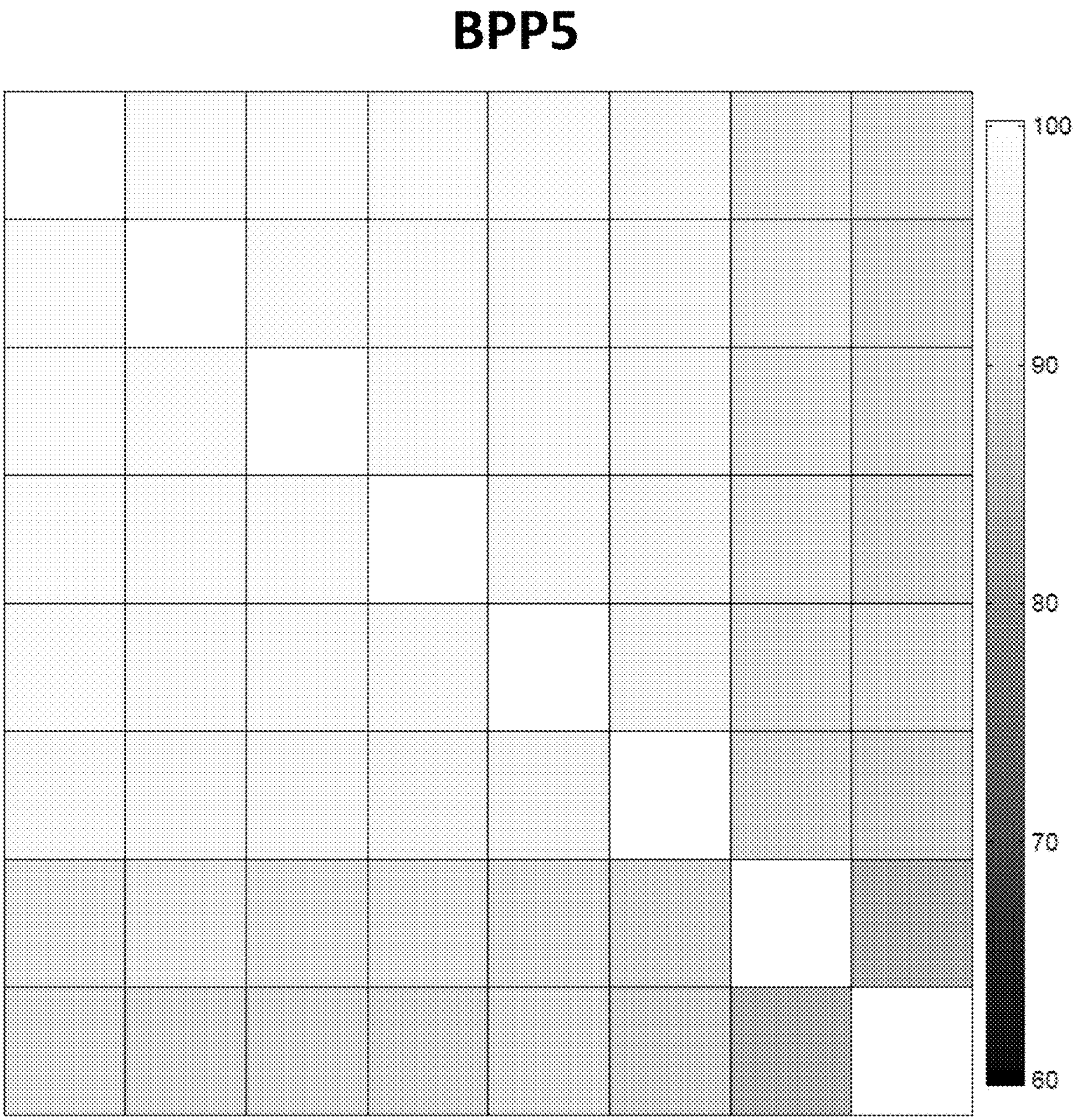

After filtering for high quality markers, a genotype matrix was assembled for BPP5 (FIG. 16E). Across the BPP5 population, the average pairwise genetic uniformity as measured by the Jaccard similarity coefficient was 94.2%. These data are illustrated by the population uniformity graph in FIG. 21 and the matrix in FIG. 19E.

Figure 19F:
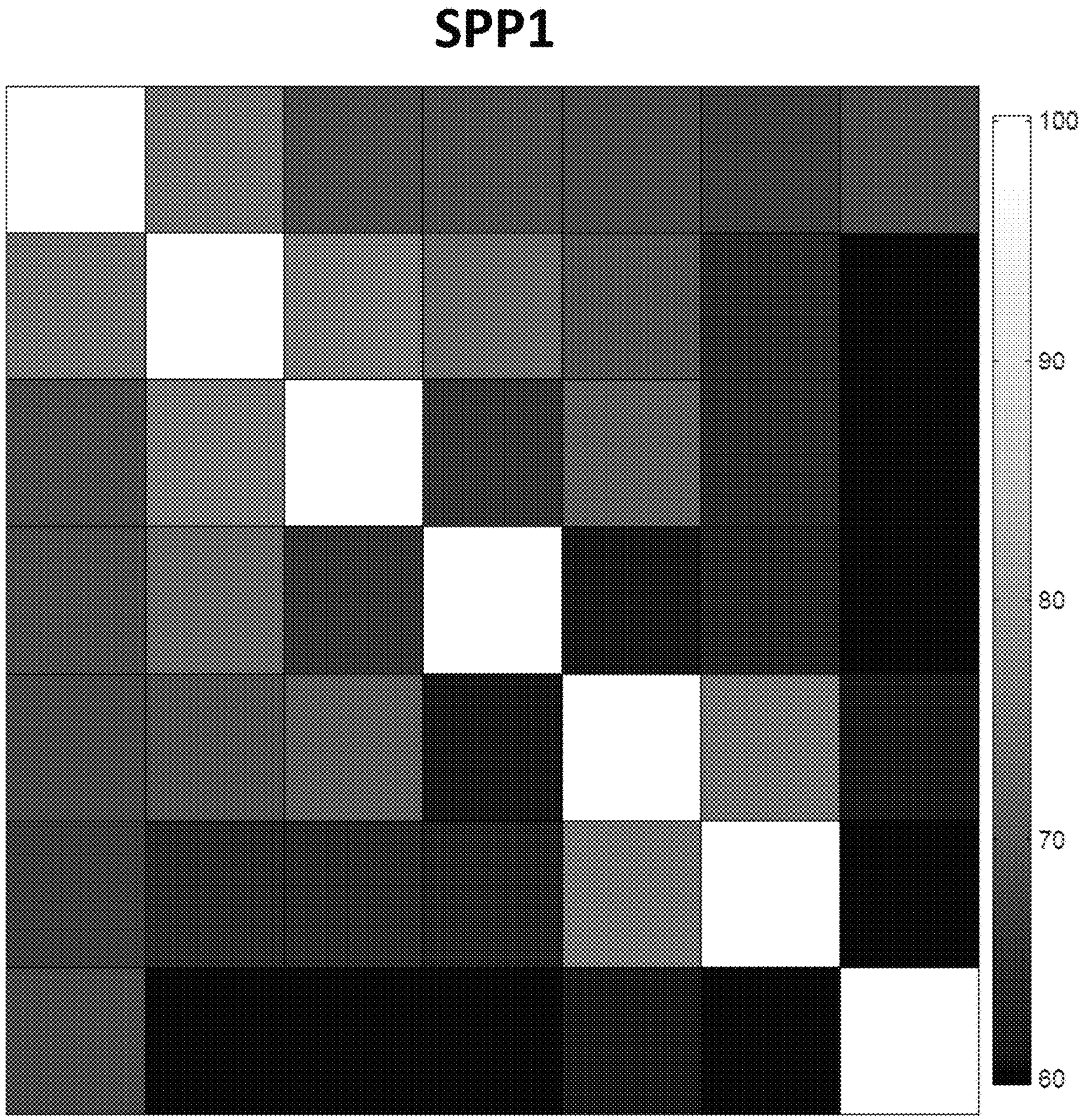
Figure 19G:
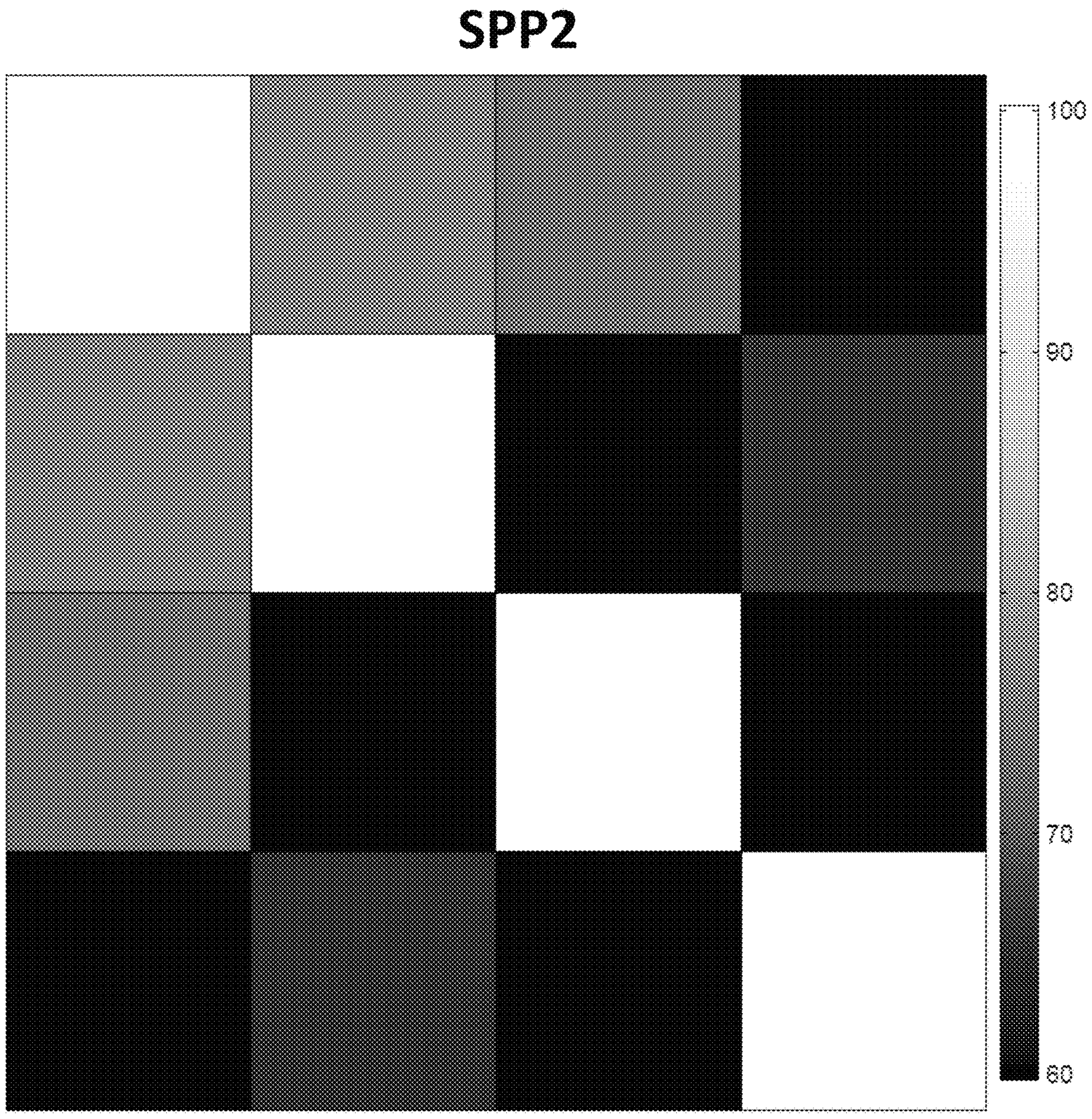

Regarding the control populations, after filtering for high quality markers, the average pairwise genetic uniformity as measured by the Jaccard similarity coefficient for the SPP1 and SPP2 populations was 65.9% and 65.4%, respectively (uniformity by pairwise genetic matrix visualized in FIG. 19F and FIG. 19G, respectively). These data are illustrated by the population uniformity graph in FIG. 21.

PR6a: Phenotypic Evaluation of BPP1

Figure 17A:
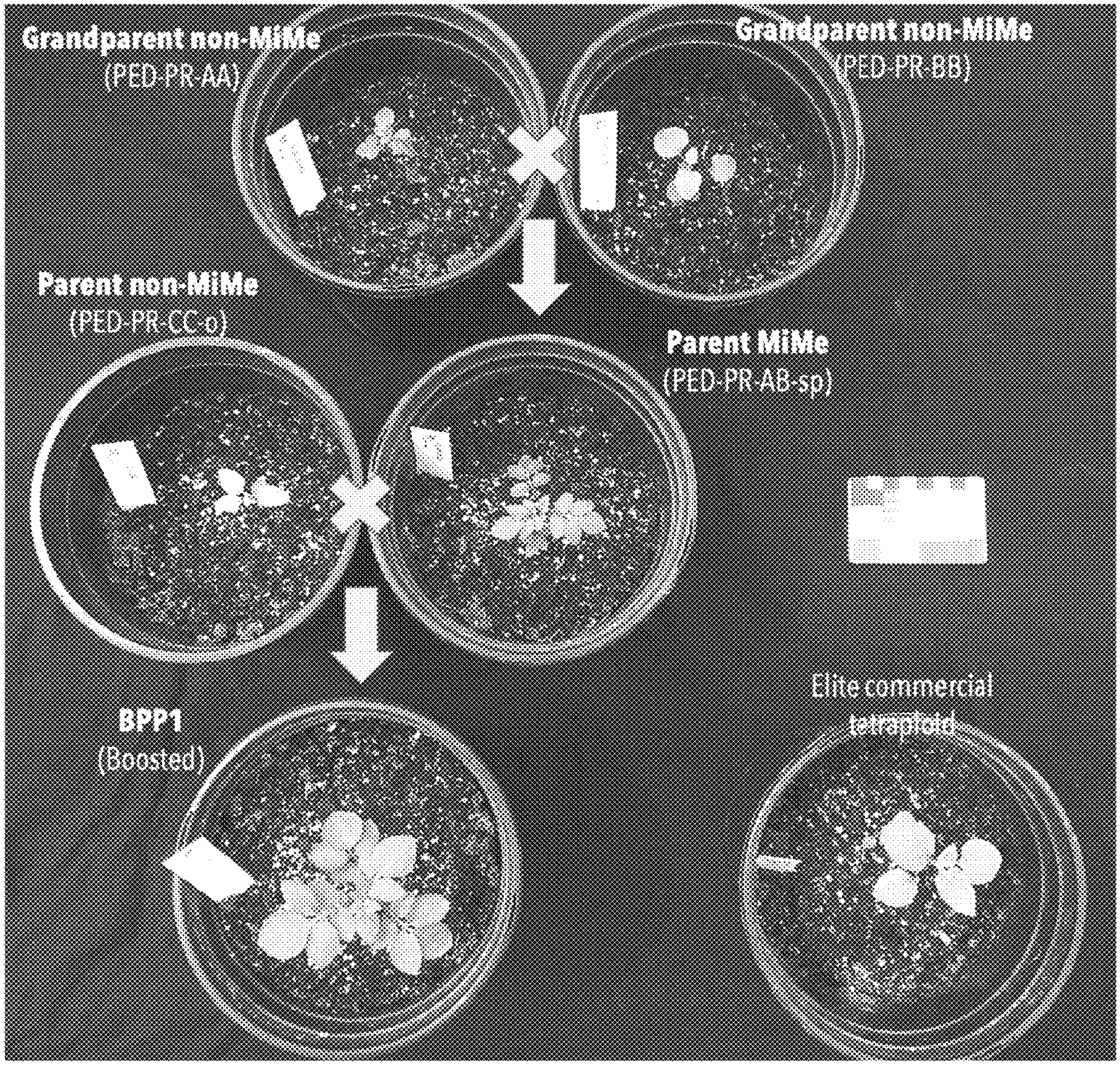
FIGS. 17A-17K show images of generated MiMe potato plants of population BPP1 compared to parent, grandparent, and tetraploid potato lines, and leaf area calculated based on said images.
Figure 17B:
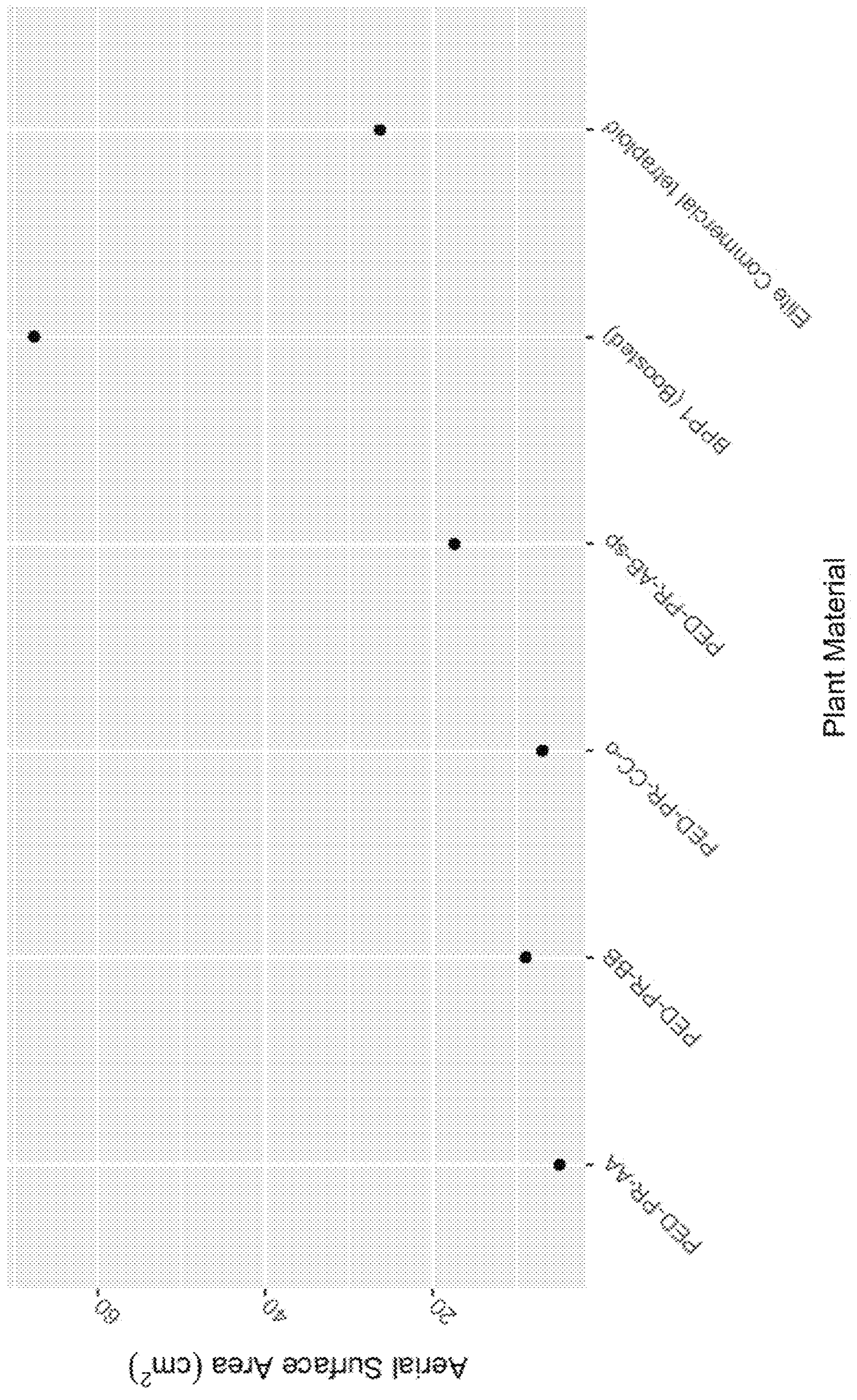
Figure 17C:
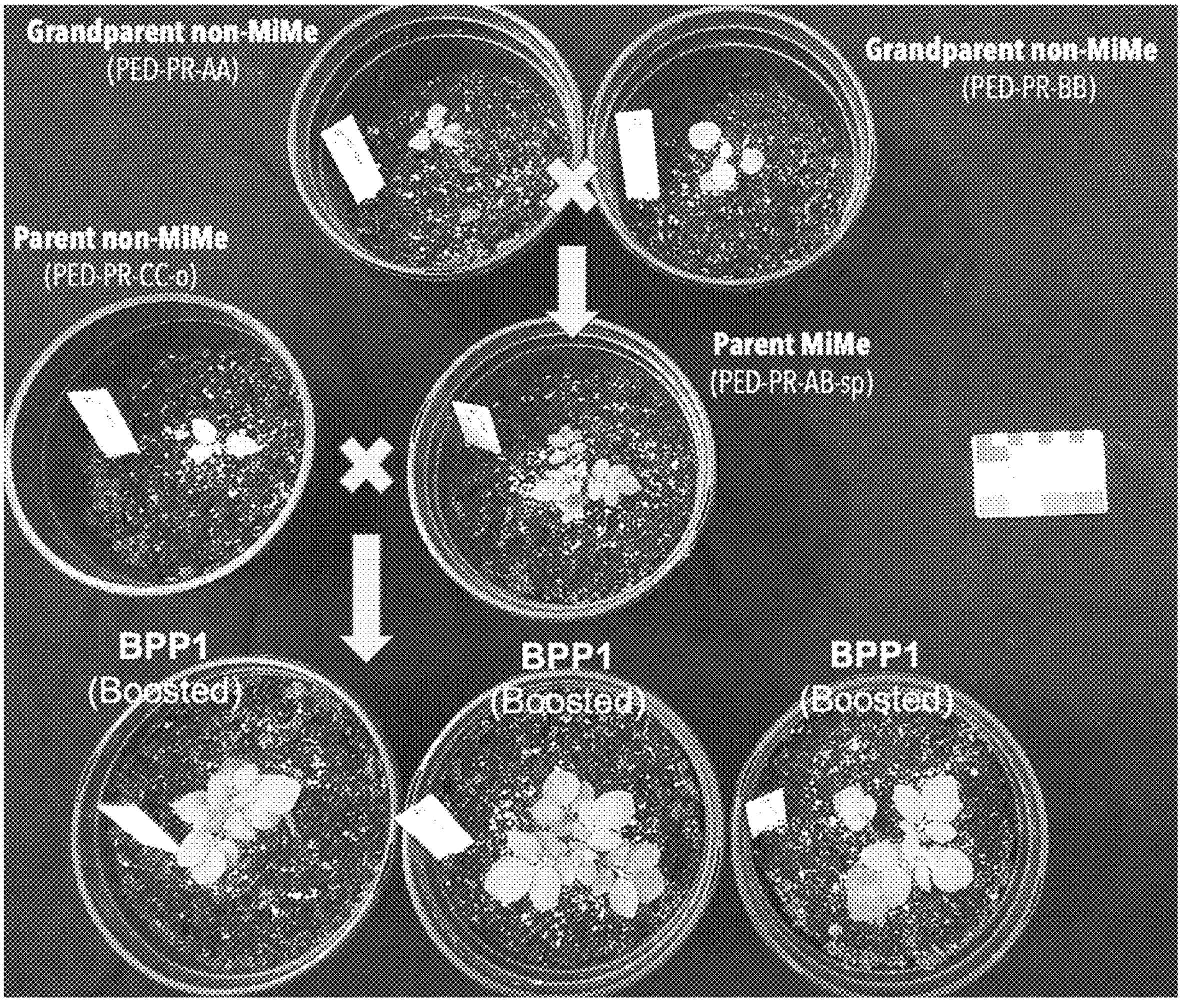
Figure 17D:
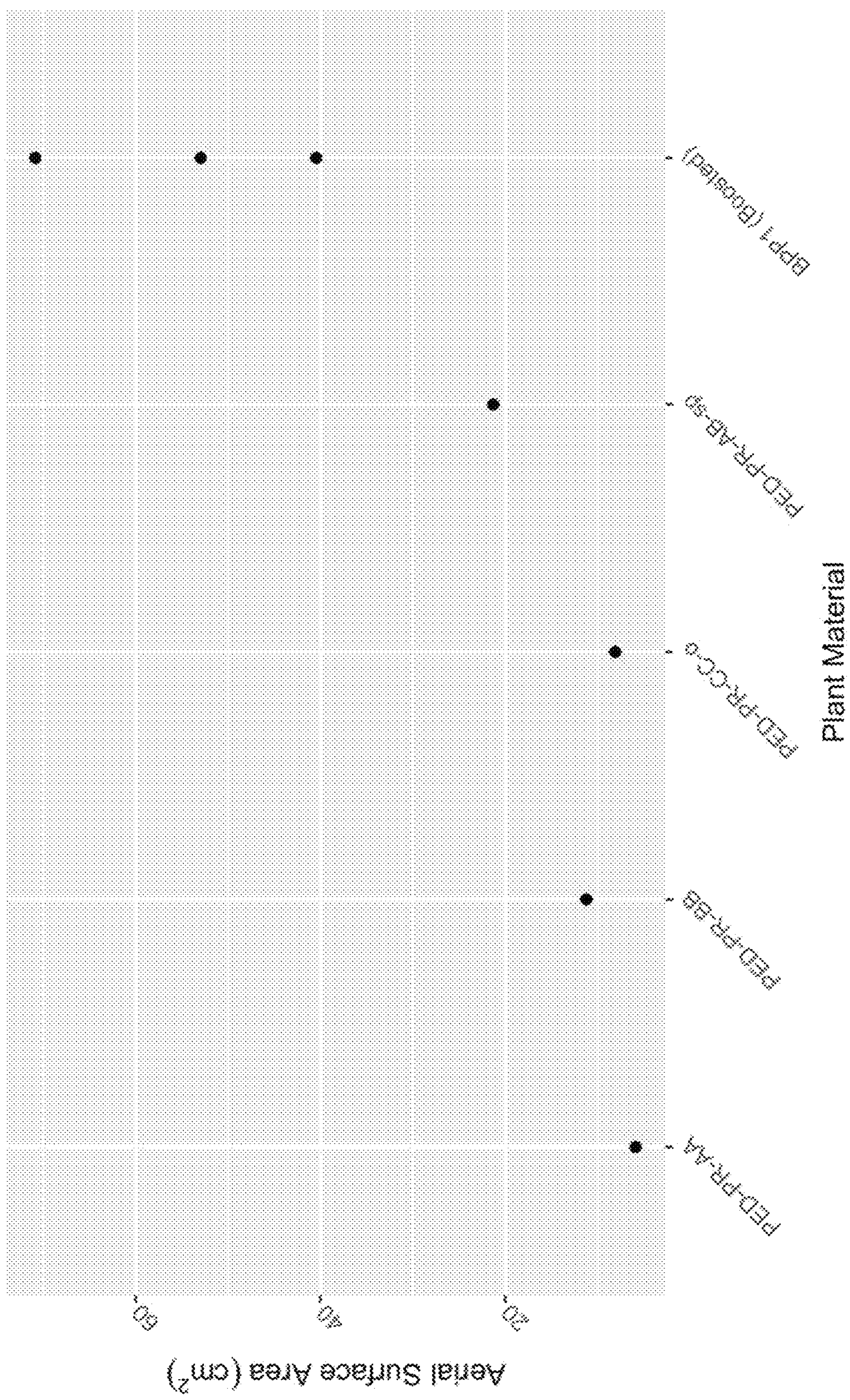
Figure 17E:
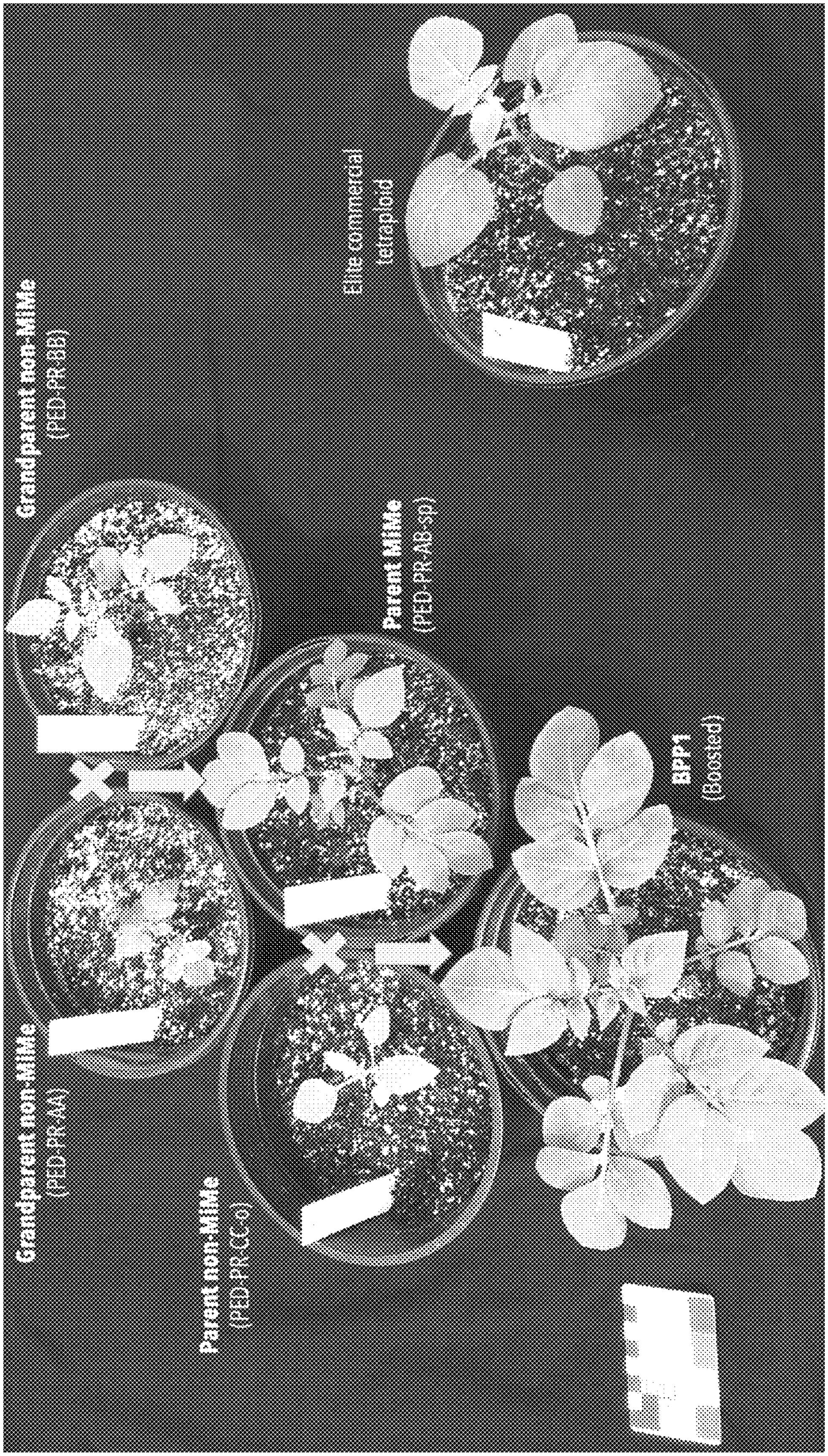
Figure 17F:
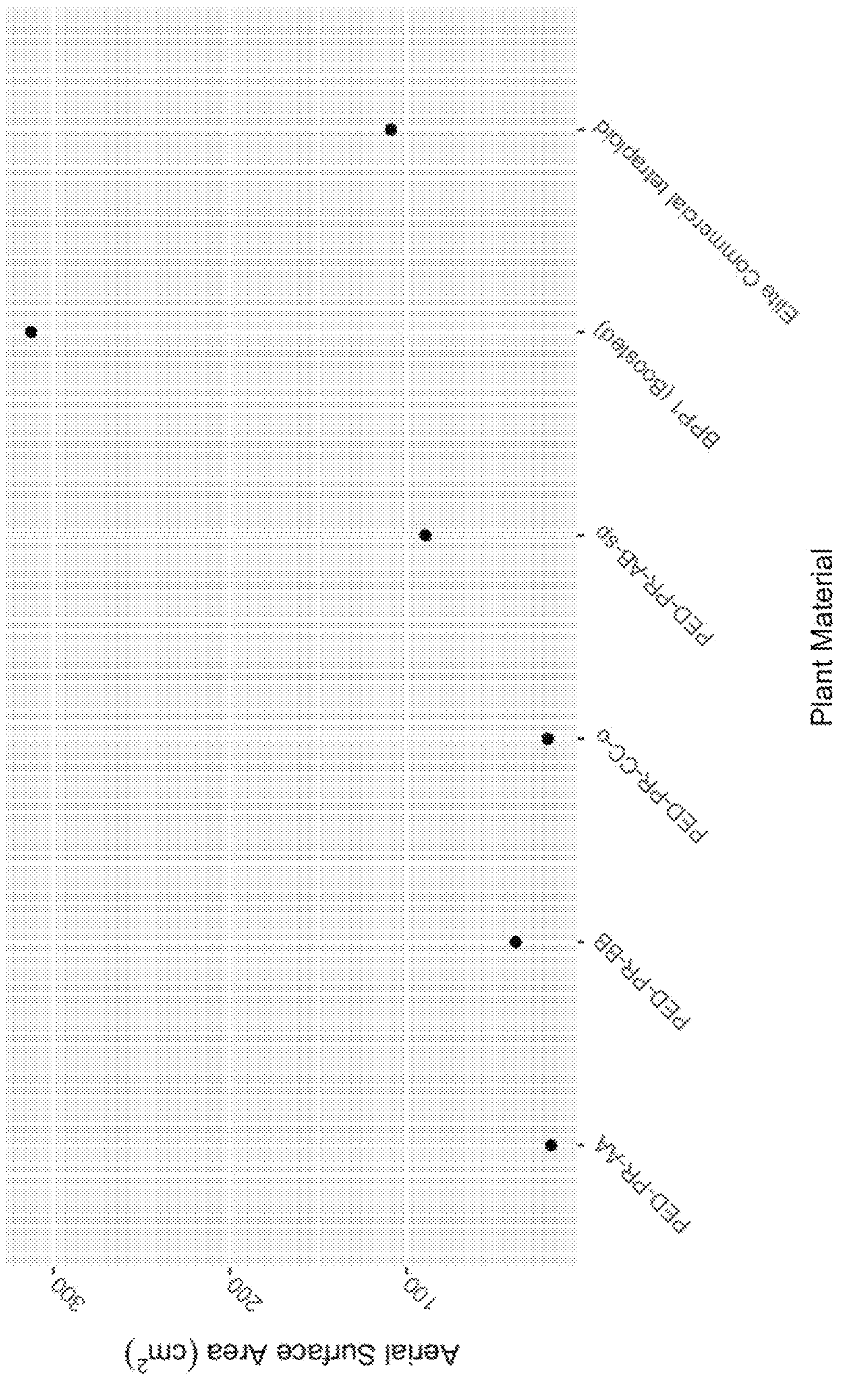
Figure 17G:
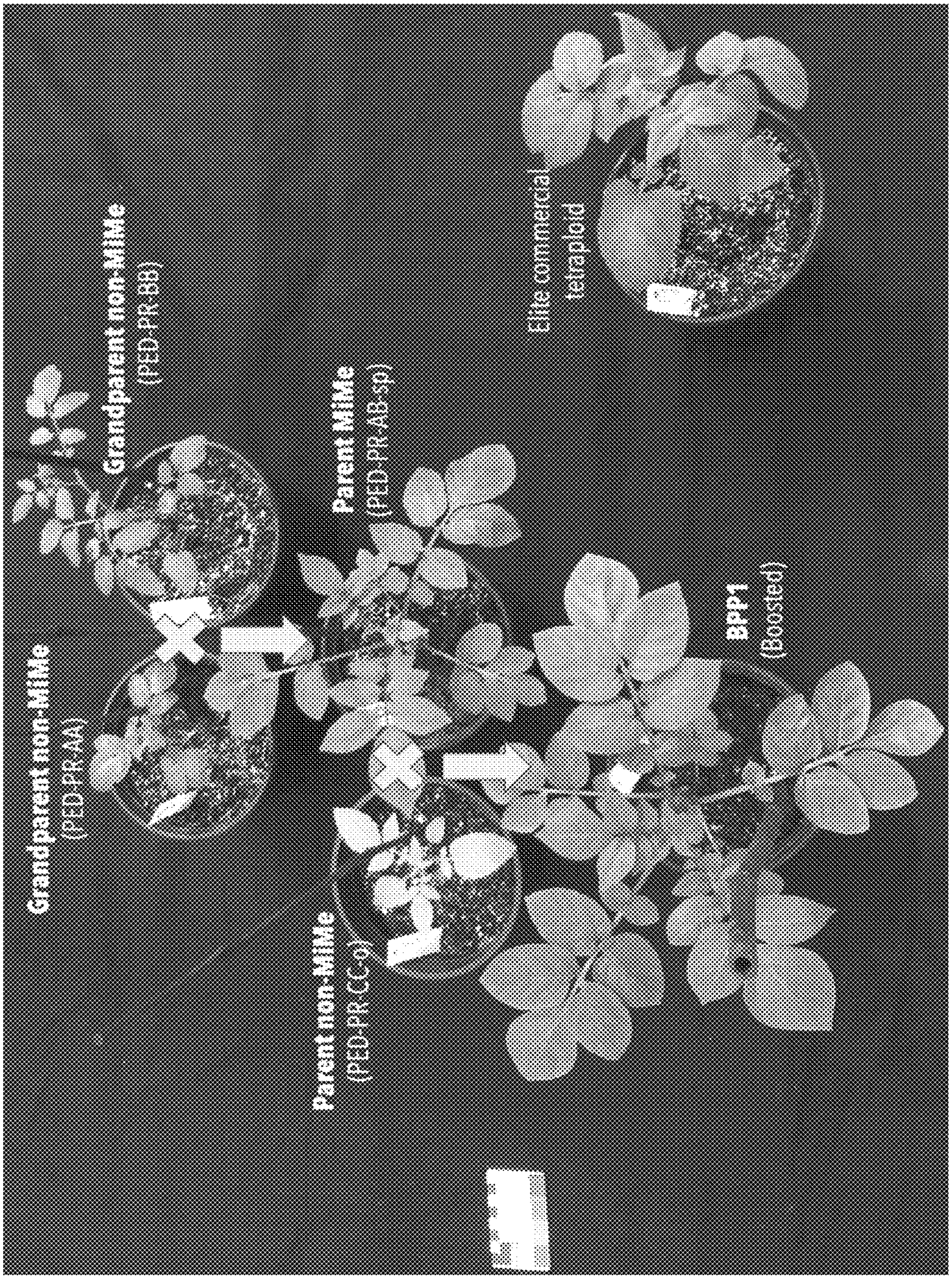

A potato plant from BPP1 is shown in FIG. 17A, FIG. 17E, and FIG. 17G adjacent to its grandparent plants, parent plants and an elite commercial tetraploid variety. For each figure, all plants are either 12 days post-planting (FIG. 17A), 19 days post-planting (FIG. 17E), or 26 days post-planting (FIG. 17G), respectively. For each figure, FIG. 17A, FIG. 17E, and FIG. 17G, respectively, (i) the plant on the top left of the photograph is the grandparent non-MiMe plant PED-PR-AA (doubled monoploid DM1-3 516 R44), (ii) the plant on the top right of the photograph, PED-PR-BB (selfed M6), is representative of the grandparent non-MiMe plant (M6), (iii) the plant on the middle left of the photograph is the parent non-MiMe plant PED-PR-CC-o, (iv) the plant on the middle right of the photograph is the parent MiMe plant PED-PR-AB-sp (spo11-1/ps), (v) the plant on the bottom left of the photograph is the BPP1 plant (labeled "BPP1 (Boosted)"), and (vi) the plant on the bottom right is an unrelated elite commercial tetraploid variety.

Figure 17H:
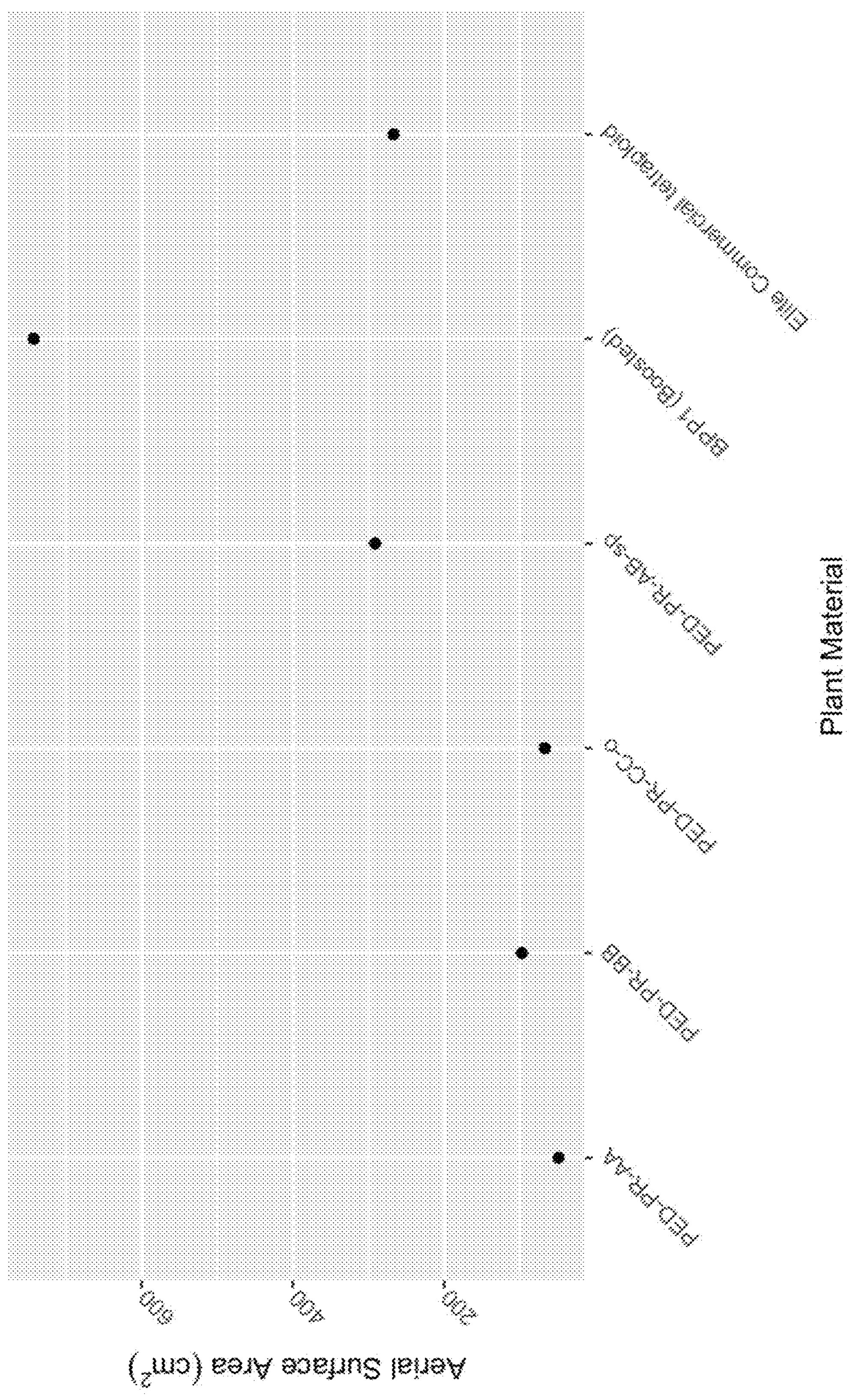
Figure 17I:
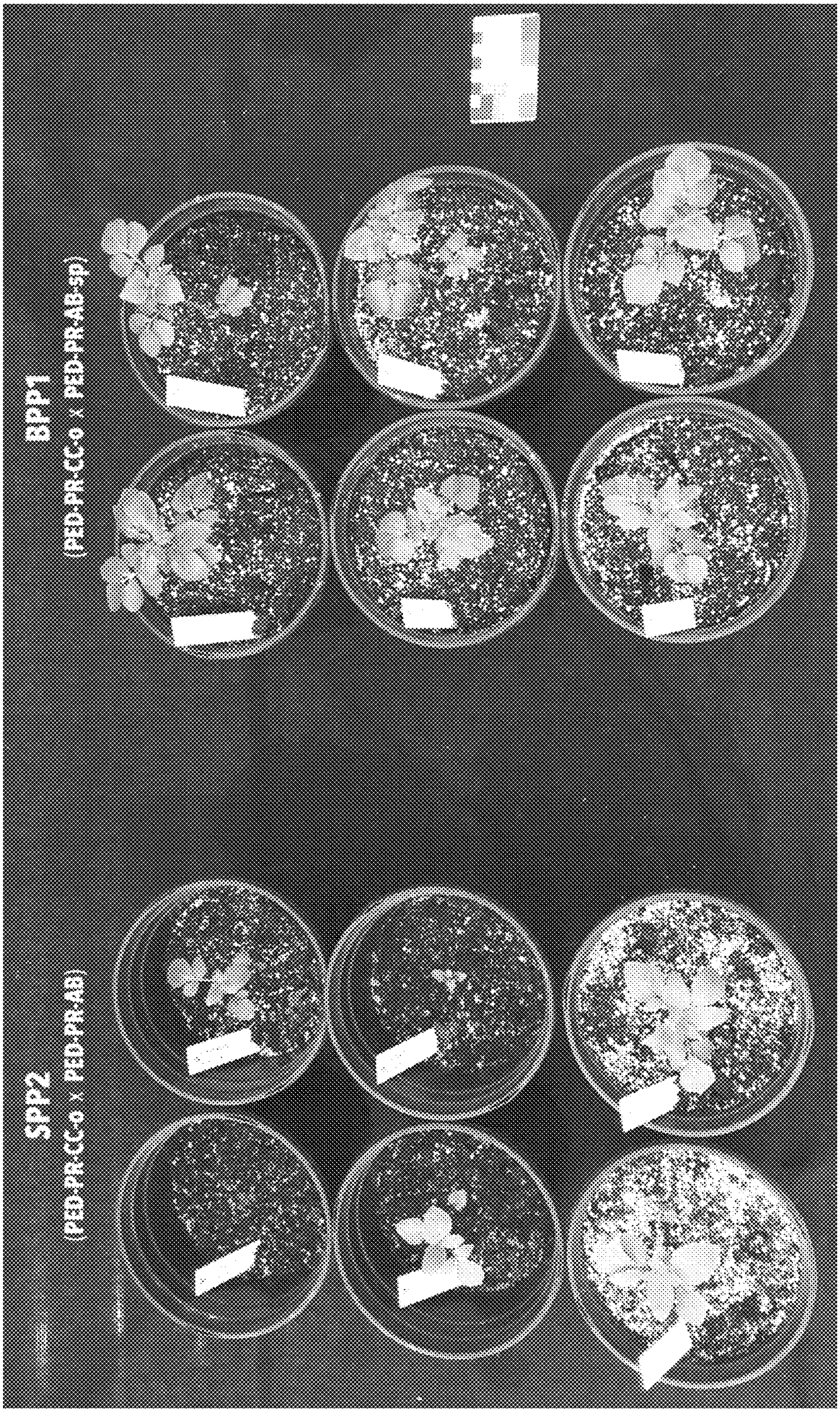
Figure 17J:
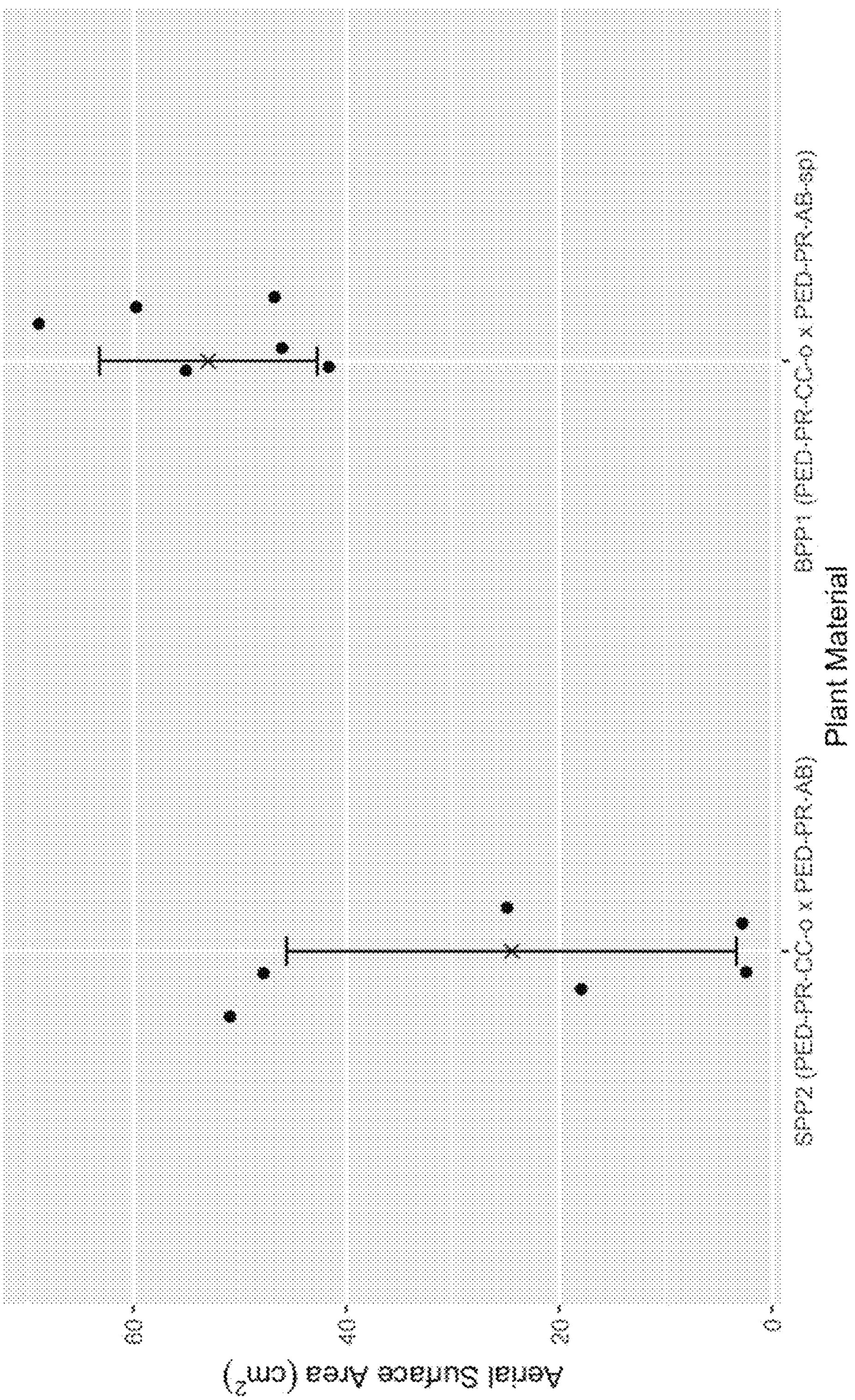
Figure 17K:

Six potato plants from BPP1 are shown in FIG. 17I and FIG. 17K compared to six plants resulting from SPP2. For each figure, all plants are either 16 days post-planting (FIG. 17I), or 23 days post-planting (FIG. 17K), respectively. The BPP1 plants demonstrated a phenotypically uniform size, growth, and appearance, whereas SPP2 plants were variable in size, growth, and appearance.

PR6b: Phenotypic Evaluation of BPP2

Figure 18A:
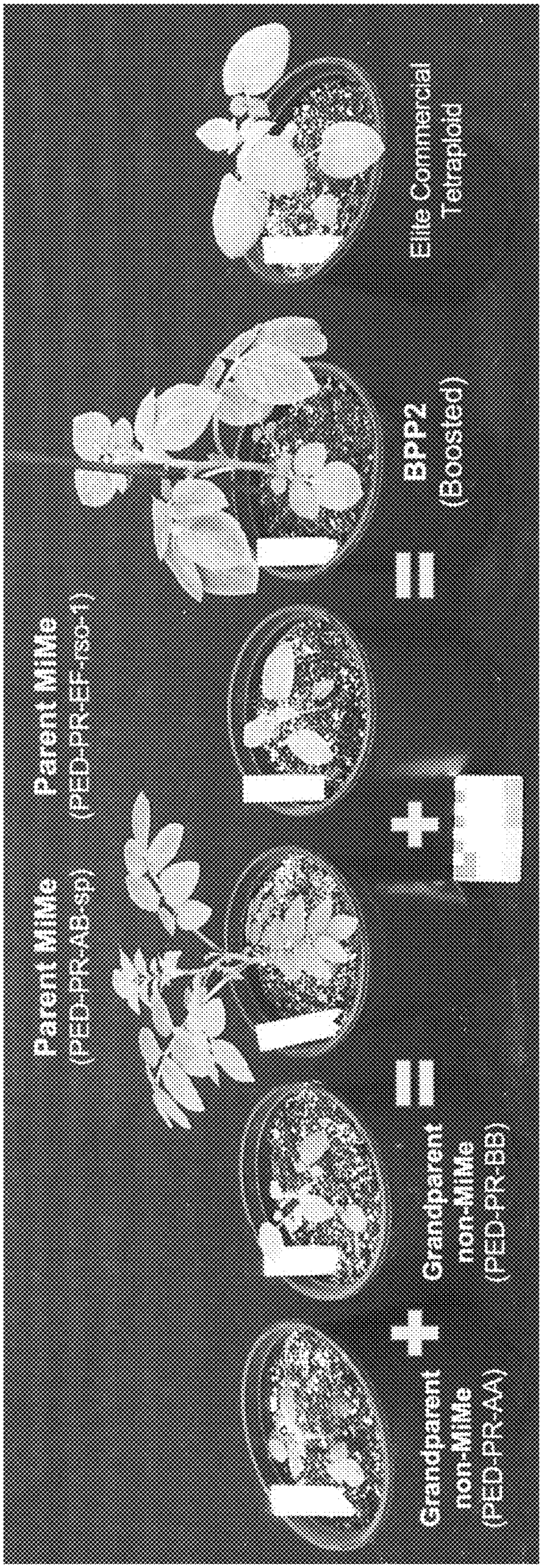
FIGS. 18A-18I show images of generated MiMe potato plants of population BPP2 compared to parent, grandparent, and tetraploid potato lines, and leaf area calculated based on said images.
Figure 18B:
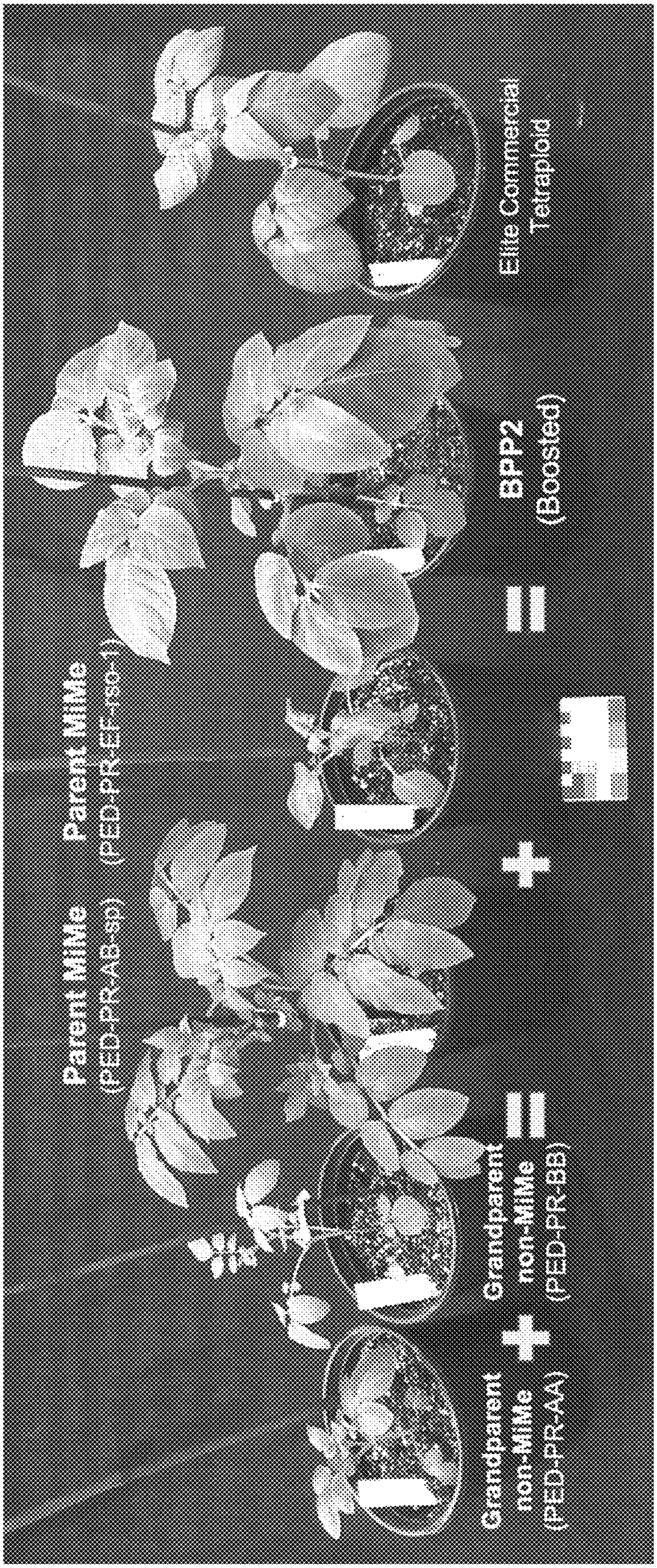

A potato plant from BPP2 is shown in FIG. 18A (23 days after planting) and FIG. 18B (29 days after planting) in the same photograph as its grandparent non-MiMe plants, parent MiMe plants and an elite commercial tetraploid variety. From left to right, the plants in FIG. 18A and FIG. 18B are (i) a grandparent non-MiMe plant (the doubled monoploid DM 1-3 516 R44), (ii) a selfed M6 representative of the grandparent non-MiMe plant (M6), (iii) a parent MiMe plant PED-PR-AB-sp (spo11-1/ps), (iv) a parent MiMe plant PED-PR-EF-rso-1 (rec8/spo11-1/os), (v) a BPP2 plant (labeled "BPP2 (Boosted)"), and (vi) an unrelated elite commercial tetraploid variety.

Figure 18C:
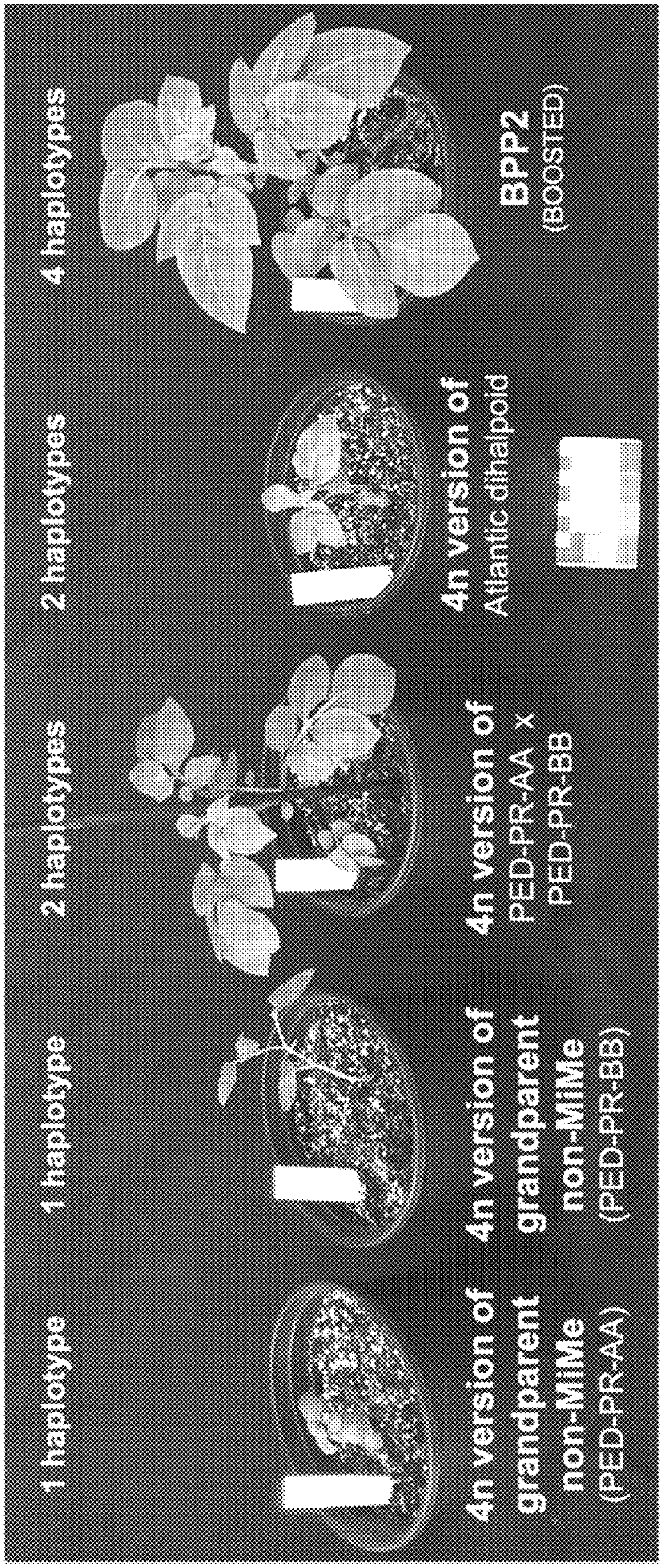
Figure 18D:
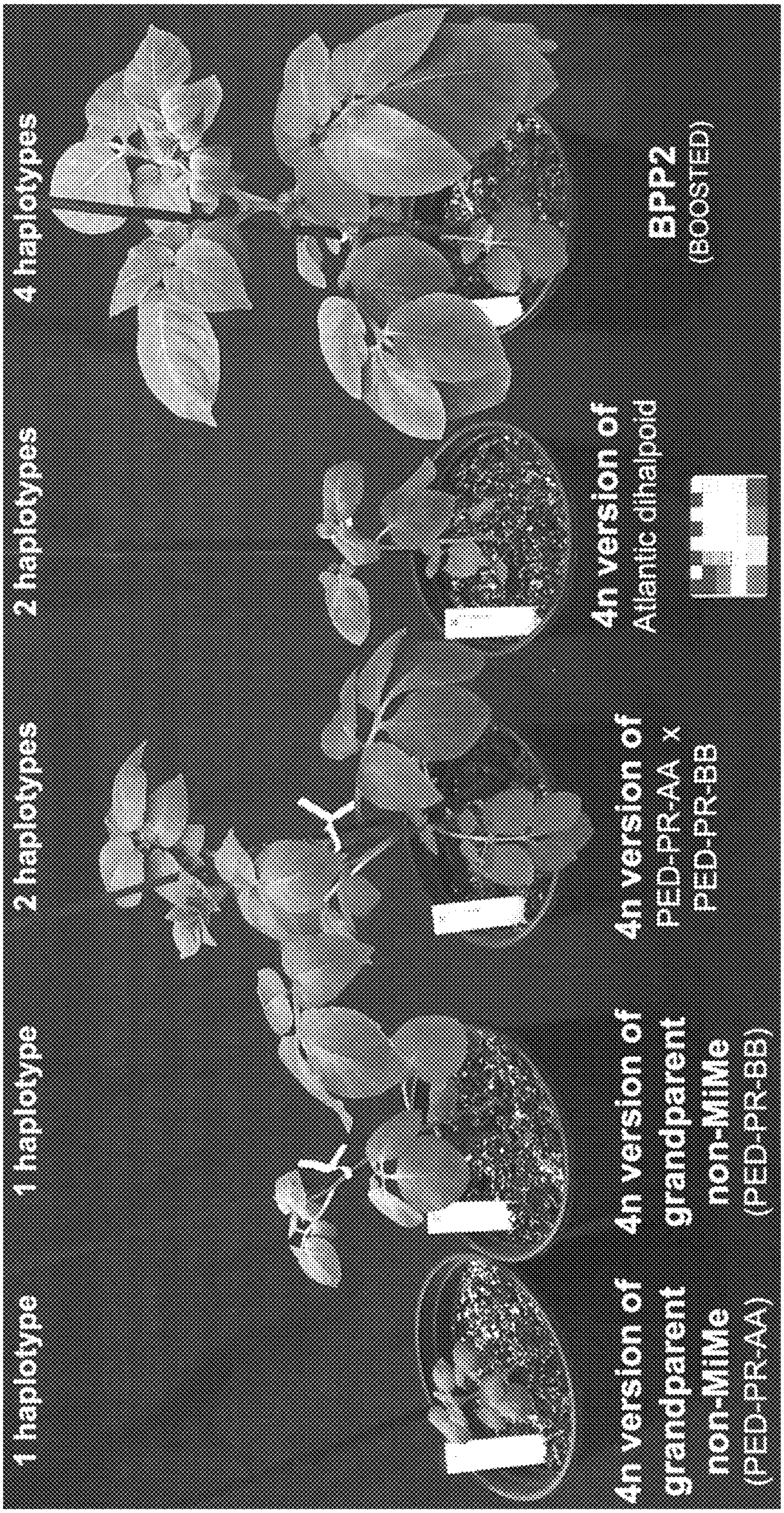

A potato plant from BPP2 is also shown in FIG. 18C (23 days after planting) and FIG. 18D (29 days after planting) in the same photograph as tetraploid versions of its grandparent non-MiMe plants and tetraploid versions of its parent MiMe plants. From left to right, the plants in FIG. 18C and FIG. 18D are (i) tetraploid (4n) version of the grandparent non-MiMe plant (the doubled monoploid DM 1-3 516 R44), (ii) tetraploid (4n) version of a twice selfed M6 representative of the grandparent non-MiMe plant (M6), (iii) tetraploid (4n) version of the DM1-3 516 R44×M6 F1 hybrid (same parents as PED-PR-AB-sp which was also derived from a DM1-3 516 R44×M6 F1 hybrid), (iv) PED-PR-EEFF, a tetraploid (4n) version of the Atlantic dihaploid from which PED-PR-EF-rso-1 was also derived), (v) a BPP2 plant (labeled "BPP2 (Boosted)").

Figure 18E:
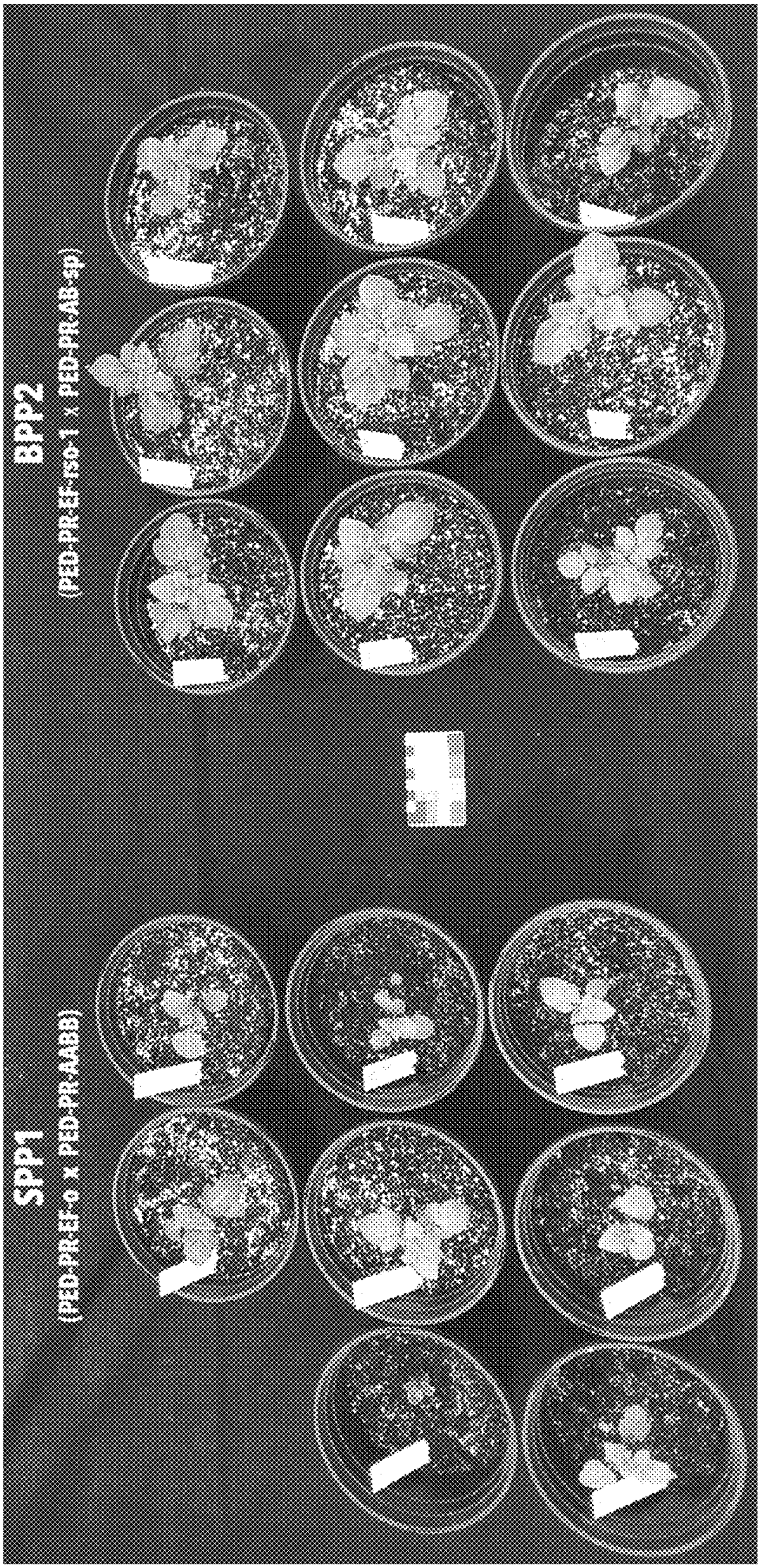
Figure 18F:
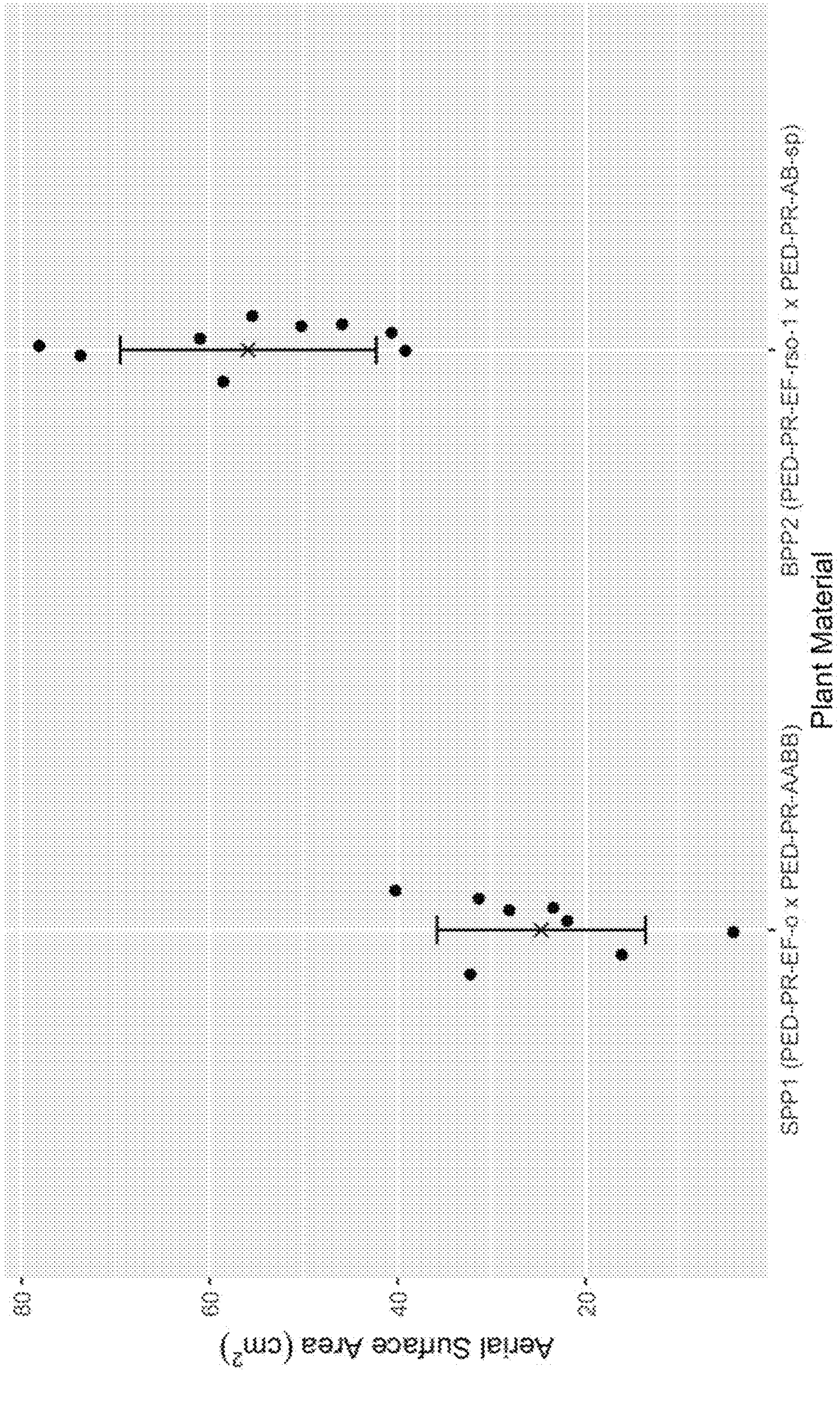
Figure 18G:
Figure 18H:
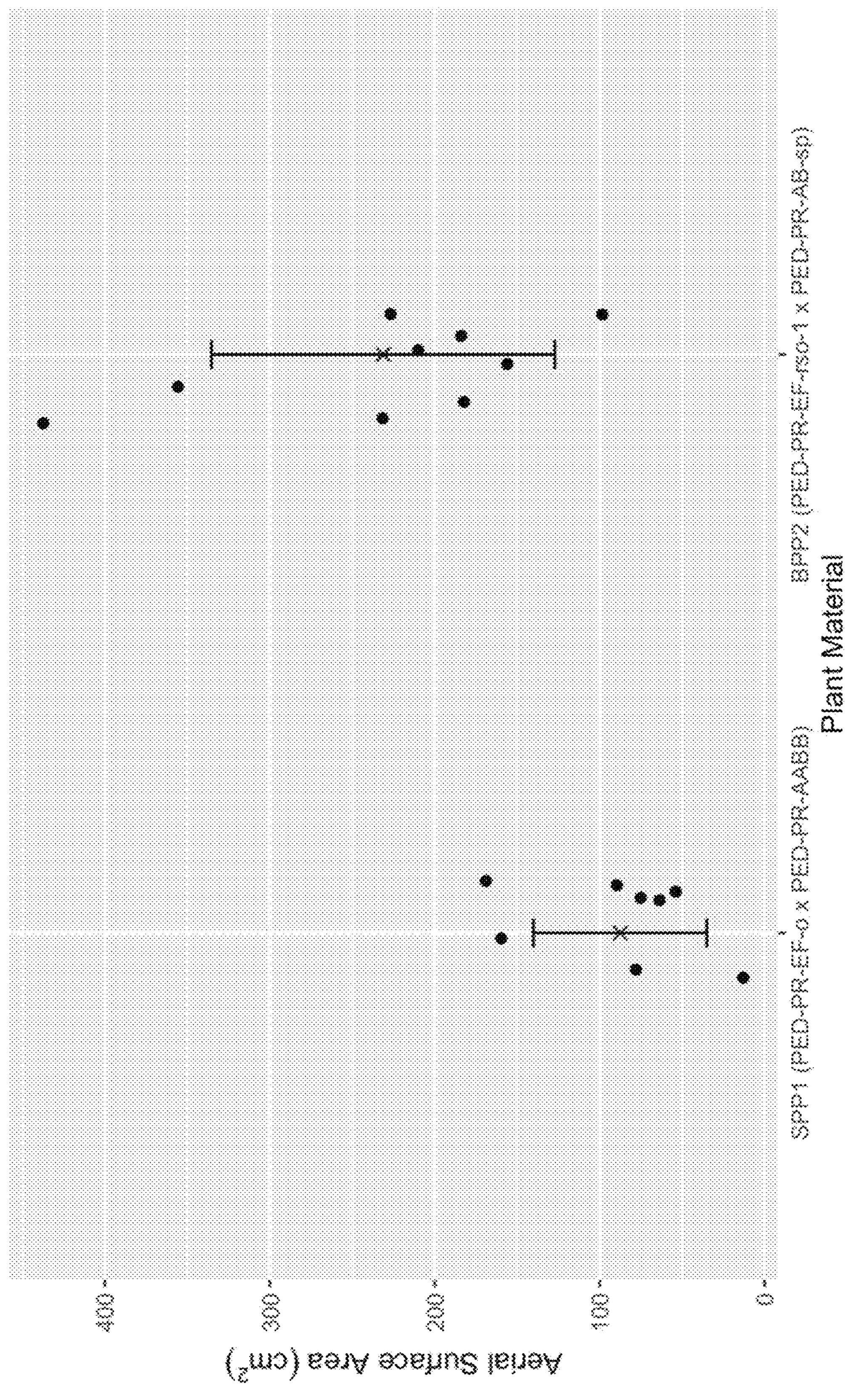
Figure 18I:
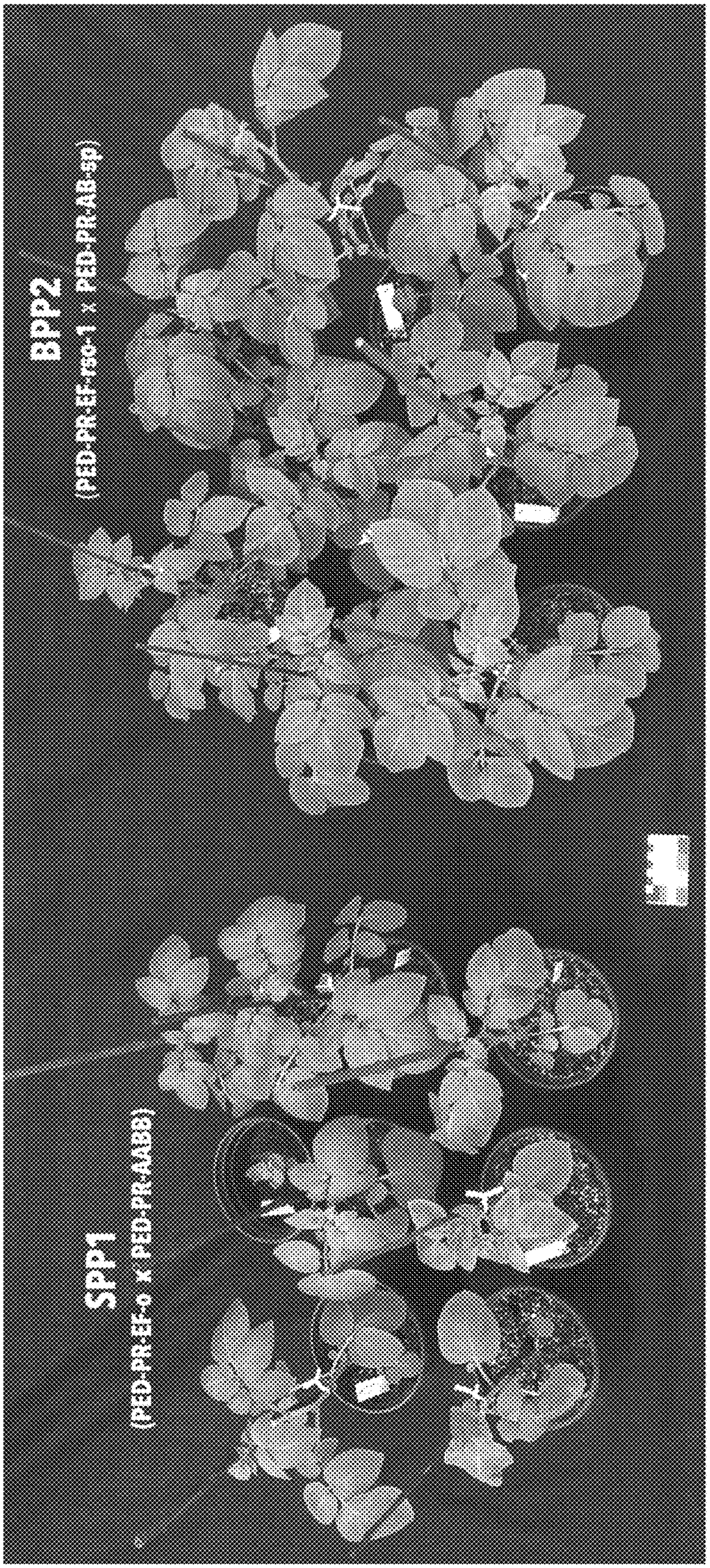

Nine potato plants from BPP2 are shown in FIG. 18E and FIG. 18G, and eight potato plants from BPP2 are shown in FIG. 18I, compared to eight plants from SPP1. For each figure, all plants are either 16 days post-planting (FIG. 18E), 23 days post-planting (FIG. 18G), or 29 days post-planting (FIG. 18I) respectively. The BPP2 plants demonstrated a phenotypically uniform size, growth and appearance, whereas the SPP1 plants were variable in size, growth and appearance.

PC: Conclusions

Alongside improved genetic and phenotypic uniformity, the BPP1 plants having three haplotypes exhibit many superior traits compared to both parent lines and grandparent plants. FIGS. 17A and 17C show that even by 12 days post-planting, relative to all compared plants, BPP1 plants have higher vigor, exhibit more dense foliage, and exhibit higher leaf surface area (quantified in FIGS. 17B and 17D).

Figure 17L:
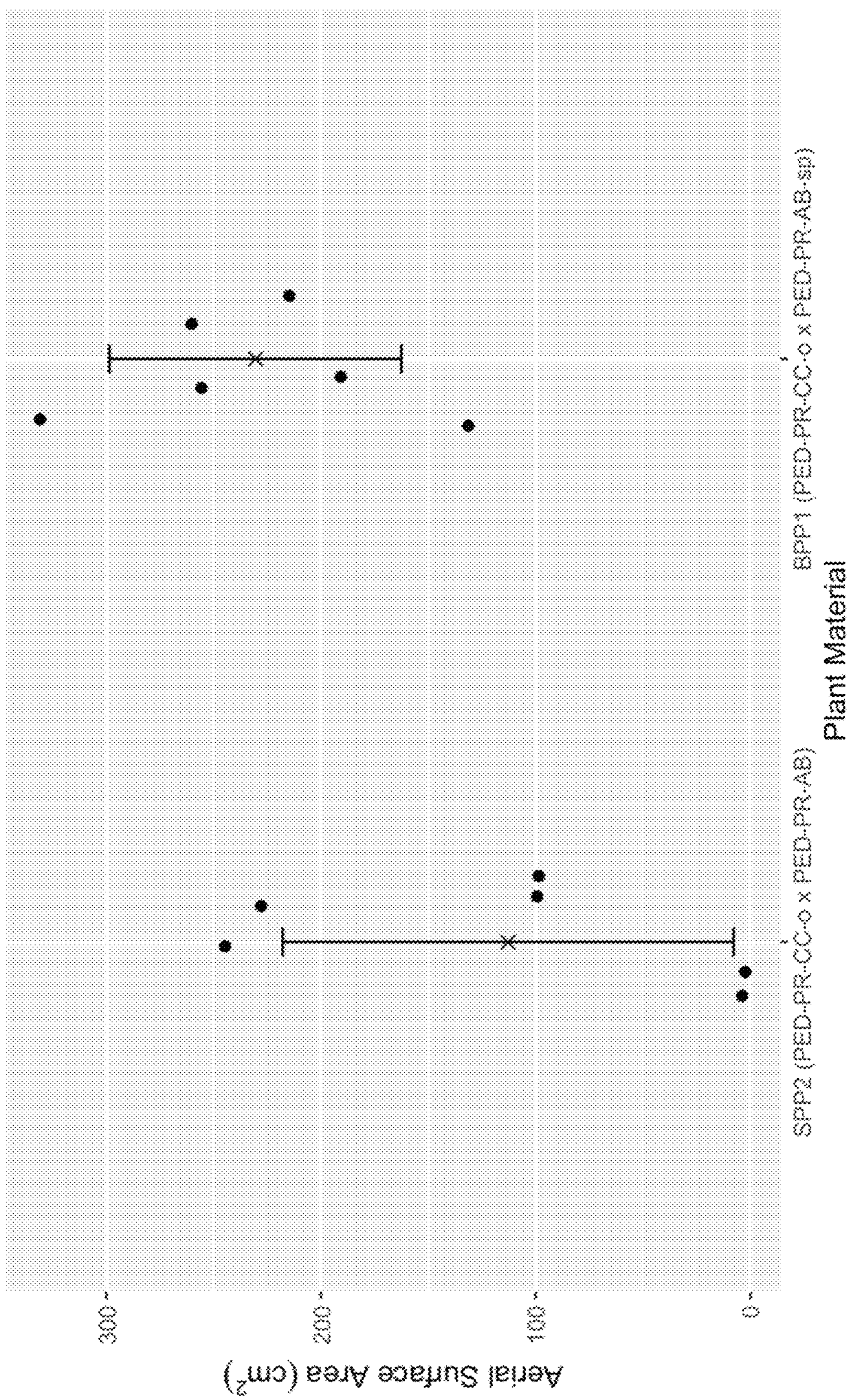
FIG. 17L shows measurements of leaf surface area visible in FIG. 17K, comparing the aerial surface area ($cm^2$) for each individual plant from the photograph in FIG. 17K using ImageJ software. The aerial surface area mean and standard deviation for each plant population are represented in the graph by a cross and error bars, respectively.
Figure 20A:
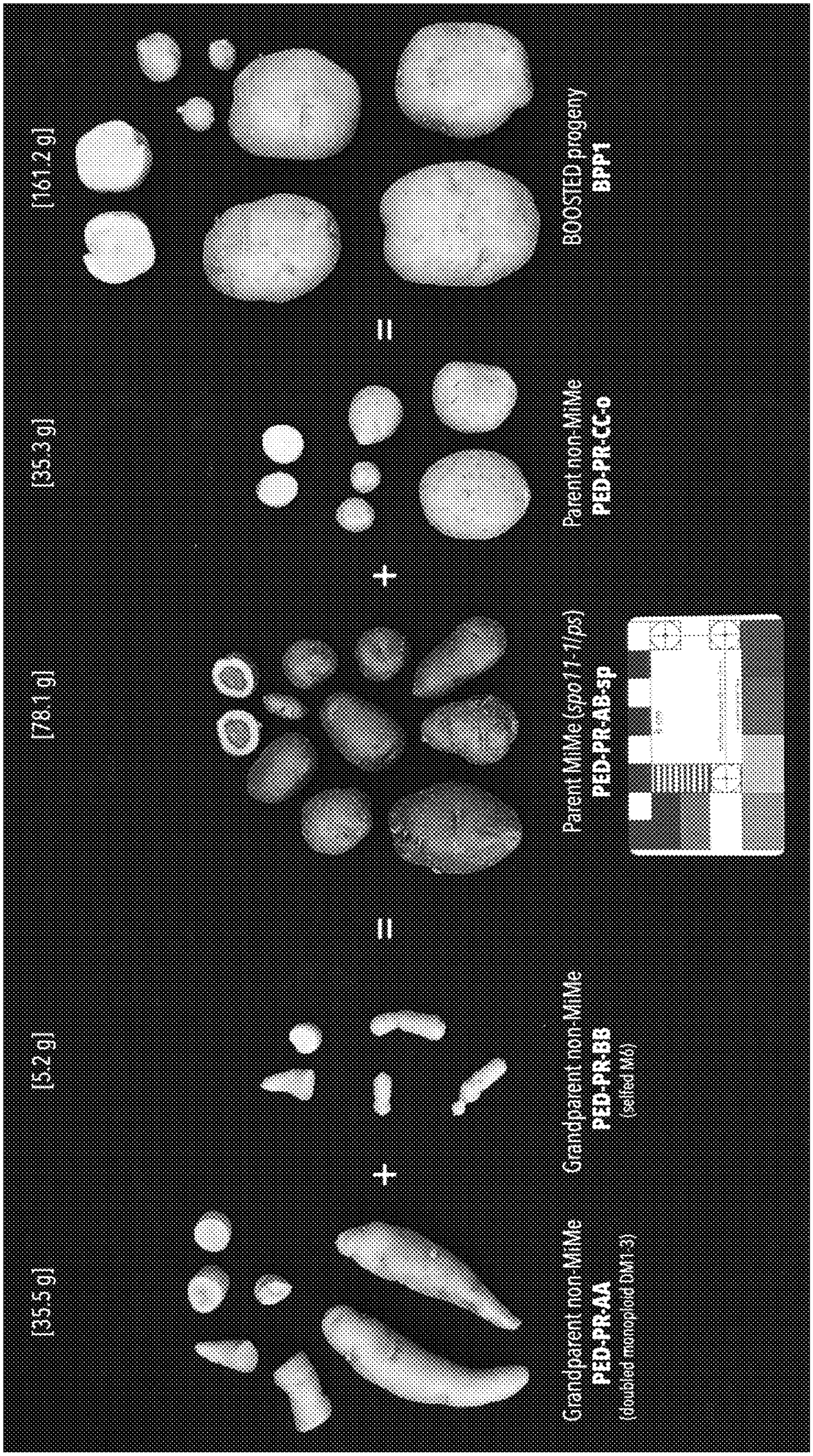
FIG. 20A-20B show and measure the comparative tuber sizes of BPP1 and the crosses that generate BPP1.
Figure 20B:
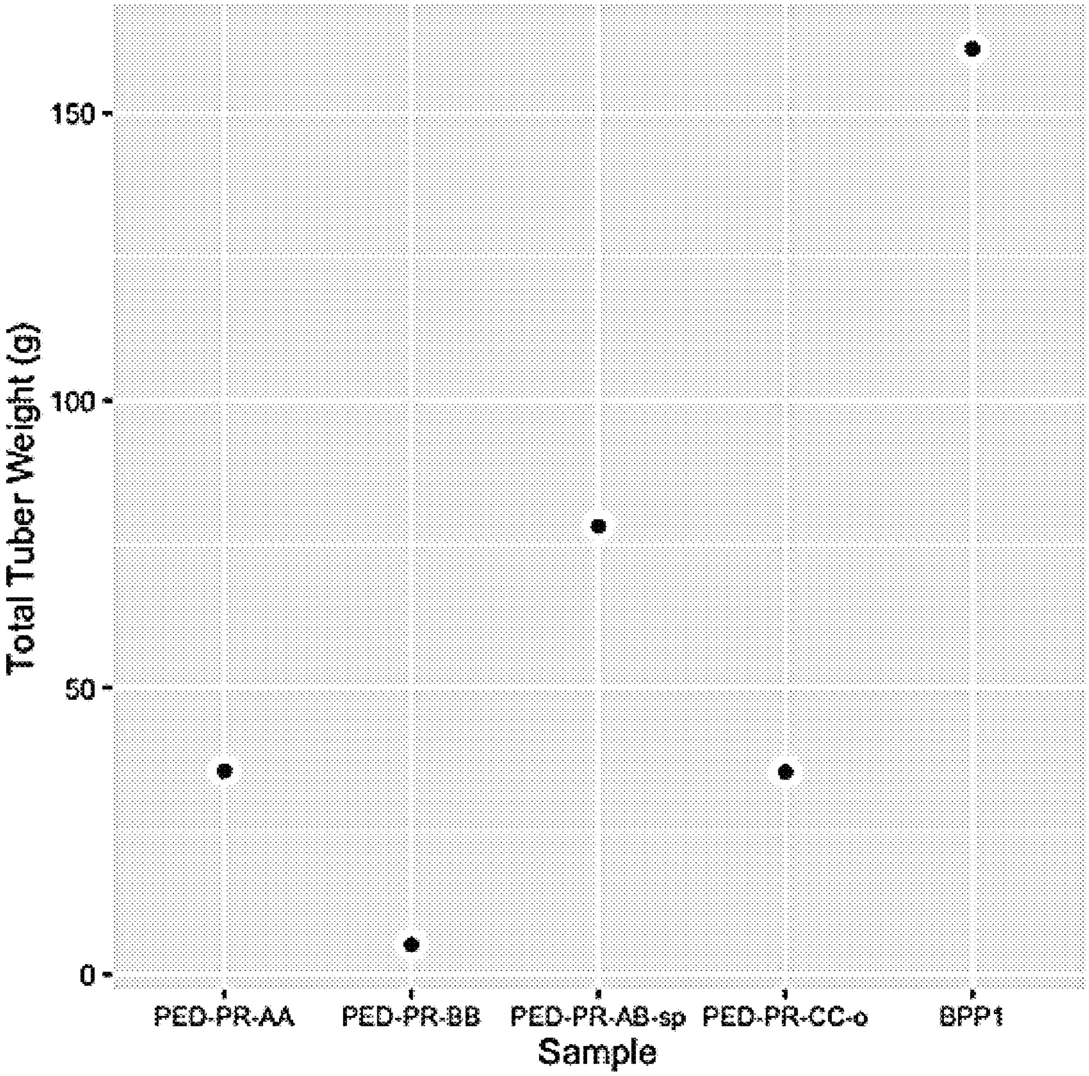

This trend intensifies through further days post-planting. By 19 and 26 days post-planting (FIG. 17E and FIG. 17G, respectively), the BPP1 plant has higher vigor, more nodes, more leaves, more leaf surface area (quantified in FIGS. 17F and 17H), and a more spreading growth habit than the compared plants. By 16 days post-planting, BPP1 plants exhibit these same superior traits when compared to the diploid SPP2 potato plants created from a non-MiMe cross of the wild-type version of same parents used in BPP1 (i.e. SPP2 is a cross between PED-PR-CC-o (selfed M18) and PED-PR-AB (an F1 hybrid of DM1-3xM6 without a MiMe genotype)) (FIG. 17I), and this continues at 23 days post-planting (FIG. 17K). The BPP1 plants' greater surface area per leaf is quantified in FIGS. 17J and 17L. The BPP1 plants also exhibited remarkable phenotypic uniformity, as compared to a cross of the wild-type version of the same parent plants that comprise the three haplotypes between them. At 16 days after planting, as shown in FIG. 17I, on the left, six representative progeny of SPP2, a cross between PED-PR-CC-o (selfed M18) and PED-PR-AB (an F1 hybrid of DM1-3xM6 without a MiMe genotype) exhibit very different phenotypes in terms of vigor, nodes, leaf number and leaf surface area. The phenotypic variability in SPP2 reflects the recombination between the two haplotypes present in the F1 hybrid and reduction leading to segregating recombined haploid gametes, "breaking" the two haplotypes of the heterozygous parent and preventing them from being passed to the progeny intact, and resulting in a lack of both genotypic (FIGS. 35 and 30G) and phenotypic (FIG. 17I) uniformity in SPP2. By contrast, on the right of FIG. 17I, six representative progeny of BPP1 (i.e., a cross between PED-PR-CC-o, selfed M18, and PED-PR-AB-sp, an F1 hybrid of DM1-3xM6 having a MiMe genotype) having three haplotypes shows both phenotypic uniformity and, on average, greater leaf surface area than the non-MiMe cross on the left, as quantified in FIG. 17J. Similar results are observed at 23 days after planting (FIGS. 17K and 17L). Finally, tubers harvested from BPP1 plants exhibit a remarkable increase in weight as compared to its parent and grandparent plants, showing the benefits of progressive heterosis of the three haplotypes of the BPP1 plants (FIGS. 20A-20B) and suggesting that potato plants comprising three or more haplotypes may have superior yield over diploid varieties and for one skilled in the art this shows the potential for superior yield and performance over cultivated tetraploids through successive generations of breeding. Furthermore, these results suggest that progressive heterosis can be maximized through the system described herein by combining the intact haplotypes of parents comprising superior diploid F1 hybrids with a MiMe genotype/phenotype with a third or fourth haplotype from either an inbred or a second superior diploid F1 hybrid with a MiMe genotype/phenotype to maximize variety performance as well as phenotypic and genotypic uniformity from true seed.

Similar to BPP1 plants, BPP2 plants having four haplotypes also exhibited superior traits compared to parent plants, grandparent plants, and elite commercial tetraploid plants. By 23 and 29 days post-planting, the BPP2 plants exhibit more vigor, taller height, and higher total leaf surface area than all compared plants (FIGS. 18A and 18B), even in crosses where the grandparent plants and parent plants are all tetraploid as well (FIGS. 18C and 18D). This shows that the improved performance is not simply due to an effect of ploidy (e.g. larger cells), but is also due to the composition of the plants having four haplotypes and improved progressive heterosis. Also, similar to BPP1 plants, representative BPP2 plants showed remarkably superior phenotypic uniformity, as compared to a cross of the wild-type version of the same parent plants that comprise the four haplotypes between them, as well as greater leaf surface area at both 16 (FIGS. 18E and 18F) and 23 (FIGS. 18G and 18H) days post-planting. At the time of filing the present disclosure, tuber data were not yet available for BPP2. However, given the superior tuber weight data observed for BPP1 having three haplotypes, those skilled in the art can readily expect that the combination of four haplotypes in BPP2 to exhibit superior tuber weight as well.

These experiments and associated figures demonstrate that despite the tested plants all being of the same age, grown in the same conditions, and produced from crosses using the same varieties of plant, the application of the MiMe genotype to generate a population of genetically-uniform polyploid seed having three or four haplotypes results in plants that display successful and superior progressive heterosis. These results show the surprisingly superior traits that can be achieved in plants grown from the populations of polyploid potato seed generated using the methods described herein. Provided that the source varieties for these experiments were chosen on a basis of availability rather than maximizing desired or specific phenotypes, those skilled in the art can readily appreciate that application of this disclosure to more precise breeding will yield even more superior stock.

What is claimed is:

1. A population of polyploid potato seed comprising genetically uniform polyploid potato seed in an amount of at least 70% of the total number of seeds, wherein the population is all of the seeds obtained from crossing a first diploid parent MiMe potato plant having MiMe alleles on both sets of chromosomes with a second diploid parent MiMe potato plant having MiMe alleles on both sets of chromosomes, the first and second diploid parent MiMe potato plants together comprising three or four haplotypes, wherein the genetically uniform polyploid potato seed is tetraploid and comprises the three or four haplotypes and the MiMe alleles on all sets of chromosomes, the MiMe alleles comprising:

(1) a genetic modification at a REC8 locus that eliminates the expression of, or the function of, a REC8 protein encoded by the REC8 locus, wherein the REC8 protein comprises an amino acid sequence having at least 95% identity to the sequence of SEQ ID NO: 1;

(2) a genetic modification at a SPO11-1 locus that eliminates the expression of, or the function of, a SPO11-1 protein encoded by the SPO11-1 locus, wherein the SPO11-1 protein comprises an amino acid sequence having at least 95% identity to the sequence of SEQ ID NO: 2; and (3) a genetic modification at a CYCA1 locus that eliminates the expression of, or the function of, a CYCA1 protein encoded by the CYCA1 locus, wherein the CYCA1 protein comprises an amino acid sequence having at least 95% identity to the amino acid sequence of SEQ ID NO: 5, to the amino acid sequence of SEQ ID NO: 6, or to the amino acid sequence of SEQ ID NO: 7.

2. The population of claim 1, wherein the population of polyploid potato seed comprises the genetically uniform polyploid potato seed in an amount of at least 90%, at least 95%, at least 96%, at least 97%, at least 98%, or at least 99% of the total number of seeds.

3. The population of claim 1, wherein:

(1) the genetic modification at the REC8 locus comprises a deletion or one or more nucleotide changes positioned in the first 500 nucleotides of a nucleotide sequence encoding the REC8 protein following the start codon in the 3' direction;

(2) the genetic modification at the SPO11-1 locus comprises a deletion or one or more nucleotide changes positioned in the first 500 nucleotides of a nucleotide sequence encoding the SPO11-1 protein following the start codon in the 3' direction; and/or (3) the genetic modification at the CYCA1 locus comprises a deletion or one or more nucleotide changes positioned in the first 500 nucleotides of a nucleotide sequence encoding the CYCA1 protein following the start codon in the 3' direction.

4. The population of claim 3, wherein:

(i) the genetic modification at the CYCA1 locus comprises a polynucleotide sequence selected from the group consisting of SEQ ID NOs: 143, 144, 149, and 150;

(ii) the genetic modification at the REC8 locus comprises a polynucleotide sequence selected from the group consisting of SEQ ID NOs: 145, 146, 151, and 152; and (iii) the genetic modification at the SPO11-1 locus comprises a polynucleotide sequence selected from the group consisting of SEQ ID NOs: 147, 148, 153, and 154.

5. The population of claim 1, wherein:

(1) the genetic modification at the REC8 locus comprises a deletion or one or more nucleotide changes positioned in the first 500 nucleotides of a nucleotide sequence encoding the REC8 protein following the start codon in the 3' direction;

(2) the genetic modification at the SPO11-1 locus comprises a deletion or one or more nucleotide changes positioned in the first 500 nucleotides of a nucleotide sequence encoding the SPO11-1 protein following the start codon in the 3' direction; and (3) the genetic modification at the CYCA1 locus comprises a deletion or one or more nucleotide changes positioned in the first 500 nucleotides of a nucleotide sequence encoding the CYCA1 protein following the start codon in the 3' direction.

* * * * *